US010865216B2

(12) United States Patent
Bensen et al.

(10) Patent No.: US 10,865,216 B2
(45) Date of Patent: Dec. 15, 2020

(54) TRICYCLIC GYRASE INHIBITORS

(71) Applicants: MERCK SHARP & DOHME CORP., Rahway, NJ (US); LAWRENCE LIVERMORE NATIONAL SECURITY, LLC, Livermore, CA (US)

(72) Inventors: Daniel Bensen, Carlsbad, CA (US); Allen Borchardt, San Diego, CA (US); Zhiyong Chen, San Diego, CA (US); John M. Finn, Encinitas, CA (US); Thanh To Lam, San Diego, CA (US); Suk Joong Lee, San Diego, CA (US); Xiaoming Li, San Diego, CA (US); Leslie William Tari, San Diego, CA (US); Min Teng, San Diego, CA (US); Michael Trzoss, San Diego, CA (US); Junhu Zhang, San Diego, CA (US); Michael E. Jung, Los Angeles, CA (US); Felice C. Lightstone, Fremont, CA (US); Sergio E. Wong, San Jose, CA (US); Toan B. Nguyen, San Ramon, CA (US)

(73) Assignees: MERCK SHARP & DOHME CORP., Rahway, NJ (US); LAWRENCE LIVERMORE NATIONAL SECURITY, LLC, Livermore, CA (US)

(*) Notice: Subject to any disclaimer, the term of this patent is extended or adjusted under 35 U.S.C. 154(b) by 0 days.

(21) Appl. No.: 14/427,611

(22) PCT Filed: Sep. 11, 2013

(86) PCT No.: PCT/US2013/059310
§ 371 (c)(1),
(2) Date: Mar. 11, 2015

(87) PCT Pub. No.: WO2014/043272
PCT Pub. Date: Mar. 20, 2014

(65) Prior Publication Data
US 2015/0246934 A1 Sep. 3, 2015

Related U.S. Application Data

(60) Provisional application No. 61/700,159, filed on Sep. 12, 2012.

(51) Int. Cl.
| | |
|---|---|
| C07D 487/04 | (2006.01) |
| C07D 519/00 | (2006.01) |
| C07D 515/22 | (2006.01) |
| C07D 487/16 | (2006.01) |
| C07D 487/22 | (2006.01) |
| C07D 498/22 | (2006.01) |

(52) U.S. Cl.
CPC ......... *C07D 519/00* (2013.01); *C07D 487/04* (2013.01); *C07D 487/16* (2013.01); *C07D 487/22* (2013.01); *C07D 498/22* (2013.01); *C07D 515/22* (2013.01)

(58) Field of Classification Search
CPC .................................................... C07D 487/04
See application file for complete search history.

(56) References Cited

U.S. PATENT DOCUMENTS

2012/0238751 A1* 9/2012 Phillipson et al. .. C07D 487/14
540/600
2016/0222015 A1* 8/2016 Zhang et al. ........ C07D 487/04

FOREIGN PATENT DOCUMENTS

| CN | 103562208 A | 2/2014 | | |
|---|---|---|---|---|
| IN | 157280 A | 2/1986 | | |
| WO | 2005037825 A2 | 4/2005 | | |
| WO | 2011032050 A2 | 3/2011 | | |
| WO | WO 2012/125746 A1 * | 9/2012 | ........... | C07D 487/04 |
| WO | WO-2012125746 A1 * | 9/2012 | ........... | C07D 487/04 |

OTHER PUBLICATIONS

Patani, G.A., et al. "Bioisosterism: A Rational Approach in Drug Design." Chem. Rev. (c) 1996, vol. 96, pp. 3147-3176.*
Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Tessier, P.R., Nicolau, D.P. "In Vitro Activity of Novel Gyrase Inhibitors against a Highly Resistant Population of Pseudomonas aeruginosa". Antimicrobial Agents and Chemotherapy. (Jun. 2013), vol. 57, No. 6, pp. 2887-2889. (Year: 2013).*
Venugopalan, B., et al., Synthesis of 6,7-Dimethoxypyrimido[4,5-b]-indoles as Potential Antihypertensive Agents, Journal of Heterocyclic Chemistry, 1988, 1633-1639, 25.
Tessier et al., "In Vitro Activity of Novel Gyrase Inhibitors against a Highly Resistant Population of Pseudomonas Aeruginosa," Antimicrobial Agents and Chemotherapy (2013); 57(6):2887-2889.
STN Registry (Feb. 14, 1987); 2 pages.

* cited by examiner

*Primary Examiner* — John S Kenyon
(74) *Attorney, Agent, or Firm* — Fox Rothschild LLP

(57) ABSTRACT

Disclosed herein are compounds having the structure of Formula I and pharmaceutically suitable salts, esters, and prodrugs thereof that are useful as antibacterially effective tricyclic gyrase inhibitors. In addition, species of tricyclic gyrase inhibitors compounds are also disclosed herein.
Related pharmaceutical compositions, uses and methods of making the compounds are also contemplated.

16 Claims, 3 Drawing Sheets

TRICYCLIC GYRASE INHIBITORS

This application is a U.S. national phase under 35 U.S.C. § 371 of International Application No. PCT/US2013/059310, entitled "TRICYCLIC GYRASE INHIBITORS," filed Sep. 11, 2013, which claims priority under 35 U.S.C. § 119(e) to U.S. Provisional Application No. 61/700,159, filed Sep. 12, 2012. The contents of each of these applications are incorporated herein by reference in their entireties.

BACKGROUND

Field

The present disclosure relates to the field of medicinal chemistry and in particular to compounds, and pharmaceutical compositions thereof, that are useful as antibiotics. Particularly, tricyclic gyrase compounds inhibit DNA Gyrase B (GyrB) and Topoisomerase IV (ParE) enzymes. Related methods of treating bacterial infections and methods of making the compounds using novel intermediates are also contemplated.

Description of the Related Art

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

One target for development of anti-bacterial drugs has been DNA Gyrase B (GyrB) and Topoisomerase IV (ParE) enzymes necessary for DNA replication. Gyrase inhibitors have been disclosed in RE40,245, which is hereby incorporated by reference in its entirety.

The GyrB enzymatic pocket has been characterized in detail in Wigley, D. B. et al., Nature, 351(6328), 624-629, 1991. See also, Tsai F T, et al., *The high-resolution crystal structure of a 24-kDa gyrase B fragment from E. coli complexed with one of the most potent coumarin inhibitors, clorobiocin*, Proteins. 1997 May; 28(1):41-52.

The ParE enzymatic pocket has been characterized in detail in Bellon, S., et al. *Crystal structures of Escherichia coli topoisomerase IV ParE subunit (24 and 43 kilodaltons): a single residue dictates differences in novobiocin potency against topoisomerase IV and DNA gyrase*, Antimicrob. Agents Chemother. 48: 1856-1864 (2004). These references are hereby incorporated by reference in their entirety.

In contrast, patent publications naming Hurley et al. as inventors, are directed to protein kinase inhibitors that are useful for protein kinase-mediated diseases and conditions such as cancer. See, e.g., US 2008/0051414, US 2009/0143399, and US 2009/0099165.

PCT/US2012/029104, filed by the same assignees in the present application, discloses tricyclic gyrase inhibitors and is incorporated herein by reference in its entirety.

SUMMARY

Tricyclic gyrase compounds of Formula I, including compounds herein, inhibit DNA Gyrase B (GyrB) and Topoisomerase IV (ParE) enzymes.

In some aspects, the claims do not include the compounds disclosed in PCT/US2012/029104, with the exception of unexpectedly advantageous species of compounds, which have not been previously disclosed but may fall within the genus of compounds disclosed in PCT/US2012/029104. For example, in some aspects, the present claims do not include: A compound having the structure of Formula I'

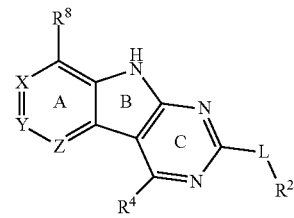

Formula I' or pharmaceutically suitable salts, esters, and prodrugs thereof, wherein

L is O or S;

$R^8$ is H or an interacting substituent having a length of about 1 Å to about 5 Å from the carbon attachment point on the A Ring to the terminal atom in $R^8$ and a width of about 3.3 Å or less;

X, Y and Z are independently selected from the group consisting of N, $CR^X$, $CR^Y$, and $CR^Z$, provided that no more than two of X, Y and Z are N, wherein $R^X$ is H or an interacting substituent having a length of about 1 Å to about 2 Å from the carbon in $CR^X$ to the terminal atom in $R^X$;

wherein $R^Y$ is H or an interacting substituent having a length of about 1 Å to about 3 Å from the carbon in $CR^Y$ to the terminal atom in $R^Y$;

wherein $R^Z$ is H or an interacting substituent having a length of about 1 Å to about 2 Å from the carbon in $CR^Z$ to the terminal atom in $R^Z$;

$R^2$ is a 6-membered aryl or heteroaryl ring containing 0-3 O, S, or N heteroatoms, optionally substituted with 0-3 noninterfering substituents, wherein 2 adjacent noninterfering substituents on $R^2$ may form one or more fused rings with the 6-membered aryl or heteroaryl ring;

wherein the 6-membered aryl or heteroaryl ring of $R^2$ has a CH at the positions immediately adjacent the position where $R^2$ attaches to L;

$R^4$ is:

H;

an optionally substituted $OR^a$;

an optionally substituted secondary or tertiary amine attached to the C Ring through the secondary or tertiary amine N; or an optionally substituted 5-10 membered unsaturated cyclic or heterocyclic residue containing 0-3 N, O or S heteroatoms;

wherein the optional substituent is 0-3 noninterfering substituents;

wherein $R^a$ is a 5-6 membered aryl or heteroaryl containing 0-3 O, S, or N heteroatoms optionally substituted with 0-3 noninterfering substituents;

wherein the $R^4$ substituent does not project greater than about 3 Å below the plane of the A, B and C Rings toward the GyrB/ParE binding pocket floor in the bound conformation; and wherein $R^4$ does not sterically interfere with $R^2$ or Z when the compound is in the bound conformation.

Compounds herein may have the structure of Formula I:

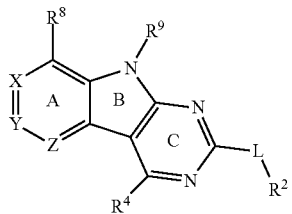

Formula I or pharmaceutically suitable salts, esters, and prodrugs thereof,
wherein
L is:
a) O or S; or
b) NH, $CH_2$, CHF, $CF_2$, $SCH_2$, $OCH_2$, $NCH_2$, $NHCH_2$, CH=CH, $CH_2CH_2$, $SCH_2CONH$, $OCH_2CONH$, $NHCH_2CONH$, $OCH_2CH$=CH, or $SCH_2CH$=CH;
$R^8$ is:
a) H or an interacting substituent having a length of about 1 Å to about 5 Å from the carbon attachment point on the A Ring to the terminal atom in $R^8$ and a width of about 3.3 Å or less; or
b) a prodrug-containing substituent, wherein the compound has the structure of Formula II:

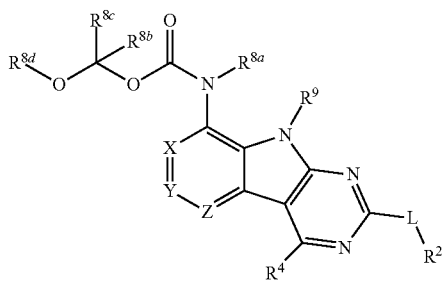

Formula II or a pharmaceutically acceptable salt thereof;
wherein $R^8$ is H or an interacting substituent having a length of about 1 Å to about 3.3 Å from the adjacent nitrogen to the terminal atom in $R^8$ and a width of about 3.3 Å or less;
wherein $R^{8b}$ and $R^{8c}$ are independently H or C1-C6 alkyl;
wherein $R^{8d}$ is

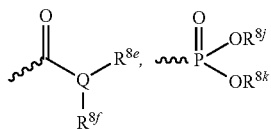

or a pharmaceutically acceptable salt thereof;
wherein Q is CH or N;
wherein $R^{8e}$ is $(CR^{8g}_2)_n$-basic amine, wherein each $R^{8g}$ may be independently H or C1-C3 alkyl;
wherein n is 0-2;
wherein $R^{8f}$ is hydrogen or C1-C6 alkyl optionally substituted with OH or $NH_2$;
wherein $R^{8e}$ and $R^{8f}$ may join to form a C3-C12 hydrocarbyl ring containing 0-3 heteroatoms selected from O, N and S optionally substituted with 0-3 noninterfering substituents;
wherein $R^8$ and $R^{8k}$ are independently H or C1-C8 hydrocarbyl residue;
c) a prodrug-containing substituent, wherein the compound has the structure of Formula II':

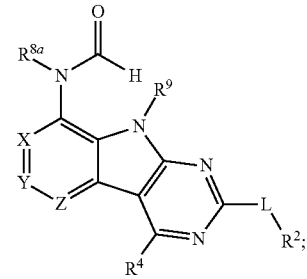

Formula II' or
d) linked to $R^9$ to form a prodrug-containing substituent, wherein the compound has the structure of Formula III:

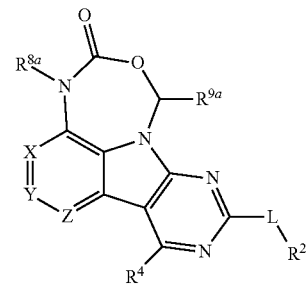

Formula III wherein $R^{9a}$ is H or C1-4 alkyl;
$R^9$ is:
a) H;
b) linked to an N in $R^8$ to form a prodrug-containing substituent, wherein the compound has the structure of Formula III;
$R^2$ is
a) a 6-membered aryl or heteroaryl ring containing 0-3 O, S, or N heteroatoms, optionally substituted with 0-3 noninterfering substituents,
wherein the 6-membered aryl or heteroaryl ring of $R^2$ has a CH at each position immediately adjacent the position where $R^2$ attaches to L, if L is O or S;
b) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S;
c) a 6-membered aryl or heteroaryl ring containing 0-3 O, S, or N heteroatoms, optionally substituted with 0-3 noninterfering substituents,
wherein the 6-membered aryl or heteroaryl ring of $R^2$ has a CH or CF independently at each position immediately adjacent the position where $R^2$ attaches to L, if L is NH, $CH_2$, CHF, or $CF_2$;
d) a 5-membered heteroaryl ring containing 1-4 O, S, or N heteroatoms, optionally substituted with 0-2 noninterfering substituents;

wherein the 5-membered heteroaryl ring of R² has O, S, N, NH, CH, CF, or CCl, independently at each of the positions immediately adjacent the position where R² attaches to L, if L is O, S, NH, CH₂, CHF, or CF₂;

e) a 6-membered or 5-membered non-aryl or non-heteroaryl ring containing 0-3 O, S, or N heteroatoms, optionally substituted with 0-3 noninterfering substituents;

wherein the 6-membered or 5-membered non-aryl or non-heteroaryl ring of R² has O, S, N, NH, CH, CF, or CH₂, independently at each position immediately adjacent the position where R² attaches to L, if L is O, S, NH, CH₂, CHF, or CF₂;

f) i) a 6-membered aryl or heteroaryl ring containing 0-3 O, S, or N heteroatoms, optionally substituted with 0-3 noninterfering substituents, ii) a 5-membered heteroaryl ring containing 1-4 O, S, or N heteroatoms, optionally substituted with 0-2 noninterfering substituents, or iii) a 6-membered or 5-membered non-aryl or non-heteroaryl ring containing 0-3 O, S, or N heteroatoms, optionally with 0-3 noninterfering substituents, when L contains two or more members in the backbone thereof in any of f)i) to f)iii);

wherein 2 adjacent noninterfering substituents of R² in a)-f) may form one or more fused rings with the 6-membered aryl or heteroaryl ring, the 5-membered heteroaryl ring, or the 6-membered or 5-membered non-aryl or non-heteroaryl ring;

g) a prodrug-containing substituent, wherein the compound has the structure of Formula IV:

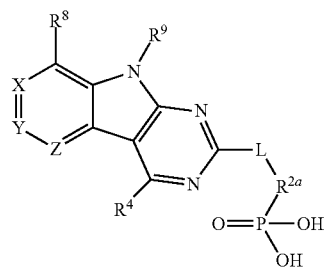

Formula IV or a pharmaceutically acceptable salt thereof;
wherein R²ᵃ contains an oxygen residue derived from an R² as in a)-f),
wherein R² has an OH group, wherein the R² OH is replaced with an oxygen residue in R²ᵃ, and wherein the oxygen residue is linked to P;

h) joined with R⁴ to form a fused ring, wherein R² is a ring as recited in a)-f) attached to R⁴; wherein if a 6-membered ring of R² is attached to L and R⁴, R⁴ is attached through the meta or para position of the 6-membered ring with respect to the point of attachment to L;

i)

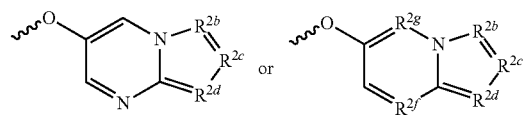

wherein R²ᵇ, R²ᶜ, R²ᵈ, R²ᶠ and R²ᵍ independently may be each N or CR²ᵉ wherein R²ᵉ is H or C1-C4 alkyl optionally substituted with a noninterfering substituent; or j) selected from the group consisting of

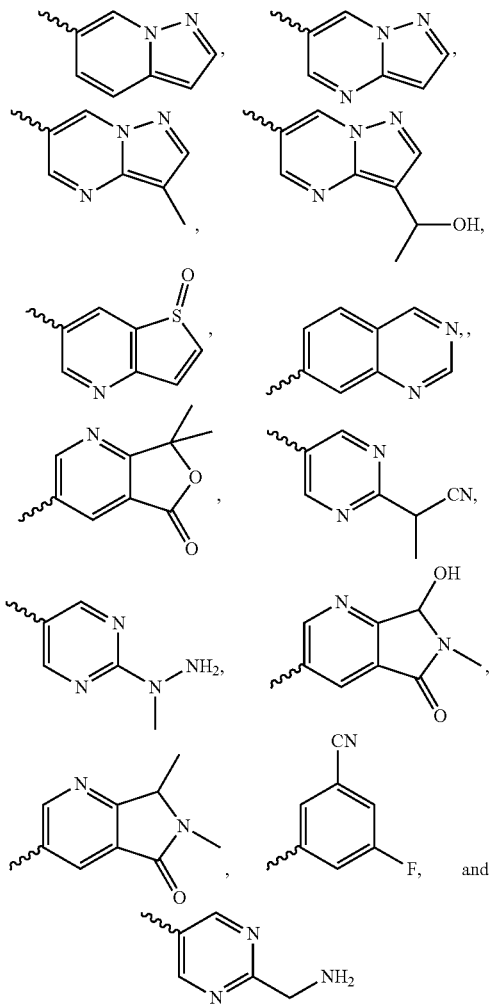

R⁴ is:
a) H;
b) an optionally substituted ORa; wherein Ra is a 5-6 membered aryl or heteroaryl containing 0-3 O, S, or N heteroatoms optionally substituted with 0-3 noninterfering substituents;
c) an optionally substituted secondary or tertiary amine attached to the C Ring through the secondary or tertiary amine N;
d) an optionally substituted 5-10 membered unsaturated cyclic or heterocyclic residue containing 0-3 N, O or S heteroatoms;
  wherein the optional substituent is 0-3 noninterfering substituents;
  wherein the R⁴ substituent of a)-d) does not project greater than about 3 Å below the plane of the A, B and C Rings toward the GyrB/ParE binding pocket floor in the bound conformation; and
  wherein R⁴ does not sterically interfere with R² or Z when the compound is in the bound conformation;
e) a prodrug-containing substituent, wherein the compound has the structure of Formula V or Formula V':

Formula V

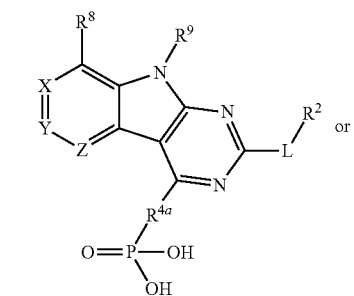

or

Formula V'

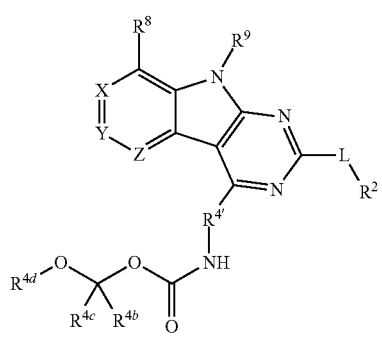

or a pharmaceutically acceptable salt thereof;
wherein $R^{4a}$ contains an oxygen residue derived from a non-prodrug $R^4$ as in b)-d) or g)-i), wherein the non-prodrug $R^4$ has an OH group, wherein the $R^4$ OH is replaced with an oxygen residue in $R^{4a}$, and wherein the oxygen residue is linked to P;
wherein $R^{4'}$—NH is derived from a non-prodrug $R^4$ as in b)-d) or g)-i), wherein the non-prodrug $R^4$ contains a primary amine and wherein the NH in the primary amine links the $R^4$ residue to the C=O;
wherein $R^{4b}$ and $R^{4c}$ are independently H or C1-C6 alkyl;
wherein $R^{4d}$ is

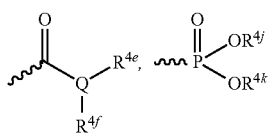

or a pharmaceutically acceptable salt thereof;
  wherein Q is CH or N;
  wherein $R^{4e}$ is $(CR^{4g}_2)_n$-basic amine, wherein each $R^{4g}$ may be independently H or C1-C3 alkyl;
  wherein n is 0-2;
  wherein $R^{4f}$ is hydrogen or C1-C6 alkyl optionally substituted with OH or $NH_2$;
  wherein $R^{4e}$ and $R^{4f}$ may join to form a ring;
  wherein $R^{4j}$ and $R^{4k}$ are independently H or C1-C8 hydrocarbyl residue;
f) a prodrug-containing substituent, wherein the compound has the structure of Formula II"

Formula II"

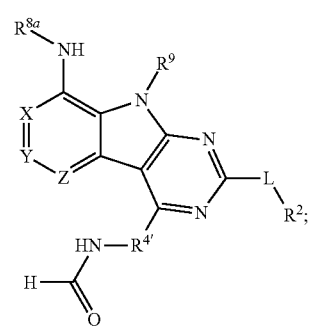

g) joined with $R^2$ to form a fused ring, wherein $R^4$ is a 5- to 15-member hydrocarbyl linker containing 0-6 O, S or N atoms in the backbone of the linker that attaches to the $R^2$ group wherein atoms in the 5- to 15-member hydrocarbyl linker are optionally substituted with a noninterfering substituent;

h) joined with Z to form a fused ring; or i) selected from the group consisting of

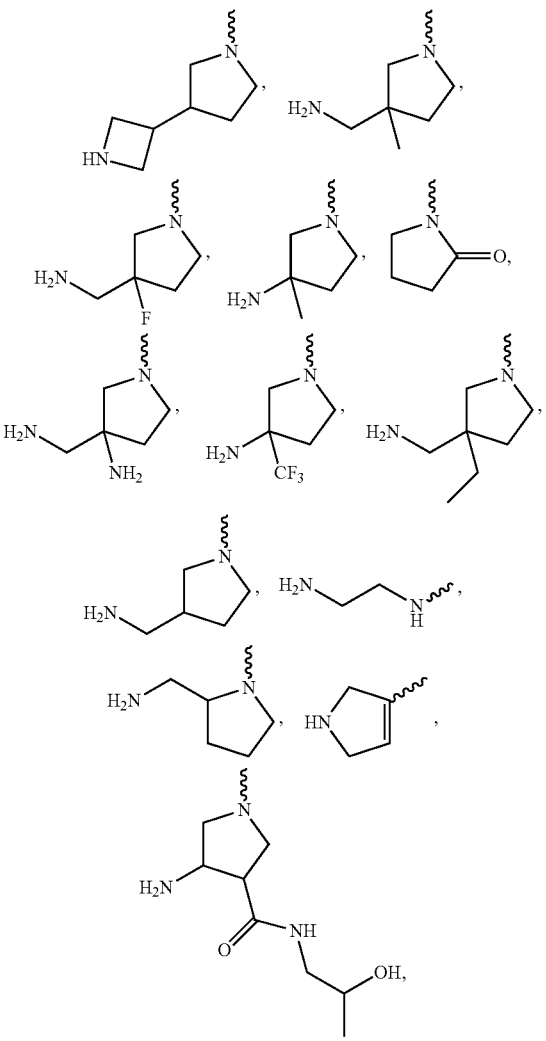

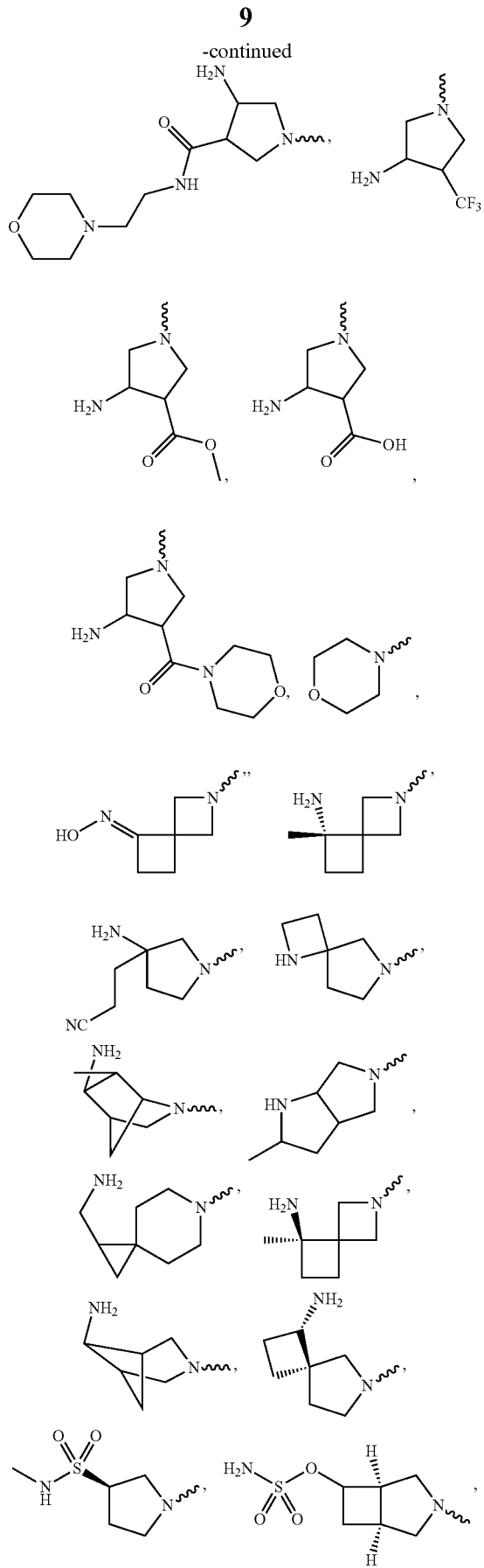

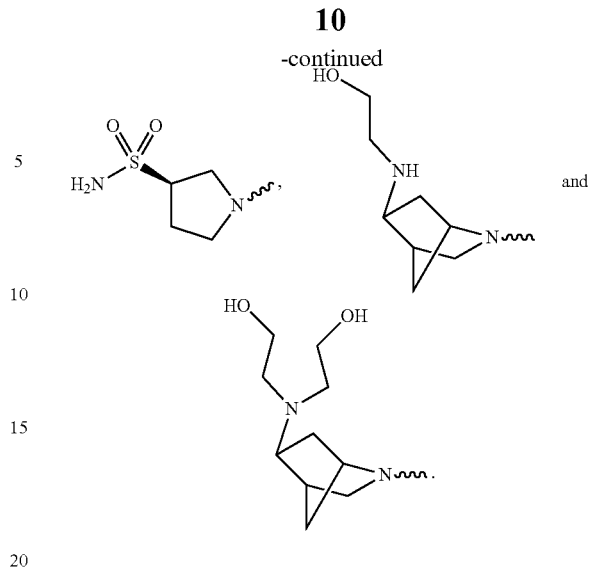

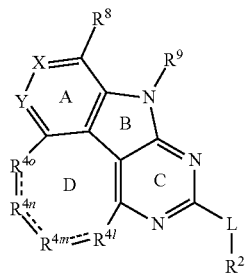

X is N or $CR^X$, wherein $R^X$ is H or an interacting substituent having a length of about 1 Å to about 2 Å from the carbon in $CR^X$ to the terminal atom in $R^Y$;

Y is N or $CR^Y$, wherein $R^Y$ is H or an interacting substituent having a length of about 1 Å to about 3 Å from the carbon in $CR^Y$ to the terminal atom in $R^Y$;

Z is:
a) N or $CR^Z$ wherein $R^Z$ is H or an interacting substituent having a length of about 1 Å to about 2 Å from the carbon in $CR^Z$ to the terminal atom in $R^Z$; or
b) C linked to $R^4$, wherein the compound has the structure of Formula VI Formula VI wherein $R^{4l}$ is $CR^{10}$, $CR^{10}CR^{11}$, $R^{12}$, O or S;
wherein $R^{4m}$ is $CR^{10}$, $CR^{10}CR^{11}$, or $NR^{12}$;
wherein $R^{4n}$ is $CR^{10}$, $CR^{10}CR^{11}$, $NR^{12}$, O or S
wherein each of $R^{10}$, $R^{11}$ and $R^{12}$ is independently H or a noninterfering substituent;
wherein 2 adjacent noninterfering substituents on either $R^{4l}$ and $R^{4m}$ or $R^{4m}$ and $R^{4n}$ may form one or more fused rings;
the dashed lines indicate an optional double bond when two adjacent $R^{4l}$, $R^{4m}$, and $R^{4n}$ are $CR^{10}$ and $R^{4o}$ is CH or N;
wherein $R^{4o}$ is:
1) a bond, wherein a 7-membered D ring is formed, wherein $R^{4n}$ may be CH, $CH_2$, S, NH, O, CHF, or $CF_2$; or
2) a 1 member link in the backbone of the D ring wherein an 8-membered D Ring is formed, wherein the 1 member link may be CH, $CH_2$, S, NH, O, CHF, or $CF_2$;
3) a 2 member link in the backbone of the D ring that forms a 9-membered D Ring, wherein the member adjacent the A Ring may be CH, $CH_2$, S, NH, O, CHF, or $CF_2$; wherein the D Ring contains at least one N in the backbone or wherein a substituent on the D Ring contains at least one N;

wherein the D ring does not project greater than about 3 Å below the plane of the A, B and C Rings toward the GyrB/ParE binding pocket floor in the bound conformation; and wherein the D ring does not sterically interfere with $R^2$ when the compound is in the bound conformation;

provided that no more than two of X, Y and Z are N wherein the compound of Formula I has least one of the following moieties i)-vi):

i) L is NH, $CH_2$, CHF, $CF_2$, $SCH_2$, $OCH_2$, $NHCH_2$, CH=CH, $CH_2CH_2$, $SCH_2CONH$, $OCH_2CONH$, $NHCH_2CONH$, $OCH_2CH=CH$, or $SCH_2CH=CH$;

ii) $R^8$ is:

a. a prodrug-containing substituent, wherein the compound has the structure of Formula II:

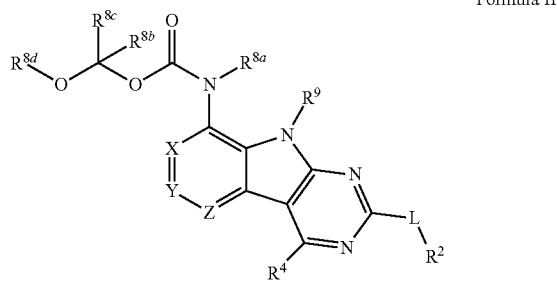

Formula II wherein $R^{8a}$ is H or an interacting substituent having a length of about 1 Å to about 3.3 Å from the adjacent nitrogen to the terminal atom in $R^{8a}$ and a width of about 3.3 Å or less;

wherein $R^{8b}$ and $R^{8c}$ are independently H or C1-C6 alkyl;

wherein $R^{8d}$ is

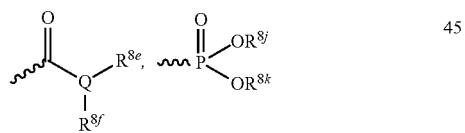

or a pharmaceutically acceptable salt thereof;

wherein Q is CH or N;

wherein $R^{8e}$ is $(CR^{8g}_2)_n$-basic amine, wherein each $R^{8g}$ may be independently H or C1-C3 alkyl;

wherein n is 0-2;

wherein $R^{8f}$ is hydrogen or C1-C6 alkyl optionally substituted with OH or $NH_2$;

wherein $R^{8e}$ and $R^{8f}$ may join to form a C3-C12 hydrocarbyl ring containing 0-3 heteroatoms selected from O, N and S optionally substituted with 0-3 noninterfering substituents;

wherein $R^8$ and $R^{8k}$ are independently H or C1-C8 hydrocarbyl residue; or e) a prodrug-containing substituent, wherein the compound has the structure of Formula II':

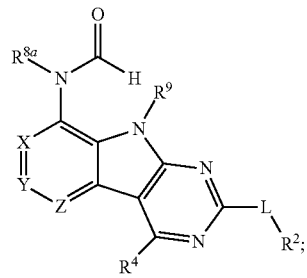

Formula II' or c) linked to $R^9$ to form a prodrug-containing substituent, wherein the compound has the structure of Formula III:

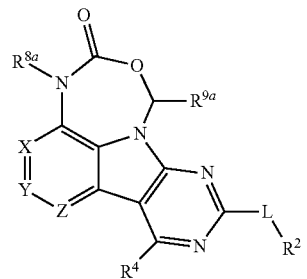

Formula III wherein $R^{9a}$ is H or C1-4 alkyl;

iii) $R^9$ is linked to an N in $R^8$ to form a prodrug-containing substituent, wherein the compound has the structure of Formula III;

iv) $R^2$ is b. a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S;

c. a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH or CF independently at each position immediately adjacent the position where $R^2$ attaches to L, if L is NH, $CH_2$, CHF, or $CF_2$;

d. a 5-membered heteroaryl ring containing 1-4 O, S, or N heteroatoms, optionally substituted with 0-2 noninterfering substituents;

wherein the 5-membered heteroaryl ring of $R^2$ has O, S, N, NH, CH, CF, or CCl, independently at each of the positions immediately adjacent the position where $R^2$ attaches to L, if L is O, S, NH, $CH_2$, CHF, or $CF_2$;

e. a 6-membered or 5-membered non-aryl or non-heteroaryl ring containing 0-3 O, S, or N heteroatoms, optionally substituted with 0-3 noninterfering substituents;

wherein the 6-membered or 5-membered non-aryl or non-heteroaryl ring of $R^2$ has O, S, N, NH, CH, CF, or $CH_2$, independently at each position immediately adjacent the position where $R^2$ attaches to L, if L is O, S, NH, $CH_2$, CHF, or $CF_2$;

f i. a 6-membered aryl or heteroaryl ring containing 0-3 O, S, or N heteroatoms, optionally substituted with 0-3 noninterfering substituents,
  ii. a 5-membered heteroaryl ring containing 1-4 O, S, or N heteroatoms, optionally substituted with 0-2 noninterfering substituents, or
  iii. a 6-membered or 5-membered non-aryl or non-heteroaryl ring containing 0-3 O, S, or N heteroatoms, optionally with 0-3 noninterfering substituents,
when L contains two or more members in the backbone thereof in any of e.i. to e.iii.;
wherein 2 adjacent noninterfering substituents of $R^2$ in a.-e. may form one or more fused rings with the 6-membered aryl or heteroaryl ring, the 5-membered heteroaryl ring, or the 6-membered or 5-membered non-aryl or non-heteroaryl ring;
g. a prodrug-containing substituent, wherein the compound has the structure of Formula IV:

Formula IV

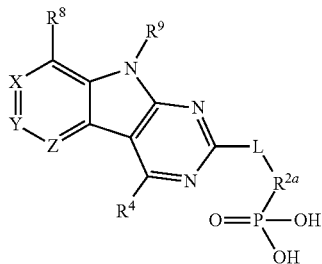

or a pharmaceutically acceptable salt thereof;
  wherein $R^{2a}$ contains an oxygen residue derived from an $R^2$ as in a)-f), wherein $R^2$ has an OH group, wherein the $R^2$ OH is replaced with an oxygen residue in $R^{2a}$, and wherein the oxygen residue is linked to P, which is discussed below in more detail;
h. joined with $R^4$ to form a fused ring, wherein $R^2$ is a ring as recited in a)-f) attached to $R^4$; wherein if a 6-membered ring of $R^2$ is attached to L and $R^4$, $R^4$ is attached through the meta or para position of the 6-membered ring with respect to the point of attachment to L;
i.

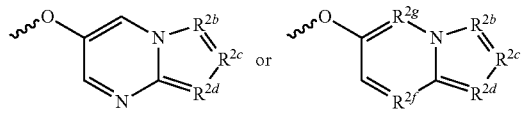

wherein $R^{2b}$, $R^{2c}$, $R^{2d}$, $R^{2f}$ and $R^{2g}$ independently may be each N or $CR^{2e}$ wherein $R^{2e}$ is H or C1-C4 alkyl optionally substituted with a noninterfering substituent, such as, $R^{2b}$ may be N, or such as $R^{2b}$ may be N and $R^{2c}$ and $R^{2d}$ may each be $CR^{2e}$, for example, CH; or
  i. selected from the group consisting of

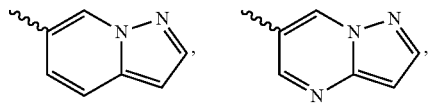

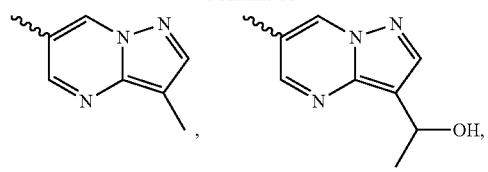

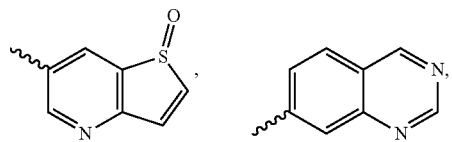

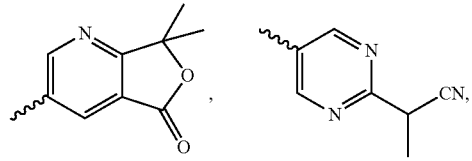

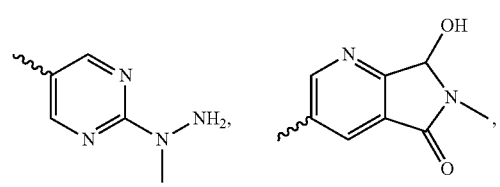

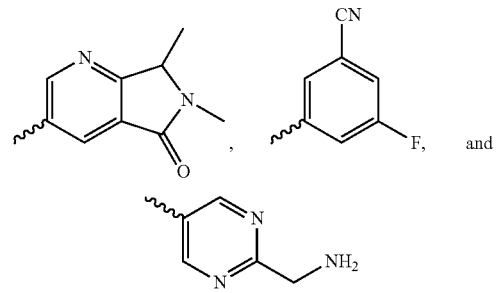

F, and v) $R^4$ is:
  a. a prodrug-containing substituent, wherein the compound has the structure of Formula V or Formula V':

Formula V

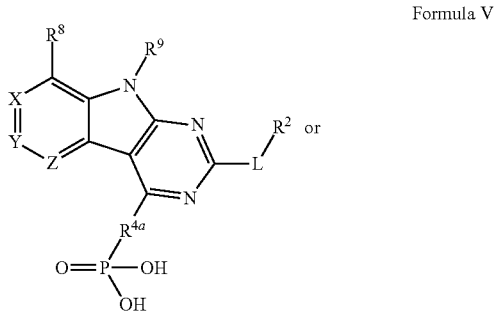

-continued

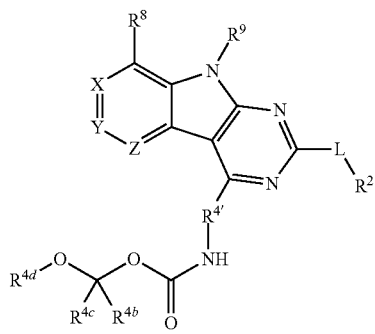

Formula V' or a pharmaceutically acceptable salt thereof;
wherein $R^{4a}$ contains an oxygen residue derived from a non-prodrug $R^4$ as in b)-d) or g)-i), wherein the non-prodrug $R^4$ has an OH group, wherein the $R^4$ OH is replaced with an oxygen residue in $R^{4a}$, and wherein the oxygen residue is linked to P;
wherein $R^{4'}$—NH is derived from a non-prodrug $R^4$ as in b)-d) or g)-i), wherein the non-prodrug $R^4$ contains a primary amine and wherein the NH in the primary amine links the $R^4$ residue to the C=O;
wherein $R^{4b}$ and $R^{4c}$ are independently H or C1-C6 alkyl;
wherein $R^{4d}$ is

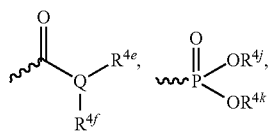

or a pharmaceutically acceptable salt thereof;
wherein Q is CH or N;
wherein $R^{4e}$ is $(CR^{4g}_2)_n$-basic amine, wherein each $R^{4g}$ may be independently H or C1-C3 alkyl;
wherein n is 0-2;
wherein $R^{4f}$ is hydrogen or C1-C6 alkyl optionally substituted with OH or $NH_2$;
wherein $R^{4e}$ and $R^{4f}$ may join to form a ring;
wherein $R^{4j}$ and $R^{4k}$ are independently H or C1-C8 hydrocarbyl residue; or
b. a prodrug-containing substituent, wherein the compound has the structure of Formula II''

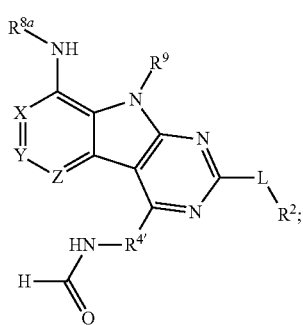

Formula II'' c. joined with $R^2$ to form a fused ring, wherein $R^4$ is a 5- to 15-member hydrocarbyl linker containing 0-6 O, S or N atoms in the backbone of the linker that attaches to the $R^2$ group wherein atoms in the 5- to 15-member hydrocarbyl linker are optionally substituted with a noninterfering substituent; or
d. joined with Z to form a fused ring;
e. selected from the group consisting of:

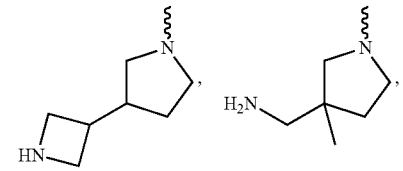

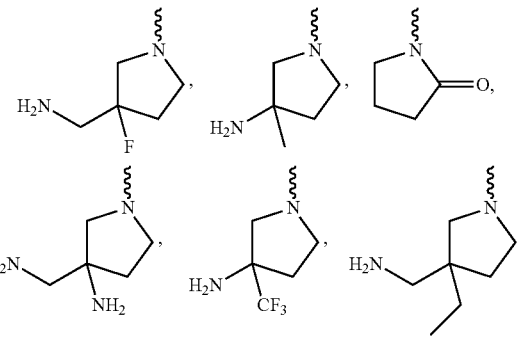

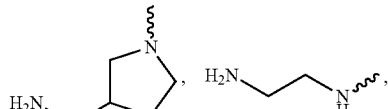

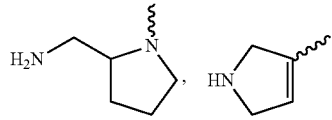

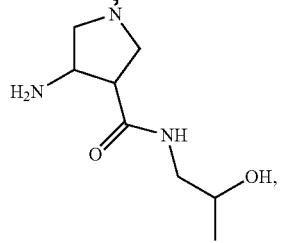

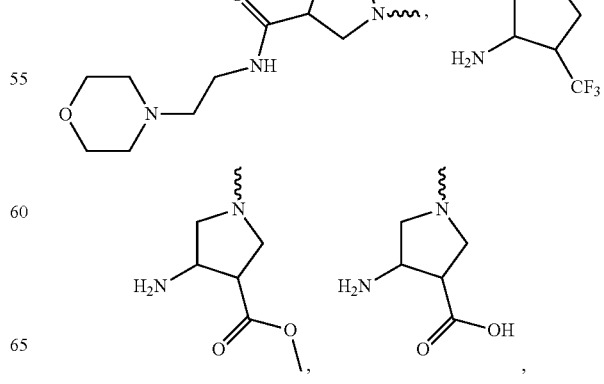

-continued

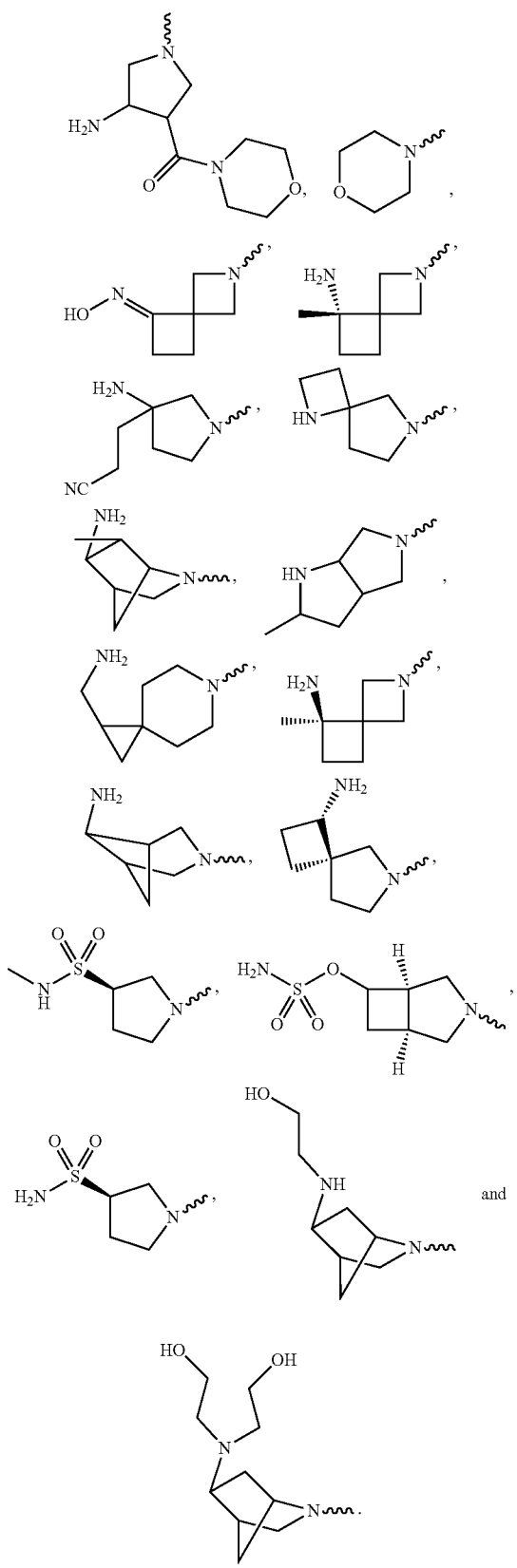

vi) Z is C linked to R⁴, wherein the compound has the structure of Formula VI

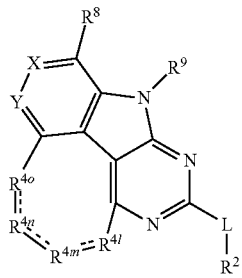

Formula VI wherein $R^{4l}$ is $CR^{10}$, $CR^{10}CR^{11}$, $NR^{12}$, O or S;
wherein $R^{4m}$ is $CR^{10}$, $CR^{10}CR^{11}$, or $NR^{12}$
wherein $R^{4n}$ is $CR^{10}$, $CR^{10}CR^{11}$, $NR^{12}$, O or S
wherein each of $R^{10}$, $R^{11}$ and $R^{12}$ is independently H or a noninterfering substituent;
wherein 2 adjacent noninterfering substituents on either $R^{4l}$ and $R^{4m}$ or $R^{4n}$ and $R^{4m}$ may form one or more fused rings;
the dashed lines indicate an optional double bond when two adjacent $R^{4l}$, $R^{4m}$, and $R^{4n}$ are $CR^{10}$ and $R^{4o}$ is CH or N;
wherein $R^{4o}$ is:
1) a bond, wherein a 7-membered D ring is formed, wherein $R^{4n}$ may be CH, $CH_2$, S, NH, O, CHF, or $CF_2$;
2) a 1 member link in the backbone of the D ring wherein an 8-membered D Ring is formed, wherein the 1 member link may be CH, $CH_2$, S, NH, O, CHF, or $CF_2$;
3) a 2 member link in the backbone of the D ring that forms a 9-membered D Ring, wherein the member adjacent the A Ring may be CH, $CH_2$, S, NH, O, CHF, or $CF_2$;
wherein the D Ring contains at least one N in the backbone or wherein a substituent on the D Ring contains at least one N;
wherein the D ring does not project greater than about 3 Å below the plane of the A, B and C Rings toward the GyrB/ParE binding pocket floor in the bound conformation; and
wherein the D ring does not sterically interfere with $R^2$ when the compound is in the bound conformation.

In addition, species of tricyclic gyrase inhibitors compounds not previously disclosed in PCT/US2012/029104 are also disclosed herein.

Methods of using the compound to treat antibacterial infections and methods of making the compounds using novel intermediates are also contemplated.

These and other related aspects are set forth in more detail below.

DETAILED DESCRIPTION

Figure 1:
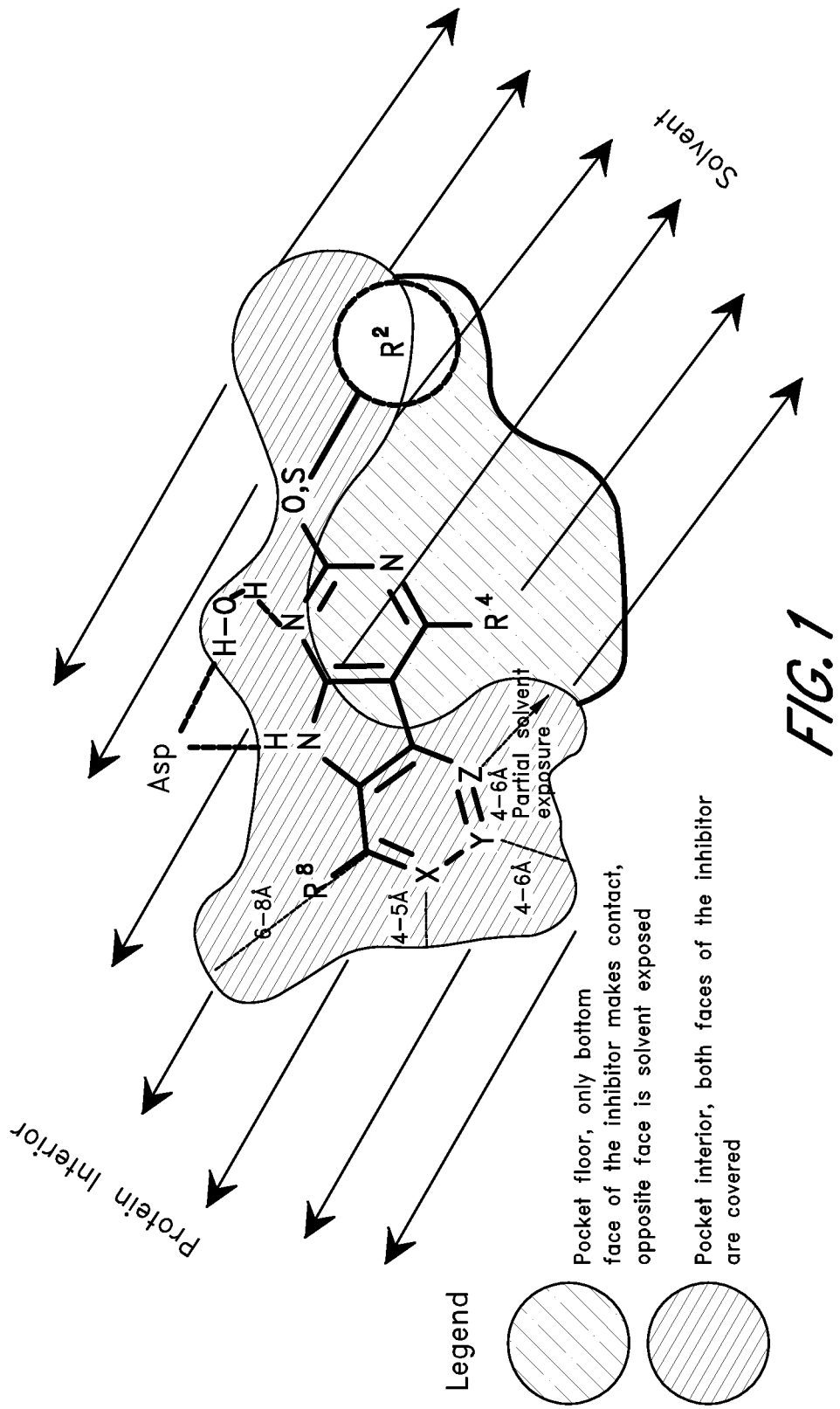
FIG. 1 illustrates a schematic representation of the receptor constraints on the compound, particularly, the binding modes of the tricyclic inhibitors to the GyrB/ParE active-site pocket (from crystallographic data). The measurements provided for the lengths are measured from atom center of the A Ring member to the atom center of the nearest non-hydrogen atom on the active site pocket. The figure indicates a length of about 6 Å to about 8 Å from the C atom attached to $R^8$ to the atom on the active site pocket; about 4 Å to about 5 Å from the A Ring atom of X to the atom on the active site pocket; about 4 Å to about 6 Å from the A Ring atom of Y to the atom on the active site pocket; and about 4 Å to about 6 Å from the A Ring atom of Z to the atom on the active site pocket. The relative positions of the $R^8$, $R^4$, and cyclic $R^2$ substituents are shown. The approximate shape of a cross-section of a representative GyrB/ParE active-site pocket in and above the plane of the tricyclic scaffold (i.e., the A, B and C Rings) is shown. The hatched area having unbroken lines depicts regions of the inhibitor that are covered on both surfaces by the active-site pocket. In addition, the approximate shape of a cross-section of a representative GyrB/ParE active-site pocket below the plane of the tricyclic scaffold is shown. The hatched area having dashed lines depict regions of the inhibitor that make contact with the floor surface of the active-site pocket, while the plane above the tricyclic ring system is solvent exposed. The approximate position of the conserved substrate-binding Asp side-chain and structural water molecule are shown in FIG. 1, along with the constellation of potential hydrogen-bonds (depicted as dotted lines) observed between the tricyclic scaffold and the Asp and water. The solvent exposed and solvent sheltered faces of the active-site pocket are highlighted. The solvent refers to the in vivo surroundings of GyrB/ParE active site as part of a protein, which generally includes an aqueous environment in which the protein is situated within a cell. Also, the $R^4$ moiety in some aspects does not project atoms greater than about 3 Å below the plane of the tricyclic ring system towards the GyrB/ParE binding pocket floor in the bound state.

Compounds of Formula I herein include in some aspects, one or more of the variables in the Formula I', i.e., L, X, Y, Z, $R^2$, $R^4$, or $R^8$, disclosed in PCT/US2012/029104, which has been replaced with one or more "new" variable substituents.

In addition, species of compounds not found in PCT/US2012/029104 have unexpected activity, such as

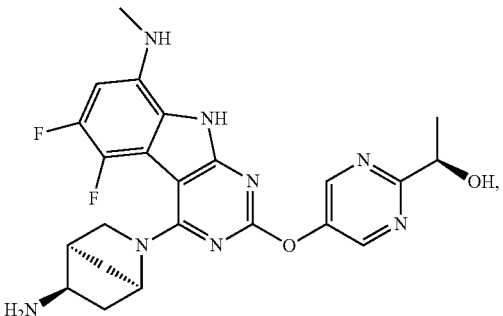

Compound 9.1

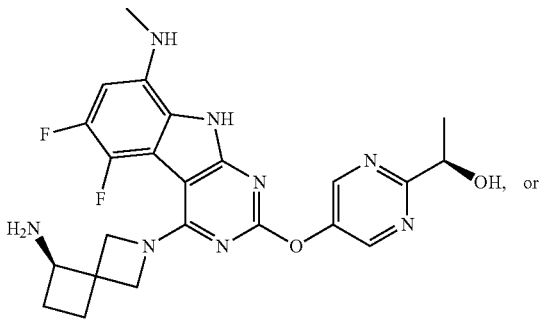

Compound 9.2

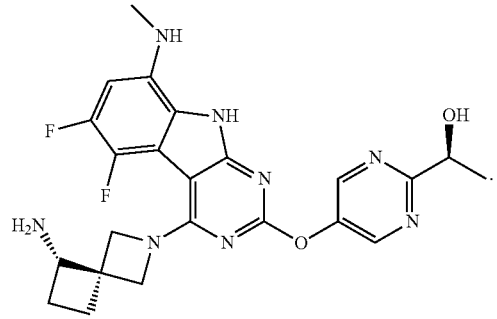

Compound 10.118

Cardiovascular side effects are a major reason for drug failures. Inhibition of hERG (human ether a go-go related gene) is used as a predictive in vitro enzymatic screen to eliminate compounds with cardiovascular side effects especially prolongation of the QTc interval (Valentin, J. *British Journal of Pharmacology* 2010, 159, 5-11). Compounds 9.1 and 9.2 were found to be unexpectedly and significantly more selective in the hERG assay than previous compounds in the series. These compounds also have excellent broad-spectrum antibacterial activity.

Certain aspects of the compounds of Formula I are elaborated below. In Formula I above, L is a linker that bridges $R^2$ to the C Ring. As recited and exemplified in PCT/US2012/029104 and herein, L may be O or S. An O linker provides potent compounds. In addition, an S linker also provides potent compounds, for example, if $R^2$ is a 5-membered ring. In some aspects, the linker may also be NH, $CH_2$, CHF, $CF_2$, $SCH_2$, $OCH_2$, $NHCH_2$, CH=CH, $CH_2CH_2$, $SCH_2CONH$, $OCH_2CONH$, $NHCH_2CONH$, $OCH_2CH$=CH, or $SCH_2CH$=CH. Without being bound by theory, these linkers may impart additional flexibility between the scaffold and $R^2$, which may improve dual targeting between ParE and GyrB active-sites.

For example, compounds having a CH₂ linker include:
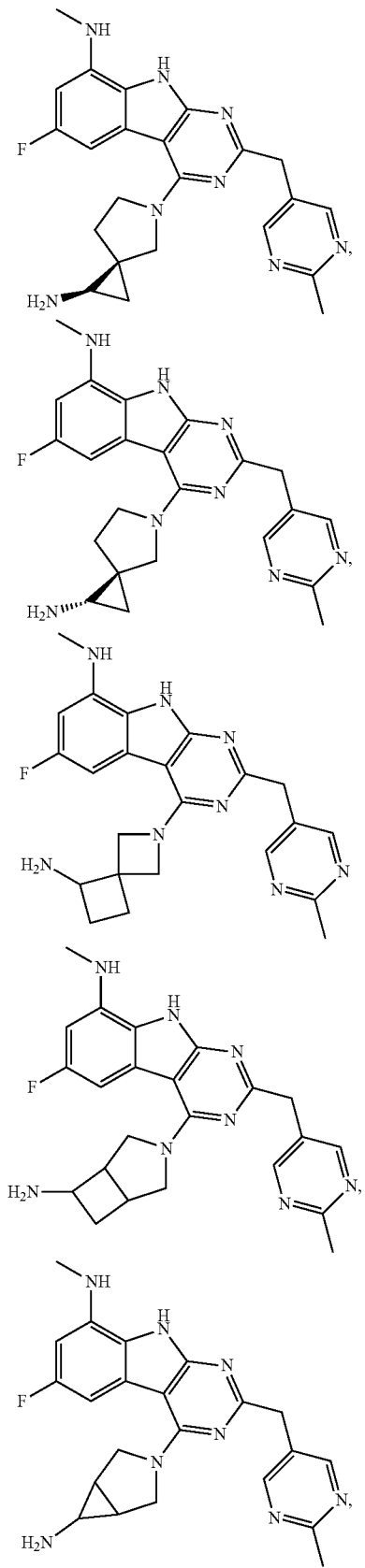
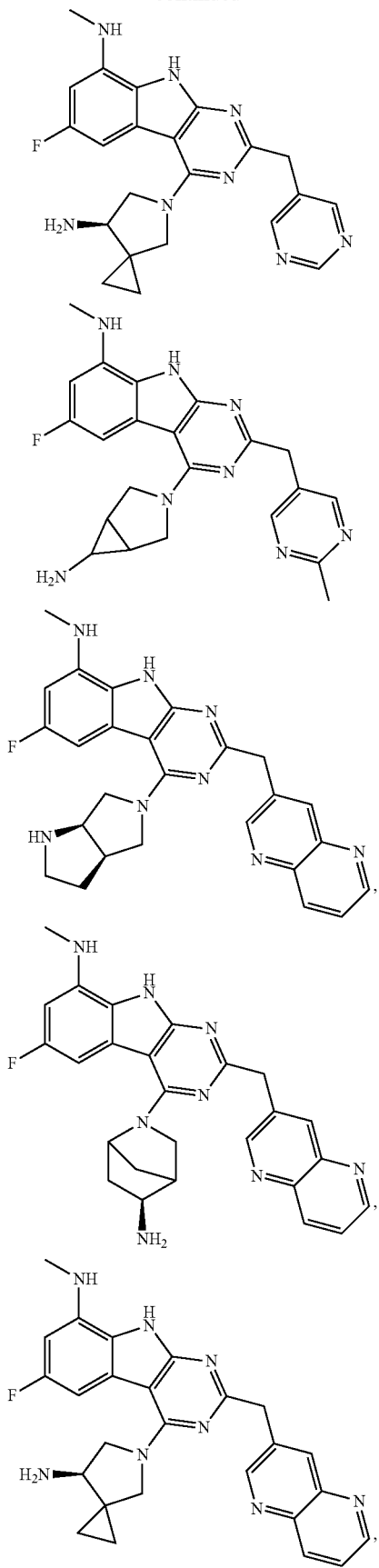

-continued
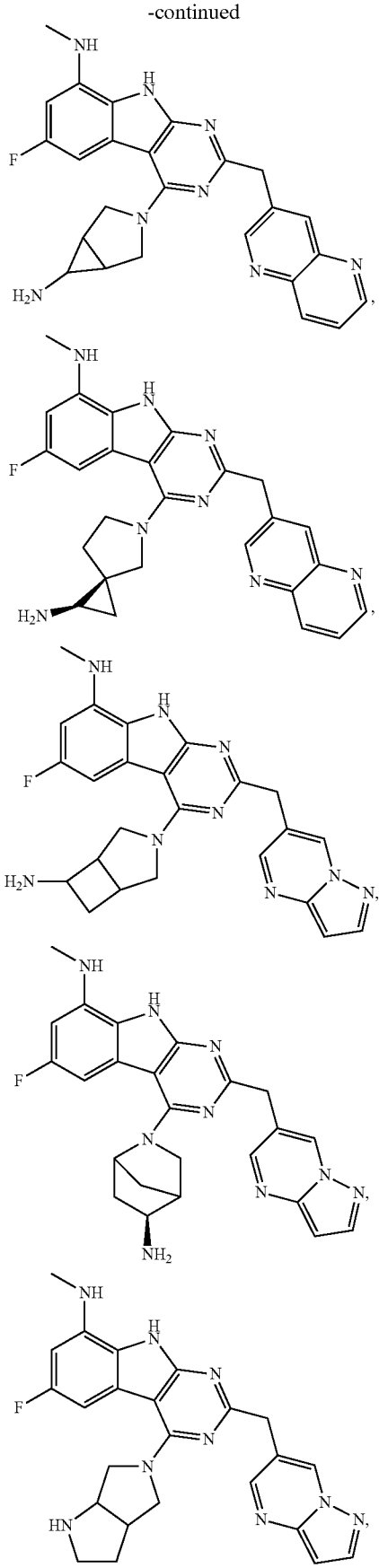
-continued
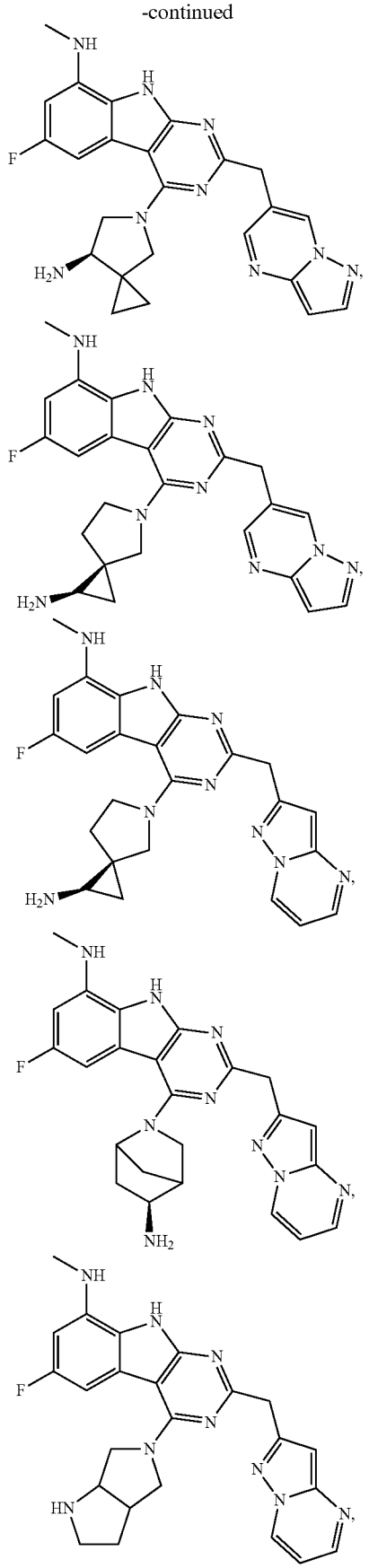

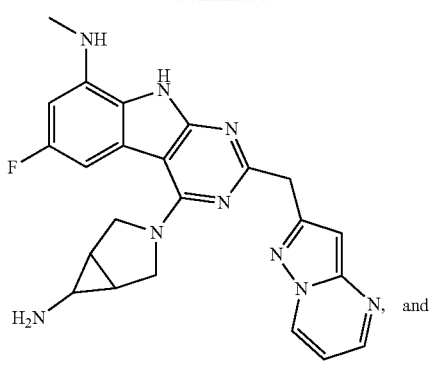

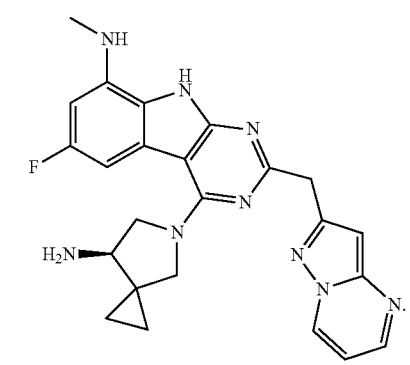

In addition, compounds having a NH linker include:

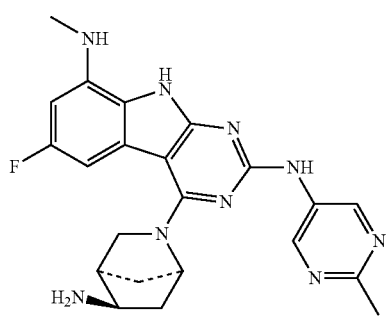

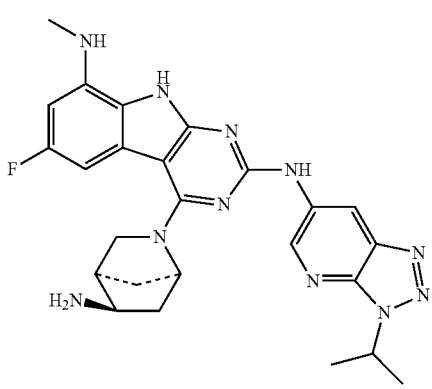

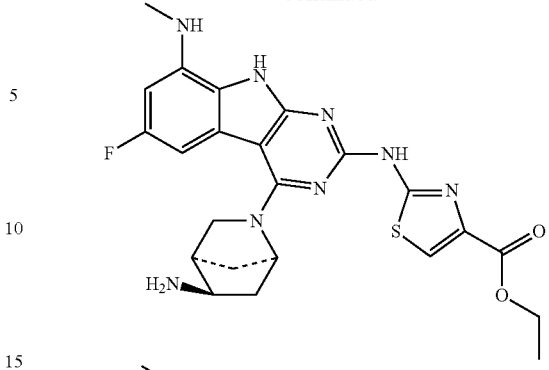

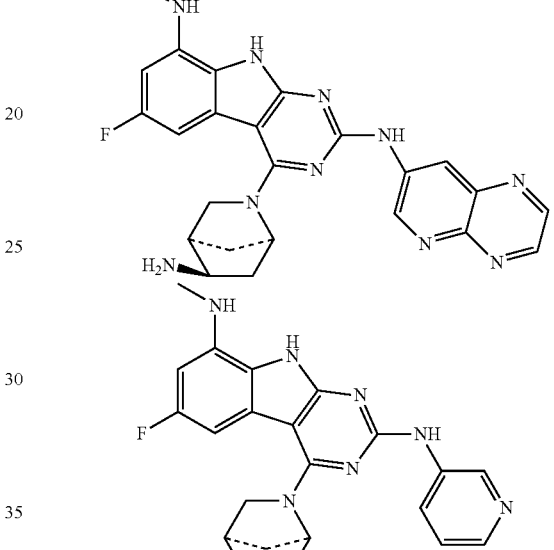

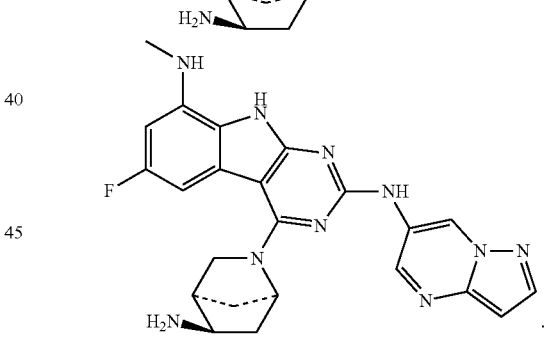

As used herein, the term "aryl" refers to optionally-substituted monocyclic and fused bicyclic hydrocarbyl moiety. Any monocyclic or fused ring bicyclic system which has the characteristics of aromaticity in terms of electron distribution throughout the ring system is included in this definition. Typically, the ring systems contain 5-12 ring member atoms. "Heteroaryl" refers to optionally-substituted aromatic monocyclic and fused bicyclic heterocycles containing one or more heteroatoms selected from N, O and S. The inclusion of a heteroatom permits inclusion of 5-membered rings as well as 6-membered rings.

As used herein, the term "alkyl," include straight- and branched-chain and cyclic monovalent substituents. Examples include methyl, ethyl, propyl, isopropyl, and cyclopropyl. Where indicated, the alkyl substituents may contain 1-10C (1 to 10 carbon atoms) such as 1-3C, 1-6C, or 1-8C.

As used herein, "hydrocarbyl residue" refers to a residue which contains only carbon and hydrogen. The hydrocarbyl residue may be saturated or unsaturated, aliphatic or aromatic, straight-chain, branched-chain, or cyclic including a single ring, a fused ring system, a bridge ring system, or a spiro ring system, or a combination hydrocarbyl groups. The hydrocarbyl residue, when so stated however, may contain heteroatoms over and above the carbon and hydrogen members of the substituent residue. Thus, when specifically noted as containing such heteroatoms, the hydrocarbyl residue may also contain heteroatoms such as O, S or N within the "backbone" of the hydrocarbyl residue. A hydrocarbyl group may include a combination hydrocarbyl containing moieties such as a heterocyclic group, linked to a heteroalkyl containing a combination of a straight chain alkyl and a cycloalkyl group.

As used herein, "cyclic residue" refers to a cyclic hydrocarbyl residue, which contains only carbon and hydrogen. The cyclic residue, when so stated however, may contain heteroatoms over and above the carbon and hydrogen members of the substituent residue. Thus, when specifically noted as containing such heteroatoms, the heterocyclic residue may also contain heteroatoms such as O, S or N within the "backbone" of the cyclic residue. In some aspects, when so stated, the cyclic residue is a cycloaliphatic or cycloheteroaliphatic residue. A saturated cycloaliphatic or saturated cycloheteroaliphatic residue refers to a ring containing saturated bonds between each ring member.

As used herein, "unsaturated cyclic residue" refers to an at least partially unsaturated or aromatic cyclic hydrocarbyl residue, which contains only carbon and hydrogen. The unsaturated cyclic residue, when so stated however, may contain heteroatoms over and above the carbon and hydrogen members of the substituent residue. Thus, when specifically noted as containing such heteroatoms, the unsaturated heterocyclic residue may also contain heteroatoms such as O, S or N within the "backbone" of the unsaturated cyclic residue.

The term "members" or "membered" in the context of heterocyclic and heteroaryl groups refers to the total atoms, carbon and heteroatoms N, O and/or S, which form the ring. Thus, an example of a 6-membered saturated cycloheteroaliphatic ring is piperidine and an example of a 6-membered heteroaryl ring is pyridine.

The bound conformation refers to the conformation (i.e., the spatial arrangement of atoms) the tricyclic gyrase compound would assume if it was bound to the GyrB/ParE active-site pocket in the enzyme's interior. In use, the compound may interact with the active site pocket and inhibit the ATPase activity. When the compound is bound to the GyrB/ParE active-site pocket, some substituents interact with certain amino acids and thus the substituents' ability to rotate freely about a bond is constrained. Thus, more useful measurements may be made to determine distances relevant for determining the dimensions of proper substituents. When indicated, measurements are based on the relative positions of substituents on the compound while hypothetically bound to the GyrB/ParE active-site pocket. References to the bound conformation with respect to the compound should not be interpreted as literally encompassing the GyrB/ParE active-site pocket in combination with the compound. The bound conformation is characterized via measurements derived from the three dimensional structure from x-ray crystallographic data on the inhibitor complexed with a protein construct that typically encompasses the 24 or 46 kDa ATP-binding domain of one or more representative bacterial GyrB or ParE orthologs. Given the high degree of sequence identity between GyrB and ParE enzymes in most pathogenic organisms of interest, structural information derived from a protein ortholog from any pathogen of clinical relevance should be sufficient to describe the bound conformation. Briefly, crystallographic structures are generated using the following methods: Proteins of interest (e.g., E. faecalis GyrB, E. coli GyrB, F. tularensis ParE or E. coli ParE) are generated in a standard E. coli expression system. The open reading frames are cloned into an expression plasmid (e.g., pET28a), and expressed in and appropriate E. coli expression strain (e.g., BL21 (DE3)). For crystallography the 24 kDa and 46 kDa ATP binding domains are cloned with a $C(His)_6$ tag to aid purification by metal affinity chromatography. This robust chromatography step typically yields greater than 80% pure protein. Polishing steps including ion exchange and size exclusion chromatography, are performed as needed until satisfactory (>95%) purity is achieved. Once purified protein is available, complexes of GyrB or ParE and the inhibitor molecule of interest are generated by mixing a stoichiometric excess of the inhibitor of interest with the recombinant protein target in solution and crystallizing the complex using established crystallization methods (typically vapor diffusion, as described in Drenth J. (1999) In Principles of protein x-ray crystallography. $2^{nd}$ ed. Springer, New York). Once crystallized, x-ray diffraction data are collected on single crystals of the protein-inhibitor complexes using monochromatic x-rays generated by a rotating anode or synchrotron radiation source. X-ray data processing, analysis and subsequent structure solution and refinement are carried out using well established computational methods (reviewed in Drenth J. (1999) In Principles of protein x-ray crystallography. $2^{nd}$ ed. Springer, New York).

Interacting substituents on the compound that interact with the GyrB/ParE active-site pocket include those substituents that would be located within the protein's interior when the compound is in the bound conformation. Interactions of interacting substituents generally include hydrophobic interactions (which favor the apposition of lipophilic surfaces on the inhibitor and active-site pocket), and electrostatic interactions such as Van der Waals, dipole-dipole, coulombic interactions or hydrogen-bonding between atoms on the compound and atoms in the GyrB/ParE active-site pocket. For example, $R^8$, $R^X$, $R^Y$, and $R^Z$ interact with various portions of the protein's interior. If $R^8$, $R^X$, $R^Y$, or $R^Z$ is $NH_2$ or NHR (where R is, for example, a small alkyl group), the H atom(s) on the nitrogen may interact with electronegative atoms, such as nitrogen or oxygen, proximally located in the GyrB/ParE active-site pocket to which the compound may bind. When $R^8$, $R^X$, $R^Y$, and $R^Z$ are non-polar (e.g., a methyl group), the interacting substituent may also electrostatically interact with an atom in the protein's interior via Van der Waals interactions, and desolvate complementary lipophilic surfaces in the active-site pocket to form favorable hydrophobic interactions. Additionally, in some aspects, the shape and size of the active-site may place restrictions on the dimensions of compound's substituents that would be sterically compatible with the active-site pocket.

Where indicated, the dimensions of a substituent may be provided and are associated with the dimensions of the pocket in which the compound would be situated if in a bound conformation. For example, the length of a substituent may be given based on its distance from the atom on the tricyclic scaffold to the substituent's atom that is positioned farthest from the tricyclic scaffold, i.e., the terminal atom. The distance is measured based on the center of a first atom such as a C on the tricyclic scaffold, to the center of the terminal atom. The distance is measured from point to point in a straight line regardless of the fact that the bonds in the substituent are not linearly aligned, such as an ethyl or OH substituent.

The width of the $R^8$ substituent may be understood with respect to the dimension of the active site pocket in which $R^8$ resides ($R^8$ pocket), and with respect to the $R^8$ substituent when it adopts a conformation in the $R^8$ pocket, when the compound in the bound conformation. The $R^8$ substituent generally projects into the $R^8$ pocket along an axis that projects through the C atom on the A Ring that is attached to $R^8$, and the C atom on the same ring in the meta position that shares a common C atom with the B ring when the compound is in bound conformation. The width of the $R^8$ substituent refers to the width at its widest point measured from atom center to atom center that are farthest apart approximately perpendicularly about such an axis, when the compound is in the bound conformation. Thus, the $R^8$ substituent may be able to adopt a conformation, when the compound is in the bound conformation, having a width that does not exceed about 3.3 Å. For example, the NHMe moiety on $R^8$ has a width of approximately 2.8 Å. This width is derived by summing the distance of atom center of a methyl proton oriented trans to the N—H proton perpendicularly from the axis described above, with the distance of the center of the N—H proton perpendicularly from the same axis. Further, the width of a cyclopropyl substituent would be approximately 3.1 Å, measured as the distance between the centers of protons on adjacent carbon atoms on opposite faces of the cyclopropyl ring.

$R^8$ may be H or an interacting substituent having a length of about 1 Å to about 5 Å from the carbon attachment point on the A Ring to the terminal atom in $R^8$ and a width of about 3.3 Å or less. The length of $R^8$ is appropriate for the length from the tricyclic scaffold carbon to the active site pocket based on crystallographic data, which is about 6 Å to about 8 Å as shown in FIG. 1. In some aspects, $R^8$ is H, Cl, F, Br, $NH_2$, OH, 1-3C alkyl, amino-1-3C alkyl, aminocyclopropyl, $OCH_3$, $OCH_2CH_3$, cyclopropyl, $CH_2$cyclopropyl, $CH_2Cl$, $CH_2F$, $CHF_2$, $CF_3$, $CH_2CH_2F$, $CH_2CHF_2$, $CH_2CF_3$, $NHNH_2$, NHOH, $NHNHCH_3$, $NHOCH_3$, $NHCD_3$, $SCH_3$, or NHCOH, where D is deuterium. In some aspects, $R^8$ is H, Cl, F, Br, $NH_2$, 1-3C alkyl, amino-1-3C alkyl, aminocyclopropyl, $OCH_3$, $OCH_2CH_3$, cyclopropyl, $CH_2$cyclopropyl, $CH_2Cl$, $CHCl_2$, $CH_2F$, $CHF_2$, $CF_3$, $CH_2CH_2F$, $CH_2CHF_2$, $CH_2CF_3$, $CHCH_2$, $NHNH_2$, NHOH, $NHNHCH_3$, $NHOCH_3$, $NHCD_3$, $SCH_3$, or NHCOH. For instance, $R^8$ may be H, $CH_3$, $CH_2CH_3$, Cl, $OCH_3$, $NHCD_3$, $NHCH_3$, $NHCH_2CH_3$, or $NH_2$, such as $NHCH_3$.

In some aspects, $R^8$ may be a prodrug-containing substituent, wherein the prodrug is cleaved to form a compound that has dimensions appropriate for the length from the tricyclic scaffold carbon to the active site pocket based on crystallographic data as described above. These prodrugs, such as Formula II, among others, are described in more detail below.

$R^9$ may be H or may be linked to $R^8$ to form a prodrug-containing substituent, such as a compound having the structure of Formula III described in more detail below.

X, Y and Z may be independently selected from the group consisting of N, $CR^X$, $CR^Y$, and $CR^Z$, provided that no more than two of X, Y and Z are N. $R^X$ may be H or is an interacting substituent having a length of about 1 Å to about 2 Å from the carbon in $CR^X$ to the terminal atom in $R^X$. $R^Y$ may be H or an interacting substituent having a length of about 1 Å to about 3 Å from the carbon in $CR^Y$ to the terminal atom in $R^Y$. For example, $R^Y$ would not be a methoxy substituent because a methoxy substituent is longer than 3 Å. $R^Z$ may be H or is an interacting substituent having a length of about 1 Å to about 2 Å from the carbon in $CR^Z$ to the terminal atom in $R^Z$. These lengths of $CR^X$, $CR^Y$, and $CR^Z$ are appropriate in comparison to the lengths from the tricyclic scaffold carbon to the active site pocket based on crystallographic data shown in FIG. 1. In some aspects, X, Y and Z are $CR^X$, $CR^Y$, and $CR^Z$ respectively. $R^X$ may be H, $CH_3$, Cl, Br, or F, such as H or F. $R^Y$ may be H, $CH_3$, $CHF_2$, $CF_3$, CN, $CH_2CH_3$, Cl, Br, or F, such as H, F, Cl, or $CF_3$. $R^Z$ may be H, $CH_3$, CN, Cl, Br, or F, such as H, $CH_3$ or F.

Z may be C linked to $R^4$. Although not being bound by theory, the potency and/or selectivity may be increased because the conformational entropy is reduced when Z joins with $R^4$ to form a fused ring. In some aspects, Z may be C linked to $R^4$, wherein the compound has the structure of Formula VI

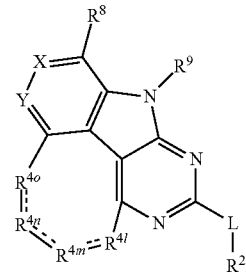

Formula VI $R^{4l}$ may be $CR^{10}$, $CR^{10}CR^{11}$, $NR^{12}$, O or S. $R^{4m}$ may be $CR^{10}$, $CR^{10}CR^{11}$, or $NR^{12}$. $R^{4n}$ may be $CR^{10}$, $CR^{10}CR^1$, $R^{12}$, O or S. Each of $R^1$, $R^{11}$ and $R^{12}$ is independently H or a noninterfering substituent. Noninterfering substituents include amine, C1-C10 hydrocarbyl, halogen such as F or Cl, alkyl amine such as C1-C4 alkylamine, for example, methylamine. In some aspects, optionally substituted $R^{4l}$ may be O, CH, NH, or $NCH_3$. Optionally substituted $R^{4m}$ may be CH, $CHCH_2NH_2$, or C=NH. Optionally substituted $R^{4n}$ may be CH, NH, $CH_2$ or $CHNH_2$.

Two adjacent noninterfering substituents on $R^{4l}$ and $R^{4m}$ may form one or more fused rings. The dashed lines indicate an optional double bond when two adjacent $R^{4l}$, $R^{4m}$, and $R^{4n}$ are $CR^{10}$ and $R^{4o}$ is CH or N. Thus, in some aspects Formula VI may have the structure of Formula VIa:

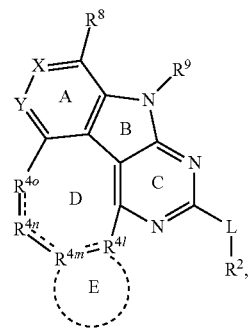

Formula VIa

The dotted lines indicate substituents on $R^{4l}$ and $R^{4m}$ that form a fused ring E that may be optionally substituted with a noninterfering substituent.

In some aspects, the portion of the E Ring linking $R^{4l}$ and $R^{4m}$ is a C1-C15 hydrocarbyl residue containing 0-5 O, S, or N heteroatoms, attached to the D Ring at $R^{4l}$ and $R^{4m}$, optionally substituted with OH, CN, =O, $NH_2$, =NOH, =$NNH_2$, =NH, =$NOCH_3$, Br, F, Cl, $SO_3H$, or $NO_2$.

For example, $R^{4l}$ and $R^{4m}$ together with two noninterfering substituents may form a fused aromatic six membered E Ring containing 0-1 N atoms, optionally substituted with halogen, such as chloro. Also, $R^{4l}$ and $R^{4m}$ together with two noninterfering substituents may form a fused five-membered unsaturated, partially unsaturated, or saturated E Ring comprising 0-2 heteroatoms selected from O, S and N. For example, $R^{4l}$ may be N and together with $R^{4m}$ and two noninterfering substituents may form a fused five-membered saturated heterocyclic E Ring. Additional examples of $R^{4l}$ and $R^{4m}$ together with two noninterfering substituents include saturated 5-, 6-, 7-, 8-, or 9-membered rings that may be fused, spiro or bridged optionally containing an amine substituent.

When $R^{4n}$ is NH or $CH_2$, attached to $R^{4o}$ through the C or N, —$R^{4n}$—$R^{4m}$—$R^{4l}$ may be selected from the following moieties, for example, forming an E Ring:

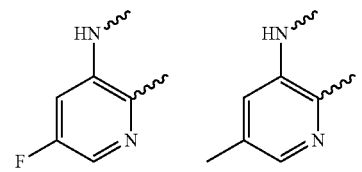
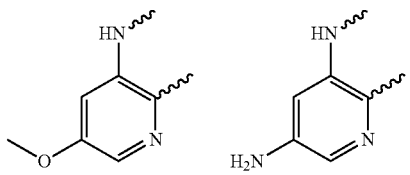
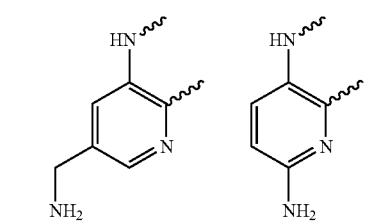
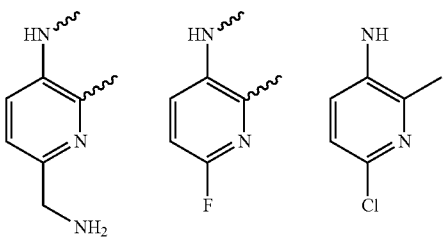

-continued

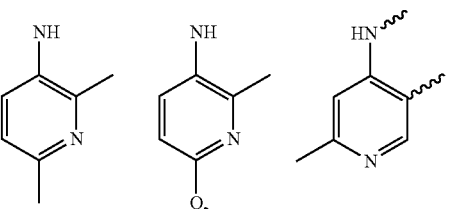
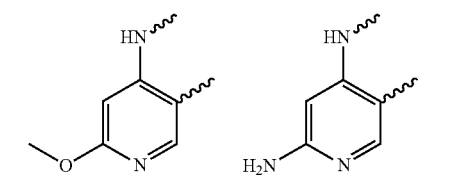
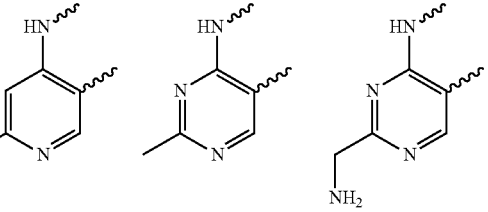
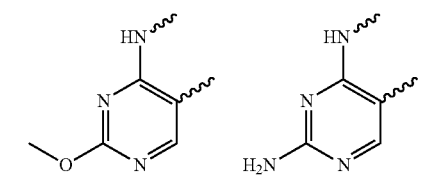

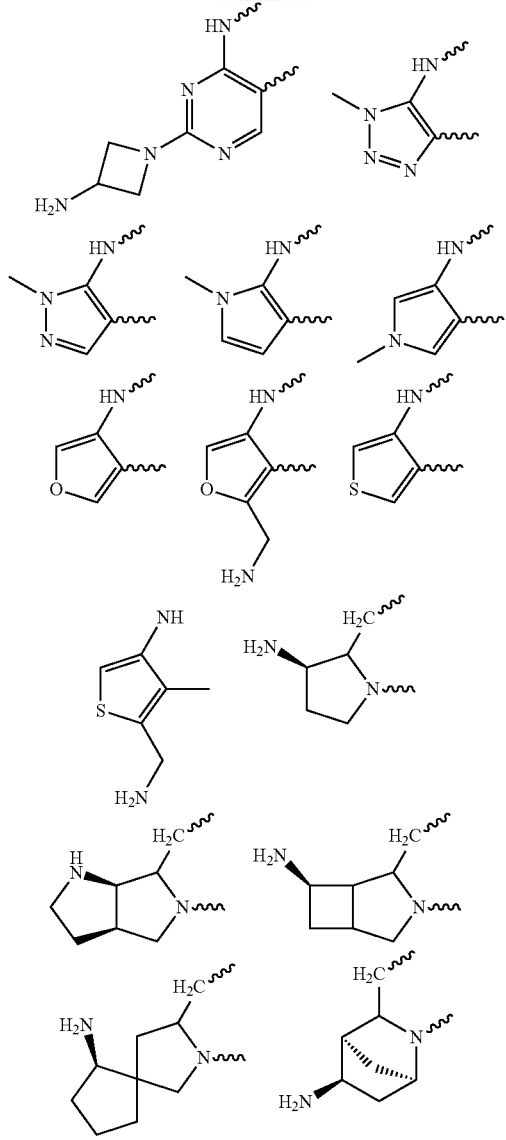

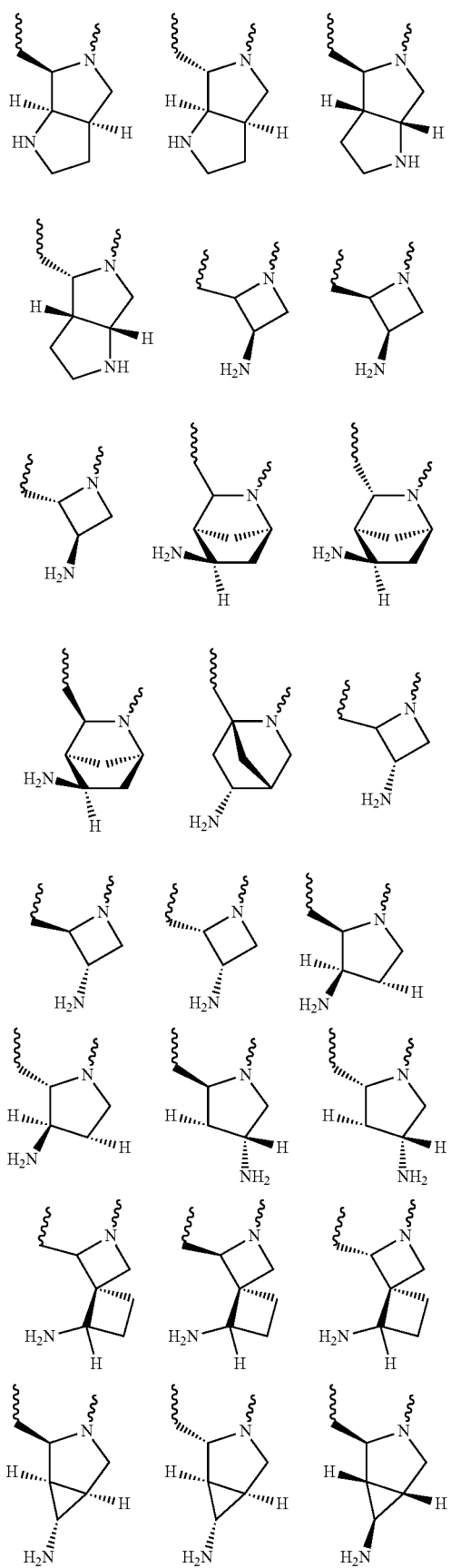

For each of these moieties above where $R^{4n}$ is NH, $R^{4n}$ may be replaced with $CH_2$. Similarly, where $R^{4n}$ is $CH_2$, $R^{4n}$ may be replaced with NH.

$R^{4o}$ may be a) a bond, wherein a 7-membered D ring is formed, wherein $R^{4n}$ may be CH, $CH_2$, S, NH, O, CHF, or $CF_2$; b) a 1 member link in the backbone of the D ring wherein an 8-membered D Ring is formed, wherein the 1 member link may be CH, $CH_2$, S, NH, O, CHF, or $CF_2$; c) a 2 member link in the backbone of the D ring that forms a 9-membered D Ring, wherein the member adjacent the A Ring may be CH, $CH_2$, S, NH, O, CHF, or $CF_2$.

In addition, $-R^{4o}-R^{4n}-R^{4m}-R^{4l}-$, i.e.,

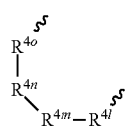

may be selected from the following moieties,

-continued

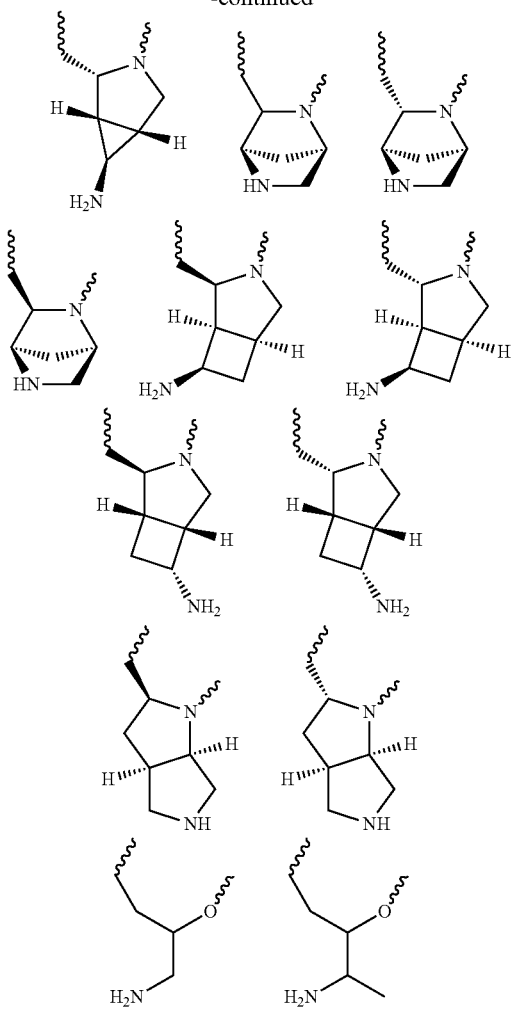

In some aspects, D Ring contains at least one N in the backbone, or a substituent on the D Ring contains at least one N.

In some aspects, two adjacent noninterfering substituents on $R^{4m}$ and $R^{4n}$ may form one or more fused rings. The dashed lines indicate an optional double bond when two adjacent $R^{4l}$, $R^{4m}$ and $R^{4n}$ are $CR^{10}$ and $R^{4o}$ is CH or N. Thus, in some aspects Formula VI may have the structure of Formula VIb:

Formula VIb

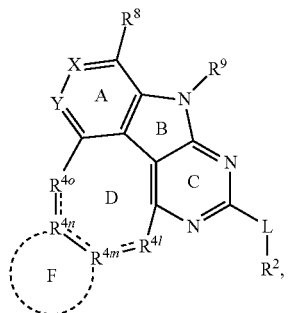

In some aspects, the portion of the F Ring linking $R^{4m}$ and $R^{4n}$ is a C1-C15 hydrocarbyl residue containing 0-5 O, S, or N heteroatoms, attached to the D Ring at $R^{4m}$ and $R^{4n}$, optionally substituted with OH, CN, =O, NH$_2$, =NOH, =NNH$_2$, =NH, =NOCH$_3$, Br, F, Cl, SO$_3$H, or NO$_2$.

Although not being bound by theory, it is useful when the F Ring avoids steric hindrance and avoids interference with the compound's binding to the enzyme's active site. Thus, in some aspects, if an F Ring is present, $R^{4o}$ may not be a bond. If $R^{4o}$ is a 1 member link, the portion of the F Ring linking $R^{4m}$ and $R^{4n}$, if present, may be an unsubstituted C1 residue or C1 substituted with a small substituent such as F or NH$_2$ substituent forming an unsubstituted cyclopropyl residue with $R^{4m}$ and $R^{4n}$. If $R^{4o}$ is a 1 member link, the portion of the F Ring linking $R^{4m}$ and $R^{4n}$ may be a C2-C15 hydrocarbyl residue containing 0-5 O, S, or N heteroatoms, however, the position on the F ring immediately adjacent $R^{4n}$ may be unsubstituted or substituted with a small substituent such as F or NH$_2$. If $R^{4o}$ is a 2 member link and the F Ring is present, any substituents on the F Ring may be sufficiently distal to avoid steric hindrance and other interference with enzyme binding.

For example, $R^{4m}$ and $R^{4n}$ together with two noninterfering substituents may form a fused 6-membered unsaturated, partially unsaturated, or saturated F Ring such as an aromatic 6-membered F Ring containing 0-1 N atoms, optionally substituted with halogen, such as fluoro or NH$_2$. Also, $R^{4m}$ and $R^{4n}$ together with two noninterfering substituents may form a fused five-membered unsaturated, partially unsaturated, or saturated F Ring comprising 0-2 heteroatoms selected from O, S and N. For example, $R^{4m}$ and $R^{4n}$ may both be CH and together with two noninterfering substituents may form a fused five-membered saturated heterocyclic F Ring. Additional examples of $R^{4m}$ and $R^{4n}$ together with two noninterfering substituents include saturated 5-, 6-, 7-, 8-, or 9-membered rings that may be fused, spiro or bridged optionally containing an amine substituent.

Although not being bound by theory, it is useful when the D Ring avoids steric hindrance and avoids interference with the compound's binding to the enzyme's active site. In some aspects, the D ring does not project greater than about 3 Å below the plane of the A, B and C Rings toward the GyrB/ParE binding pocket floor in the bound conformation; and the D ring does not sterically interfere with $R^2$ when the compound is in the bound conformation.

In some aspects, the compound of Formula VI may be selected from the group consisting of:

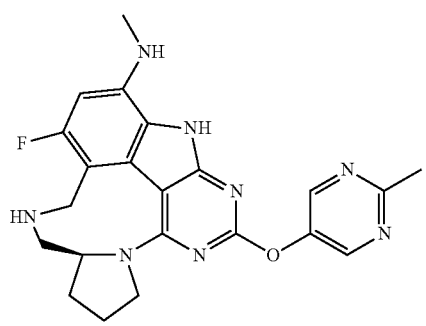

37
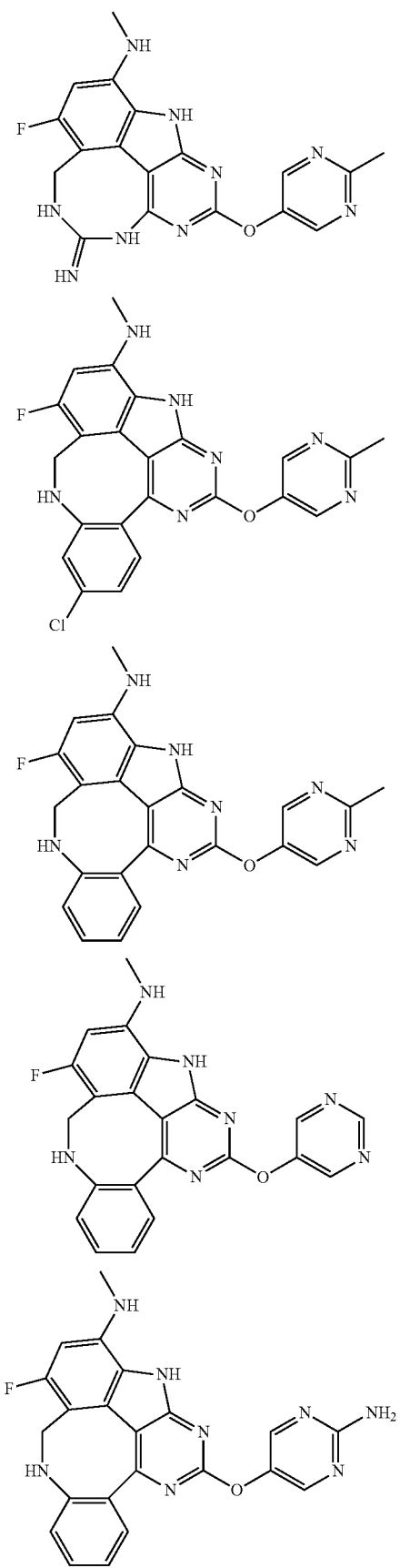
38
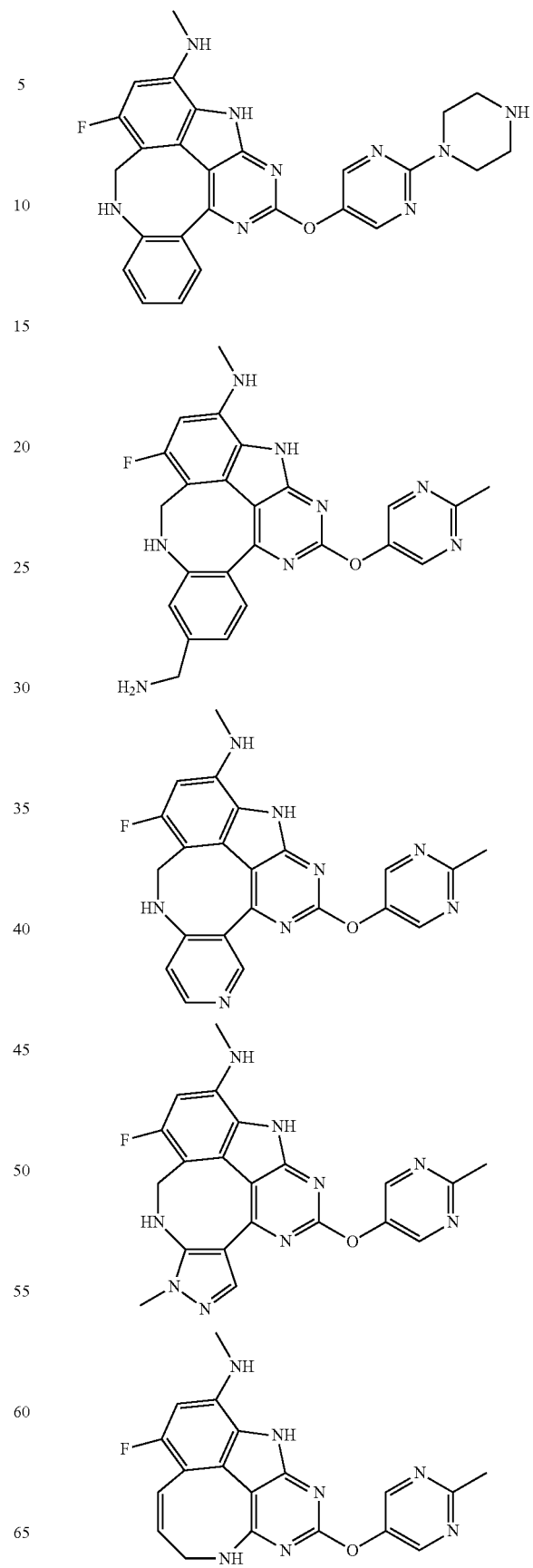

-continued
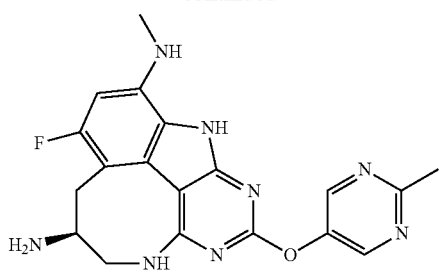
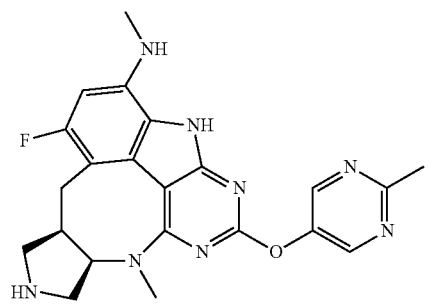
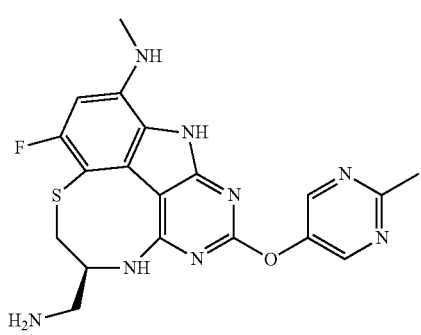
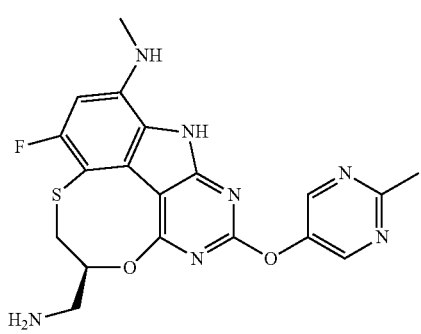
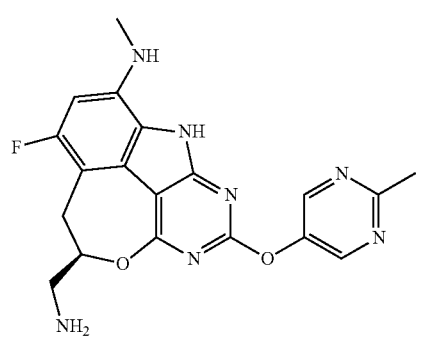
-continued
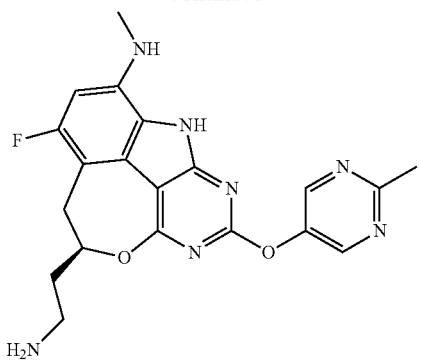
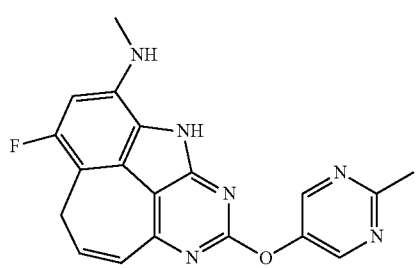
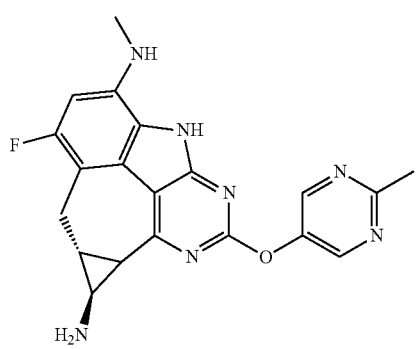
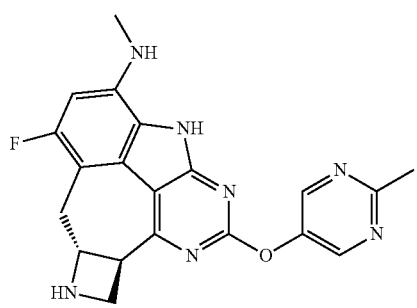
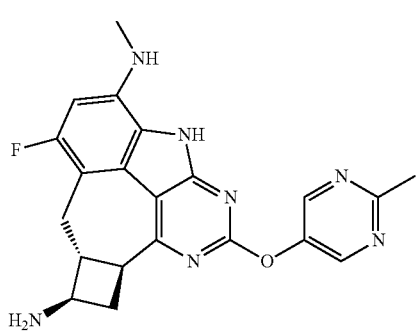

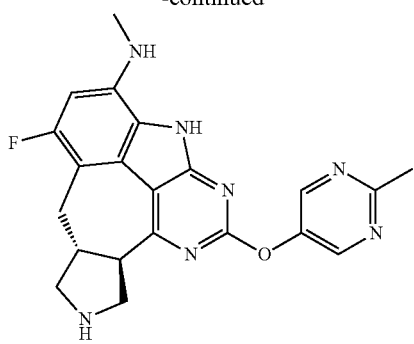
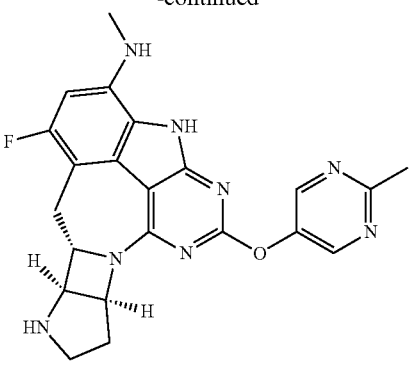
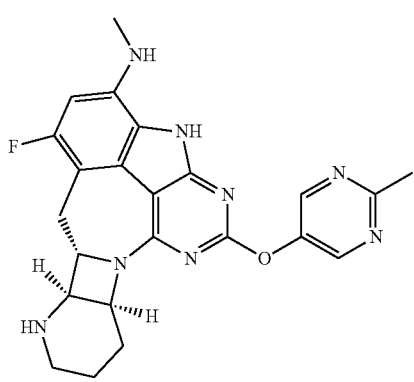
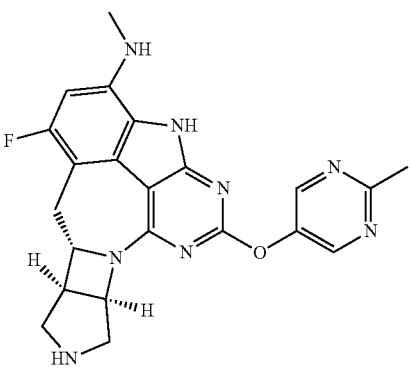
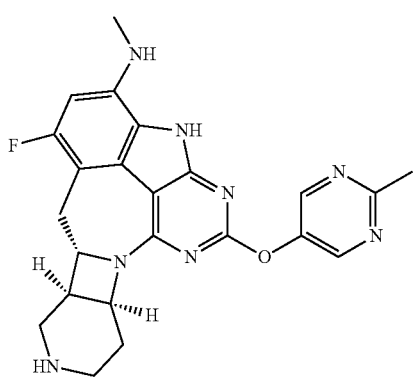
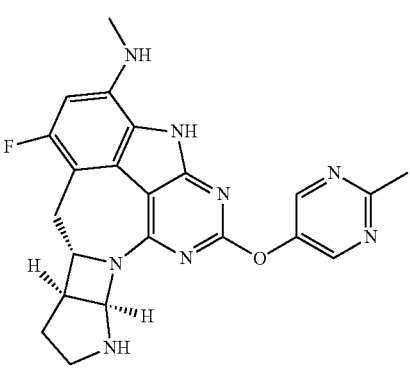
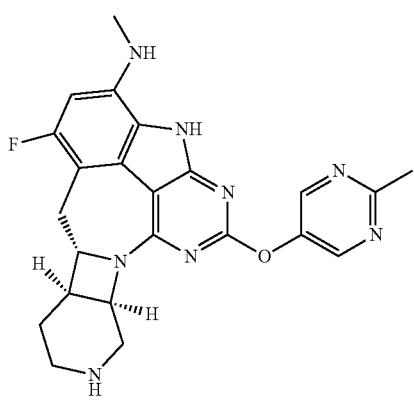
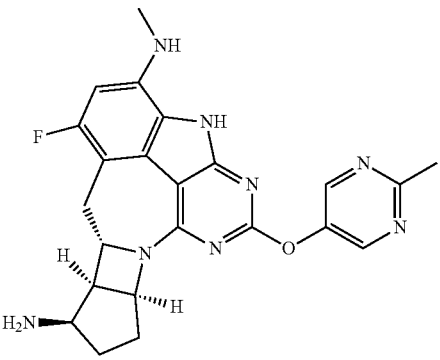

-continued

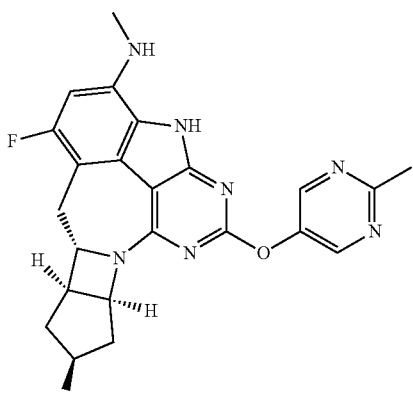

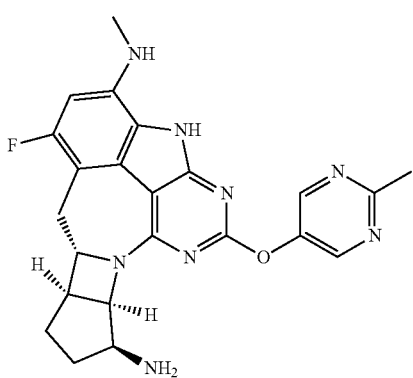

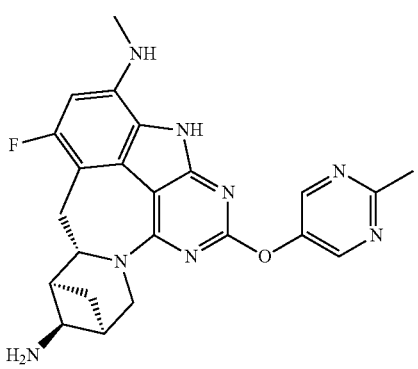

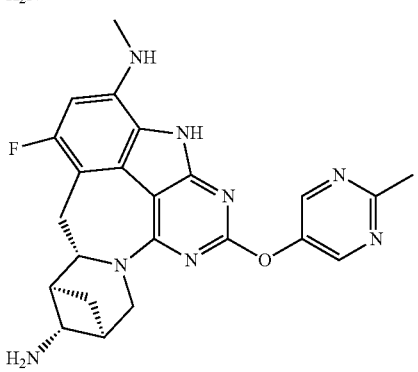

-continued

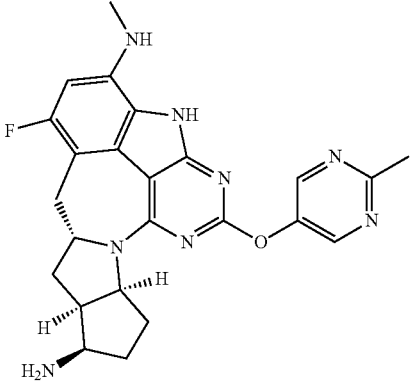

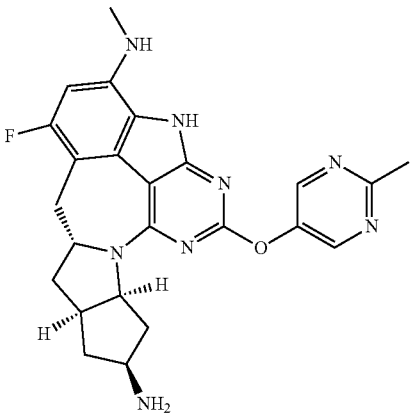 [SMILES: CNc1cc(F)c2c3c1[nH]c1nc(Oc4cnc(C)nc4)nc(c13)N1[C@@H](C2)C[C@@H]2C[C@H](N)C[C@@H]21]

The above compounds may also be made using other $R^2$ substituents as described herein.

Without being bound by theory, $R^2$ may be useful for conferring selectivity and potency against eukaryotic ATP binding proteins, such as kinases and HSP90. Thus, one of the compounds' benefits includes avoiding toxicity due to off target binding, such as to a kinase, due in part to $R^2$'s selectivity as part of the compound. Generally, in some aspects, the compounds are not potent inhibitors for eukaryotic kinases. In some aspects, $R^2$ is a 6-membered aryl or heteroaryl ring containing 0-3 O, S, or N heteroatoms, optionally substituted with 0-3 noninterfering substituents, wherein 2 adjacent noninterfering substituents on $R^2$ may form one or more fused rings with the 6-membered aryl or heteroaryl ring. For example, $R^2$ may be an optionally substituted 6-membered aryl or heteroaryl ring containing 0-3 O, S, or N heteroatoms such as optionally substituted pyrimidinyl, phenyl, or pyridyl. In some aspects, $R^2$ is a heteroaryl ring such as 6-membered heteroaryl. In some aspects, $R^2$ may be attached to L through a carbon atom in the 6-membered aryl or heteroaryl ring. Without being bound by theory, solvent sheltered faces of the GyrB/ParE active-site pockets may restrict the size of substituents on the compound proximal those solvent sheltered faces. Thus, with respect to $R^2$, the 6-membered aryl or heteroaryl ring may contain a CH at the ring positions immediately adjacent the position where $R^2$ attaches to L. In some aspects, there is no N on the 6-membered aryl or heteroaryl ring of $R^2$ at the ring positions immediately adjacent the ring position where $R^2$ attaches to L.

Figure 2:
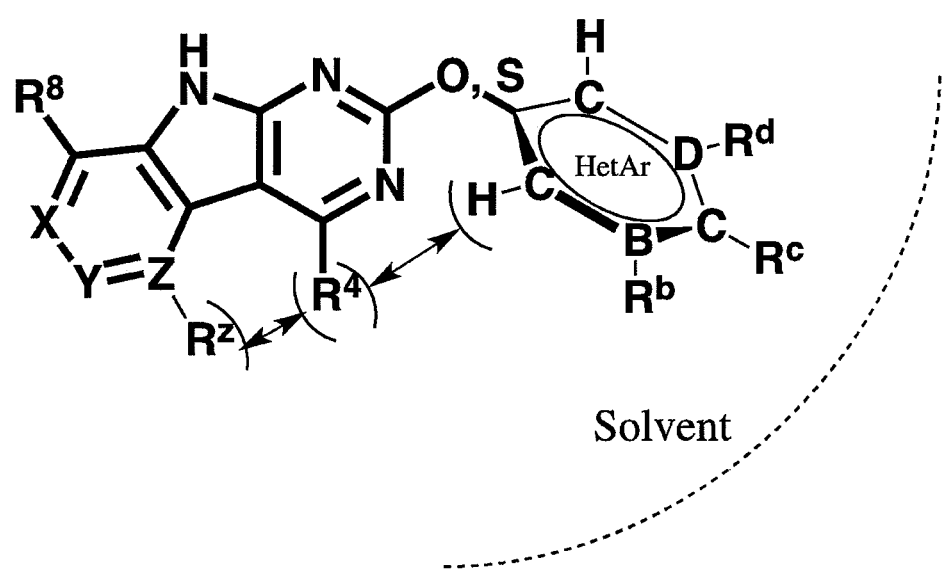
FIG. 2 illustrates a schematic representation of the intramolecular constraints on the compound wherein $R^2$ is a 6-membered ring. Specifically, the molecular geometry and the conformations of R-groups necessary to allow binding of tricyclic inhibitors to the GyrB/ParE active-site pockets constrain the size and composition of substituents at certain positions on the inhibitor scaffold. This figure illustrates regions of potential steric interference between the $R^4$ substituent and the $R^2$ or $R^Z$ substituent in the bound conformation.
Figure 3:
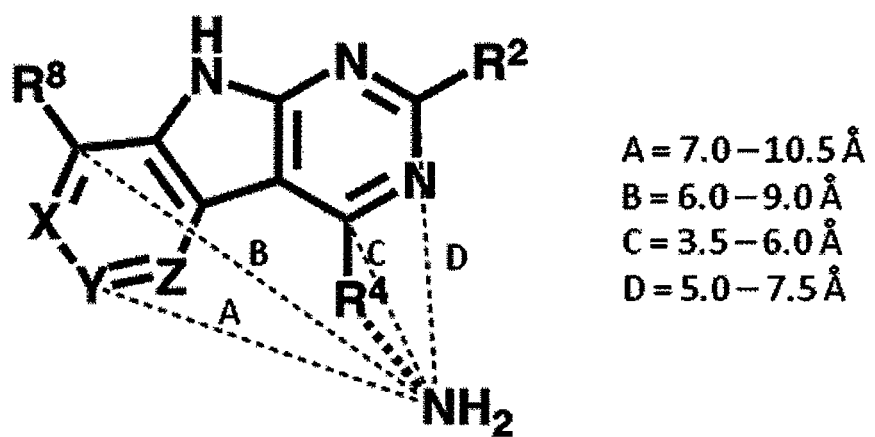
FIG. 3 illustrates an example of relative positions of a primary amine that is encompassed within $R^4$ when bound to GyrB/ParE. This illustration also applies to a secondary amine, which is not shown in FIG. 3. The volume occupied by the $R^4$ amine with respect to the tricyclic scaffold across the amines was determined using a four point trilateration procedure based on distances between the $R^4$ amine and four different atoms on the tricyclic scaffold from 17 different crystal structures of complexes of *E. faecalis* GyrB with tricyclic inhibitors containing a diverse set of $R^4$ amines comprising a secondary or tertiary amine attached to the C Ring through the secondary or tertiary amine N and a primary or secondary amine that is not attached to the C Ring. The relative position of the primary (or secondary, not shown) amine would be above the plane of the tricyclic scaffold, to avoid impinging the floor of the active site.

FIG. 2 illustrates $R^2$ as an optionally substituted 6-membered heteroaryl ring, although the positioning of the substituents also applies to a 6-membered aryl ring. In this illustration, A and E are C. $R^b$ and Re face the solvent in the bound conformation, and thus the substituents at this position may be varied and may include prodrugs. Cyclization between $R^b$ and $R^c$ may be permitted. $R^d$ is partially solvent exposed, and cyclization between $R^c$ and $R^d$ (for example, with an H-bond acceptor in the $R^d$ position) may be permitted. Large substituents such as large branched groups at $R^d$ may collide with the outer rim of the pocket.

In some aspects, the optionally substituted 6-membered aryl or heteroaryl ring of $R^2$ in combination with the one or more fused rings formed from optional substituents may be selected from the group consisting of optionally substituted indolyl, azaindolyl, pyrimidopyridyl, quinazolinyl, quinoxalinyl, naphthyridinyl, purinyl, imidizopyridinyl, furopyridinyl, isoindolylinyl, benzodioxinyl, dihydrobenzodioxinyl, benzothiazolyl, pyrrolopyridinyl, dihydropyrrolopyridinyl, benzoimidazolyl, imidazopyridinyl, dihydroimidazopyridinyl, tetrahydroisoindolyl, chromenyl, benzthiophene, benztriazolyl, benzfuranyl, benzoxadiazolyl, indazolyl, quinolinyl, isoquinolinyl, indoline, azaindolinyl, or

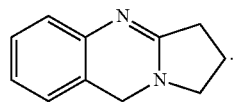 [SMILES: c1ccc2c(c1)CN1CCCC1=N2]

Similarly, $R^2$ may be a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S.

In some aspects, $R^2$ does not include the 6-membered aryl or heteroaryl groups in PCT/US2012/029104.

In some aspects, $R^2$ may be a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S.

When L contains one member in the backbone thereof, $R^2$ may be a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH or CF independently at each position immediately adjacent the position where $R^2$ attaches to L, if L is NH, $CH_2$, CHF, or $CF_2$.

When L contains one member in the backbone thereof, $R^2$ may be a 5-membered heteroaryl ring containing 1-4 O, S, or N heteroatoms, optionally substituted with 0-2 noninterfering substituents; wherein the 5-membered heteroaryl ring of $R^2$ has O, S, N, NH, CH, CF, or CCl, independently at each of the positions immediately adjacent the position where $R^2$ attaches to L, if L is O, S, NH, $CH_2$, CHF, or $CF_2$.

In some aspects, to maintain heteraromaticity, if $R^2$ contains O or S in the backbone of the 5-membered heteroaryl, one O or S may be present.

Further, when L contains one member in the backbone thereof, $R^2$ may be a 6-membered or 5-membered non-aryl or non-heteroaryl ring containing 0-3 O, S, or N heteroatoms, optionally substituted with 0-3 noninterfering substituents; wherein the 6-membered or 5-membered non-aryl or non-heteroaryl ring of $R^2$ has a O, S, N, NH, CH, CF, or $CH_2$, independently at each position immediately adjacent the position where $R^2$ attaches to L, if L is O, S, NH, $CH_2$, CHF, or $CF_2$.

When L contains two or more members in the backbone thereof, $R^2$ may be a 6-membered aryl or heteroaryl ring containing 0-3 O, S, or N heteroatoms, optionally substituted with 0-3 noninterfering substituents; a 5-membered heteroaryl ring containing 1-4 O, S, or N heteroatoms, optionally substituted with 0-2 noninterfering substituents, or a 6-membered or 5-membered non-aryl or non-heteroaryl ring containing 0-3 O, S, or N heteroatoms, optionally with 0-3 noninterfering substituents.

Examples of 5-membered heterocycles include thiadiazole, oxadiazole, isoxazole, tetrazole, imidazole, pyrrole, pyrazole, thiazole, oxazole, isothiazole, triazole, furan and thiophen.

Adjacent noninterfering substituents of $R^2$ may form one or more fused rings with the 6-membered aryl or heteroaryl ring, the 5-membered heteroaryl ring, or the 6-membered or 5-membered non-aryl or non-heteroaryl ring. Examples of 5/6 fused rings include indole, azaindole, purine, imidazolepyrimidine, furopyridinyl, azabenzothiazole, pyrrolopyridinyl, azabenzoimidazole, imidazopyridine, azabenzthiophene, azabenztriazole, azabenzfuran, azabenzoxazole, or azaindazole.

Some species of $R^2$ may include

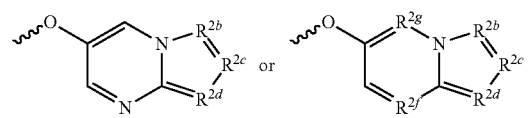

$R^{2b}$, $R^{2c}$, $R^{2d}$, $R^{2f}$ and $R^{2g}$ independently may be each N or $CR^{2e}$ wherein $R^{2e}$ is H or C1-C4 alkyl optionally substituted with a noninterfering substituent, such as OH, $CH_3$ or $CH_2OH$. In comparison to the leading compounds in PCT/US2012/029104, many compounds containing these $R^2$ species are significantly more potent against certain bacteria. In some aspects, $R^{2b}$ is N. In some aspects, $R^{2d}$ is N. In addition, $R^{2b}$ may N and $R^{2c}$ and $R^{2d}$ may each be $CR^{2e}$, for example, CH. Examples of $R^2$ include

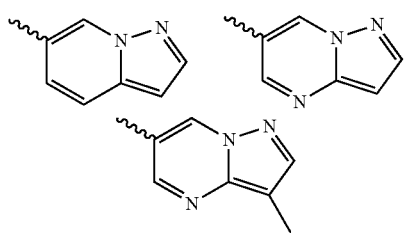

Species of compounds that may be covered by the genus but are not disclosed in PCT/US2012/029104, may also be included herein. For example, new species include:

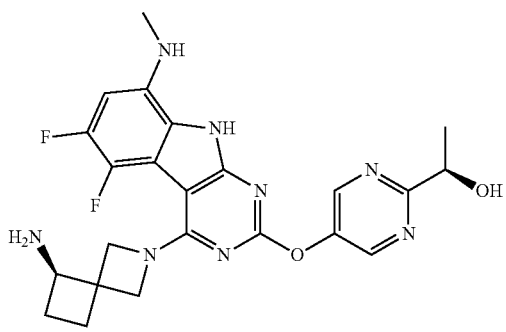

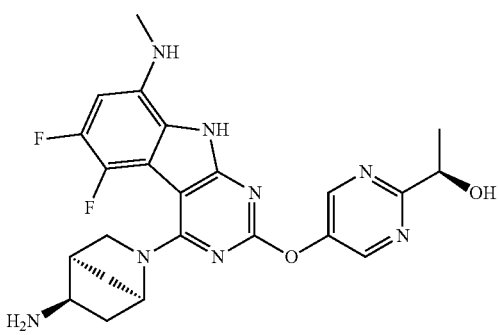

In some aspects, compounds wherein $R^2$ may be a 5-membered heteroaryl ring containing 1-4 O, S, or N heteroatoms, optionally substituted with 0-2 noninterfering substituents, or a 6-membered or 5-membered non-aryl or non-heteroaryl ring containing 0-3 O, S, or N heteroatoms, may have the following structures of Formula VII, Formula VIII and Formula IX:

Formula VII

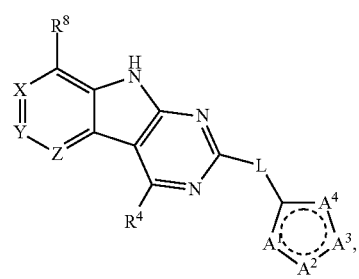

Formula VIII

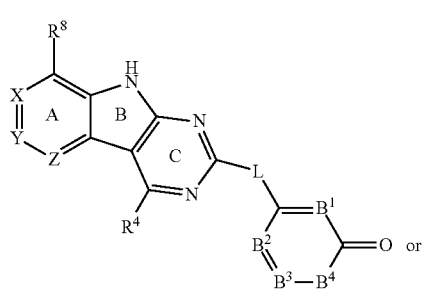

Formula IX

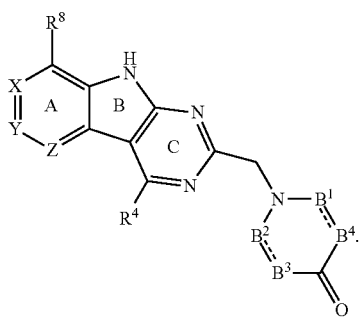

The dashed lines may indicate at least one optional double bond. If one of $A^1$ and $A^2$ is a carbon atom substituted with =O, at least one double bond would not be needed. $A^1$, $A_2$, $A^3$, $A^4$ $B^1$, $B^2$, $B^3$ and $B^4$ are independently optionally substituted CH, $CH_2$, NH, N, O or S, wherein the optional substituents are noninterfering substituents. Noninterfering substituents may include C1-C12 hydrocarbyl group containing 0-6 hetero atoms such as O, S, or N, such as a C1-C6 alkyl or a 5-membered or a 6-membered carbocyclic, aromatic or hetero aromatic ring, which may in turn be optionally substituted with a noninterfering substituent. Noninterfering substituents may also include =O, halo, hydroxy, C1-C6 alkoxy, amino, CN, or $N_3$, such as =O. Two adjacent noninterfering substituents on $R^2$ may form one or more fused rings.

$R^2$ may also include:

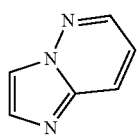

imidazo[1,2-b]pyridazine

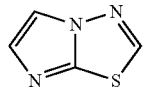

imidazo[2,1-b][1,3,4]thiadiazole

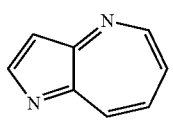

pyrrolo[3,2-b]azepine 5-membered non-aromatic rings may include:

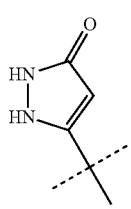

1H-pyrazol-3(2H)-one

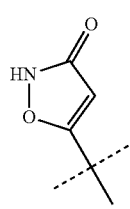

isoxazol-3(2H)-one 6-membered non-aromatic rings may include:
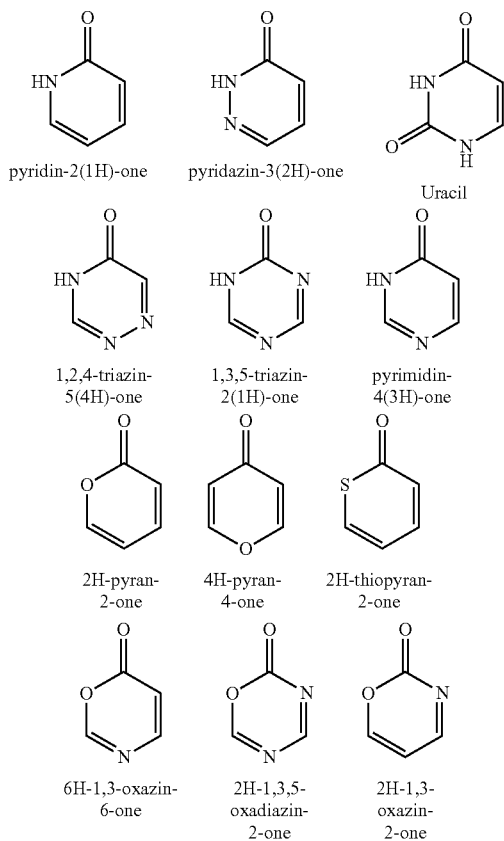
Examples of optionally substituted R² groups include:
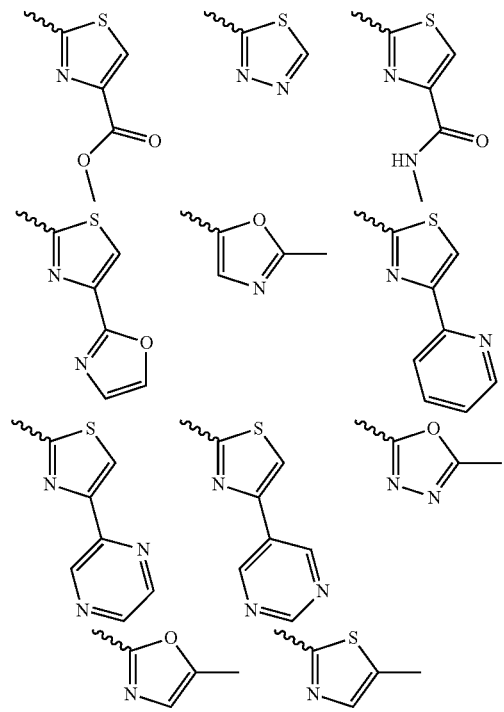
-continued
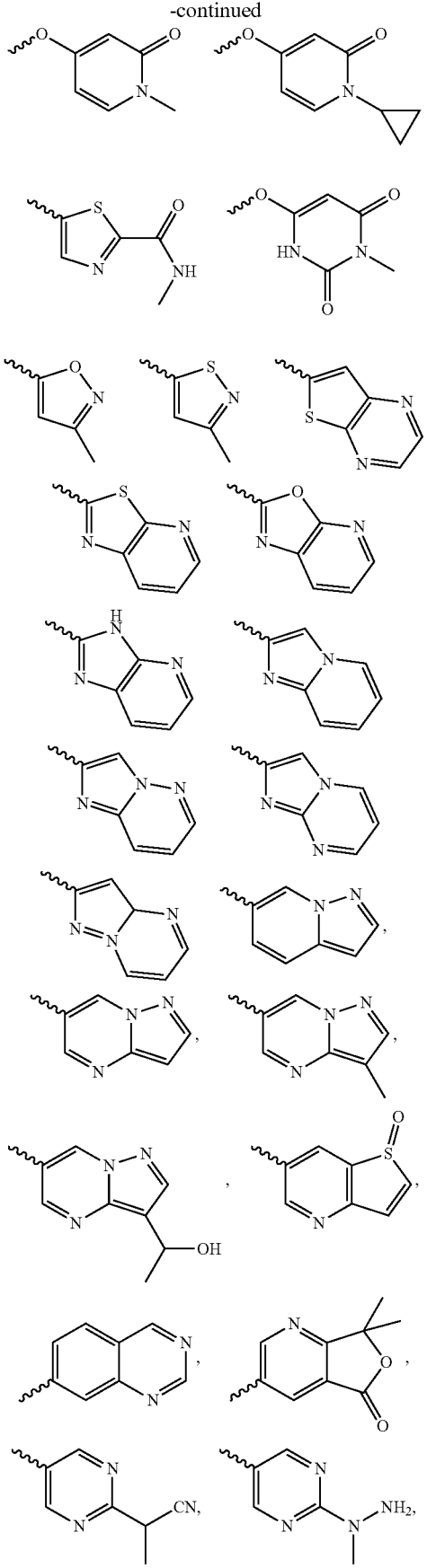

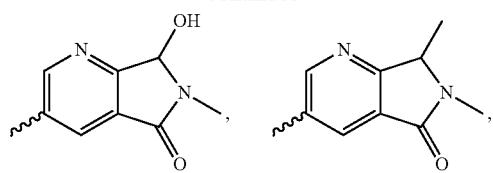
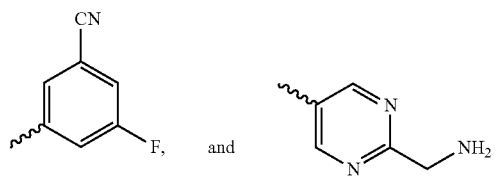
Compounds wherein R² a 5-membered heteroaryl ring containing 1-4 O, S, or N heteroatoms, optionally substituted with 0-2 noninterfering substituents, or a 6-membered or 5-membered non-aryl or non-heteroaryl ring containing 0-3 O, S, or N heteroatoms, optionally with 0-3 noninterfering substituents include:
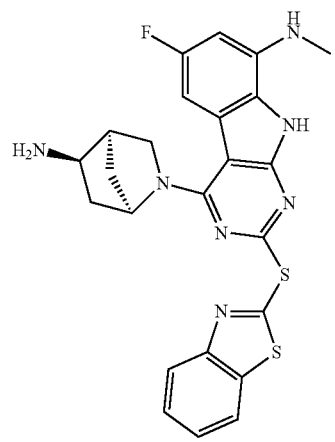
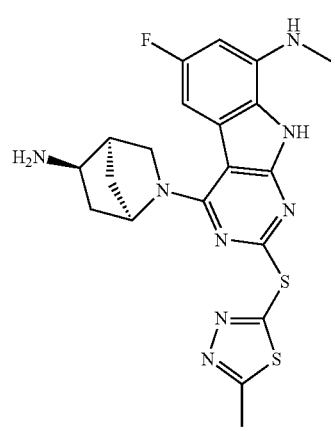
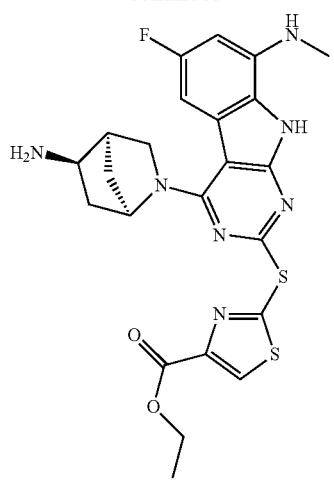
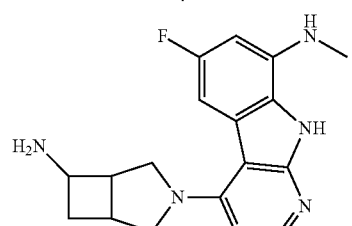
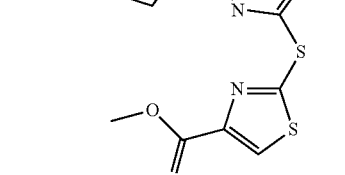

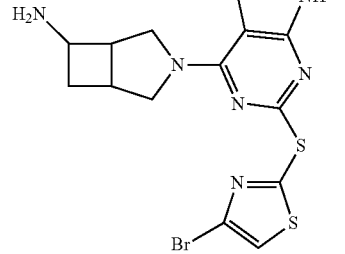

53
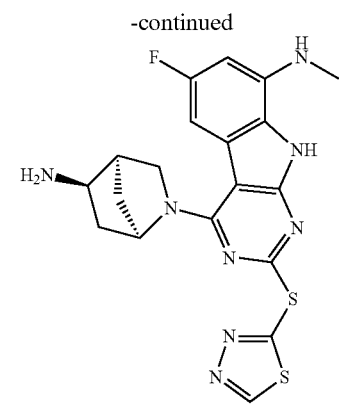
54
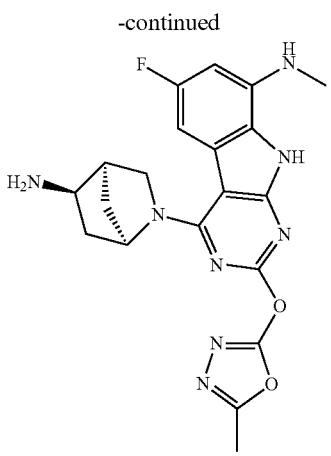
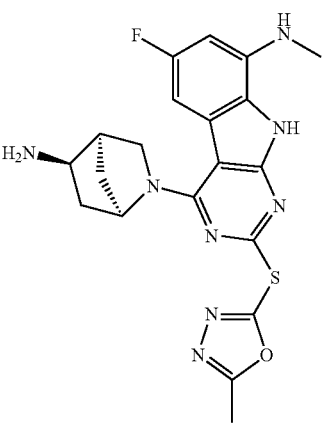
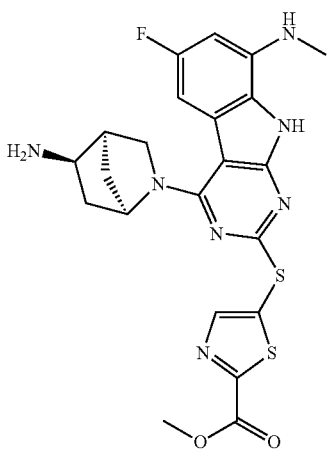
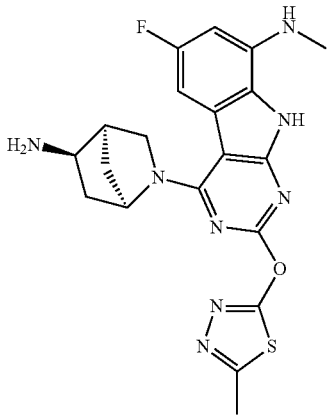

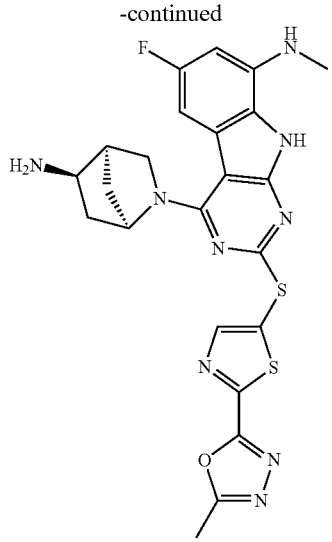

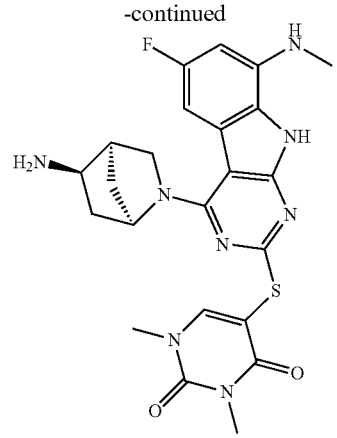

Solvent exposed faces of the GyrB/ParE active-site pockets allow portions of the compound to be exposed to a solvent environment when in use as illustrated in FIG. 1. In some aspects, noninterfering substituents may be water soluble to afford compatibility with an aqueous solvent environment. Proportions of the substituents in the direction of a potential solvent environment are not critical but one skilled in the art would understand that sterically unhindered substituents are useful. Thus, proportions of the solvent-exposed substituents may be diverse.

In contrast to an "interacting substituent," certain positions of the molecule may be described as permitting "noninterfering substituents." This terminology is used because the substituents in these positions generally speaking are less relevant to the activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound herein such as compounds of Formula I to inhibit bacterial growth of at least one type of bacterium qualitatively intact. For example, the noninterfering substituent would leave the ability of the compound to provide antibacterial efficacy based on a minimum inhibitory concentration (MIC) of less than 32 µg/ml, or based on inhibition of ATPase activity of DNA Gyrase B (GyrB) or Topoisomerase IV (ParE) of less than 10 nm. Thus, the substituent may alter the degree of inhibition based on MIC or ATPase activity. However, as long as the compound herein such as compounds of Formula I retains the ability to inhibit bacterial/ATPase activity, the substituent will be classified as "noninterfering." A number of assays for determining the MIC or the ability of any compound to inhibit ATPase activity of DNA Gyrase B (GyrB) or Topoisomerase IV (ParE) are available in the art, and some are exemplified in the Examples below. For instance, a coupled spectrophotometric assay, in which the enzyme-dependent release of inorganic phosphate from ATP hydrolysis is measured, determines the inhibitor activity of an arbitrarily chosen compound during incubation with GyrB or ParE upon the addition of ATP. The features related to the molecule's activity are tightly defined. The positions which are occupied by "noninterfering substituents" can be substituted by conventional moieties as is understood in the art. It is irrelevant to test the outer limits of such substitutions. The relevant features of the compounds are those set forth with particularity herein.

In some aspects, substituents that are noninterfering substituents on one R group may also be noninterfering substituents on another R group, subject to the steric hindrances, size limitations and the ability to inhibit bacteria as discussed herein. For example, the noninterfering substituents on $R^2$ may also be noninterfering substituents on $R^4$.

$R^2$ may have 0-3 noninterfering substituents on a ring. For instance, $R^2$ may have a noninterfering substituent selected from the group consisting of OH, $CO_2H$, CN, $NH_2$, Br, Cl, F, $SO_3H$, $SO_2NH_2$, $SO_2CH_3$, $SOCH_3$, NHOH, $NHOCH_3$, and $NO_2$. $R^2$ may also have a substituent that is an optionally substituted C1-15 hydrocarbyl residue containing 0-5 O, S, or N heteroatoms, optionally substituted with OH, CN, =O, $NH_2$, NHOH, =NOH, $=NNH_2$, $=NOCH_3$, Br, F, Cl, $SO_3H$, or $NO_2$. Substitutions may be on a carbon atom or a heteroatom thus permitting groups such as S=O. In cases where the heteroaryl contains a pyridine ring, the nitrogen atom may be oxidized to a pyridine N-oxide; thus, an OH substituent may be in the form of an oxide, thus for example, permitting a pyridyl having an N-oxide wherein the N is a ring heteroatom.

The C1-15 hydrocarbyl residue containing 0-5 O, S, or N heteroatoms may included a combination of hydrocarbyl groups such as a combination of aliphatic rings or chains and aromatic rings linked together.

In some aspects, two adjacent noninterfering substituents on $R^2$ form one or more fused rings. For example, the combination of the one or more fused rings with the 6-membered aryl or heteroaryl ring of $R^2$ contains 5-15 members, and 0-5 O, S, or N heteroatoms, optionally substituted, such as with OH, =O, CN, $NH_2$, Br, F, or Cl.

The optional substituents may occupy all positions of the $R^2$ ring structure that are not adjacent L such as one position, 1-2 positions, or 1-3 positions. In some aspects, one position is optionally substituted. These substituents may be optionally substituted with substituents similar to those listed. Of course, some substituents, such as halo, are not further substituted, as known to one skilled in the art.

In some aspects, $R^2$ may be pyrimidinyl or pyridinyl optionally substituted with $CH(OH)CH_3$, $C(OH)(CH_3)_2$, $OCH_3$, CN, $CH_3$, $CH_2CH_3$, O-cyclopropyl, $SCH_3$, Br, Cl, F, or $NH_2$.

The noninterfering substituents on $R^2$'s ring that may be solvent exposed in the bound conformation may include large substituents such as prodrugs.

In some aspects $R^2$ may be selected from the substituents in the following Chart 1.

Chart 1

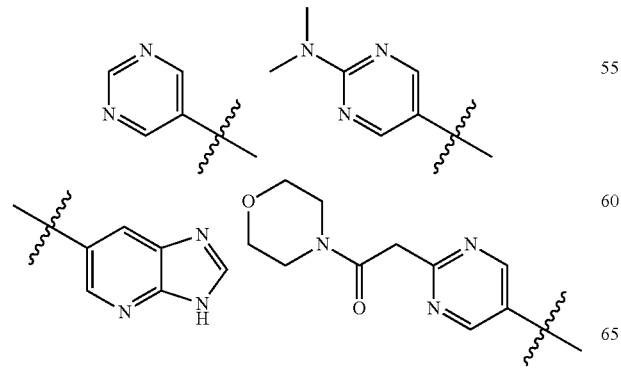

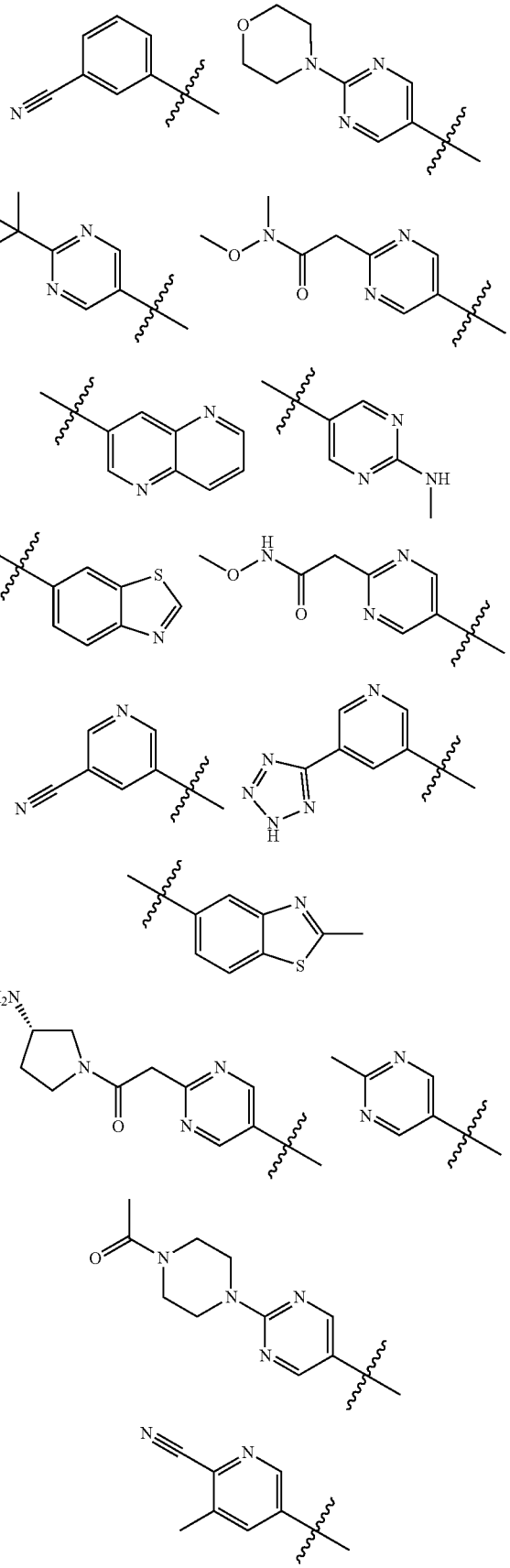

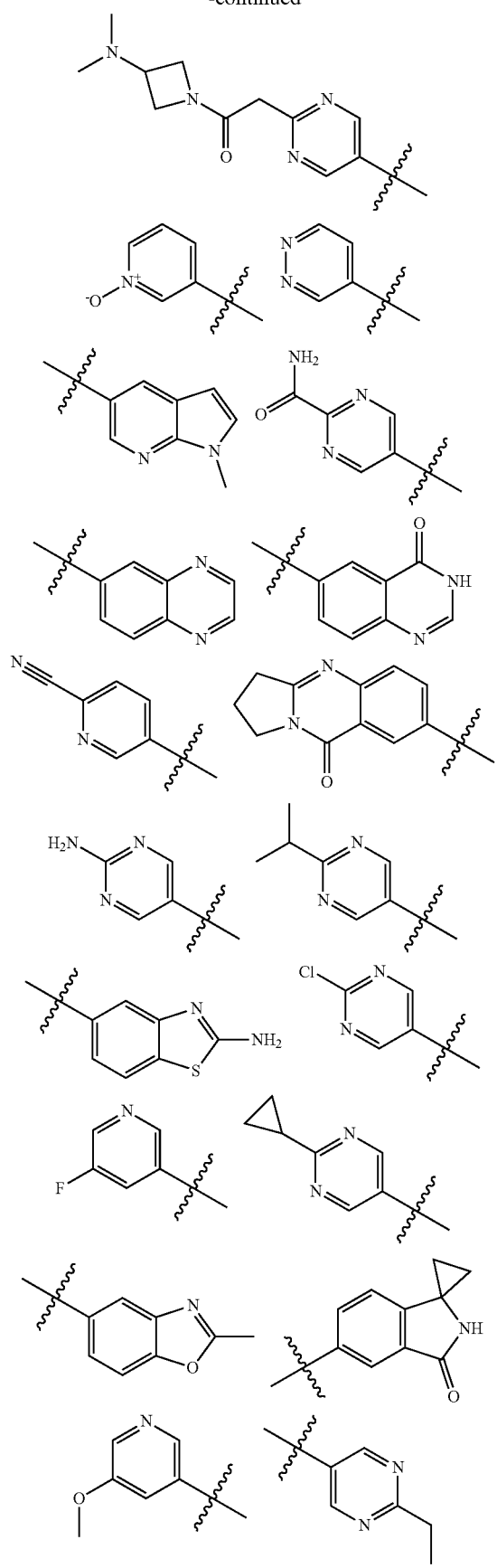
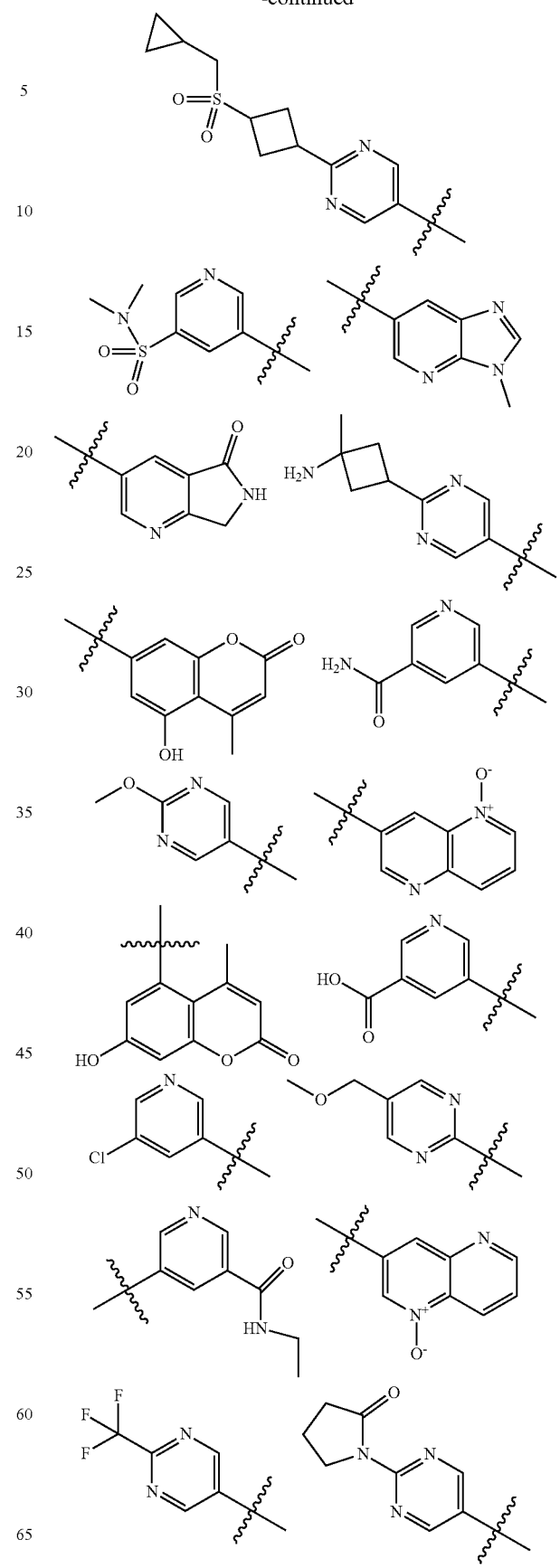

61
-continued
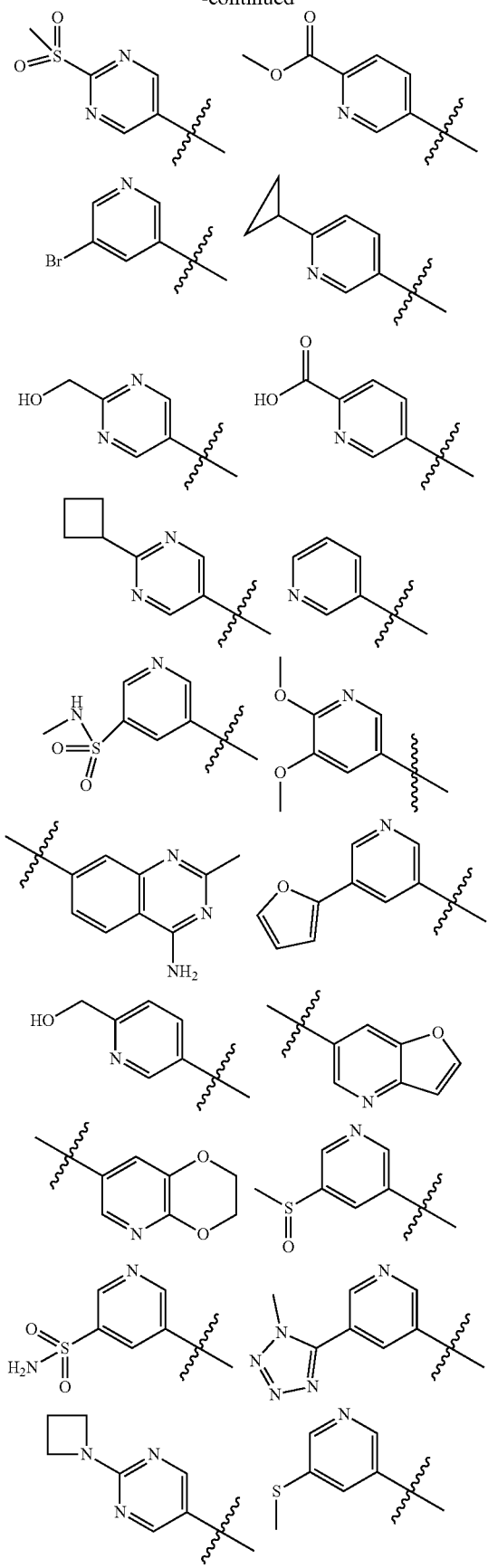
62
-continued
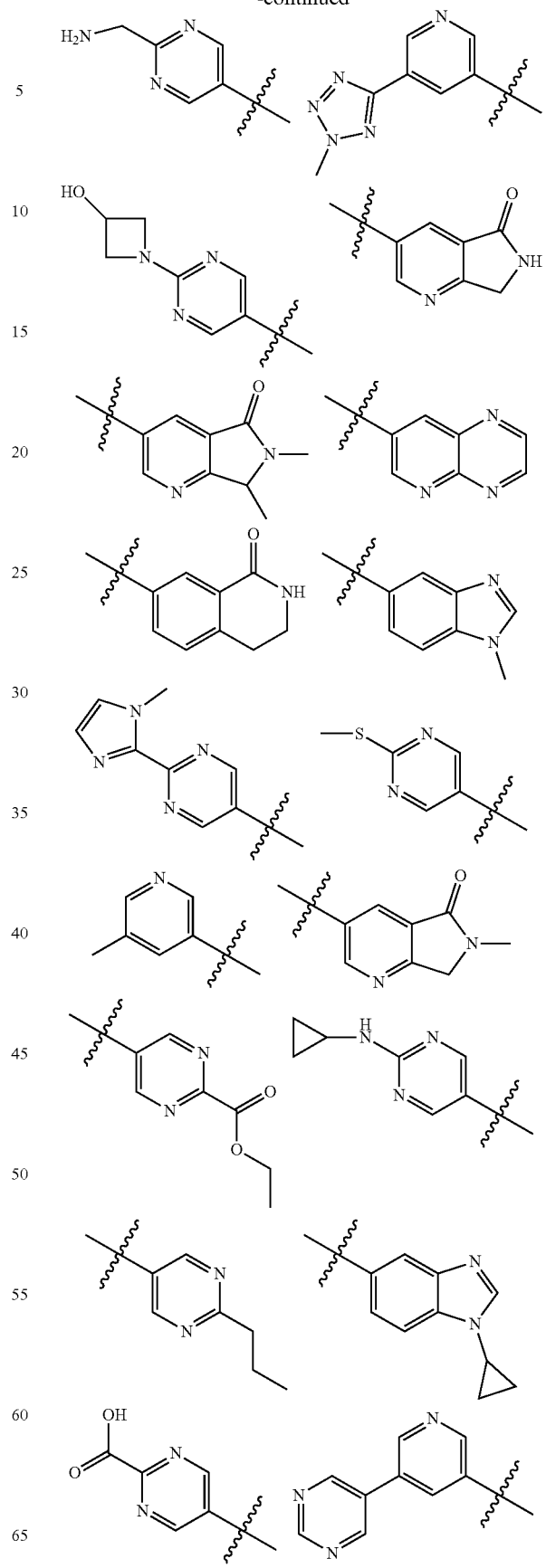

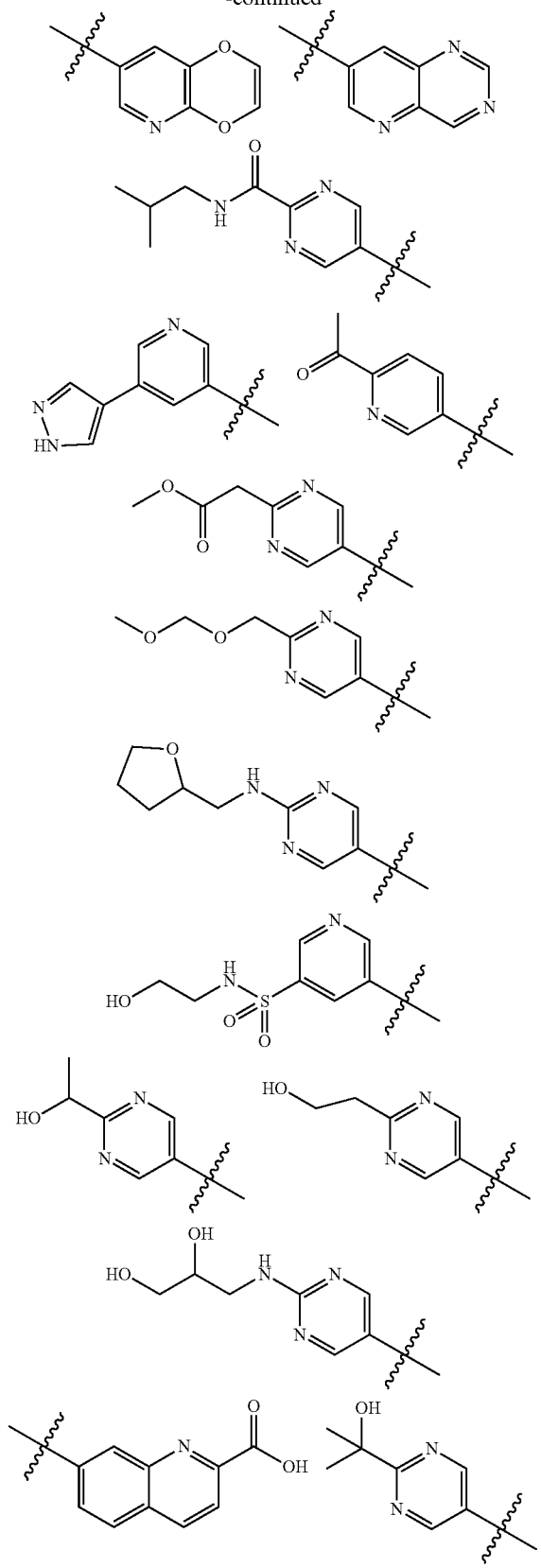
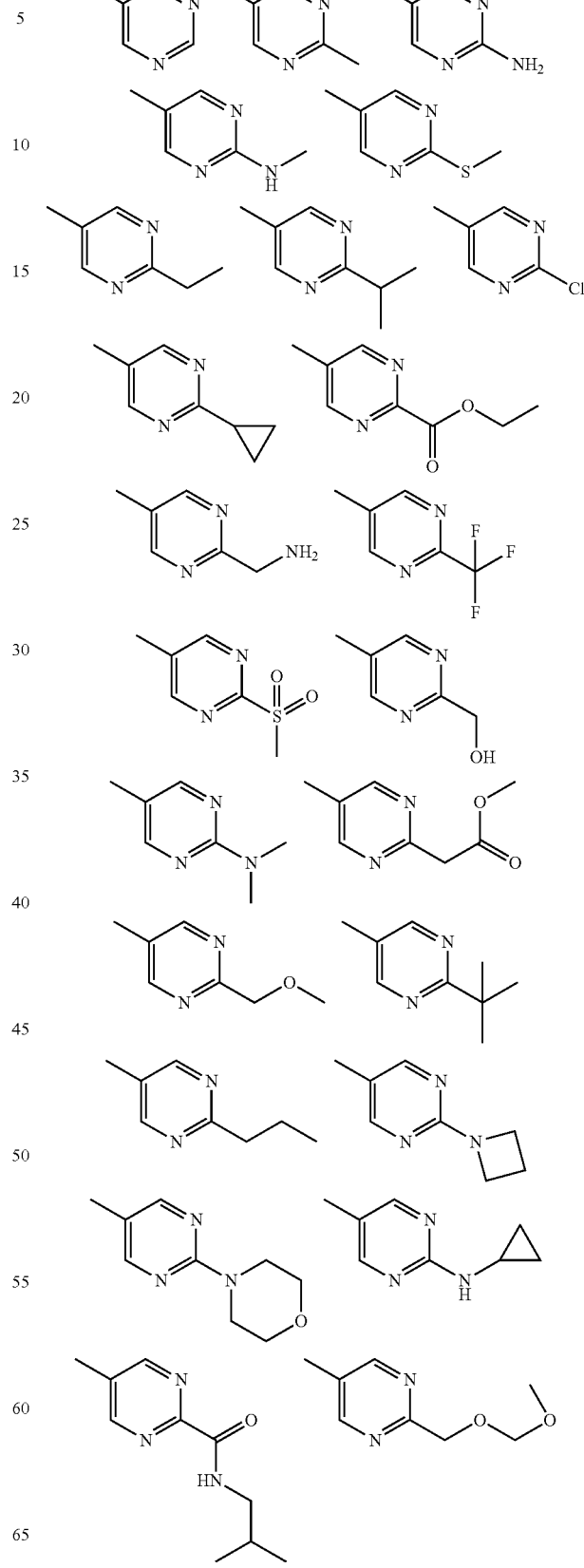
Chart 2
In some aspects R² may be selected from the substituents in the following Chart 2.

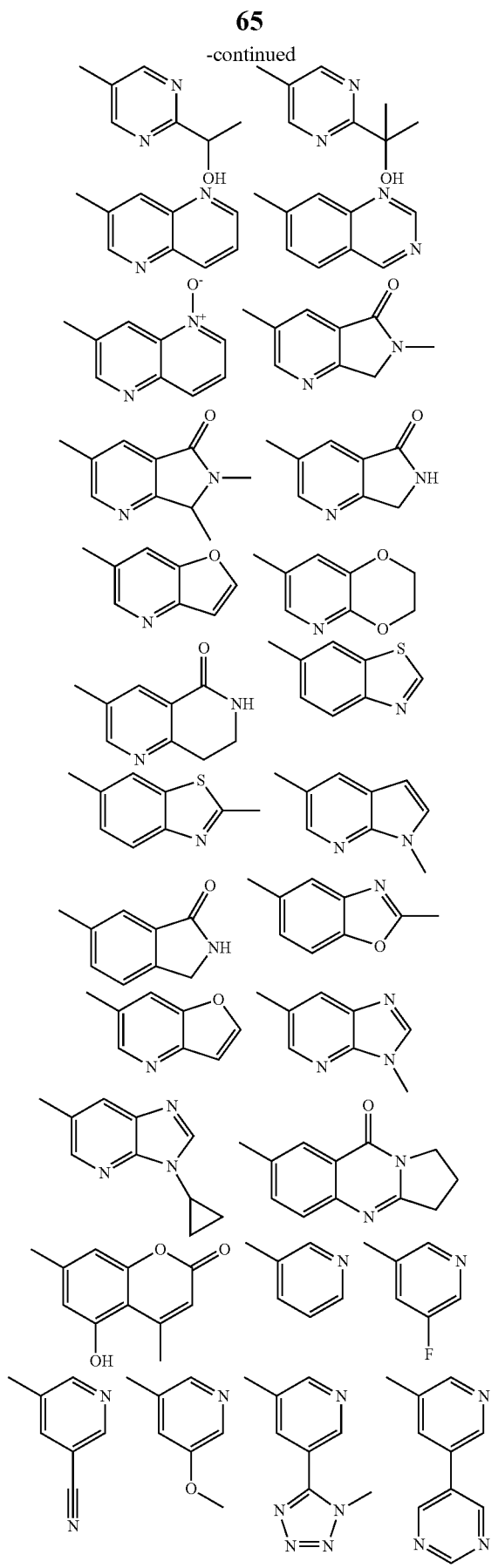
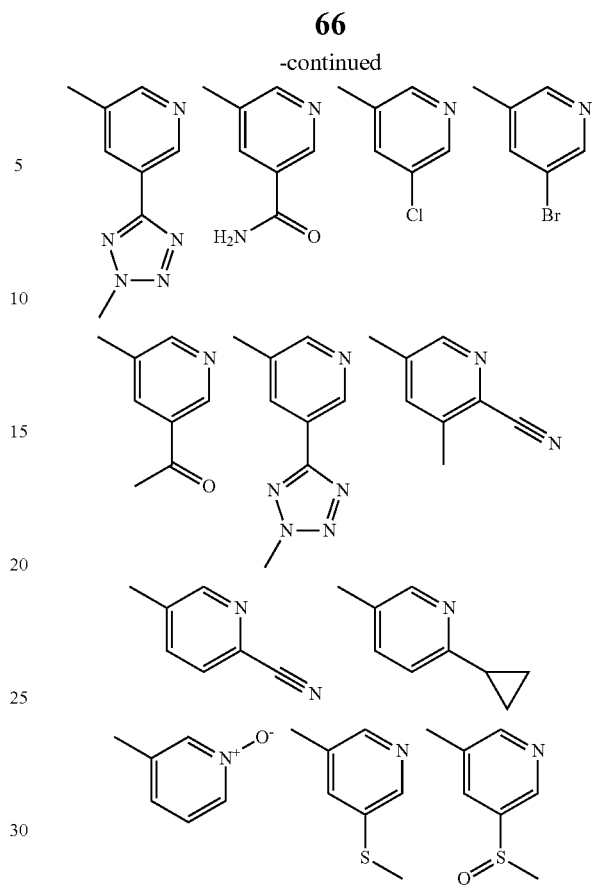
In some aspects R² may be selected from the substituents in the following Charts 2a and 2b. These R² groups include an OH so are useful for making prodrugs.
Chart 2a
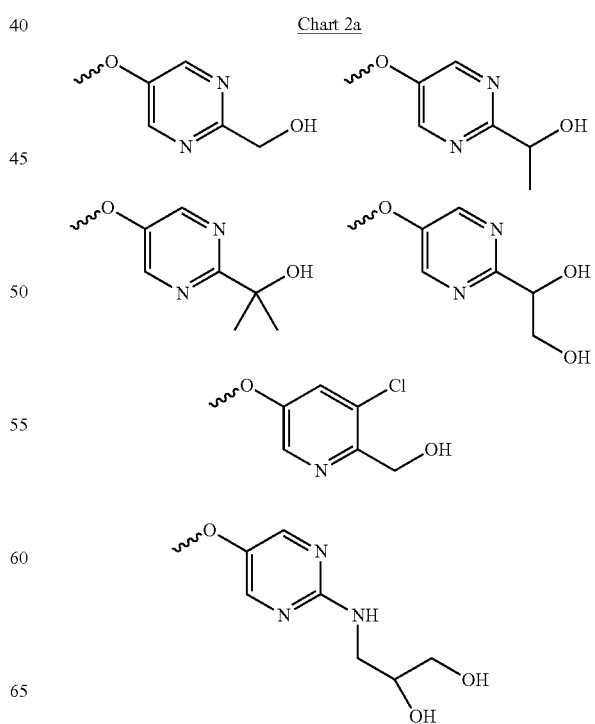

-continued

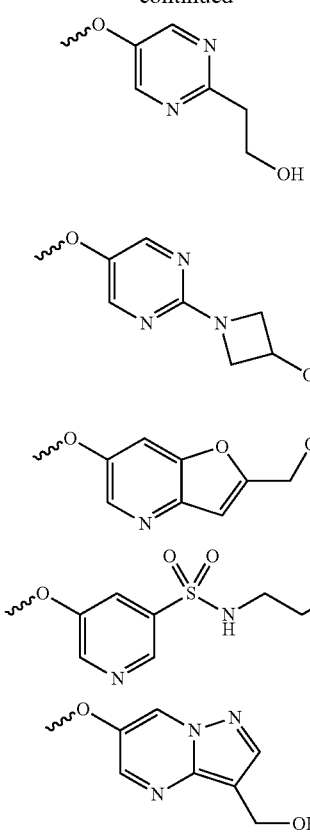

Chart 2b

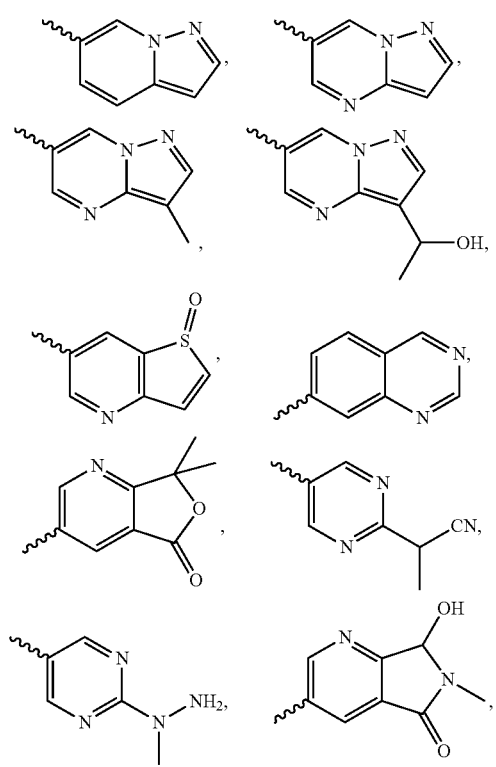

-continued

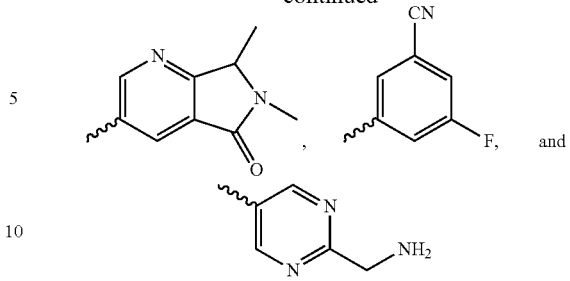

In another aspect, L-R² includes:

FIGS. 1 and 2 show that the compound is solvent exposed in the bound conformation along the R⁴ bond axis and in a 0-90° counterclockwise sweep from the R⁴ bond axis. Choices for prodrugs and substituents on R⁴, therefore, may be varied. In selecting the R⁴ substituent, in some aspects the R⁴ groups do not sterically interfere with R² or Z groups in the bound conformation, which is illustrated in FIG. 2. A skilled artisan would understand that to avoid steric interference, atoms on R⁴ should not approach atoms on R² or R^z (in the bound conformation) such that the interatomic distances of the closest atoms are less than the sums of their Van der Waals radii.

In addition, in some aspects, the R⁴ substituent does not project greater than about 3 Å below the plane of the A, B and C Rings toward the GyrB/ParE binding pocket in the bound conformation. "Toward the GyrB/ParE binding floor pocket" refers to not projecting greater than about 3 Å below the plane within about 5-6 bonds from the point of attachment of R⁴ to the scaffold. Thus, portions of R⁴ that extend greater than about 5-6 bonds away from the point of attachment of R⁴ to the C Ring may project greater than about 3 Å below the plane of the A, B and C Rings as these portions are not constrained by the floor of the GyrB/ParE binding pocket.

The distance is defined as the perpendicular distance from the plane aligned with atom centers of the tricyclic scaffold to the center of the most distal atom (from the plane) on the R⁴ substituent in the bound conformation.

In some aspects, R⁴ may be H.

In some aspects, R⁴ may also be an optionally substituted OR^a; wherein R^a is a 5-6 membered aryl or heteroaryl containing 0-3 O, S, or N heteroatoms optionally substituted with 0-3 noninterfering substituents. In some aspects, the ring positions adjacent the position where O attaches to R^a, may be substituted with small substituents such as those having 2 atoms in the backbone, such as OCH₃, CH₃, CH₂CH₃, OH, NH₂, F, Cl, Br, I, or NO.

In the remaining positions, substituents can be larger and diverse as substituents in these positions are solvent exposed in the bound conformation. In some aspects, R^a is an optionally substituted pyrimidinyl or pyridinyl, such as unsubstituted pyrimidinyl or pyridinyl substituted with CH₃ or NH₂. In some aspects, OR^a is one of the following substituents in Chart 3.

Chart 3

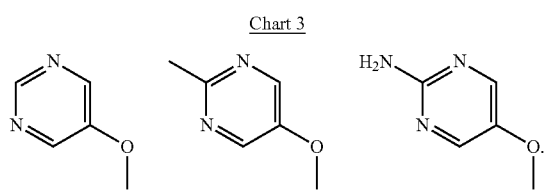

In some aspects, $R^4$ may be an optionally substituted secondary or tertiary amine attached to the C Ring through the secondary or tertiary amine N. "Secondary amine" refers to an N-containing substituent that contains one H attached to the secondary amine N when the substituent is attached to the remainder of the molecule. "Tertiary amine" refers to an N-containing substituent that contains no H attached to the tertiary amine N when the substituent is attached to the remainder of the molecule.

When $R^4$ is the optionally substituted secondary or tertiary amine attached to the C Ring through the secondary or tertiary amine N, $R^4$ may further comprise a primary or secondary amine, wherein the primary or secondary amine is not directly attached to the C Ring. "Primary amine" refers to an amine group that contains two H atoms attached to the primary amine N when attached to the remainder of the substituent. With respect to the "secondary amine" that is not directly attached to the C Ring, in this instance, the secondary amine refers to an amine group that contains one H atom attached to the secondary amine N when attached to the remainder of the substituent. The primary or secondary amine that is not directly attached to the C Ring may be positioned in the compound in the bound conformation wherein:
  a) the distance between the C or N atom of Y and the primary or secondary amine N is about 7 Å to about 10.5 Å;
  b) the distance between the C atom to which $R^8$ is attached and the primary or secondary amine N is about 6 Å to about 9 Å;
  c) the distance between the C atom to which $R^4$ is attached and the primary or secondary amine N is about 3.5 Å to about 6 Å; and
  d) the distance between the C atom to which $R^2$ is attached and the primary or secondary amine N is about 5 Å to about 7.5 Å.

"Not directly attached to the C Ring" with regard to the primary or secondary amine refers to the lack of a bond joining the primary or secondary amine to the C Ring.

In some aspects, $R^4$ may be an optionally substituted tertiary amine that is an optionally substituted 4-14 membered saturated cycloheteroaliphatic tertiary amine ring system containing 1-3 N atoms, 0-3 O atoms and 0-1 S atoms; and wherein the 4-14 membered saturated cycloheteroaliphatic ring system is a single ring, a fused ring system, a bridge ring system, or a spiro ring system.

In some aspects, $R^4$ may be the optionally substituted tertiary amine attached to the C ring through the tertiary amine N, wherein the optionally substituted tertiary amine contains at least one additional N separated from the tertiary amine N by 2-3 atoms. The atoms separating the N's need not be located in the same ring. For example, one atom separating the N's may be in a ring and the second atom may be found in a substituent, or both atoms separating the N's may be in the backbone in, or a substituent on, the same or different rings.

In some aspects, the optionally substituted secondary or tertiary amine of $R^4$ is one of the following substituents in Chart 4.

Chart 4

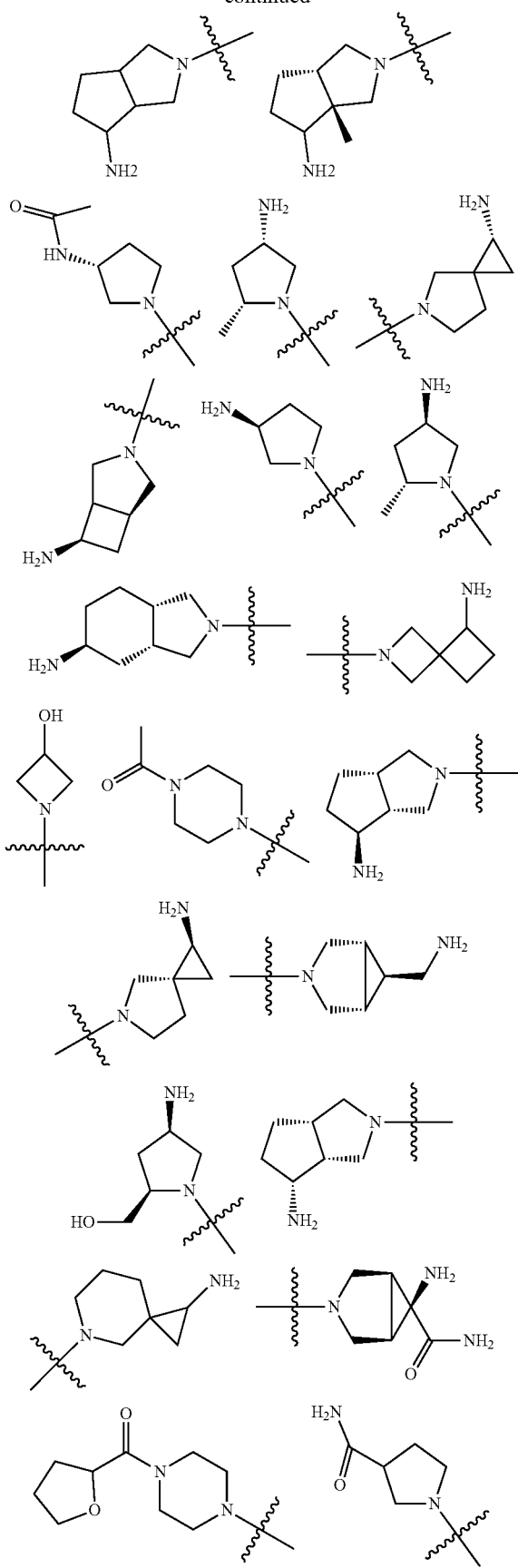
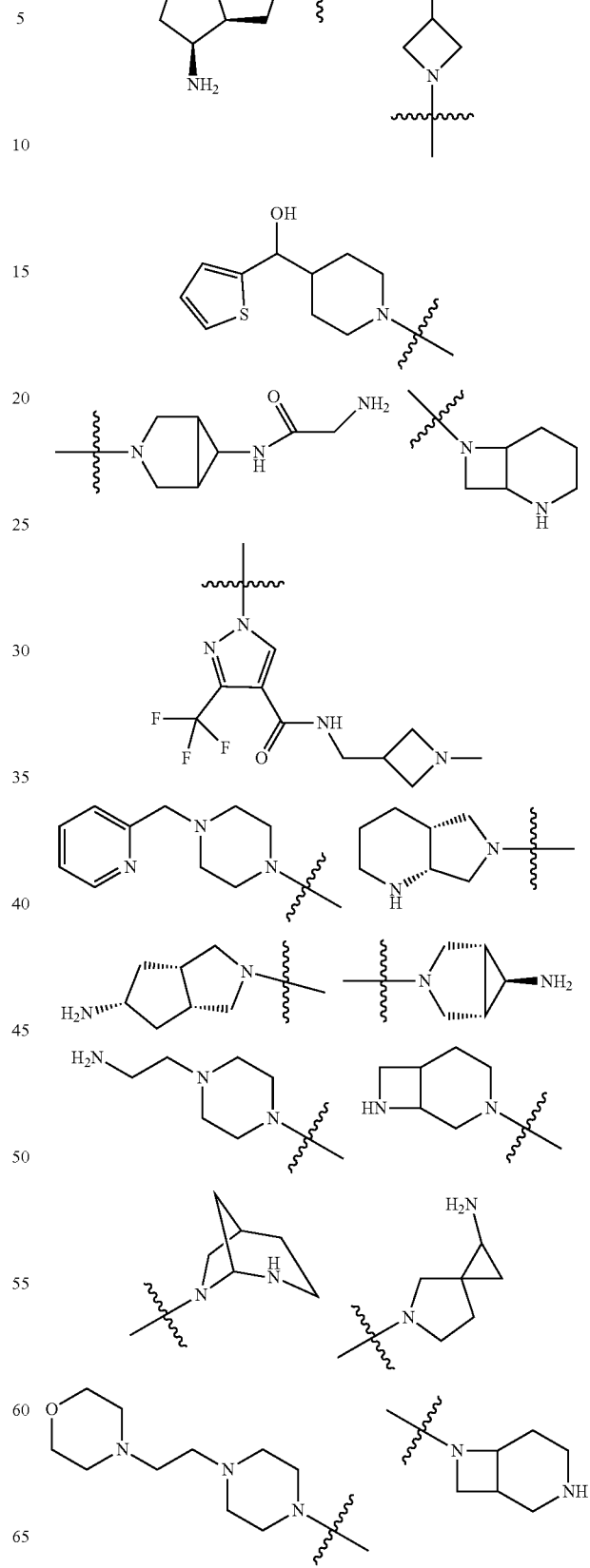

73
-continued
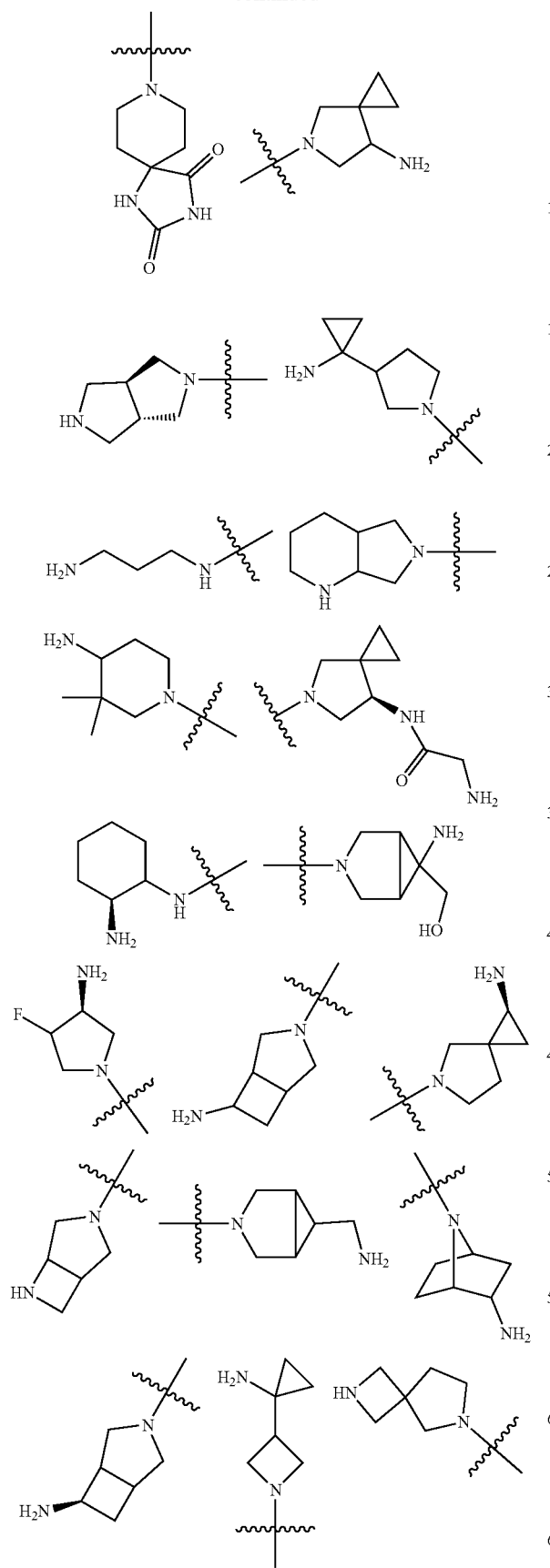
74
-continued
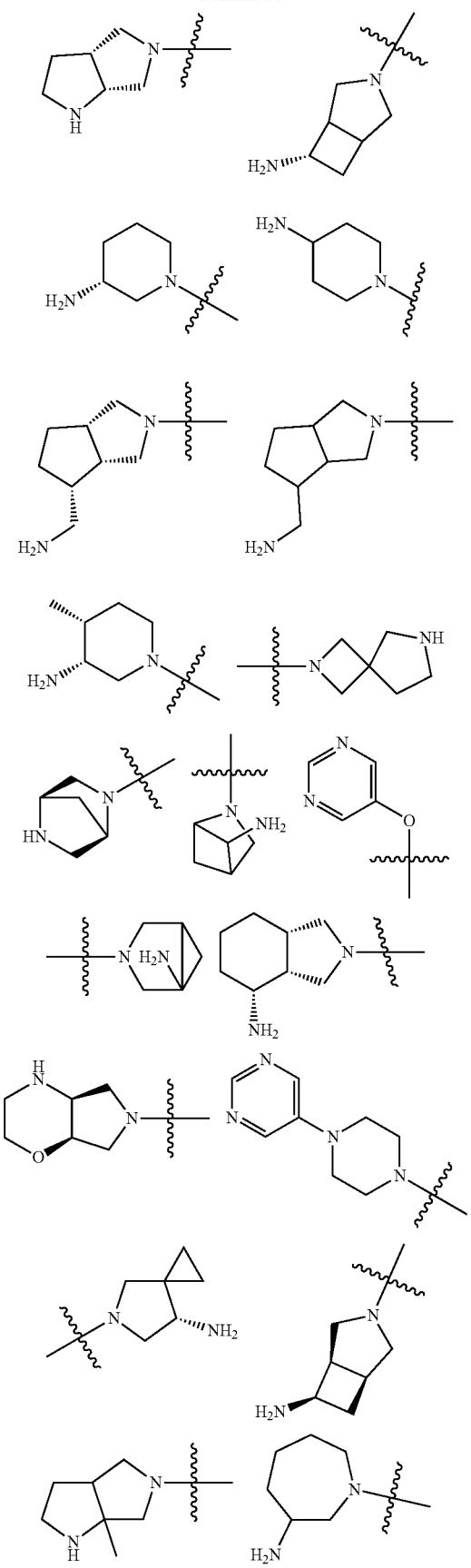

75
-continued
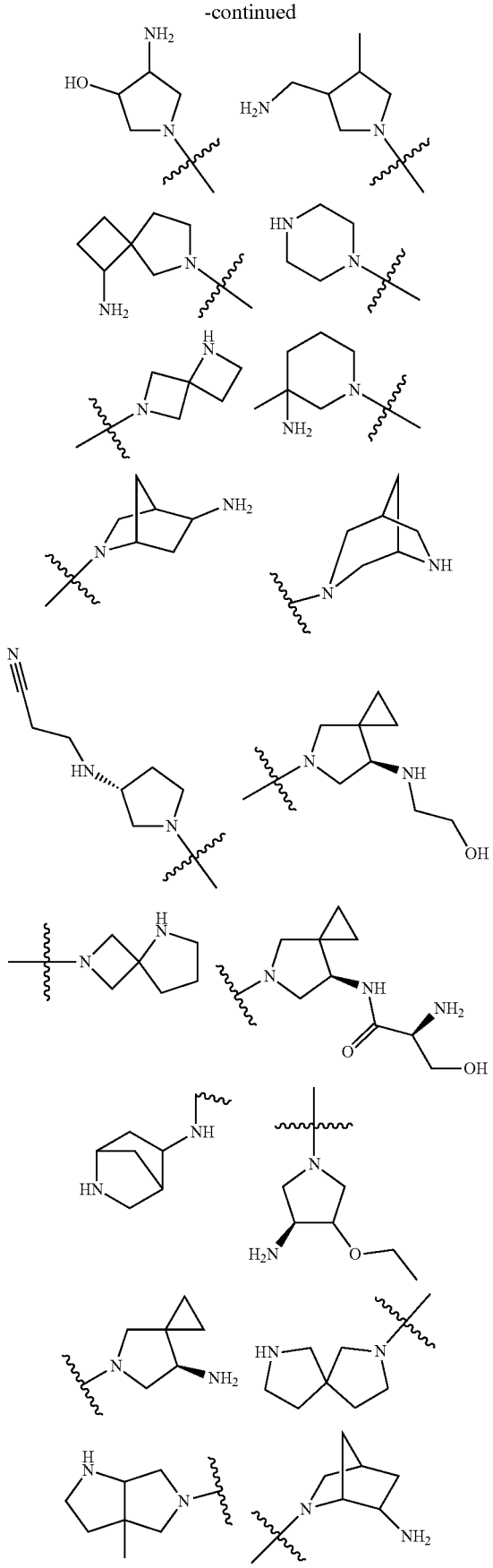
76
-continued
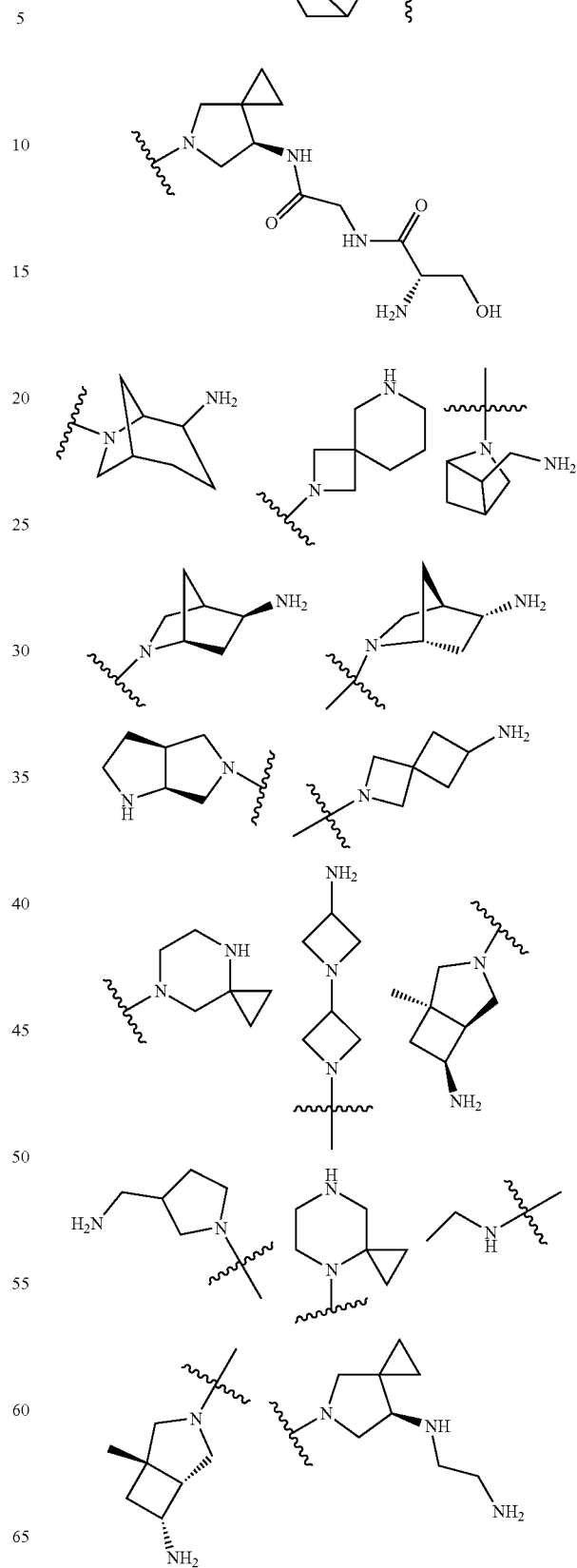

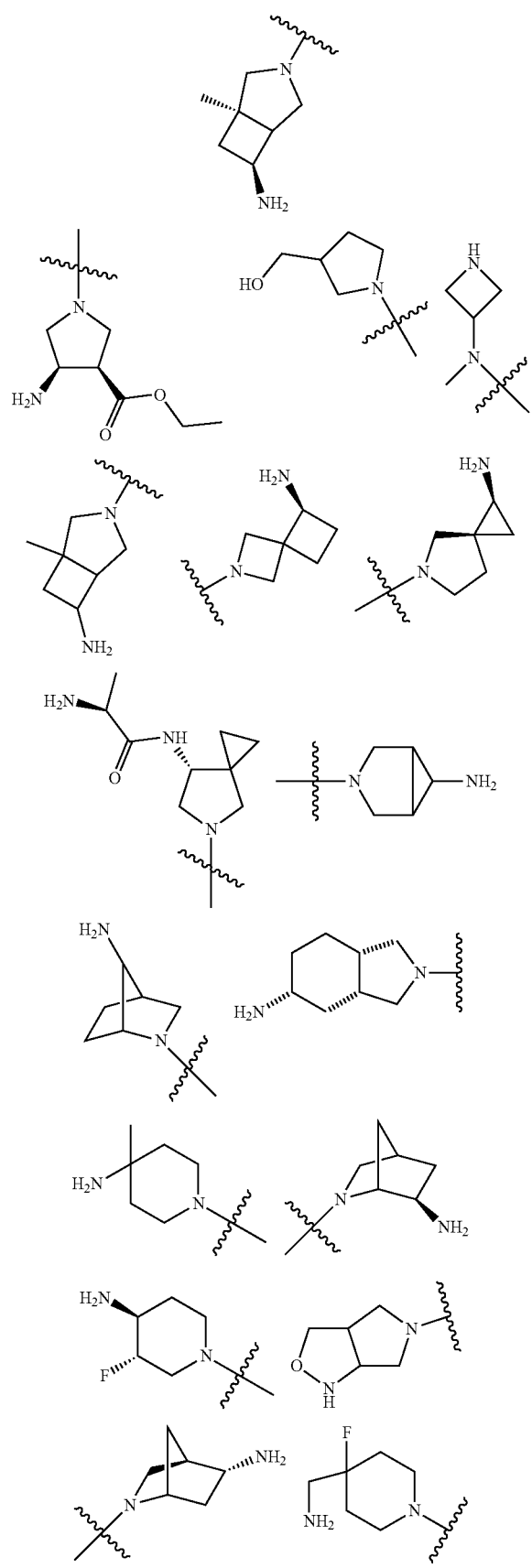
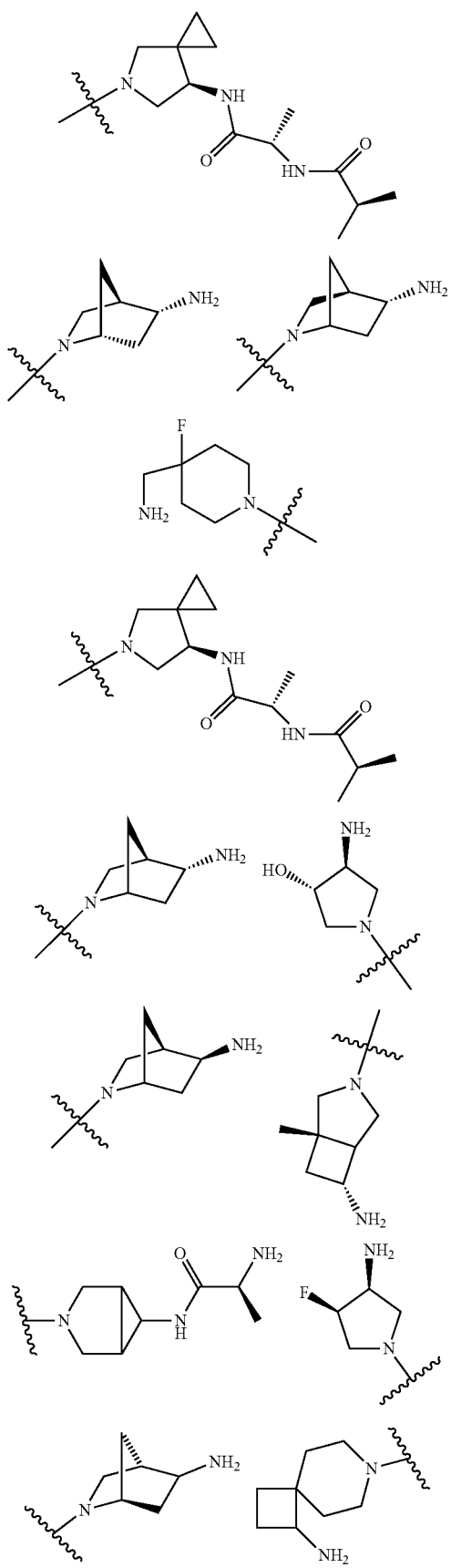

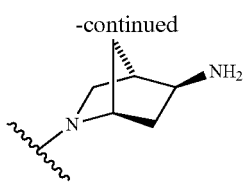

In some aspects, $R^4$ may be selected from the group consisting of optionally substituted pyrazolyl, phenyl, piperazinyl, pyridinyl, and tetrahydropyridinyl.

In some aspects, $R^4$ may be an optionally substituted 5-10 membered unsaturated cyclic or heterocyclic residue containing 0-3 N, O or S heteroatoms. The optional substituents may include 0-2 optional substituents selected from the group consisting of $CH_3$, $NH_2$, F, Cl, and $CH_2NH_2$. In some aspects, the optionally substituted 5-10 membered unsaturated cyclic or heterocyclic residue containing 0-3 N, O or S heteroatoms of $R^4$ is one of the following substituents in Chart 5.

Chart 5

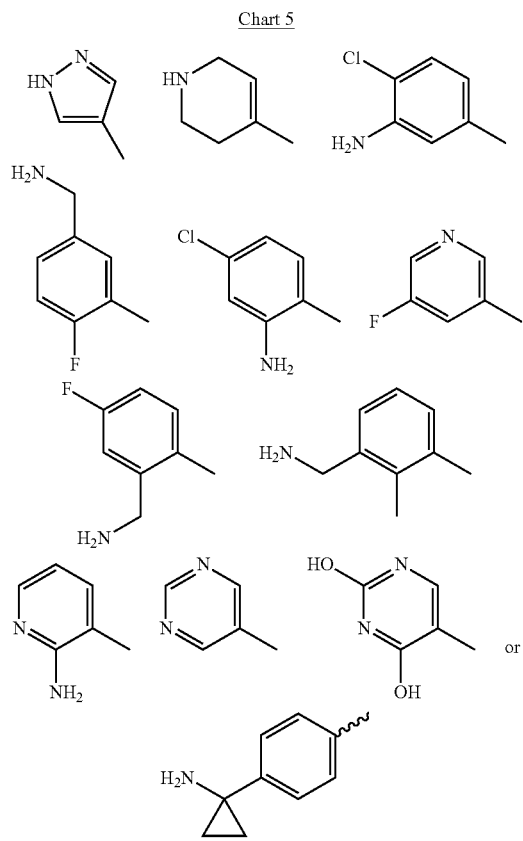

The optional substituent on R4 may include 0-3 noninterfering substituents. A noninterfering substituent on R4 may be a substituent selected from the group consisting of OH, NO, CO2H, CN, NH2, Br, Cl, F, SO3H, and NO2, or is a C1-15 hydrocarbyl residue containing 0-5 O, S, or N heteroatoms, optionally substituted with OH, CN, =O, NH2, =NOH, =NNH2, =NOCH3, Br, F, Cl, SO3H, or NO2. Substitutions may be on a C or a heteroatom thus permitting groups such as S=O. In addition, an OH substituent may be in the form of an oxide, thus for example, permitting a pyridyl having an N-oxide wherein the N is a ring heteroatom. The C1-15 hydrocarbyl residue containing 0-5 O, S, or N heteroatoms may include a combination of hydrocarbyl groups such as a combination of aliphatic rings or chains and aromatic rings linked together.

In some aspects, $R^4$ may be selected from the substituents in the following Chart 6.

Chart 6

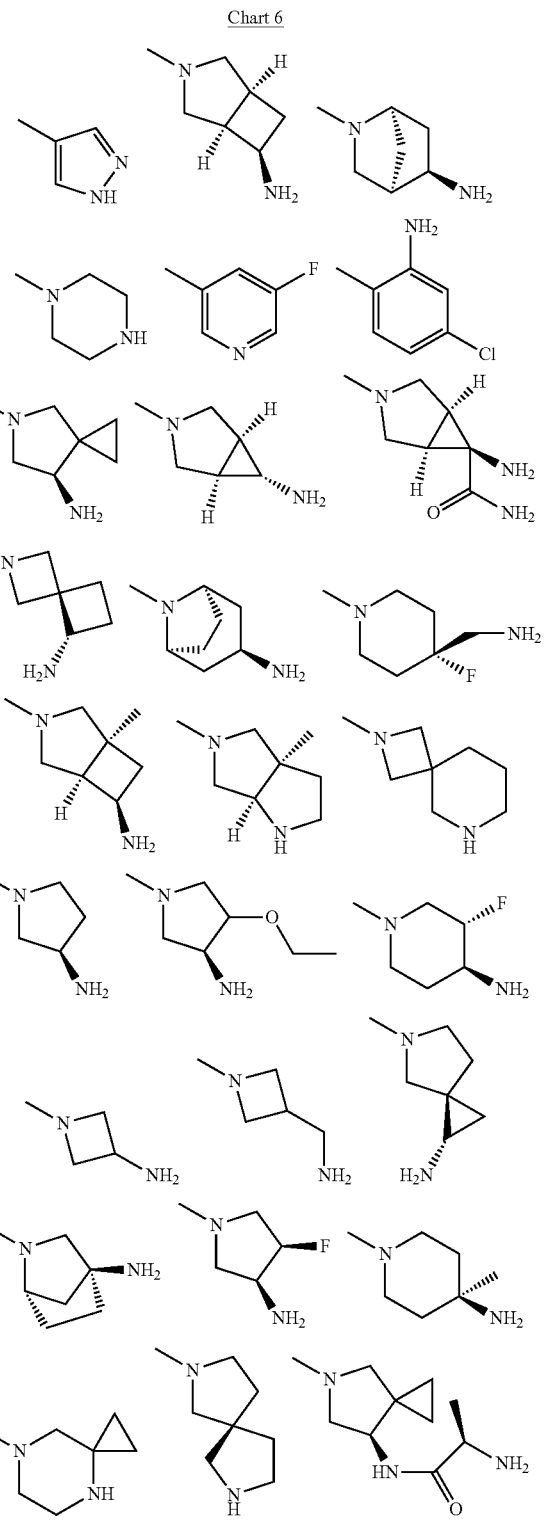

81
-continued
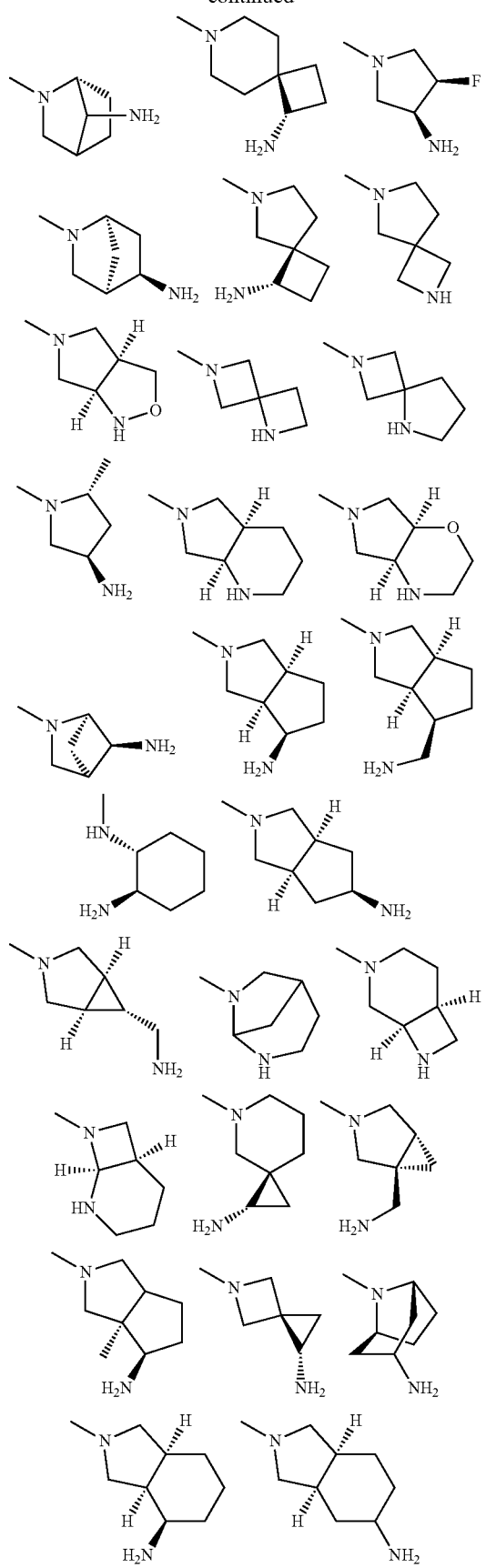
82
-continued
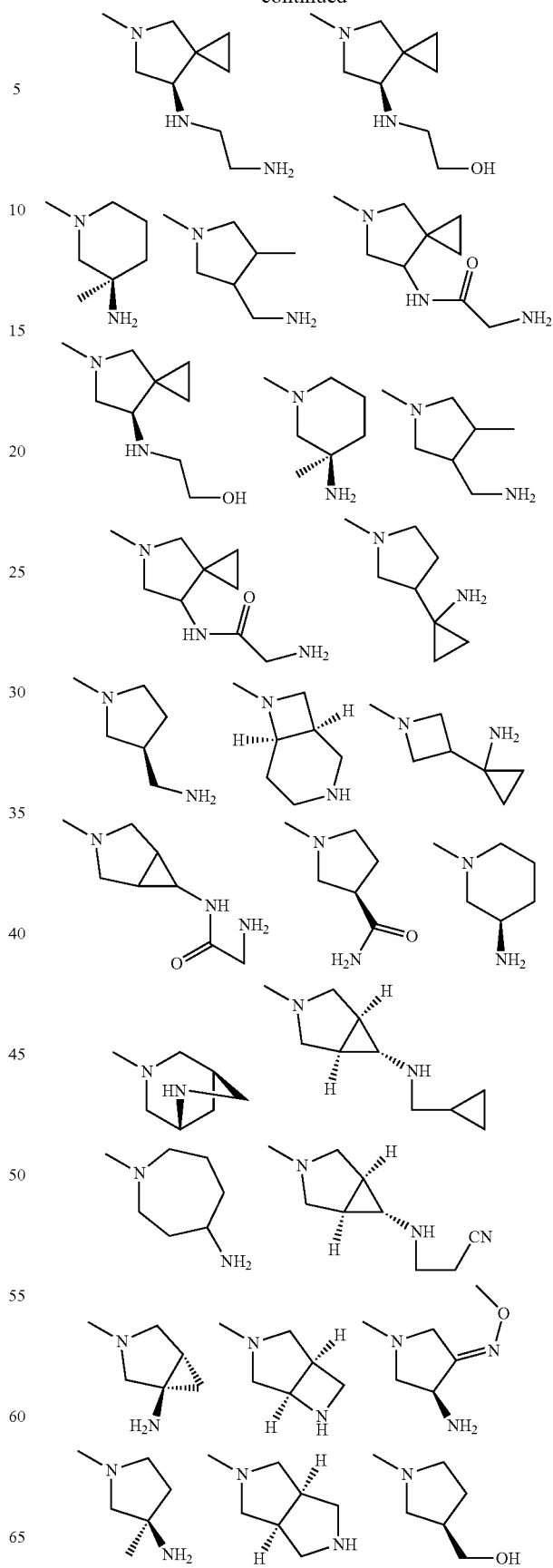

-continued
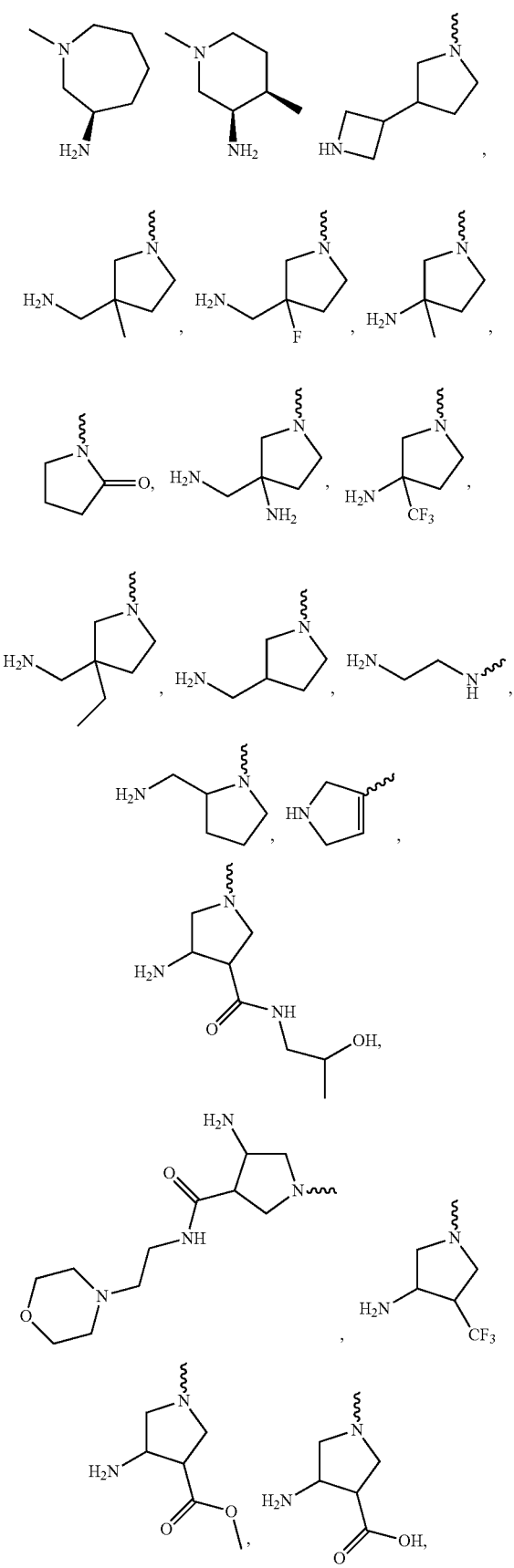
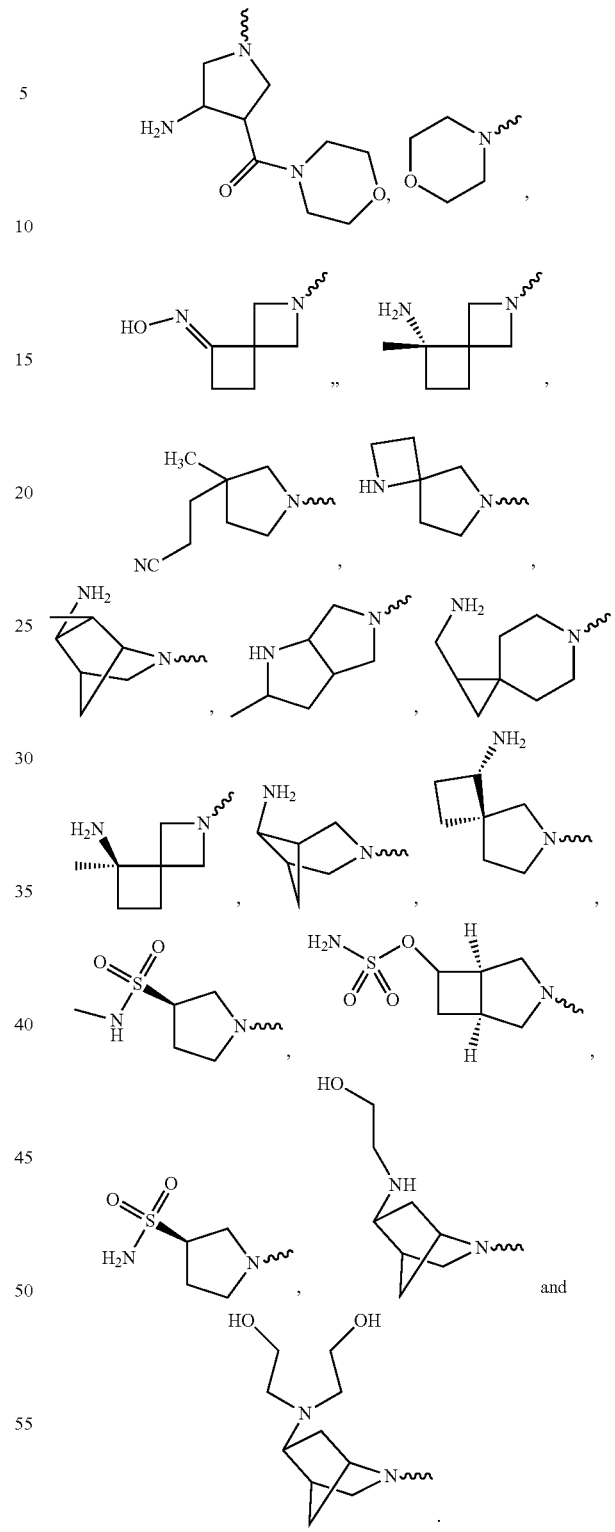
In addition to the species of $R^4$ that are disclosed in PCT/US2012/029104 and herein, $R^4$ may include $R^4$ substituents that are substituted with =O, such as pyrrolidinone or piperidinone.
$R^4$ may also be a prodrug-containing substituent, wherein the compound has the structure of Formula V or Formula V':

Formula V

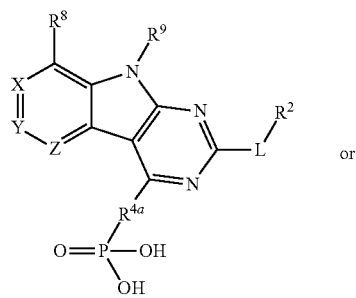

or

Formula V'

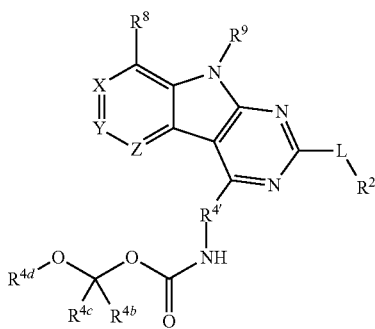

or a pharmaceutically acceptable salt thereof;

wherein $R^{4a}$ contains an oxygen residue derived from a non-prodrug $R^4$ as in b)-d) or g)-i), wherein the non-prodrug $R^4$ has an OH group, wherein the $R^4$ OH is replaced with an oxygen residue in $R^{4a}$, and wherein the oxygen residue is linked to P;

wherein $R^{4'}$—NH is derived from a non-prodrug $R^4$ as in b)-d) or g)-i), wherein the non-prodrug $R^4$ contains a primary amine and wherein the NH in the primary amine links the $R^4$ residue to the C=O;

wherein $R^{4b}$ and $R^{4c}$ are independently H or C1-C6 alkyl;

wherein $R^{4d}$ is

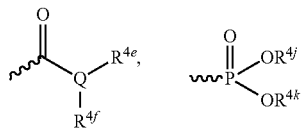

or a pharmaceutically acceptable salt thereof;

wherein Q is CH or N;

wherein $R^{4e}$ is $(CR^{4g}_2)_n$-basic amine, wherein each $R^{4g}$ may be independently H or C1-C3 alkyl;

wherein n is 0-2;

wherein $R^{4f}$ is hydrogen C1-C6 alkyl optionally substituted with OH or $NH_2$;

wherein $R^{4e}$ and $R^{4f}$ may join to form a ring;

wherein $R^{4j}$ and $R^{4k}$ are independently H or C1-C8 hydrocarbyl residue;

$R^4$ may also be a prodrug-containing substituent, wherein the compound has the structure of Formula II''

Formula II''

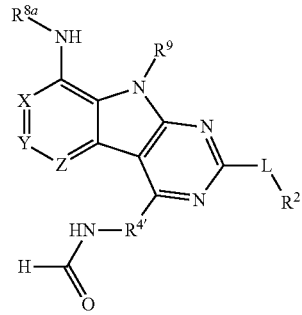

wherein the substituents are the same as those defined herein.

$R^4$ may also be joined with $R^2$ to form a fused ring, wherein $R^4$ is a 5- to 15-member hydrocarbyl linker containing 0-6 O, S or N atoms in the backbone of the linker that attaches to the $R^2$ group wherein atoms in the 5- to 15-member hydrocarbyl linker are optionally substituted with a noninterfering substituent. This fused ring is discussed in more detail in the above. $R^4$ may also be joined with Z to form a fused ring, discussed in more detail herein.

The compound may be one of the compounds exemplified in the Examples.

In some aspects, the compounds of Chart 7, or any compound recited in PCT/US2012/029104, may be the active moiety associated with the new prodrugs described herein.

Chart 7

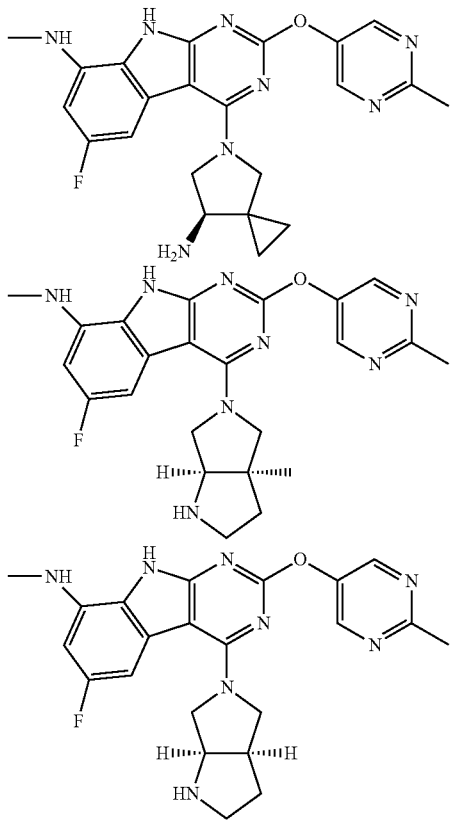

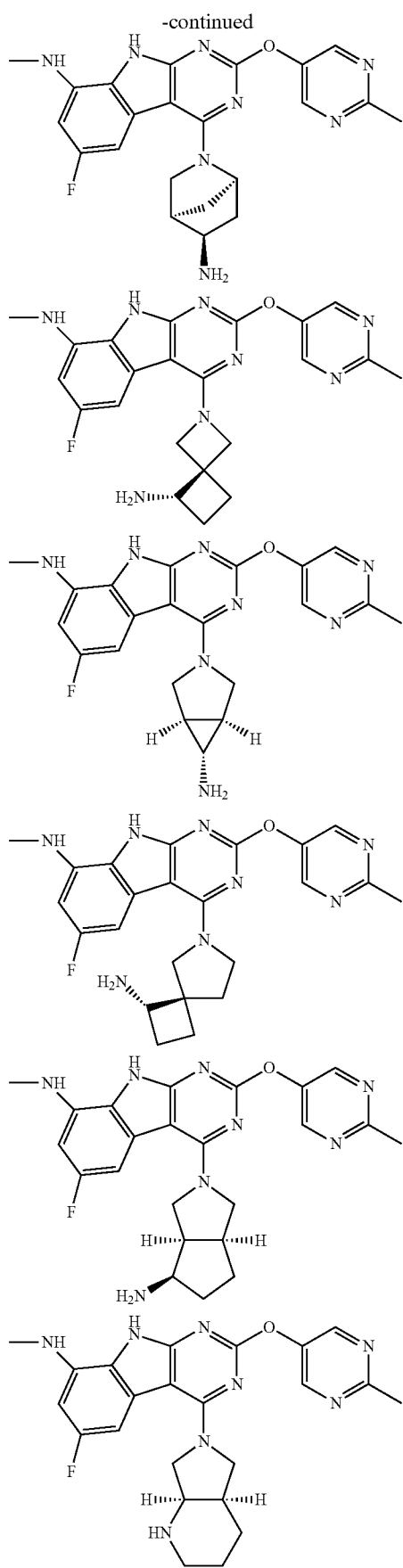
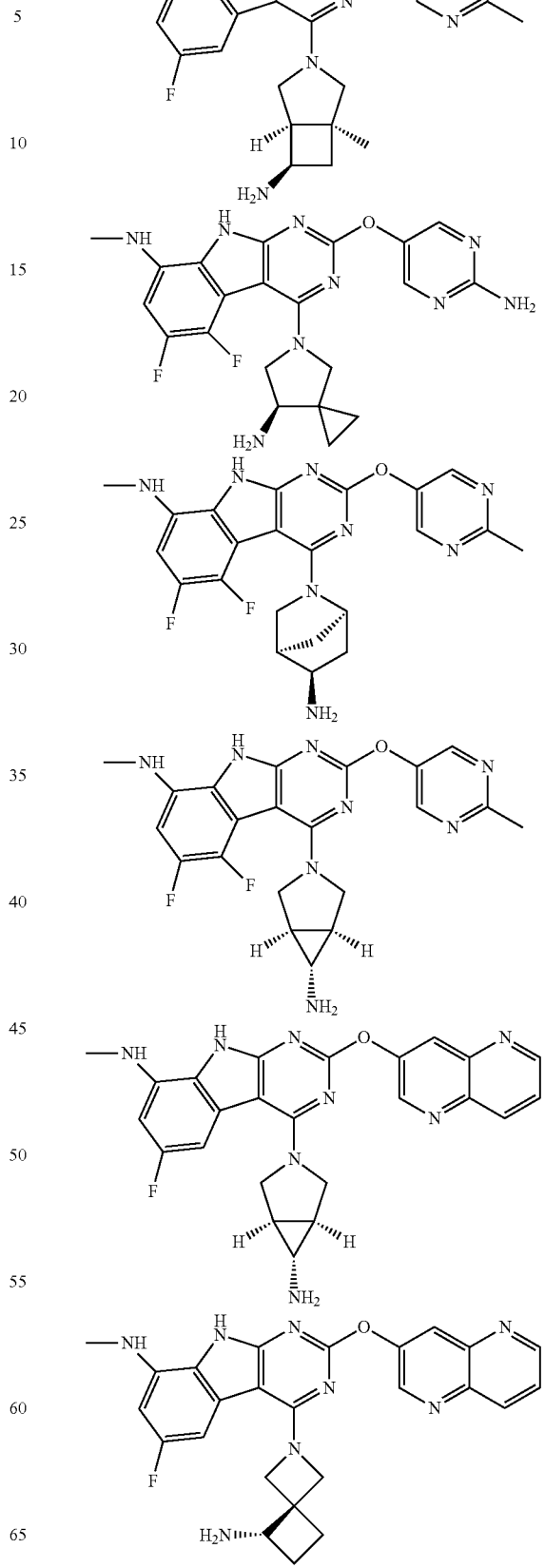

89
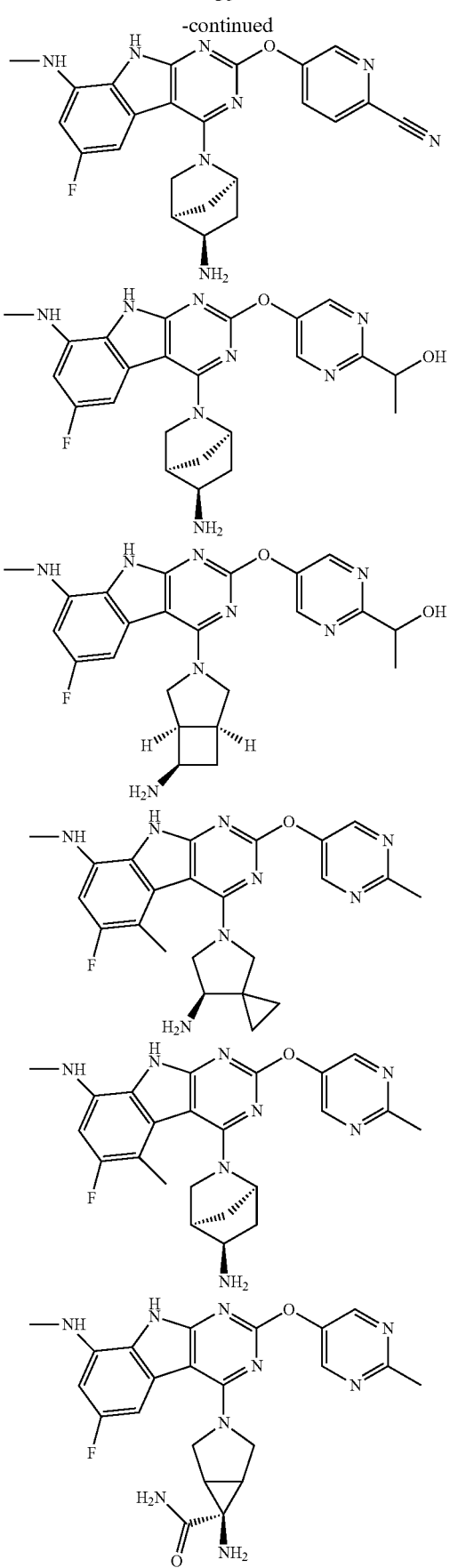
90
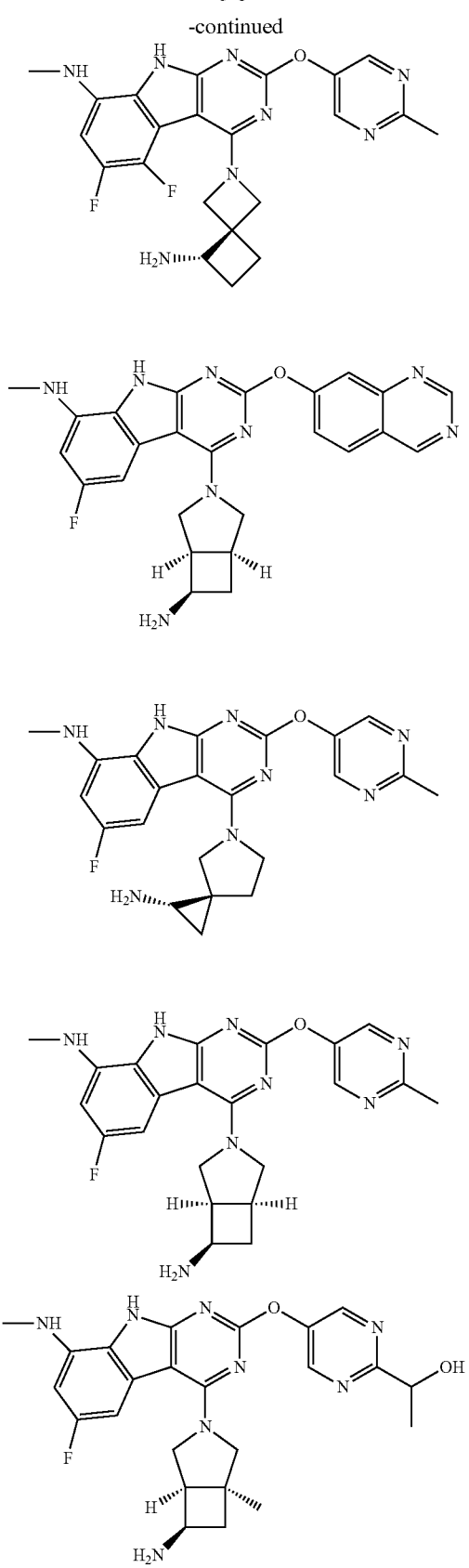
New species of compounds in Chart 8 below are not disclosed in PCT/US2012/029104.

CHART 8
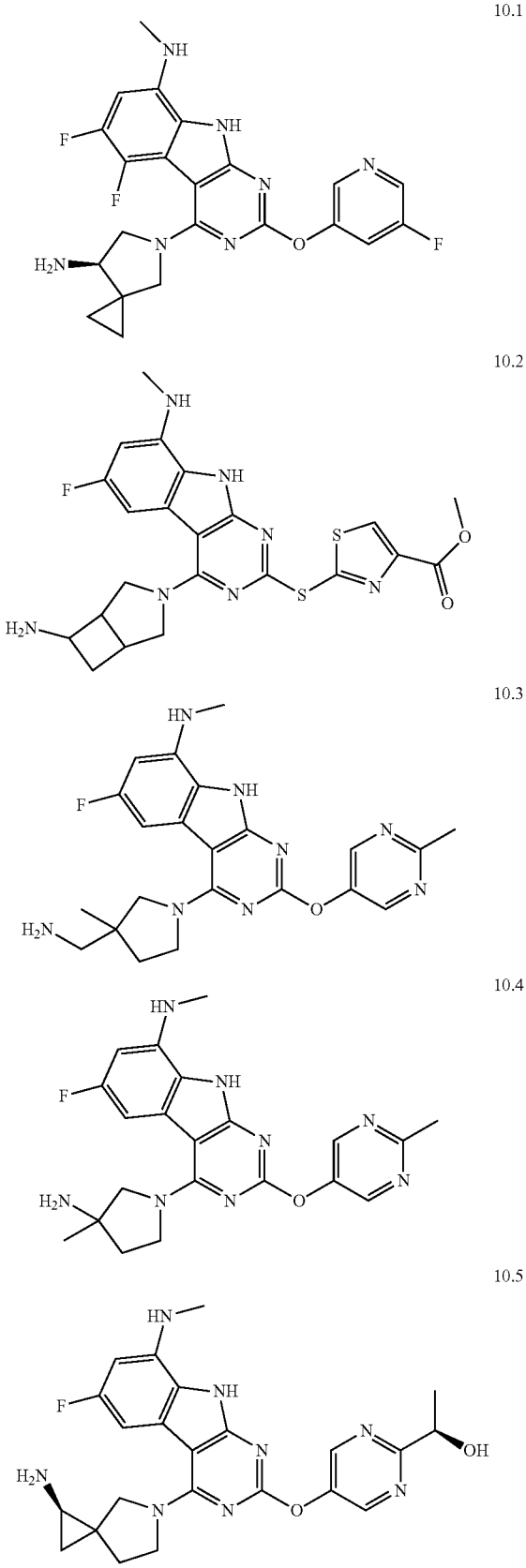
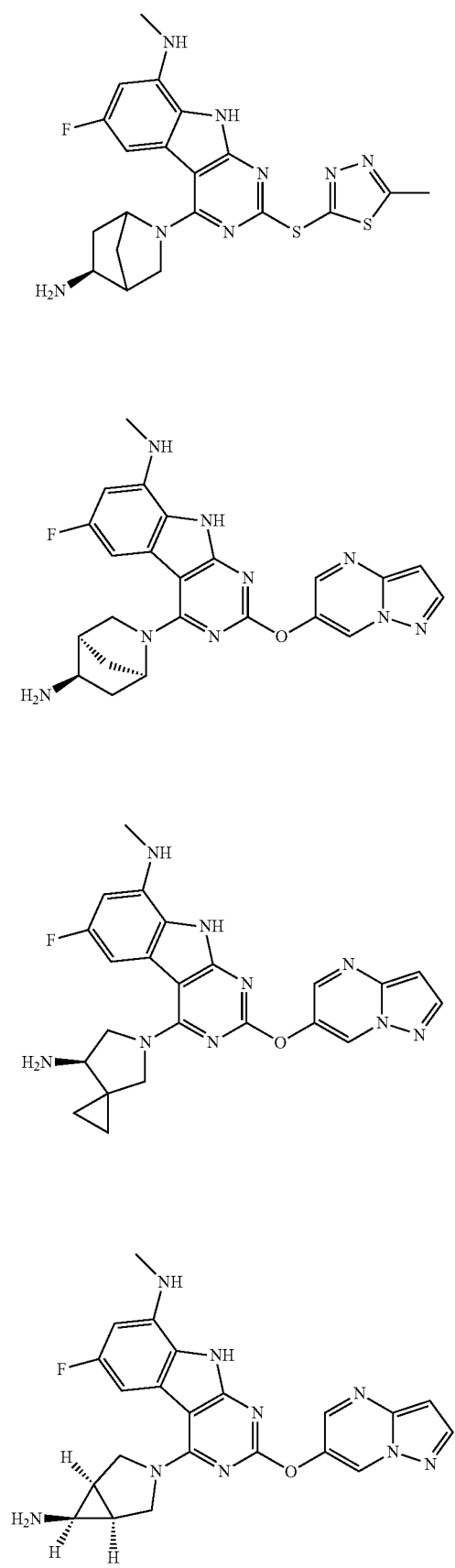

10.10
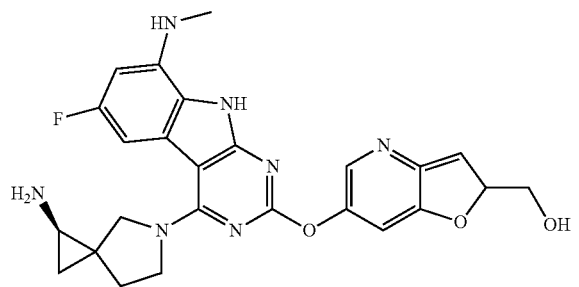
10.11
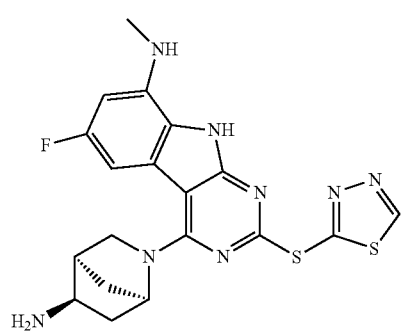
10.12
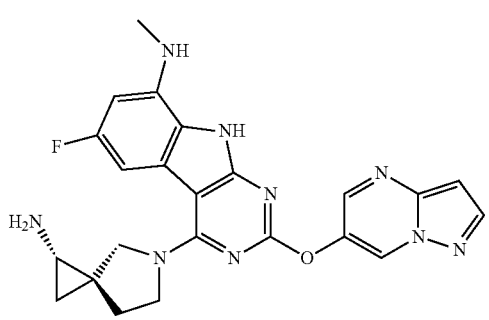
10.13
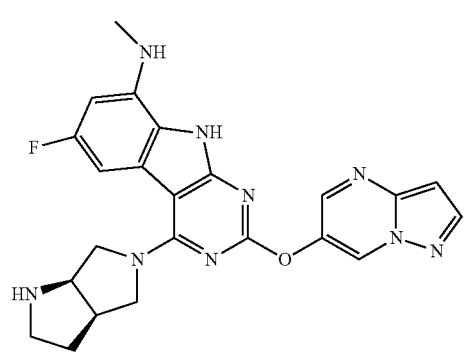
10.14
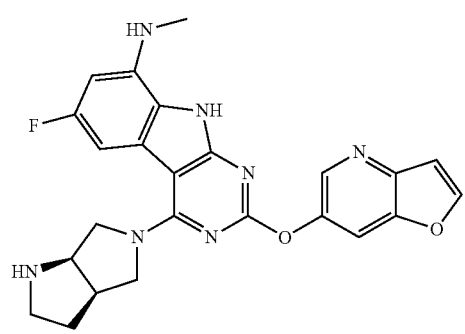
10.15
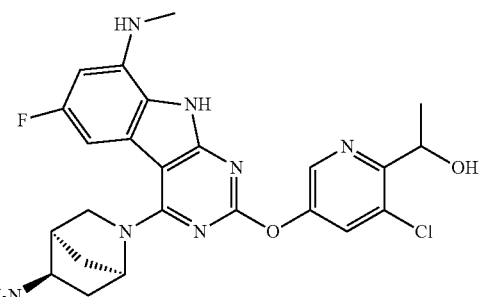
10.16
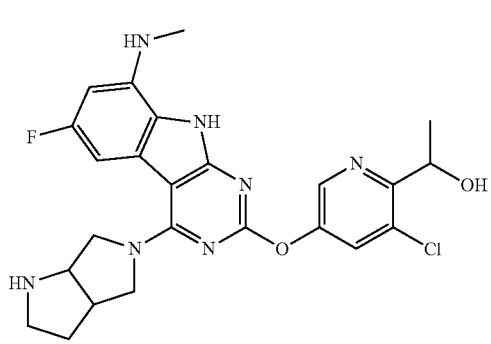
10.17
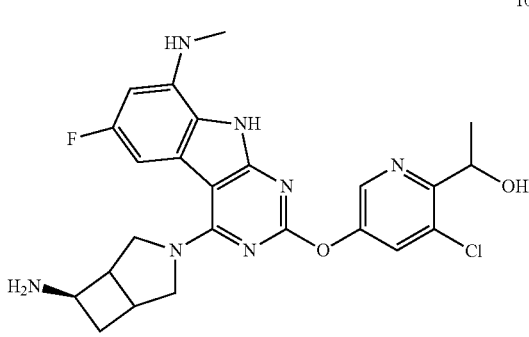
10.18
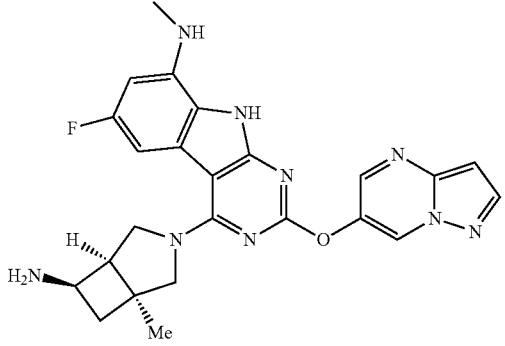
10.19
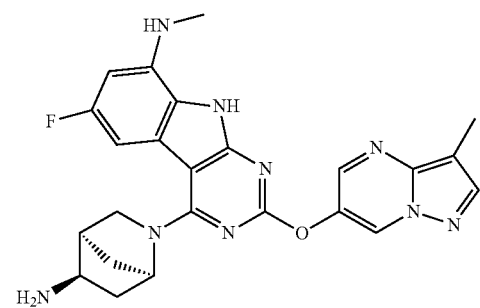

-continued
10.20
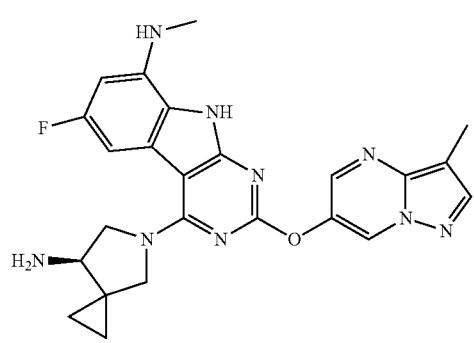
10.21
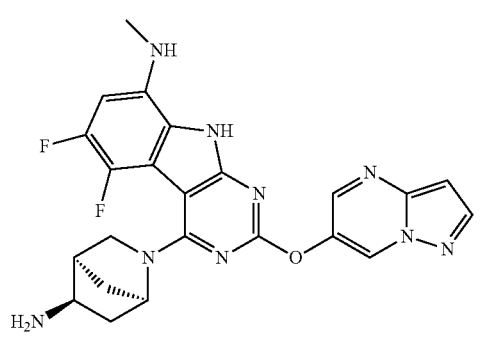
10.22
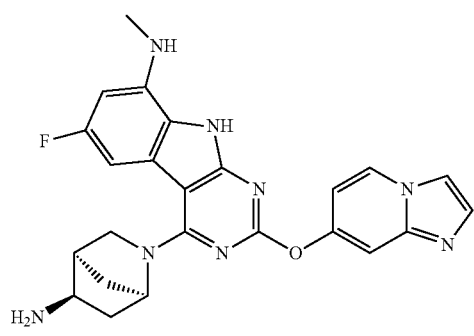
10.23
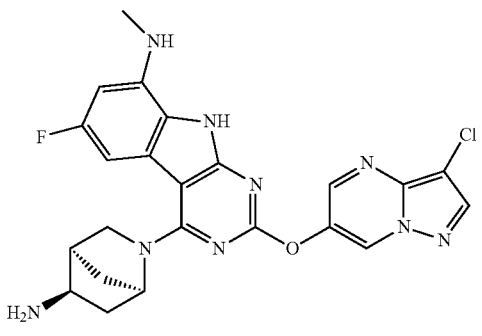
10.24
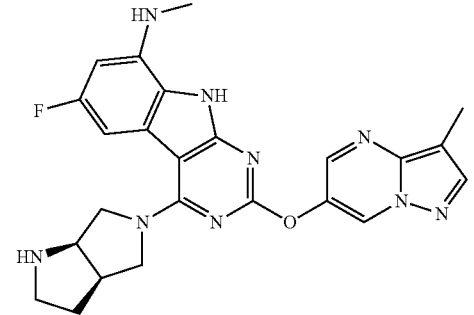
-continued
10.25
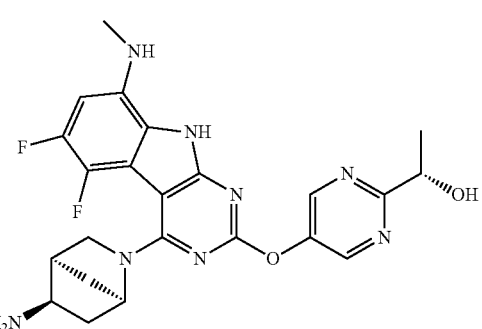
10.26
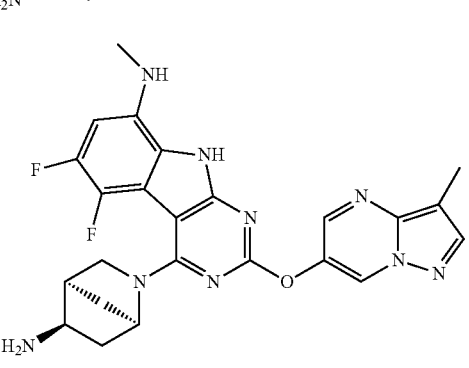
10.27
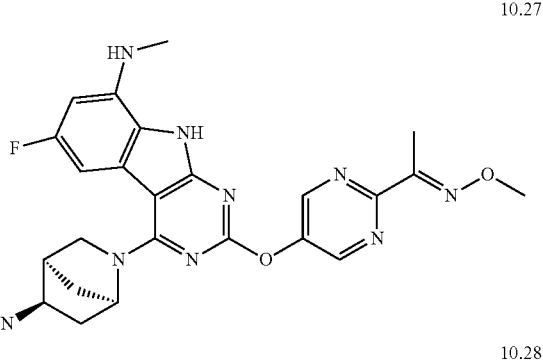
10.28
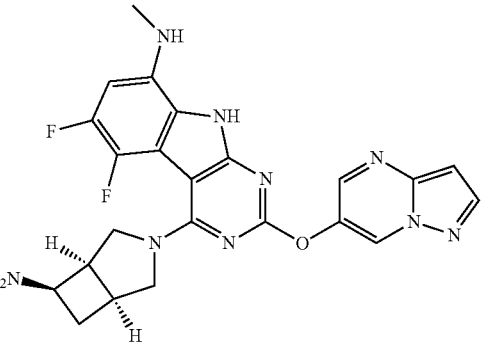
10.29
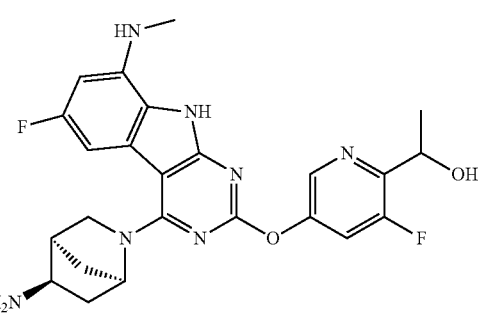

10.30
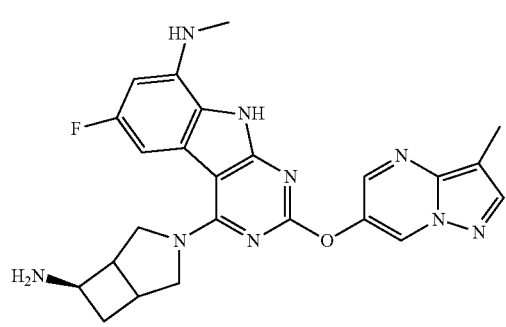
10.31
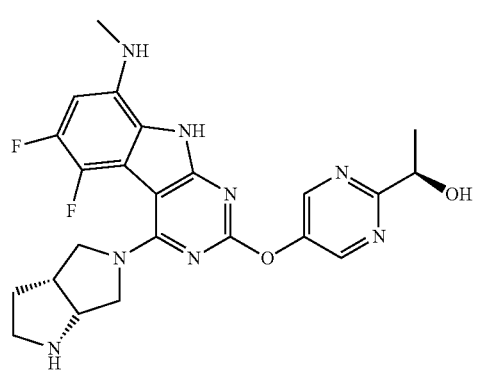
10.32
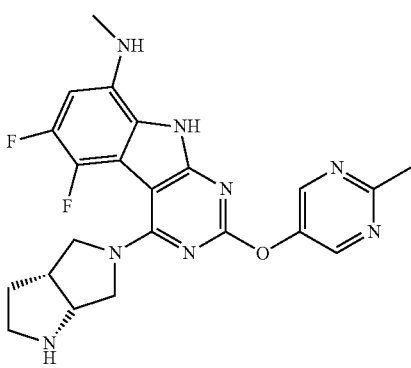
10.33
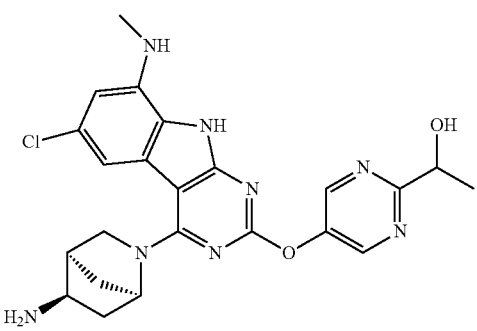
10.34
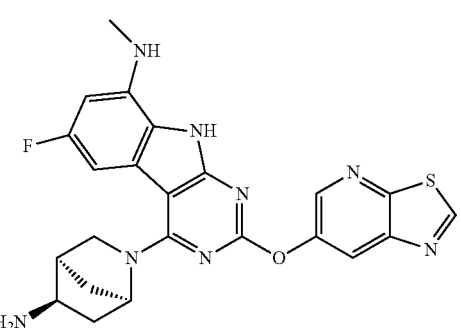
10.35
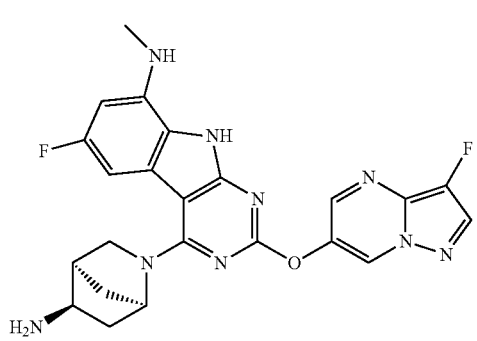
10.36
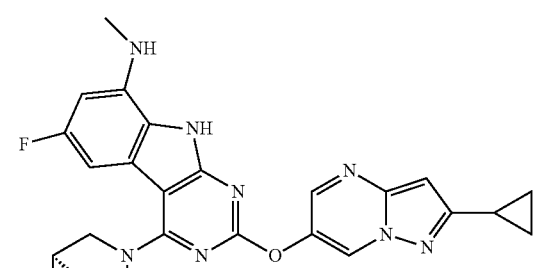
10.37
10.38
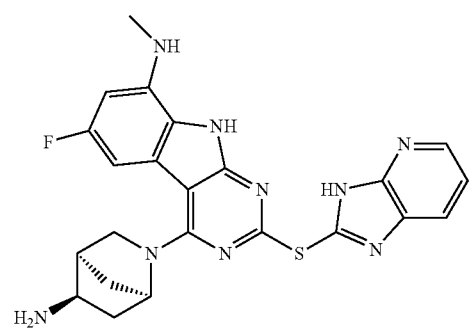

-continued
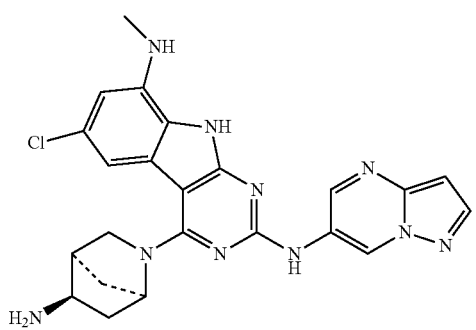
10.39
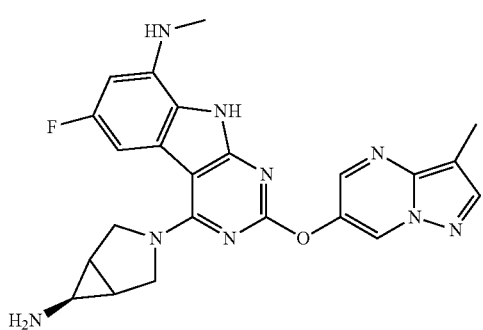
10.40
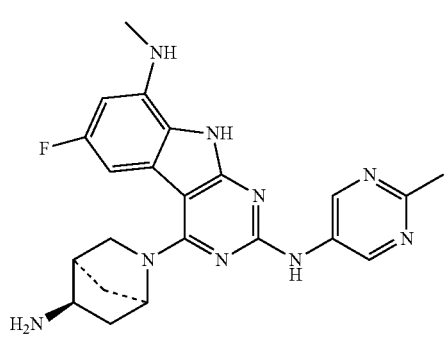
10.41
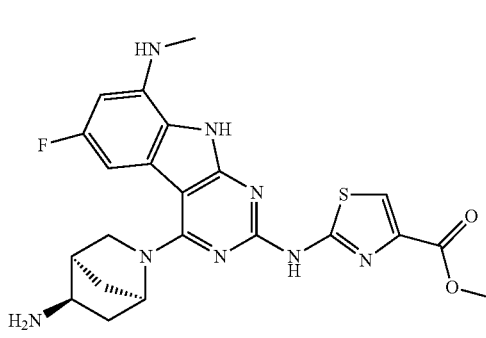
10.42
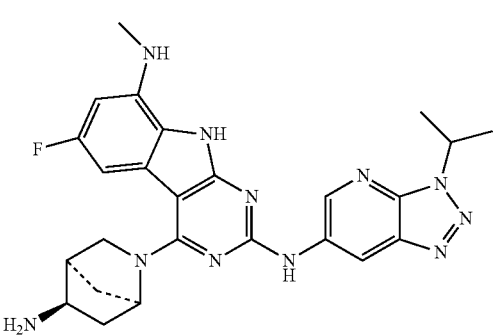
10.43
-continued
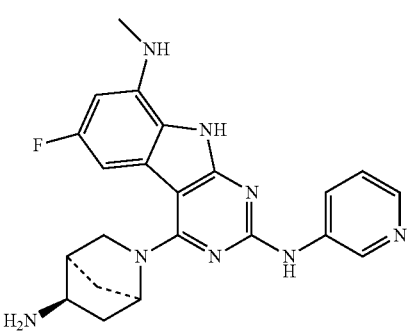
10.44
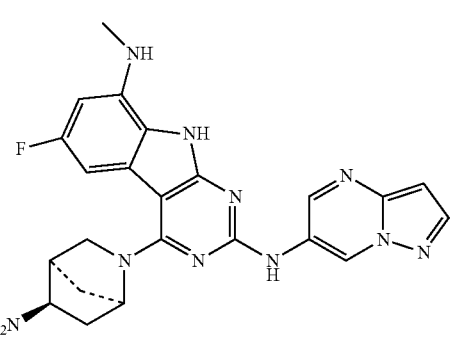
10.45
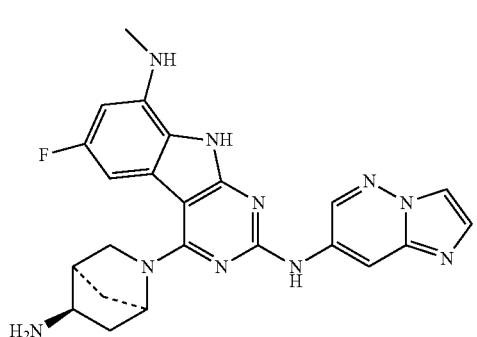
10.46
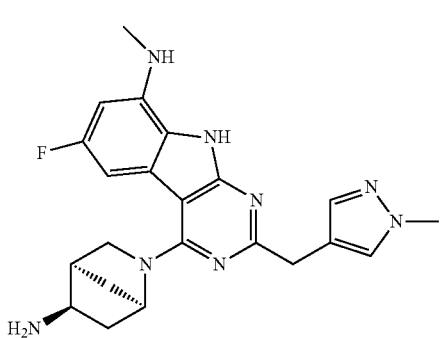
10.47
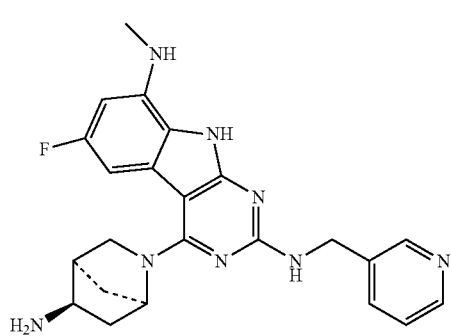
10.48

10.49
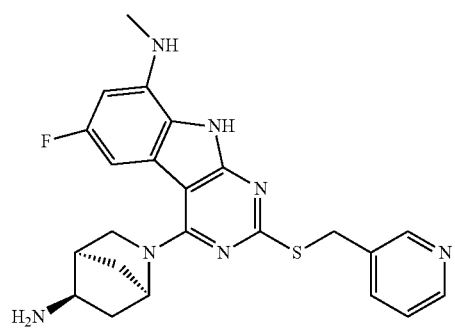
10.50
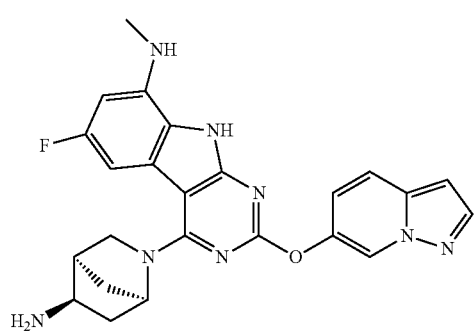
10.51
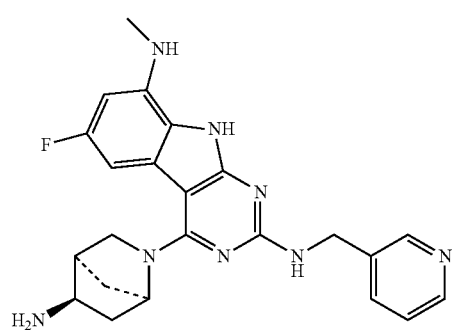
10.52
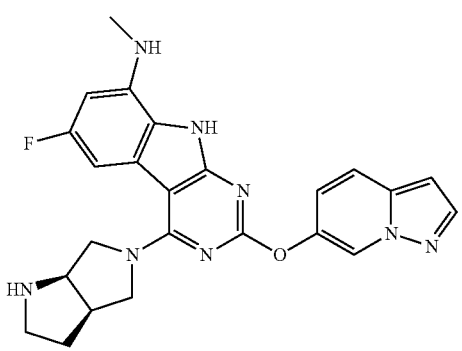
10.53
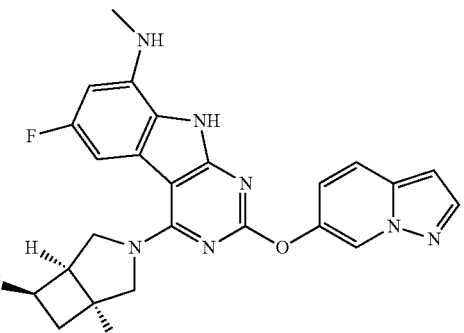
10.54
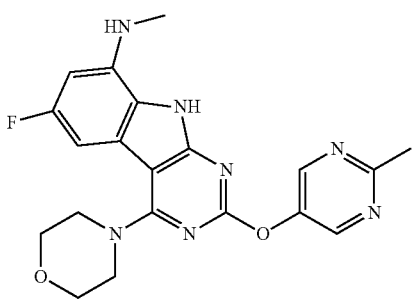
10.55
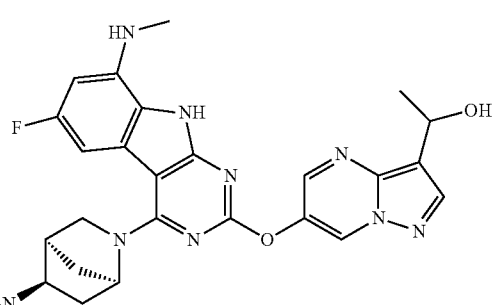
10.56
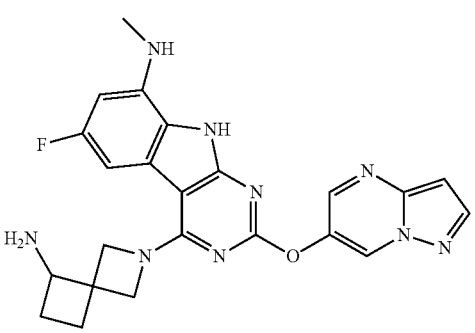
10.57
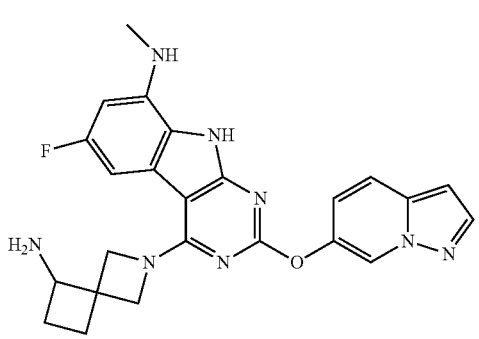

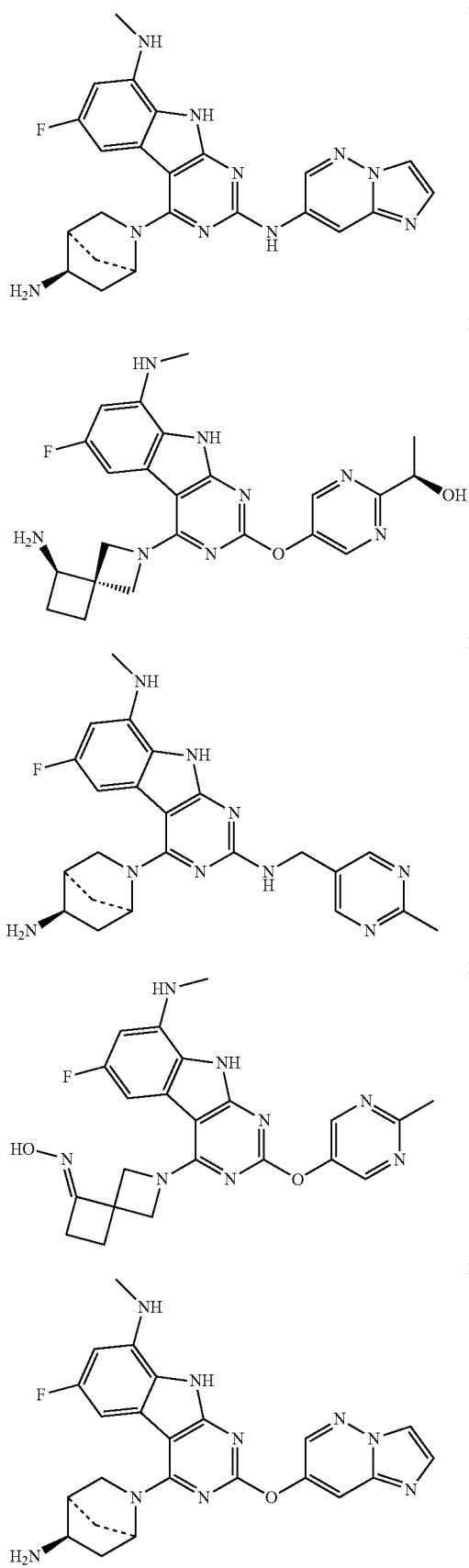
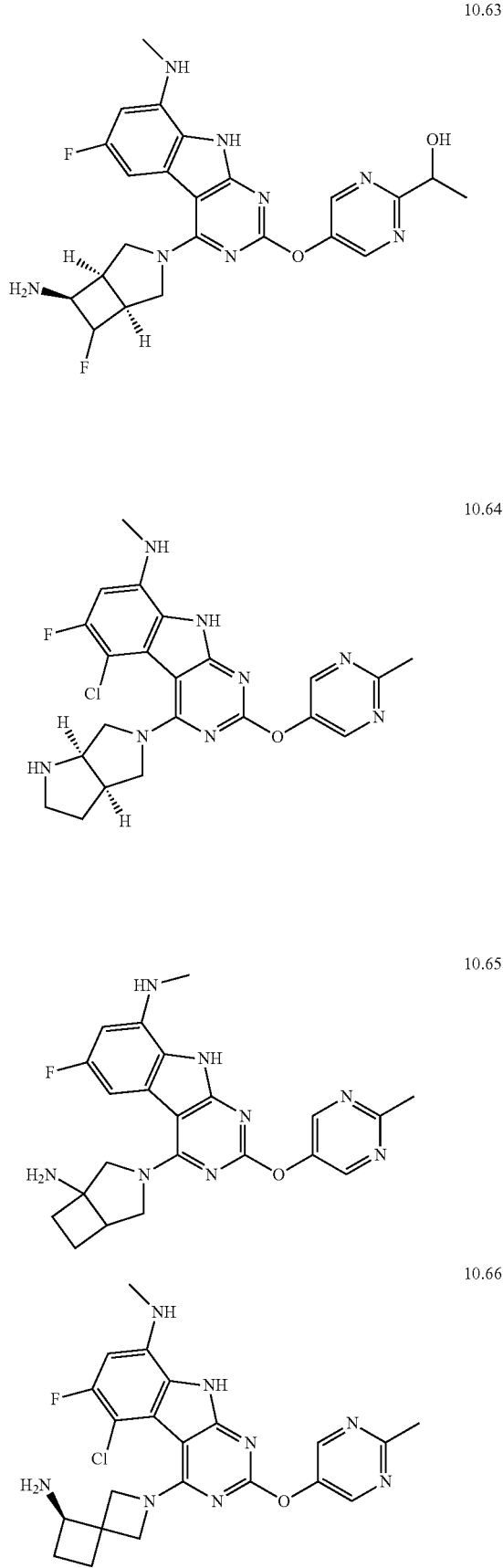

-continued
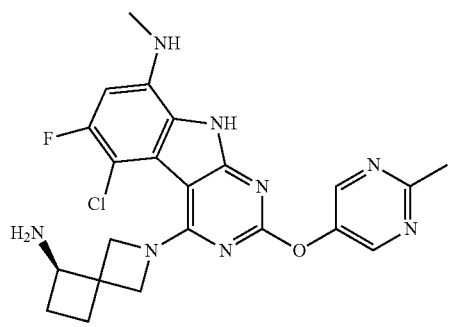
10.67
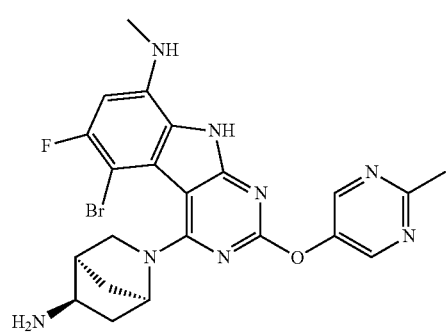
10.68
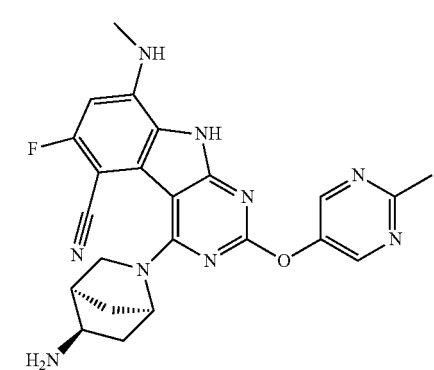
10.69
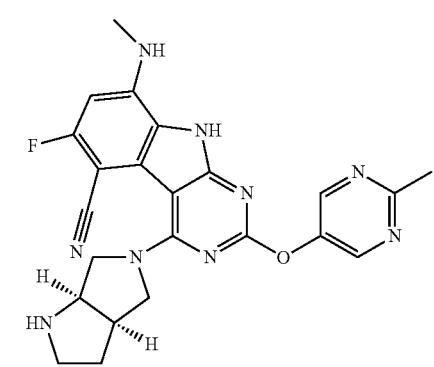
10.70
-continued
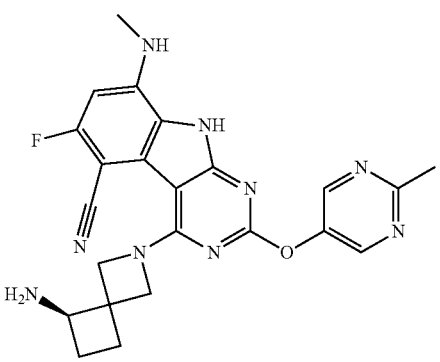
10.71
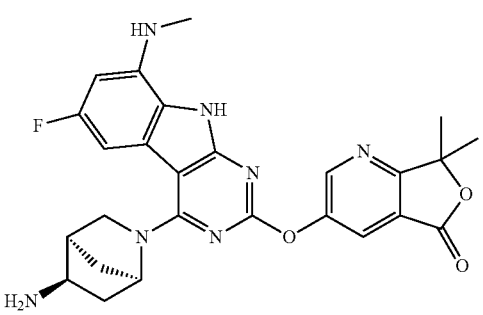
10.72
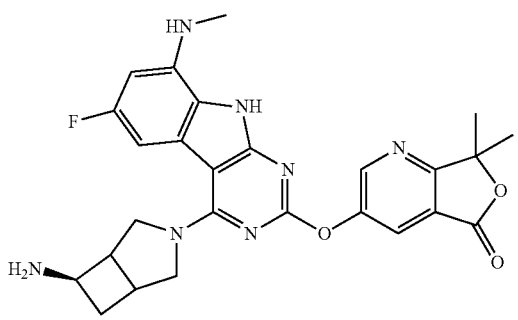
10.73
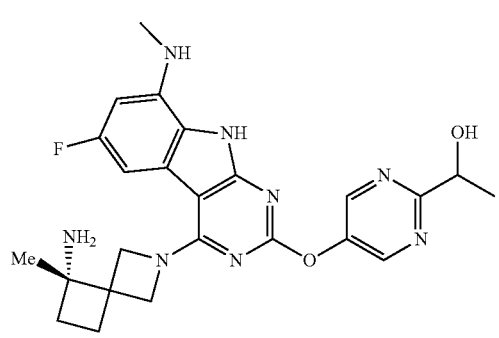
10.74

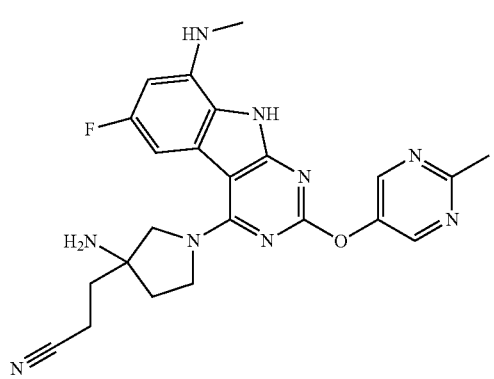
10.75
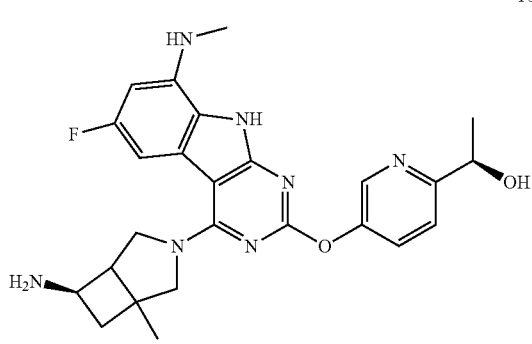
10.76
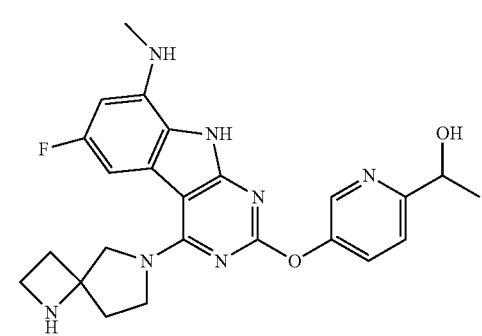
10.77
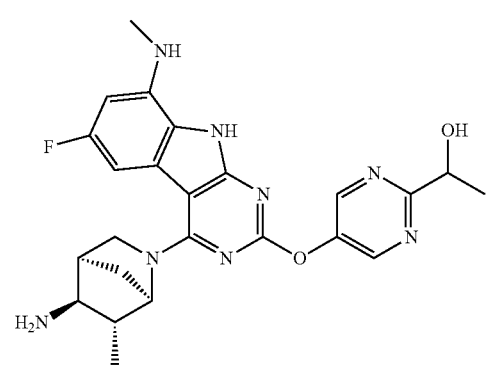
10.78
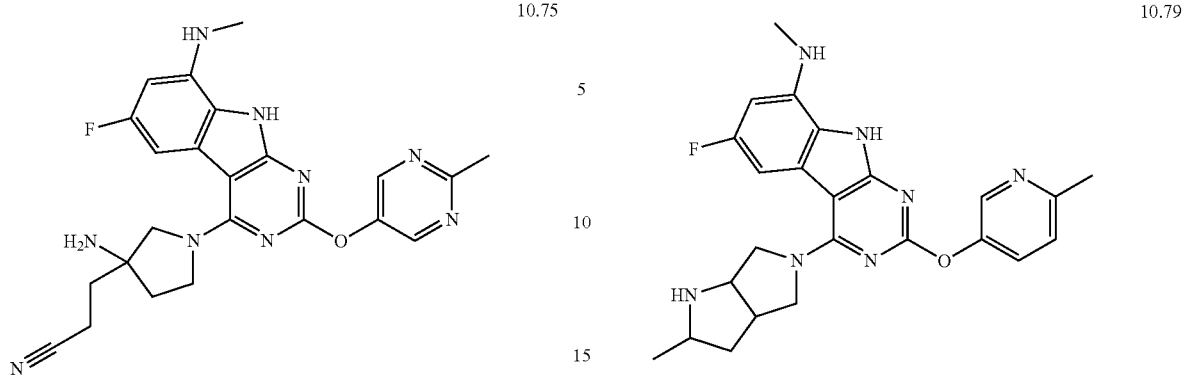
10.79
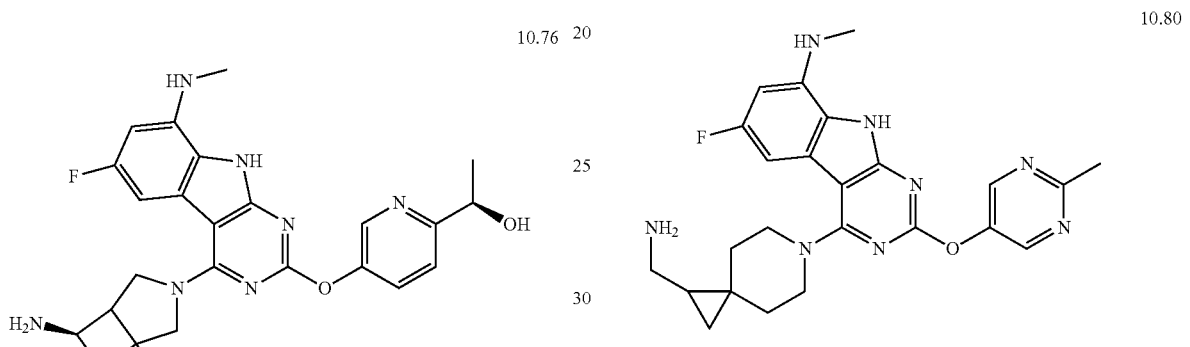
10.80
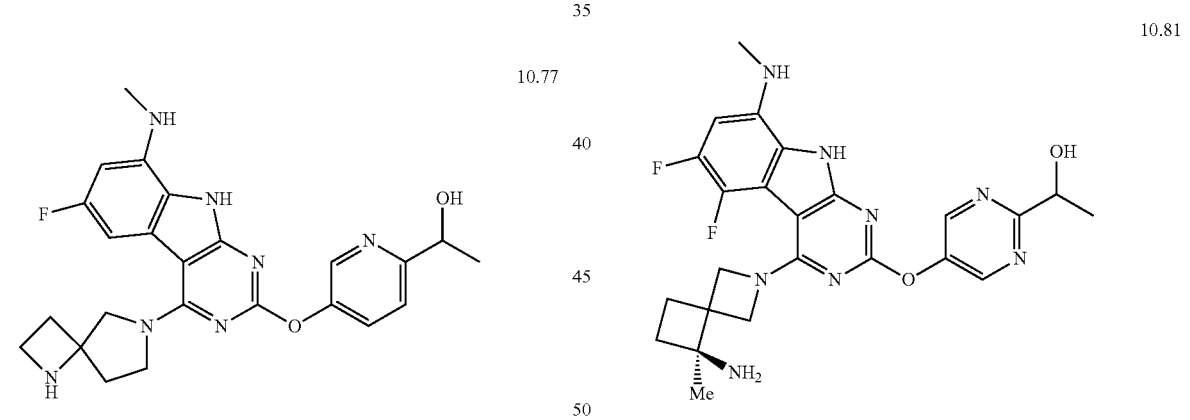
10.81
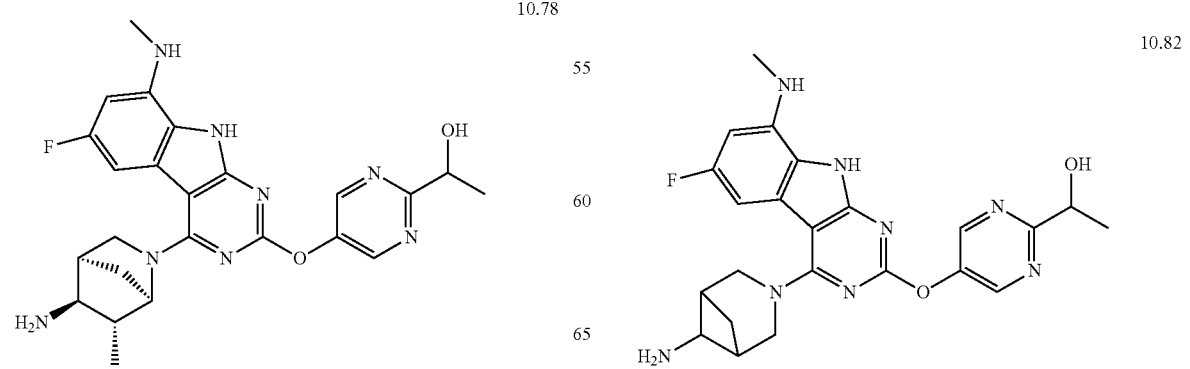
10.82

-continued
10.83
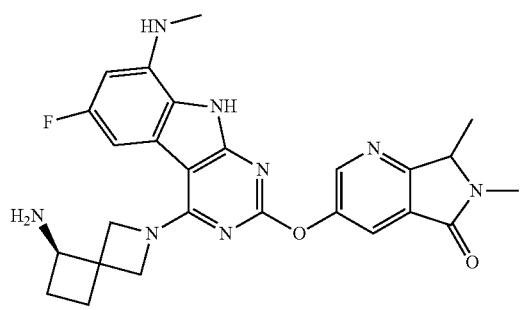
10.84
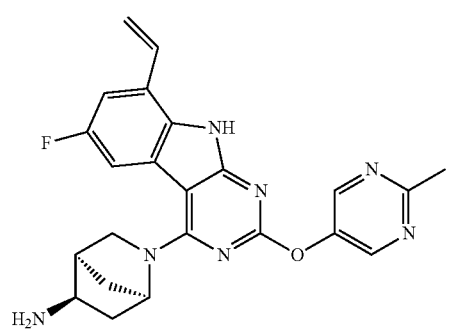
10.85
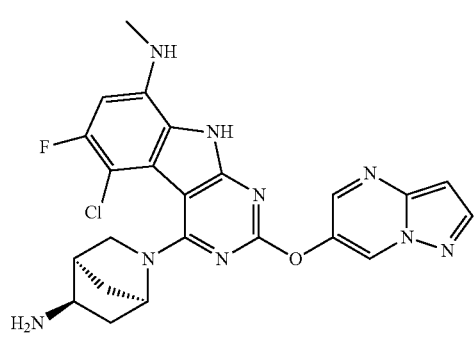
10.86
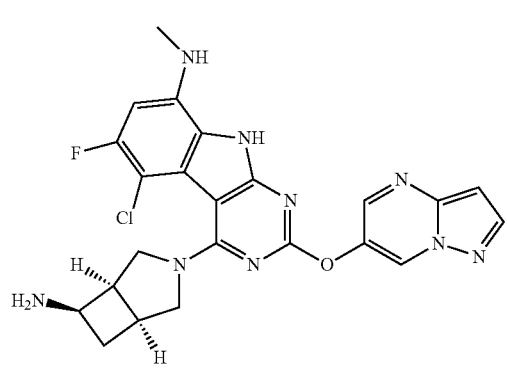
-continued
10.87
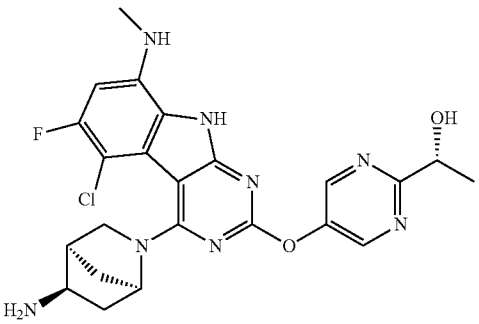
10.88
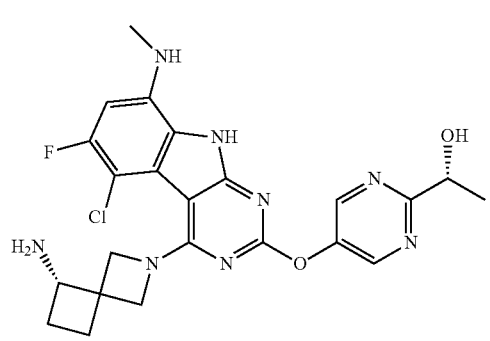
10.89
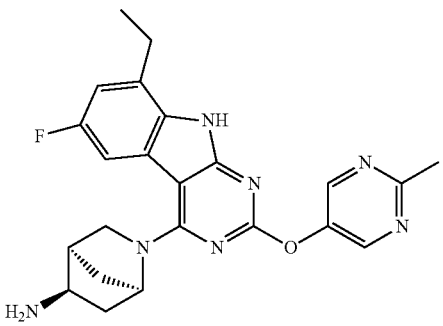
10.90
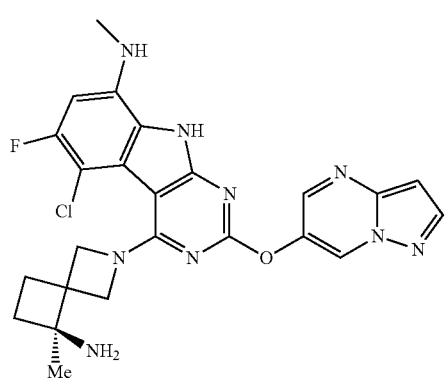

| | |
|---|---|
| 10.91 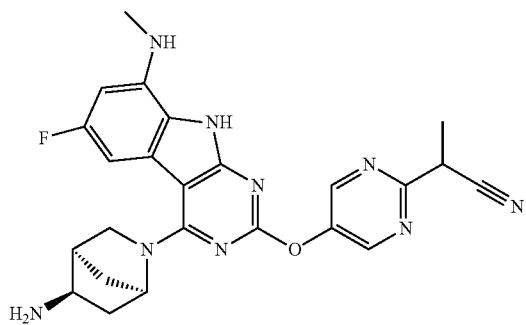 | 10.95 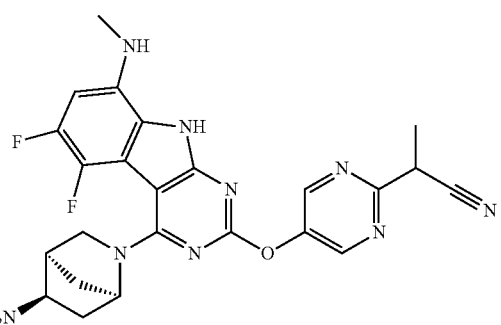 |
| 10.92 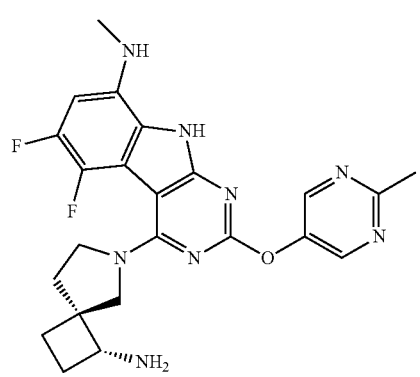 | 10.96 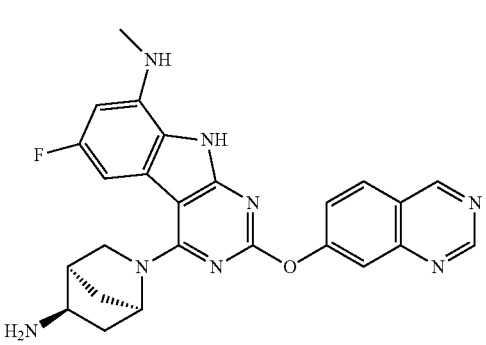 |
| 10.93 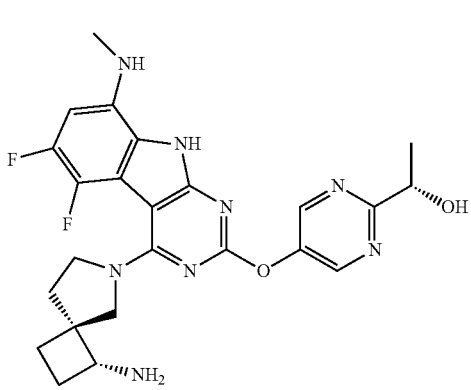 | 10.97 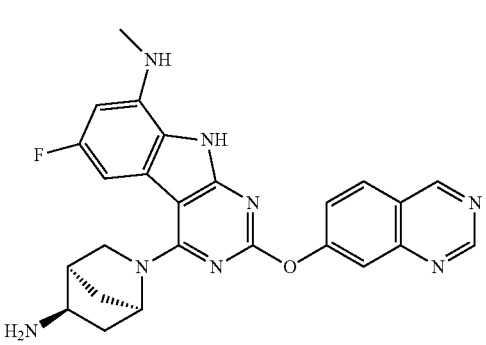 |
| 10.94 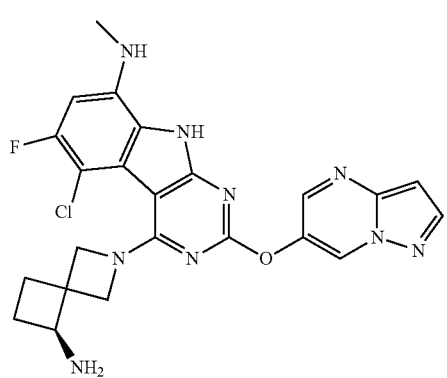 | 10.98 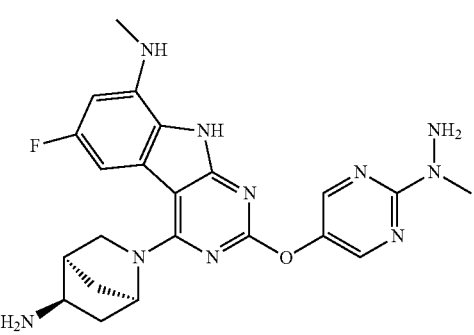 |

10.99
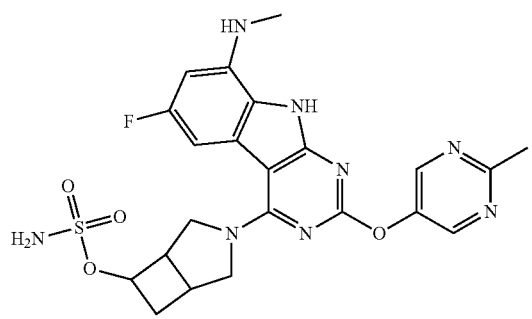
10.100
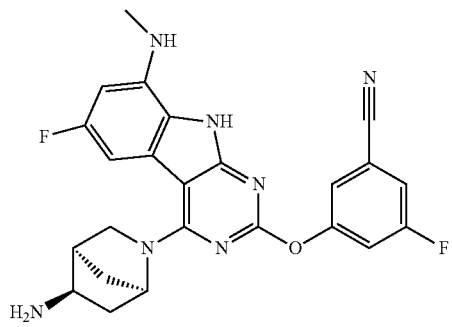
10.101
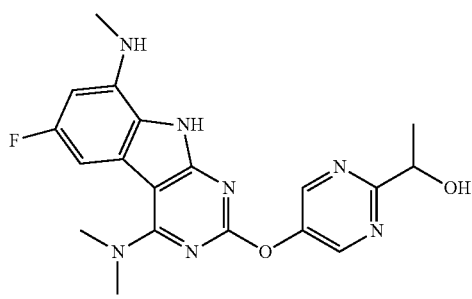
10.102
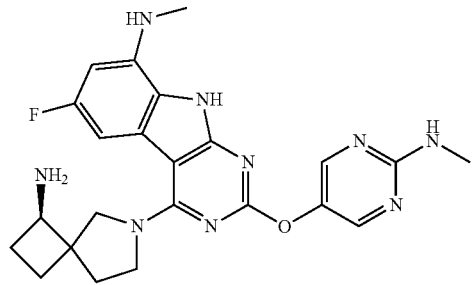
10.103
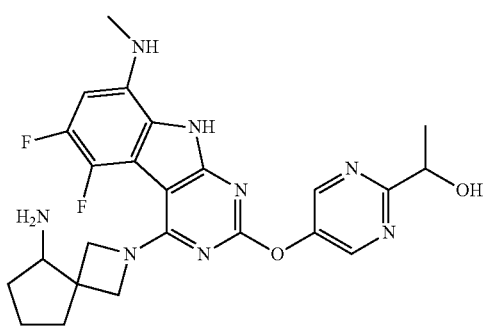
10.104
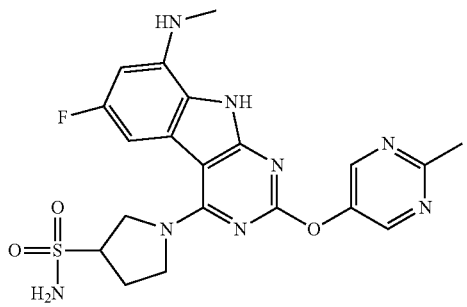
10.105
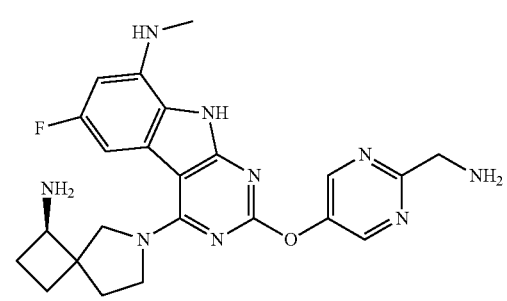
10.106
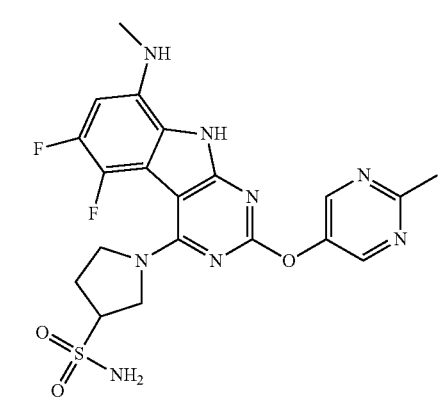
10.107
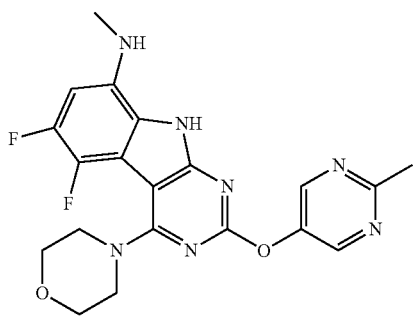

10.108
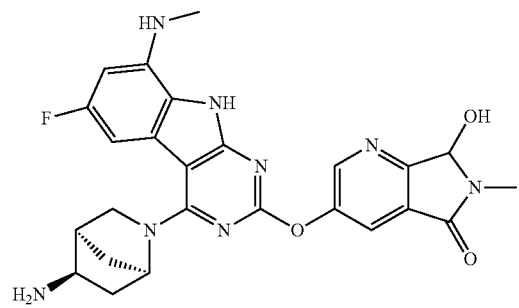
10.109
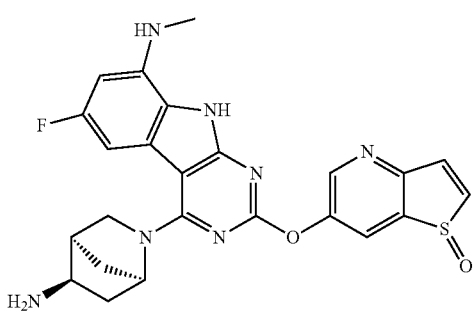
10.110
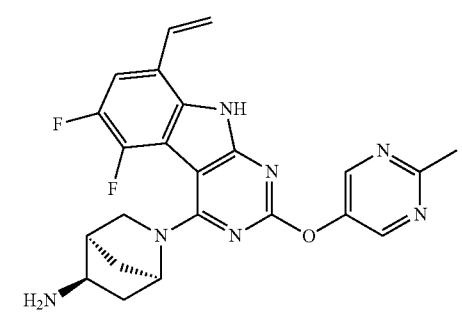
10.111
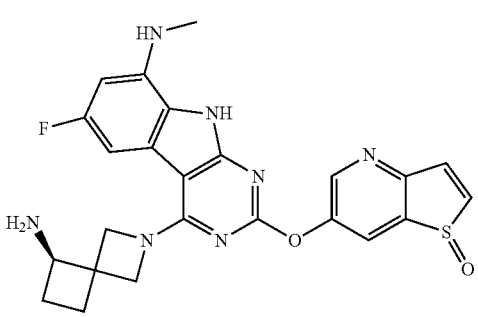
10.112
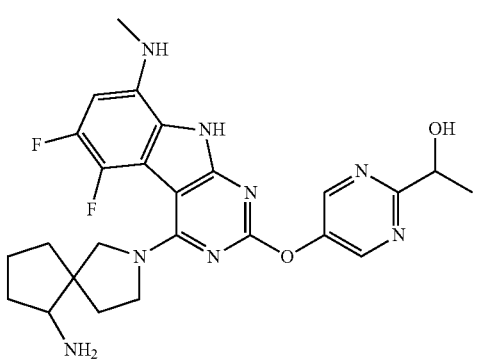
10.113
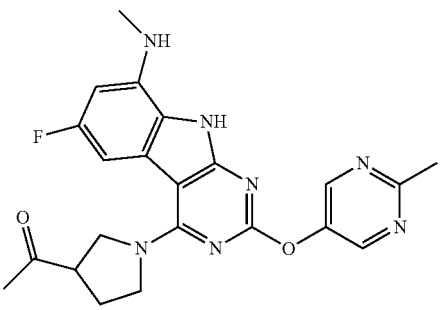
10.114
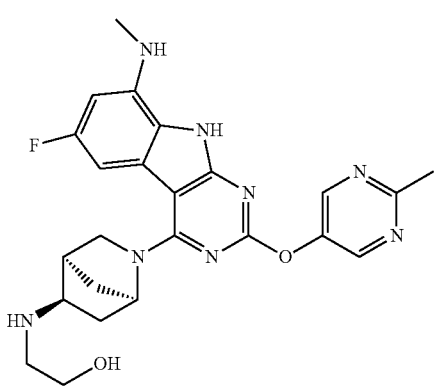
10.115
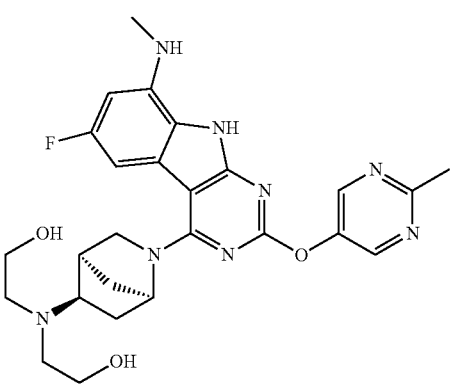
10.116
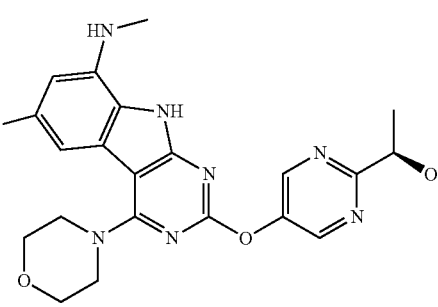
10.117
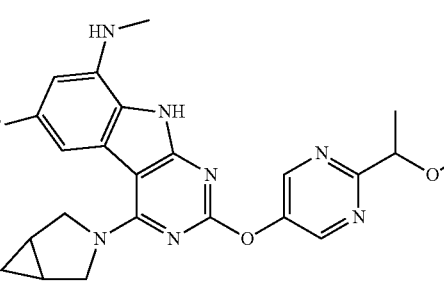

-continued

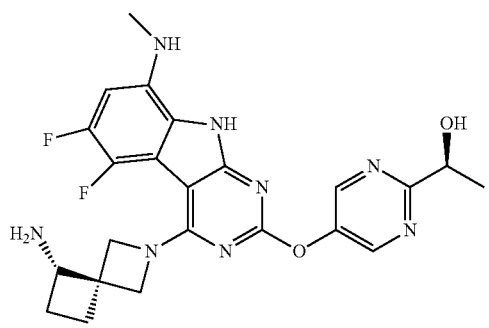

10.118

In some aspects, the compounds in Chart 8 have either unexpectedly higher activity than the most active species of compounds disclosed in PCT/US2012/029104, or were expected to have lower activity than compounds disclosed in PCT/US2012/029104 but had unexpectedly higher activity. In some aspects, the hERG IC50 values of compounds in Chart 8, or other compounds herein, are unexpectedly higher than the most active species of compounds disclosed in PCT/US2012/029104.

When the compounds herein, such as compounds having Formula I, contain one or more chiral centers, optically pure forms as well as mixtures of stereoisomers or enantiomers are also contemplated.

$R^2$ may join with $R^4$ to form a fused ring with the ABC ring. Although not being bound by theory, the potency and/or selectivity may be increased because the conformational entropy is reduced when $R^2$ joins with $R^4$ to form a fused ring. The oversimplified structure below, which does not show the details of L, $R^2$ and $R^4$, illustrates $R^2$ joined with $R^4$ forming a ring that is fused with the ABC ring:

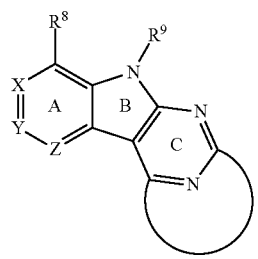

When part of the fused ring, $R^2$ may be a ring as recited herein. Although not being bound by theory, it is useful when the attachment point of $R^2$ to $R^4$ avoids steric hindrance and avoids interference with the compound's binding to the enzyme's active site. In one aspect, L may have a single member in its backbone such as O, S, NH, $CH_2$, CHF, or $CF_2$. In this case, if a 6-membered ring of $R^2$ is attached to L and $R^4$, $R^4$ may be attached through the meta or para position of the 6-membered ring with respect to the point of attachment to L. If a 5-membered ring of $R^2$ is attached to L and $R^4$, $R^4$ may be attached through any position on $R^2$'s 5-membered ring except the position where L attaches to $R^2$. Of course, for 5-membered rings, it is possible to have the attachment point at the atom that is two atoms removed from the atom that attaches to L. The attachment point to $R^2$'s 6-membered or 5-membered ring may be a carbon or an appropriate heteroatom such as nitrogen in the ring.

For example, if $R^2$ is a 6-membered ring as described herein, e.g., a 6-membered aryl, heteroaryl, non-aryl or non-heteroaryl ring, $R^2$ may be attached to $R^4$ through the meta or para position of $R^2$'s 6-membered ring with respect to the point of attachment to L.

As an illustration, an example of compounds where $R^2$ may join with $R^4$ to form a fused ring at the meta position include the first compound below. Examples of compounds where $R^2$ may join with $R^4$ to form a fused ring at the para position include the last three compounds below.

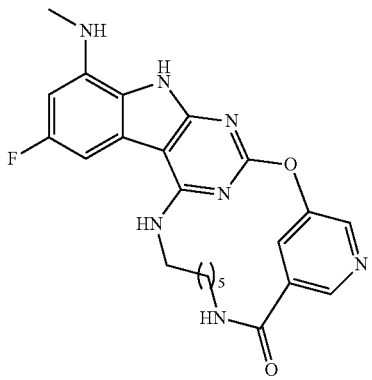

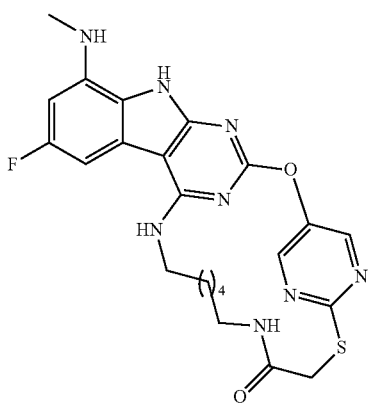

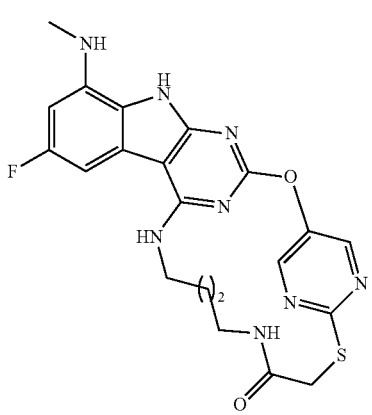

-continued

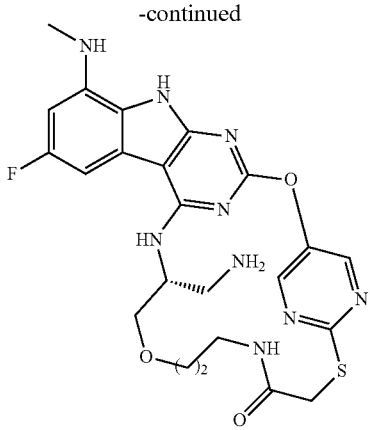

If L has a single member in its backbone and if $R^2$ is a 5-membered ring as described herein, e.g., a 5-membered aryl, heteroaryl, non-aryl or non-heteroaryl ring, the first position is the ring member attached to L. The second position is the ring member at the position in the five membered ring adjacent to the first position. The third position is the ring member at the position in the five membered ring adjacent to the second position. In some aspects, when L contains a single member in its backbone, $R^2$ may be attached to $R^4$ through the third position in the five membered ring to avoid any stearic hindrance or interfere with enzyme binding.

However, $R^2$ may contain more than one ring. If $R^2$ is a multi-ring substituent, the attachment point to $R^4$ may be sufficiently distal to avoid steric hindrance and other interference with enzyme binding, if the attachment point in not in a ring that is adjacent L. In addition, in some aspects when L has more than one member in its backbone such as $SCH_2$, $OCH_2$, $NHCH_2$, $CH=CH$, $CH_2CH_2$, $SCH_2CONH$, $OCH_2CONH$, $NHCH_2CONH$, $OCH_2CH=CH$, or $SCH_2CH=CH$, the attachment point of $R^2$ to $R^4$ may be sufficiently distal to avoid steric hindrance and other interference with enzyme binding.

$R^4$ in this case may be a 5- to 15-membered, such as a 9- to 12-membered hydrocarbyl residue linker and may contain 0-6 O, S or N atoms in the backbone of the hydrocarbyl residue linker that attaches to the $R^2$ group wherein atoms in the 5-15 member hydrocarbyl residue linker are optionally substituted with noninterfering substituents. In some aspects, the hydrocarbyl residue linker may be saturated, partially unsaturated, or unsaturated.

Optional substituents include any noninterfering substituents recited herein including hydrocarbyl residues optionally containing heteroatoms in the backbone which, in turn, may be optionally substituted with noninterfering substituents. Hydrocarbyl residues may be C1-C10 hydrocarbyl residues for example C1-C10 alkyl, for example C3-C6 Cycloalkyl and C1-C6 alkyl. Adjacent optional substituents may form a fused ring. Examples of optional substituents may be one or more of halogen, for example Cl or F, amide, OH, =O, amino, amino C1-C6 cycloalkyl and amino C1-C6 alkyl. In some aspects, an amide may be formed, for example, when C=O is adjacent to a nitrogen in the backbone of the hydrocarbyl residue linker.

When in the bound conformation, the $R^4$ linker will be open to the solvent space above the plane of the A, B and C Rings so little interference is expected with the GyrB/ParE binding pocket floor, regardless of the size of the optionally substituted linker. In addition, at a distance of about 5 Å from the C to which the $R^4$ linker is attached, a portion of the GyrB/ParE binding pocket floor is open to solvent space, allowing the linker freedom of movement both above and below the plane of the A, B, and C Rings. Of course, practical considerations in drug design may limit the size of the linker, such as size of the resulting pharmaceutical, which may increase costs.

Various processes of making the compounds are also contemplated. Processes for species of compounds covered by a genus of compounds in PCT/US2012/029104, may be made by processes disclosed therein. The substituents unless noted are the same substituents as in Formula I. In some aspects wherein $R^4$ is an optionally substituted secondary or tertiary amine attached to the C Ring through the secondary or tertiary amine N, the process comprises treating

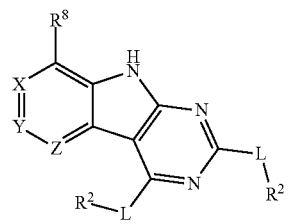

with $HR^4$ to make the compound of Formula I; and optionally further comprising, before the treating step, protecting $R^8$ with a protecting group, or protecting an amine in $R^4$ which is not the secondary or tertiary amine N, if present, with a protecting group; and optionally removing the protecting groups after the treating step.

Protecting groups are useful for chemoselectivity and are known in the art. Typical protecting groups included tert-butyloxycarbonyl (BOC) and carbobenzyloxy (Cbz). When the protecting group is BOC, an acid may be used for deprotection, protecting group is Cbz, catalytic hydrogenation may be used for deprotection.

Before the treating step immediately above, the process may further comprise reacting the compound of Formula XX Formula XX

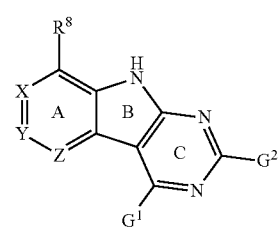

with $R^2LH$ under basic conditions, wherein $G^1$ and $G^2$ are leaving groups independently selected from the group consisting of Cl, Br, F, I, SR, SOR, $SO_2R$, $OSO_2R$, and 0-benzotriazole (OBt); wherein R may be C1-8 alkyl, aryl, or heteroaryl containing 0-5, O, S, or N atoms optionally substituted with C1-4 alkyl, C1-4 alkyloxy, Cl, Br, F, I, or $NO_2$, such as methyl, benzyl and p-methoxybenzyl, to make the compound having the structure

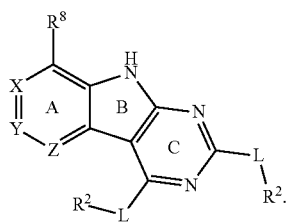

In some aspects, the compounds wherein $R^4$ is an optionally substituted secondary or tertiary amine attached to the C Ring through the secondary or tertiary amine N, may also be made using a process comprising treating

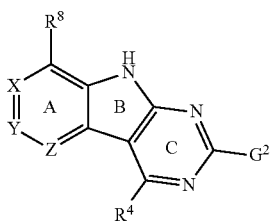

with $R^2LH$ under basic conditions such as with the anion of phenol, thiophenol, heteroaryl hydroxy or heteroarylthiol, wherein $G^2$ is a leaving group selected from the group consisting of Cl, Br, F, and I; and optionally further comprising, before the treating step immediately above, protecting $R^8$ with a protecting group, or protecting an amine in $R^4$ which is not the secondary or tertiary amine N, if present, with a protecting group; and deprotecting $R^8$ and $R^4$ after the treating step.

Before the treating step immediately above, the process may further comprise reacting the compound of Formula XX Formula XX

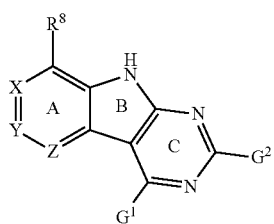

with $HR^4$ to make

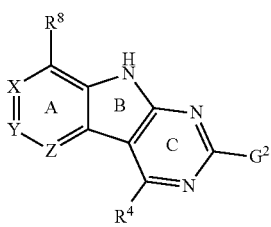

wherein $G^1$ is a leaving group selected from the group consisting of Cl, Br, F, and I.

In some aspects, when L is S, a process of making the compound wherein $R^4$ is an optionally substituted secondary or tertiary amine attached to the C Ring through the secondary or tertiary amine N, may comprise treating

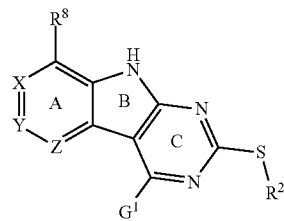

wherein $G^1$ is a leaving group derived from $SO_2$halide, bis(2-oxo-3-oxazolidinyl)phosphine (BOP), or benzotriazol-1-yl-oxytripyrrolidinophosphonium hexafluorophosphate (pyBOP), with $HR^4$ to make the compounds herein. This process may also optionally further comprise, before the treating step immediately above, protecting $R^8$ with a protecting group, or protecting an amine in $R^4$ which is not the secondary or tertiary amine N, if present, with a protecting group; and deprotecting $R^8$ and $R^4$ after the treating step.

Before the treating step immediately above, the process may further comprise reacting

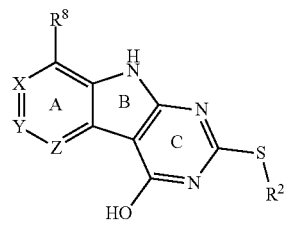

with $G^1X^1$ to provide

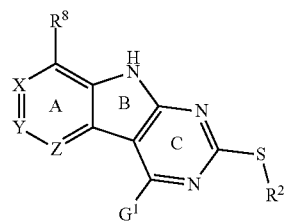

wherein $G^1X^1$ is $SO_2$halide, bis(2-oxo-3-oxazolidinyl)phosphine (BOP), or benzotriazol-1-yl-oxytripyrrolidinophosphonium hexafluorophosphate (pyBOP).

Before the treating step immediately above, the process may further comprise coupling

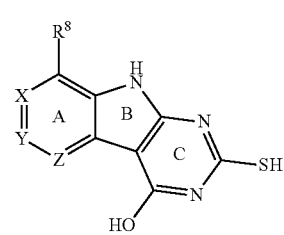

with $R^2X^2$ wherein $X^2$ is Br or I to form

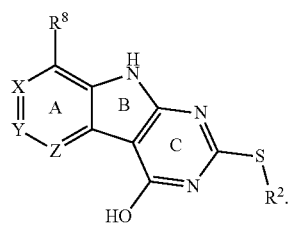

In another aspect, an intermediate compound has the structure of Formula XX:

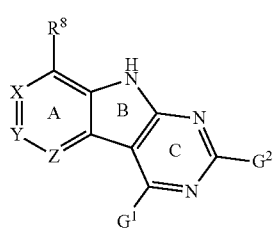

Formula XX or an amine-protected intermediate thereof, wherein: $G^1$ and $G^2$ are leaving groups independently selected from the group consisting of SH, OH, Cl, Br, F, I, SR, SOR, $SO_2R$, $OSO_2R$, OAr, and OBt; R is C1-8 alkyl, aryl, or heteroaryl; Ar is aryl or heteroaryl containing 0-5 O, S, or N atoms optionally substituted with C1-4 alkyl, C1-4 alkoxy, halo or $NO_2$; Bt is benzotriazole; $R^8$ is an interacting substituent having a length of about 1 Å to about 5 Å from the carbon attachment point on the A Ring to the terminal atom in $R^8$ and a width of about 3.3 Å or less; and X, Y and Z are independently selected from the group consisting of N, $CR^X$, $CR^Y$, and $CR^Z$ respectively, provided that no more than two of X, Y and Z are N, wherein $R^X$ is H or an interacting substituent having a length of about 1 Å to about 2 Å from the carbon in $CR^X$ to the terminal atom in $R^X$; wherein $R^Y$ is H or an interacting substituent having a length of about 1 Å to about 3 Å from the carbon in $CR^Y$ to the terminal atom in $R^Y$; wherein $R^Z$ is H or an interacting substituent having a length of about 1 Å to about 2 Å from the carbon in $CR^Z$ to the terminal atom in $R^Z$; with a proviso wherein $R^8$ is not $CH_3$, and with a proviso when $R^8$ is $OCH_3$, then $R^X$ and $R^Y$ are not OH.

When the intermediate compound is an amine-protected intermediate, one or more nitrogens in the compound may be protected with carbobenzyloxy (Cbz) or BOC. $G^1$ and $G^2$ may be leaving groups independently selected from the group consisting tosylate, mesylate, triflate, O-pyrimidine, O-phenyl and O-pyridine.

The following schemes outline aspects of reaction steps to make the starting materials, intermediates and compounds herein, which are detailed in the Examples.

The starting materials for the $R^2$ and $R^4$ substituents are available commercially or can be made by a skilled artisan using methods reported in the literature.

1. General Procedures for the Preparation of the Tricyclic Pymirido[4,5-b]indole Core A wide variety of amines and substituted amines can be introduced into the A Ring of the pyrimidoindole system as shown in Scheme 1. Ortho-fluoro-nitrobenzenes S1 can be readily displaced by amines to yield the orthoamino analogs S2. A protecting group can be introduced by incorporation in the starting material (as in S3b) or introduced after the fluoroaryl displacement reaction (as in S 3c). With an alkyl or alkoxy $R^8$ group, nitration may be used to introduce the nitro group ortho to the $R^8$ group S3d. When the nitration reaction provides mixtures of regioisomers, chromatography may be used to isolate the desired isomer.

Scheme 1: General procedure for preparing substituted phenyl starting materials

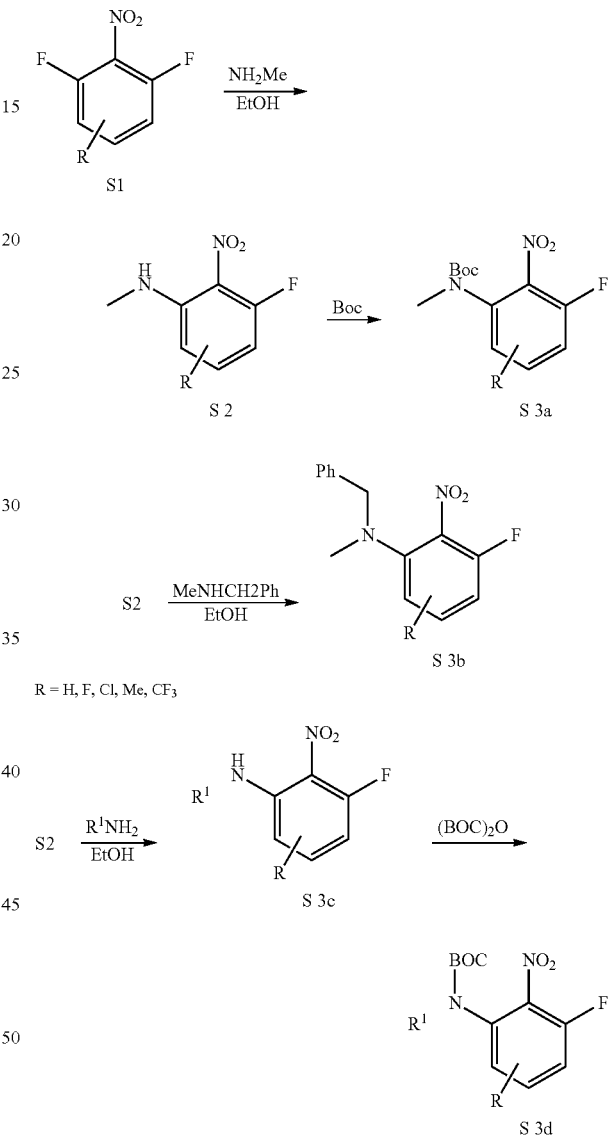

Scheme 2 outlines the general methods for preparing a wide variety of pyridine and pyrimidine starting materials. Nitration of 4,6-dihydroxypyrimidine followed by conversion of the hydroxyl groups to a chloro group with $POCl_3$ affords intermediate S4c. The chloro is readily displaced by amines and alcohols to provide the desired intermediate S3e. In a similar fashion, commercially available pyridine S4d is readily substituted with amines and alcohols to form intermediate S3f.

Scheme 2: General procedure for preparing substituted pyrimidine and pyridine starting materials

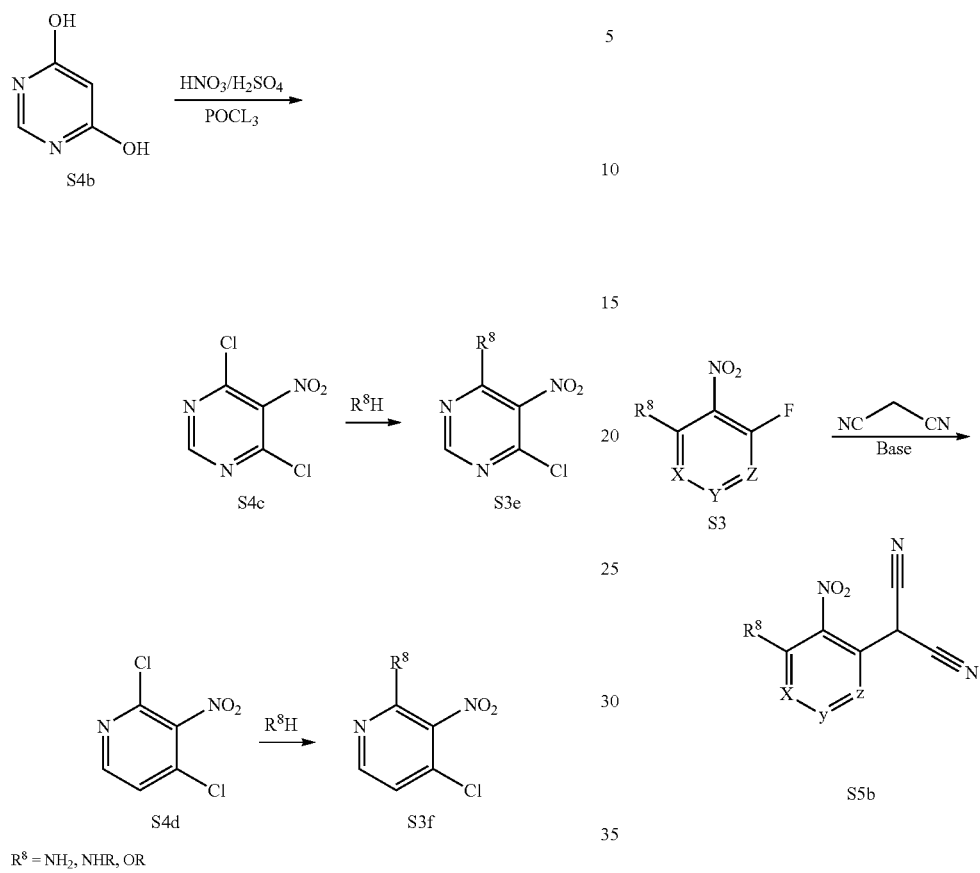

$R^8$ = $NH_2$, NHR, OR

The orthofluoro-nitroaromatics S3 are converted (Scheme 2) to indoles, and nitrogen substituted indoles S6a and S6b (pyrrolopyrimidines and pyrrolopyridines) by treatment with cyano ethyl acetate or cyanomalonate followed by reduction with zinc in acetic acid alternatively the nitro group can be reduced with many alternative reduction agents such as sodium bisulfite.

Scheme 3: Formation of indole intermediates

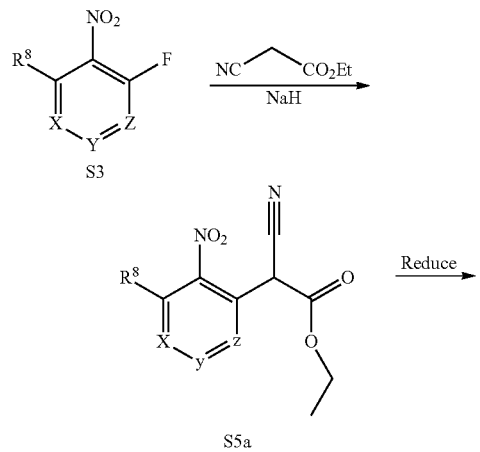

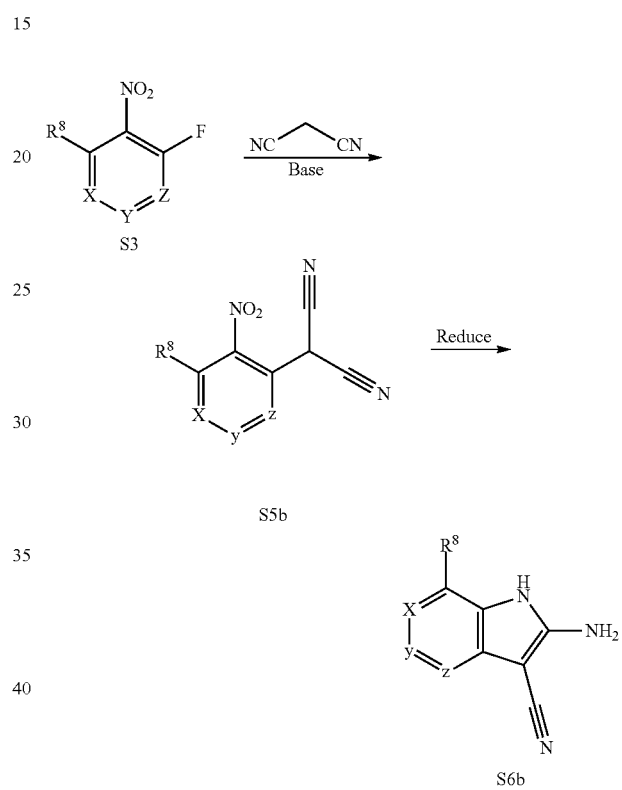

The indole intermediates are converted to tricyclic intermediates as shown in Scheme 4. Reaction of an amino ester indole S6a with an acylisothiocynate followed by treatment with base provides the tricycle S8a with an SH at the 2 position and an OH in the 4 position. Alternatively, treatment with an acylisocynate followed by base provides S8b with an OH substituent at both the 2 and 4 positions of the tricycle. These are versatile intermediates as S8a can be converted to a bis-sulfone by first alkylation at the 2-position sulfur, followed by activation of the 4-position with a reagent such as BOP or mesyl chloride followed by displacement with a sulfide then oxidation to the bis-sulfone S8f with a reagent such as sulfone.

Scheme 4. Preparation of Tricyclic Intermediates

Alternatively, the dihydroxy core S8b can be converted to the dichloro-tricycle S8g. Amino nitrile indole intermediates S6b may be converted to the bissulfone by treatment with carbon disulfide and an alkoide to provide the anion of the 2,4 dithiol tricylcle. This intermediate can be alkylated in situ and then oxidized to provide the bissulfone S8f.

Scheme 4
Preparation of tricyclic intermediates
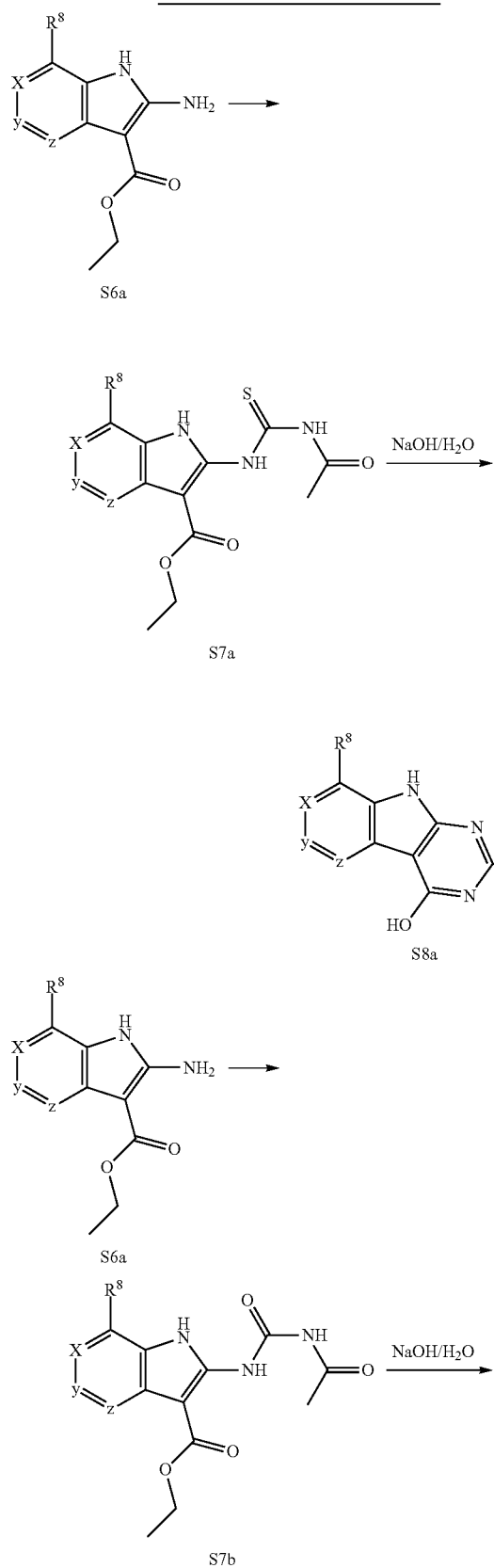
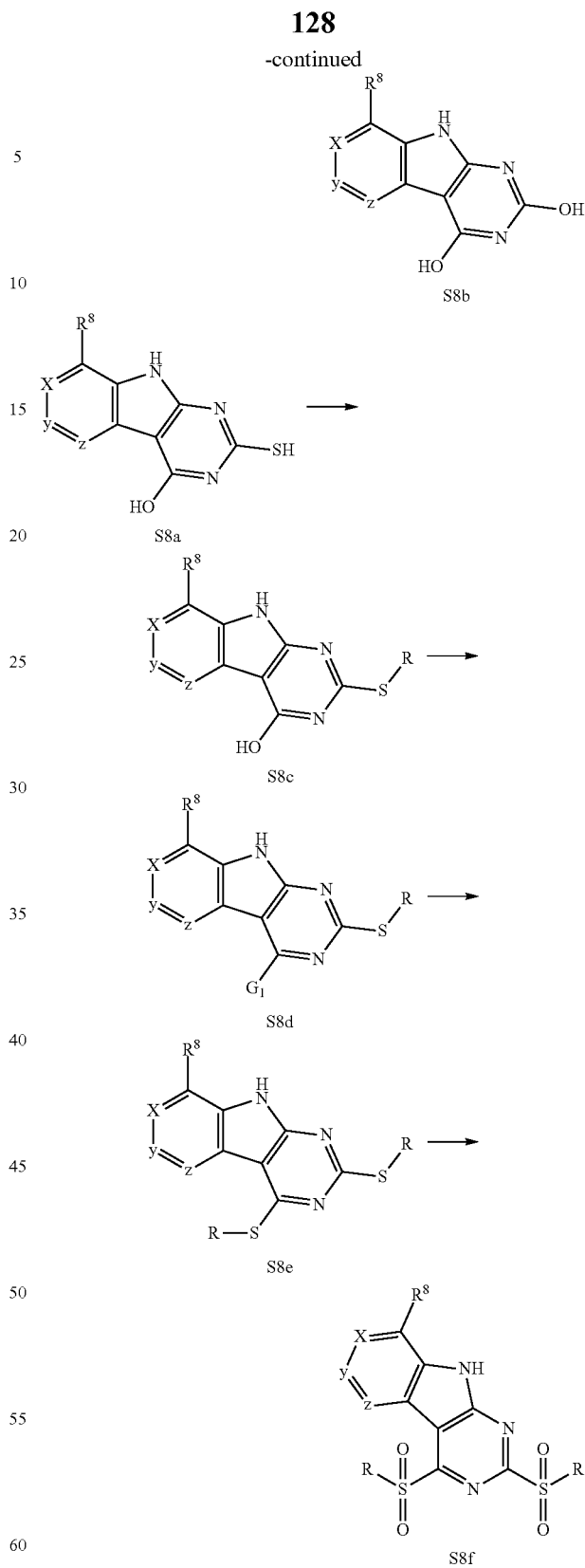
2. General Procedures for Conversion of Tricyclic Cores to Formula I Compounds
There are multiple methods for converting key tricyclic intermediates to Formula I compounds.

In Scheme 5, either intermediate S8f or S8g may be converted to the bis-aryloxy compound 9. The Aryloxy group in the 4 position can be displaced by amines or alcohols to provide the desired Formula I compound when $R^4$ is either an amine of an alkoxide. In some cases it is desirable to use protection groups on the S8 intermediates and/or the $R^4$ group. In those cases, an additional step may be required to remove the protecting group.

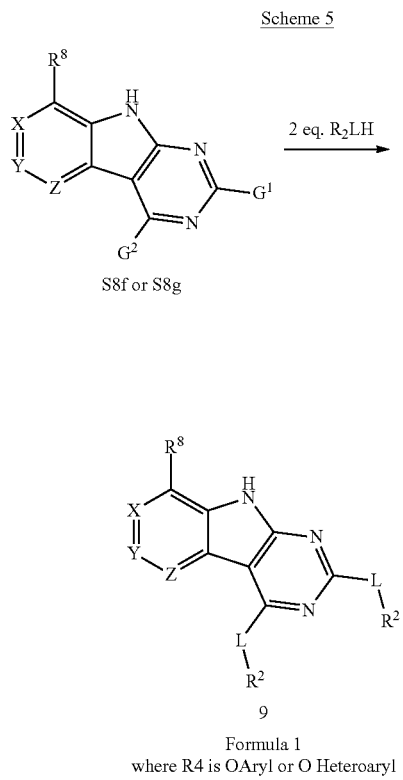

Scheme 5

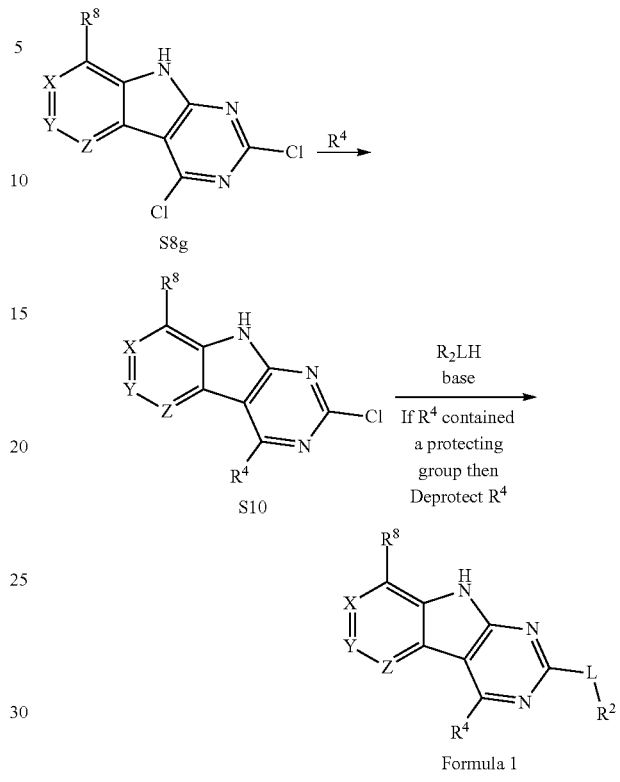

Scheme 6

In cases where L is S, the Formula I compounds can be prepared directly from S8a by the method in Scheme 7. In this method the sulfide is coupled to an aryl halide (preferably an iodo or bromo aromatic). Activation of the 4 position hydroxyl group by reagents such as a sulfonylhalide or a coupling reagent such as BOP followed by displacement with an amine provides the desired Formula I compound.

As an alternative method, the dichloro tricyclic intermediate S8g may be treated with the $R^4$ group first, then followed by displacement of at the 2 position with an alkoxide of $R^2OH$ (Scheme 6). Typically this method requires protecting groups especially when a diamine is used as the $R^4$ group. In these cases, removal of the protecting groups provides Formula I compound. This method is particularly useful when a costly $R^2OH$ group is used or the $R^2$ group is electron rich.

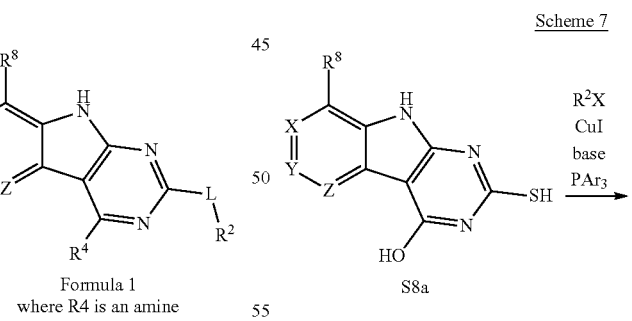

Scheme 7

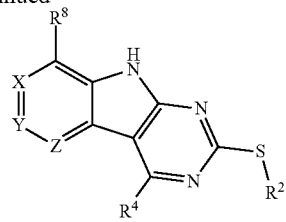

Formula 1
where R⁴ is an amine

Formula I compounds where R⁴ is an aryl or heteroaryl may be made as shown in Scheme 8. In this case, the dichloro intermediate S8g is coupled to a boronic acid using Suzuki coupling conditions. The resulting product is then treated with an alkoxide to provide the Formula I compound.

Scheme 8

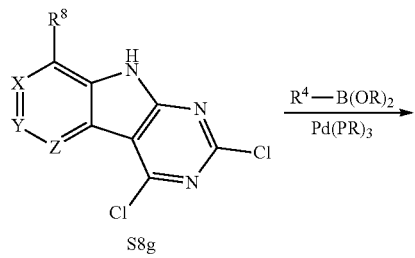

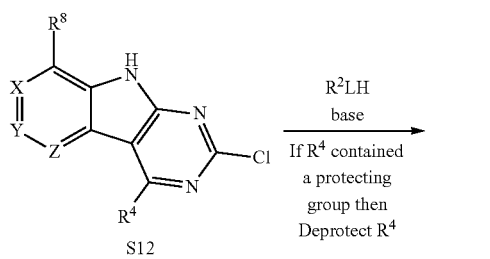

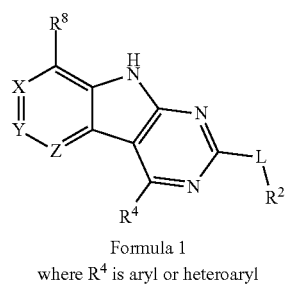

Formula 1
where R⁴ is aryl or heteroaryl

3. General Procedures for the Preparation of R² Intermediates

The cyclic amine in Scheme 9 below may be treated with bromomalonaldehyde to generate a 6/5 bicyclic compound. Palladium or base catalyzed hydrolysis of the bromobicyclic compound may be used to lead to the alcohol final product.

Scheme 9

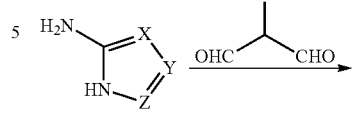

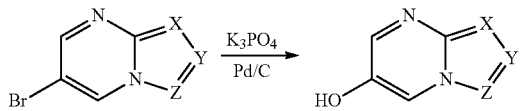

According to Scheme 10, the halide starting material may undergo Stille Coupling, for example, with (1-ethoxyvinyl) triethylstannane by catalyzed palladium, followed by acid hydrolysis to form a ketone intermediate. Then the ketone intermediate may be reduced to alcohol, for example, by sodium borohydride.

Scheme 10

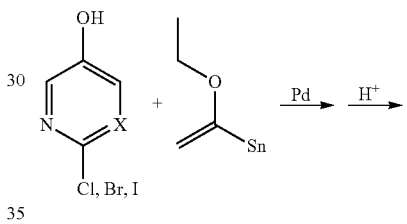

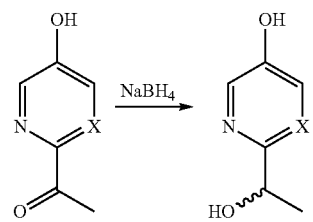

4. General Procedures for Conversion of Tricyclic Cores to Formula I (L=NH, or L=CH₂) Compounds According to Scheme 11 below, the bis-sulfone was treated with the diamine R⁴ and base. Then the amino R² was added. Acid deprotection may give the desired products. More particularly, one equivalent of HR⁴ may be added to a stirring mixture of bis-sulfone and one equivalent of K₂CO₃ in NMP at room temperature. After 12 hours, LC/MS may indicate the completed reaction. Two more equivalent of K₂CO₃ and at least three more equivalents of H₂NR² may be added. The mixture may then heated at least 110 C for more than 3 hours, cooled to room temperature, TFA may be added to the mixture to remove the protection groups. The resulting mixture may be concentrated under the reduced pressure and pre-HPLC separation afforded the target compounds.

Scheme 11

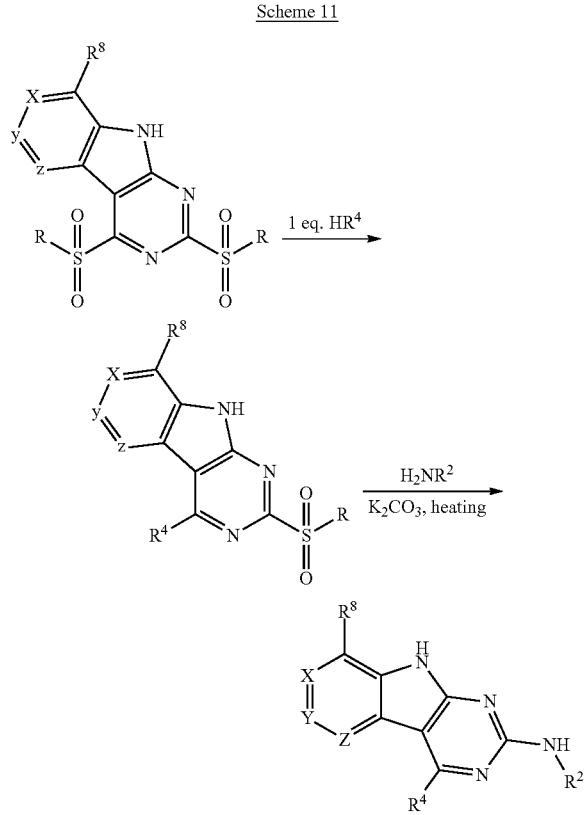

According to Scheme 12 below, the Boc protected methylamine-indole carboxylic ester and the nitrile was dissolved into HCl (g) in dioxane, and stirred for overnight. The resulting solution may be concentrated and the resulting residue may be redissolved with the mixture solution of 1:1 5% NaOH in H₂O and MeOH, then the solution may be heated to reflux, and LCMS may be used to monitor the progress of the reaction. After completing the reaction, the solution may be neutralized, such as with HCl, and concentrated. The residue may be purified, e.g., by reverse phase column to provide the triclyco pyrimidine core. Then the triclyco core may be dissolved in NMP, and coupling reagents BOP and base such as K₂CO₃ may be added. The resulting intermediate may be treated with 1 to 2 equivalent mono-protected diamine, the resulting solution may be stirred for overnight, TFA may be added to the mixture to remove the protection groups. The resulting mixture may be concentrated under the reduced pressure and pre-HPLC separation to afford the target compounds.

Scheme 12

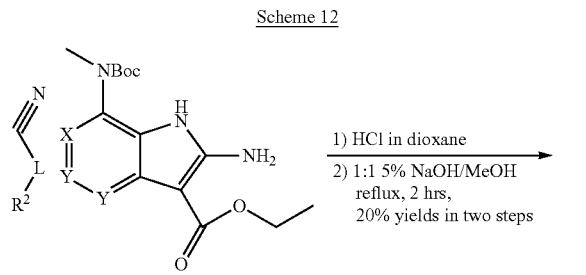

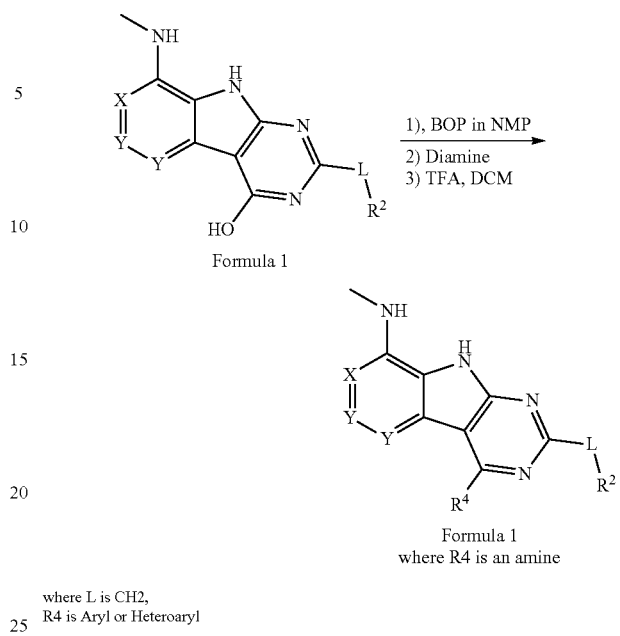

where L is CH2,
R4 is Aryl or Heteroaryl

Similar methods, using the bis-sulfone or the dichloro tricyclic core, are used to make compounds having the following linkers: CHF, CF₂, SCH₂, OCH₂, NHCH₂, CH=CH, CH₂CH₂, SCH₂CONH, OCH₂CONH, NHCH₂CONH, OCH₂CH=CH, or SCH₂CH=CH.

5. General Procedures for Conversion of Tricyclic Cores to Formulae II, III, IV, V, and V', Prodrug Compounds According to Scheme 13 below, the bis sulfone is deprotected for example with an acid. The deprotected compound is then treated with HLR² and a base, followed by HR⁴. This compound is treated with a chloroalkylchloroformate such as chloromethylchloroformate. The chlorine is displaced with R⁸ᵈO— and base. Any protecting groups on R⁴ and R⁸ᵈ may be removed.

Scheme 13

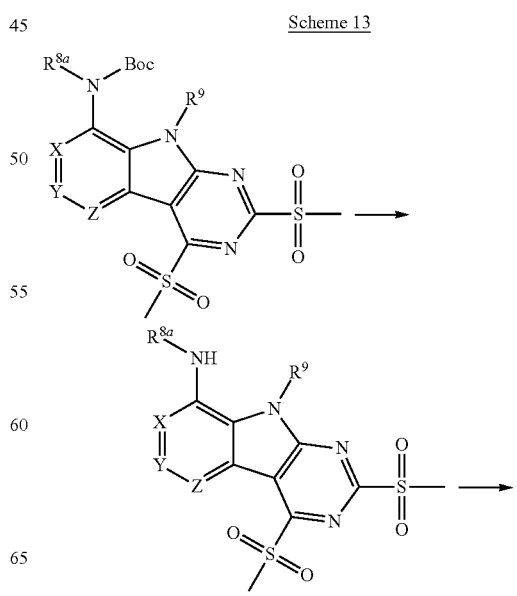

-continued

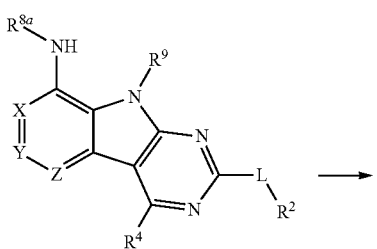

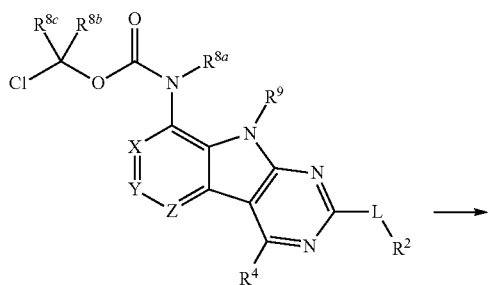

Formula II

According to Scheme 14 below, the chlorine is displaced by nitrogen (R⁹=H) via intramolecular cyclization in the presence of an iodide salt such as sodium iodide. The protecting group in R⁴ may be removed under acidic condition such as trifluoroacetic acid.

Scheme 14

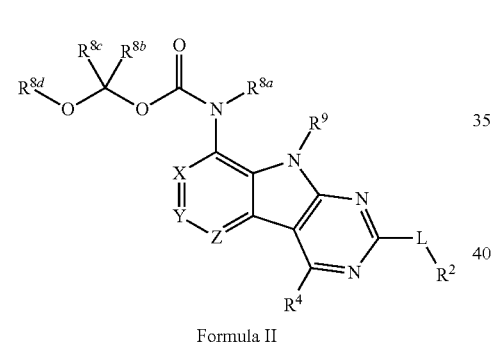

-continued

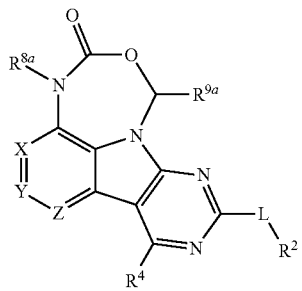

Formula III

According to Scheme 15 below, the bis sulfone is converted to $R^2$ and $R^4$ via the displacement with $R^2$LH followed by amination with free amine in $R^4$. The compound is treated with chloro alkylchloroformate in the presence of organic base such as NEt(i-Pr)$_2$. The chlorine is displaced by a protected salt of a phosphoric acid diester $R^{8d}O^-NR_4^+$ the presence of sodium iodide. The protecting groups in $R^8$ and phosphate protecting group in $R^{8d}$ may be removed under acidic conditions. "$R^{4'}$—NH" in the scheme below represents a non-prodrug $R^4$ group having an NH attached to the prodrug.

Scheme 15

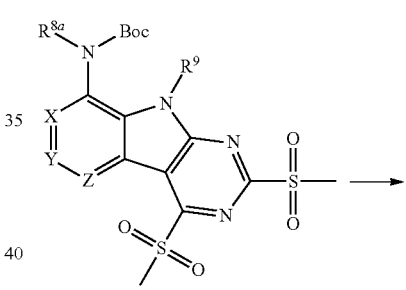

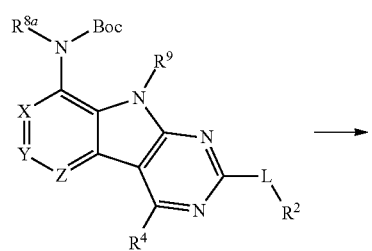

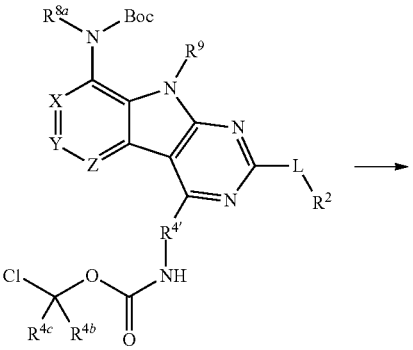

-continued

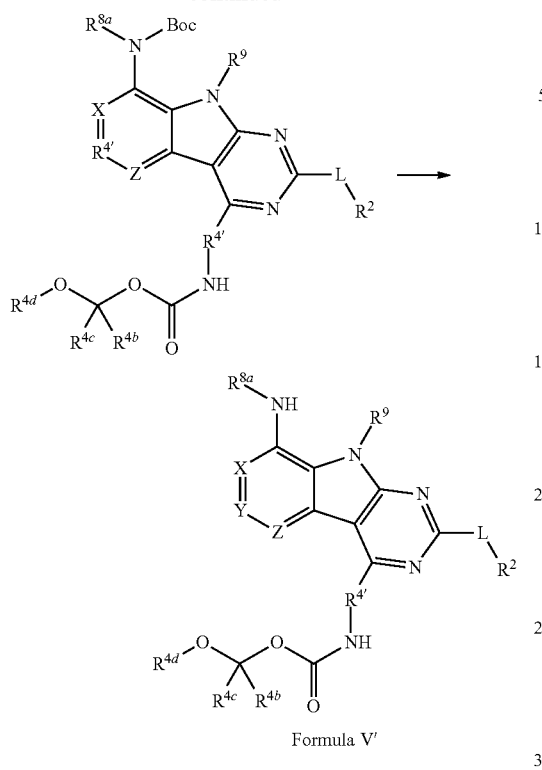

Formula V′

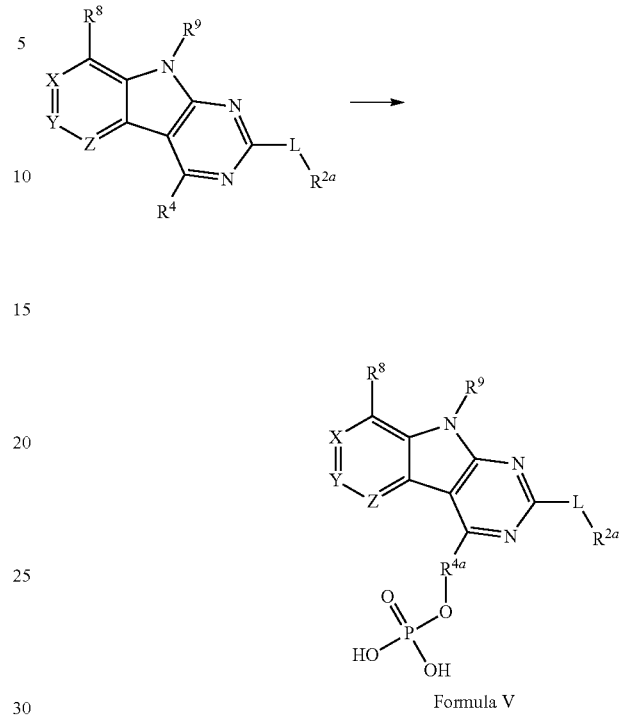

Scheme 17

Formula V

According to Scheme 16 below, the hydroxyl group in $R^{2a}$ is converted to the corresponding dialkylphosphate in the presence of alkyl phosphorochloridate and a base. The protecting groups in $R^8$, $R^4$ and phosphate protecting group in $R^{2a}$ may be removed under acidic conditions.

According to Scheme 17a below, the hydroxyl group in $R^4$ is converted to the corresponding dialkylphosphate in the presence of alkyl phosphorochloridate and a base. The protecting groups in $R^8$, $R^4$ and phosphate protecting group in $R^4$ may be removed under acidic conditions.

Scheme 16

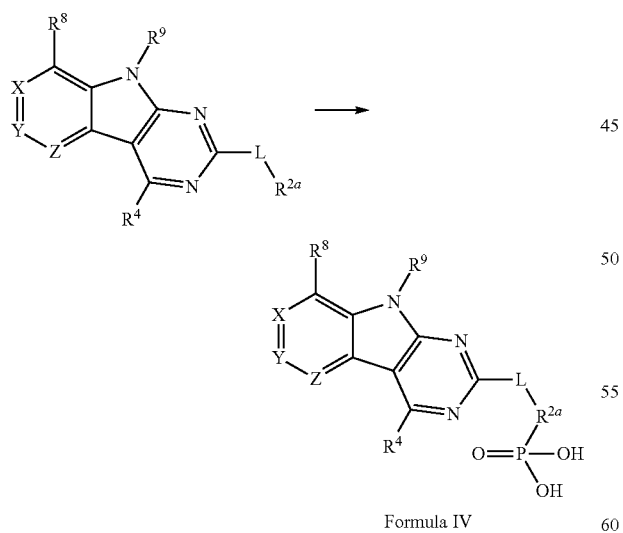

Formula IV

According to Scheme 17 below, the hydroxyl group in $R^4$ is converted to the corresponding dialkylphosphate in the presence of alkyl phosphorochloridate and a base. The protecting groups in $R^8$, $R^4$ and phosphate protecting group in $R^4$ may be removed under acidic conditions.

Scheme 17a

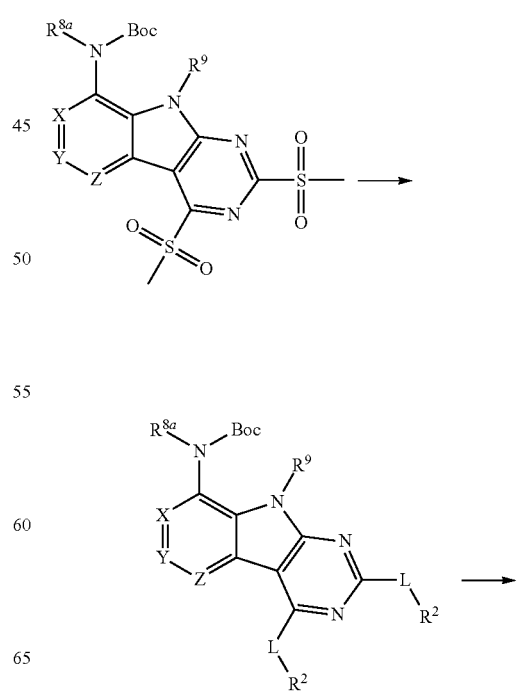

139

-continued

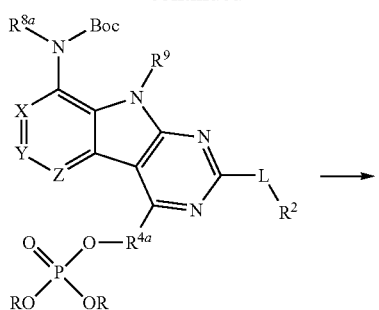

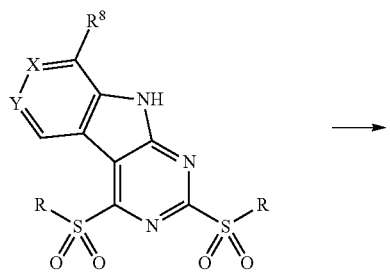

Formula V

6. General Procedures for Conversion of Tricyclic Cores to Formula I where Z is joined to $R^4$ as in Formula VI The bis-sulfone intermediate in Scheme 18a below can be used as starting material to make compounds of Formula I where Z is joined to $R^4$. The bis-sulfone can be first treated with arylthio or alkylthio and potassium carbonate. The reaction is carried out at room temperature with an equivalent amount of the thio reagent to regioselectively substitute the $R_4$ sulfone. In-situ, $HLR_2$ group is then added and heat is applied to help the displacement of the $R_2$ sulfone with $LR_2$. The sulfide group of the product is then oxidized by mCPBA to the resulting sulfone which is in turn hydrolyzed by lithium hydroxy. $POCl_3$ is used to transform the hydroxy functional group to Cl. Then the $R^{4l}$—$R^{4n}$ is attached to the core via $R^{4l}$. It can take place by a metal-complex catalyzed coupling or by an amine substitution. The D ring can be formed by coupling the $R^{4n}$ to the A ring via $R^{4o}$. For example, where $R^{4n}$ is an amine, it can be treated with formaldehyde and catalytic amount of TFA to form the resulting imine which is spontaneously cyclized to A ring.

Scheme 18a

140

-continued

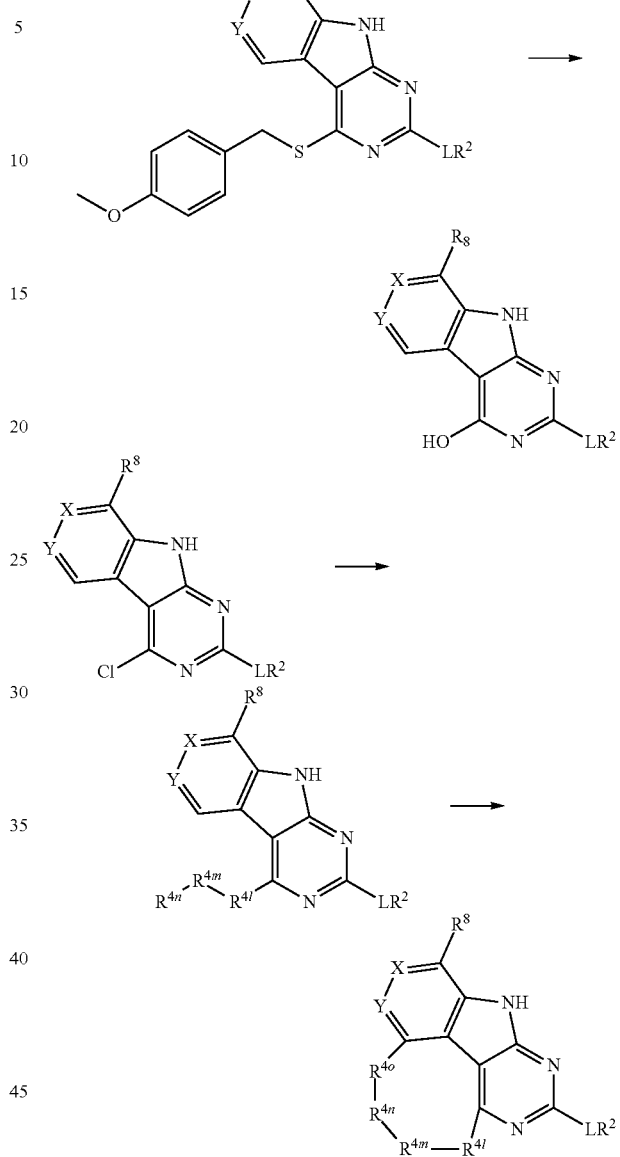

In Scheme 18b below, intermediate bis-methylsulfonyl 18.1 was used as starting material to prepare Formula VI compounds. The $R^4$ methylsulfonyl of 18.1 was selectively replaced by 2-methylpyrimidin-5-ol in the presence of potassium carbonate at room temperature to afford product 18.3. Regioselective bromination of 18.3 by NBS was then carried out at 40° C. in DMF giving rise compound 18.4, which was then converted to the vinyl compound 18.5 by Stille coupling. Dihydroxylation in situ followed by oxidative cleavage of 18.5 directly provided aldehyde 18.6. Different $R^2$ fragments can be then installed at this stage of the synthesis. Typically, an $OR_2$ can replace the $R^2$ methylsulfonyl of compound 18.6 by heating the reaction at 90° C. in the presence of base. When $R_2$ was different from $R^4$ 2-methylpyrimidin-5-ol, more than 3 equivalences of $R_2OH$ were used to minimize the bis-methylpyrimidine product. The product 18.7 of the substitution was then treated with amine 18.8 to convert into 18.9. Temperature of the reaction varied from room temperature to 80° C. depended on the reactivity of amine 18.8. Cyclic compound 18.12 was prepared from 18.9 via C—H carbene insertion through in situ three-step sequence of imination of 18.9, formation of diazonium 18.11, and the insertion of 18.11 to form 18.12. The Boc protecting group of compound 18.12 was then removed by TFA at room temperature to afford Formula VIa compound.

Scheme 18b

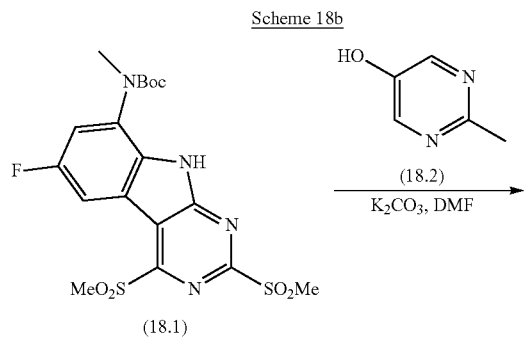
(18.1)

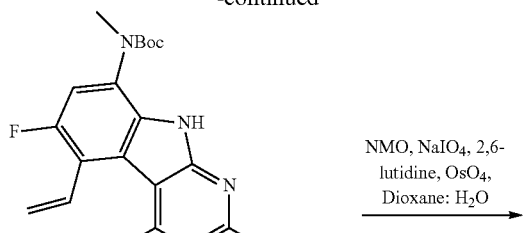
(18.5)

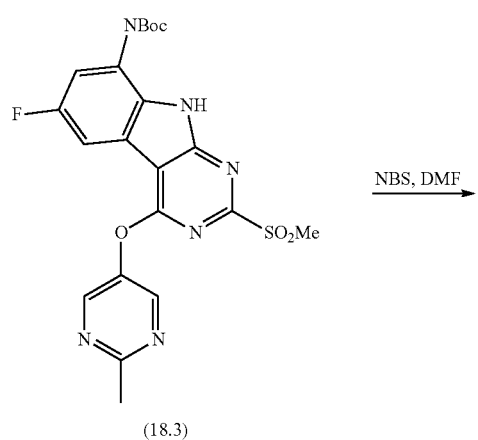
(18.3)

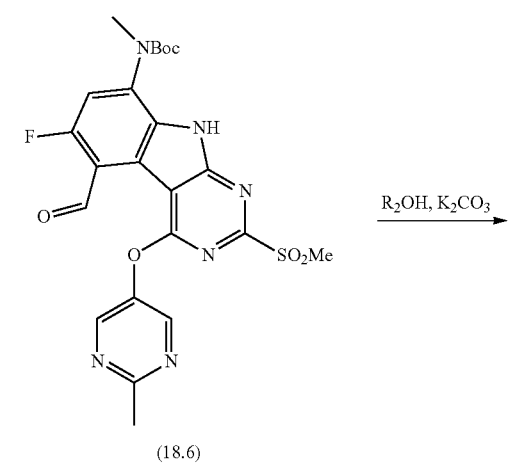
(18.6)

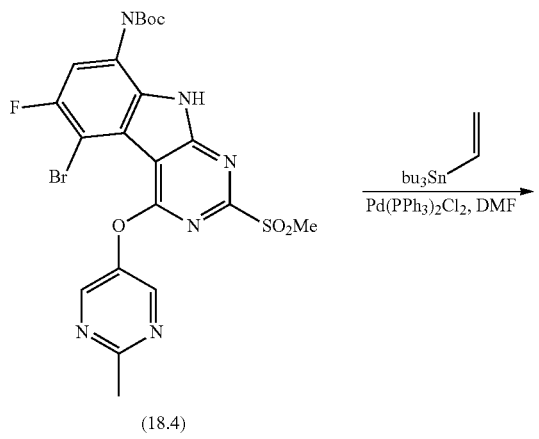
(18.4)

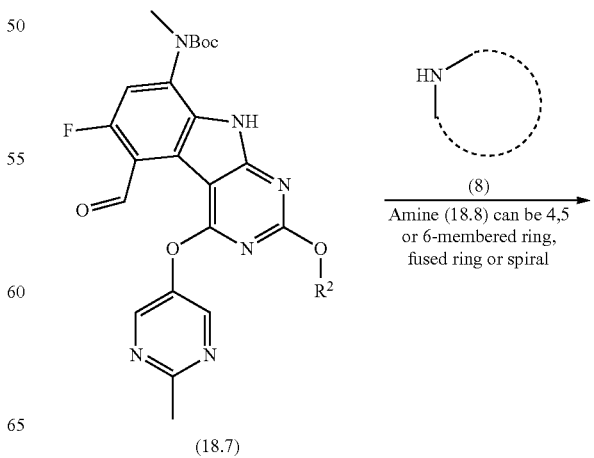
(18.7)

Amine (18.8) can be 4,5 or 6-membered ring, fused ring or spiral

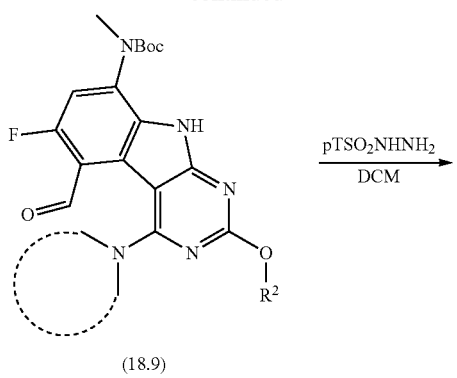

(18.9)

pTSO₂NHNH₂
DCM
→

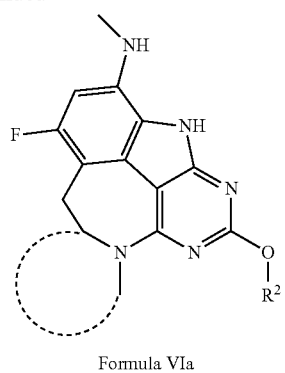

(Formula VIa)

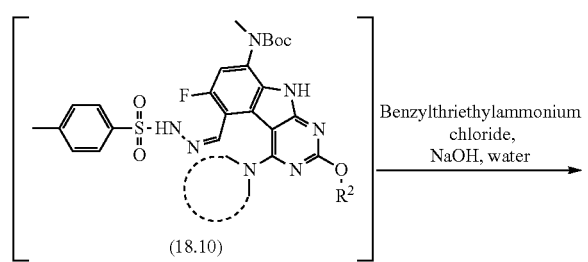

(18.10)

Benzylthriethylammonium chloride, NaOH, water
→

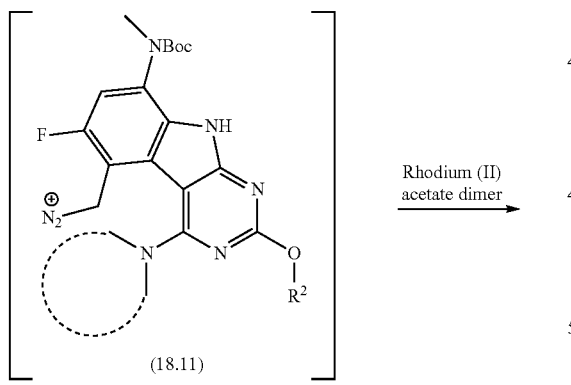

(18.11)

Rhodium (II) acetate dimer
→

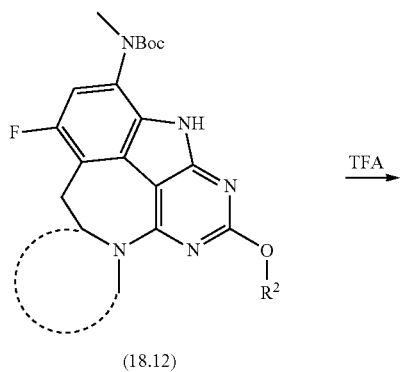

(18.12)

TFA
→

Intermediate 18.4 in Scheme 18c below was used to prepare compound 18.17. The compound was first converted into the corresponding allyl 18.13 by Stille coupling. The R₂ methylsulfonyl of 18.13 was then substituted by an OR₂ in the presence of potassium carbonate at 100° C. to afford product 18.14. The dihydroxylation of 18.14 by NMO and OsO₄ provided the diol 18.15. Upon in situ treated with NaOH aqueous solution and heat, diol 18.15 cylized into Boc-protected 18.16. Expectedly, in addition to 18.17, other analogs can be made from 18.16 through the transformation of its hydroxy group.

$R^{4a}$ is a solubilizing group such as —HNCH₃, —NH₂, —NHCH₂CH₃, —NHCH₂CH₂OH,

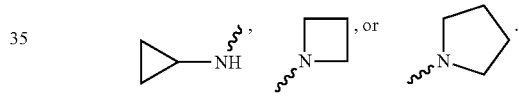

Scheme 18c

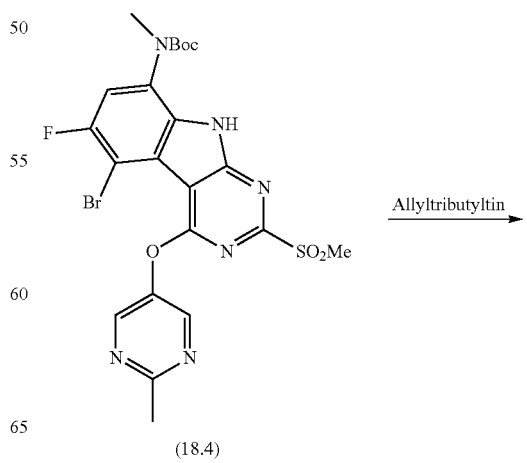

(18.4)

Allyltributyltin
→

145
-continued
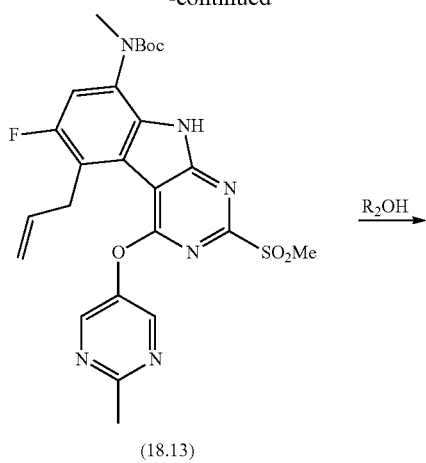
(18.13)
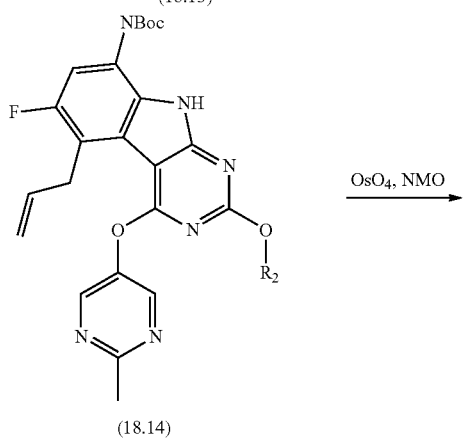
(18.14)
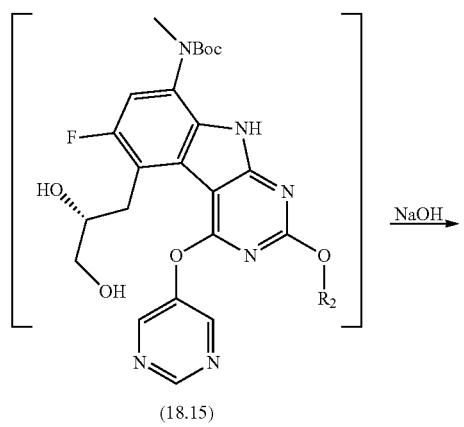
(18.15)
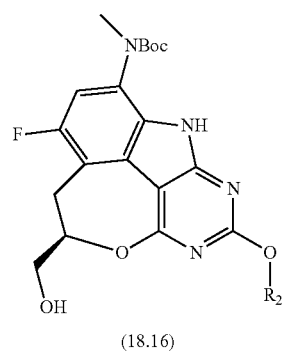
(18.16)
R₂OH →
OsO₄, NMO →
NaOH →
- - →
146
-continued
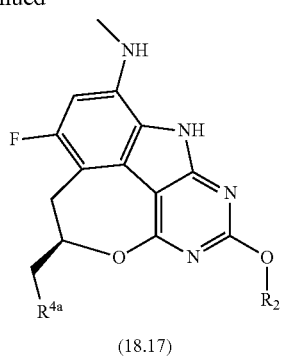
(18.17)
Compounds that may be made using Scheme 18c include:
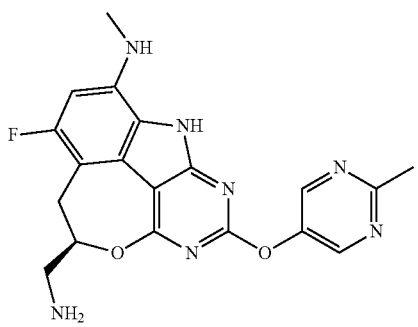
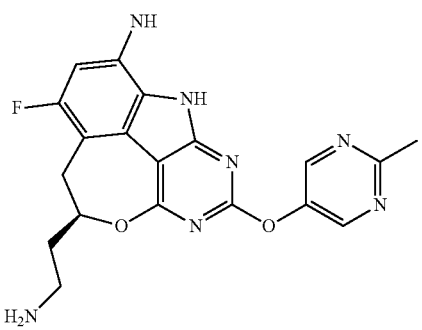
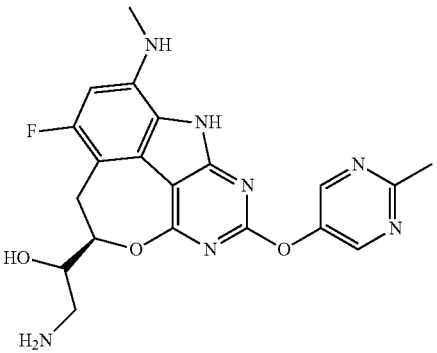

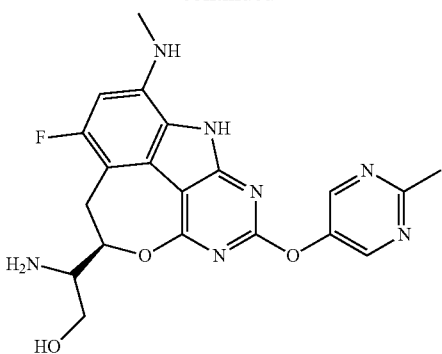

By changing the R[2] groups additional compounds may also be made with various R[2] groups.

Intermediate 18.14 in Scheme 18d below can be used to prepare the core of 18.22. The R[4] group of 18.14 can be selectively hydrolyzed to form the hydroxy 18.18, which upon treated with $POCl_3$ turns into Cl 18.19. Suzuki coupling of 18.19 with vinyl boronic acid or Stille coupling of 18.19 with tributyl(vinyl)tin provides the vinyl 18.20. The compound is then subjected to ring-closing metathesis to form the advance intermediate 18.21. 18.22 compounds can arise from 18.21 via variety of reaction of alkene such as hydroamination, Diels-Alder reaction, cyclopropanation, etc.

Scheme 18d

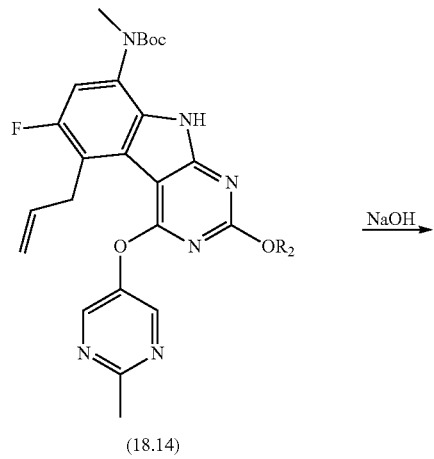

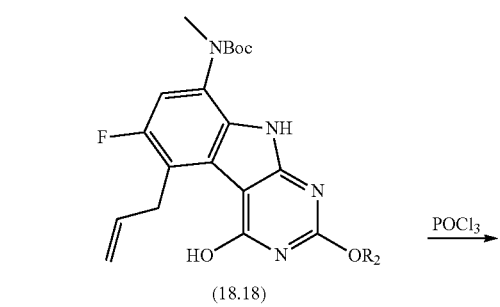

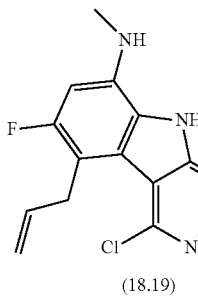

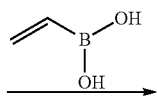

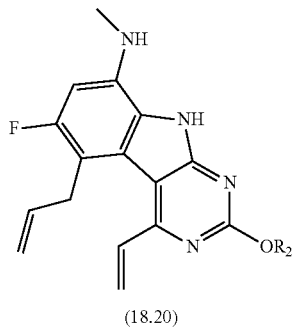

(18.20)

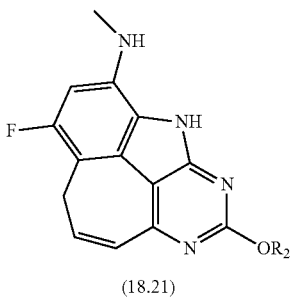

(18.21)

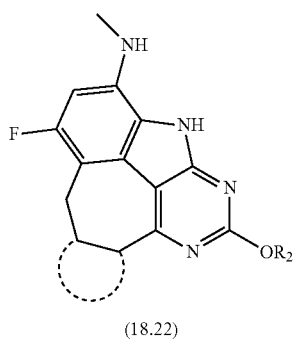

(18.22)

Compounds that can be made by using Scheme 18d include:

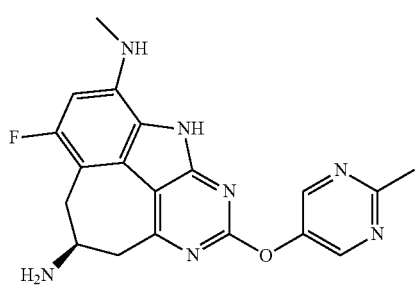

149
-continued
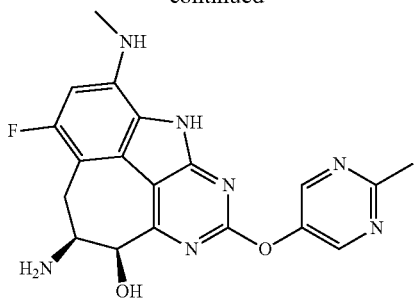
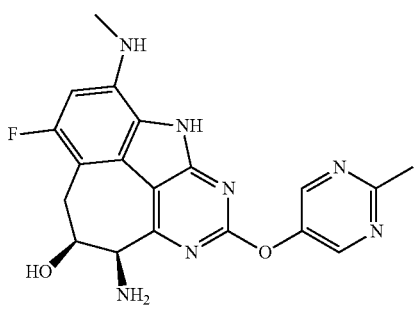
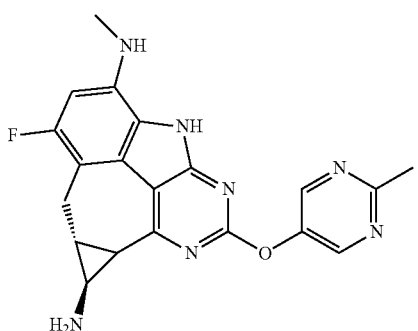
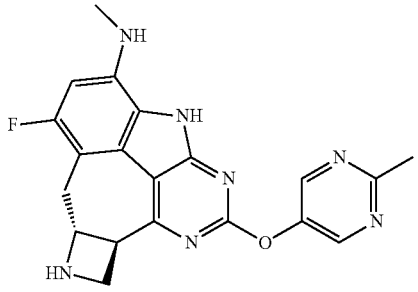
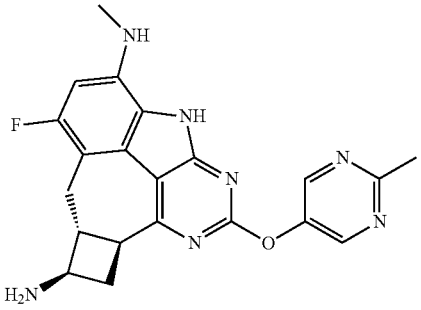
150
-continued
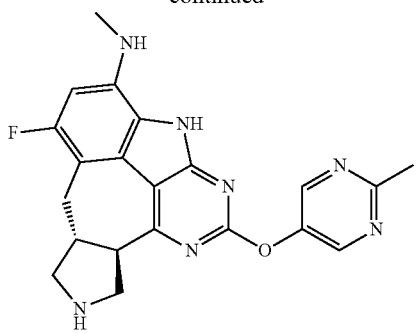
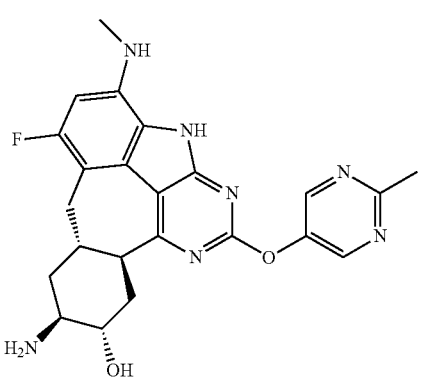
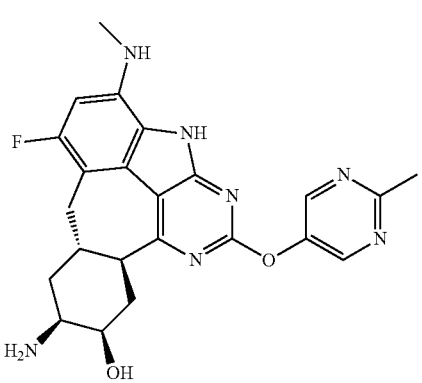
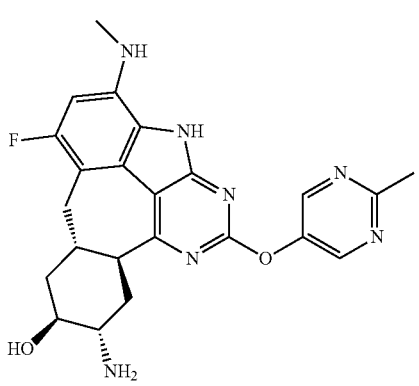

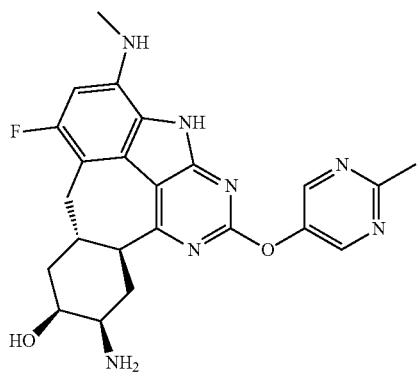

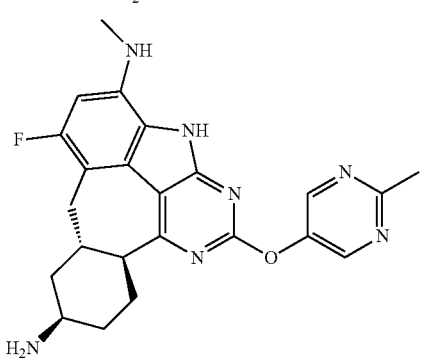

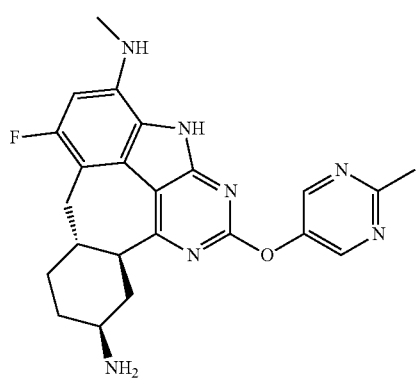

By changing the R² groups additional compounds may also be made with various R² groups.

According to Scheme 19 below, compounds of Formula I where Z is joined to R⁴ can be prepared from the dichloro intermediate.

Scheme 19

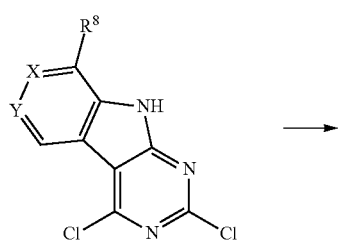

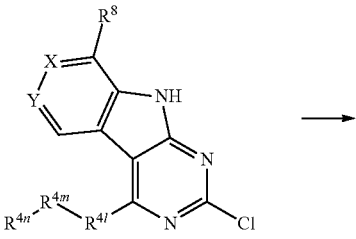

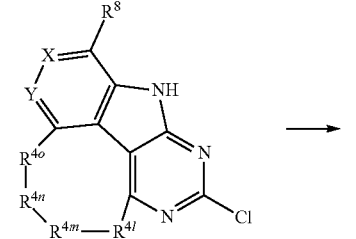

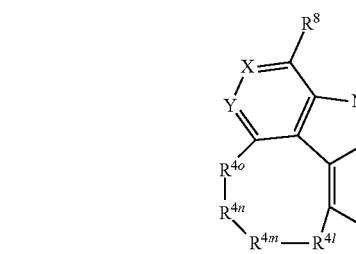

Formula VIa in Scheme 20 below can be synthesized by two different routes. On the first route before cyclization in Scheme 18, the E ring is formed to join $R^{4l}$ and $R^{4m}$. The cyclization takes place as in Scheme 18.

Formula VIa in Scheme 20 below also can be synthesized by another route. Using a di-chloro intermediate (shown in Scheme 19), the E ring is first connected to the core by a metal-complex catalyzed coupling followed by the D ring formation. HLR² group is then assembled via its substitution with Cl in the presence of base and heat.

Scheme 20

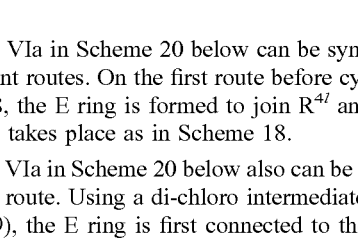

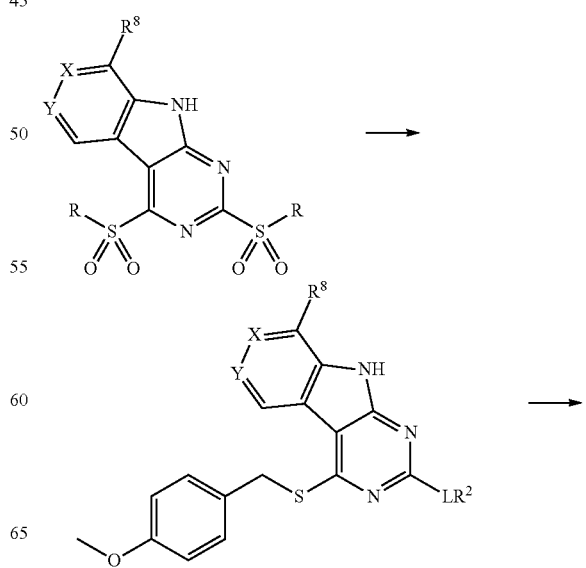

-continued

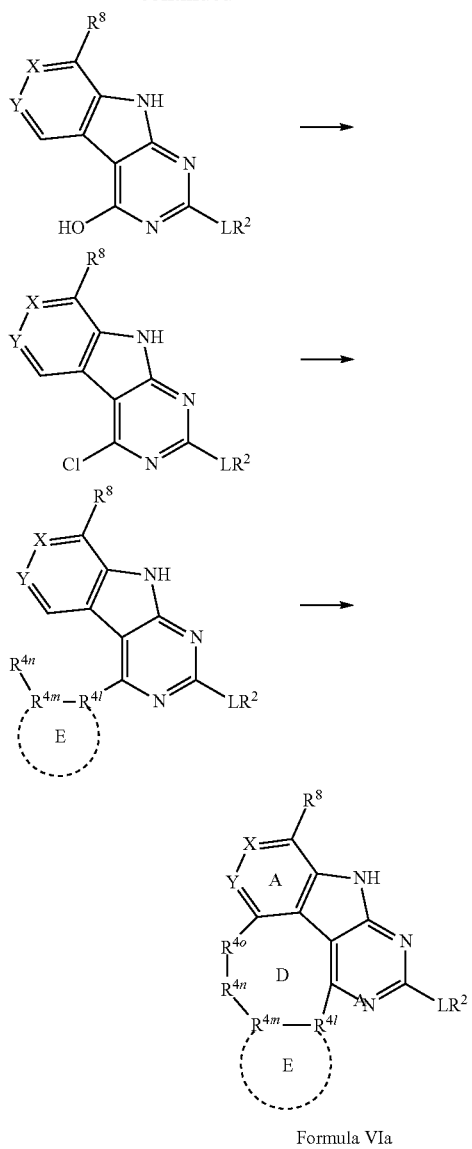

Formula VIa

According to Scheme 21 below, the dichloro intermediate can be used to prepare Formula VIb. It is first reacted with the F ring via a double substitution or double metal-complex catalyzed coupling or via a combination of the substitution and the coupling. HLR2 group is then attached to the core in a known manner of the substitution of Cl.

Scheme 21

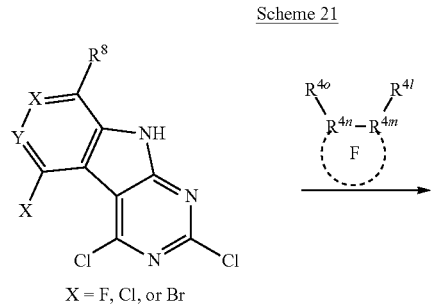

X = F, Cl, or Br

-continued

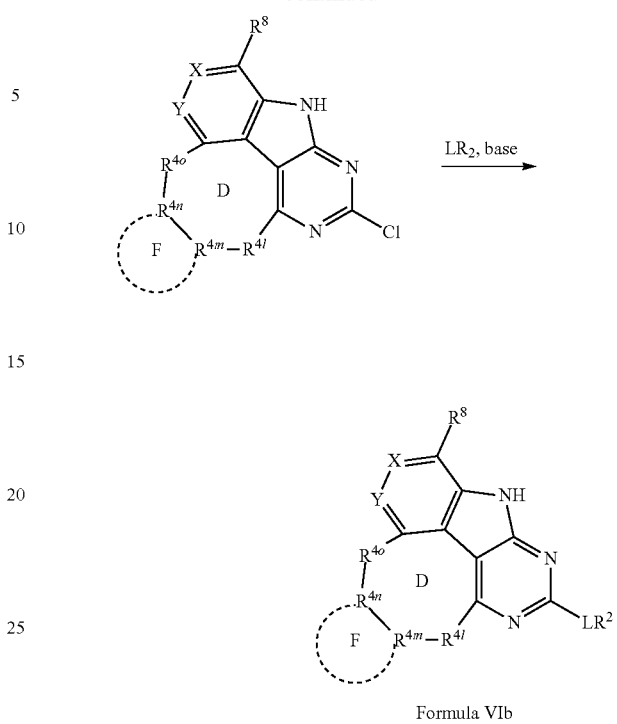

Formula VIb

7. General Procedure for Conversion of Tricyclic Cores to Formula I Compounds where $R^2$ is Joined to $R^4$ The bis-sulfone intermediate in Scheme 22 below can be treated with a thiol (in this example benzylthiol) and base (for example $K_2CO_3$) to substitute the 4-position sulfone. After completion, $HLR^2$ and base (for example $K_2CO_3$) can be added to introduce $LR^2$ into the 2-position. $R^2$ may bear a functional group, which can be optionally protected. This functional group could be, for example, a double bond, a carboxylic acid, a thiol, an amine or another functional group. In the next step, the thiol at the 4-position can be converted to a leaving group, for example, by oxidation to a sulfone using MCPBA. This leaving group can now be displaced by $HR^4$, with $R^4$ bearing a functional group (for example a double bond, a carboxylic acid, a thiol, an amine or another functional group). The functional groups at $R^2$ and $R^4$ can now be further modified or extended to be ready for the macrocyclization. The macrocycle can be formed by using methods available to those skilled in the art, for example ring-closing-metathesis or macro lactamization.

Scheme 22

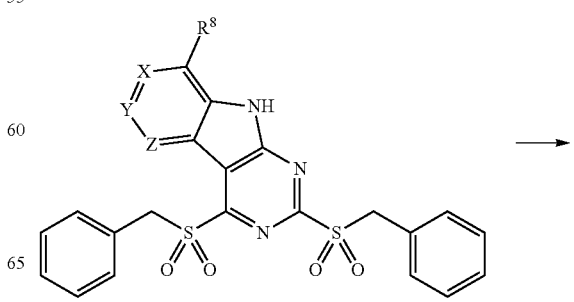

155

-continued

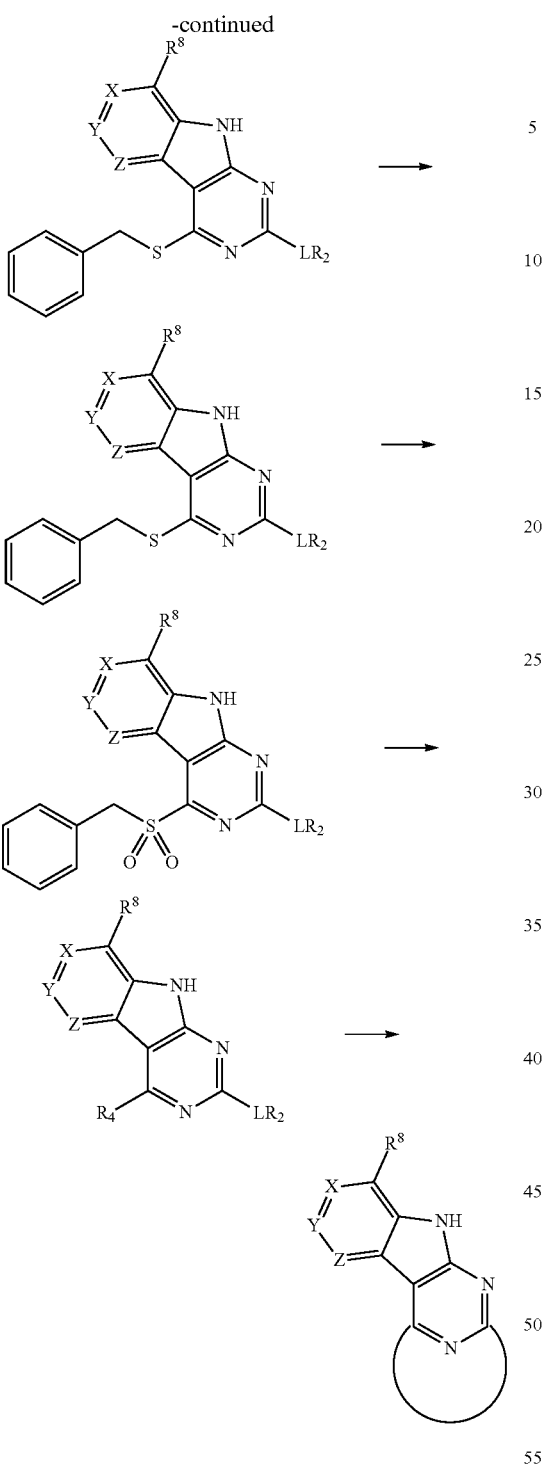

Prodrugs may also be prepared from the compounds of Formula I' or I. The term "prodrug," as used herein, represents compounds which can be transformed in vivo to the active parent compounds defined herein.

In addition, prodrugs may have increased oral bioavailability compared to the parent drug. Although the benefits of prodrugs are widely recognized, often prodrugs fail to achieve these advantages. Thus, significant effort and research are needed to develop an effective prodrug.

The prodrugs herein have significantly less antibacterial activity than the parent antibacterial agent and, consequently, less disruptive to the digestive tract. Because these prodrugs are converted in blood to the active antibacterial agent, they are active systemically. Thus, the prodrug may maintain the beneficial effects of curing the bacterial infection while avoiding the significant side effects of the parent antibacterial agent on the gastrointestinal tract.

In addition, the prodrug may have increased the water solubility compared to the parent antibacterial agent, thereby enabling a better formulation for intravenous administration.

In some aspects, a prodrug may have the structure of Formula II or Formula V':

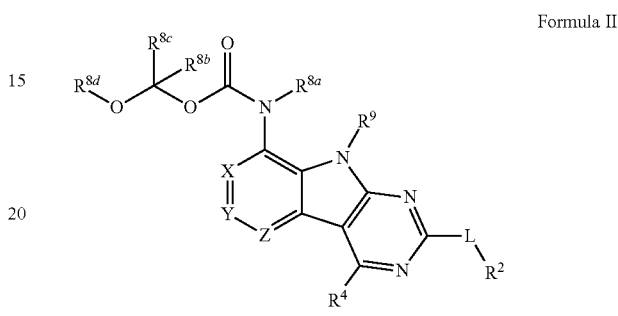

Formula II

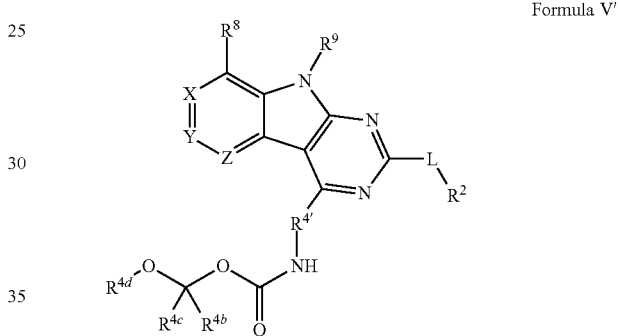

Formula V'

$R^2$, $R^4$, and $R^9$ are described herein.

The drug of Formula II or Formula V' maybe cleaved by an esterase in the blood and converted to the active antibacterial agent having the following Formula IIa or Formula IIa' respectively:

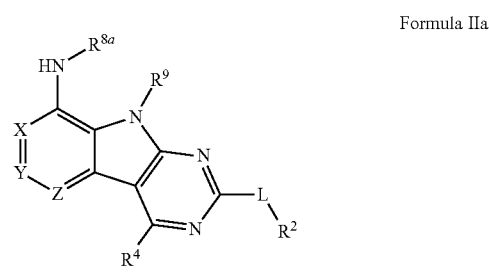

Formula IIa

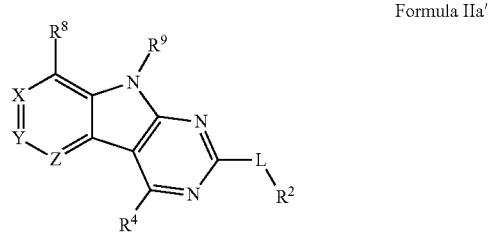

Formula IIa'

$R^{8a}$ has dimensions such that it binds to the enzymatic pocket when in the bound conformation, once the prodrug is cleaved in vivo. For example, $R^{8a}$ may be H or an interacting substituent having a length of about 1 Å to about 3.3 Å from the adjacent nitrogen to the terminal atom in $R^{8a}$ and a width of about 3.3 Å or less. In some aspects, $R^{8a}$ is H, methyl, ethyl, or cyclopropyl, such as methyl.

$R^{8b}$ or $R^{8c}$ may be each independently H or C1-C6 alkyl, for example, C1-C4 alkyl, such as methyl, ethyl, or tertiary butyl. For example, $R^{8b}$ may be methyl, $R^{8c}$ may be H; or $R^{8c}$ may be tertiary butyl and $R^{8c}$ may be H. In some instances, one of $R^{8b}$ or $R^{8c}$ is H, or both are H.

In some aspects, $R^{8d}$ is

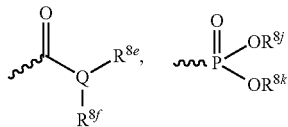

or a pharmaceutically acceptable salt thereof. Pharmaceutically acceptable salts are known in the art and include metal cations, for example a sodium, magnesium, calcium or potassium salt, and also include amine cations such as $NH_4^+$ or alkylated amines.

Q may be CH or N, such as CH.

$R^{8e}$ may be $(CR^{8g}_2)_n$-basic amine, wherein n is 0-2, such as 1, and wherein each $R^8$ may be independently H or C1-C3 alkyl, such as $H_2$, $HCH_2$ or $CH_2CH_2$. A basic amine is a solubilizing group that increases the solubility of the prodrug in aqueous environments such as blood upon administration to the subject.

The basic amine may be $NR^{8h}R^{8i}$ wherein $R^{8h}$ and $R^{8i}$ are independently selected from the group consisting of H, optionally substituted C1-C4 alkyl, wherein optional substituents may be OH, $NH_2$, or $NHCH_3$ wherein $R^{8h}$ and $R^{8i}$ may join to form a fused ring containing 1-3 N, or 0-3 O or S heteroatoms. For example, basic amines may include piperzinyl, morpholinyl, C1-C2 alkyl amine such as methyl amine, C1-C2 dialkyl amine such as dimethylamine, or $NH_2$.

For example, $R^{8d}$ may be

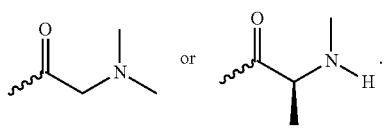

In some aspects, $R^{8f}$ is hydrogen or C1-C6 alkyl, such as methyl, ethyl, propyl, or iso-propyl, or a C1-C6 alkyl, such as methyl, ethyl, propyl, or iso-propyl, optionally substituted with OH or $NH_2$. For example, $R^{8f}$ may be $CH_2OH$, $CHOHCH_3$, or $(CH_2)_4NH_2$. $R^{8f}$ also may be methyl.

In addition, $R^{8e}$ and $R^{8f}$ may join to form a ring; for example, $R^{8d}$ may be

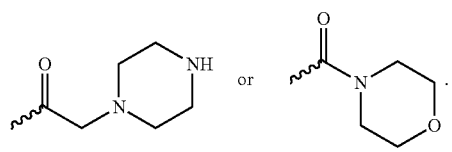

$R^{8c}$ may be

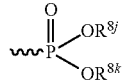

such as

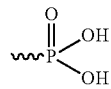

or a pharmaceutically acceptable salt thereof as described herein. $R^{8j}$ and $R^{8k}$ may be independently H, C1-C8 hydrocarbyl residue such as C1-C8 alkyl, for example tertiary butyl, or benzyl.

For example, in some aspects, $R^{8c}$ may be

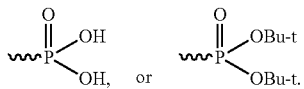

Similarly, $R^4$ has dimensions such that it binds to the enzymatic pocket when in the bound conformation, once the prodrug is cleaved in vivo.

$R^{4b}$ or $R^{4c}$ may be each independently H or C1-C6 alkyl, for example, C1-C4 alkyl, such as methyl, ethyl, or tertiary butyl. For example, $R^{4b}$ may be methyl, $R^{4c}$ may be H; or $R^{4c}$ may be tertiary butyl and $R^{4c}$ may be H. In some instances, one of $R^{4b}$ or $R^{4c}$ is H, or both are H.

In some aspects, $R^{4d}$ is

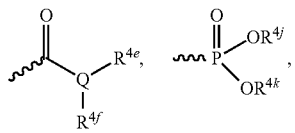

or a pharmaceutically acceptable salt thereof. Pharmaceutically acceptable salts are known in the art and include metal cations, for example a sodium, magnesium, calcium or potassium salt, and also include amine cations such as $NH_4^+$ or alkylated amines.

Q may be CH or N, such as CH.

$R^{4c}$ may be $(CR^{4g}_2)_n$-basic amine, wherein n is 0-2, such as 1, and wherein each $R^{4g}$ may be independently H or C1-C3 alkyl, such as $H_2$, $HCH_2$ or $CH_2CH_2$. A basic amine is a solubilizing group that increases the solubility of the prodrug in aqueous environments such as blood upon administration to the subject.

The basic amine may be $NR^{4h}R^{4i}$ wherein $R^{4h}$ and $R^{4i}$ are independently selected from the group consisting of H, optionally substituted C1-C4 alkyl, wherein optional substituents may be OH, $NH_2$, or $NHCH_3$ wherein $R^{4h}$ and $R^{4i}$ may join to form a fused ring containing 1-3 N, or 0-3 O or S heteroatoms. For example, basic amines may include piperzinyl, morpholinyl, C1-C2 alkyl amine such as methyl amine, C1-C2 dialkyl amine such as dimethylamine, or $NH_2$.

For example, $R^{4d}$ may be

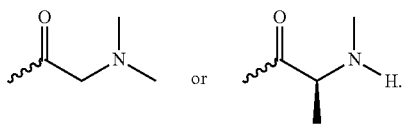 or

In some aspects, $R^{4f}$ is hydrogen or C1-C6 alkyl, such as methyl, ethyl, propyl, or iso-propyl, or a C1-C6 alkyl, such as methyl, ethyl, propyl, or iso-propyl, optionally substituted with OH or $NH_2$. For example, $R^{4f}$ may be $CH_2OH$, $CHOHCH_3$, or $(CH_2)_4NH_2$. $R^{4f}$ also may be methyl.

In addition, $R^{4e}$ and $R^{4f}$ may join to form a ring; for example, $R^{4d}$ may be

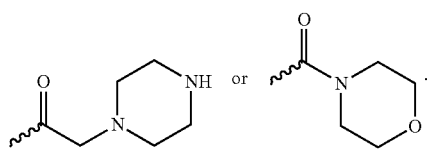

$R^{4c}$ may be

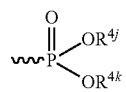

such as

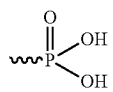

or a pharmaceutically acceptable salt thereof as described herein. $R^{4j}$ and $R^{4k}$ may be independently H, C1-C8 hydrocarbyl residue such as C1-C8 alkyl, for example tertiary butyl, or benzyl.

For example, in some aspects, $R^{4c}$ may be

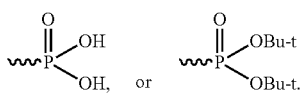

Examples of the compound of Formula II or V' include

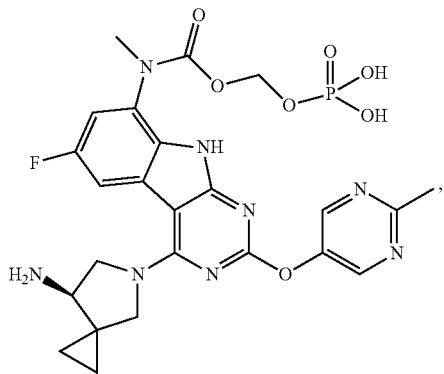

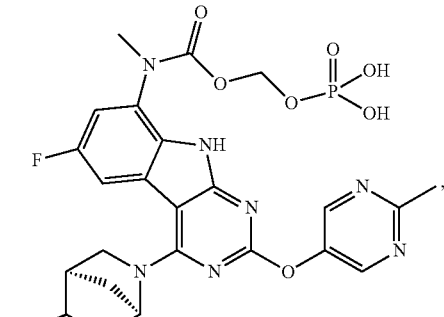

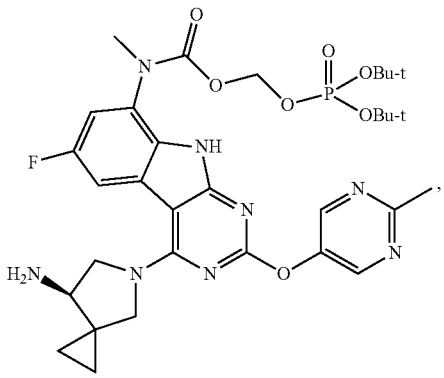

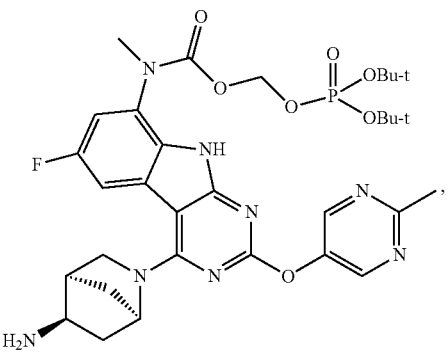

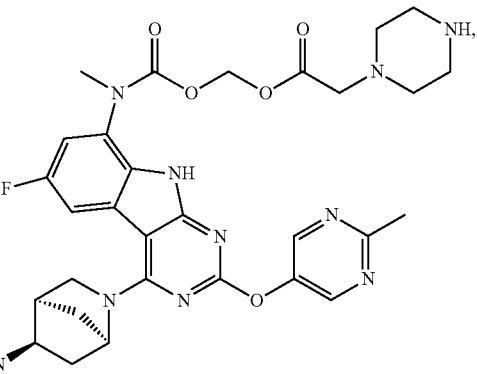

-continued

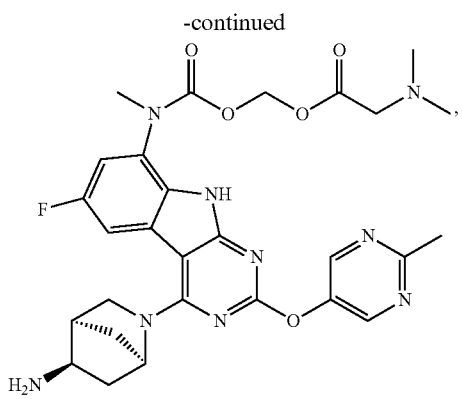

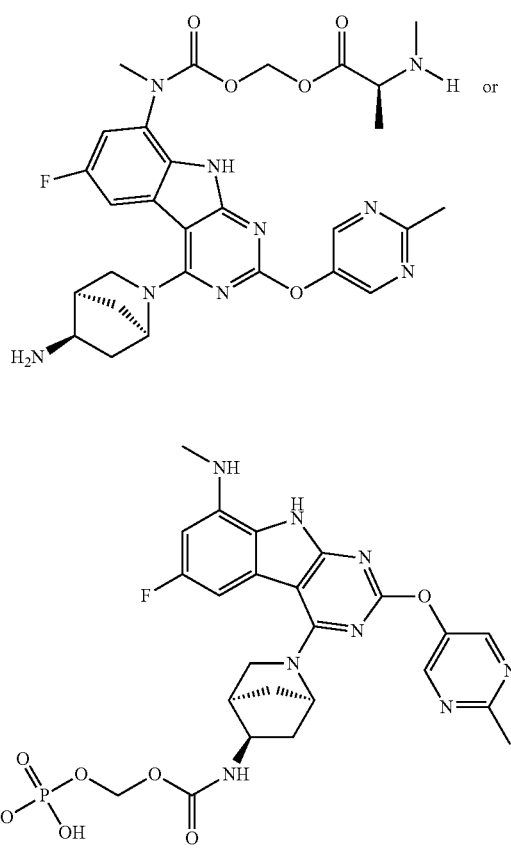

In some aspects, a prodrug may have the structure of Formula II', II" or II''':

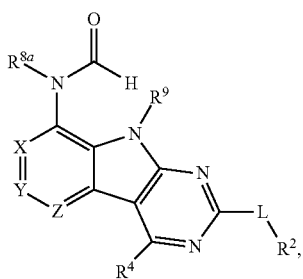

Formula II'

-continued

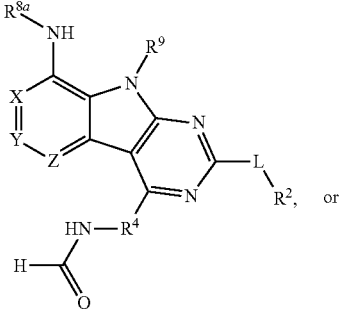

Formula II"

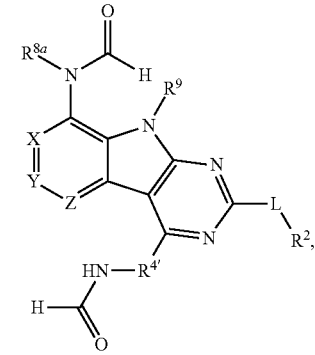

Formula II''' where the R groups are as defined herein.

Generally, as illustrated above but not limited thereto, more than one prodrug substituent may be present on the compound.

In some aspects, a prodrug has the structure of Formula III:

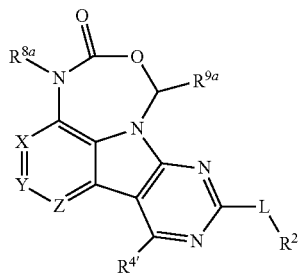

Formula III $R^{8a}$ is the same as recited above for Formula II. $R^{9a}$ may be H, or C1-C4 such as methyl, ethyl, or tertiary butyl. Similarly, the drug of Formula III maybe cleaved by an esterase in the blood and converted to the active antibacterial agent having Formula IIa above.

An example of the compound of Formula III is

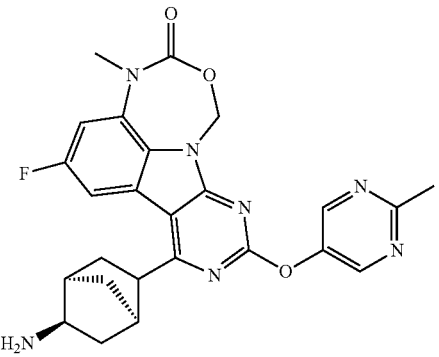 [SMILES: Cc1ncc(Oc2nc(C3C[C@H]4C[C@@H]3C[C@H]4N)c3c4cc(F)cc5c4n(c3n2)COC(=O)N5C)cn1]

A prodrug also may have the structure of Formula IV or V:

Formula IV

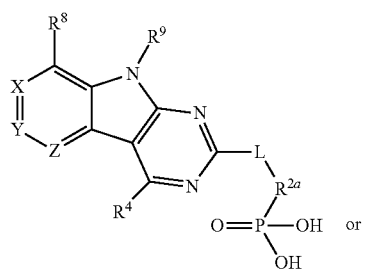

or

Formula V

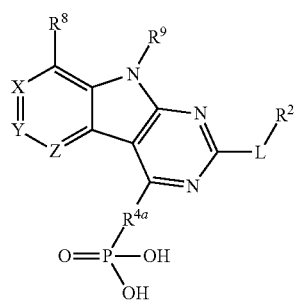

or a pharmaceutically acceptable salt thereof as described herein.

Any suitable $R^2$ herein comprising an OH group or substituted with an OH may allow phosphorylation to arrive at Formula IV. Thus, $R^{2a}$ contains an oxygen residue derived from an $R^2$ wherein $R^2$ has an OH group, wherein $R^2$'s OH is replaced with an oxygen residue in $R^{2a}$, upon phosphorylation, and wherein the oxygen residue is linked to P in the phosphate group.

Examples of suitable $R^2$ groups include the following, which are shown below as attached to an O linker although other linkers may be used:

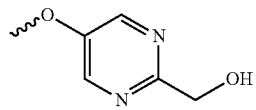

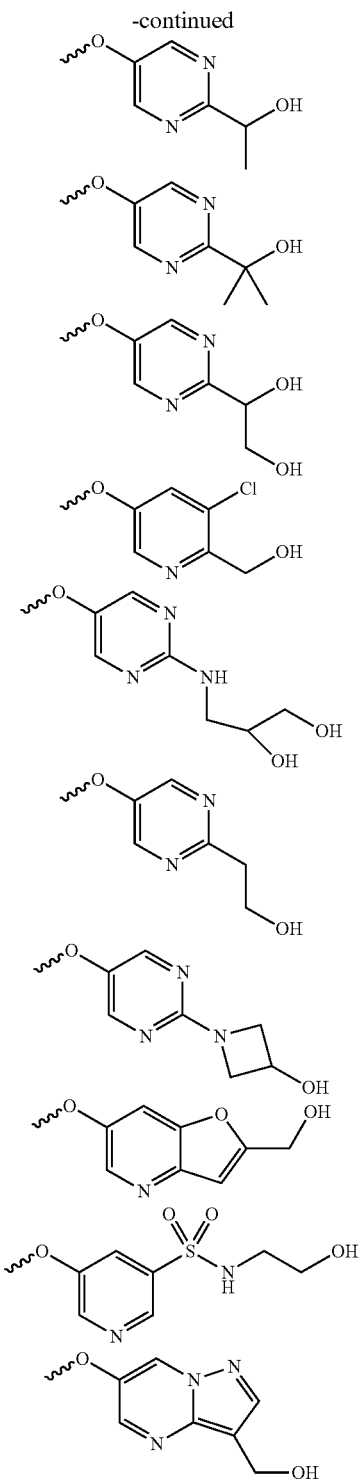

Any suitable $R^4$ herein comprising an OH group or substituted with an OH group may allow phosphorylation to arrive at Formula V. Thus, $R^{4a}$ contains an oxygen residue derived from a non-prodrug $R^4$. Thus, if the non-prodrug $R^4$ has an OH group, $R^4$'s OH is replaced with an oxygen residue in $R^{4a}$, upon phosphorylation, wherein the oxygen residue is linked to P in the phosphate group.

$R^2$ and $R^4$ substituents that are disclosed in PCT/US2012/029104 maybe further substituted with —OH as known in the art.

The prodrug of Formula IV or Formula V maybe cleaved by a phosphatase in the blood and converted to the active antibacterial agent having an R² or R⁴ group respectively containing a hydroxy group. R$^{2a}$ or R$^{4a}$ may be derived from an active antibacterial compound having an hydroxy substituted R² or R⁴ group respectively, wherein upon the formation of the prodrug, the hydroxy becomes the point of attachment to the phosphate.

An example of a compound having Formula IV is

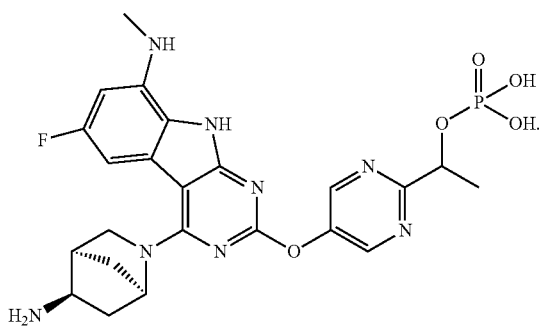 [SMILES: CNc1cc(F)cc2c1[nH]c1nc(Oc3cnc(C(C)OP(=O)(O)O)nc3)nc(N3C[C@H]4C[C@@H]3C[C@H]4N)c12]

An example of a compound having Formula V is

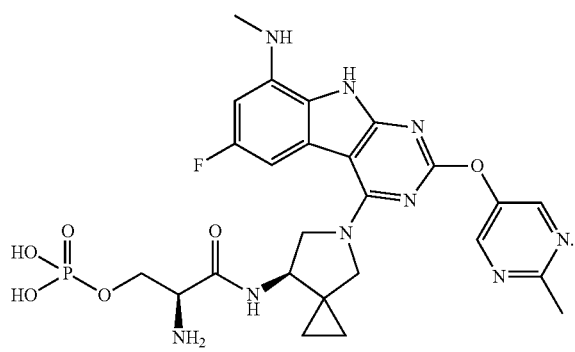 [SMILES: CNc1cc(F)cc2c1[nH]c1nc(Oc3cnc(C)nc3)nc(N3C[C@H](NC(=O)[C@@H](N)COP(=O)(O)O)C4(CC4)C3)c12]

An example of a compound having Formula V' is

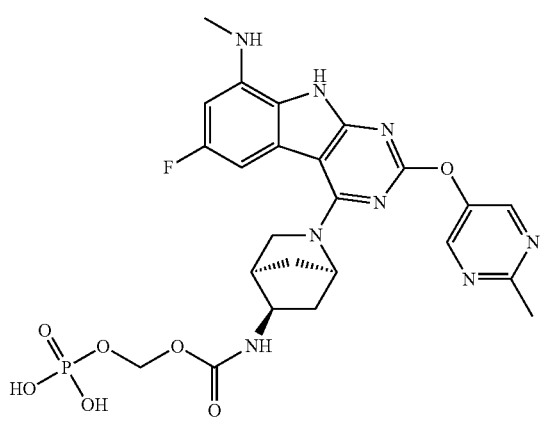 [SMILES: CNc1cc(F)cc2c1[nH]c1nc(Oc3cnc(C)nc3)nc(N3C[C@H]4C[C@@H]3C[C@H]4NC(=O)OCOP(=O)(O)O)c12]

When a prodrug formula, e.g. Formula II-V or V', includes an R², R⁴, or R⁸ group, any appropriate R², R⁴, or R⁸ group herein may be used.

General Schemes for making prodrugs are indicated above.

Additional examples of prodrugs for example on R⁴ include NHNHCH₃,

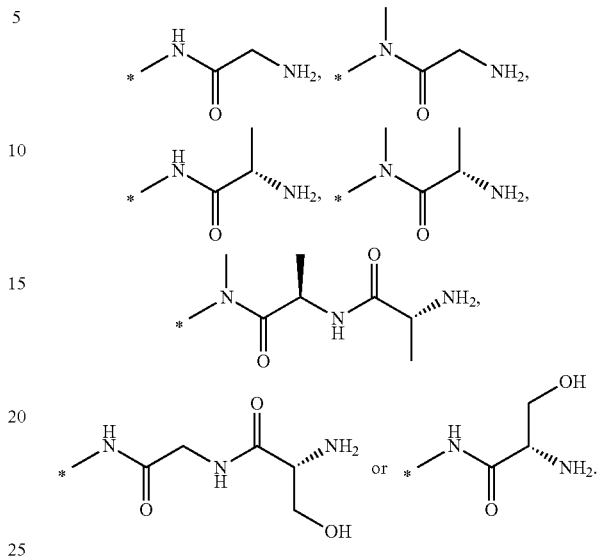

A pharmaceutically-acceptable salt, ester, or prodrug of the compounds herein is also contemplated. Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}$C for carbon, $^{15}$N for nitrogen, or $^{32}$P for phosphorus) known as "isotopomers" can also be readily produced. All such derivatives are contemplated within the scope of this disclosure.

Many of the compounds may be in the form of a salt, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499 discuss such salts in detail.

Compounds herein include those structures that are set out throughout the examples, and pharmaceutically acceptable salts, esters and prodrugs thereof. In some embodiments, the compound is in a pharmaceutical composition or a dosage form, wherein the pharmaceutical composition or dosage form provides an effective antibiotic amount of the compound for treating or preventing infection.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner. Administration to the buccal mucosa and sublingually are contemplated.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria including *H. influenzae, E. coli, S. aureus, E. faecalis, E. facium, K. pneumonia, A. baumannii, S. pneumoniae,* and *P. aeruginosa*. The compounds show activity against most resistant strains for example methicillin resistant *Staphylococcus aureus* (MRSA). In addition, the compounds show broad-spectrum activity against all Category A, B, and C bacterial biodefense pathogens including *B. anthracis, B. pseudomallei, B. mallei, F. tularensis* and *Y. psetis*. See the Examples. The compounds have excellent relative antibiotic activity with a relatively low concentration. Further, the compounds may exert potent antibacterial activity versus various human and animal pathogens, including Gram-positive and Gram-negative bacteria. In an embodiment, the bacterial infection that may be treated or ameliorated is MRSA.

Methods of treating bacterial infections also include intraabdominal infection, a urinary tract infection, or melioidosis. Intraabdominal infections include various infections such as peritonitis, appendicitis, abscesses, sepsis, and cholecystitis, which may be complicated or uncomplicated. The compound here in may also be used to treat urinary tract infections, which may be caused by *E. coli*. In addition, the compounds herein are useful to treat melioidosis, which may be caused by *B. pseudomallei*.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions.

Therefore, in some embodiments, "substantially pure" refers to the amount of purity required for formulating pharmaceuticals, which may include, for example, a small amount of other material that will not affects the suitability for pharmaceutical use. In some embodiments, the substantially pure compound contains at least about 96% of the compound by weight, such as at least about 97%, 98%, 99%, or 100% of the compound.

The terms "approximately," "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXPERIMENTAL SECTION

Example 1: Preparation of Compounds

Example 1a—Preparation of $R^2$ Group

Preparation of Pyrazolo[1,5-a]pyrimidin-6-ol

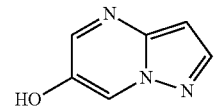

Commercially available 6-bromopyrazolo[1,5-a]pyrimidine (1 g, 5.05 mmol) was dissolved in a solution of KOH (1.7 g, 30.3 mmol) and methanol (25 mL), then heated in a 65° C. oil bath until the reaction was complete by LCMS (3 h). Work-up: cooled to room temperature, filtered to remove KBr salt, neutralized with conc. HCl, removed 50% of MeOH by rotary evaporation, diluted with EtOAc and water, extracted with EtOAc (5×50 mL), dried over Na2SO4, concentrated until a solid formed, sonicated, and filtered, yielding 1.13 g of off white solid. A second crop with a mass of 0.091 g was obtained. Total yield of the title compound was 1.22 g (89%), which used without further purification. LCMS m/z: 134.20 (M+).

Example 1b—Preparation of $R^2$ group Preparation of Thiazolo[5,4-b]pyridin-6-ol

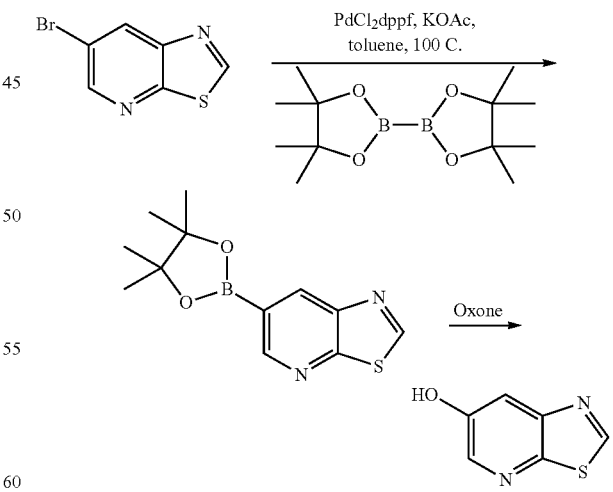

6-(4,4,5,5-tetramethyl-1,3,2-dioxaborolan-2-yl)thiazolo[5,4-b]pyridine

A round bottom flask was charged with 6-bromothiazolo[5,4-b]pyridine (430 mg, 2.00 mmol), 4,4,4',4',5,5,5',5'-octamethyl-2,2'-bi(1,3,2-dioxaborolane) (660 mg, 2.6 mmol), KOAc (392 mg, 4.00 mmol), toluene (10 ml), vacuum flushed with nitrogen (3×), and treated with PdCl₂dppf (82 mg, 0.100 mmol), vacuum flushed (3×), and placed in a 100° C. oil bath. After 1.5 h reaction was complete by LCMS. Work-up: filtered, concentrated, and purified by flash chromatography (5-95% EtOAc/Hex). 610 mg (116%) of colorless oil was obtained, that was contaminated boron derived side products. This material was used in the next step without further purification.

Thiazolo[5,4-b]pyridin-6-ol

To a solution of 6-(4,4,5,5-tetramethyl-1,3,2-dioxaborolan-2-yl)thiazolo[5,4-b]pyridine (524 mg, 2.0 mmol), dissolved in acetone (10 ml), was added a solution of Oxone (0.2M, 10 mL, 2.0 mmol), at room temperature. LCMS showed disappearance of all starting material after 10 min. Work-up: the reaction was acidified with 1N HCl, extracted with ether (5×25 mL), dried of Na₂SO₄, and purified by RPLC. Yield of yellow powder was 48 mg (16%).

Example 1c—Preparation of R² Group

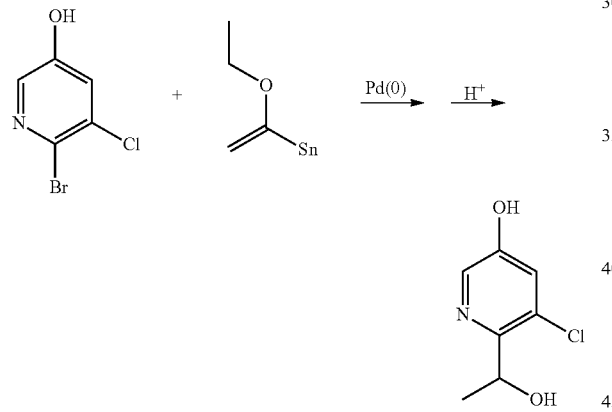

5-chloro-6-(1-hydroxyethyl)pyridin-3-ol

Step 1. To a solution of 5-Cl-6-Bromopyridine-3-ol (1.1 g, 5.28 mmol) in DMF (10 mL) was added 2-ethoxyvinyl-tributyltin (2.86 g, 7.93 mmol) and PdCl₂(PPh₃)₂ (185 mg, 0.26 mmol). The mixture was heated at 110 C for 5 h. The mixture was concentrated under vacuum and dissolved in acetone (10 mL). 2N HCl (3 mL) was added. The mixture was then stirred at room temp for 3 h. The mixture was concentrated, neutralized to PH 7 and extracted with ethyl acetate. The organic layer was dried and concentrated to give black oil which was chromatographed on silica gel to give the methyl ketone as a pale yellow solid (1.0 g).

Step 2. To a solution of ketone (1.0 g, 5.84 mmol) in methanol (10 ml) was added NaBH₄ (666 mg, 17.5 mmol). The mixture was heated at 50 C for 30 min. After this period, the mixture was concentrated and partitioned between ethyl acetate and water. The water layer was neutralized with 2N HCl and extracted with ethyl acetate. The organic layers were dried and concentrated. Silica gel chromatography of the residue gave the title compound as a pale red solid (470 mg, 48%). ¹H-NMR (400 MHz) δ 8.12 (d, 1H), 7.23 (d, 2H), 5.20 (brs, 1H), 5.09 (m, 1H), 4.16 (d, 1H), 1.45 (d, 3H).

Example 1d—Preparation of R² Group

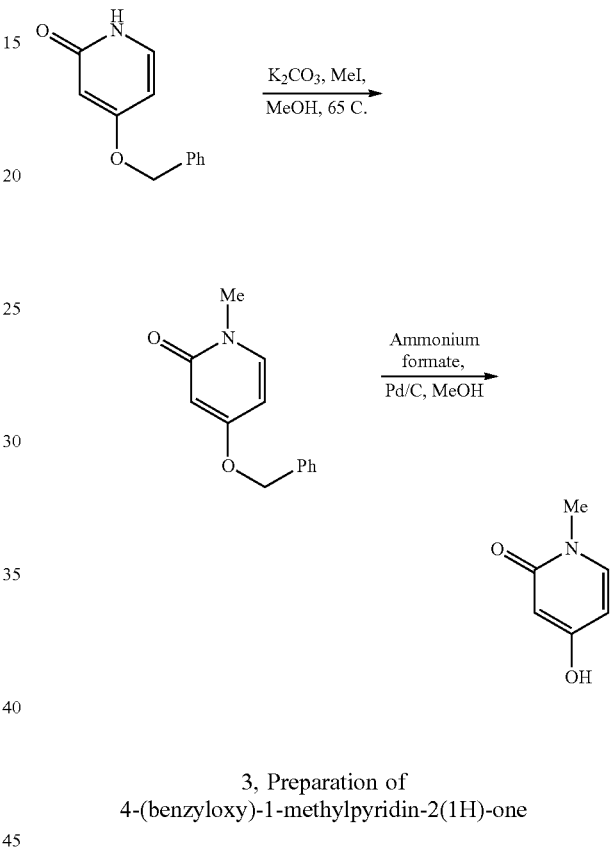

3, Preparation of 4-(benzyloxy)-1-methylpyridin-2(1H)-one

A round bottom flask equipped with condenser was charged with 4-(benzyloxy)pyridin-2(1H)-one (2.012 g, 10.0 mmol), K₂CO₃ (2.76 g, 20.0 mmol), MeI (2.129 g, 15.0 mmol), and MeOH (12.5 mL, 0.8M), then heated at 65° C. overnight, at which time LCMS showed clean conversion to product. Work-up: the reaction was filtered through celite. The filtrate was concentrated to an oil that solidified on standing. Mass recovery=1.95 g (91%). This material was used in the next stap without further purification.

4-hydroxy-1-methylpyridin-2(1H)-one

A round bottom flask was charged with 4-(benzyloxy)-1-methylpyridin-2(1H)-one (646 mg, 3.0 mmol), Pd/C 10% (160 mg), ammonium formate (568 mg, 9.0 mmol), and methanol (15 ml, 0.2M). The resulting mixture was heated at 40° C. for 1 h, at which time LCMS showed clean conversion to product. Work-up: the mixture was filtered through celite, concentrated, and purified by RPLC, giving the title compound as a colorless oil (215 mg, 57%).

Example 1d—Preparation of Compound of Formula I

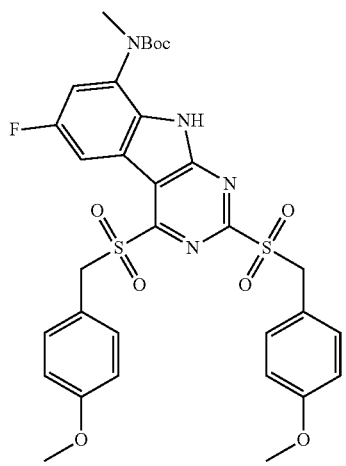

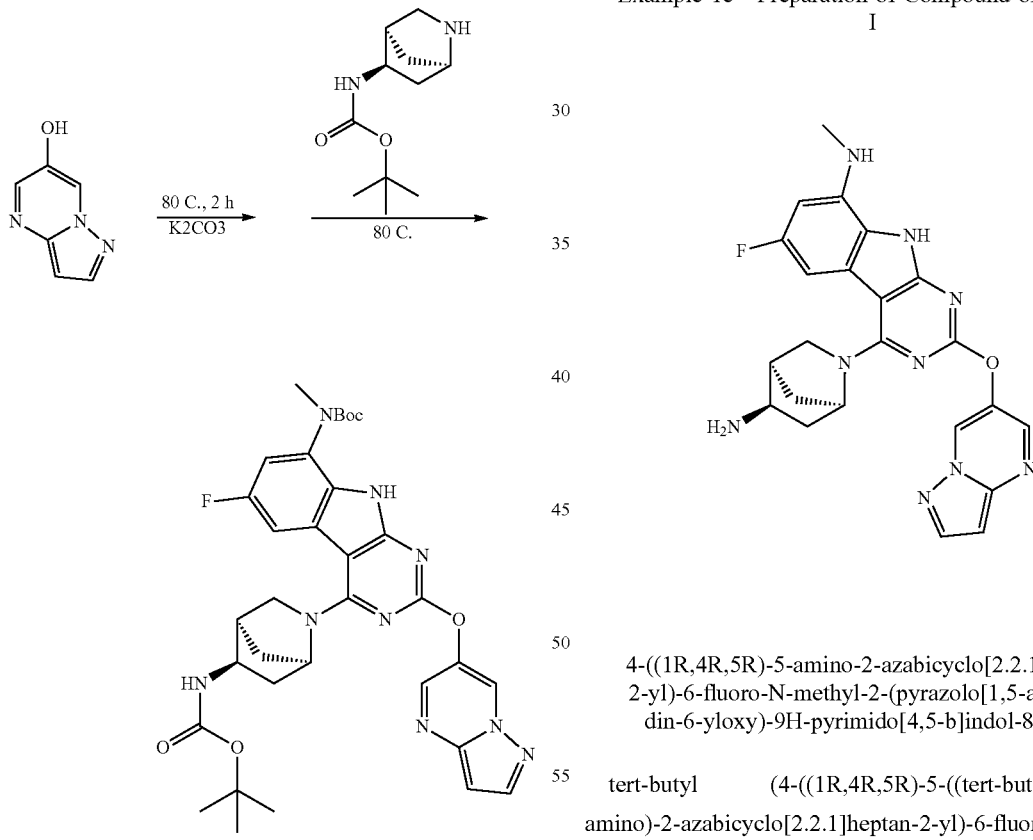

Preparation of tert-butyl (4-((1R,4R,5R)-5-((tert-butoxycarbonyl)amino)-2-azabicyclo[2.2.1]heptan-2-yl)-6-fluoro-2-(pyrazolo[1,5-a]pyrimidin-6-yloxy)-9H-pyrimido[4,5-b]indol-8-yl)(tert-butyl(4-((1R,4R,5R)

A mixture of tert-butyl (6-fluoro-2,4-bis((4-methoxybenzyl)sulfonyl)-9H-pyrimido[4,5-b]indol-8-yl)(methyl)carbamate (137 mg, 0.200 mmol), pyrazolo[1,5-a]pyrimidin-6-ol (81 mg, 0.600 mmol, preparation described below), $K_2CO_3$ (111 mg, 0.800 mmol), DMAP (2.44 mg, 0.020 mmol), and NMP (0.40 ml, 0.5M), were heated at 80° C. for 2 h at which time LCMS showed complete conversion to tert-butyl (6-fluoro-2,4-bis(pyrazolo[1,5-a]pyrimidin-6-yloxy)-9H-pyrimido[4,5-b]indol-8-yl)(methyl)carbamate.

To the dark brown mixture was added tert-butyl (1R,4R,5R)-2-azabicyclo[2.2.1]heptan-5-ylcarbamate (127 mg, 0.600 mmol). Heating was continued at the same temperature until product formation was complete by LCMS (2 h). Work-up: the reaction was cooled to room temperature, neutralized with acetic acid, and purified first by RPLC (5-95% ACN/$H_2O$), and then further by flash chromatography (5-95% EtOAc/Hex). Yield off white powder was 32 mg (24%). LCMS m/z: 660.3 (M+1).

Example 1e—Preparation of Compound of Formula I 4-((1R,4R,5R)-5-amino-2-azabicyclo[2.2.1]heptan-2-yl)-6-fluoro-N-methyl-2-(pyrazolo[1,5-a]pyrimidin-6-yloxy)-9H-pyrimido[4,5-b]indol-8-amine tert-butyl (4-((1R,4R,5R)-5-((tert-butoxycarbonyl)amino)-2-azabicyclo[2.2.1]heptan-2-yl)-6-fluoro-2-(pyrazolo[1,5-a]pyrimidin-6-yloxy)-9H-pyrimido[4,5-b]indol-8-yl)(methyl)carbamate (32 mg, 0.049 mmol), was treated with 25% TFA/$CH_2Cl_2$ (1.0 mL) for 30 min, diluted with toluene (1 ml), concentrated to an oil, purified by RPLC, yield 22 mg (79%) of the title compound as an off white solid that was determined to be a mono TFA salt. LCMS m/z: 460.2 (M+1).

Example 1f—Preparation of Compound of Formula I

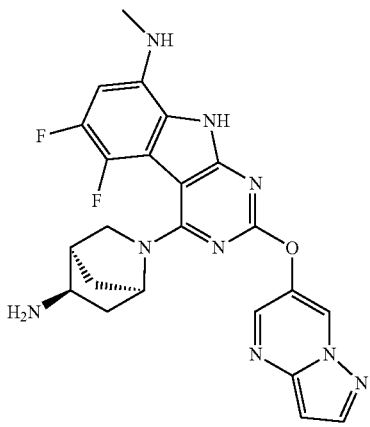 [SMILES: CNc1cc(F)c(F)c2c1[nH]c1nc(Oc3cnc4ccnn4c3)nc(N3C[C@H]4C[C@@H]3C[C@H]4N)c12]

4-((1R,4R,5R)-5-amino-2-azabicyclo[2.2.1]heptan-2-yl)-5,6-difluoro-N-methyl-2-(pyrazolo[1,5-a]pyrimidin-6-yloxy)-9H-pyrimido[4,5-b]indol-8-amine The title compound was prepared analogously to 4-((1R,4R,5R)-5-amino-2-azabicyclo[2.2.1]heptan-2-yl)-6-fluoro-N-methyl-2-(pyrazolo[1,5-a]pyrimidin-6-yloxy)-9H-pyrimido[4,5-b]indol-8-amine, where the mono flouro starting material was replaced by the difluoro core. LCMS m/z: 478.2 (M+1).

Example 1g—Preparation of Compound of Formula I

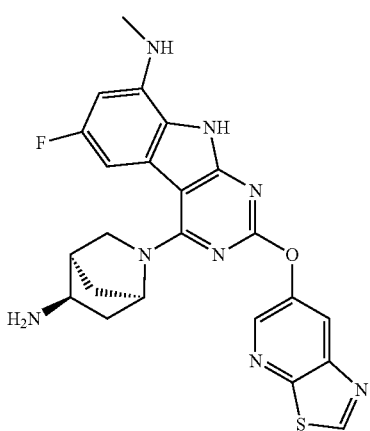 [SMILES: CNc1cc(F)cc2c1[nH]c1nc(Oc3cnc4scnc4c3)nc(N3C[C@H]4C[C@@H]3C[C@H]4N)c12]

4-((1R,4R,5R)-5-amino-2-azabicyclo[2.2.1]heptan-2-yl)-6-fluoro-N-methyl-2-(thiazolo[5,4-b]pyridin-6-yloxy)-9H-pyrimido[4,5-b]indol-8-amine The title compound was prepared analogously to 4-((1R,4R,5R)-5-amino-2-azabicyclo[2.2.1]heptan-2-yl)-6-fluoro-N-methyl-2-(pyrazolo[1,5-a]pyrimidin-6-yloxy)-9H-pyrimido[4,5-b]indol-8-amine. LCMS m/z: 477.2 (M+1).

Example 1h—Preparation of Compound of Formula I

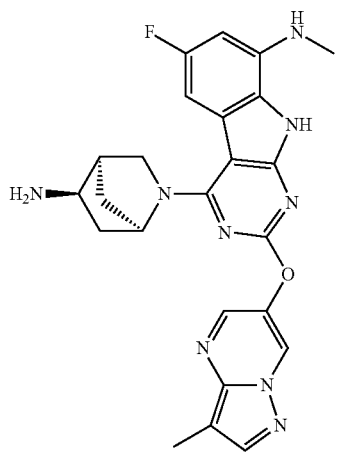 [SMILES: CNc1cc(F)cc2c1[nH]c1nc(Oc3cnc4c(C)cnn4c3)nc(N3C[C@H]4C[C@@H]3C[C@H]4N)c12]

4-((1R,4R,5R)-5-amino-2-azabicyclo[2.2.1]heptan-2-yl)-6-fluoro-N-methyl-2-(3-methylpyrazolo[1,5-a]pyrimidin-6-yloxy)-9H-pyrimido[4,5-b]indol-8-amine The title compound was prepared from the general procedure described above. LCMS m/z: 474.21 (M+1).

Example 1i—Preparation of Compound of Formula I

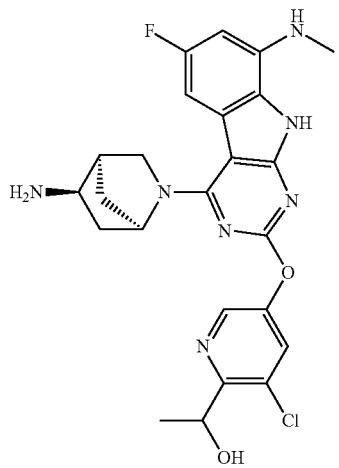 [SMILES: CNc1cc(F)cc2c1[nH]c1nc(Oc3cnc(C(C)O)c(Cl)c3)nc(N3C[C@H]4C[C@@H]3C[C@H]4N)c12]

1-(5-(4-((1R,4R,5R)-5-amino-2-azabicyclo[2.2.1]heptan-2-yl)-6-fluoro-8-(methylamino)-9H-pyrimido[4,5-b]indol-2-yloxy)-3-chloropyridin-2-yl)ethanol The title compound was prepared from the general procedure described above, yield 56 mg (30%) of the title compound as an off yellow solid. LCMS m/z: 498.20 (M+1).

Example 1j—Preparation of Compound of Formula I

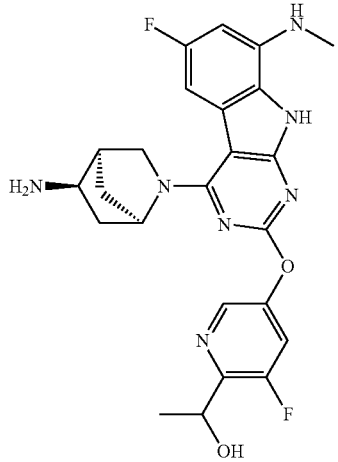 [SMILES: CNc1cc(F)cc2c1[nH]c1nc(Oc3cnc(C(C)O)c(F)c3)nc(N3C[C@H]4C[C@@H]3C[C@H]4N)c12]

1-(5-(4-((1R,4R,5R)-5-amino-2-azabicyclo[2.2.1]heptan-2-yl)-6-fluoro-8-(methylamino)-9H-pyrimido[4,5-b]indol-2-yloxy)-3-fluoropyridin-2-yl)ethanol The title compound was prepared from the general procedure described above, yield 55 mg (34%) of the title compound as an off yellow solid. LCMS m/z: 498.20 (M+1).

Example 1k—Preparation of Compound of Formula I

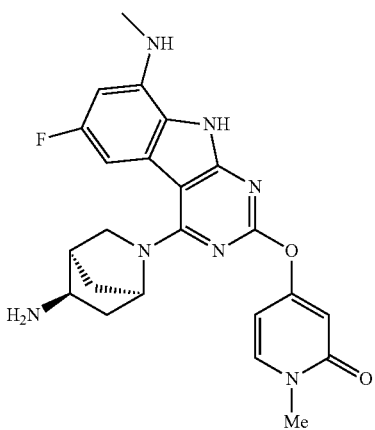 [SMILES: CNc1cc(F)cc2c1[nH]c1nc(Oc3ccn(C)c(=O)c3)nc(N3C[C@H]4C[C@@H]3C[C@H]4N)c12]

4-((4-((1R,4R,5R)-5-amino-2-azabicyclo[2.2.1]heptan-2-yl)-6-fluoro-8-(methylamino)-9H-pyrimido[4,5-b]indol-2-yl)oxy)-1-methylpyridin-2(1H)-one The title compound was prepared analogously to 4-((1R,4R,5R)-5-amino-2-azabicyclo[2.2.1]heptan-2-yl)-6-fluoro-N-methyl-2-(pyrazolo[1,5-a]pyrimidin-6-yloxy)-9H-pyrimido[4,5-b]indol-8-amine. LCMS m/z: 450.2 (M+1).

Example 1l—Preparation of Compound of Formula I

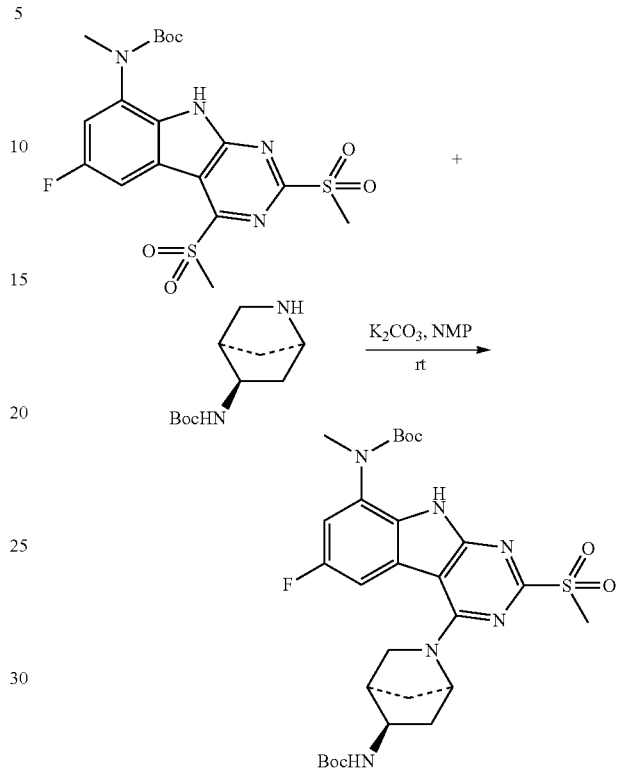

tert-butyl(4-((1R,4R,5R)-5-((tert-butoxycarbonyl)amino)-2-azabicyclo[2.2.1]heptan-2-yl)-6-fluoro-2-(methylsulfonyl)-9H-pyrimido[4,5-b]indol-8-yl)(methyl)carbamate The mixture of bis-sulfone (1.0 g, 2.12 mmol), amine (448.7 mg, 2.12 mmol) and K$_2$CO$_3$ (292.3 mg, 2.12 mmol) in NMP (7 mL) was stirred for 24 hours at room temperature. LC/MS indicated the completed reaction. Water (200 mL) was added to the mixture, and the resulting precipitate was filtered, washed with water (2×15 mL) and dried. 1.20 g of powder product was obtained (yield: 94%). MS (ESI) m/z 605 (M+H)$^+$.

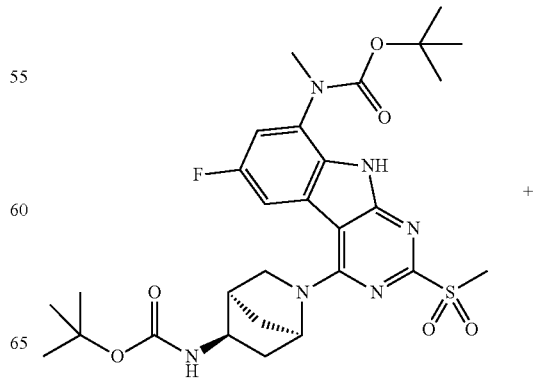

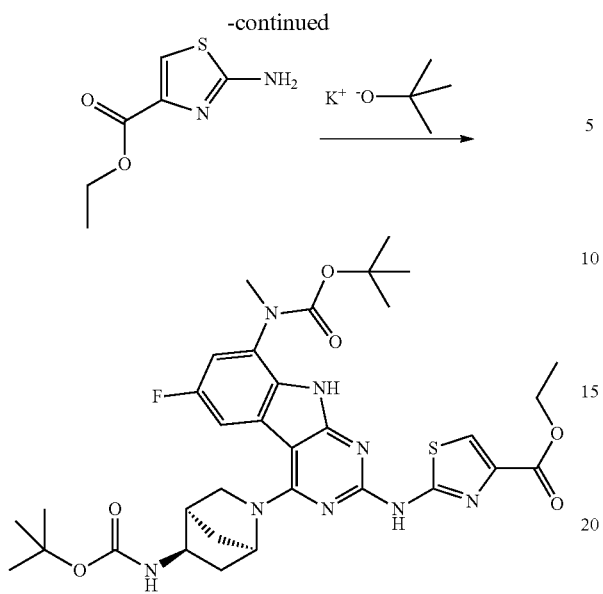

Ethyl-2-(8-(tert-butoxycarbonyl(methyl)amino)-4-(5-(tert-butoxycarbonylamino)-2-azabicyclo[2.2.1]heptan-2-yl)-6-fluoro-9H-pyrimido[4,5-b]indol-2-ylamino)thiazole-4-carboxylate The methyl sulfone starting material (30 mgs, 0.05 mmol) in DMF (0.2 mL) was added ethyl 2-aminothiazole-4-carboxylate (54 mgs, 0.3 mmol) and potassium tertbutoxide (25 mgs, 0.23 mmol). The solution was heated to 150° C. in an oil bath. After two hours, LC/MS showed formation of desired peak and consumption of starting material. Reaction was purified without aq work up. Purification was done via RP ISCO to get 8 mgs of tan solids (23%). MS (ESI) m/z 697 (M+H)$^+$.

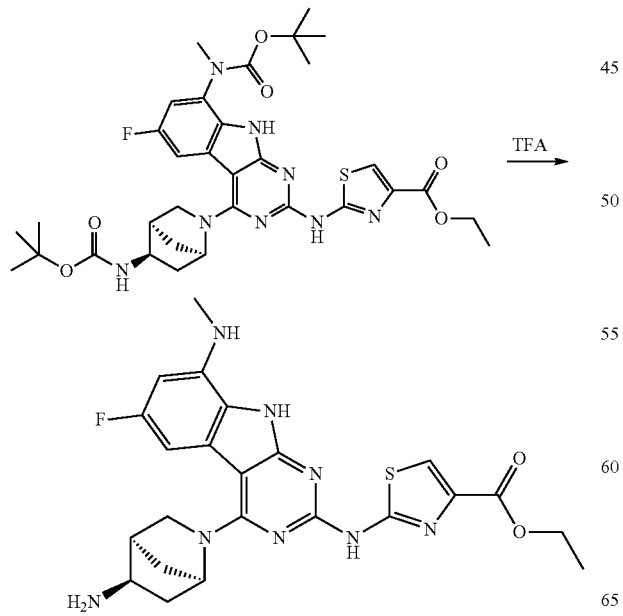

Ethyl-2-(4-(5-amino-2-azabicyclo[2.2.1]heptan-2-yl)-8-(tert-butoxycarbonyl(methyl)amino)-6-fluoro-9H-pyrimido[4,5-b]indol-2-ylamino)thiazole-4-carboxylate The starting material (25 mgs, 0.038 mmol) was treated with 2 mL of 4 N HCl in dioxane. 1 mL of MeOH was added to aid to solubility. The mixture was left at rt for 5 mins to finish. RP ISCO isolated 5.2 mgs of white solids as the TFA salt of the desired product (30%). MS (ESI) m/z 497 (M+H)$^+$.

Example 1m—Preparation of Compound of Formula I

Following the same sequence and procedure as in Example 1m, the following compound was synthesized:

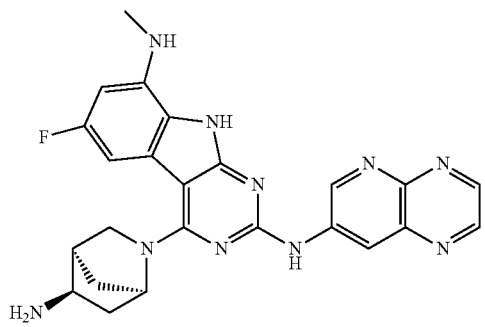 [SMILES: CNc1cc(F)cc2c1[nH]c1nc(Nc3cnc4nccnc4c3)nc(N3C[C@H]4C[C@@H]3C[C@H]4N)c12]

4-(5-amino-2-azabicyclo[2.2.1]heptan-2-yl)-6-fluoro-N8-methyl-N2-(pyrido[3,2-b]pyrazin-7-yl)-9H-pyrimido[4,5-b]indole-2,8-diamine The title compound was prepared from the general procedure described above. LCMS m/z: 471.24 (M+1).

Example 1n—Preparation of Compound of Formula I

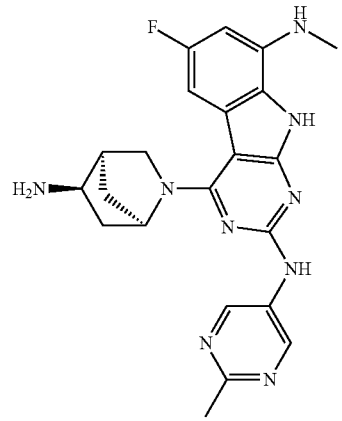 [SMILES: CNc1cc(F)cc2c1[nH]c1nc(Nc3cnc(C)nc3)nc(N3C[C@H]4C[C@@H]3C[C@H]4N)c12]

4-((1R,4R,5R)-5-amino-2-azabicyclo[2.2.1]heptan-2-yl)-6-fluoro-N8-methyl-N2-(2-methylpyrimidin-5-yl)-9H-pyrimido[4,5-b]indole-2,8-diamine The title compound was prepared from the general procedure described above. LCMS m/z: 434.44 (M+1).

Example 1o—Preparation of Compound of Formula I

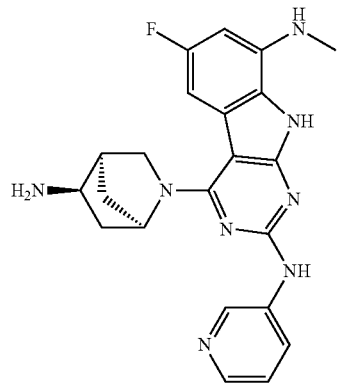 [SMILES: CNc1cc(F)cc2c1[nH]c1nc(Nc3cccnc3)nc(N3C[C@H]4C[C@@H]3C[C@H]4N)c12]

4-((1R,4R, S5R)-5-amino-2-azabicyclo[2.2.1]heptan-2-yl)-6-fluoro-N8-methyl-N2-(pyridin-3-yl)-9H-pyrimido[4,5-b]indole-2,8-diamine. The title compound was prepared from the general procedure described above. LCMS m/z: 419.22 (M+1).

Example 1p—Preparation of Compound of Formula I

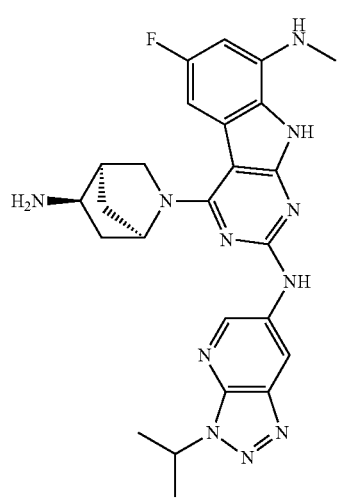 [SMILES: CNc1cc(F)cc2c1[nH]c1nc(Nc3cnc4c(c3)nnn4C(C)C)nc(N3C[C@H]4C[C@@H]3C[C@H]4N)c12]

4-((1R,4R,5R)-5-amino-2-azabicyclo[2.2.1]heptan-2-yl)-6-fluoro-N2-(3-isopropyl-3H-[1,2,3]triazolo[4,5-b]pyridin-6-yl)-N8-methyl-9H-pyrimido[4,5-b]indole-2,8-diamine.

The title compound was prepared from the general procedure described above. LCMS m/z: 502.26 (M+1).

Example 1q—Preparation of Compound of Formula I

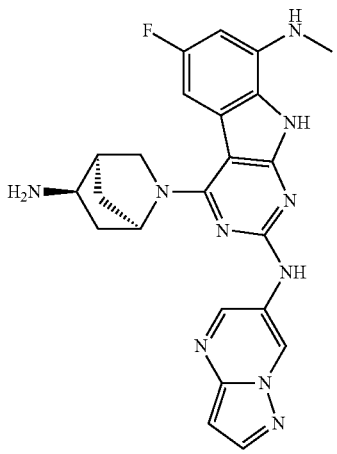

4-((1R,4R,5R)-5-amino-2-azabicyclo[2.2.1]heptan-2-yl)-6-fluoro-N8-methyl-N2-(pyrazolo[1,5-a]pyrimidin-6-yl)-9H-pyrimido[4,5-b]indole-2,8-diamine. The title compound was prepared from the general procedure described above. LCMS m/z: 459.21 (M+1).

Example 1r—Preparation of Compound of Formula I

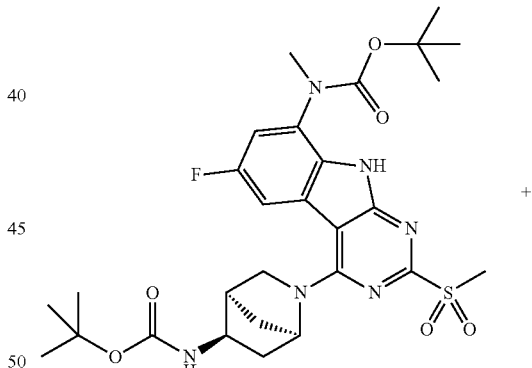

+

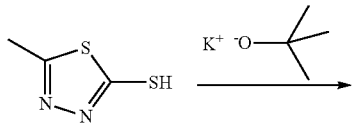

187
-continued

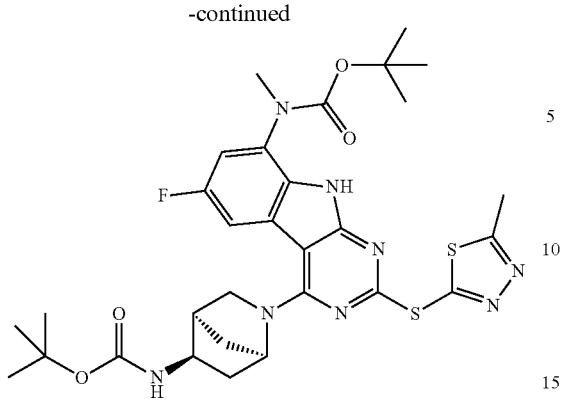

The methyl sulfone starting material (40 mgs, 0.06 mmol) in DMF (0.3 mL) was added 5-methyl-1,3,4-thiadiazole-2-thiol (20 mgs, 0.152 mmol) and potassium tertbutoxide (17 mgs, 0.152 mmol). The solution was heated to 150° C. in an oil bath. After two hours, LC/MS showed formation of desired peak and consumption of starting material. Reaction was purified without aq work up. Purification was done via RP ISCO to get 25 mgs of tan solids (58%). LC/MS 657 (M$^+$+1).

Example 1s—Preparation of Compound of Formula I

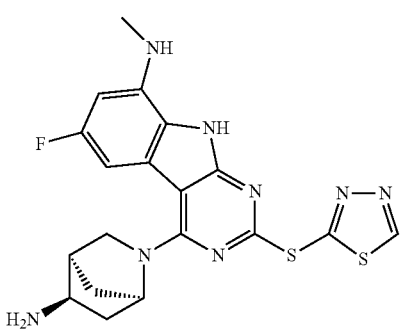 [SMILES: CNc1cc(F)cc2c1[nH]c1nc(Sc3nncs3)nc(N3C[C@H]4C[C@@H]3C[C@H]4N)c12]

The starting material (25 mgs, 0.038 mmol) was treated with 2 mL of 4 N HCl in dioxane. 1 mL of MeOH was added to aid to solubility. The mixture was left at rt for 5 mins to finish. RP ISCO isolated 5.2 mgs of white solids as the TFA salt of the desired product (30%). LC/MS 557 (M$^+$+1).

188

Example 1t—Preparation of Compound of Formula I

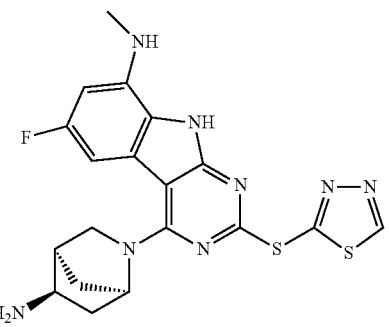

The title compound was prepared from the general procedure described above. LCMS m/z: 443.12 (M+1).

Example 1u—Preparation of Compound of Formula I

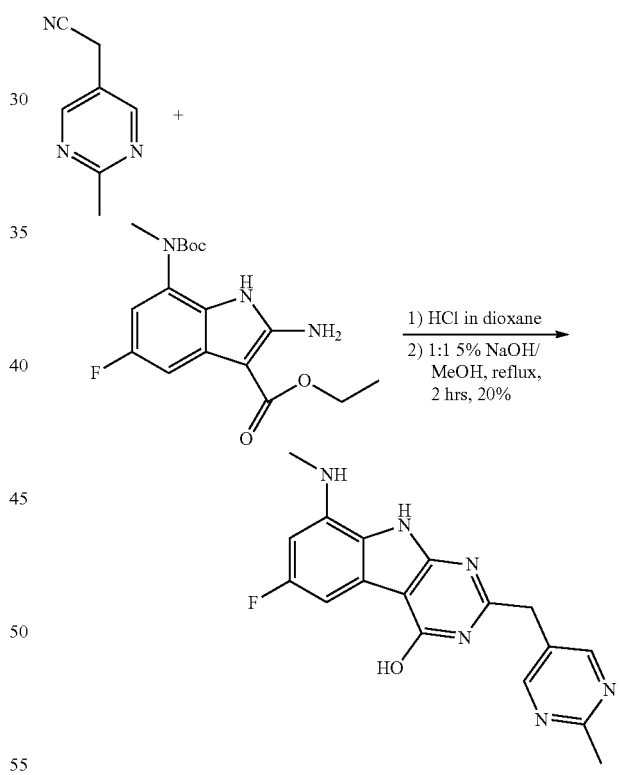

6-Fluoro-8-(methylamino)-2-((2-methylpyrimidin-5-yl)methyl)-9H-pyrimido[4,5-b]indol-4-ol The ethyl 2-amino-7-((tert-butoxycarbonyl)(methyl)amino)-5-fluoro-1H-indole-3-carboxylate (3.51 g, 10 mmol) and 2-(2-methylpyrimidin-5-yl)acetonitrile (1.50 g, 1 mmol, 1.1 equi.) was added into 50 ml 4M dioxane solution, the mixture was stirred at room temperature for 24 hours, then removed excess dioxane solvent, the residue was re-dissolved into 50 ml 5% NaOH in H2O and 50 ml Methanol, the solution was heated to reflux for 2 hours, then the solution was neutralized with 6M HCl, the resulting solution was concentrated. The residue was purified by reverse phase column to provide the desired product 6-fluoro-8-(methylamino)-2-((2-methylpyrimidin-5-yl)methyl)-9H-pyrimido[4,5-b]indol-4-ol (680 mg, 20% yield in over two steps), MS (ESI) m/z 339 (M+H)+.

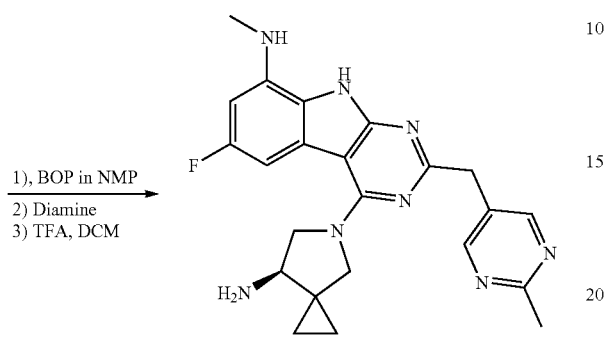

(R)-4-(7-amino-5-azaspiro[2.4]heptan-5-yl)-6-fluoro-N-methyl-2-((2-methylpyrimidin-5-yl)methyl)-9H-pyrimido[4,5-b]indol-8-amine (6)

To a solution of 6-fluoro-8-(methylamino)-2-((2-methylpyrimidin-5-yl)methyl)-9H-pyrimido[4,5-b]indol-4-ol (34 mg, 0.1 mmol) in 5 ml NMP under ice water bath was added into 42 mg (0.3 mmol) K2CO3, followed 45 mg BOP (0.1 mmol), the solution was stirred for 30 min, then (R)-tert-butyl 5-azaspiro[2.4]heptan-7-ylcarbamate (22 mg, 0.1 mmol) was added to above solution, then the mixture was warmed to 40 degree and stirred for overnight (12 hours), the reaction mixture was purified by HPLC to provide (R)-tert-butyl (5-(6-fluoro-8-(methylamino)-2-((2-methylpyrimidin-5-yl)methyl)-9H-pyrimido[4,5-b]indol-4-yl)-5-azaspiro[2.4]heptan-7-yl)carbamate, 33 mg, 60% yield).

The Boc protected compounds 5 (30 mg) was dissolved into 2 ml 50% TFA in DCM, the mixture was stirred for one 1 hours, then concentrated, the residue was purified by reverse HPLC to provide final compound 6(12 mg, yield 46%).

Example 1v—Preparation of R⁴

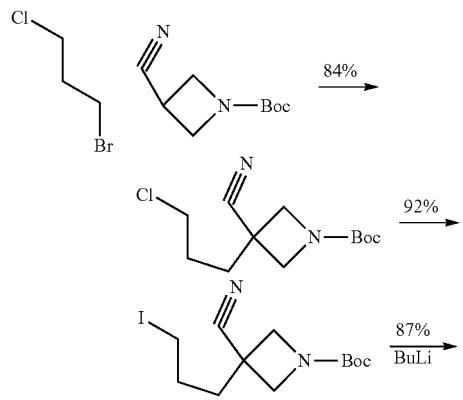

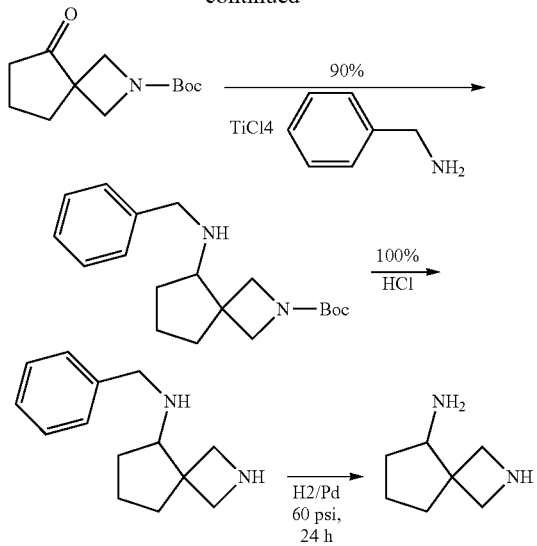

tert-butyl 3-(3-chloropropyl)-3-cyanoazetidine-1-carboxylate

A solution of tert-butyl 3-cyanoazetidine-1-carboxylate (3.15 g, 17.3 mmol), in THF (70 ml), at −78 C, was treated with lithium bis(trimethylsilyl)amide 1M (19.0 mL, 19.0 mmol). After 30 min 1-bromo-3-chloropropane (3.40 mL, 34.6 mmol) was added. The mixture was slowly warmed to RT. After 1 hr the reaction was quenched with saturated aqueous ammonium chloride, extracted with ethyl ether, dried over sodium sulfate, concentrated, purified by flash chromatography with ethyl acetate/hexanes, yielding 3.75 g (84% yield) of mmol the product as a colorless oil. LCMS m/z: 259.7 (M+1).

tert-butyl 3-cyano-3-(3-iodopropyl)azetidine-1-carboxylate

A solution of tert-butyl 3-(3-chloropropyl)-3-cyanoazetidine-1-carboxylate (3.75 g, 14.5 mmol), in acetone (60 ml), was treated with sodium iodide (6.52 g, 43.5 mmol), then refluxed overnight. The reaction was diluted with ether, washed with water, dried over sodium sulfate, concentrated, and purified by flash chromatography with ethyl acetate/hexanes, yielding 4.68 g (92% yield) of the product as a colorless oil. LCMS m/z: 351.2 (M+1).

tert-butyl 5-oxo-2-azaspiro[3.4]octane-2-carboxylate

A solution of tert-butyl 3-cyano-3-(3-iodopropyl)azetidine-1-carboxylate (4.68 g, 13.4 mmol), in dry THF (54 ml), was cooled to −78 C, then slowly treated with n-butyllithium 2.5M in hexanes (10.7 mL, 26.7 mmol). TLC after 15 minutes shows no starting material. The reaction was quenched with acetic acid (1.53 mL, 26.7 mmol), warmed to room temperature, diluted with ether, washed with brine, dried over sodium sulfate, concentrated, and purified by flash chromatography with ethyl acetate/hexanes, yielding 2.61 g (87% yield) of product. LCMS m/z: 226.3 (M+1).

tert-butyl 5-(benzylamino)-2-azaspiro[3.4]octane-2-carboxylate 2,2,2-trifluoroacetate A solution of tert-butyl 5-oxo-2-azaspiro[3.4]octane-2-carboxylate (0.243 g, 1.08 mmol), and benzylamine (0.139 g, 1.29 mmol) in dry methylene chloride (4.3 ml), was cooled to 0 C, then slowly treated with titanium tetrachloride (0.102 g, 0.539 mmol), then heated to reflux. After 3 h the reaction was cooled to room temperature, diluted with ether (white ppt forms), and filtered with the aid of celite. The light yellow filtrate was concentrated to an oil, dissolved in MeOH (5 mL), cooled to 0 C with an ice bath, then treated with sodium borohydride (0.041 g, 1.08 mmol). LCMS after 1 hr shows a major peak corresponding to product. The reaction was diluted with DMF (0.75 mL), concentrated, and purified by reverse phase liquid chromatography (5-95% acetonitrile/water), giving the title compound as a light yellow solid (420 mg, 90% yield) after concentration by rotary evaporator. LCMS m/z: 317.4 (M+1).

N-benzyl-2-azaspiro[3.4]octan-5-amine dihydrochloride

A flask charged with methanol (5 mL) was treated with acetyl chloride (0.5 mL), followed by tert-butyl 5-(benzylamino)-2-azaspiro[3.4]octane-2-carboxylate 2,2,2-trifluoroacetate (0.420 mg, 0.98 mmol). After 30 min the mixture is stripped of solvent giving product as a white powder (280 mg, quantitavive yield). LCMS m/z: 217.3 (M+1). 2-azaspiro[3.4]octan-5-amine dihydrochloride:

A Parr shaker flask was charged with N-benzyl-2-azaspiro [3.4]octan-5-amine dihydrochloride (286 mg, 0.99 mmol), 10% Pd/C (300 mg), and methanol (10 mL), then shook under a hydrogen atmosphere at 60 psi. After 24 h the mixture was filtered through celite, giving product as a white powder (197 mg, quantitavive yield). LCMS m/z: 127.2 (M+1).

Example 1w—Preparation of Compounds of Formula I

Additional compounds were prepared by the general procedure as below:

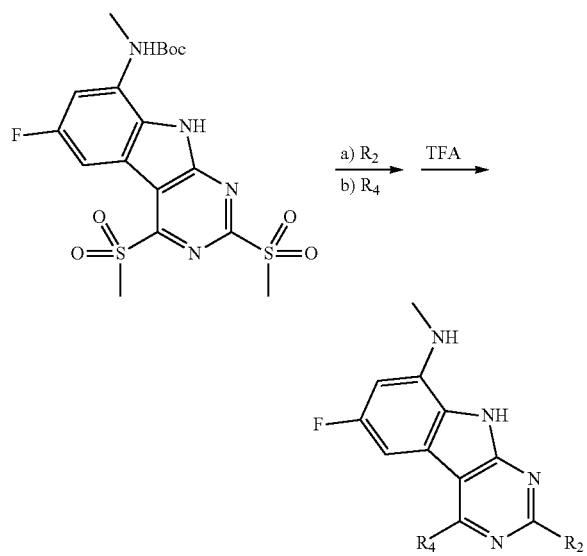

The bissulfone was first treated with R² and K₂CO₃, then following by addition of R⁴ in one pot. The final product was obtained by Boc deprotection with TFA.

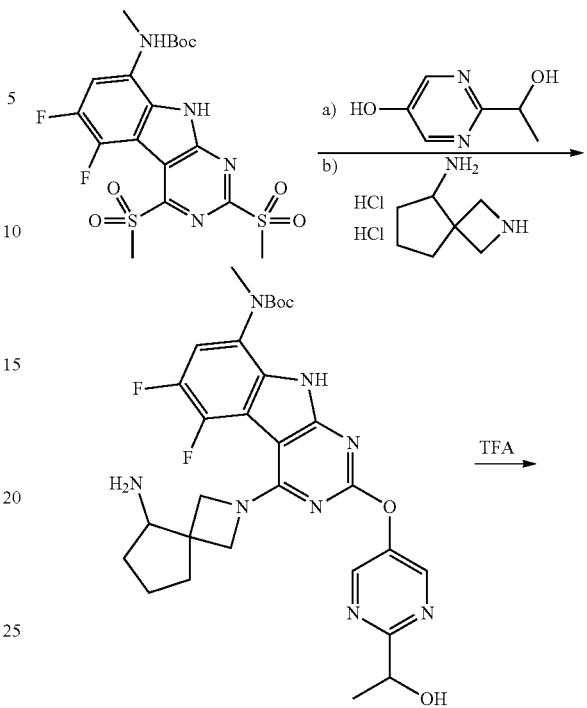

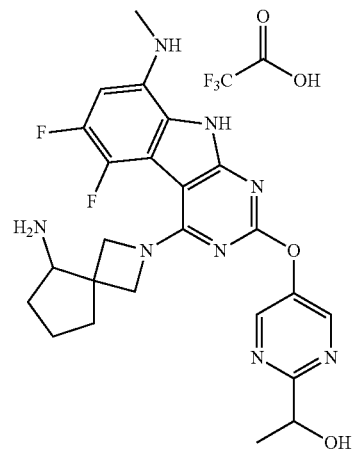

1-(5-((4-(5-amino-2-azaspiro[3.4]octan-2-yl)-5,6-difluoro-8-(methylamino)-9H-pyrimido[4,5-b]indol-2-yl)oxy)pyrimidin-2-yl)ethanol A mixture of 5,6-difluoro-N-methyl-2,4-bis(methylsulfonyl)-9H-pyrimido[4,5-b]indol-8-amine (172 mg, 0.352 mmol), 2-(1-hydroxyethyl)pyrimidin-5-ol (148 mg, 1.055 mmol), potassium carbonate (194 mg, 1.406 mmol), and NMP (0.70 mL) were heated at 90° C. for 30 min, then treated with 2-azaspiro[3.4]octan-5-amine dihydrochloride (140 mg, 0.703 mmol). After 1 h the reaction was complete by LCMS. The crude mixture was purified directly reverse phase liquid chromatography (5-95% acetonitrile/water), giving the title compound as a light yellow solid (73 mg, 29% yield) after lyophylization. LCMS m/z: 497.2 (M+1).

Example 1x—Preparation of R²

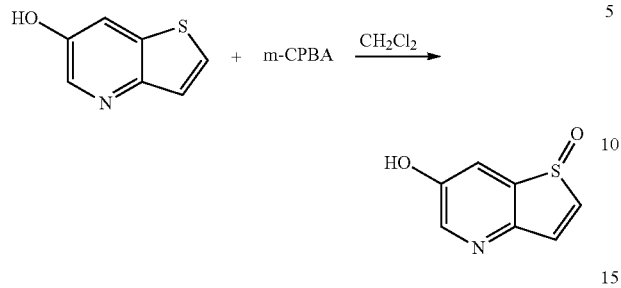

To thieno[3,2-b]pyridin-6-ol (500 mg, 3.31 mmol) in DCM (30 mL) was added m-CPBA (1.14 g, 4.97 mmol) at rt and stirred at rt for overnight. The reaction was washed with sat. NaHCO3 and extracted into ethyl acetate. The organic layer was washed with brine, dried and concentrated. The product was purified by silica gel column chromatography. yield: 80%.

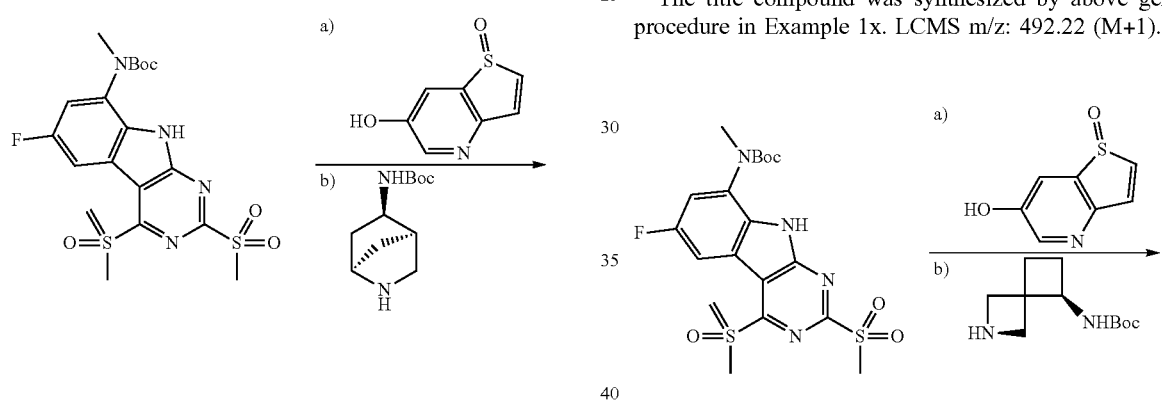

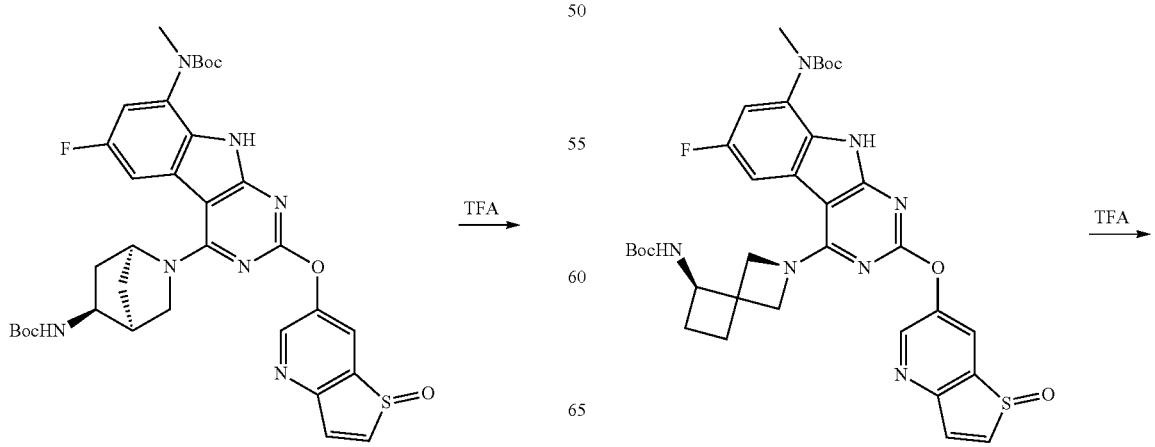

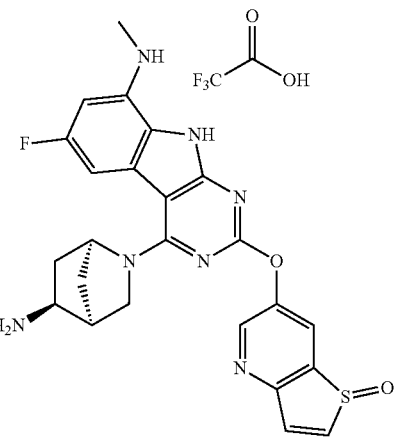

Example 1y—Preparation of Compound of Formula I

The title compound was synthesized by above general procedure in Example 1x. LCMS m/z: 492.22 (M+1).

Example 1aa—Preparation of Compound of Formula I

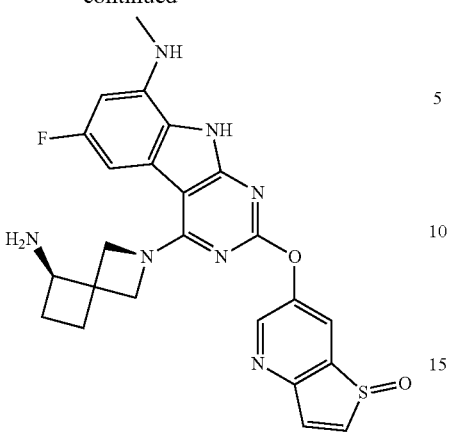

The title compound was synthesized by above general procedure Example 1x. LCMS m/z: 492.15 (M+1).

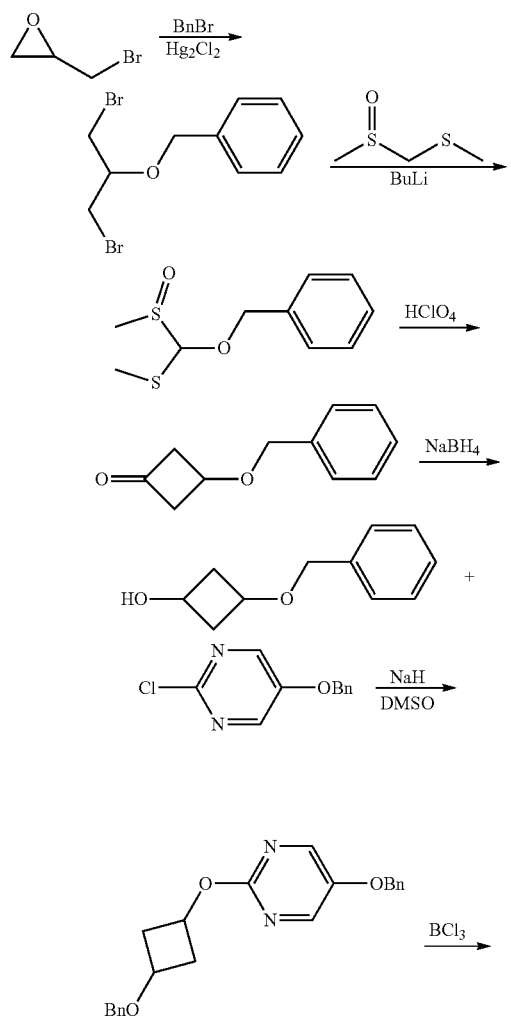

Example 1bb—Preparation of $R^2$

Synthesis of 2-bromo-1-(bromomethyl)-1-(phenylmethoxy)ethane

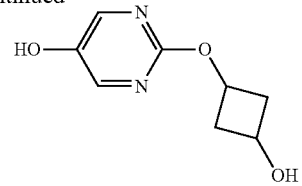

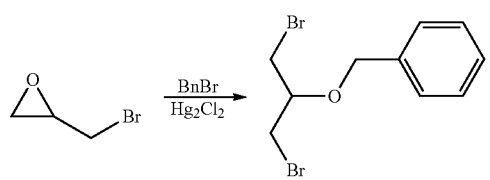

The mixture of 1 (60.1 g, 0.47 mol), benzyl bromide (80 g, 0.47 mol) and $Hg_2Cl_2$ (100 mg, 0.2 mmol) was heated to 150° C. over night. TLC showed the reaction was completed. The product 2 (98 g, 70% yield) was obtained by distillation (180° C.) in vacuum as a colorless oil.

$^1$H NMR (400 MHz, $CDCl_3$):7.37-7.28 (m, 5H), 4.65 (s, 2H), 3.82-3.77 (m, 1H), 3.56 (d, 4H, J=5.2 Hz).

Synthesis of 1-(methylsulfinyl)-1-methylthio-3-(phenylmethoxy)cyclobutane

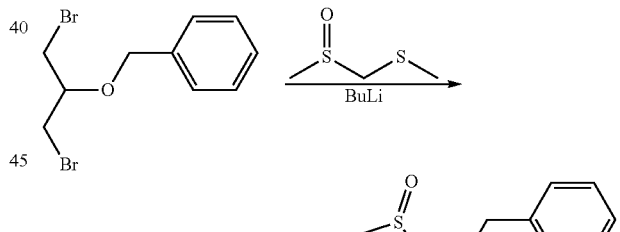

To the mixture of 3 (45.1 g, 0.36 mol) in THF (400 mL) was added n-BuLi (145 mL, 0.36 mol, 2.5 M) at −10° C. under $N_2$ drop wise. It was stirred further 2 h at this temperature. And then it was cooled to −78° C. and the mixture of 2 (46.2 g, 0.15 mol) in THF (100 mL) was added drop wise over 0.5 h. The result mixture was stirred further 2 h at −78° C. and over night at r.t. It was quenched by the addition of $H_2O$ (100 mL) and the mixture was extracted with EtOAc (300 mL*3). The combined extracts were dried over $Na_2SO_4$ and concentrated in vacuo to give the crude product. It was purified by column chromatography (Eluan: EtOAc/Pet.ether=1/2, v/v) to give the product 4 (30 g, 73% yield) as a yellow oil.

$^1$H NMR (400 MHz, $CDCl_3$):7.36-7.26 (m, 5H), 4.47 (d, 2H), 4.38-4.31 (m, 0.6H), 4.21-4.18 (m, 0.4H), 3.10-2.98

(m, 0.8H), 2.78-2.64 (m, 1.2H), 2.55 (s, 1.2H), 2.44 (s, 1.8H), 2.42-2.15 (m, 2H), 2.12 (d, 3H).

Synthesis of 3-(phenylmethoxy)cyclobutan-1-one

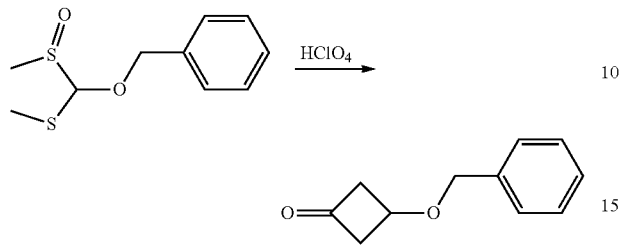

To a solution of compound 4 (30 g, 0.11 mol) in dry ether (500 mL) was HClO4 (22.5 mL, 35%) at 0° C. drop wise, while keep the temperature bellow 10° C. It was stirred further 2 h at 0° C. and over night at r.t. Solid NaHCO3 and MgSO4 were added and the resulting mixture was stirred further 0.5 h at r.t. It was filtered and the cake was washed with ether. The filtrate was concentrate in vacuo to give the crude product. It was purified by column chromatography (Eluant: EtOAc/Pet.ether=1/4, v/v) to give the product 5 (14.0 g, 72% yield) as a yellow oil.

$^1$H NMR (400 MHz, CDCl$_3$): 7.39-7.25 (m, 5H), 4.52 (s, 2H), 4.40-4.34 (m, 1H), 3.26-3.10 (m, 4H).

Synthesis of 3-(phenylmethoxy)cyclobutan-1-ol

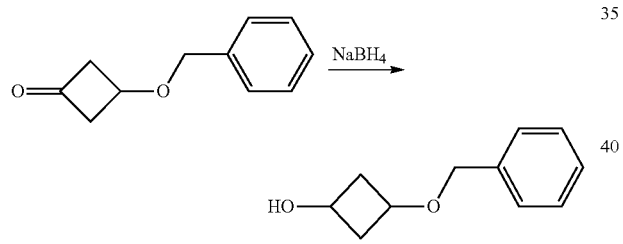

To the mixture of 5 (14.0 g, 79.46 mmol) in EtOH (150 mL) was added NaBH4 (3.32 g, 87.40 mmol) at 0° C. over 0.5 h. The resulting mixture was stirred further 2 h at 0° C. and TLC showed the reaction was completed. The solvent was removed in vacuo and the residue was diluted with MeOH (100 mL) and quenched by HCl (1M). The organic solvent was removed in vacuo and the residue was extracted with EtOAc (200 mL*3). The combined extracts were dried over Na2SO4 and concentrated in vacuo to give the crude product. It was purified by column chromatography (Eluant: EtOAc/Pet.ether=1/4, v/v) to give the product 6 (14 g, 99% yield) as a yellow oil.

$^1$H NMR (400 MHz, CDCl$_3$): 7.39-7.27 (m, 5H), 4.43 (s, 2H), 3.94-3.83 (m, 1H), 3.68-3.59 (m, 1H), 2.76-2.67 (m, 2H), 2.37 (br, 1H), 2.05-1.89 (m, 2H).

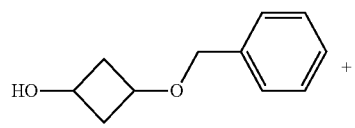

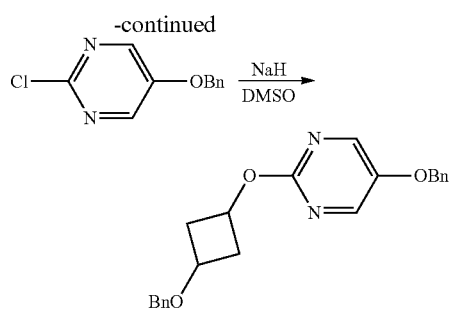

Synthesis of 5-(phenylmethoxy)-2-[3-(phenylmethoxy)cyclobutoxy]pyrimidine

To the mixture of 6 (10.5 g, 58.93 mmol) in DMSO (100 mL) was added NaH (3.06 g, 60%, 76.61 mmol) at r.t. The resulting mixture was stirred for 0.5 h at r.t, and then the mixture of 7 (13.0 g, 58.93 mmol) in DMSO (50 mL) was added drop wise over 10 min. The whole mixture was stirred further 0.5 h, TLC showed the reaction was completed. It was quenched by the addition of H2O (200 mL) and the mixture was extracted with EtOAc (200 mL*3). The combined extracts were dried over Na2SO4 and concentrated in vacuo to give the crude product. It was purified by column chromatography (Eluant: EtOAc/Pet.ether=1/5, v/v) to give the product 8 (10.0 g, 47% yield) as a white solid. [0308]$^1$H NMR (400 MHz, CDCl$_3$): 8.19 (s, 2H), 7.38-7.25 (m, 10H), 5.05 (s, 2H), 4.76-4.68 (m, 1H), 4.43 (s, 2H), 3.82-3.75 (m, 1H), 2.87-2.81 (m, 2H), 2.24-2.17 (m, 2H).

Synthesis of 2-(3-hydroxycyclobutoxyl)pyrimidin-5-ol

To the mixture of 8 (8.84 g, 24.42 mmol) in dry DCM (250 mL) was added BCl3 (100 mL, 1M in DCM, 0.1 mol) at −20° C. under N2. The resulting mixture was stirred further 0.5 h at −20° C. TLC showed the reaction was completed, and then it was quenched by the addition of MeOH (20 mL). The solvent was removed in vacuo to give the crude product. It was diluted with DCM (50 ml) and the solid was filtered out by filtration. The cake was suspended in H2O (20 mL) and filtered, dried in vacuo to give the product (2.2 g, 50% yield) as a white solid.

$^1$H NMR (400 MHz, DMSO-d$_6$): 9.76 (s, 1H), 8.12 (s, 2H), 5.07 (br, 1H), 4.59-4.52 (m, 1H), 3.85-3.78 (m, 1H), 2.76-2.72 (m, 2H), 1.91-1.85 (m, 2H). LCMS [mobile phase: from 50% water (0.1% TFA) and 50% CH3CN to 5% water (0.1% TFA) and 95% CH₃CN in 6.0 min, finally under these conditions for 0.5 min.] purity is >95%, Rt=1.84 min; MS Calcd.: 182.2; MS Found: 183.1

Example 1cc—Preparation of Compound of Formula I

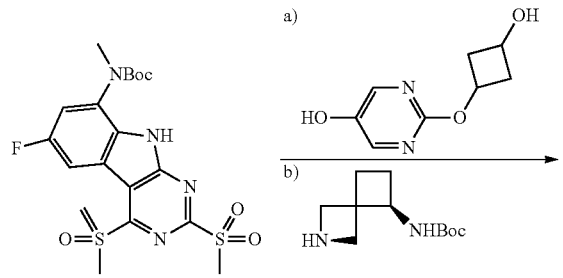

Example 1dd—Preparation of Compound of Formula I

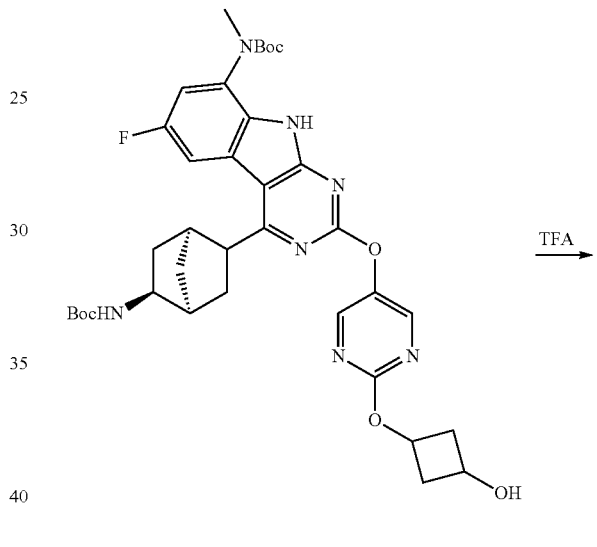

The title compound was synthesized by the above general procedure in Example 1x. LCMS m/z: 507.12 (M+1).

The title compound was synthesized by the above general procedure. LCMS m/z: 507.21 (M+1).

201
Example 1ee—Preparation of Compound of Formula I

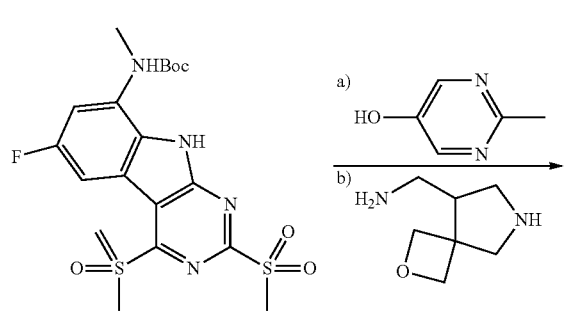

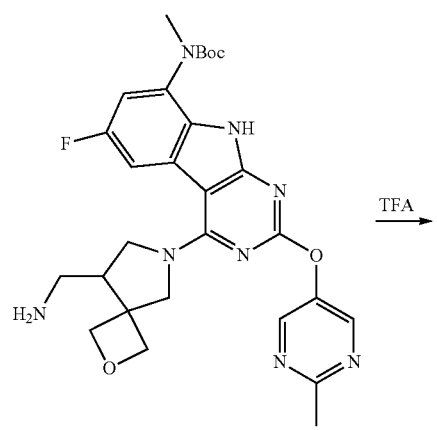

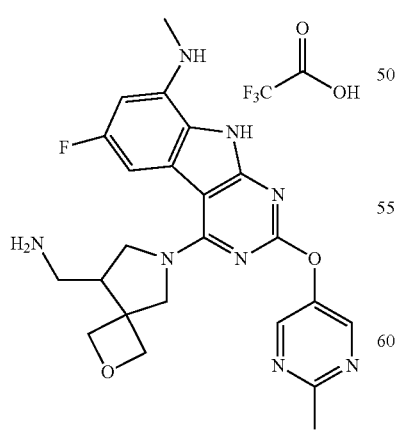

The title compound was synthesized by the above general procedure. LCMS m/z: 465.50 (M+1).

202
Example 1ff—Preparation of Compound of Formula I

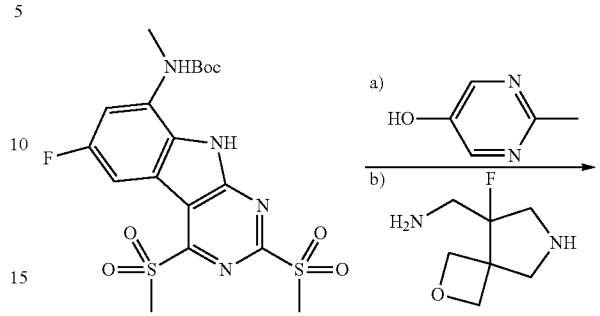

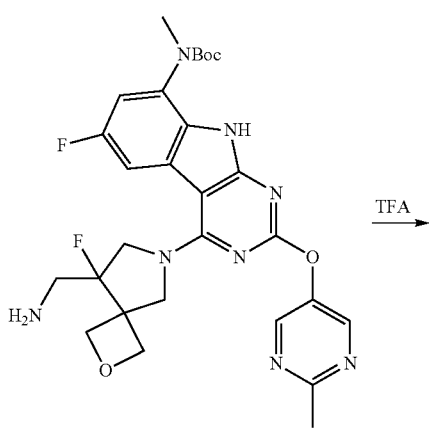

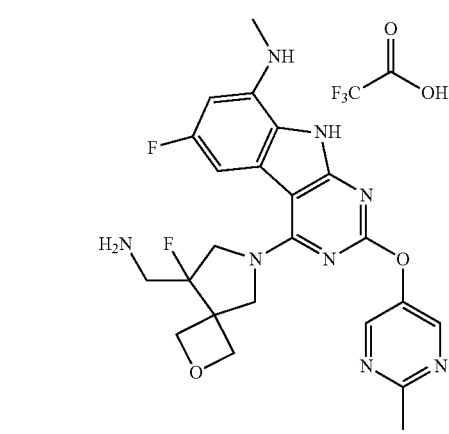

The title compound was synthesized by the above general procedure. LCMS m/z: 483.49 (M+1).

Example 1gg—Preparation of Compounds of Formula I with N-Linker

The following compounds have also been made using the procedures herein.

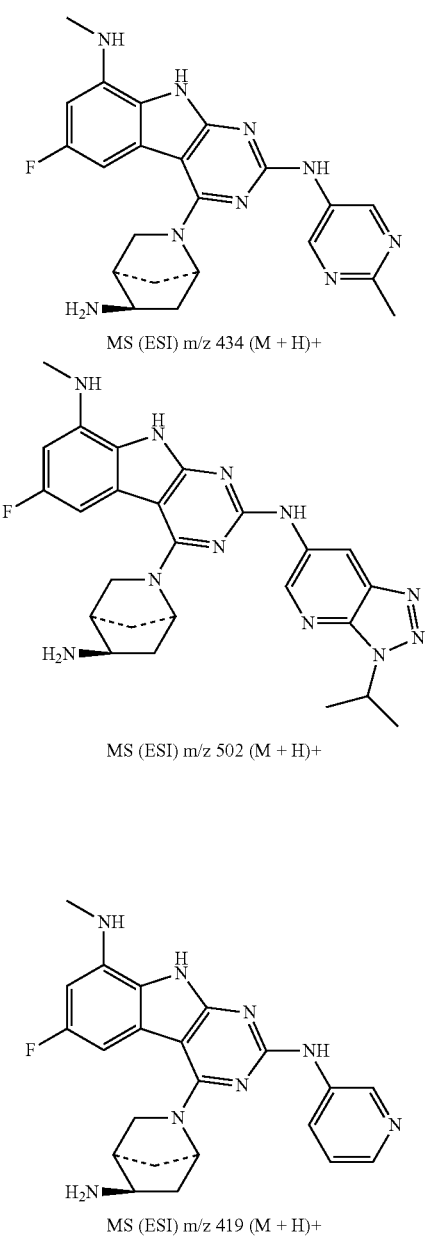

MS (ESI) m/z 434 (M + H)+

MS (ESI) m/z 502 (M + H)+

MS (ESI) m/z 419 (M + H)+

MS (ESI) m/z 459 (M + H)+

Example 1hh—Preparation of Compounds of Formula I

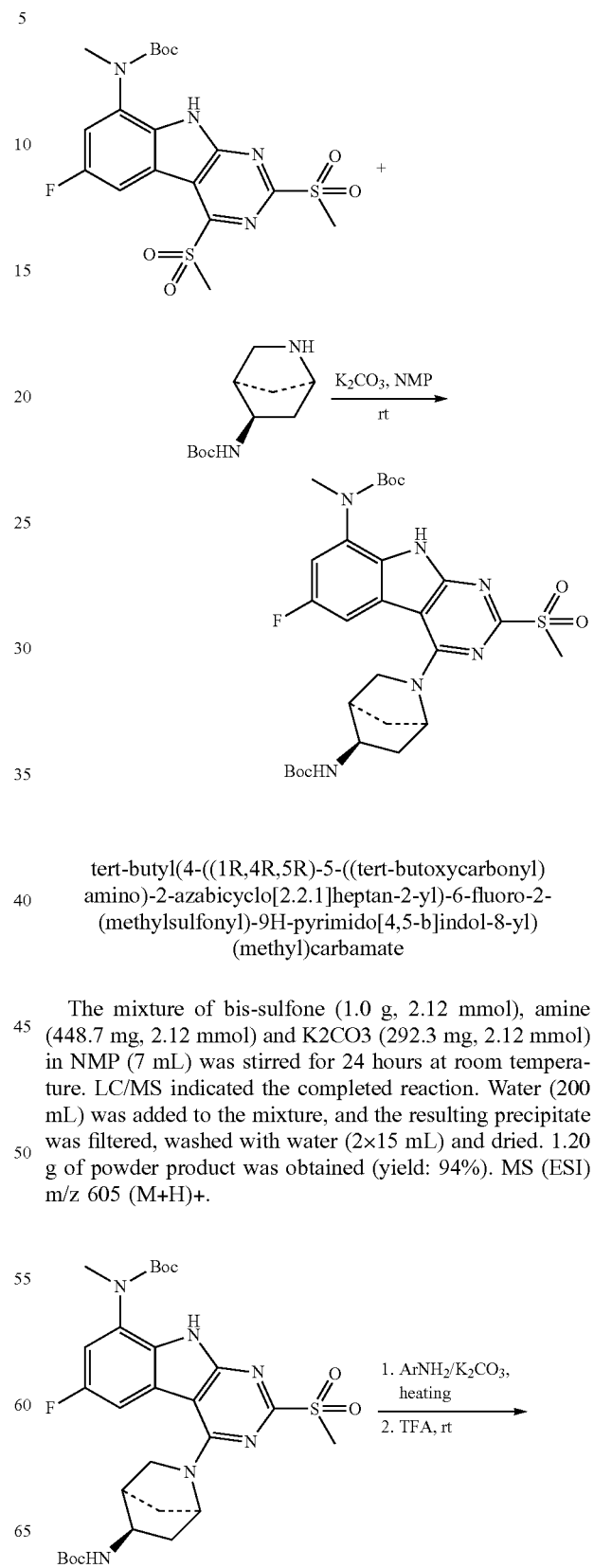

tert-butyl(4-((1R,4R,5R)-5-((tert-butoxycarbonyl)amino)-2-azabicyclo[2.2.1]heptan-2-yl)-6-fluoro-2-(methylsulfonyl)-9H-pyrimido[4,5-b]indol-8-yl)(methyl)carbamate The mixture of bis-sulfone (1.0 g, 2.12 mmol), amine (448.7 mg, 2.12 mmol) and K2CO3 (292.3 mg, 2.12 mmol) in NMP (7 mL) was stirred for 24 hours at room temperature. LC/MS indicated the completed reaction. Water (200 mL) was added to the mixture, and the resulting precipitate was filtered, washed with water (2×15 mL) and dried. 1.20 g of powder product was obtained (yield: 94%). MS (ESI) m/z 605 (M+H)+.

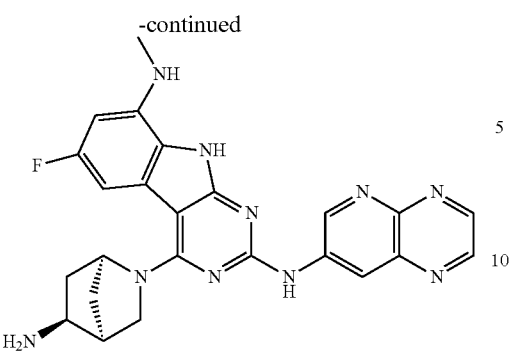

The mixture of mono-sulfone (60.5 mg, 0.1 mmol), hetero aromatic amine (1.0 mmol), and K₂CO₃ (138.1 mg, 1.0 mmol) in NMP (0.5 mL) was heated to 140 C for 17 hrs, cooled to room temperature, and TFA (15 mL) was added and stirred for 5 minutes. After removal of the solvent, prep-HPLC of the residue gave the desired product. MS (ESI) m/z 471.22 (M+H)+.

Example 1ii—Preparation of Compounds of Formula I

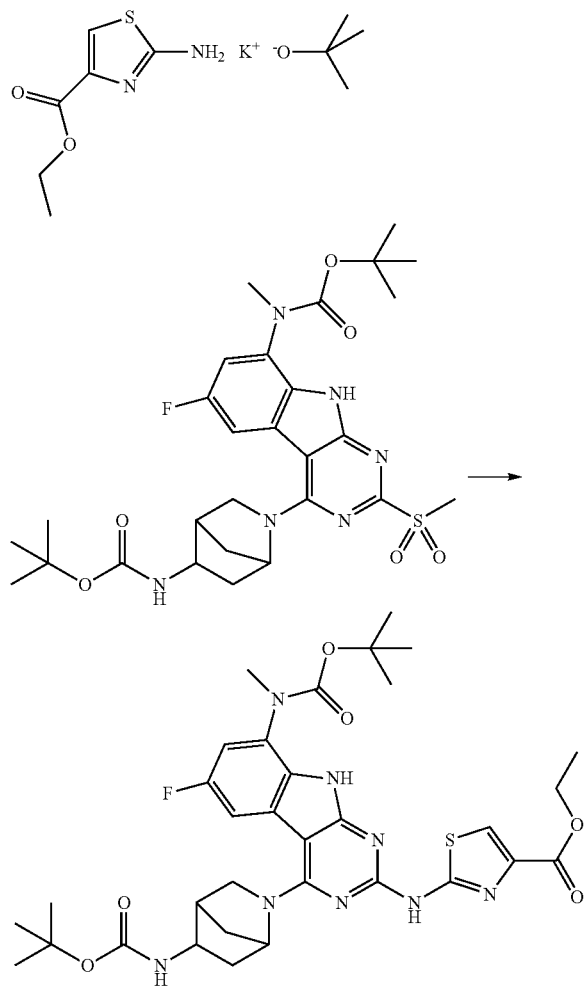

The methyl sulfone starting material (30 mgs, 0.05 mmol) in DMF (0.2 mL) was added ethyl 2-aminothiazole-4-carboxylate (54 mgs, 0.3 mmol) and potassium tertbutoxide (25 mgs, 0.23 mmol). The solution was heated to 150° C. in an oil bath. After two hours, LC/MS showed formation of desired peak and consumption of starting material. Reaction was purified without a 1 h work up. Purification was done via RP ISCO to get 8 mgs of tan solids (23%). MS (ESI) m/z 697 (M+H)+.

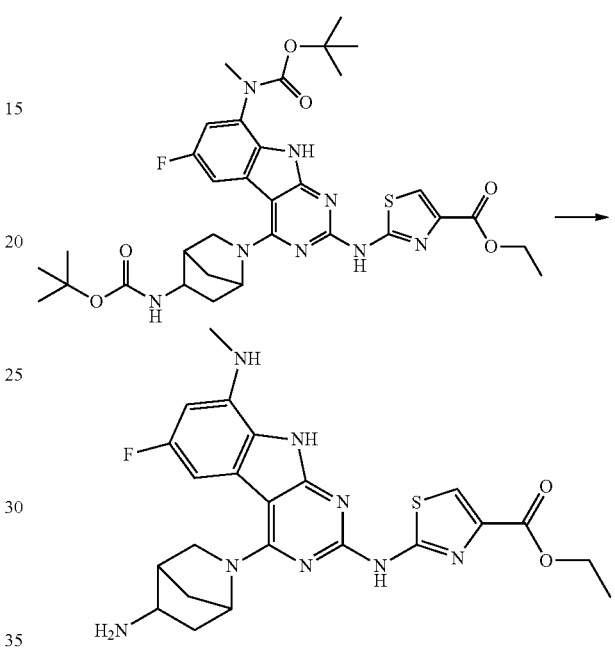

The lit brown goo starting material (25 mgs, 0.038 mmol) was treated with 2 mL of 4 N HCl in dioxane. 1 mL of MeOH was added to aid to solubility. The mixture was left at rt for 5 mins to finish. RP ISCO isolated 5.2 mgs of white solids as the TFA salt of the desired product (30%). MS (ESI) m/z 497 (M+H)+.

Example 2: Synthesis of Prodrugs

Example 2a—Preparation of Prodrug at R⁸

6-Fluoro-N-methyl-2,4-bis(methylsulfonyl)-9H-pyrimido[4,5-b]indol-8-amine (2)

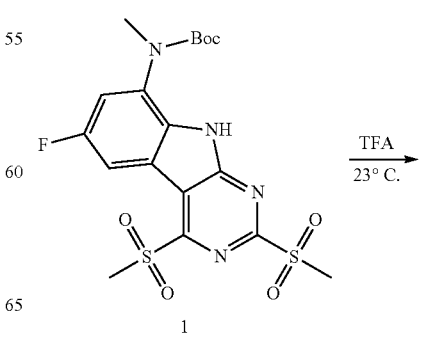

1

-continued

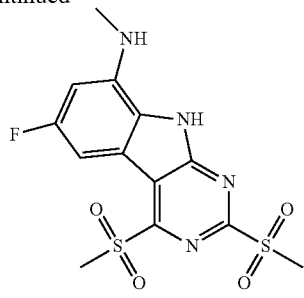

2

The mixture of 1 (2.25 g, 4.76 mmol) in trifluoroacetic acid (3.0 mL) were stirred for 30 min at 23° C. Trifluoroacetic acid was evaporated by reduced pressure to provide 2 (quantitative yield) as deep orange solid. This crude material was used for next reaction without further purification. LC/MS (ESI, M+H$^+$)=373.

tert-Butyl (1R,4R,5R)-2-(6-fluoro-8-(methylamino)-2-(2-methylpyrimidin-5-yloxy)-9H-pyrimido[4,5-b]indol-4-yl)-2-azabicyclo[2.2.1]heptan-5-ylcarbamate (3)

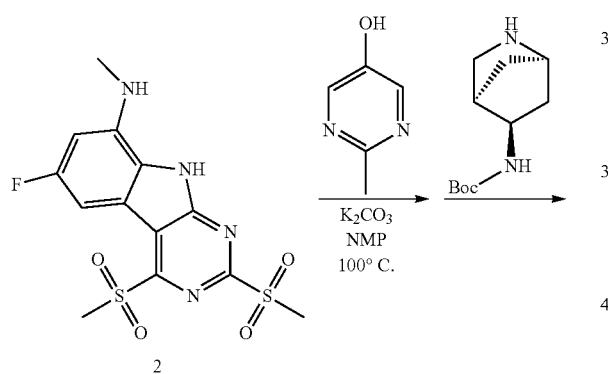

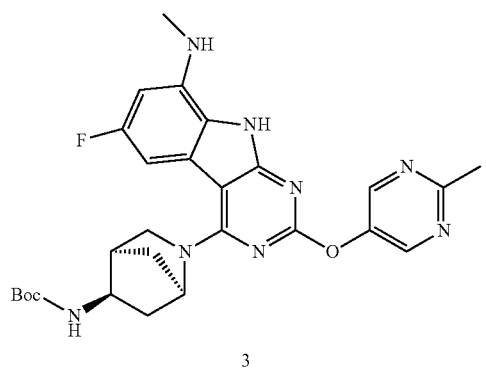

3

The mixture of 2 (1.77 g, 4.76 mmol, 1.0 eq.), 2-methylpyrimidin-5-ol (1.57 g, 14.3 mmol, 3.0 eq.) and K$_2$CO$_3$ (2.63 g, 19.0 mmol, 4.0 eq.) in NMP (15.0 mL) were stirred for 2 hr at 100° C. After being stirred for 2 hr, the reaction was checked by LC/MS. tert-Butyl (1R,4R,5R)-2-azabicyclo[2.2.1]heptan-5-ylcarbamate (3.03 g, 14.3 mmol, 3.0 eq.) was added at once, the mixture was allowed to stir for 1 hr at 100° C. The resulting heterogeneous mixture was cooled to 23° C. and purified by HPLC to provide 3 (1.34 g, 2.50 mmol, 53%) as light yellow solid. LC/MS (ESI, M+H$^+$)=535.

Chloromethyl 4-((1R,4R,5R)-5-Boc-amino-2-azabicyclo[2.2.1]heptan-2-yl)-6-fluoro-2-(2-methylpyrimidin-5-yloxy)-9H-pyrimido[4,5-b]indol-8-yl(methyl)carbamate (4)

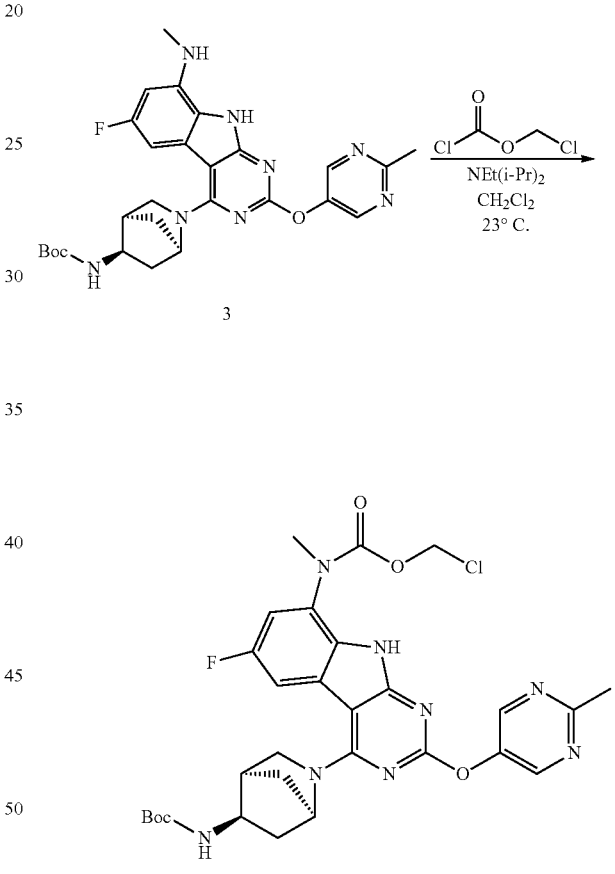

The mixture of 3 (0.69 g, 1.30 mmol) and di-isopropylethylamine (0.67 g, 5.20 mmol) in CH$_2$Cl$_2$ (25 mL) were cooled to 0° C. under nitrogen atmosphere. Chloromethyl chloroformate (0.17 mL, 1.95 mmol) dissolved in CH$_2$Cl$_2$ (1.0 mL) was dropwise added into the reaction mixture via syringe. The resulting yellow solution was stirred for 1 hr and then concentrated under reduced pressure. The crude product as yellow solid was purified by column chromatography (SiO$_2$, n-Hex:EtOAc 20:80 (v/v)) to give 4 (0.41 g, 0.65 mmol, 50%) as white solid. LC/MS (ESI, M+H$^+$)=628.

209

(di-tert-Butoxyphosphoryloxy)methyl 4-((1R,4R, 5R)-5-Boc-amino-2-azabicyclo[2.2.1]heptan-2-yl)-6-fluoro-2-(2-methylpyrimidin-5-yloxy)-9H-pyrimido [4,5-b]indol-8-yl(methyl)carbamate (5)

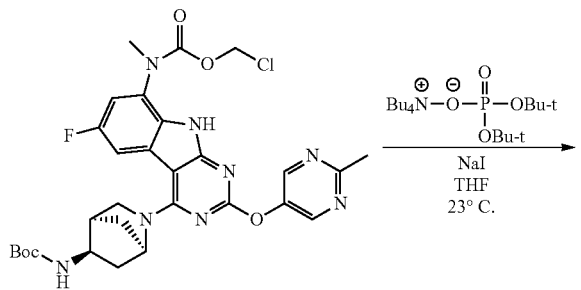

The mixture of 4 (0.051 g, 0.082 mmol), sodium iodide (0.020 g, 0.133 mmol) and tetra-n-butylammonium di-tert-butylphosphate (0.123 g, 0.265 mmol) in anhydrous THF (7.0 mL) were stirred for 3 hr at 23° C. After being stirred for 3 hr, the resulting heterogeneous mixture was filtered and purified by HPLC to provide 5 (0.054 g, 0.067 mmol, 82%) as light yellow solid. LC/MS (ESI, M+H$^+$)=801.

Phosphonooxymethyl 4-((1R,4R,5R)-5-amino-2-azabicyclo[2.2.1]heptan-2-yl)-6-fluoro-2-(2-methylpyrimidin-5-yloxy)-9H-pyrimido[4,5-b]indol-8-yl (methyl)carbamate (6)

210

The mixture of 5 (0.054 g, 0.067 mmol) in trifluoroacetic acid (1.5 mL) were stirred for 15 min at 23° C. Trifluoroacetic acid was evaporated by reduced pressure and the crude product was purified by HPLC to give 6 (0.037 g, 0.062 mmol, 93%) as white solid. LC/MS (ESI, M+H$^+$)=589.

Examples 2b and 2c—Preparation of Prodrugs at R$^8$

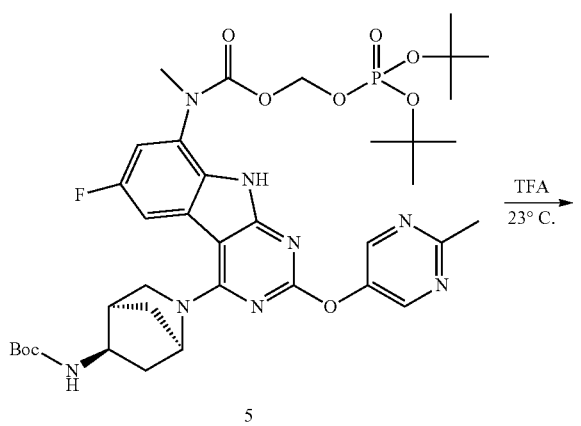

The prodrugs above—(LC/MS (ESI, M+H$^+$)=589) and —(LC/MS (ESI, M+H$^+$)=589) were prepared using procedures similar to that described in Example 2a.

Example 2d—Preparation of Prodrug at R[8]

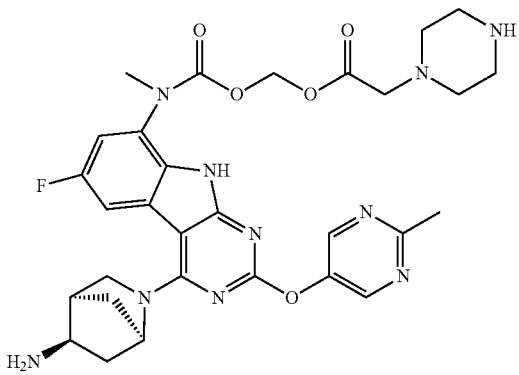 [SMILES: Cc1ncc(Oc2nc(N3C[C@H]4C[C@@H]3C[C@H]4N)c3c(n2)[nH]c2c(N(C)C(=O)OCOC(=O)CN4CCNCC4)cc(F)cc23)cn1]

tert-Butyl 4-(2-(((4-((1R,4R,5R)-5-(tert-butoxycarbonylamino)-2-azabicyclo[2.2.1]heptan-2-yl)-6-fluoro-2-(2-methylpyrimidin-5-yloxy)-9H-pyrimido[4,5-b]indol-8-yl)(methyl)carbamoyloxy)methoxy)-2-oxoethyl)piperazine-1-carboxylate (7)

The mixture of 4 (0.250 g, 0.400 mmol), sodium iodide (0.100 g, 0.667 mmol) and cesium 2-(4-(tert-butoxycarbonyl)piperazin-1-yl)acetate (0.487 g, 1.300 mmol; prepared as described in WO 2008/014108 A2) in anhydrous DMF (10.0 mL) were stirred for 24 hr at 23° C. under nitrogen atmosphere. After being stirred for 24 hr, the resulting mixture was purified by HPLC to provide 7 (0.181 g, 0.217 mmol, 54%) as white solid. LC/MS (ESI, M+H$^+$)=835.

((4-((1R,4R,5R)-5-Amino-2-azabicyclo[2.2.1]heptan-2-yl)-6-fluoro-2-(2-methylpyrimidin-5-yloxy)-9H-pyrimido[4,5-b]indol-8-yl)(methyl)carbamoyloxy)methyl 2-(piperazin-1-yl)acetate (8)

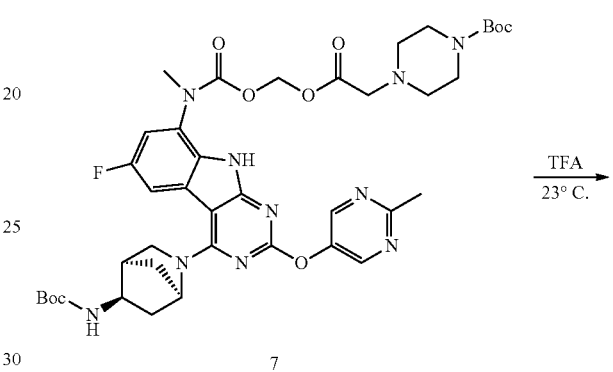

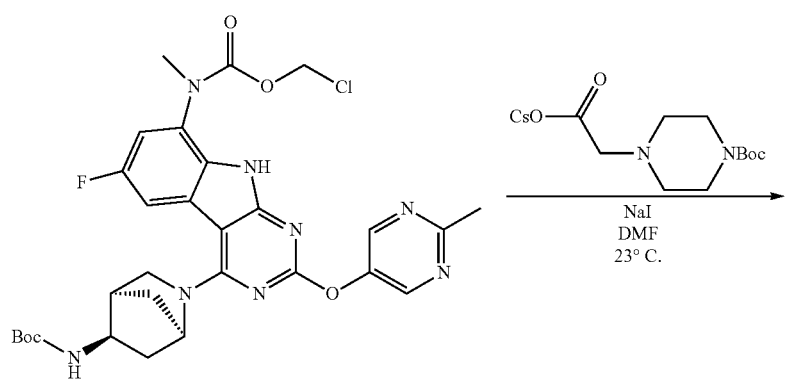

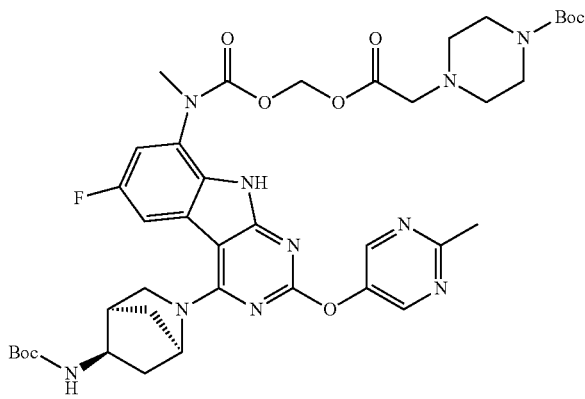

213
-continued

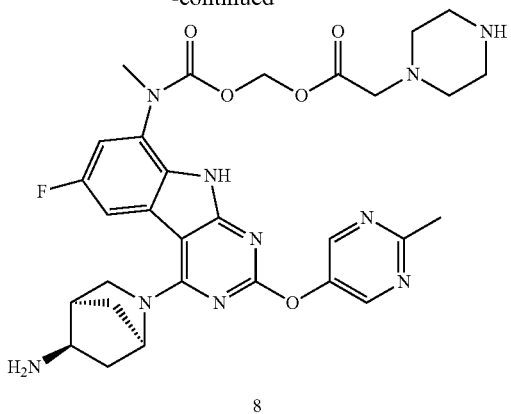

8

The mixture of 7 (0.181 g, 0.217 mmol) in trifluoroacetic acid (1.5 mL) were stirred for 15 min at 23° C. Trifluoroacetic acid was evaporated by reduced pressure and the crude product was purified by HPLC to give 8 (0.105 g, 0.165 mmol, 76%) as white solid. LC/MS (ESI, M+H$^+$)= 635.

Example 2e—Preparation of Prodrug at R$^8$

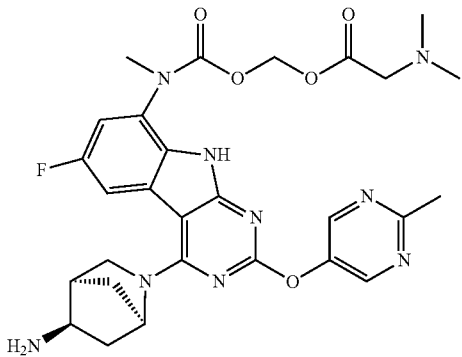 [SMILES: Cc1ncc(Oc2nc(N3C[C@H]4C[C@@H]3C[C@H]4N)c3c(n2)[nH]c2c(N(C)C(=O)OCOC(=O)CN(C)C)cc(F)cc23)cn1]

The prodrug above (LC/MS (ESI, M+H$^+$)=594) was prepared using procedures similar to that described in Example 2d.

Example 2f—Preparation of Prodrug at R$^8$

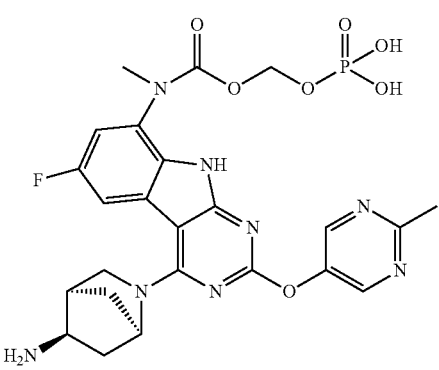 [SMILES: Cc1ncc(Oc2nc(N3C[C@H]4C[C@@H]3C[C@H]4N)c3c(n2)[nH]c2c(N(C)C(=O)OCOP(=O)(O)O)cc(F)cc23)cn1]

214

6-Fluoro-N-methyl-2,4-bis(methylsulfonyl)-9-pyrimido[4,5-b]indol-8-amine (2)

The mixture of 1 (2.25 g, 4.76 mmol) in trifluoroacetic acid (3.0 mL) were stirred for 30 min at 23° C. Trifluoroacetic acid was evaporated by reduced pressure to provide 2 (quantitative yield) as deep orange solid. This crude material was used for next reaction without further purification. LC/MS (ESI, M+H+)=373.

tert-Butyl (1R,4R,5R)-2-(6-fluoro-8-(methylamino)-2-(2-methylpyrimidin-yloxy)-9H-pyrimido[4,5-b]indol-4-yl)-2-azabicyclo[2.2.1]heptan-5-ylcarbamate (3)

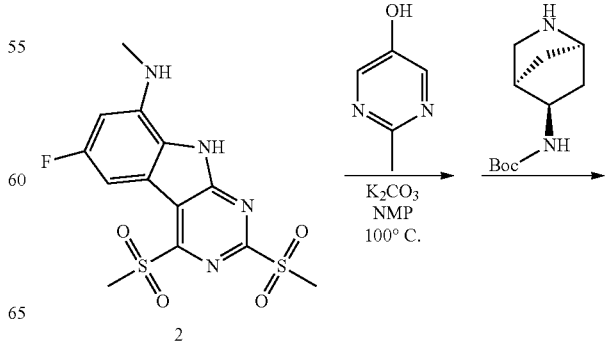

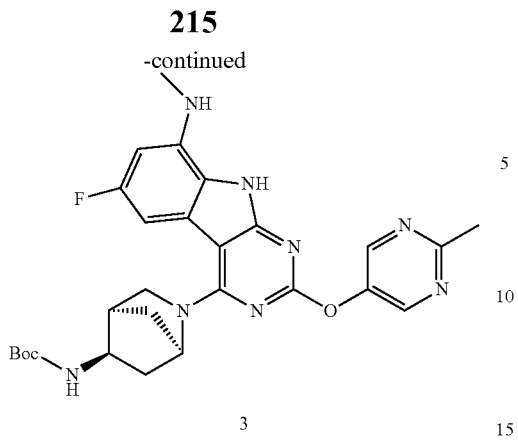

The mixture of 2 (1.77 g, 4.76 mmol, 1.0 eq.), 2-methylpyrimidin-5-ol (1.57 g, 14.3 mmol, 3.0 eq.) and K₂CO₃ (2.63 g, 19.0 mmol, 4.0 eq.) in NMP (15.0 mL) were stirred for 2 hr at 100° C. After being stirred for 2 hr, the reaction was checked by LC/MS. tert-Butyl (1R,4R,5R)-2-azabicyclo[2.2.1]heptan-5-ylcarbamate (3.03 g, 14.3 mmol, 3.0 eq.) was added at once, the mixture was allowed to stir for 1 hr at 100° C. The resulting heterogeneous mixture was cooled to 23° C. and purified by HPLC to provide 3 (1.34 g, 2.50 mmol, 53%) as light yellow solid. LC/MS (ESI, M+H+) =535.

Chloromethyl 4-((1R,4R,5R)-5-Boc-amino-2-azabicyclo[2.2.1]heptan-2-yl)-6-fluoro-2-(2-methylpyrimidin-5-yloxy)-9H-pyrimido[4,5-b]indol-8-yl (methyl)carbamate (4)

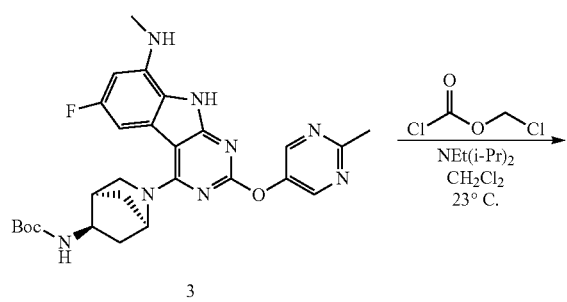

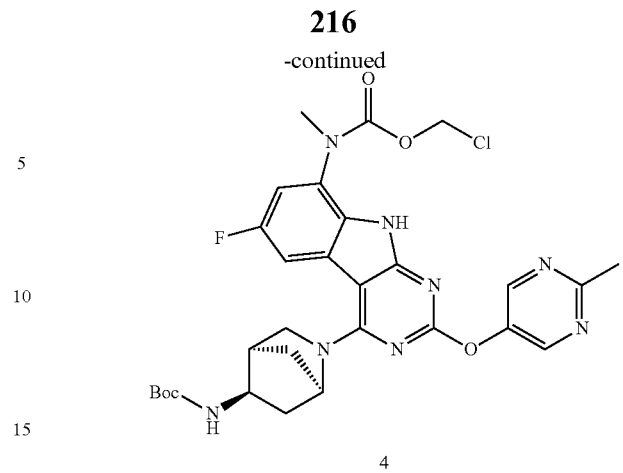

The mixture of 0 (0.69 g, 1.30 mmol) and di-isopropylethylamine (0.67 g, 5.20 mmol) in CH₂Cl₂ (25 mL) were cooled to 0° C. under nitrogen atmosphere. Chloromethyl chloroformate (0.17 mL, 1.95 mmol) dissolved in CH₂Cl₂ (1.0 mL) was dropwise added into the reaction mixture via syringe. The resulting yellow solution was stirred for 1 hr and then concentrated under reduced pressure. The crude product as yellow solid was purified by column chromatography (SiO₂, n-Hex:EtOAc 20:80 (v/v)) to give 4 (0.41 g, 0.65 mmol, 50%) as white solid. LC/MS (ESI, M+H+)=628.

(di-tert-Butoxyphosphoryloxy)methyl 4-((1R,4R,5R)-5-Boc-amino-2-azabicyclo[2.2.1]heptan-2-yl)-6-fluoro-2-(2-methylpyrimidin-5-yloxy)-9H-pyrimido[4,5-b]indol-8-yl(methyl)carbamate (5)

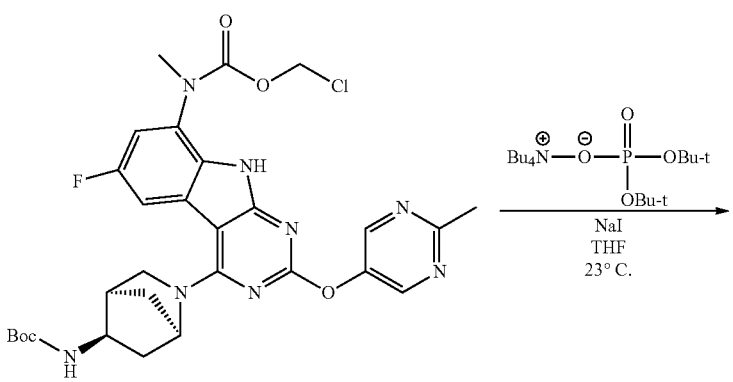

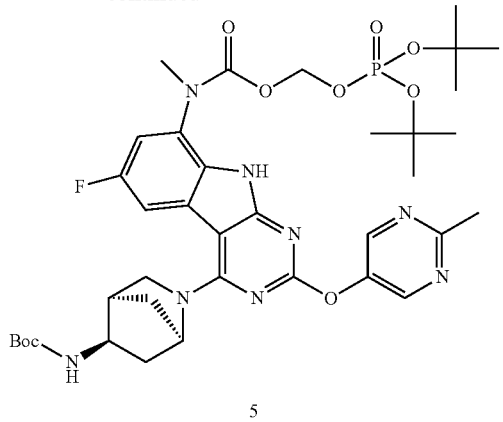

5

The mixture of 4 (0.051 g, 0.082 mmol), sodium iodide (0.020 g, 0.133 mmol) and tetra-n-butylammonium di-tert-butylphosphate (0.123 g, 0.265 mmol) in anhydrous THF (7.0 mL) were stirred for 3 hr at 23° C. After being stirred for 3 hr, the resulting heterogeneous mixture was filtered and purified by HPLC to provide 5 (0.054 g, 0.067 mmol, 82%) as light yellow solid. LC/MS (ESI, M+H+)=801.

Phosphonooxymethyl 4-((1R,4R,5R)-5-amino-2-azabicyclo[2.2.1]heptan-2-yl)-6-fluoro-2-(2-methylpyrimidin-5-yloxy)-9H-pyrimido[4,5-b]indol-8-yl (methyl)carbamate (6)

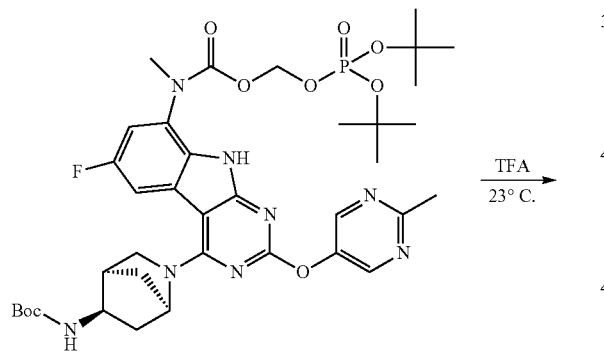

5

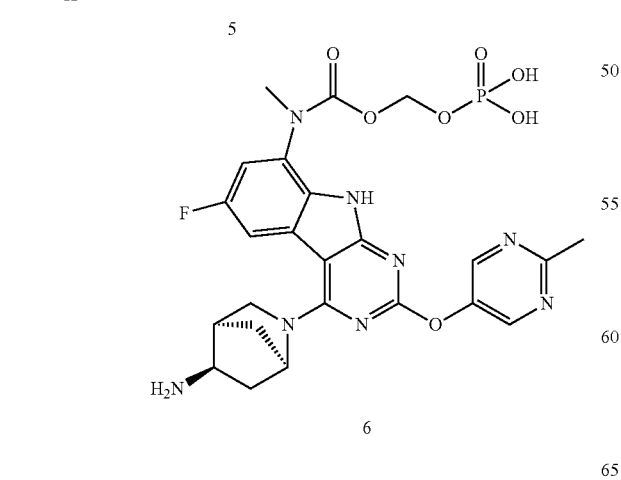

6

The mixture of 5 (0.054 g, 0.067 mmol) in trifluoroacetic acid (1.5 mL) were stirred for 15 min at 23° C. Trifluoroacetic acid was evaporated by reduced pressure and the crude product was purified by HPLC to give 6 (0.037 g, 0.062 mmol, 93%) as white solid. LC/MS (ESI, M+H+) =589.

Examples 2g and 2h—Preparation of Prodrugs at $R^8$

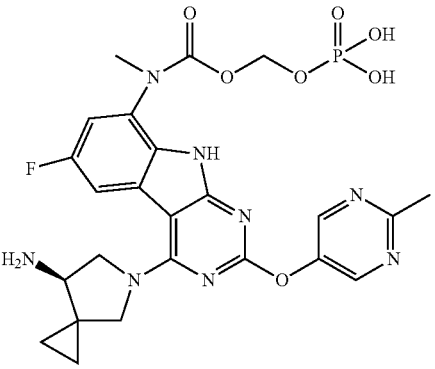

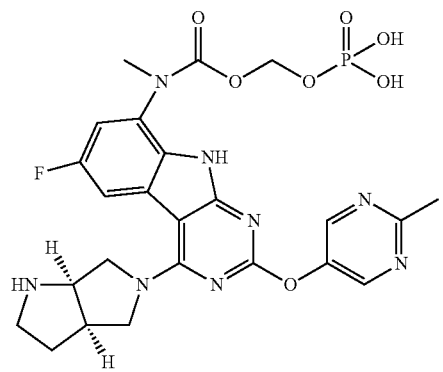

219

-continued

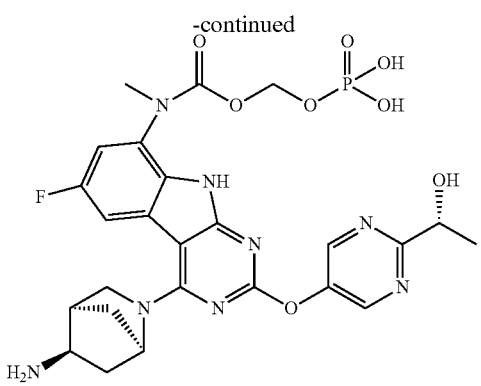

The prodrugs above (LC/MS (ESI, M+H+)=589), (LC/MS (ESI, M+H+)=589) and (LC/MS (ESI, M+H+)=619), respectively, were prepared using procedures similar to that described in Example 2f.

220

Example 2i—Preparation of Prodrugs at R⁸

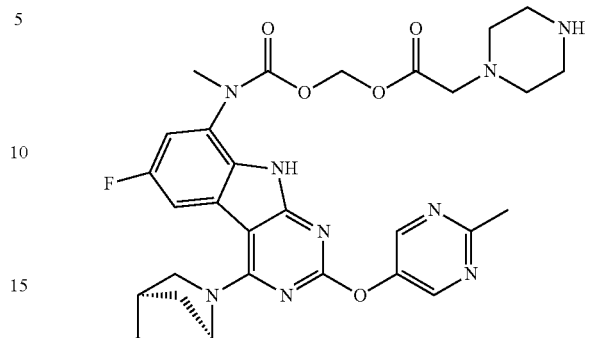

tert-Butyl 4-(2-(((4-(((1R,4R,5R)-5-(tert-butoxycarbonylamino)-2-azabicyclo[2.2.1]heptan-2-yl)-6-fluoro-2-(2-methylpyrimidin-5-yloxy)-9H-pyrimido[4,5-b]indol-8-yl)(methyl)carbamoyloxy)methoxy)-2-oxoethyl)piperazine-1-carboxylate (7)

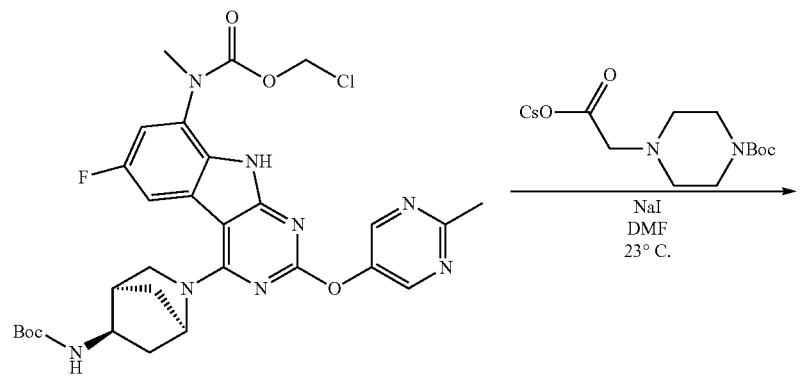

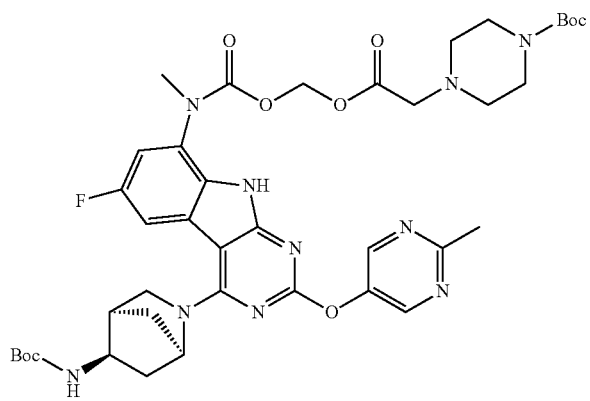

The mixture of 4 (0.250 g, 0.400 mmol), sodium iodide (0.100 g, 0.667 mmol) and cesium 2-(4-(tert-butoxycarbonyl)piperazin-1-yl)acetate (0.487 g, 1.300 mmol; prepared as described in Pat. WO 2008/014108 A2) in anhydrous DMF (10.0 mL) were stirred for 24 hr at 23° C. under nitrogen atmosphere. After being stirred for 24 hr, the resulting mixture was purified by HPLC to provide 7 (0.181 g, 0.217 mmol, 54%) as white solid. LC/MS (ESI, M+H+)= 835.

((4-((1R,4R,5R)-5-Amino-2-azabicyclo[2.2.1]heptan-2-yl)-6-fluoro-2-(2-methylpyrimidin-5-yloxy)-9H-pyrimido[4,5-b]indol-8-yl)(methyl)carbamoyloxy)methyl 2-(piperazin-1-yl)acetate (8)

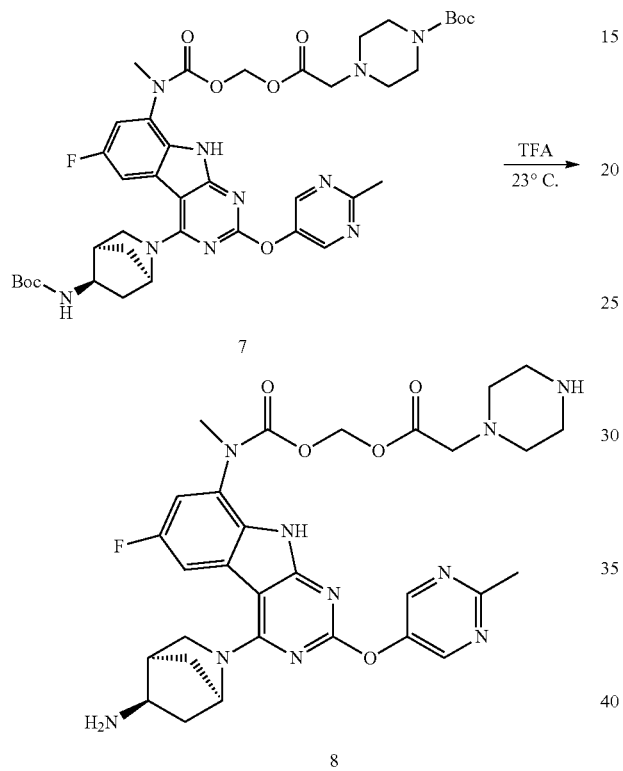

The mixture of 7 (0.181 g, 0.217 mmol) in trifluoroacetic acid (1.5 mL) were stirred for 15 min at 23° C. Trifluoroacetic acid was evaporated by reduced pressure and the crude product was purified by HPLC to give 8 (0.105 g, 0.165 mmol, 76%) as white solid. LC/MS (ESI, M+H+)= 635.

Example 2j—Preparation of Prodrugs at $R^8$

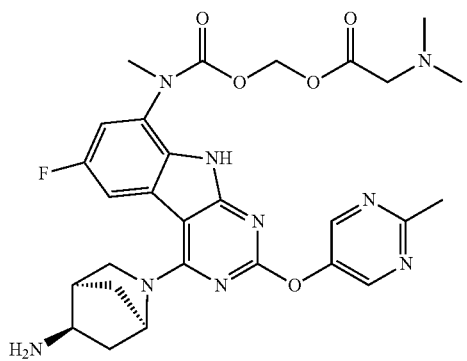 [SMILES: Cc1ncc(Oc2nc(N3C[C@H]4C[C@@H]3C[C@H]4N)c3c(n2)[nH]c2c(N(C)C(=O)OCOC(=O)CN(C)C)cc(F)cc23)cn1]

The prodrug above (LC/MS (ESI, M+H+)=594) was prepared using procedures similar to that described in Example 2i.

Example 2k—Preparation of Prodrugs at $R^8$

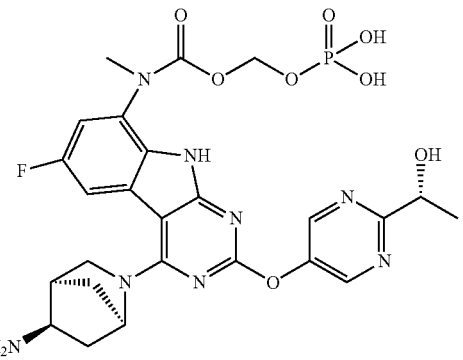

The prodrug above (LC/MS (ESI, M+H+)=619) was prepared using procedures similar to that described in Example 2f.

Example 2l—Preparation of Prodrugs at $R^8$ and $R^2$

The general scheme follows:

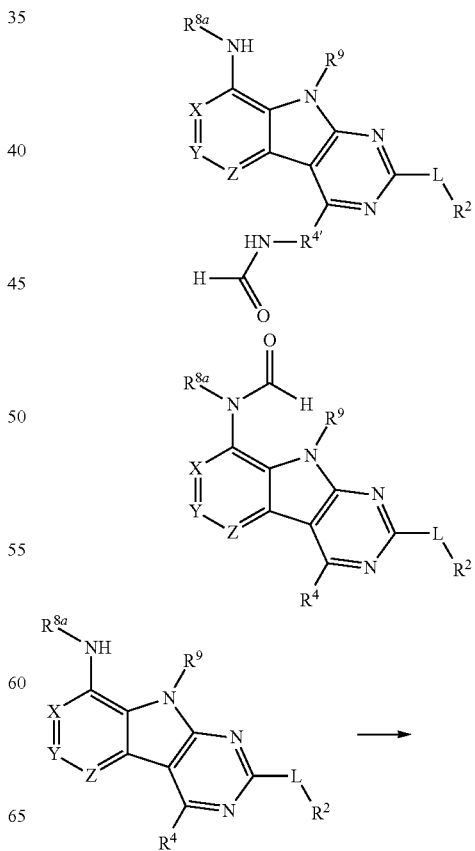

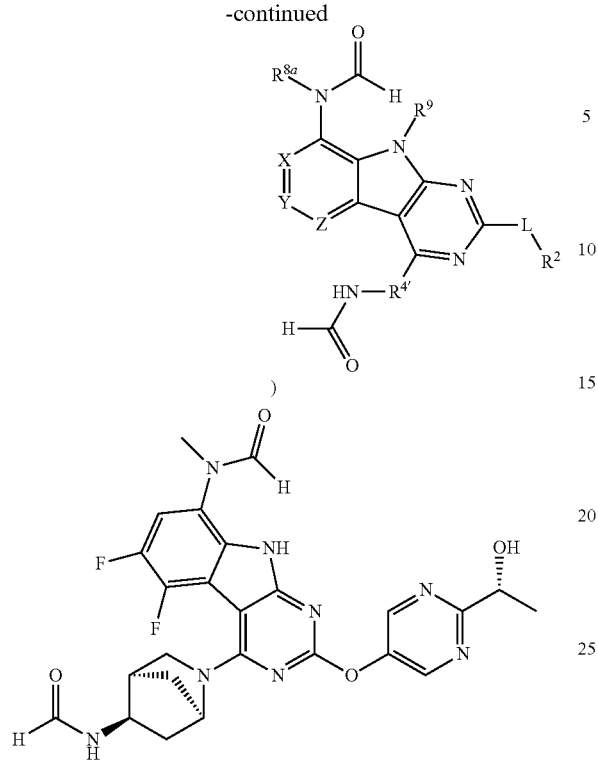
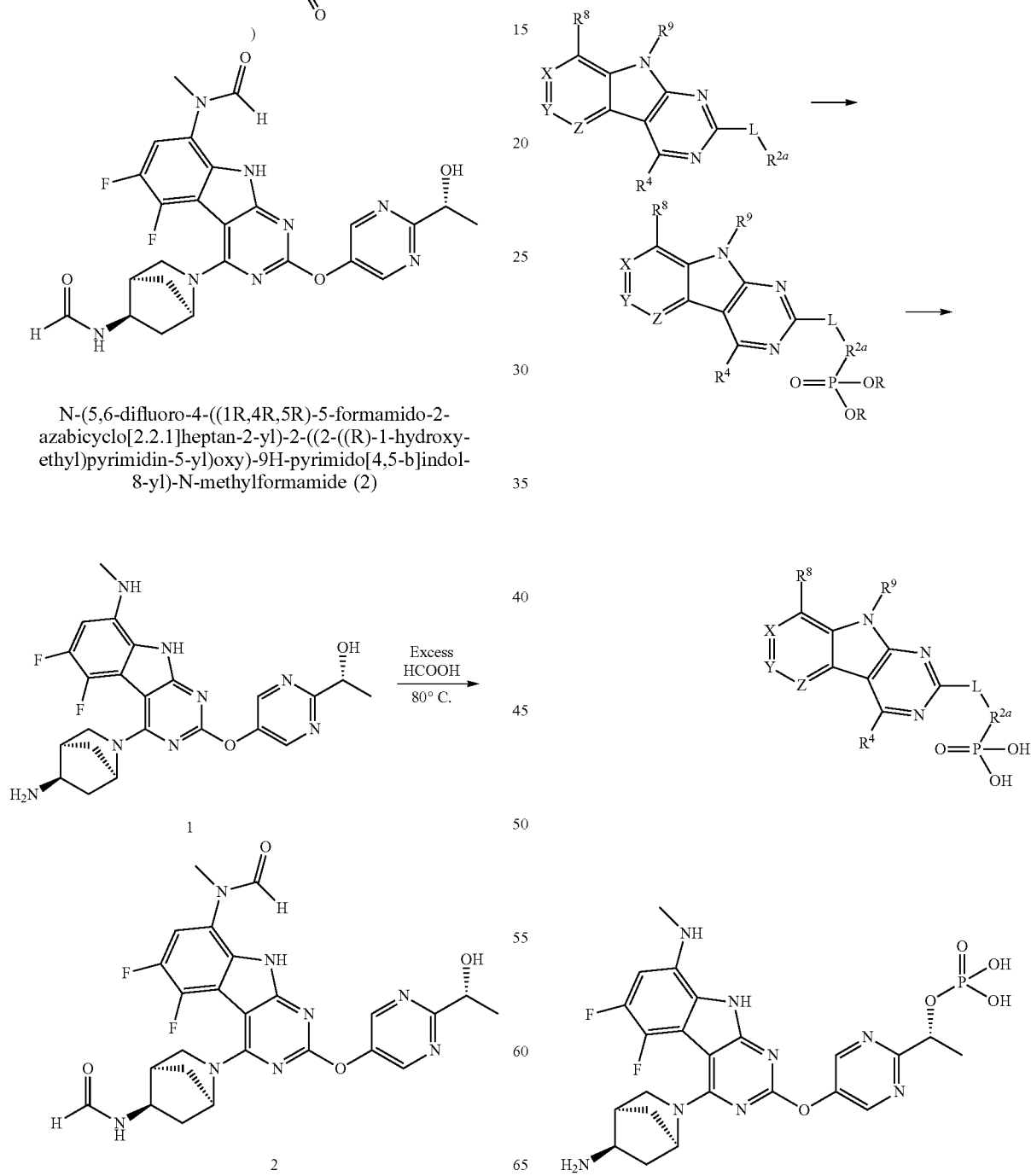
The mixture of 1 (0.167 g, 0.346 mmol) in formic acid (1.5 mL) was stirred for 6 hr at 80° C. under nitrogen atmosphere. Excess formic acid was evaporated by reduced pressure and the crude product was purified by HPLC to give a di-formyl adduct 2 (0.130 g, 0.241 mmol, 70%) as white solid (LC/MS (ESI, M+H$^+$)=539).
Example 2m—Preparation of Prodrug at R$^2$
General Scheme tert-butyl (4-((1R,4R,5R)-5-((tert-butoxycarbonyl)amino)-2-azabicyclo[2.2.1]heptan-2-yl)-2-((2-((R)-1-((diisopropoxyphosphoryl)oxy)ethyl)pyrimidin-5-yl)oxy)-5,6-difluoro-9H-pyrimido[4,5-b]indol-8-yl)(methyl)carbamate (2)

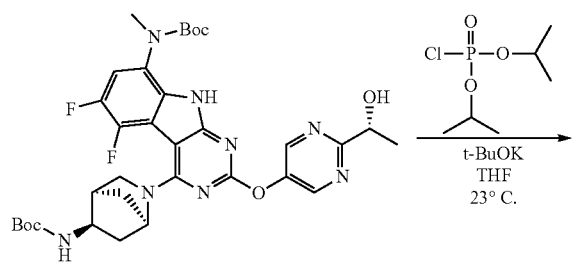

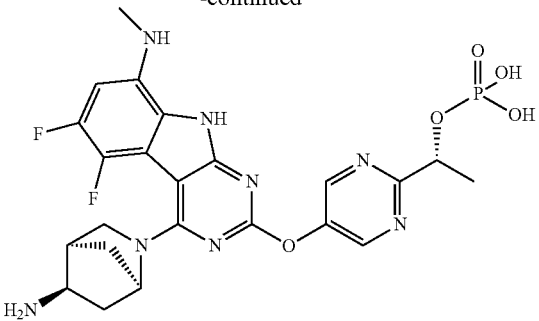

To a solution of 1 (0.250 g, 0.366 mmol) in anhydrous THF (7.0 mL) was added t-BuOK (0.732 mL, 0.732 mmol, 1.0 M solution in THF) under nitrogen atmosphere at 23° C. The resulting mixture was stirred for 10 min and then diisopropyl phosphorochloridate (0.147 g, 0.732 mmol) dissolved in THF (0.5 mL) was dropwise added by syringe. After being stirred for 15 min, the mixture was treated with ice water (25 mL) and was extracted with EtOAc (100 mL×3). The combined organic layers were dried over MgSO4, filtered, and concentrated in vacuo. The crude product was purified by column chromatography (SiO2, 100% EtOAc) to give 2 (0.237 g, 0.280 mmol, 77%) as white solid. LC/MS (ESI, M+H+)=847.

(R)-1-(5-((4-((1R,4R,5R)-5-amino-2-azabicyclo[2.2.1]heptan-2-yl)-5,6-difluoro-8-(methylamino)-9H-pyrimido[4,5-b]indol-2-yl)oxy)pyrimidin-2-yl)ethyl dihydrogen phosphate (3)

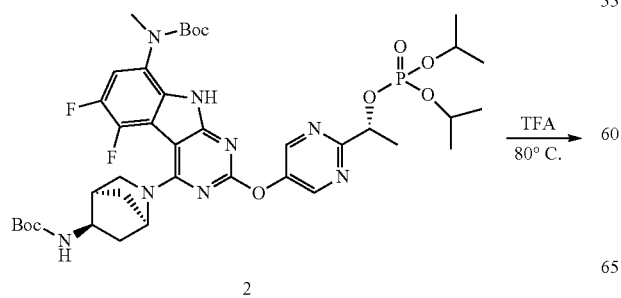

The reaction mixture of 2 (0.237 g, 0.280 mmol) in trifluoroacetic acid (7.0 mL) was stirred for 16 hr at 80° C. under nitrogen atmosphere. Trifluoroacetic acid was evaporated by reduced pressure and the crude product was purified by HPLC to give (R)-1-(5-((4-((1R,4R, S5R)-5-amino-2-azabicyclo[2.2.1]heptan-2-yl)-5,6-difluoro-8-(methylamino)-9H-pyrimido[4,5-b]indol-2-yl)oxy)pyrimidin-2-yl) ethyl dihydrogen phosphate 3 (0.112 g, 0.200 mmol, 71%) as white solid (LC/MS (ESI, M+H+)=563).

Using the same method, starting with compound 10.25

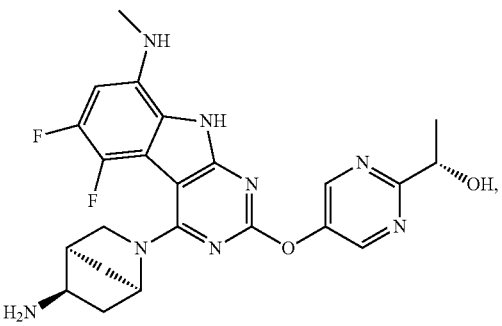 [SMILES: CNc1cc(F)c(F)c2c1[nH]c1nc(Oc3cnc([C@H](C)O)nc3)nc(N3C[C@H]4C[C@@H]3C[C@H]4N)c12]

the following prodrug may be made:

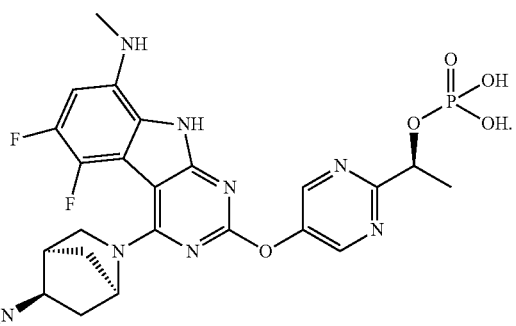

Example 2n—Preparation of Prodrug at R[2]

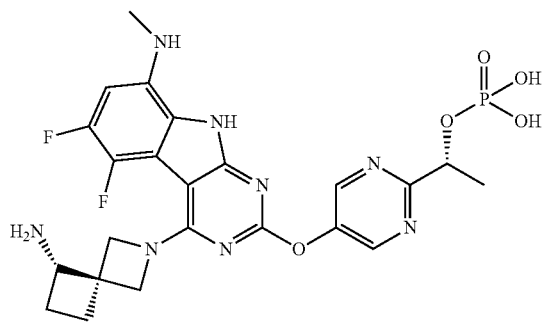

The prodrug above (LC/MS (ESI, M+H+)=563) was prepared with di-tert-butyl phosphorochloridate using procedures similar to that described in Example 2m.

Using the same method, starting with compound 10.118

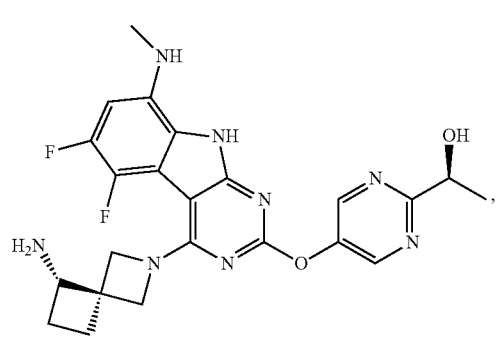

the following prodrug may be made:

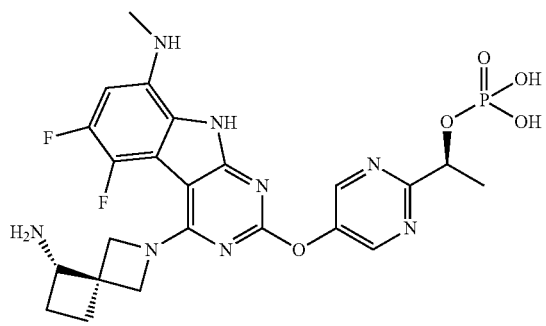

Example 2o—Preparation of Prodrug at R[2]

tert-Butyl (4-((1R,4R,5R)-5-((tert-butoxycarbonyl)amino)-2-azabicyclo[2.2.1]heptan-2-yl)-2-((2-((1R)-1-((ethoxy(hydroxy)phosphoryl)oxy)ethyl)pyrimidin-5-yl)oxy)-6-fluoro-9H-pyrimido[4,5-b]indol-8-yl)(methyl)carbamate (2)

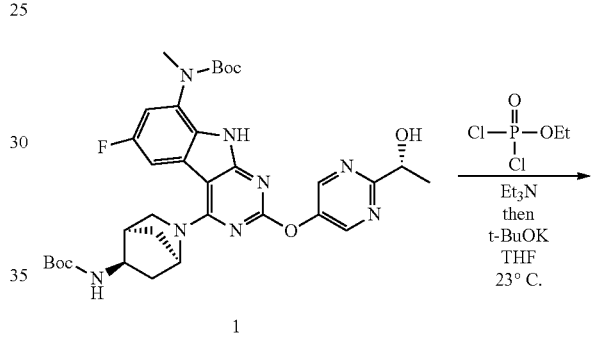

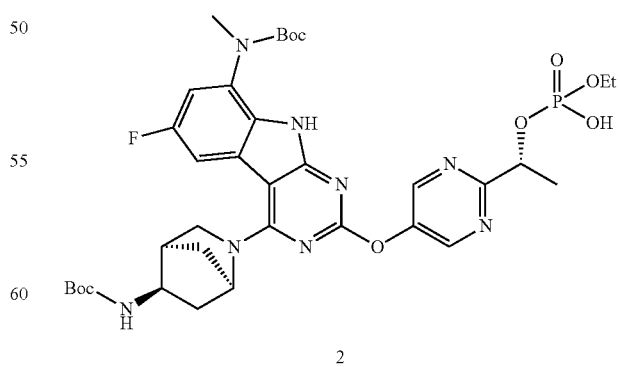

To a solution of 1 (0.120 g, 0.180 mmol) from prior step and Et$_3$N (0.036 g, 0.360 mmol) in anhydrous THF (5.0 mL) was added ethyl phosphorodichloridate (0.029 g, 0.180 mmol) under nitrogen atmosphere at 23° C. The resulting mixture was stirred for 5 hr and then t-BuOK (0.360 mL, 0.360 mmol, 1.0 M solution in THF) was added into the mixture. After being stirred for 30 min, the mixture was treated with ice water (1.0 mL) and was extracted with EtOAc (50 mL×3). The combined organic layers were dried over MgSO₄, filtered, and concentrated in vacuo. The crude product was purified by column chromatography (SiO₂, EtOAc:MeOH 75:25 (v/v)) to give 2 (0.025g, 0.032 mmol, 18%) as white solid. LC/MS (ESI, M+H⁺)=773.

(R)-1-(5-((4-((1R,4R,5R)-5-Amino-2-azabicyclo [2.2.1]heptan-2-yl)-6-fluoro-8-(methylamino)-9H-pyrimido[4,5-b]indol-2-yl)oxy)pyrimidin-2-yl)ethyl ethyl hydrogen phosphate (3)

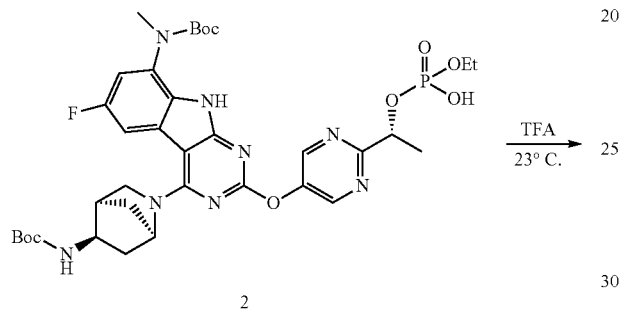

2

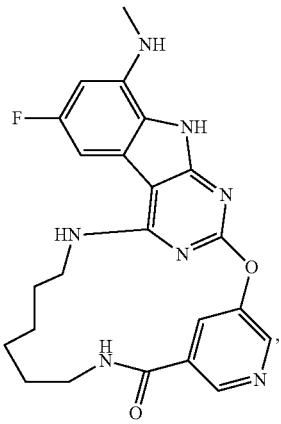

3

The reaction mixture of 2 (0.043 g, 0.055 mmol) in prior step in trifluoroacetic acid (3.0 mL) was stirred for 15 min at 23° C. under nitrogen atmosphere. Trifluoroacetic acid was evaporated by reduced pressure and the crude product was purified by HPLC to give 3 (0.030 g, 0.052 mmol, 95%) as white solid (LC/MS (ESI, M+H⁺)=573).

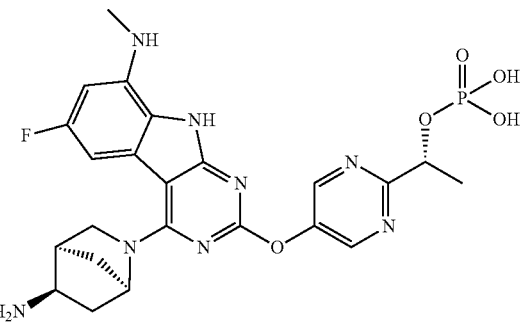

The prodrug above (LC/MS (ESI, M+H⁺)=545) was prepared using procedures similar to that described in Example 2m.

Example 3: Synthesis of Compounds of Formula I where R² and R⁴ are Joined

The following compounds were made:

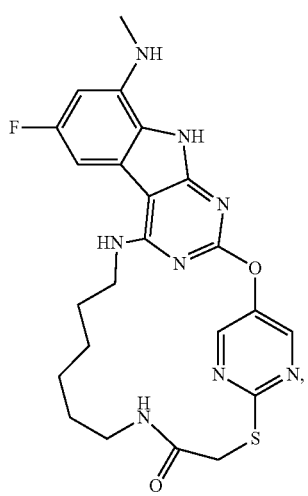

231
-continued
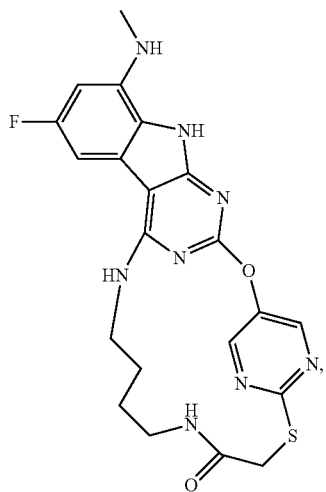
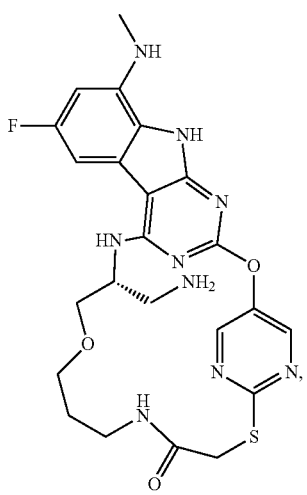
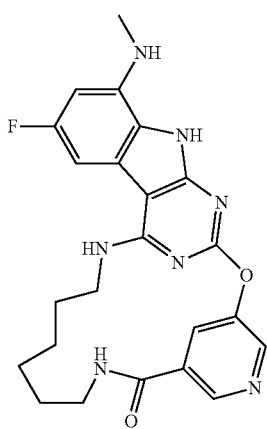
232
-continued
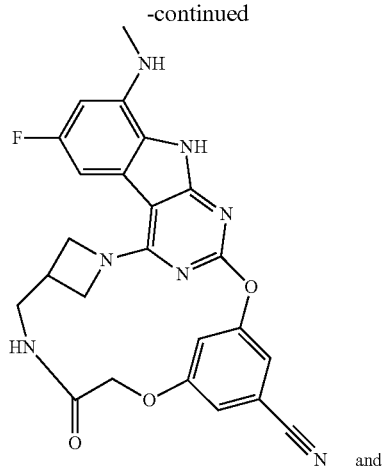
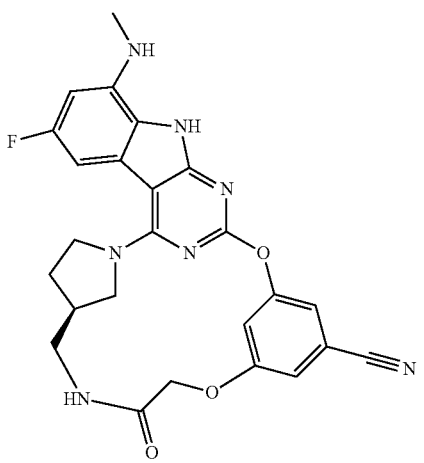
Example 3a—Process to make

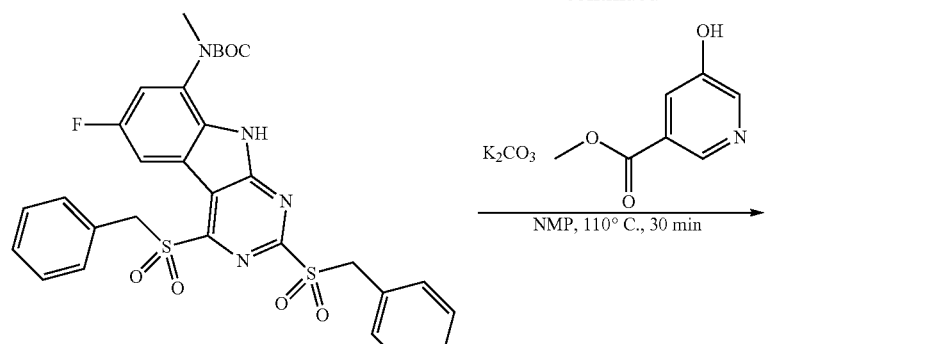
-continued
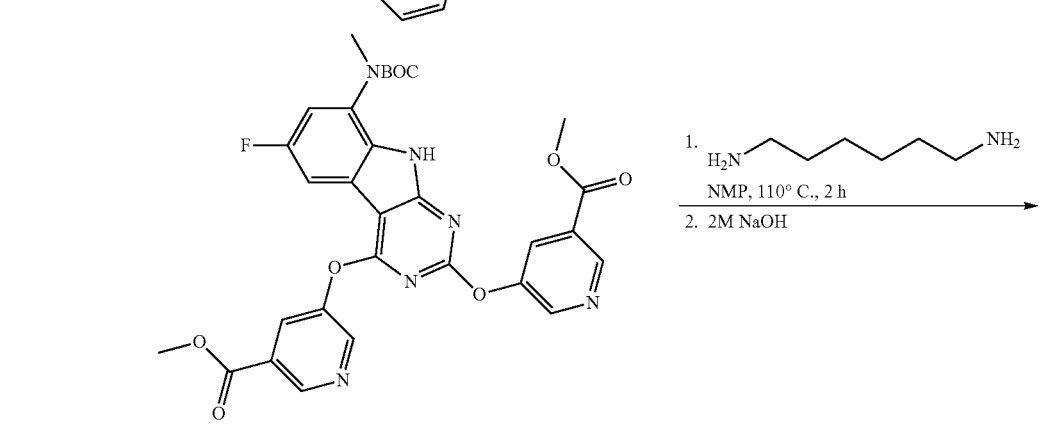
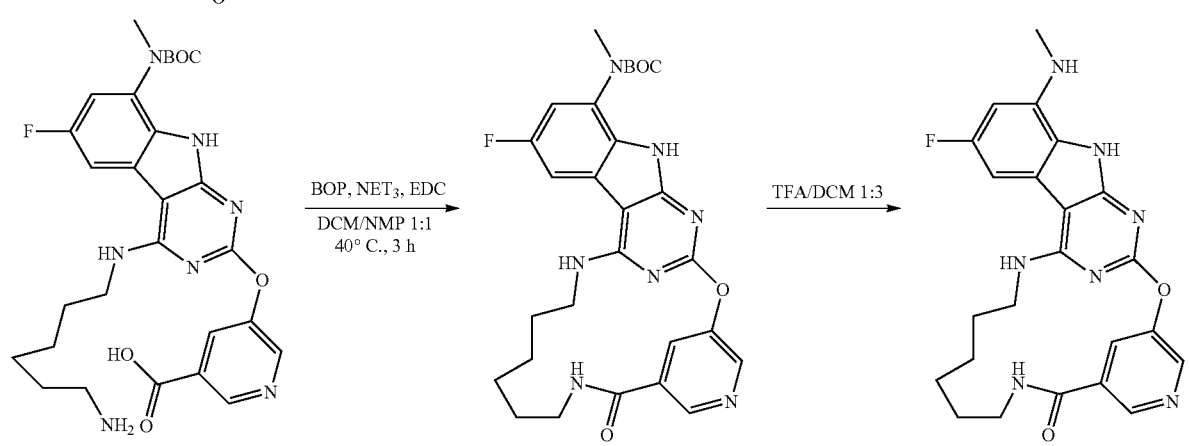
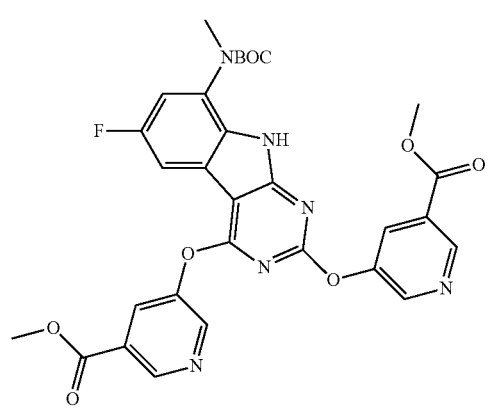

Synthesis of dimethyl 5,5'-((8-((tert-butoxycarbonyl)(methyl)amino)-6-fluoro-9H-pyrimido[4,5-b]indole-2,4-diyl)bis(oxy))dinicotinate tert-butyl (2,4-bis(benzylsulfonyl)-6-fluoro-9H-pyrimido[4,5-b]indol-8-yl)(methyl)carbamate (91 mg, 0.146 mmol), methyl 5-hydroxynicotinate (157 mg, 1.022 mmol) and potassium carbonate (121 mg, 0.876 mmol) were mixed in NMP (1.5 ml) and heated at 110° C. for 30 min. The crude reaction mixture was purified by RPLC to yield the title compound (40 mg, 0.065 mmol, 44%). LCMS m/z: 619.1 (M+1).

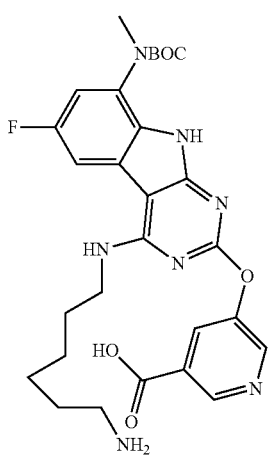

Synthesis of dimethyl 5-((4-((6-aminohexyl)amino)-8-((tert-butoxycarbonyl)(methyl)amino)-6-fluoro-9H-pyrimido[4,5-b]indol-2-yl)oxy)nicotinic acid 5,5'-((8-((tert-butoxycarbonyl)(methyl)amino)-6-fluoro-9H-pyrimido[4,5-b]indole-2,4-diyl)bis(oxy))dinicotinate (40 mg, 0.065 mmol) and hexane-1,6-diamine (75 mg, 0.647 mmol) were mixed in NMP (1 ml) and heated at 110° C. for 2 hours. 2M NaOH (excess) was added and the mixture was heated at 100° C. for 5 min. The crude reaction mixture was purified by RPLC to yield the title compound (21 mg, 0.052 mmol, 72%). LCMS m/z: 568.2 (M+1).

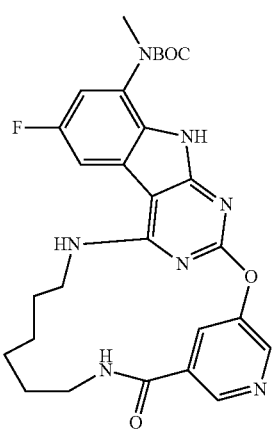

Macrocyclization:

5-((4-(6-aminohexyl)amino)-8-((tert-butoxycarbonyl)(methyl)amino)-6-fluoro-9H-pyrimido[4,5-b]indol-2-yl)oxy)nicotinic acid (21 mg, 0.037 mmol), triethylamine (11.2 mg, 0.111 mmol) and BOP (49.1 mg, 0.111 mmol) were mixed in DCM/NMP (1:1, 2 ml) at 0° C. The mixture was warmed to 40° C. over a period of 1 h. LCMS indicated only traces of product formation. EDC (42.6 mg, 0.222 mmol) was added and the mixture was heated at 40° C. for a period of 2 h. NMP (1 ml) was added and the DCM removed under reduced pressure. The crude reaction mixture was purified by RPLC to yield the macrocyclic compound (15 mg, 0.027 mmol, 74%). LCMS m/z: 550.2 (M+1).

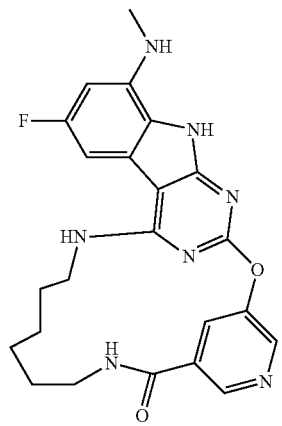 [SMILES: CNc1cc(F)cc2c1[nH]c1nc3nc(c12)NCCCCCCNC(=O)c1cncc(c1)O3]

Boc-Deprotection of the Macrocyclic Compound:

The Boc-protected macrocycle (15 mg, 0.027 mmol) was mixed with DCM/TFA (4:1, 1 ml) and heated at 40° C. for 15 min. To the stirring mixture was added diethyl ether (8 ml) and hexane (2 ml). The precipitated deprotected macrocycle was isolated in form of its TFA salt by filtration (13 mg, 0.023 mmol, 85%). LCMS m/z: 449.1 (M+1).

Example 3b—Process to Make
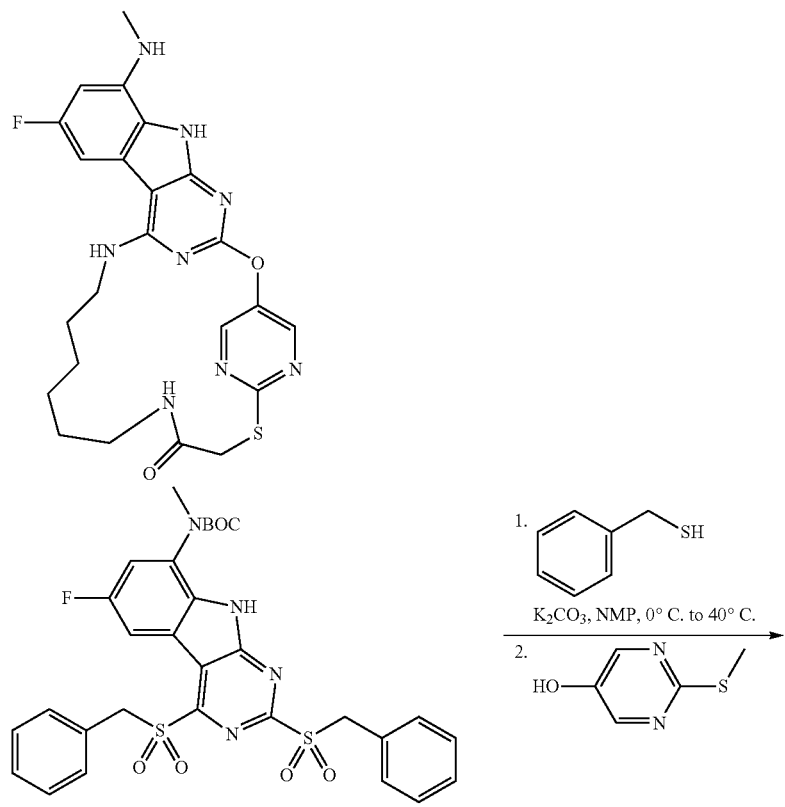
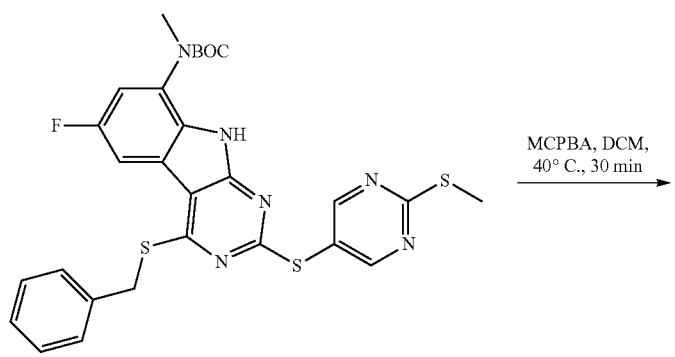
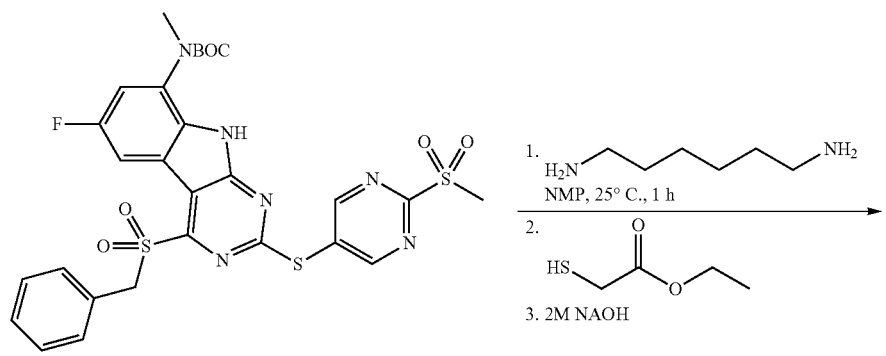

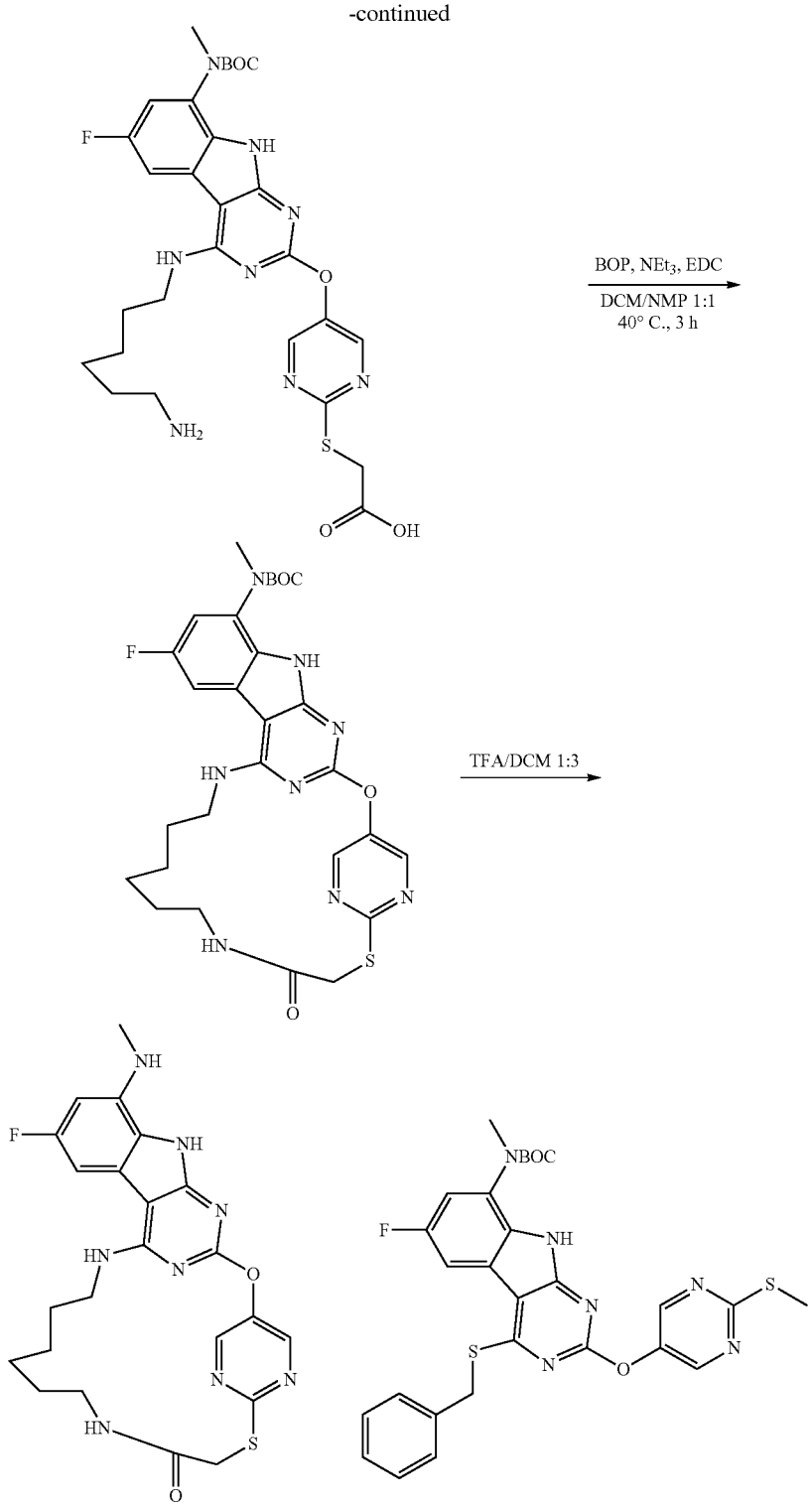

Tert-butyl (4-(benzylthio)-6-fluoro-2-((2-(methylthio)pyrimidin-5-yl)oxy)-9H-pyrimido[4,5-b]indol-8-yl)(methyl)carbamate tert-butyl (2,4-bis(benzylsulfonyl)-6-fluoro-9H-pyrimido[4,5-b]indol-8-yl)(methyl)carbamate (365 mg, 0.584 mmol), phenylmethanethiol (72.6 mg, 0.584 mmol) and potassium carbonate (81 mg, 0.584 mmol) were mixed in NMP (4 ml) at 0° C. The mixture was warmed to 40° C. over a period of 1 h. To the mixture was added 2-(methylthio)pyrimidin-5-ol (249 mg, 1.753 mmol) and potassium carbonate (283 mg, 2.045 mmol) and it was heated at 110° C. for 2 hours. The crude reaction mixture was purified by RPLC to yield the title compound (230 mg, 0.397 mmol, 68%). LCMS m/z: 579.3 (M+1).

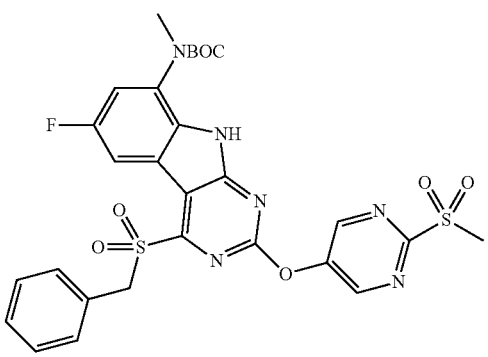

Tert-butyl (4-(benzylsulfonyl)-6-fluoro-2-((2-(methylsulfonyl)pyrimidin-5-yl)oxy)-9H-pyrimido[4,5-b]indol-8-yl)(methyl)carbamate Tert-butyl (4-(benzylthio)-6-fluoro-2-((2-(methylthio)pyrimidin-5-yl)oxy)-9H-pyrimido[4,5-b]indol-8-yl)(methyl)carbamate (230 mg, 0.397 mmol) and 3-chlorobenzoperoxoic acid (77%, 401 mg, 1.789 mmol) were mixed in DCM (4 ml) at 0° C. The mixture was warmed to 40° C. over a period of 2h. The crude reaction mixture was purified by LC to yield the title compound (180 mg, 0.280 mmol, 70%). LCMS m/z: 643.1 (M+1).

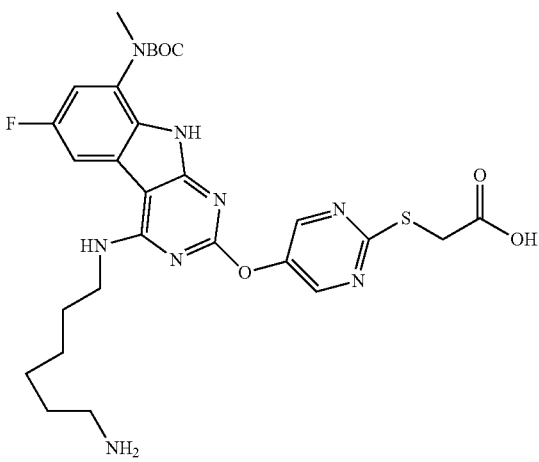

2-((5-((4-((6-aminohexyl)amino)-8-((tert-butoxycarbonyl)(methyl)amino)-6-fluoro-9H-pyrimido[4,5-b]indol-2-yl)oxy)pyrimidin-2-yl)thio)acetic acid tert-butyl (4-(benzylsulfonyl)-6-fluoro-2-((2-(methylsulfonyl)pyrimidin-5-yl)oxy)-9H-pyrimido[4,5-b]indol-8-yl)(methyl)carbamate (65 mg, 0.101 mmol) and hexane-1,6-diamine (70.5 mg, 0.607 mmol) were mixed in NMP (1.5 ml) and stirred at 25° C. for 1 hour. Ethyl 2-mercaptoacetate (122 mg, 1.011 mmol) was added and the mixture was heated at 60° C. for 1 hour. 2M NaOH (excess) was added and the mixture was heated at 100° C. for 5 min. The crude reaction mixture was purified by RPLC to yield the title compound (37 mg, 0.06 mmol, 60%). LCMS m/z: 615.1 (M+1).

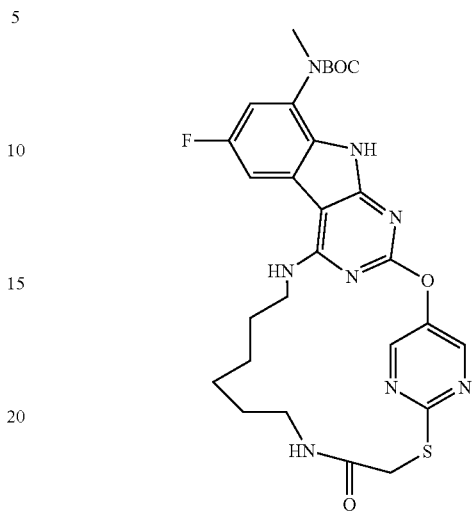

Macrocyclization:

2-((5-((4-(6-aminohexyl)amino)-8-((tert-butoxycarbonyl)(methyl)amino)-6-fluoro-9H-pyrimido[4,5-b]indol-2-yl)oxy)pyrimidin-2-yl)thio)acetic acid (37 mg, 0.06 mmol), triethylamine (18.3 mg, 0.181 mmol) and BOP (80 mg, 0.181 mmol) were mixed in DCM/NMP (1:1, 2 ml) at 0° C. The mixture was warmed to 40° C. over a period of 1 h. LCMS indicated only traces of product formation. EDC (69.2 mg, 0.361 mmol) was added and the mixture was heated at 40° C. for a period of 2h. NMP (1 ml) was added and the DCM removed under reduced pressure. The crude reaction mixture was purified by RPLC to yield the macrocyclic compound (26 mg, 0.044 mmol, 72%). LCMS m/z: 597.1 (M+1).

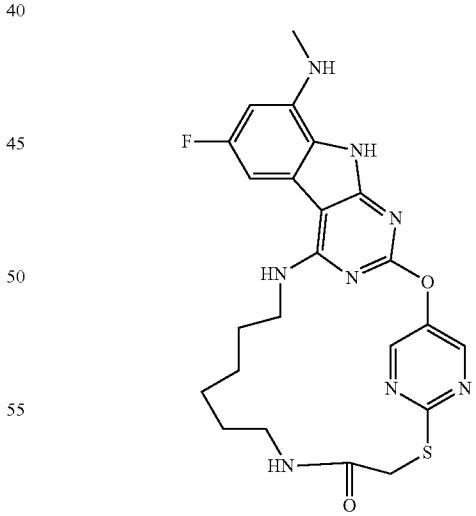

Boc-Deprotection of the Macrocyclic Compound:

The Boc-protected macrocycle (26 mg, 0.044 mmol) was mixed with DCM/TFA (4:1, 1 ml) and heated at 40° C. for 15 min. To the stirring mixture was added diethyl ether (8 ml) and hexane (2 ml). The precipitated deprotected macrocycle was isolated in form of its TFA salt by filtration (22 mg, 0.036 mmol, 83%). LCMS m/z: 497.1 (M+1).

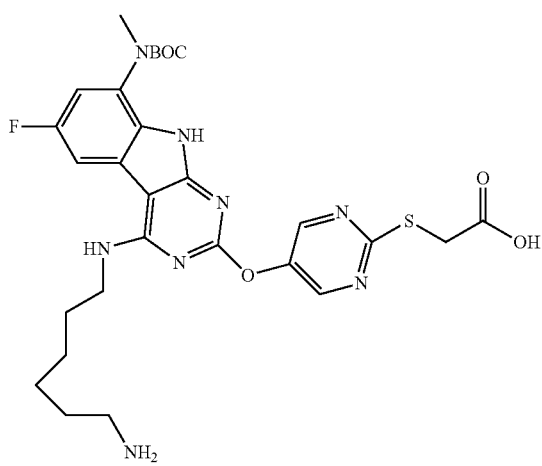

2-((5-((4-((4-aminobutyl)amino)-8-((tert-butoxycarbonyl)(methyl)amino)-6-fluoro-9H-pyrimido[4,5-b]indol-2-yl)oxy)pyrimidin-2-yl)thio)acetic acid tert-butyl (4-(benzyl sulfonyl)-6-fluoro-2-((2-(methyl sulfonyl)pyrimidin-5-yl)oxy)-9H-pyrimido[4,5-b]indol-8-yl)(methyl)carbamate (65 mg, 0.101 mmol) and butane-1,4-diamine (53.5 mg, 0.607 mmol) were mixed in NMP (1.5 ml) and stirred at 25° C. for 1 hour. Ethyl 2-mercaptoacetate (122 mg, 1.011 mmol) was added and the mixture was heated at 60° C. for 1 hour. 2M NaOH (excess) was added and the mixture was heated at 100° C. for 5 min. The crude reaction mixture was purified by RPLC to yield the title compound (43 mg, 0.073 mmol, 73%). LCMS m/z: 615.1 (M+1).

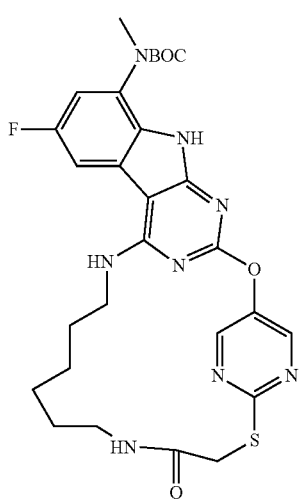

Macrocyclization:
2-((5-((4-((4-aminobutyl)amino)-8-((tert-butoxycarbonyl)(methyl)amino)-6-fluoro-9H-pyrimido[4,5-b]indol-2-yl)oxy)pyrimidin-2-yl)thio)acetic acid (43 mg, 0.073 mmol), triethylamine (22.25 mg, 0.220 mmol) and BOP (97 mg, 0.220 mmol) were mixed in DCM/NMP (1:1, 2 ml) at 0° C. The mixture was warmed to 40° C. over a period of 1 h. LCMS indicated only traces of product formation. EDC (84 mg, 0.440 mmol) was added and the mixture was heated at 40° C. for a period of 2h. NMP (1 ml) was added and the DCM removed under reduced pressure. The crude reaction mixture was purified by RPLC to yield the macrocyclic compound (14 mg, 0.025 mmol, 34%). LCMS m/z: 569.1 (M+1).

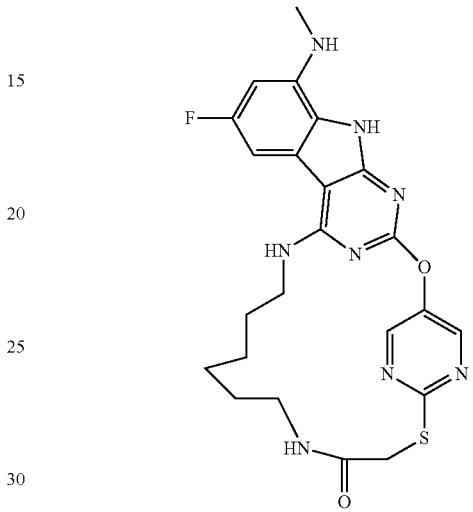

Boc-Deprotection of the Macrocyclic Compound:
The Boc-protected macrocycle (14 mg, 0.025 mmol) was mixed with DCM/TFA (4:1, 1 ml) and heated at 40° C. for 15 min. To the stirring mixture was added diethyl ether (8 ml) and hexane (2 ml). The precipitated deprotected macrocycle was isolated in form of its TFA salt by filtration (13 mg, 0.022 mmol, 91%). LCMS m/z: 469.2 (M+1).

Example 3c—Process to Make

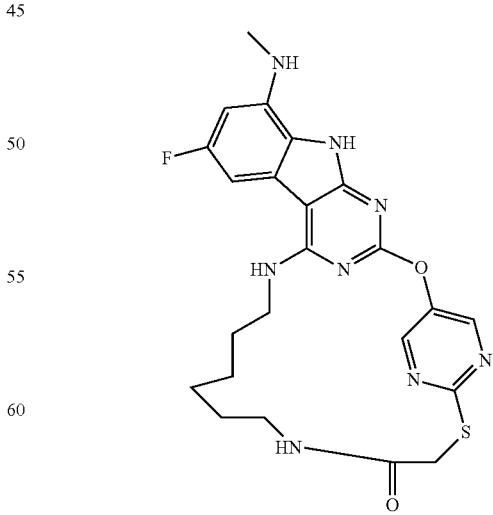

Using a Similar Process as in Example 3b, the Above Compound was Made.

Example 3d—Process to Make
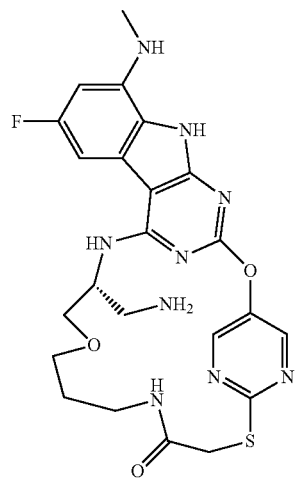
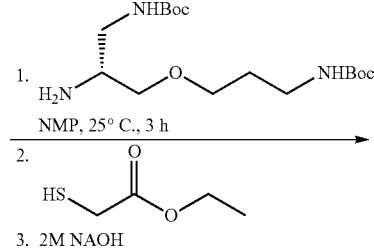
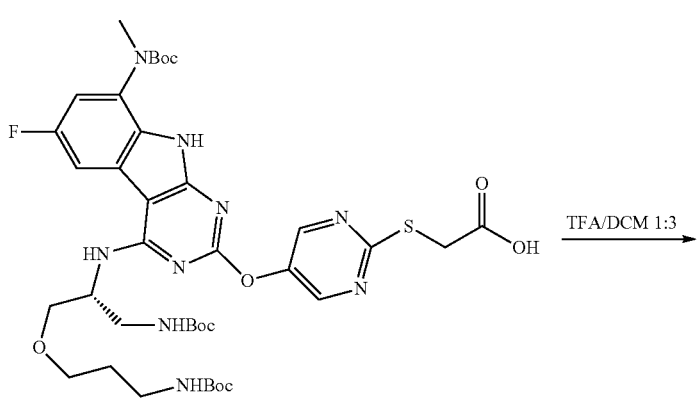
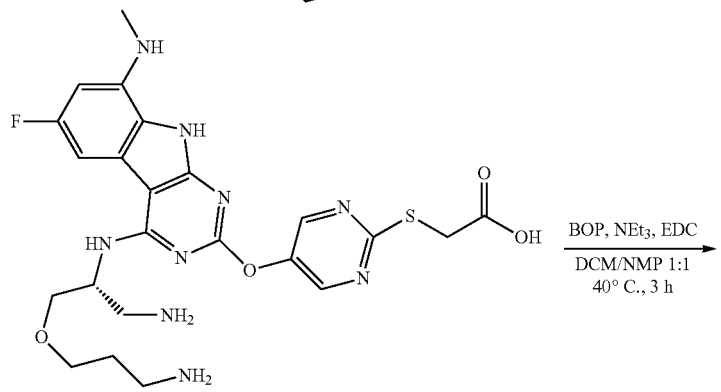
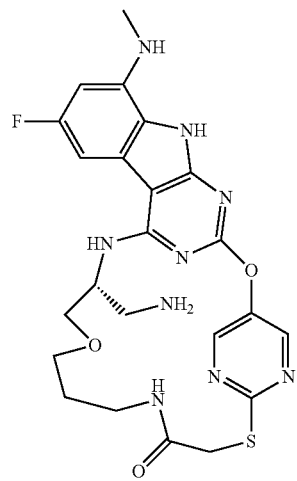

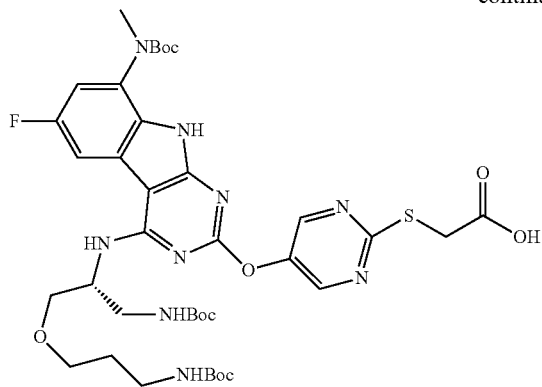

(R)-2-((5-((8-((tert-butoxycarbonyl)(methyl)amino)-6-fluoro-4-((2,2,16,16-tetramethyl-4,14-dioxo-3,9,15-trioxa-5,13-diazaheptadecan-7-yl)amino)-9H-pyrimido[4,5-b]indol-2-yl)oxy)pyrimidin-2-yl)thio) acetic acid tert-butyl (4-(benzyl sulfonyl)-6-fluoro-2-((2-(methylsulfonyl)pyrimidin-5-yl)oxy)-9H-pyrimido[4,5-b]indol-8-yl)(methyl)carbamate (80 mg, 0.124 mmol) and (R)-tert-butyl (2-amino-3-(3-Boc-aminopropoxy)propyl)carbamate (173 mg, 0.498 mmol) were mixed in NMP (1.5 ml) and stirred at 25° C. for 3 hours. Ethyl 2-mercaptoacetate (150 mg, 1.245 mmol) was added and the mixture was heated at 60° C. for 1 hour. 2M NaOH (excess) was added and the mixture was heated at 100° C. for 5 min. The crude reaction mixture was purified by RPLC to yield the title compound (73 mg, 0.086 mmol, 69%). LCMS m/z: 846.3 (M+1).

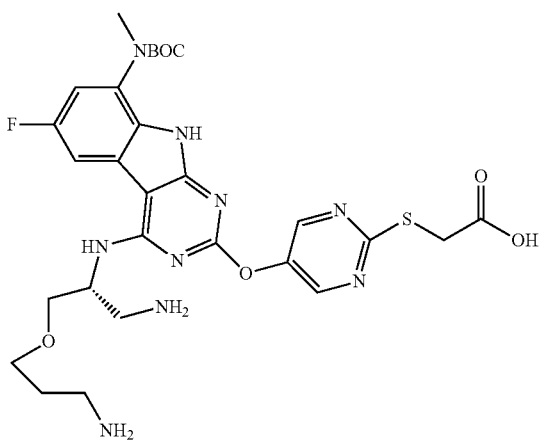

(R)-2-((5-((4-((1-amino-3-(3-aminopropoxy)propan-2-yl)amino)-6-fluoro-8-(methylamino)-9H-pyrimido[4,5-b]indol-2-yl)oxy)pyrimidin-2-yl)thio)acetic acid (R)-2-((5-((8-((tert-butoxycarbonyl)(methyl)amino)-6-fluoro-4-((2,2,16,16-tetramethyl-4,14-dioxo-3,9,15-trioxa-5,13-diazaheptadecan-7-yl)amino)-9H-pyrimido[4,5-b]indol-2-yl)oxy)pyrimidin-2-yl)thio)acetic acid (73 mg, 0.086 mmol) was mixed with DCM/TFA (4:1, 1.5 ml) and heated at 40° C. for 15 min. To the stirring mixture was added diethyl ether (10 ml). The precipitated title compound was isolated in form of its TFA (3×) salt by filtration (68 mg, 0.077 mmol, 89%). LCMS m/z: 469.2 (M+1).

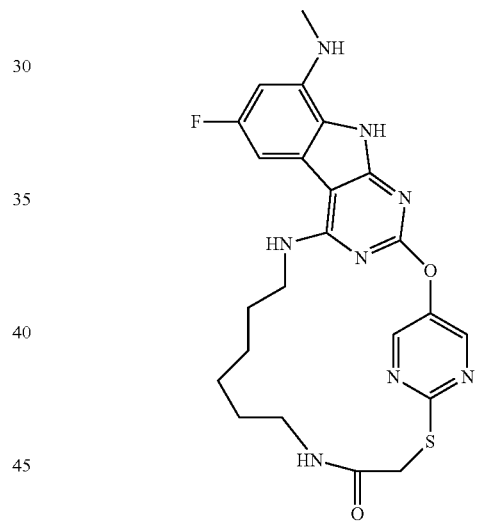

Macrocyclization:

(R)-2-((5-((4-((1-amino-3-(3-aminopropoxy)propan-2-yl)amino)-6-fluoro-8-(methylamino)-9H-pyrimido[4,5-b]indol-2-yl)oxy)pyrimidin-2-yl)thio)acetic acid (68 mg, 0.077 mmol), triethylamine (31 mg, 0.306 mmol) and BOP (102 mg, 0.230 mmol) were mixed in DCM/NMP (1:1, 2 ml) at 0° C. The mixture was warmed to 40° C. over a period of 1 h. LCMS indicated only traces of product formation. EDC (88 mg, 0.460 mmol) was added and the mixture was heated at 40° C. for a period of 2h. NMP (1 ml) was added and the DCM removed under reduced pressure. The crude reaction mixture was purified by RPLC to yield the macrocyclic compound (23 mg, 0.044 mmol, 57%). LCMS m/z: 528.1 (M+1).

Example 3e—Process to Make
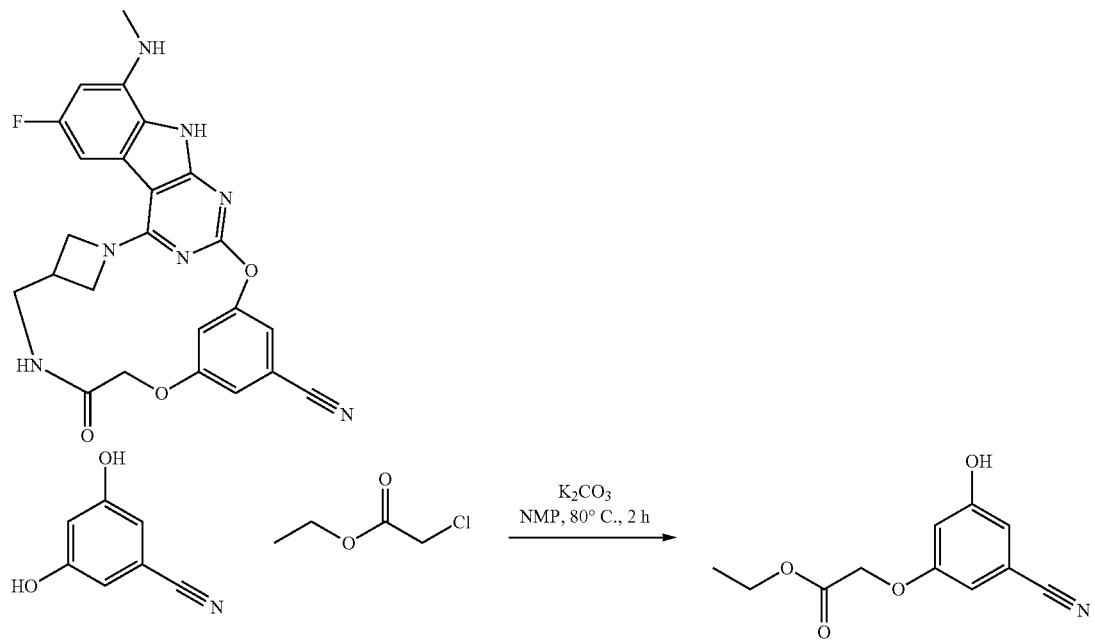
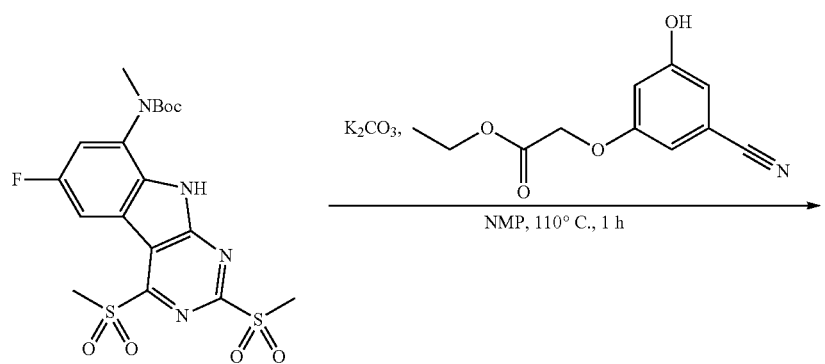
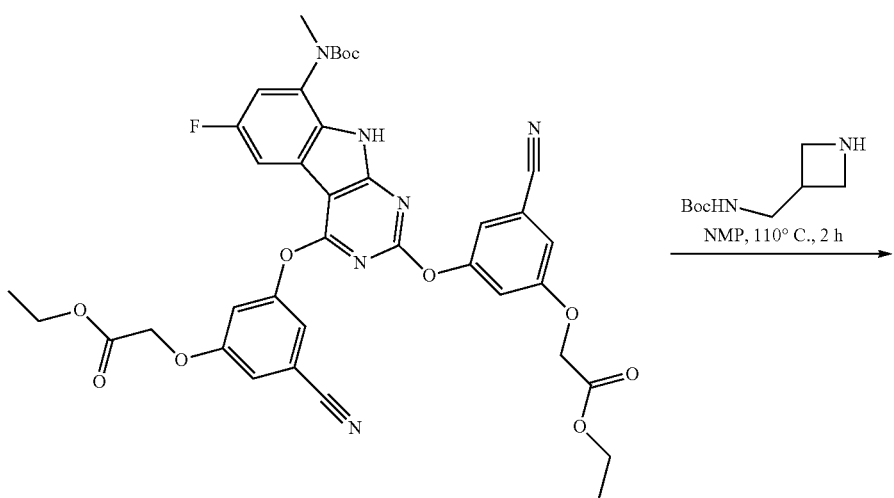

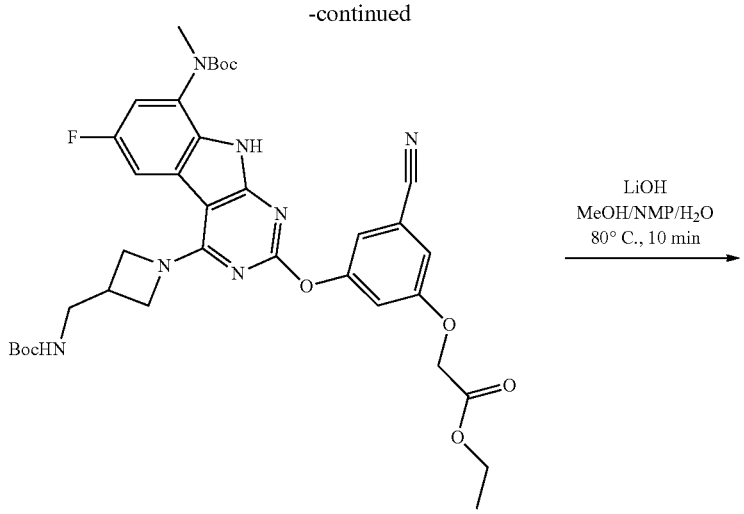
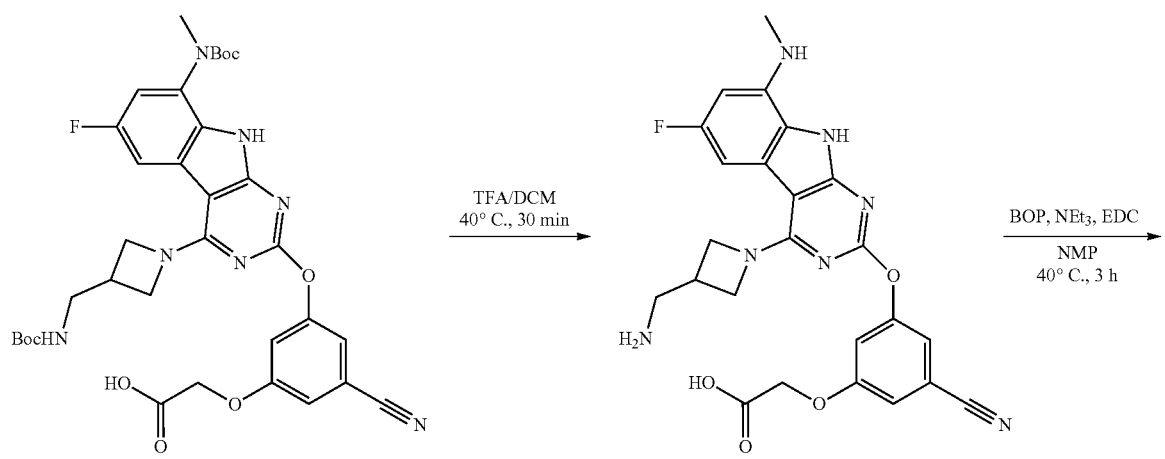
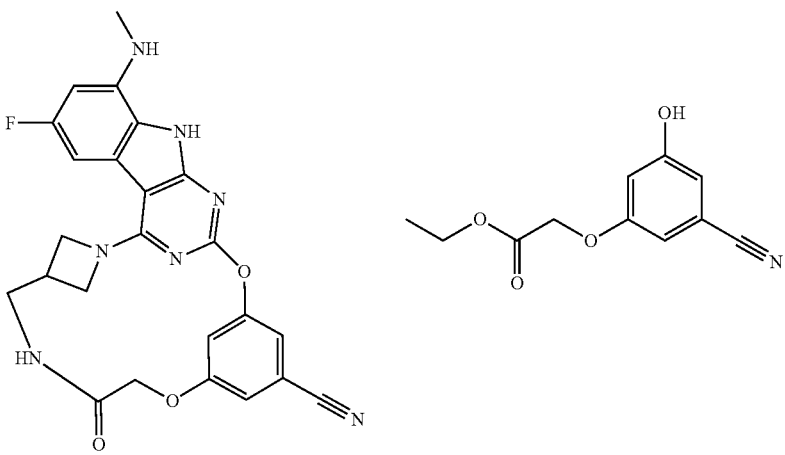
Ethyl 2-(3-cyano-5-hydroxyphenoxy)acetate
3,5-dihydroxybenzonitrile (3.0 g, 22.2 mmol) and potassium carbonate (3.68 g, 26.6 mmol) were mixed in NMP (25 ml). Ethyl 2-chloroacetate (3.27 g, 26.6 mmol) was added and the mixture was heated at 80° C. for 2 h. The crude reaction mixture was purified by flash chromatography to yield the title compound (1.8 g, 8.1 mmol, 36.6%). LCMS m/z: 222.1 (M+1).

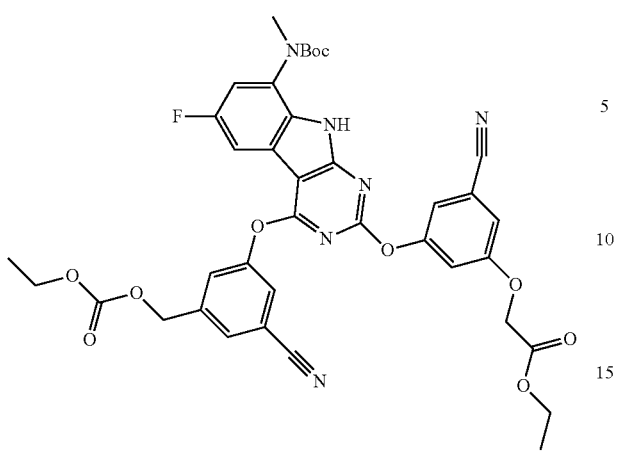

Diethyl 2,2'-((((8-((tert-butoxycarbonyl)(methyl)amino)-6-fluoro-9H-pyrimido[4,5-b]indole-2,4-diyl)bis(oxy))bis(3-cyano-5,1-phenylene))bis(oxy))diacetate tert-butyl (2,4-bis(methylsulfonyl)-6-fluoro-9H-pyrimido[4,5-b]indol-8-yl)(methyl)carbamate (1.0 g, 2.1 mmol), ethyl 2-(3-cyano-5-hydroxyphenoxy)acetate (1.8 g, 8.1 mmol) and potassium carbonate (1.3 g, 9.5 mmol) were mixed in NMP (10 ml) and heated at 110° C. for 1 h. The crude reaction mixture was purified by flash chromatography to yield the title compound (0.93 g, 1.2 mmol, 58%). LCMS m/z: 755.2 (M+1).

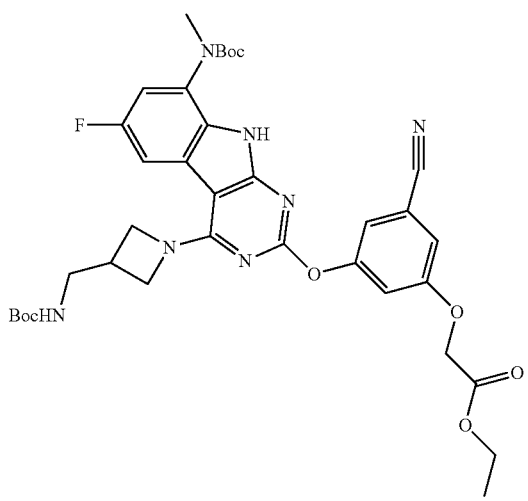 [SMILES: CCOC(=O)COc1cc(C#N)cc(Oc2nc(N3CC(CNC(=O)OC(C)(C)C)C3)c3c(n2)[nH]c2c(N(C)C(=O)OC(C)(C)C)cc(F)cc23)c1]

Ethyl 2-(3-((8-((tert-butoxycarbonyl)(methyl)amino)-4-(3-(((tert-butoxycarbonyl)amino)methyl)azetidin-1-yl)-6-fluoro-9H-pyrimido[4,5-b]indol-2-yl)oxy)-5-cyanophenoxy)acetate diethyl 2,2'-((((8-((tert-butoxycarbonyl)(methyl)amino)-6-fluoro-9H-pyrimido[4,5-b]indole-2,4-diyl)bis(oxy))bis(3-cyano-5,1-phenylene))bis(oxy))diacetate (200 mg, 0.265 mmol) and tert-butyl(azetidin-3-ylmethyl)carbamate (148 mg, 0.795 mmol) were mixed in NMP (1.5 ml) and heated at 110° C. for 2 h. The crude reaction mixture was purified by RPLC to yield the title compound (143 mg, 0.20 mmol, 75%). LCMS m/z: 720.2 (M+1).

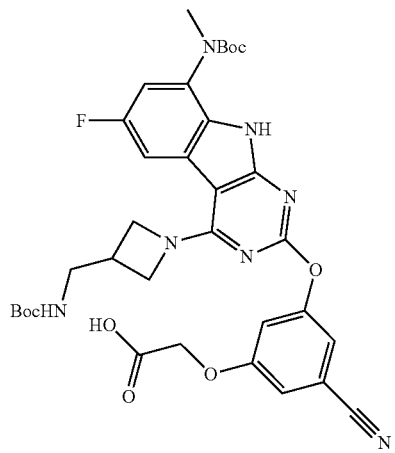 [SMILES: CN(C(=O)OC(C)(C)C)c1cc(F)cc2c1[nH]c1nc(Oc3cc(C#N)cc(OCC(=O)O)c3)nc(N3CC(CNC(=O)OC(C)(C)C)C3)c12]

2-(3-((8-((tert-butoxycarbonyl)(methyl)amino)-4-(3-(((tert-butoxycarbonyl)amino)methyl)azetidin-1-yl)-6-fluoro-9H-pyrimido[4,5-b]indol-2-yl)oxy)-5-cyanophenoxy)acetic acid ethyl 2-(3-((8-((tert-butoxycarbonyl)(methyl)amino)-4-(3-(((tert-butoxycarbonyl)amino)methyl)azetidin-1-yl)-6-fluoro-9H-pyrimido[4,5-b]indol-2-yl)oxy)-5-cyanophenoxy)acetate (143 mg, 0.20 mmol) was dissolved in NMP (1 ml). Methanol (0.5 ml), water (0.2 ml) and powdered lithium hydroxide (47.6 mg, 2.0 mmol) were added and the mixture was heated at 80° C. for 10 min. The crude reaction mixture was purified by RPLC to yield the title compound (110 mg, 0.16 mmol, 80%). LCMS m/z: 692.1 (M+1).

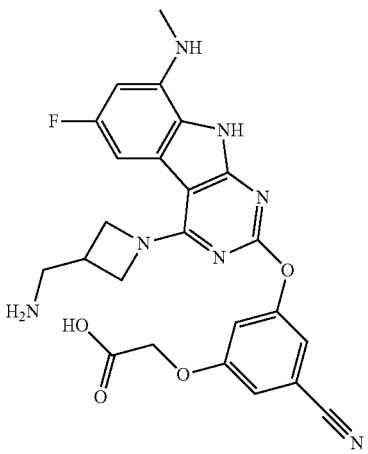 [SMILES: CNc1cc(F)cc2c1[nH]c1nc(Oc3cc(C#N)cc(OCC(=O)O)c3)nc(N3CC(CN)C3)c12]

2-(3-((4-(3-(aminomethyl)azetidin-1-yl)-6-fluoro-8-(methylamino)-9H-pyrimido[4,5-b]indol-2-yl)oxy)-5-cyanophenoxy)acetic acid 2-(3-((8-((tert-butoxycarbonyl)(methyl)amino)-4-(3-(((tert-butoxycarbonyl)amino)methyl)azetidin-1-yl)-6-fluoro-9H-pyrimido[4,5-b]indol-2-yl)oxy)-5-cyanophenoxy)acetic acid (110 mg, 0.16 mmol) was dissolved in a mixture of DCM/TFA (3:1, 2 ml) and heated at 40° C. for 30 min. To the stirring mixture was added diethyl ether (8 ml) and hexane (2 ml). The precipitated title compound was isolated in form of its TFA salt by filtration (92 mg, 0.15 mmol, 95%). LCMS m/z: 492.2 (M+1).

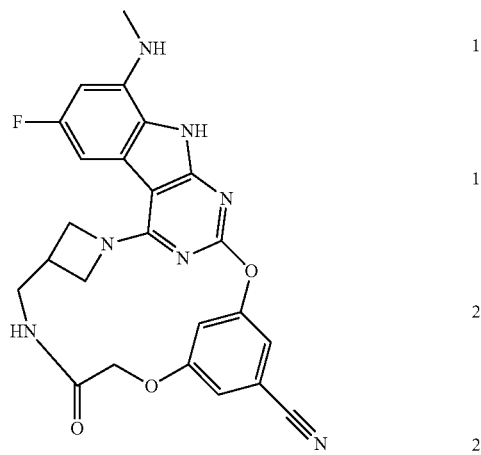

Macrocyclization:

2-(3-((4-(3-(aminomethyl)azetidin-1-yl)-6-fluoro-8-(methylamino)-9H-pyrimido[4,5-b]indol-2-yl)oxy)-5-cyanophenoxy)acetic acid (40 mg, 0.08 mmol), triethylamine (33 mg, 0.33 mmol) and BOP (72 mg, 0.16 mmol) were mixed in DCM/NMP (1:1, 2 ml) at 23° C. EDC (47 mg, 0.244 mmol) was added and the mixture was heated at 40° C. for a period of 2 h. NMP (1 ml) was added and the DCM removed under reduced pressure. The crude reaction mixture was purified by RPLC to yield the macrocyclic compound (6.4 mg, 0.014 mmol, 17%). LCMS m/z: 474.3 (M+1).

Example 3f—Process to Make

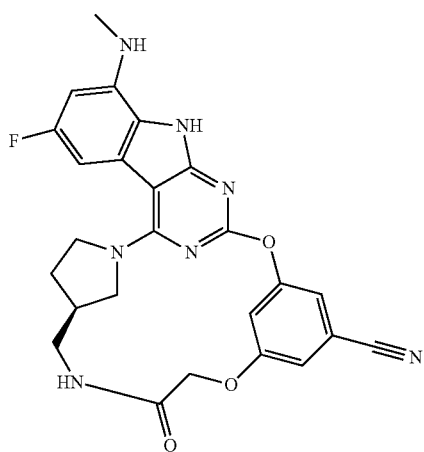 [SMILES: CNc1cc(F)cc2c1[nH]c1nc3nc(c12)N1CC[C@H](CNC(=O)COc2cc(C#N)cc(c2)O3)C1]

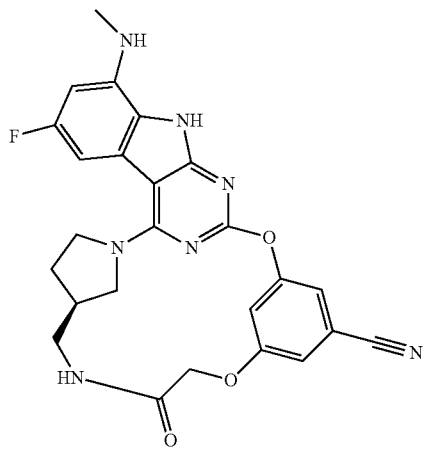

was made using a similar same process as Example 3e.

Example 4

Synthesis of Compounds of Formula I with D and E Rings

Example 4a—Process to Make

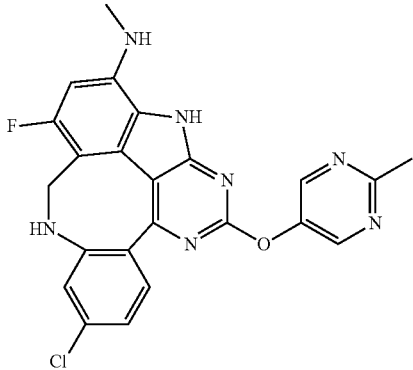

(15)

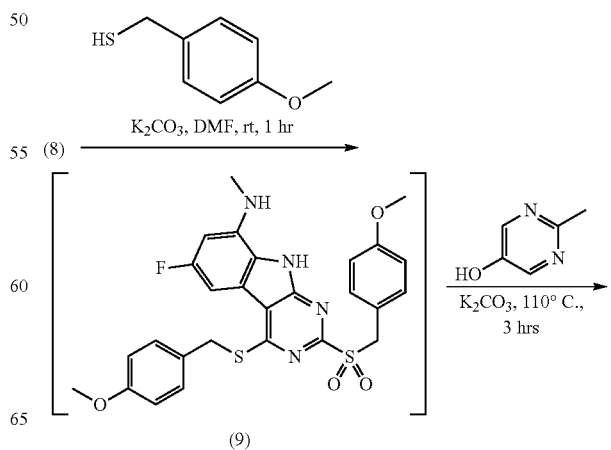

257

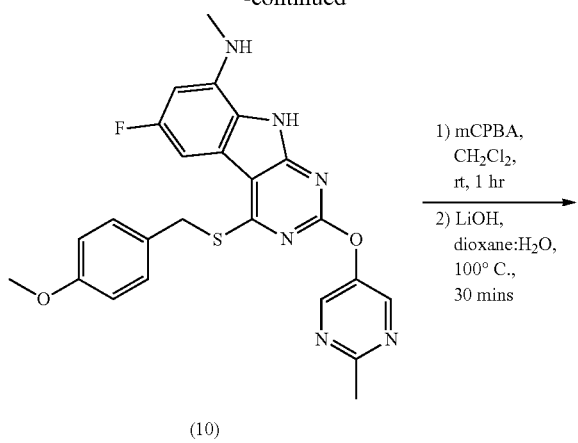
(10)

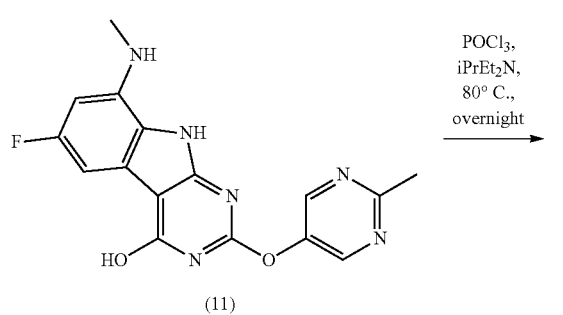
(11)

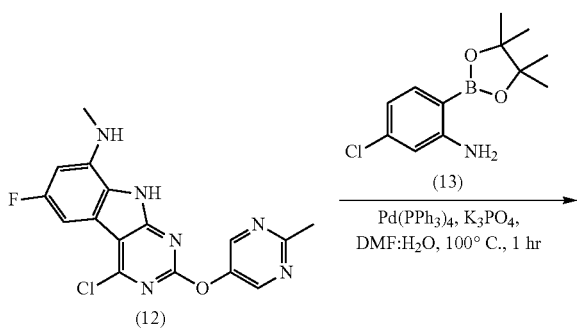
(12)

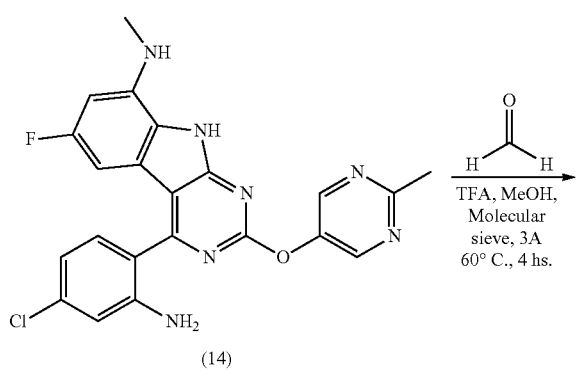
(14)

258

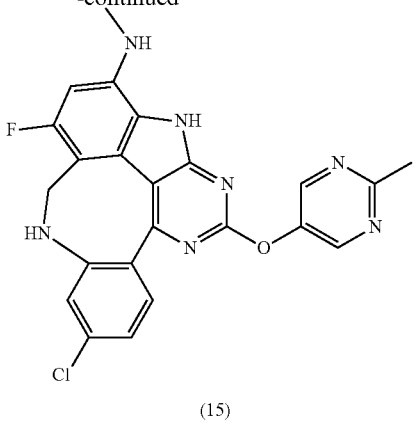
(15)

6-Fluoro-4-(4-methoxybenzylthio)-N-methyl-2-(2-methylpyrimidin-5-yloxy)-9H-pyrimido[4,5-b]indol-8-amine (10)

To the solution of compound (8) (2.923 g, 5 mmol) in NMP (12 ml) was added potassium carbonate (2.073 g, 15 mmol) followed by 4-methoxyphenyl)methanethiol (0.771 g, 5 mmol). The reaction mixture was stirred at room temperature for one hour. 2-Methylpyrimidine-5-ol (1.101 g, 10 mmol) was then added. The resulting mixture was heated at 100° C. for 3 hours. It was purified through C18 column chromatography to afford the title compound as light yellow solid (2.4 g, 83%).

6-Fluoro-8-(methylamino)-2-(2-methylpyrimidin-5-yloxy)-9H-pyrimido[4,5-b]indol-4-ol (11)

To the solution of compound (10) (2.48 g, 4.3 mmol) in dioxane (12 ml) was added 3-chloroperoxy benzoic acid (1.484 g, 8.6 mmol) by portions over 10 minutes. After the reaction was stirred at room temperature for 30 minutes, lithium hydroxide (1.8 g, 75 mmol) and water (5 ml) were added. The resulting solution was stirred at room temperature to 100° C. for one hour. It was then purified through C18 column chromatography to afford the title compound as white solid (1.39 g, 95%).

4-Chloro-6-fluoro-N-methyl-2-(2-methylpyrimidin-5-yloxy)-9H-pyrimido[4,5-b]indol-8-amine (12)

Compound (11) (1.06 g, 2.407 mmol) was dissolved in POCl$_3$ (20 ml) and N-ethyl-isopropylpropan-2-amine (0.43 g, 3.33 mmol). The mixture was heated at 50° C. for 4 hours. After the reaction was cooled down to room temperature, it was poured into a 1 L-flask containing ice (~500 g) and NaOH (20 g) and the resulting was sat for one hour. It was then extracted with ethyl acetate (100 ml×3). The combined organic layers were dried over Na$_2$SO$_4$ and concentrated by rotary evaporation to afford the title compound as white solid (492 mg, 57%).

4-(2-amino-4-chlorophenyl)-6-fluoro-N-methyl-2-(2-methylpyrimidin-5-yloxy)-9H-pyrimido[4,5-b]indol-8-amine (14)

The mixture of compound (12) (36 mg, 0.1 mmol), the boronic acid pinacol ester (13) (38 mg, 0.15 mmol), potassium phosphate (64 mg, 0.3 mmol), and catalytic amount of Pd(PPh₃)₄ was dissolved in DMF (1 ml) and water (0.3 ml). The reaction mixture was refluxed at 100° C. for one hour. It was then purified through HPLC to afford the title compound as yellow product (17 mg, 37.8%).

8-chloro-4-fluoro-N-methyl-12-((2-methylpyrimidin-5-yl)oxy)-5,6-dihydro-1H-,6,11,13-tetraazabenzo[5,6]cycloocta[1,2,3,4-def]fluoren-2-amine (15)

To the solution of compound (14) (13.5 mg, 0.3 mmol) in MeOH (30 ml) was added 37% solution of formaldehyde (0.1 ml), 2 drops of trifluoroacetic acid, and ~3.5 g of molecular sieve, 3 Å. The resulting mixture was heated at 60° C. for 7 hours. The molecular sieve was then filtered off and washed with MeOH. The filtrate was concentrated by rotary evaporation and purified by C18 column to afford the title compound as yellow solid (10.3 mg, 74%).

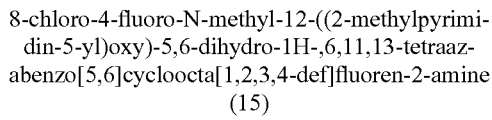

(1)

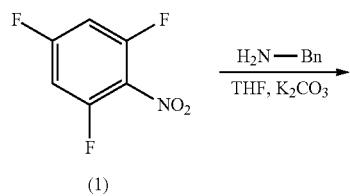

(16)

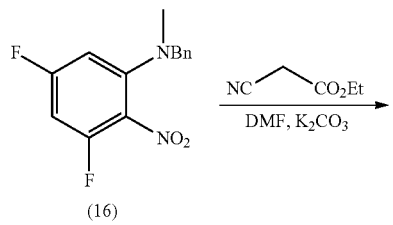

(17)

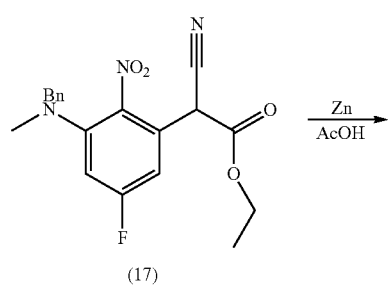

(18)

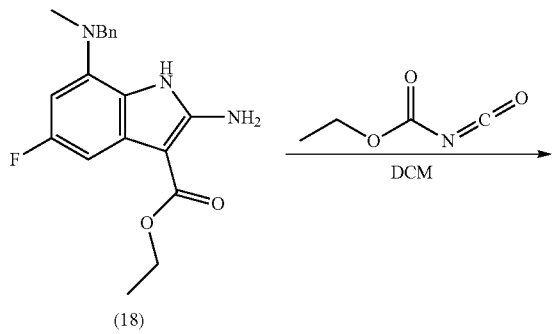

(19)

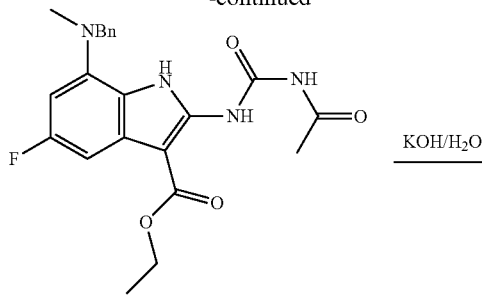

(20)

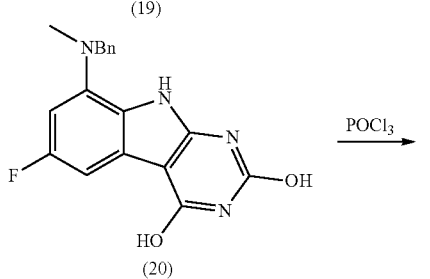

(21)

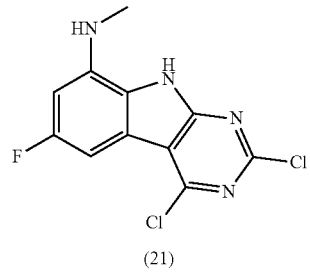

Compound (16):

To a stirred suspension of BnNHMe (34.2 g, 0.282 moL) and K₂CO₃ (50.6 g, 0.367 moL) in 400 mL of THF was added dropwise a solution of compound 1 (50.0 g, 0.282 moL) in 100 mL of THF below 10° C. After addition, the reaction was warmed to r.t. slowly and stirred overnight. TCL showed the reaction was completed; the reaction mixture was concentrated under vacuum. The residue was partitioned by ethyl acetate (300 mL) and water (500 mL), the organic layer was washed with brine (300 mL×3), dried over Na₂SO₄, filtered, and concentrated under vacuum. The crude product was purified by flash chromatography (pet. ether/EtOAc, 100/1 to 50/1, v/v) to give the product 16 as a pale yellow solid. (69.0 g, 87.9% yield). LC-MS: M+1: 279. ¹H-NMR (400 MHz, CDCl₃): δ (ppm)=7.37 (m, 5H), 6.43 (m, 2H), 4.40 (s, 2H), 2.84 (s, 3H).

Compound 17

To a stirred suspension of K₂CO₃ (57.6 g, 0.417 moL) and ethyl cyanoacetate (35.4 g, 0.313 moL) in 200 mL of DMF was added a solution of compound 16 (58.0 g, 0.208 mol) in 100 mL DMF under N₂ protection. After addition, the reaction was stirred at r.t. for two days. TLC showed the starting material was consumed, then the reaction mixture was diluted with ethyl acetate (400 ml) and water (1500 ml). The organic layer was separated, and the aqueous layer was extracted by ethyl acetate (200 ml). The combined organic layers were washed with brine (300 ml×3), dried over Na₂SO₄, and concentrated in vacuum. The crude product was purified by chromatography (pet. ether/EtOAc, 100/1 to 20/1, v/v) to give the product 17 as a pale yellow solid. (61.0 g, 79.2% yield). LC-MS: M+1: 371. ¹H-NMR (400 MHz, CDCl₃): δ (ppm)=7.33 (m, 5H), 6.92 (d, J=8 Hz, 1H), 6.84

(d, J=8 Hz, 1H), 5.13 (s, 1H), 4.37 (s, 2H), 4.30 (dd, J=14.4 Hz, 2H), 2.78 (s, 3H), 1.35 (t, J=7.2 Hz, 3H).

Compound 18:

To a stirred solution of compound 17 (61.0 g, 0.164 mol) in 400 ml of AcOH cooled on an ice bath was added 10 equivalent of zinc powder in portions.

After addition, the reaction was heated to 60° C. and stirred at this temperature for 5 h. TLC showed the reaction was completed. The reaction mixture was cooled to r.t. and filtered.

After the filtrate was concentrated by rotary evaporation, the residue was dissolved in ethyl acetate (400 ml), basified by saturated NaHCO$_3$ aqueous solution (400 ml). The organic layer was then separated, washed with brine (200 ml×3), dried over Na$_2$SO$_4$, and concentrated by rotary evaporation. The resulting dark oil was then purified by column chromatography (pet. ether/DCM, 5/1 to DCM, v/v) to give the product 18 as a pale yellow solid (26.0 g, 46.4% yield). LC-MS: M+1: 342. $^1$H-NMR (400 MHz, CDCl$_3$): δ (ppm)=8.02 (s, 1H), 7.33 (m, 5H), 6.52 (d, J=2.4 Hz, 1H), 6.49 (d, J=2.4 Hz, 1H), 5.73 (s, 2H), 4.35 (dd, J=15.2 Hz, 2H). 4.19 (s, 2H), 2.73 (s, 3H), 1.44 (t, J=7.2 Hz, 3H).

Compound 19:

To a stirred suspension of 18 (16.0 g, 46.9 mmol) in 200 mL of DCM was added dropwise ethyl isocyanatoformate (resolved in 50 ml of DCM) with an ice bath cooling. After addition, the resulting mixture was stirred at r.t. The starting material was dissolved gradually and then precipitate was generated from the reaction. 4 hours later, TLC showed the reaction was completed. The reaction mixture was filtered. The filtration was concentrated in vacuo. The residue was suspended in 50 ml of DCM, stirred then filtered. The two batch filter cakes were combined, dried in vacuo to give the product 19 as a pale yellow solid (14.4 g, 67.3% yield). LC-MS: M+1: 457. $^1$H-NMR (400 MHz, DMSO): δ (ppm) =12.01 (s, 1H), 11.12 (s, 1H), 11.06 (s, 1H), 10.41 (s, 1H), 7.33 (m, 5H), 6.63 (d, J=2.0 Hz, 1H), 6.60 (d, J=2.4 Hz, 1H), 4.34 (dd, J=7.2 Hz, 2H), 4.28 (s, 2H), 4.24 (dd, J=7.2 Hz, 2H), 4.14 (dd, J=7.2 Hz, 2H), 2.75 (s, 3H), 1.37 (t, J=7.2 Hz, 3H), 1.27 (t, J=7.2 Hz, 3H), 1.22 (t, J=6.8 Hz, 3H).

Compound 20:

To a stirred suspension of 19 (9.13 g, 20.0 mmol) in water/EtOH (75 ml/25 ml) was added a KOH solution in 20 ml of water at r.t. After addition, the resulting mixture was refluxed for 4 h. TLC showed the reaction was completed, then the reaction was cooled to r.t., acidified with 1M HCl a 1 h. until pH=5 to precipitate the product. The solid was collected by filtration, washed first with water (200 ml) then ethyl acetate (200 ml) to give the product 20 as a pale yellow solid (5.90 g, 87.1% yield). LC-MS: M−1: 337. 1H-NMR (400 MHz, DMSO): δ (ppm)=7.25 (m, 5H), 7.01 (dd, J=8.8 Hz, 1H), 6.35 (d, J=12.0 Hz, 1H), 4.45 (s, 2H), 2.76 (s, 3H).

Compound 21:

Compound 20 (2 g, 5.75 mmol), POCl$_3$ (100 ml), and few drops of N-ethyldiisopropyl amine were placed in a sealed tube. The reaction mixture was heated to at 185° C. for 10 h. The mixture was cooled and poured into ice water. The yellow solid was collected by filtration, dried under reduced press to give 21 (1.6 g, 98% yield) as a yellow solid. LC-MS: M+1: 286.02.

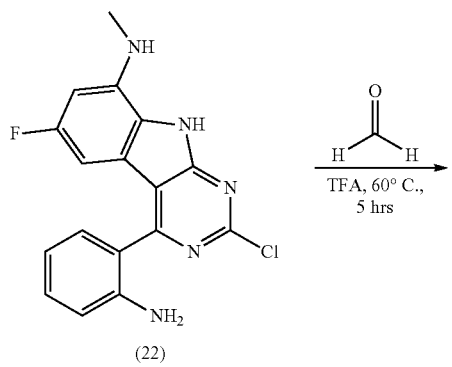

(22)

Compound 22:

The mixture of compound 21 (285 mg, 1 mmol), (2-aminophenyl)boronic acid (137 mg, 1 mmol), potassium phosphate (318 mg, 1.5 mmol), and tetrakis(triphenylphosphine) palladium (0) (35 mg, 0.16 mmol) was dissolved in dioxane (2 ml) and water (0.4 ml). It was heated at 100° C. for 1.5 hours and then purified by C18 column to afford the title product as yellow solid.

Compound 23:

To the solution of compound 22 in MeOH (30 ml) was added 37% solution of formaldehyde (0.1 ml), 2 drops of trifluoroacetic acid, and ~3.5 g of molecular sieve, 4 Å. The resulting mixture was heated at 60° C. for 5 hours. The molecular sieve was filtered off and washed with MeOH. The combined filtrates were concentrated by rotary evaporation to afford the crude yellow solid product. It was carried to the next step without purification.

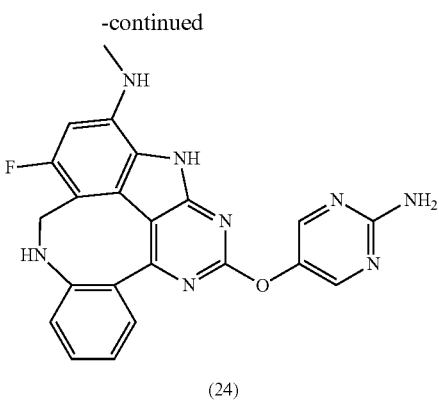

(24)

Compound 24:

To the solution of compound 23 (20 mg, 0.057 mmol) in anhydrous NMP (1 ml) and DMSO (0.1 ml) was added 2-aminopyrimidin-5-ol (21.73 mg, 0.226 mmol) and potassium carbonate (31.3 mg, 0.226 mmol). The mixture was microwaved at 180° C. for 1 hour. It was then purified by C18 column to afford the title compound as yellow solid.

Compound 25:

The mixture of compound 8 (125 mg, 0.2 mmol), 2-methylpyrimidin-5-ol (88.1 mg, 0.8 mmol) and potassium carbonate (112 mg, 0.8 mmol) was dissolved in anhydrous NMP (1 ml). It was heated at 110° C. for 30 minutes. Triethylamine (0.1 ml) and (s)-tert-butyl(pyrrolidin-2-ylmethyl)carbamate were then added. The resulting mixture was heated at 110° C. overnight. The crude product was purified through C18 column chromatography. The collected eluates were concentrated by rotary evaporation at 60° C. The residue was re-dissolved in DCM (2 ml) and TFA (0.1 ml). The mixture was stirred at 40° C. for 30 mins. DCM was then removed by evaporation, and the crude product was carried to the next step without purification.

Compound 26:

The crude product 25 in the previous step was dissolved in MeOH (30 ml) was added 37% solution of formaldehyde (0.1 ml), 2 drops of trifluoroacetic acid, and ~3.5 g of molecular sieve, 4 Å. The resulting mixture was heated at 60° C. for 6 hours. The molecular sieve was filtered off and washed with MeOH. The combined filtrates were concentrated by rotary evaporation. The residue was purified through C18 column chromatography to afford the title compound as yellow solid.

Example 4b—Process to Make

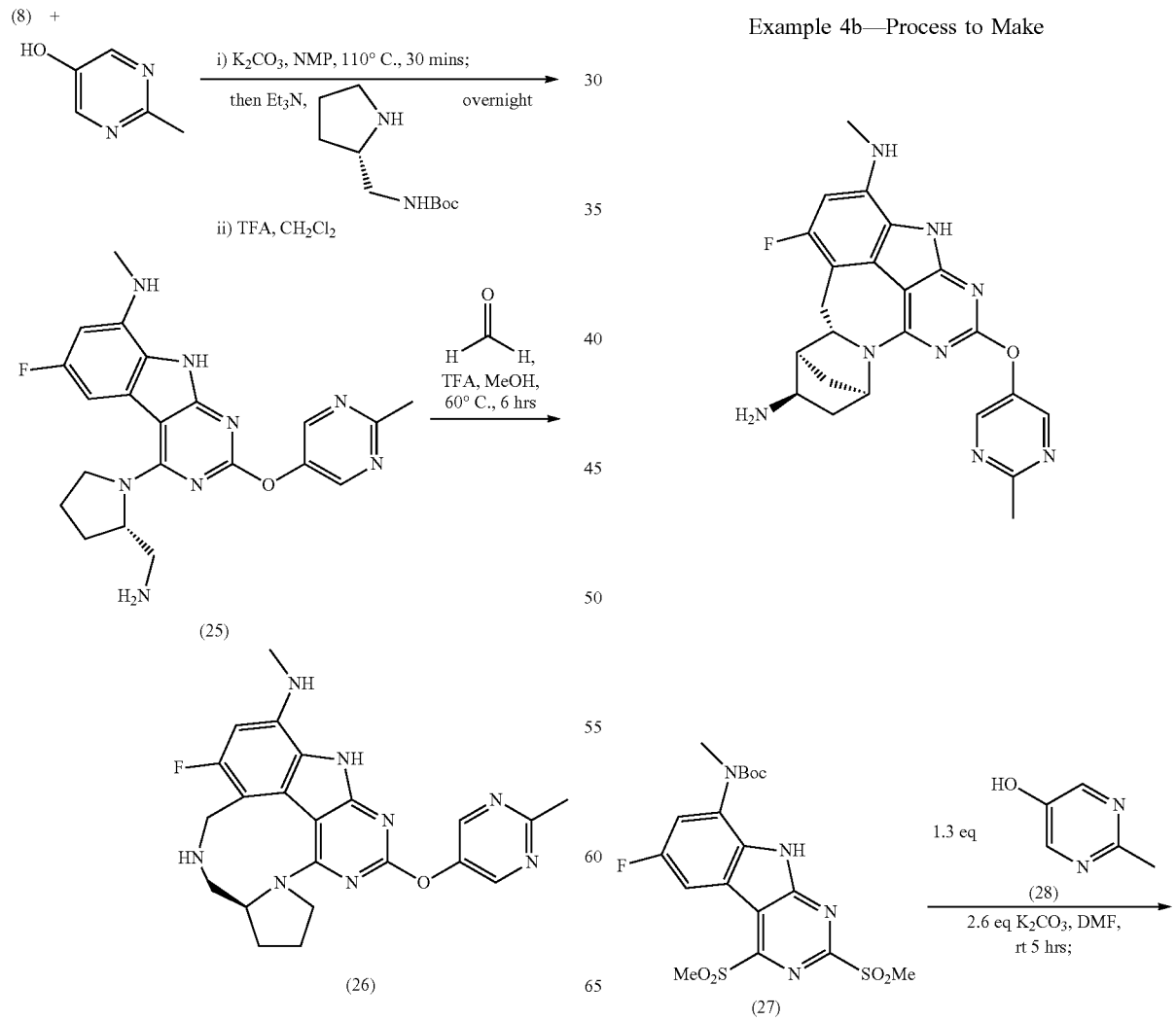

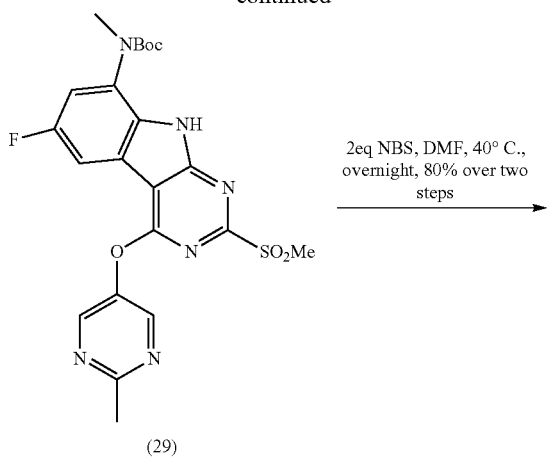

(29)

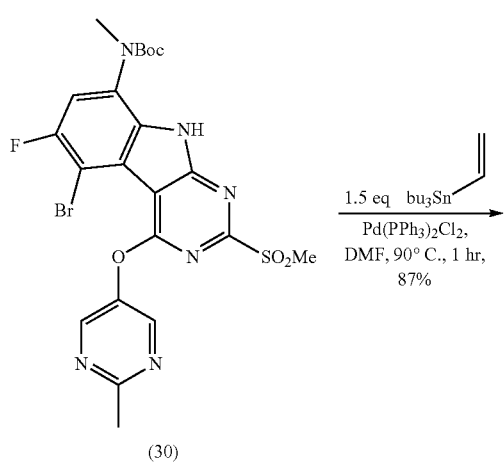

(30)

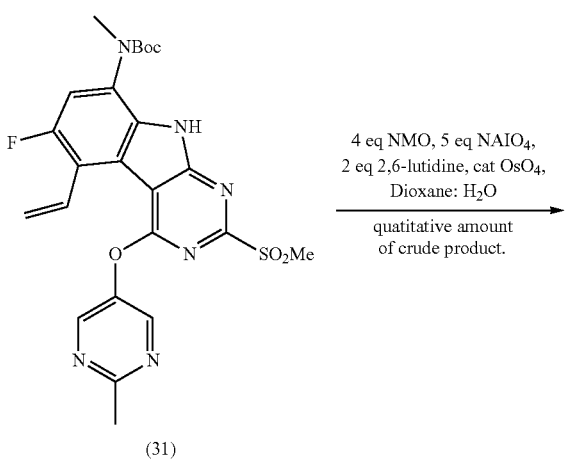

(31)

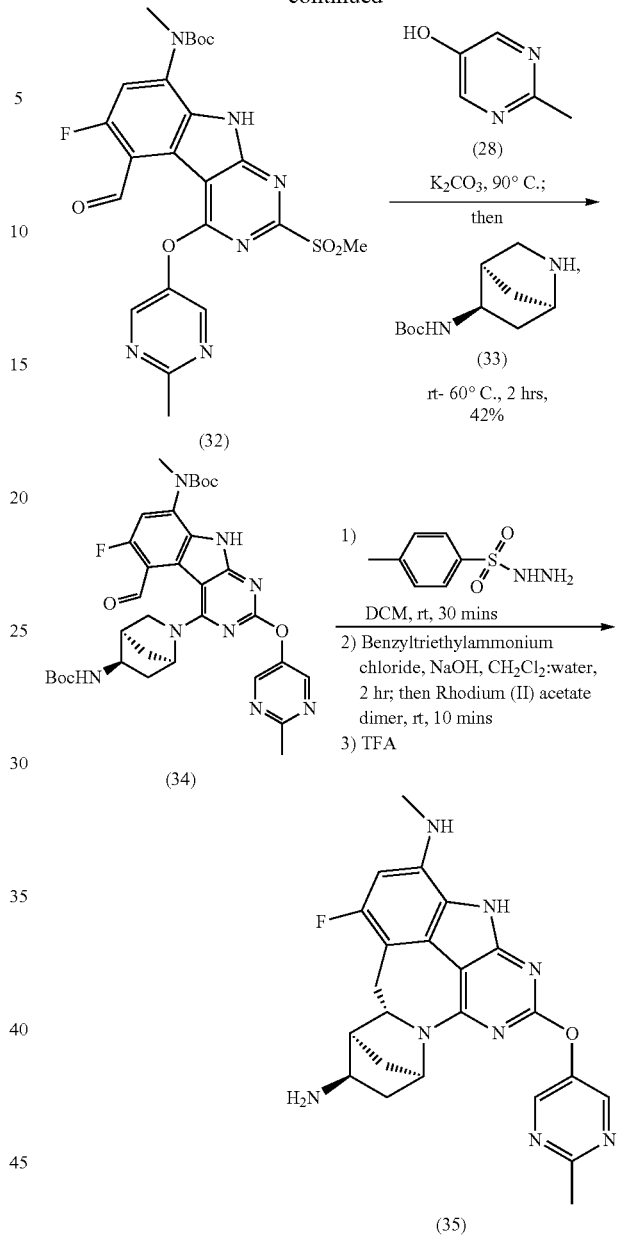

Compound 29.

To the mixture of compound 27 (14.18 g, 30 mmol) and 2-methylpyrimidin-5-ol (4.29 g, 39 mmol) in anhydrous DMF (30 ml) was added $K_2CO_3$ (10.8 g, 78 mmol). The resulting was stirred at rt for 7 hours. It was then diluted with EtOAc (100 ml) and water (100 ml). The aqueous layer was extracted and back-extracted with EtOAc (100 ml×2). The combined organic layers were dried over $Na_2SO_4$ and concentrated by rotary evaporation at 40° C. Possibly trace amount of EtOAc was further dried off through co-evaporation with dichloromethane in vacuo. The crude sticky product (17.2 g) was carried to the next step without further purification. LC-MS: M+1: 503.5

Compound 30.

To the solution of crude compound 29 in anhydrous DMF (30 ml) at 40° C. was added NBS (5.34 g, 30 mmol). The mixture was heated at 40° C. for 2 hours, and an additional amount of NBS (5.34 g, 30 mmol) was added. The reaction was continued at 40° C. overnight. It was then purified through silica gel column chromatography (40-60% EtOAc in hexane). About half of the total volume of the combined fractions were removed by rotary evaporation. The remaining solution was then washed with water (3×100 ml), dried over $Na_2SO_4$, and concentrated by rotary evaporation at 45° C. to afford the title compound as yellow solid (13.95 g, 80%). LC-MS: M+1: 582.3

Compound 31.

The solution of compound 30 (4.4 g, 7.57 mmol) in anhydrous DMF (10 ml) was heated at 90° C., and the air was purged with nitrogen. It was added with t-butylvinyl tin (3.6 g, 11.35 mmol) followed by catalytic amount of $Pd(PPh_3)_2Cl_2$ (301 mg, 0.757 mmol). The resulting mixture was heated at 90° C. for 1 hour under nitrogen. It was then purified through silica gel column chromatography (60-80% EtOAc in hexane). The combined fractions of the product were partially concentrated down to half of the total volume by rotory evaporation. It was then washed with water (3×100 ml), dried over $Na_2SO_4$, and concentrated by rotory evaporation at 45° C. to afford the title compound as yellow solid (3.48 g, 87%). LC-MS: M+1: 529.1

Compound 32.

Mixture of compound 31 (1.057 g, 2 mmol), N-methyl-morpholine-N-oxide (703 mg, 6 mmol), sodium periodate (2.14 g, 10 mmol) was suspended in dioxane (14 ml) and cooled in an ice-water bath. 2,6-lutidine (4.286 mg, 4 mmol) was added to the reaction mixture, followed by catalytic amount of 4% aqueous solution of $OsO_4$ (1 ml) and water (5 ml). After the resulting mixture was stirred for 1 hours, an additional amount of $OsO_4$ (1 ml) was added, and the reaction was continued for 2 hours. It was then poured into a beaker containing EtOAc (80 ml). The sticky mass was filtered off and washed with EtOAc. The filtrate was extracted with water (100 ml) and the aqueous layer was back-extracted with EtOAc (100 ml). The combined organic layers were dried over $Na_2SO_4$ and concentrated in vacuo at rt. The crude yellow solid product (1.06 g) was carried to the next step without further purification. LC-MS: M+1: 531.0

Compound 34.

Mixture of crude compound 32 (841 mg, assumed 1.5 mmol), 2-methylpyrimidin-5-ol (330.3 mg, 3 mmol) and $K_2CO_3$ (967.4 mg, 7 mmol) in anhydrous DMF (2 ml) was heated at 90° C. for 1 hour. After the reaction was cooled to rt, it was added with amine 13 (509.6 mg, 2.4 mmol) and was stirred at rt to 60° C. for 2 hours. The reaction was then purified by C18 column chromatography to afford the title product as yellow solid (890 mg, 65.4% over two steps). LC-MS: M+1: 561.4

Compound 35.

To the solution of compound 34 (460 mg, 0.694 mmol) in DCM (10 ml) was added p-toluenesulfonyl hydrazide (200 mg, 1.074 mmol). The mixture was stirred at rt for 30 minutes and then added with benzyltriethylammonium chloride (632.4 mg, 2.78 mmol) and 10% NaOH solution (4 ml). The mixture was stirred at rt for 2 hours then 40° C. for 3 hours. The aqueous layer was removed and back-extracted with DCM (~6 ml). Rhodium (II) acetate dimer was then added to the combined organic layers. The resulting mixture was stirred at rt for 15 minutes. It was then concentrated by rotor evaporation and purified through HPLC. The di-Boc protected product was treated with TFA (0.3 ml) at rt for 10 minutes and purified by HPLC to provide the title compound as yellow TFA salt. LC-MS: M+1: 447.0

Compounds that may also be made by this process include:

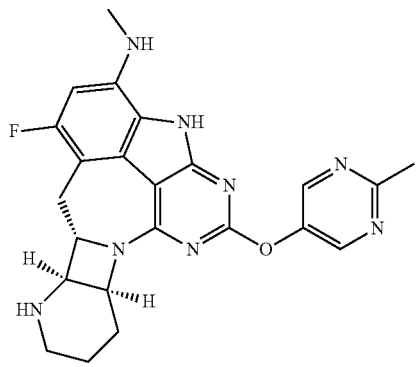

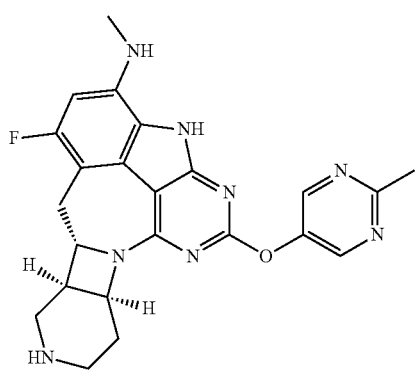

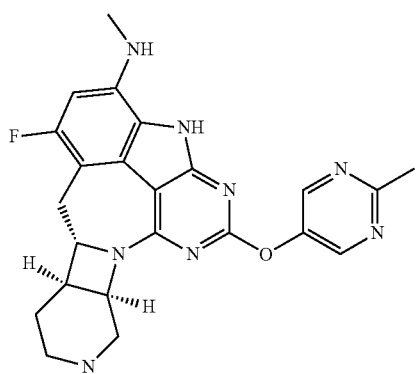

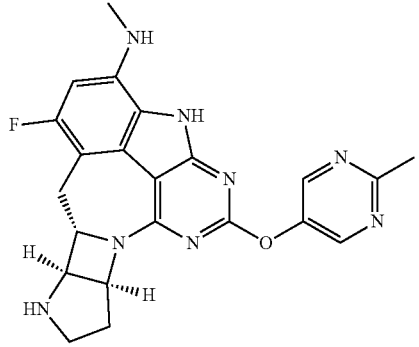

269
-continued
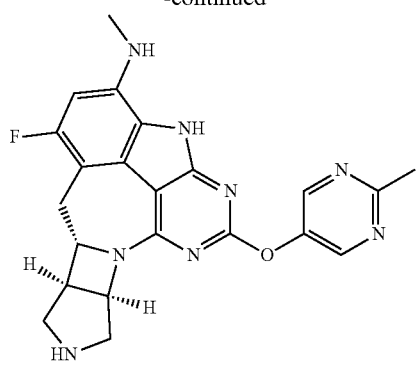
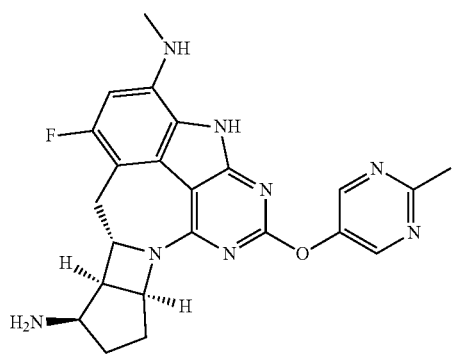
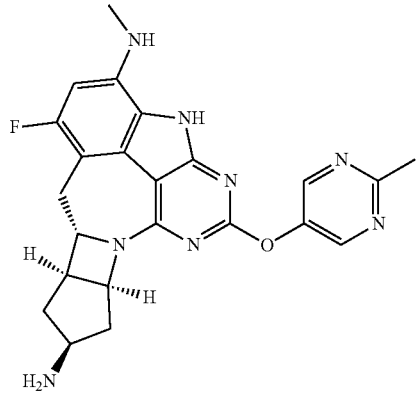
270
-continued
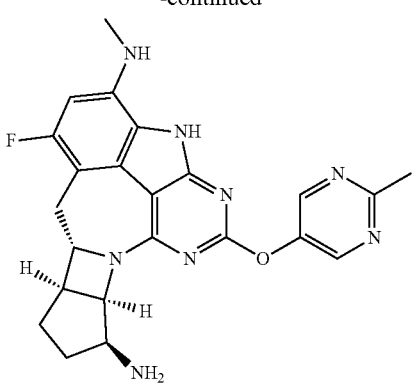
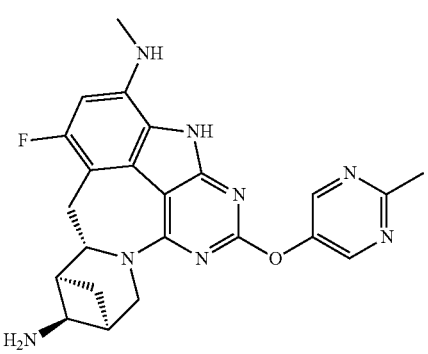
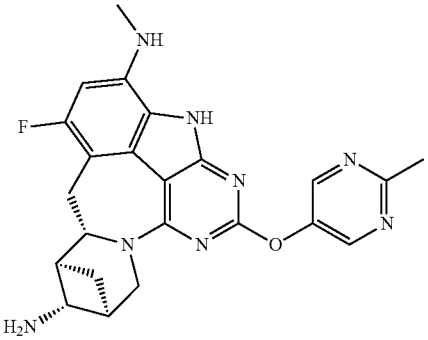
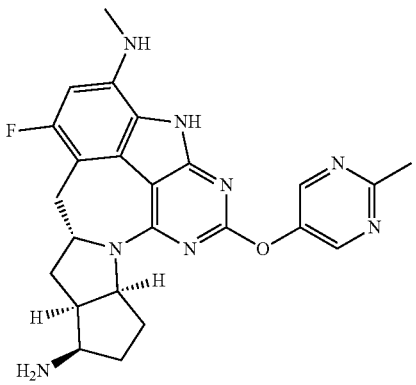

271
-continued
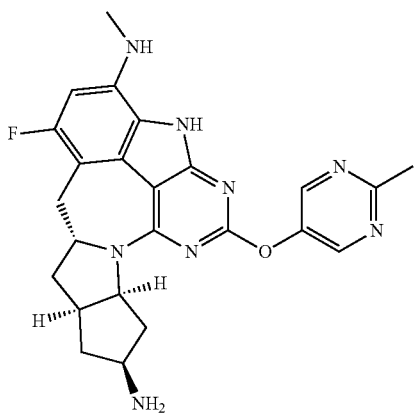
Additional compounds may be made by varying the R² group in any of the compounds above.
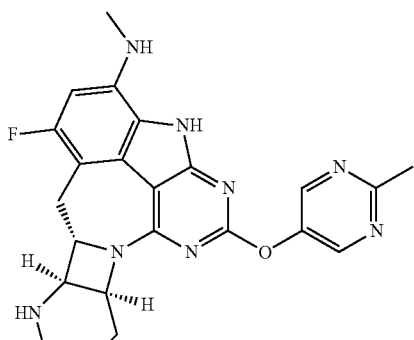
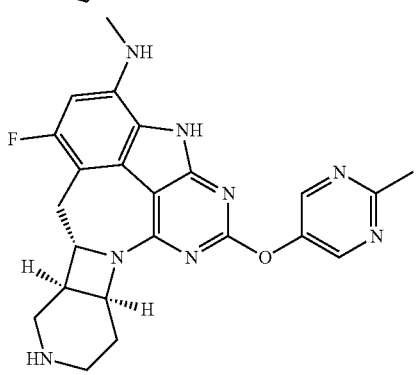
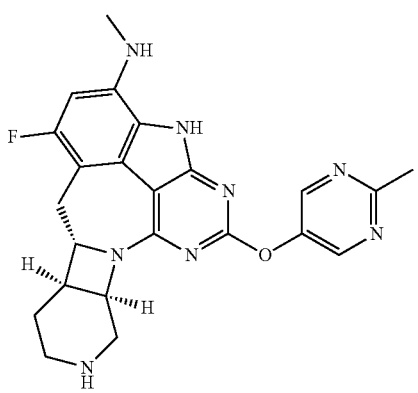
272
-continued
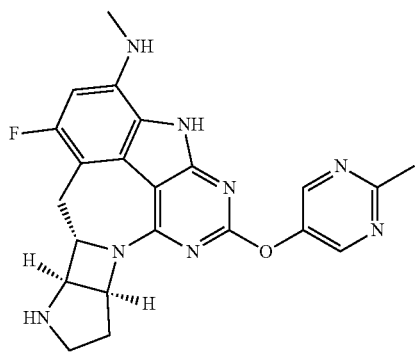
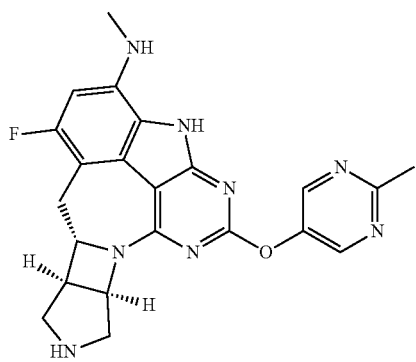
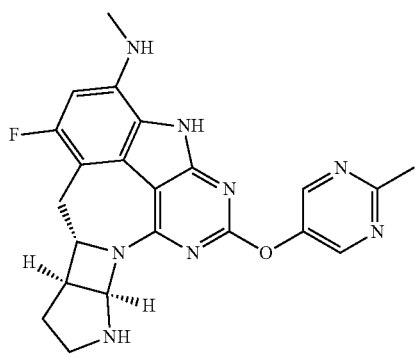
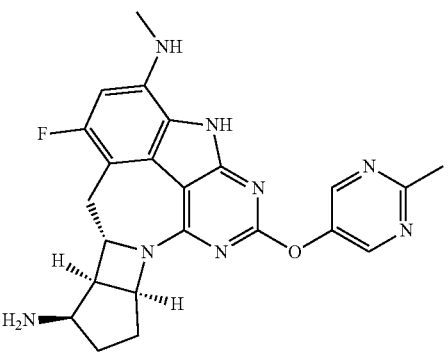

273
-continued
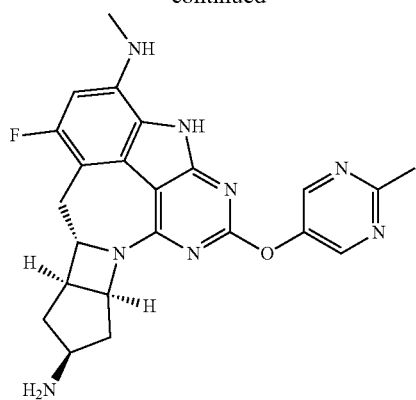
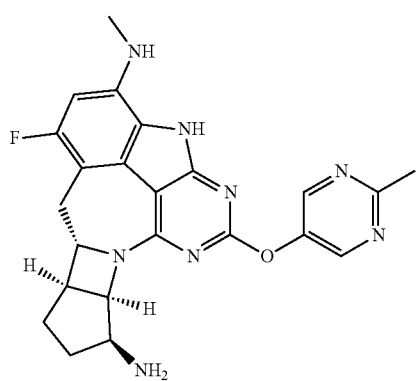
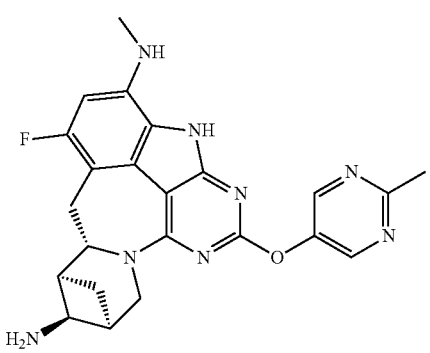
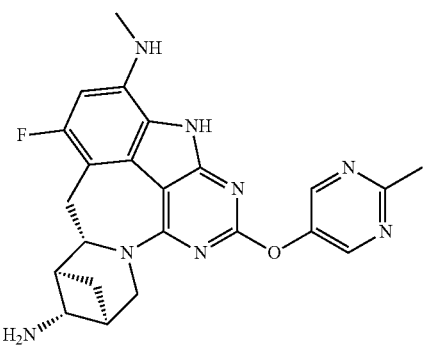
274
-continued
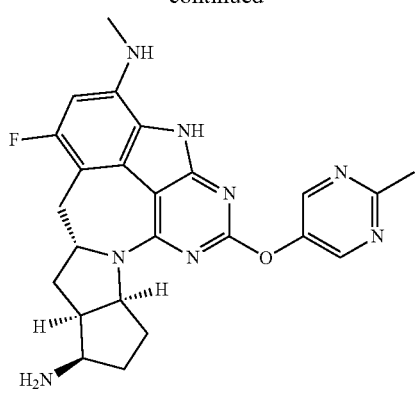
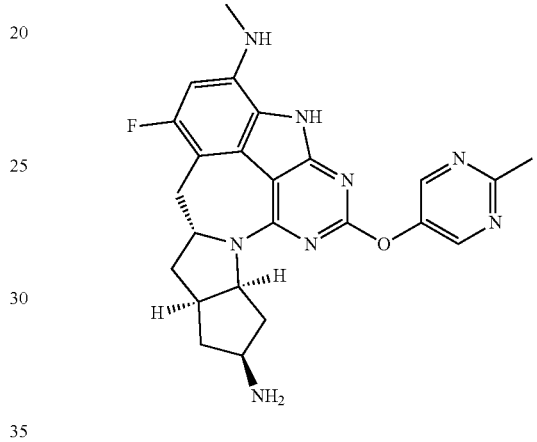
The following compounds were made using the processes herein:
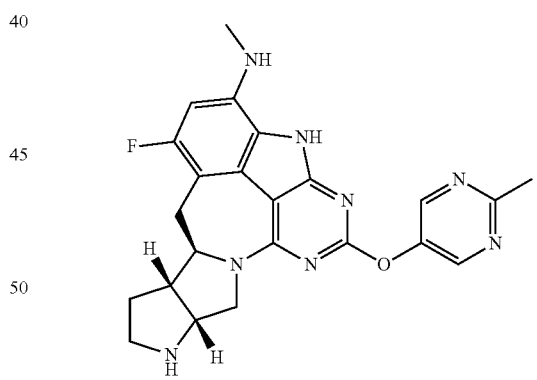
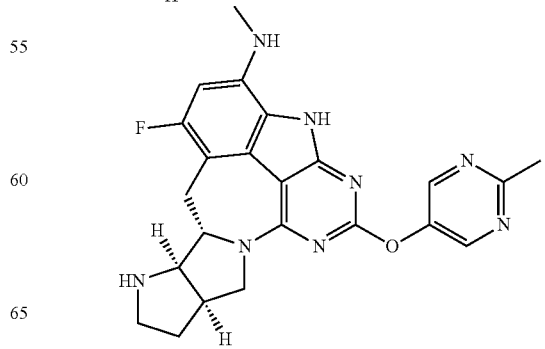

275
-continued
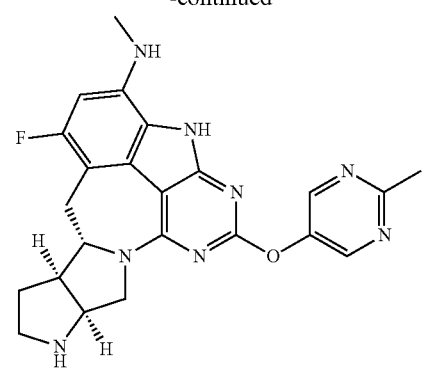
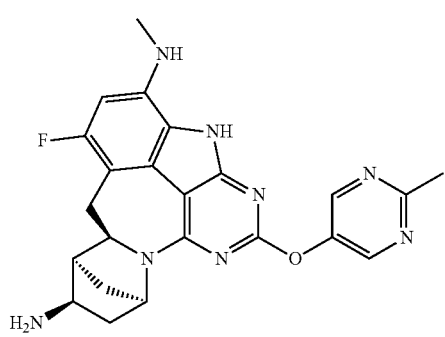
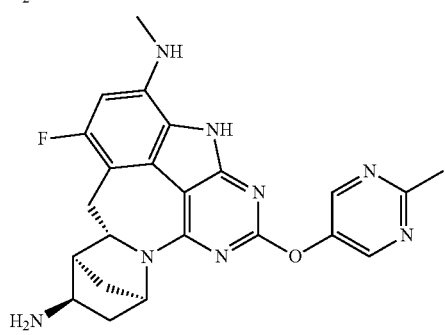
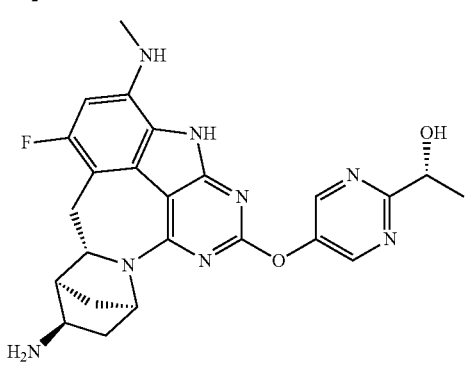
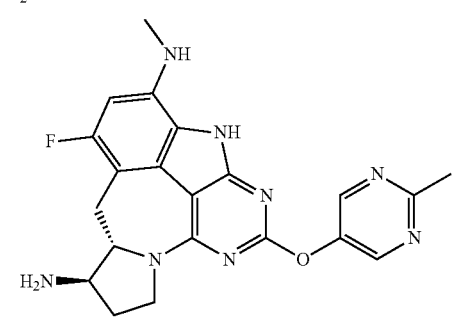
276
-continued
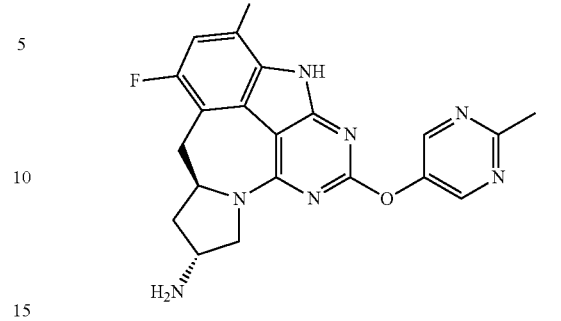
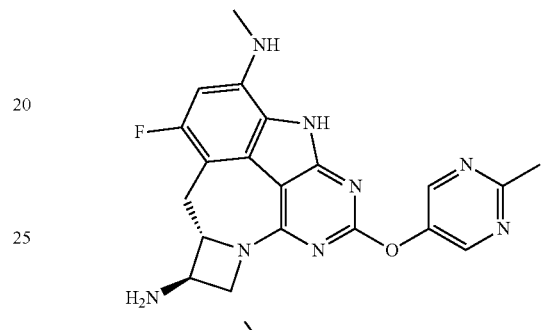
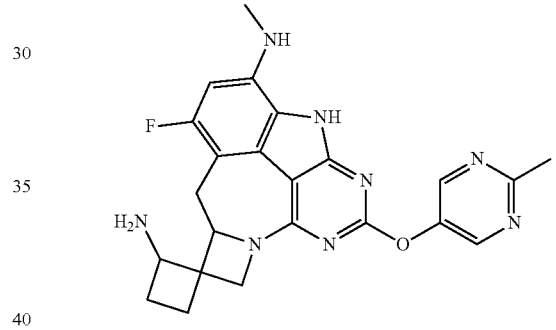
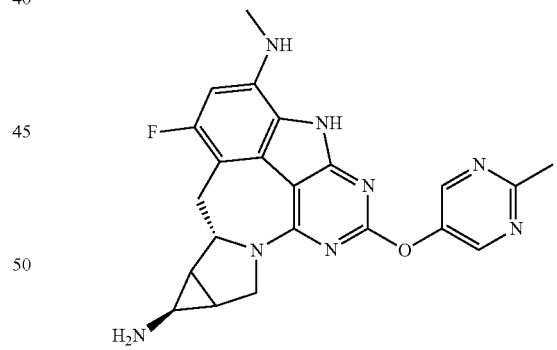
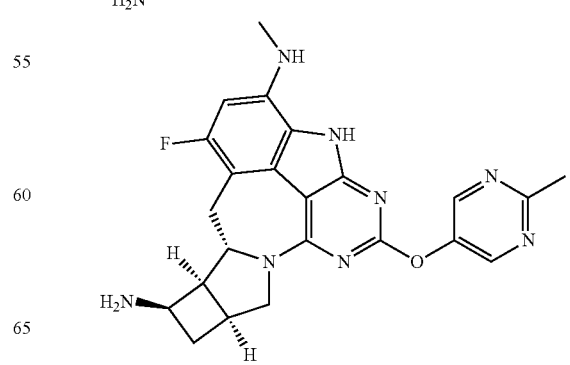

277
-continued
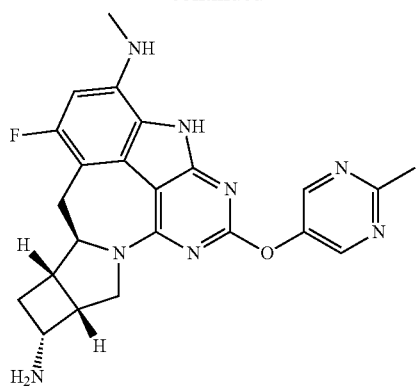
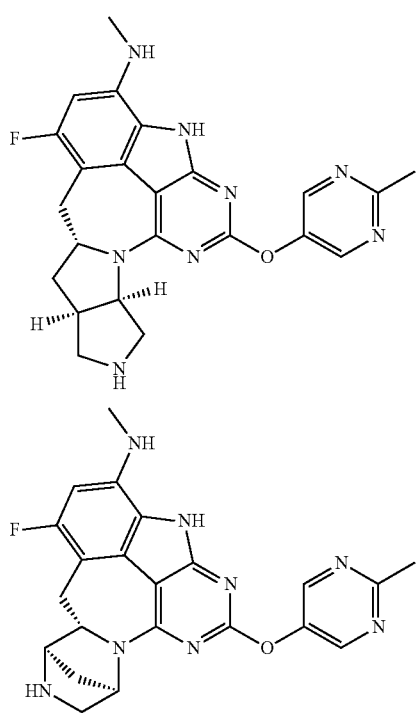
Example 4c—Process to Make
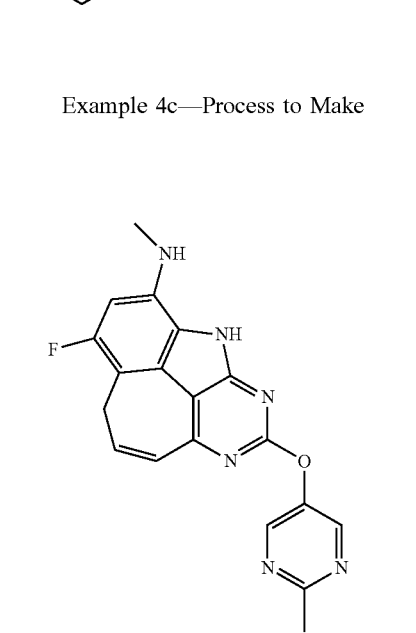
(40)
278
-continued
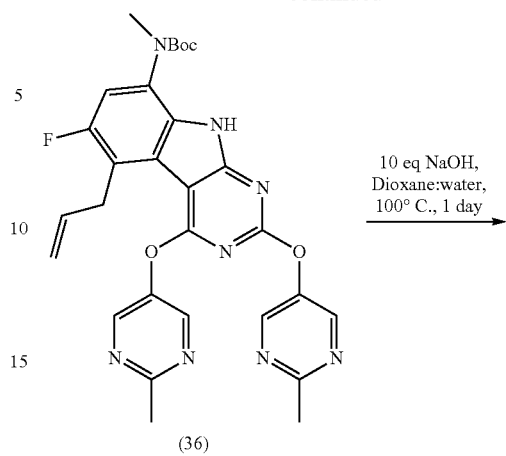
(36)
10 eq NaOH,
Dioxane:water,
100° C., 1 day →
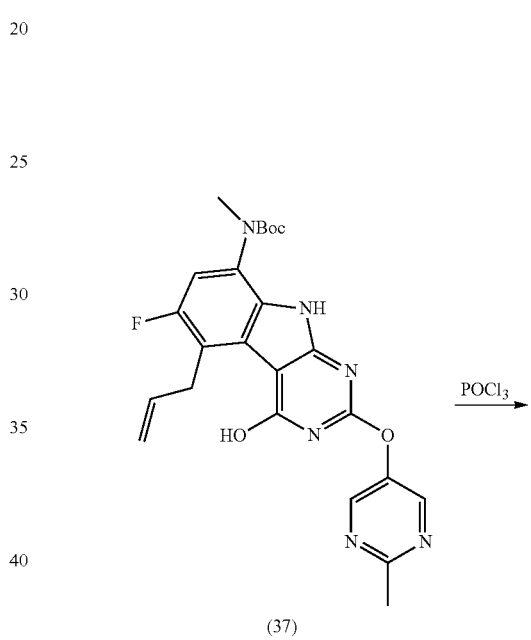
(37)
POCl₃ →
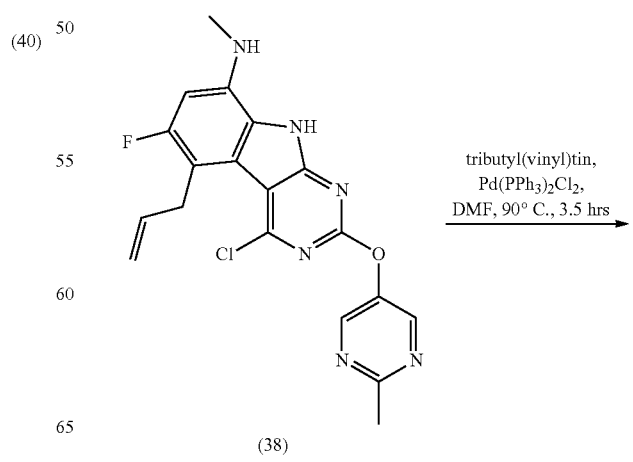
(38)
tributyl(vinyl)tin,
Pd(PPh₃)₂Cl₂,
DMF, 90° C., 3.5 hrs →

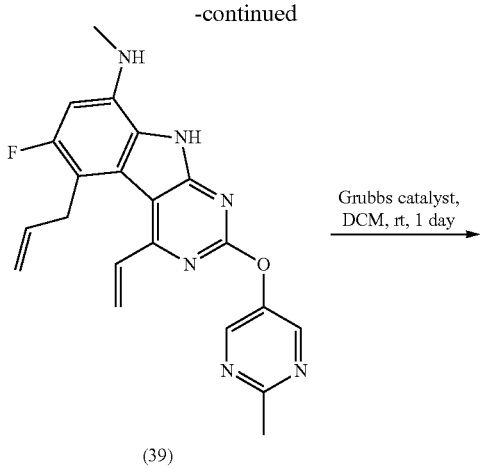

(39)

Grubbs catalyst,
DCM, rt, 1 day

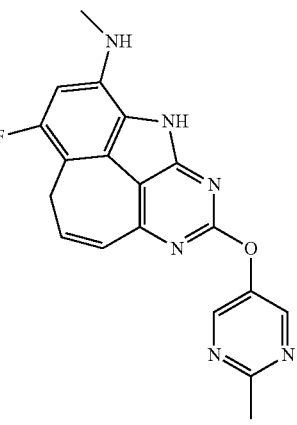

(40)

Compound 37:

The mixture of compound 36 (1.145 g, 2 mmol) and sodium hydroxide (800 mg, 20 mmol) in dioxane (10 ml) and water (10 ml) were refluxed at 100° C. for 1 day. It was then purified through C18 column chromatography. The collected fractions were extracted with DCM (100 ml), and the aqueous layer was back-extracted with DCM (50 ml×2). The combined organic layers were concentrated by rotary evaporation to afford the title compound as yellow solid (800 mg, 83.2%). LC-MS: M+1: 481.6.

Compound 38:

To the solution of compound 37 (800 mg, 1.665 mmol) in $POCl_3$ (6 ml) was added diethylisopropylamine (430 mg, 3.33 mmol). The resulting solution was heated at 70° C. for 1 hour then 80° C. for 1 day. After the reaction was cooled to rt, it was poured into a beaker containing about 100 g of ice. The precipitate was dissolved with DCM (80 ml), and the solution was then extracted. The aqueous layer was back-extracted with DCM (50 ml×2). The combined organic layers were concentrated by rotor evaporation and purified through C18 column chromatography. The collected fractions were extracted with DCM and concentrated by rotary evaporation to afforded the title product as peach color solid (525 mg, 79%). LC-MS: M+1: 399.1.

Compound 39:

To the solution of compound 38 (525 mg, 1.32 mmol) in anhydrous DMF (2 ml) was added tributyl(vinyl)tin (835 mg, 2.63 mmol). After the atmosphere of the mixture solution was purged with nitrogen, $Pd(PPh_3)_2Cl_2$ (92.1 mmol, 0.132 mmol) was added. The reaction was heated at 90° C. for 2 hours, and then an additional amount of $Pd(PPh_3)_2Cl_2$ (92.1 mmol, 0.132 mmol) was added. The reaction was continued at 90° C. for 1.5 hours. It was then cooled to rt and purified through C18 column chromatography. The collected fractions were extracted with DCM, and the organic layer was concentrated by rotary evaporation to afford the title product as red brown solid (421.3 mg, 82%). LC-MS: M+1: 391.4.

Compound 40:

To the solution of compound 39 (42.1 mg, 0.11 mmol) in DCM (2 ml) was added with Grubbs catalyst (first generation, 16.5 mg, 0.02 mmol). The mixture was stirred at rt for 1 day. It was then concentrated by rotary evaporation and purified through HPLC to afford the title compound as yellow solid (21.9 mg, 55%).

Compound 40 may be used to make various compounds via the reaction of alkene such as hydroamination, Diels-Alder reaction, cyclopropanation, etc.

Example 5

Section A

Synthesis of $R^2$ Pieces

All of the non-commercially available 2-substituted pyrimidinols were prepared in accordance with the procedures described in U.S. Pat. No. 5,162,529 or the published paper Tetrahedron, 65(4), 757-764; 2009.

General Scheme:

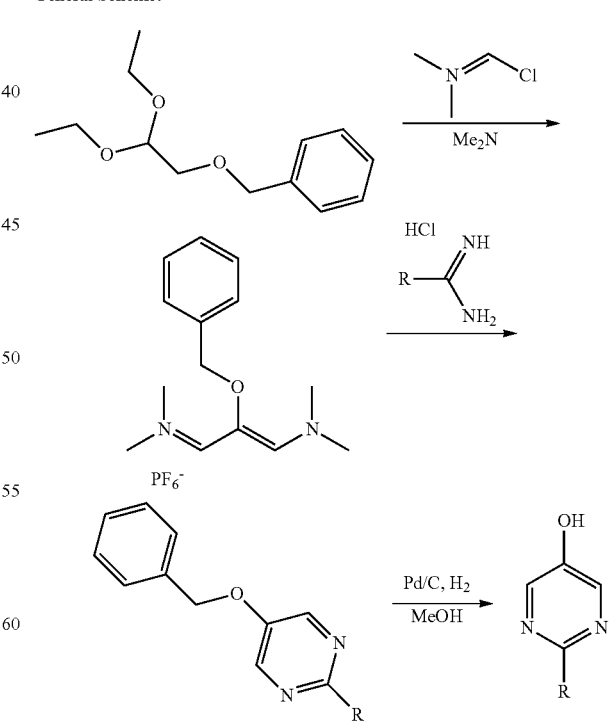

R = Cyclopropyl, Isobutyl, $CH_2OH$, $CHOHCH_3$, $C(CH_3)_2OH$, $CH_2F$, $CHF_2$, $CHF_3$

Example 5a

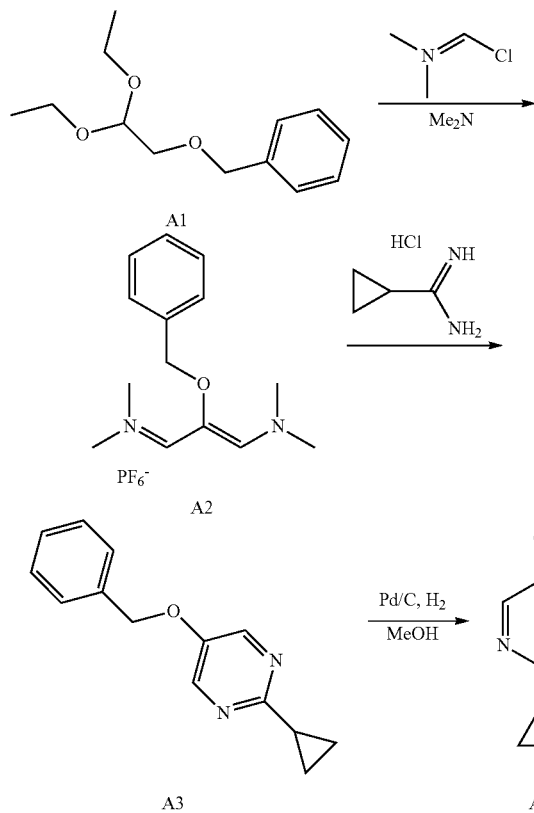

Preparation of Compound A2:

Phosphorus oxychloride (96 g, 0.62 mol) was added to anhydrous DMF (46 g, 0.62 mol) at 0° C. and the mixture was stirred at room temperature for 1 h. Then CHCl3 (500 mL) was added and benzyloxyacetaldehyde diethyl acetate (40 g, 0.18 mol) was added dropwise. Once completed, the reaction mixture was heated at reflux for 2.5 h then allowed to cool to room temperature. The orange solution was slowly poured into cold water (500 mL) at 0° C., and the biphasic mixture was stirred for 15 min. The organic phase was washed with water (500 mL). The combined aqueous layers were added dropwise to a solution of dimethylamine hydrochloride (59 g, 0.72 mol) in water (200 mL). The pH was adjusted to 8.5 by addition of a 5N sodium hydroxide aqueous solution while keeping the temperature around 15° C. The solution was stirred for 1 h and sodium hexafluorophosphate (40 g, 0.23 mol) in water (100 mL) was added. The resulting precipitate was collected by filtration, washed with water, and dried under high vacuum to give compound 2 (22 g, yield: 30%) as a pale beige solid, which was used in the next step without any further purification.

$^1$H NMR (400 MHz, DMSO-$d_6$): δ: 7.42-7.39 (m, 5H), 4.74 (s, 2H), 3.32 (s, 3H), 3.21 (s, 3H).

Preparation of Compound A3:

To a stirred suspension of compound A2 (14 g, 39 mmol) and cyclopropanecarboximidamide hydrochloride (5.65 g, 47 mmol) in CH$_3$CN (100 mL) was added potassium carbonate (16.2 g, 117 mmol). The reaction mixture was heated at 90° C. for 12 h, then cooled to room temperature, poured into ice water, extracted with ethyl acetate (2×50 mL). The organic layer was dried over Na$_2$SO$_4$, filtered and concentrated to afford the compound A3 (2.5 g, yield: 26%) as yellow solid.

$^1$H NMR (400 MHz, CDCl$_3$): δ 8.44 (s, 2H), 7.46-7.28 (m, 5H), 5.24 (s, 2H), 2.18-2.12 (m, 1H), 0.99-0.90 (m, 2H), 0.89-0.86 (m, 2H).

Preparation of Compound A4:

A solution of compound A3 (3.50 g, 15.8 mmol) in MeOH (30 mL) was added palladium on charcoal 10% (350 mg) and the mixture was stirred under hydrogen atmosphere for 4 h. The solid was filtered off and the filtrate was concentrated to get compound A4 (2.0 g, yield: 98%).

$^1$H NMR (300 MHz, DMSO-$d_6$): δ: 10.05 (s, 1H), 8.17 (s, 2H), 2.12-2.05 (m, 1H), 0.93-0.91 (m, 2H), 0.86-0.83 (m, 2H). LCMS [mobile phase: 2-60% Acetonitrile-0.05% TFA in 6 min, finally under these conditions for 0.5 min.] purity is >95%, Rt=2.564 min; MS Calcd.:136.1; MS Found: 137.1 ([M+1]$^+$)

Example 5b

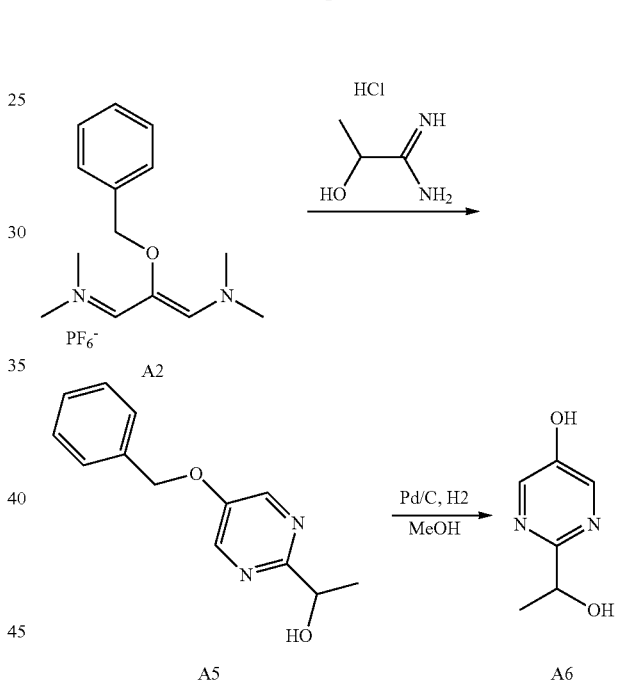

Preparation of Compound A5:

To a stirred suspension of compound A2 (14 g, 39 mmol) and 2-hydroxypropanimidamide hydrochloride (5.65 g, 47 mmol) in CH$_3$CN (100 mL) was added potassium carbonate (16.2 g, 117 mmol). The reaction mixture was heated at 90° C. for 12 h, then cooled to room temperature, poured into ice water, extracted with ethyl acetate (2×50 mL). The organic layer was dried over Na$_2$SO$_4$, filtered and concentrated to afford the compound A5 (2.5 g, yield: 26%) as yellow solid.

$^1$H NMR (300 MHz, CDCl$_3$): δ: 8.84 (s, 2H), 7.48 (m, 3H), 7.37 (m, 2H), 5.20 (s, 2H), 4.68 (m, 1H), 3.25 (m, 1H), 1.48 (d, 3H).

Preparation of Compound A6:

A solution of compound A5 (3.50 g, 15.8 mmol) in MeOH (30 mL) was added palladium on charcoal 10% (350 mg) and the mixture was stirred under hydrogen atmosphere for 4 h. The solid was filtered off and the filtrate was concentrated to get compound A6 (2.0 g, yield: 98%).

¹H NMR (400 MHz, CDCl₃): δ: 8.84 (s, 2H), 5.40 (brd, 1H), 4.66 (m, 1H), 3.25 (m, 1H), 1.46 (d, 3H). LCMS Found: 141.1 ([M+1]+)

Example 5c

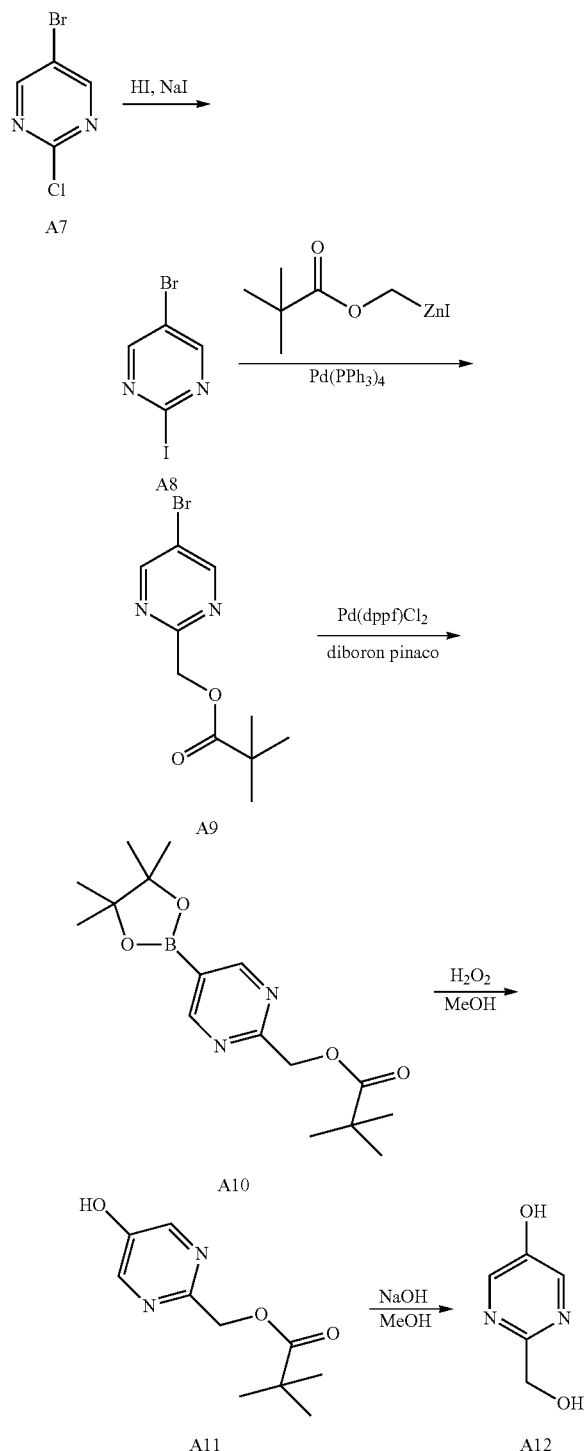

Preparation of Compound A8:
To a solution of compound A7 (50 g, 0.26 mol) in DCM (300 mL) was added NaI (80 g, 0.52 mol) at room temperature, then HI (75 g, 0.52 mol) was added. After stirred at 50° C. for 5 h, the mixture was poured into ice water and carefully neutralized by addition of solid sodium bicarbonate until mixture became colorless.

Then the mixture was extracted with DCM (2×200 mL). The organic layer was dried over Na₂SO₄, filtered and concentrated to afford compound A8 (60 g, yield: 81%) as white solid.

¹H NMR (400 MHz, CDCl₃): δ: 8.54 (s, 2H).

Preparation of Compound A9:
To the solution of compound A8 (50 g, 0.18 mol) in THF (300 mL) was added Pd(PPh₃)₄ (11.5 g, 0.01 mol), followed by addition of a solution of zinc reagent 3 (freshly prepared from iodomethyl 2,2-dimethylpropanoate) in THF (500 ml, 0.36 mol) and stirred at room temperature for 12 h. Then ice water was added and the mixture was extracted with ethyl acetate (2×200 mL). The organic layer was dried over Na₂SO₄, filtered and concentrated to afford crude product. The residue was purified by chromatography on silica gel (petroleum ether/ethyl acetate=10:1) to afford the compound A9 (41 g, yield: 85%) as yellow solid.

¹H NMR (400 MHz, CDCl₃): δ 8.75 (s, 2H), 5.26 (s, 2H), 5.06 (s, 1H), 1.28 (s, 9H).

Preparation of Compound A10:
To a stirred solution of compound A9 (15.0 g, 54.9 mmol) in dioxane (100 mL) was added bis(pinacolato)diboron (17.0 g, 65.4 mmol) under nitrogen, followed by Pd(dppf)Cl₂ (2.20 g, 2.72 mmol) and KOAc (16 g, 163 mmol). The reaction mixture was heated at 85° C. for 3 h. The black suspension was cooled to room temperature, filtered, concentrated to afford crude product. The residue was purified by chromatography on silica gel (petroleum ether/ethyl acetate=15:1) to afford compound A10 (15.4 g) as white solid, contaminated with pinacol derivatives.

¹H NMR (400 MHz, CDCl₃): δ: 8.97 (s, 2H), 5.30 (s, 2H), 1.35 (s, 9H), 1.28 (s, 9H).

Preparation of Compound A11:
To a solution of compound A10 (15.6 g, 48.7 mmol) in MeOH (100 mL) was added H₂O (16.0 g, 140 mmol). The mixture was stirred at room temperature for 12 h. 2N sodium thiosulphate (200 mL) was added and the mixture was extracted with ethyl acetate (200 mL) The aqueous phase was adjusted pH to 4-5 with 2N HCl; then the mixture was extracted with ethyl acetate (2×200 mL). The organic layer was dried over Na₂SO₄, filtered and concentrated to get compound A11 (9.4 g, yield: 82% in two steps).

¹H NMR (400 MHz, DMSO-d₆): δ: 10.48 (s, 1H), 8.31 (s, 2H), 5.11 (s, 2H), 1.21 (s, 9H).

Preparation of Compound A12:
To a solution of compound A11 (10 g, 30 mmol) in MeOH (200 mL) was added MeONa (50 ml, 1M in MeOH). After stirred at room temperature for 12 h, the mixture was poured into water and extracted with ethyl acetate (2×200 mL). The organic layer was dried over Na₂SO₄, filtered and concentrated to afford the compound A12 (7.3 g, yield: 98%) as white solid.

¹H NMR (300 MHz, CDCl₃): δ: 8.43 (s, 2H), 7.35 (d, J=8.8 Hz, 2H), 6.93 (d, J=8.8 Hz, 2H), 5.09 (s, 2H), 4.78 (s, 2H).

Example 5d

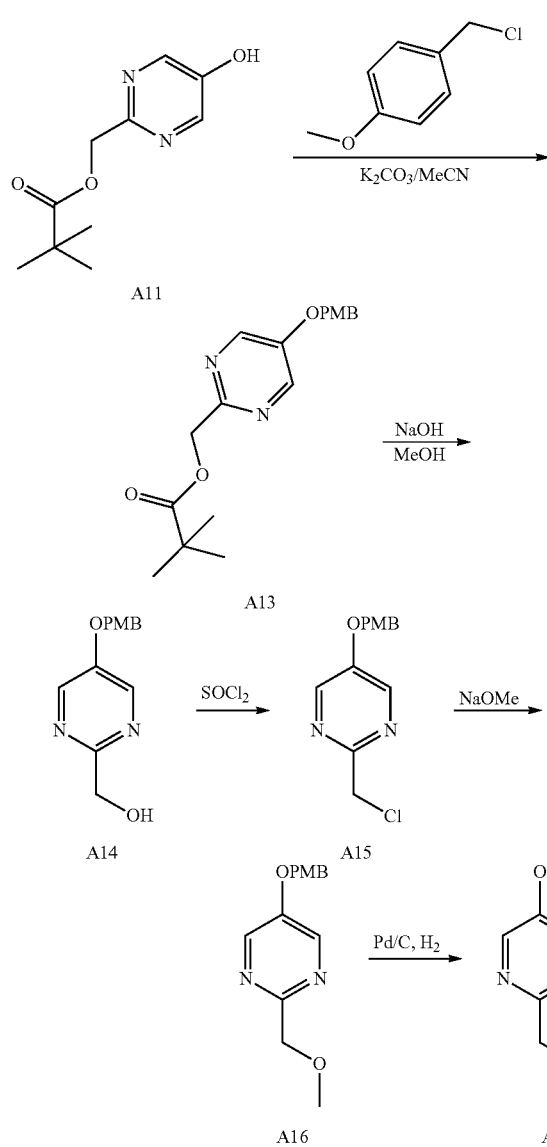

Preparation of Compound A13:

To a solution of compound A11 (12.3 g, 58.5 mmol) in CH₃CN (100 mL) was added K₂CO₃ (10.5 g, 76 mmol) and PMBCl (12 g, 76 mmol) and the mixture was stirred at room temperature for 12 h and heated to 50° C. for 3 h. Then the mixture was poured into water and extracted with ethyl acetate (2×200 mL). The organic layer was dried over Na₂SO₄, filtered and concentrated, the residue was purified by chromatography on silica gel (petroleum ether/ethyl acetate=10:1) to afford the compound A13 (10.0 g, yield: 52%) as white solid.

¹H NMR (300 MHz, CDCl₃): δ: 8.41 (s, 2H), 7.34 (d, J=8.8 Hz, 2H), 6.93 (d, J=8.8 Hz, 2H), 5.24 (s, 2H), 5.07 (s, 2H), 3.82 (s, 3H), 1.26 (s, 9H).

Preparation of Compound A14:

To a solution of compound A13 (10 g, 30 mmol) in MeOH (200 mL) was added MeONa (50 ml, 1M in MeOH). After stirred at room temperature for 12 h, the mixture was poured into water and extracted with ethyl acetate (2×200 mL). The organic layer was dried over Na₂SO₄, filtered and concentrated to afford the compound A14 (7.3 g, yield: 98%) as white solid.

¹H NMR (300 MHz, CDCl₃): δ: 8.43 (s, 2H), 7.35 (d, J=8.8 Hz, 2H), 6.93 (d, J=8.8 Hz, 2H), 4.78 (s, 2H).

Preparation of Compound A16:

To a solution of compound A14 (15 g, 61 mmol) in DCM (200 mL) was added thionyl chloride (10.8 g, 91 mmol). After stirred at room temperature for 2 h, then the mixture was poured into water and extracted with ethyl acetate (2×200 mL). The organic layer was dried over Na₂SO₄, filtered and concentrated to afford the compound A15 (16 g) as white solid. To a solution of compound A15 (15 g) in MeOH (200 mL) was added MeONa solution (50 mL, 50% in MeOH). The mixture was stirred at 50° C. for 5 h, then cooled to room temperature, concentrated to afford crude product. The residue was purified by chromatography on silica gel (petroleum ether/ethyl acetate=5:1) to afford the compound A16 (12.5 g, yield: 80%) as yellow solid.

¹H NMR (400 MHz, CDCl₃): δ: 8.45 (s, 2H), 7.34 (d, J=8.8 Hz, 2H), 6.92 (d, J=8.8 Hz, 2H), 5.08 (s, 2H), 4.64 (s, 2H), 3.82 (s, 3H), 3.52 (s, 3H).

Preparation of Compound A17:

A solution of compound A16 (3.0 g) in MeOH (30 mL) was added 10% palladium on charcoal (350 mg) and the mixture was stirred under hydrogen atmosphere for 4 h. The solid was filtered off and the filtrate was concentrated; the residue was purified by chromatography on silica gel (petroleum ether/ethyl acetate=1:1) to afford compound A17 (1.2 g, yield: 74%) as white solid.

¹H NMR (400 MHz, DMSO-d₆): δ: 10.45 (s, 1H), 8.33 (s, 2H), 4.44 (s, 2H), 3.31 (s, 3H). LCMS [mobile phase: 95-5% Acetonitrile-0.02% NH₄Ac in 6 min, finally under these conditions for 0.5 min.] purity is >95%, Rt=3.3 min; MS Calcd. 140.1.1; MS Found: 141.1 ([M+1]⁺).

General Scheme

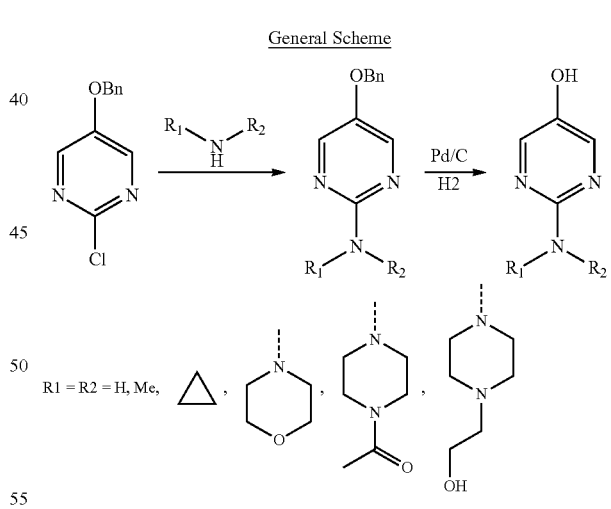

Example 5e

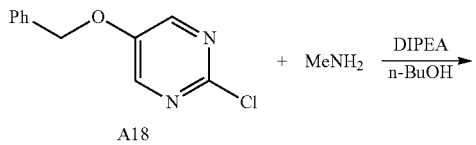

287

-continued

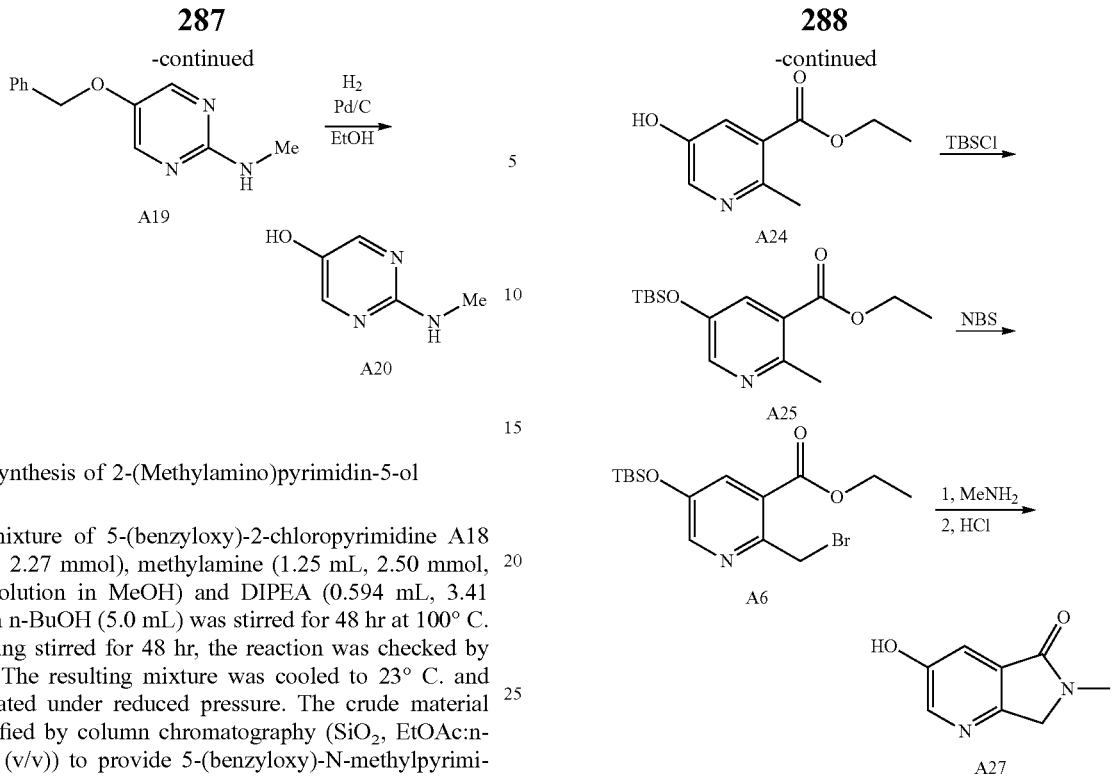

Synthesis of 2-(Methylamino)pyrimidin-5-ol

The mixture of 5-(benzyloxy)-2-chloropyrimidine A18 (0.500 g, 2.27 mmol), methylamine (1.25 mL, 2.50 mmol, 2.0 M solution in MeOH) and DIPEA (0.594 mL, 3.41 mmol) in n-BuOH (5.0 mL) was stirred for 48 hr at 100° C. After being stirred for 48 hr, the reaction was checked by LC/MS. The resulting mixture was cooled to 23° C. and concentrated under reduced pressure. The crude material was purified by column chromatography (SiO$_2$, EtOAc:n-Hex 1:1 (v/v)) to provide 5-(benzyloxy)-N-methylpyrimidin-2-amine A19 (0.355 g, 1.65 mmol, 73%) as colorless crystal. LC/MS (M+H+)=216. The mixture of palladium on carbon (0.176 g, 0.165 mmol, 10.0 mol %) and 5-(benzyloxy)-N-methylpyrimidin-2-amine A19 (0.355 g, 1.65 mmol) in ethanol (7.0 mL) was stirred for 20 h under hydrogen atmosphere at 23° C. The resulting mixture was filter through Celite and the pad was washed with methanol (25 mL). The filtrate was concentrated under reduced pressure to provide the title compound 2-(methylamino)pyrimidin-5-ol A20 (0.196 g, 1.57 mmol, 95%) as a light yellow solid. LC/MS (M+H$^+$)=126.

Example 5f

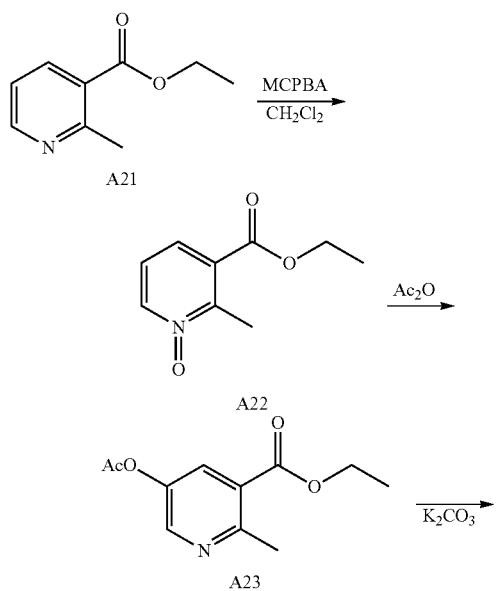

288

-continued

Preparation of Compound A22:

To a solution of A21 (50.0 g, 0.303 mol) in DCM (200 mL) was added m-CPBA (80.0 g, 0.465 mol) at 0° C. After stirred at 0° C. for 1 hour at room temperature for overnight, the mixture was poured into ice water. 2N NaOH was added to adjust the pH to 8-9 and the resultant mixture was extracted with DCM (3×200 mL). The organic layer was dried over Na$_2$SO$_4$, filtered and concentrated to afford compound A22 (50.0 g, yield: 91%) as a yellow solid.

Preparation of Compound A23:

The solution of A22 (50.0 g, 0.276 mmol) in acetic anhydride (300 mL) was heated to 90° C. for 1.5 hour. Then the mixture was concentrated and the residue was poured into ice water; 2N NaOH was added to adjust the pH to 8-9 and the resultant mixture was extracted by ethyl acetate (3×100 mL). The organic layer was dried over Na$_2$SO$_4$ and concentrated to give the cured which was purified by chromatography on silica gel (petroleum ether/ethyl acetate=5:1) to afford the compound A23 (10.0 g, yield: 16%) as a yellow oil.

$^1$H NMR (400 MHz, CDCl$_3$): δ: 8.43 (d, J=2.4 Hz, 1H), 7.99 (d, J=1.6 Hz, 1H), 4.41-4.35 (1 h, J=3.2 Hz, 3H), 2.83 (s, 3H), 2.34 (s, 3H), 1.42-4.39 (t, J=3.2 Hz, 3H).

Preparation of Compound A24:

To a solution of A23 (10.0 g, 44.8 mmol) in MeOH (300 mL) was added potassium carbonate (12.4 g, 89.8 mmol). After stirred at room temperature for 12 hour, the mixture was poured into ice water. 2N HCl was added to adjust the pH to 8-9 and the mixture was extracted with ethyl acetate (2×100 mL). The organic layer was dried over Na$_2$SO$_4$, filtered and concentrated to afford compound A24 (8.00 g, yield 99%) as yellow solid.

$^1$H NMR (400 MHz, DMSO-d$_6$): δ: 10.0 (s, 1H), 8.18 (d, J=2.4 Hz, 1H), 7.54 (d, J=2.8 Hz, 1H), 4.32-4.26 (1 h, J=3.2 Hz, 3H), 2.57 (s, 3H), 1.33-1.29 (t, J=3.2 Hz, 3H).

Preparation of Compound A25:

To a solution of compound A24 (2.50 g, 13.8 mmol) in DCM (50 mL) was added imidazole (3.00 g, 44.1 mmol) and tert-Butyldimethylsilyl chloride (2.50 g, 16.7 mmol) and the mixture was stirred at room temperature for 3 hours. Then evaporated the solvent, the residue was purified by chromatography (petroleum ether/ethyl acetate=5:1) to give compound A25 (2.80 g, yield 69%) as a yellow oil.

$^1$H NMR (400 MHz, CDCl$_3$): δ: 8.12 (d, J=2.8 Hz, 1H), 7.54 (d, J=2.8 Hz, 1H), 4.30-4.26 (1 h, J=3.2 Hz, 3H), 2.64 (s, 3H), 1.32-1.28 (t, J=3.2 Hz, 3H), 0.92 (s, 9H), 0.12 (s, 6H).

Preparation of Compound A26:

To a solution of compound A25 (2.80 g, 9.48 mmol) in CCl$_4$ (100 mL) was added azodiisobutyronitrile (280 mg) and NBS (1.80 g, 10.1 mmol), the mixture was stirred at 70° C. for 15 hours, then the solvent was evaporated, the residue was purified by chromatography (petroleum ether/ethyl acetate=5:1) to give compound A26 (1.60 g, yield 45%) as a yellow oil.

$^1$H NMR (400 MHz, CDCl$_3$): δ: 8.28 (d, J=3.2 Hz, 1H), 7.68 (d, J=3.2 Hz, 1H), 4.98 (s, 3H), 4.45-4.40 (1 h, J=3.2 Hz, 3H), 1.45-1.42 (t, J=2.8 Hz, 3H), 1.00 (s, 9H), 0.26 (s, 6H).

Preparation of Compound A27:

To a solution of compound A26 (1.60 g, 4.27 mmol) in EtOH (100 mL) was added the solution of methylamine in EtOH (1.24 g, 12.0 mmol, 30% w/w) and the mixture was stirred at room temperature for 3 hour. Then the solvent was evaporated and the residue was purified by chromatography (petroleum ether/ethyl acetate=5:1) to give compound A27a (300 mg, yield: 25%) as a yellow solid.

$^1$H NMR (400 MHz, DMSO-d$_6$): δ: 8.34 (d, J=2.8 Hz, 1H), 7.43 (d, J=2.8 Hz, 1H), 4.42 (s, 2H), 3.06 (s, 3H), 0.95 (s, 9H), 0.20 (s, 6H).

To a solution of compound A27a (300 mg, 1.14 mmol) in THF (5 mL) was added 6 N HCl (0.5 mL). After stirred at room temperature for 1 hour, the mixture was concentrated to get compound A27 (150 mg, yield 80%) as a yellow solid.

$^1$H NMR (400 MHz, DMSO-d$_6$): δ: 10.27 (s, 1H), 8.27 (d, J=2.4 Hz, 1H), 7.32 (d, J=2.8 Hz, 1H), 4.37 (s, 2H), 3.0 (s, 3H). LCMS mobile phase: from 40% water (0.05% TFA) and 60% CH$_3$CN to 10% water (0.05% TFA) and 90% CH$_3$CN in 6 min, finally under these conditions for 0.5 min.] Purity is >95%, Rt=3.7 min; MS Calcd.: 164.1; MS Found: 165.1 ([M+1]+).

Example 5g

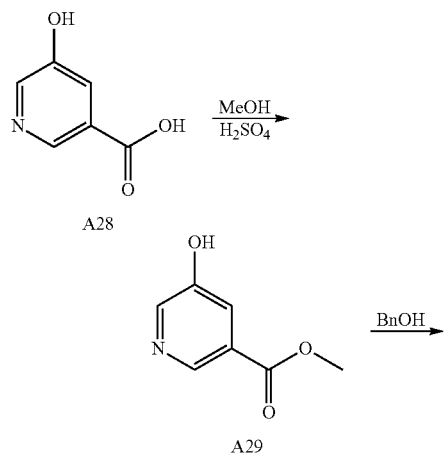

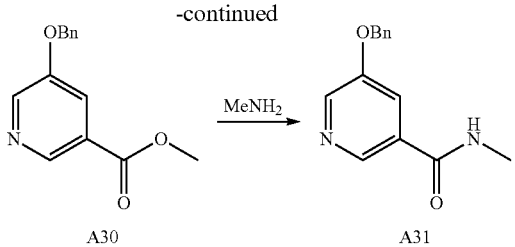

Preparation of Compound A29:

A mixture of compound A28 (25.0 g, 180 mmol) and concentrated H$_2$SO$_4$ (10 mL) in CH$_3$OH (100 mL) was heated to reflux for overnight. The mixture was concentrated, the residue was washed with aqueous NaHCO$_3$ (50 mL) and extracted with ethyl acetate (2×100 mL). The organic layer was dried over Na$_2$SO$_4$, filtered and concentrated to afford compound A29 (18.7 g, yield: 68%).

$^1$H NMR (300 MHz, DMSO-d$_6$): δ: 10.42 (s, 1H), 8.60 (d, J=1.6 Hz, 1H), 8.36 (d, J=2.8 Hz, 1H), 7.60-7.61 (m, 1H), 3.87 (s, 3H).

Preparation of Compound A30:

BnOH (3.90 g, 36.1 mmol, 1.1 eq) and PPh$_3$ (17.1 g, 65.4 mmol, 2.0 eq) was added to a solution of compound A29 (5.00 g, 32.7 mmol) in THF (100 mL), then DEAD (6.80 g, 39.2 mmol, 1.2 eq) was added at 0° C. The mixture was stirred at room temperature for overnight. The solvent was evaporated, the residue was purified by chromatography on silica gel (petroleum ether/ethyl acetate=10:1) to afford the compound A30 (5.70 g, yield: 71%) as white solid.

$^1$H NMR (300 MHz, CDCl$_3$): δ: 8.83 (d, J=1.6 Hz, 1H), 8.54 (d, J=2.8 Hz, 1H), 7.85-7.86 (m, 1H), 7.27-7.46 (m, 5H), 5.15 (s, 2H), 3.95 (s, 3H).

Preparation of Compound A31:

A solution of compound A30 (12.8 g, 52.9 mmol) in methylamine alcohol solution in sealed tube was stirred at 70° C. for overnight.

Then the mixture was cooled to room temperature and the solvent was evaporated to afford the compound A31 (12.0 g, yield: 100%).

$^1$H NMR (300 MHz, CDCl$_3$): δ: 8.50 (d, J=1.6 Hz, 1H), 8.48 (d, J=2.8 Hz, 1H), 7.73-7.74 (m, 1H), 7.73-7.74 (m, 5H), 6.16 (s, 1H), 3.15 (s, 2H), 3.04 (d, J=4.4 Hz, 3H).

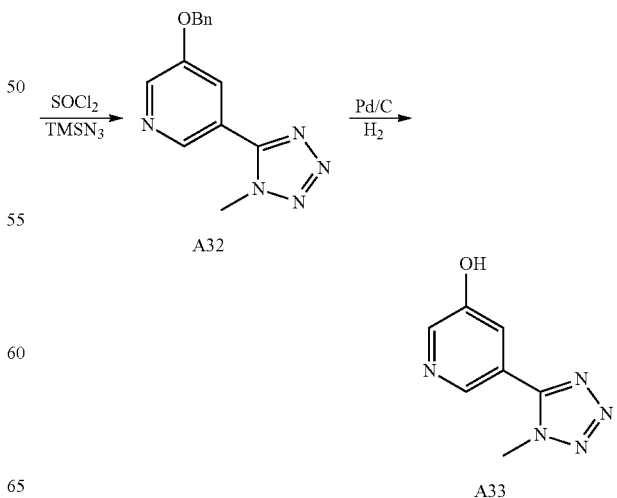

Preparation of Compound A32:

The solution of compound A31 (11.0 g, 45.5 mmol) in SOCl$_2$ (100 mL) was heated to reflux for 4 h. Then, SOCl$_2$ was removed under vacuum and the residue was dissolved in MeCN (200 mL). TMSN$_3$ (12.5 g, 90.0 mmol, 2.0 eq) was added slowly and the mixture was stirred at 90° C. for 3 h. Then the solvent was evaporated and the residue was purified by chromatography on silica gel (petroleum ether/ethyl acetate=2:3) to afford the compound A32 (9.50 g, yield: 78%).

$^1$H NMR (300 MHz, CDCl$_3$): δ: 8.59 (d, J=2.8 Hz, 1H), 8.56 (d, J=1.6 Hz, 1H), 7.68-7.69 (m, 1H), 7.3-7.46 (m, 5H), 5.21 (s, 2H), 4.17 (s, 3H).

Preparation of Compound A33:

To a solution of compound A32 (5.00 g, 18.7 mmol) in CH$_3$OH (100 mL) was added Pd(OH)$_2$ (0.50 g), The mixture was stirred at room temperature under H$_2$ atmosphere for 3 h. The solid was filtered off and the filtrate was concentrated to get compound A33 (1.60 g, yield: 48%).

$^1$H NMR (300 MHz, DMSO-d$_6$): δ: 10.56 (s, 1H), 8.49 (d, J=1.6 Hz, 1H), 8.36 (d, J=2.8 Hz, 1H), 7.61-7.62 (m, 1H), 4.19 (s, 3H).

Example 5h

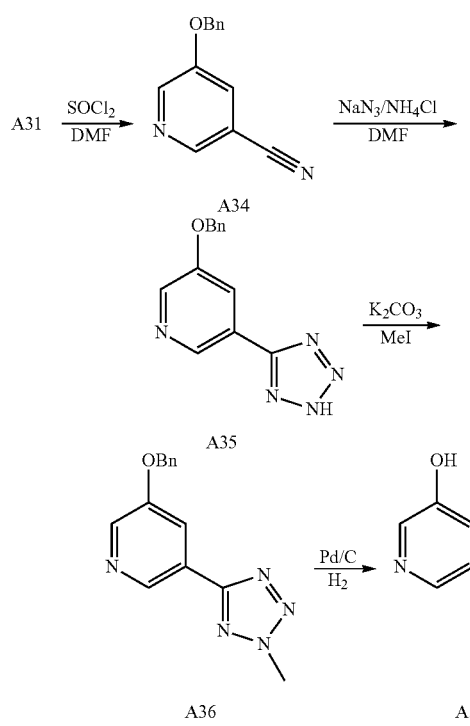

Preparation of Compound A34:

Thionyl chloride (15.0 g, 107 mmol) was added to DMF (200 mL) at 0° C., and the mixture was stirred at 0° C. for 30 min, then A31 (12.2 g, 53.5 mmol) was added to the mixture, and stirred at 0° C. for 1 h. Then the reaction mixture was poured into ice water and extracted with ethyl acetate (2×100 mL). The organic layer was dried over Na$_2$SO$_4$, filtered and concentrated to afford compound A34 (11.5 g, yield: 100%).

$^1$H NMR (300 MHz, CDCl$_3$): δ 8.57 (d, J=2.8 Hz, 1H), 8.48 (d, J=1.6 Hz, 1H), 7.45-7.39 (m, 6H), 5.15 (s, 2H).

Preparation of Compound A35:

To a solution of A34 (12.0 g, 57.1 mmol) in DMF (200 mL) was added NH$_4$Cl (5.20 g, 97.1 mmol) and NaN$_3$ (6.31 g, 97.1 mmol). The resulting mixture was heated to 100° C. for 14 h, cooled to room temperature, poured into ice water, 2N HCl was added to adjust the PH to 3-4, and extracted with ethyl acetate (2×100 mL). The organic layer was dried over Na$_2$SO$_4$, filtered and concentrated to afford compound A35 (13.0 g, yield: 90%).

$^1$H NMR (300 MHz, DMSO-d$_6$): δ: 8.82 (d, J=1.6 Hz, 1H), 8.57 (d, J=2.8 Hz, 1H), 8.04-8.02 (m, 1H), 7.52-7.35 (m, 5H), 5.30 (s, 2H).

Preparation of Compound A36:

Compound A35 (7.00 g, 27.7 mmol) was dissolved in acetone (150 mL), potassium carbonate (5.70 g, 41.2 mmol) was added to the mixture, and stirred at room temperature for 20 min, then iodomethane (5.89 g, 41.2 mmol) was added to mixture, and heated to 45° C. for 1 h, cooled to room temperature, poured into ice water, extracted with ethyl acetate (2×100 mL). The organic layer was dried over Na$_2$SO$_4$, filtered and concentrated to afford crude product, the residue was purified by chromatography on silica gel (petroleum ether/ethyl acetate=3:1) to afford the compound A36 (4.5 g, yield: 61%) as white solid.

$^1$H NMR (300 MHz, CDCl$_3$): δ: 8.97 (d, J=1.6 Hz, 1H), 8.48 (d, J=2.4 Hz, 1H), 8.00-7.99 (m, 1H), 7.47-7.26 (m, 5H), 5.19 (s, 2H), 4.43 (s, 3H).

Preparation of Compound A37:

To a solution of compound A36 (7.5 g, 28.0 mmol) in CH$_3$OH (100 mL) was added Pd(OH)$_2$(500 mg), The mixture was stirred at room temperature under H$_2$ atmosphere for 3 h. The solid was filtered off and the filtrate was concentrated to get compound A37 (4.3 g, yield: 87%). LC-MS: M+1: 178.16.

$^1$H NMR (300 MHz, DMSO-d$_6$): δ: 10.42 (s, 1H), 8.68 (d, J=1.6, 1H), 8.28 (d, J=2.8, 1H), 7.74-7.73 (m, 1H), 4.45 (s, 3H).

Example 6

SECTION B

Synthesis of Unique R$^4$ Pieces

Example 6a—Asymmetric Synthesis of (1R,4R,5R) tert-butyl 5-amino-2-azabicyclo[2.2.1]heptane-2-carboxylate General Scheme:

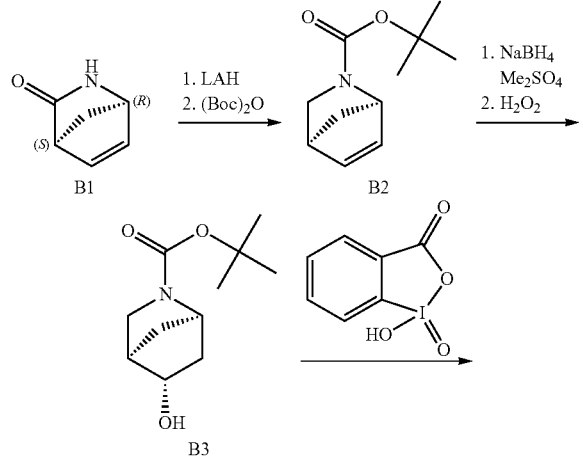

293

-continued

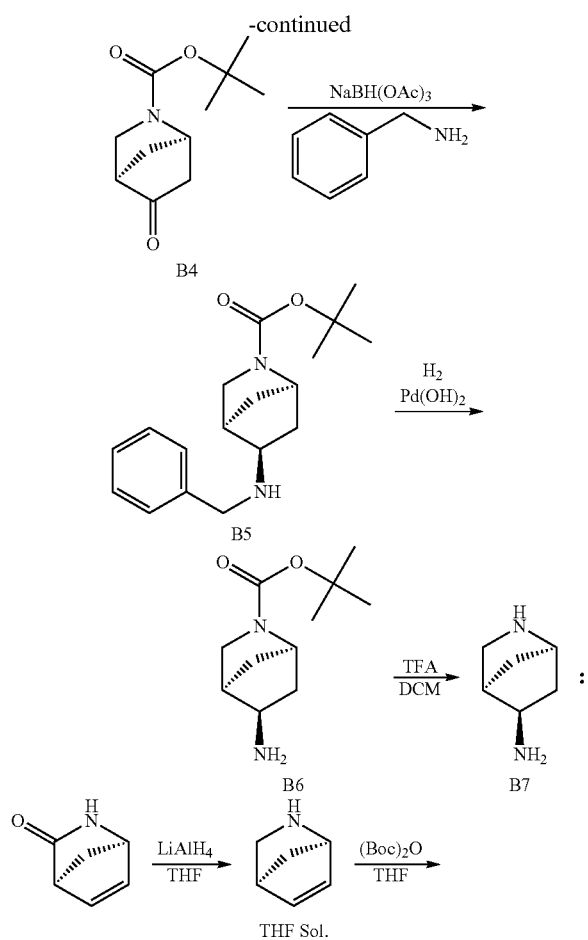

(1R,4S)-tert-Butyl 2-azabicyclo[2.2.1]hept-5-ene-2-carboxylate (B2)

(1R)-(−)-2-Azabicyclo[2.2.1]hept-5-en-3-one (5.00 g, 45.8 mmol, ee=99%) dissolved in anhydrous THF (15.0 mL) was slowly added to a solution of lithium aluminum hydride (57.3 mL, 57.3 mmol, 1M solution in THF) in anhydrous THF (35.0 mL) under nitrogen atmosphere at 0° C. After the addition was successfully completed, the mixture was stirred for 3 h at 23° C. and then heated at 60° C. for 12 h. The resulting heterogeneous mixture was cooled to 0° C. and H₂O (5.00 mL) was carefully added to the mixture via syringe. The white colored suspension was filtered through a Celite filter aid and the pad was washed with anhydrous diethyl ether (50.0 mL). The filtrate was then treated with (Boc)₂O (15.0 g, 68.7 mmol) and stirred for 24 h at 23° C. The mixture was concentrated in vacuo and the crude material was purified by column chromatography (SiO₂, EtOAc:n-Hex 1:7 (v/v)) to provide the title compound B2 as a colorless crystal. (After the solvent was evaporated by rotavap, the resulting colorless oil quickly crystallized at 23° C.)

294

(1R,4R,5S)-tert-Butyl 5-hydroxy-2-azabicyclo[2.2.1]heptanes-2-carboxylate (B3)

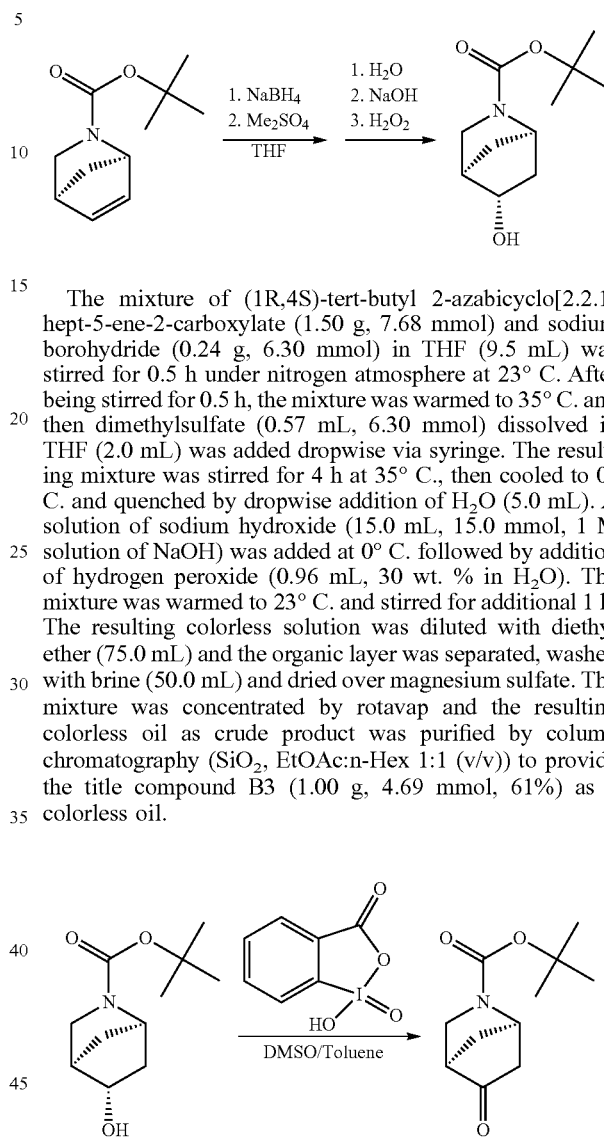

The mixture of (1R,4S)-tert-butyl 2-azabicyclo[2.2.1]hept-5-ene-2-carboxylate (1.50 g, 7.68 mmol) and sodium borohydride (0.24 g, 6.30 mmol) in THF (9.5 mL) was stirred for 0.5 h under nitrogen atmosphere at 23° C. After being stirred for 0.5 h, the mixture was warmed to 35° C. and then dimethylsulfate (0.57 mL, 6.30 mmol) dissolved in THF (2.0 mL) was added dropwise via syringe. The resulting mixture was stirred for 4 h at 35° C., then cooled to 0° C. and quenched by dropwise addition of H₂O (5.0 mL). A solution of sodium hydroxide (15.0 mL, 15.0 mmol, 1 M solution of NaOH) was added at 0° C. followed by addition of hydrogen peroxide (0.96 mL, 30 wt. % in H₂O). The mixture was warmed to 23° C. and stirred for additional 1 h. The resulting colorless solution was diluted with diethyl ether (75.0 mL) and the organic layer was separated, washed with brine (50.0 mL) and dried over magnesium sulfate. The mixture was concentrated by rotavap and the resulting colorless oil as crude product was purified by column chromatography (SiO₂, EtOAc:n-Hex 1:1 (v/v)) to provide the title compound B3 (1.00 g, 4.69 mmol, 61%) as a colorless oil.

(1R,4R)-tert-Butyl 5-oxo-2-azabicyclo[2.2.1]heptanes-2-carboxylate (B4)

2-Iodoxybenzoic acid (3.43 g, 5.52 mmol, 45 wt. % (SIBX)) was added to a solution of (1R,4R,5S)-tert-butyl 5-hydroxy-2-azabicyclo[2.2.1]heptanes-2-carboxylate (0.87 g, 4.09 mmol) dissolved in dimethylsulfoxide (5.0 mL) and toluene (10.0 mL) under nitrogen atmosphere at 23° C. The mixture was stirred for 3 h at 60° C. and cooled to 23° C. The resulting mixture was treated with saturated sodium carbonate (a 1 h.) (50.0 mL) and filtered under reduced pressure to remove a white solid. The filtrate was extracted with ethyl acetate (75.0 mL×3) and the organic extracts were washed with brine, dried over magnesium sulfate and concentrated in vacuo. The crude material as colorless oil was purified by column chromatography (SiO₂, EtOAc:n-Hex 1:2 (v/v)) to provide the title compound B4 (0.62 g, 2.91 mmol, 71%) as a white solid.

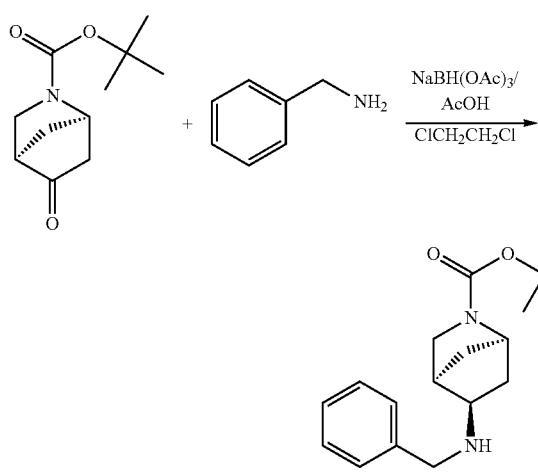

(1R,4R,5R)-tert-Butyl 5-(benzylamino)-2-azabicyclo[2.2.1]heptanes-2-carboxylate (B5)

Sodium triacetoxyborohydride (23.4 g, 105 mmol) and glacial acetic acid (4.66 g, 77.6 mmol) were added to a solution of (1R,4R)-tert-butyl 5-oxo-2-azabicyclo[2.2.1]heptane-2-carboxylate (16.4 g, 77.6 mmol) and benzylamine (8.32 g, 77.6 mmol) in 1,2-dichloroethane (250 mL) under nitrogen atmosphere at 23° C. The resulting mixture was stirred for 5 h at 23° C. and then quenched with saturated sodium bicarbonate (a 1 h.) (300 mL). The mixture was extracted with ethyl acetate (350 mL×3) and the organic extracts were washed with brine, dried over magnesium sulfate and concentrated in vacuo. The crude material was purified by column chromatography (SiO$_2$, EtOAc:n-Hex. 9:1 (v/v)) to provide the title compound B5 (20.0 g, 66.1 mmol, 85%) as colorless oil.

$^1$H NMR (300 MHz, CDCl$_3$): δ 7.35-7.27 (m, 5H), 4.21 (s, 0.5H), 4.08 (s, 0.5H), 3.80-3.68 (m, 2H), 3.58 (d, J=10.0 Hz, 1H), 3.28-3.22 (m, 1H), 3.20-3.11 (m, 1H), 2.62 (m, 1H), 2.05-1.97 (m, 1H), 1.76-1.69 (m, 1H), 1.55-1.51 (m, 1H), 1.48 (s, 9H), 1.30-1.14 (m, 1H).

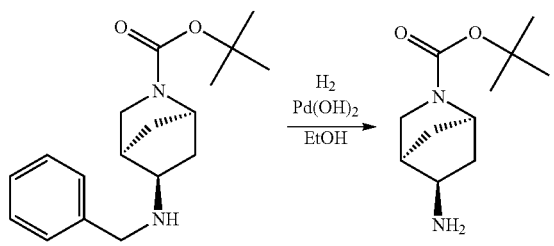 [SMILES: "EtOH" ; CC(C)(C)OC(=O)N1C[C@H]2C[C@@H]1C[C@H]2NCc1ccccc1 ; CC(C)(C)OC(=O)N1C[C@H]2C[C@@H]1C[C@H]2N]

(1R,4R,5R)-tert-Butyl 5-amino-2-azabicyclo[2.2.1]heptanes-2-carboxylate (B6)

The mixture of palladium hydroxide (4.30 g, 6.12 mmol, 10.0 mol %, 20 wt. % on carbon, 50% wet) and (1R,4R,5R)-tert-butyl 5-(benzylamino)-2-azabicyclo[2.2.1]heptane-2-carboxylate (18.5 g, 61.2 mmol) in ethanol (100 mL) was stirred for 36 h under hydrogen atmosphere at 23° C. The resulting mixture was filter through Celite and the pad was washed with ethyl acetate (500 mL). The filtrate was concentrated under reduced pressure to provide the title compound B6 (12.8 g, 60.3 mmol, 99%) as a colorless crystal.

$^1$H NMR (300 MHz, MeOD): δ 4.11 (s, 1H), 3.56-3.51 (m, 1H), 3.43-3.39 (m, 1H), 3.18-3.15 (m, 1H), 2.49 (bs, 1H), 2.14-2.05 (m, 1H), 1.74-1.68 (m, 1H), 1.61 (d, J=10.0 Hz, 1H), 1.48 (s, 9H), 1.18-1.10 (m, 1H).

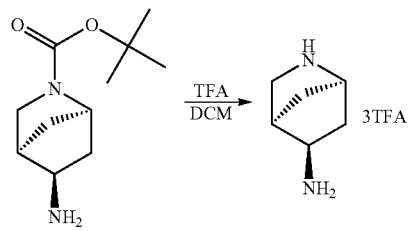

Preparation of (1R,4R,5R)-2-azabicyclo[2.2.1]heptan-5-amine (B7): The Boc protected amine (200 mg, 0.94 mmol) in CH$_2$Cl$_2$ (10 mL) was added dropwise of TFA (5 mL) and the mixture was stirred at RT for 10 minutes. The solvent was removed at vacuum and the amine (100 mg, 99%) was used for the reactions without further purification.

Example 6b

Synthesis of octahydrocyclopenta[c]pyrrol-4-amine

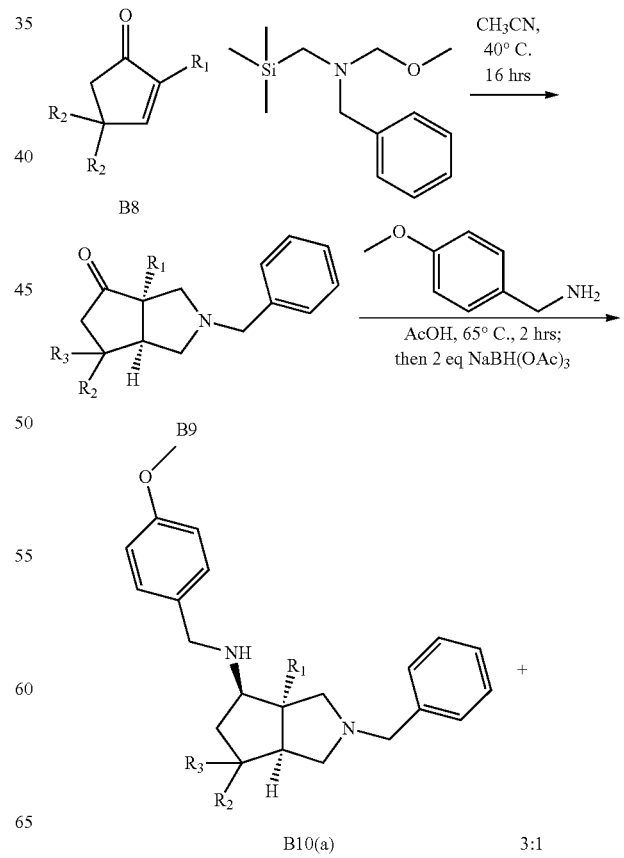

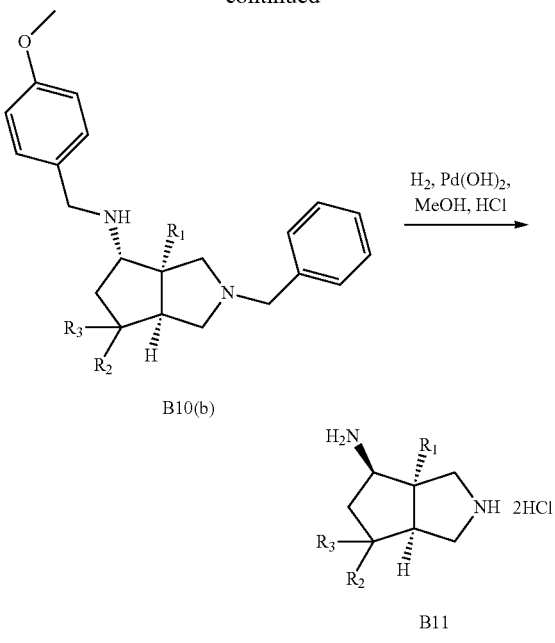

B10(b)

$R_1, R_2, R_3 = H$ or $CH_3$ (3aR,6aS)-2-benzylhexahydrocyclopenta[c]pyrro-4-(5H)-one (B9)

To a solution of N-methoxymethyl)-N-(trimethylsilylmethyl)benzyl amine (50 g, 0.21 mol) in acetonitrile (134 ml) was added 2-cyclopenten-1-one. The mixture was stirred under argon at 45° C. overnight. After the solvent was removed by rotary evaporation, the residue was purified through C18 column chromatography to afford the title compound as clear oil (30 g, 66.4%). The chirality was resolved by chiral HPLC to obtain the desired enantiomer (B9) with an ee of >99%.

(3aR,4R,6aS)-2-benzyl-N-(4-methoxybenzyl)octahydrocyclopenta[c]pyrrol-4-amine B10(a) and B10(b)

To the solution of compound (B9) (2.9 g, 13.43 mmol) in acetic acid (25 ml) was added 4 Å molecular sieve (5.7 g) and 4-methoxy benzylamine (2.76 g, 20.15 mmol). After the mixture was stirred at 75° C. for one hour, it was added with sodium triacetoxyborohydride by portion of total 1.2 equivalences (285 mg, 1.35 mmol in every 20 minutes interval). The reaction was continued at 75° C. to room temperature overnight. The molecular sieve was filtered off and washed with MeOH. The solution was concentrated by rotary evaporation, and the resulting residue was purified through C18 column chromatography. The PH of the combined collected eluents was adjusted to slightly basic by sodium carbonate and extracted with DCM (150 ml×3). The combined organic layers were dried over sodium sulfate and concentrated by rotary evaporation to afford the title product B10(a) as yellow oil (2.56 g, 56.7%).

(3aR,4R,6aS)-octahydrocyclopenta[c]pyrrol-4-amine HCl salt (B11)

To the solution of compound B10(a) (2.56 g, 7.61 mmol) in MeOH (100 ml) was added Pd(OH)$_2$ on 20% carbon-50% water (2 g) followed by the slow addition of concentrated HCl 37% (3 g). Hydrogen from a double-layer balloon was bubbled through the reaction mixture for 16 hours. Palladium on carbon was filtered out and washed with MeOH (10 ml). The filtrate was concentrated by rotary evaporation and excess HCl was removed through MeOH-toluene azeotrope to yield the tile compound (B11) as light yellow HCl salt (1.51 g, 100% yield).

Example 6c—Asymmetric Synthesis of tert-butyl (1R,4R,5R)-2-azabicyclo[2.2.1]heptan-5-ylcarbamate

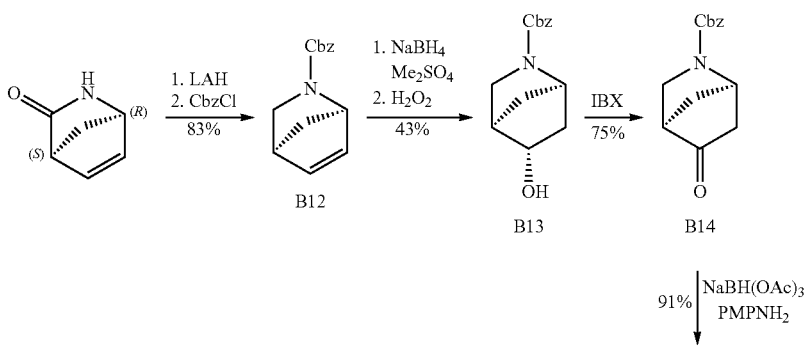

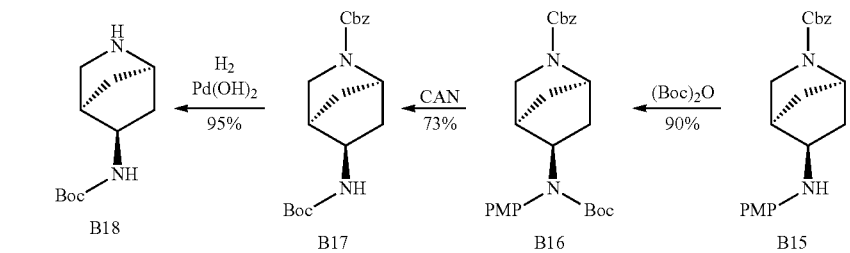

Asymmetric Synthesis of tert-butyl (1R,4R,5R)-2-azabicyclo[2.2.1]heptan-5-ylcarbamate

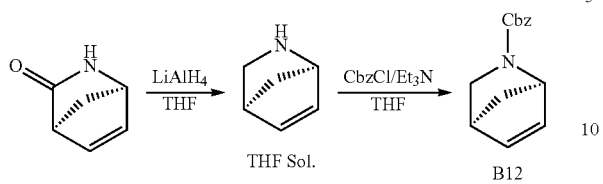

(1R,4S)-Benzyl 2-azabicyclo[2.2.1]hept-5-ene-2-carboxylate (B12)

(1R)-(−)-2-Azabicyclo[2.2.1]hept-5-en-3-one (5.00 g, 45.8 mmol, ee=99%) dissolved in anhydrous THF (45.0 mL) was slowly added to a solution of lithium aluminum hydride (28.7 mL, 57.3 mmol, 2M solution in THF) in anhydrous THF (50.0 mL) under nitrogen atmosphere at 0° C. After the addition was successfully completed, the mixture was stirred for 3 h at 23° C. and then heated for 24 h at 60° C. The resulting heterogeneous mixture was cooled to 0° C. and $H_2O$ (5.00 mL) was carefully added to the mixture via syringe. The white suspension was filtered through a Celite filter aid and the pad was washed with anhydrous THF (250.0 mL). The filtrate as a clear solution was cooled to 0° C. and then treated with triethylamine (12.8 mL, 91.6 mmol) and CbzCl (10.3 mL, 68.7 mmol) in that order. The resulting heterogeneous mixture including a white precipitate was slowly warmed to 23° C. and allowed to stir for 48 h. The white precipitates were filtered by reduced pressure and the resulting clear solution was concentrated in vacuo. The crude material as light yellow oil was purified by column chromatography ($SiO_2$, EtOAc:n-Hex 1:4 (v/v)) to provide the title compound B12 (8.68 g, 37.9 mmol, 83%) as a colorless oil.

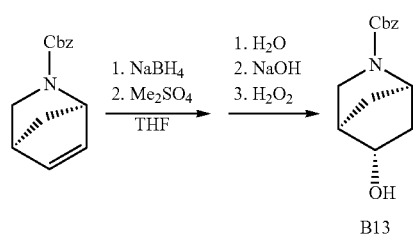 [SMILES: O=C(OCc1ccccc1)N1C[C@@H]2C=C[C@H]1C2 ; "B13" ; O=C(OCc1ccccc1)N1C[C@H]2C[C@@H]1C[C@@H]2O ; "THF"]

(1R,4R,5S)-Benzyl 5-hydroxy-2-azabicyclo[2.2.1]heptane-2-carboxylate (B13)

The mixture of (1R,4S)-benzyl 2-azabicyclo[2.2.1]hept-5-ene-2-carboxylate (8.679 g, 37.86 mmol) and sodium borohydride (1.17 g, 31.0 mmol) in THF (60.0 mL) was stirred for 0.5 h under nitrogen atmosphere at 23° C. After being stirred for 0.5 h, the mixture was warmed to 35° C. and then dimethylsulfate (2.93 mL, 31.0 mmol) dissolved in THF (2.0 mL) was added dropwise via syringe. (Note: dimethylsulfate was slowly added due to gas evolution) The resulting heterogeneous mixture was stirred for 4 h at 35° C., then cooled to 0° C. and quenched by dropwise addition of $H_2O$ (5.0 mL). A solution of sodium hydroxide (80.0 mL, 80.0 mmol, 1 M solution of NaOH) was added at 0° C. followed by addition of hydrogen peroxide (5.0 mL, 30 wt. % in $H_2O$). The mixture was warmed to 23° C. and stirred for additional 1 h. The resulting colorless solution was diluted with ethylacetate (250 mL) and the organic layer was separated, washed with brine (150 mL) and dried over magnesium sulfate. The mixture was concentrated by rotavap and the resulting colorless oil as crude product was purified by column chromatography ($SiO_2$, EtOAc:n-Hex 1:1 (v/v)) to provide the title compound B13 (4.02 g, 16.3 mmol, 43%) as a colorless oil.

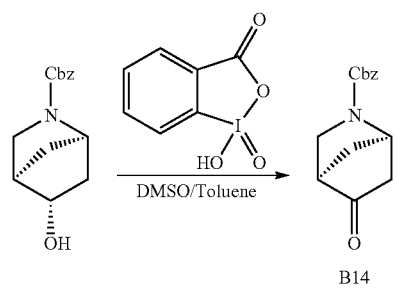

(1R,4R)-Benzyl 5-oxo-2-azabicyclo[2.2.1]heptanes-2-carboxylate (B14)

2-Iodoxybenzoic acid (13.7 g, 22.0 mmol, 45 wt. % (SIBX)) was added to a solution of (1R,4R,5S)-benzyl 5-hydroxy-2-azabicyclo[2.2.1]heptanes-2-carboxylate (4.02 g, 16.3 mmol) dissolved in dimethylsulfoxide (20.0 mL) and toluene (40.0 mL) under nitrogen atmosphere at 23° C. The mixture was stirred for 3 h 30 min at 60° C. and then cooled to 23° C. The resulting heterogeneous mixture was treated with saturated sodium carbonate (a 1 h.) (250 mL) and filtered under reduced pressure to remove a white solid. The filtrate was extracted with ethyl acetate (250 mL×3) and the organic extracts were washed with brine, dried over magnesium sulfate and concentrated in vacuo. The crude material as colorless oil was purified by column chromatography ($SiO_2$, EtOAc:n-Hex 1:2 (v/v)) to provide the title compound B14 (2.99 g, 12.2 mmol, 75%) as a colorless oil.

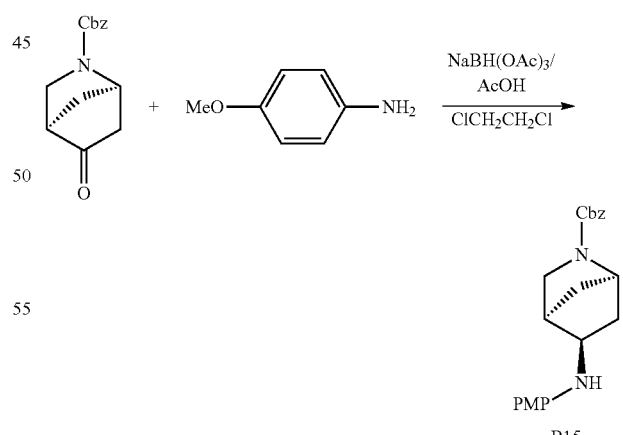

(1R,4R,5R)-Benzyl 5-(4-methoxyphenylamino)-2-azabicyclo[2.2.1]heptanes-2-carboxylate (B15)

Sodium triacetoxyborohydride (0.904 g, 4.05 mmol) and glacial acetic acid (0.180 g, 3.00 mmol) were added to a solution of (1R,4R)-benzyl 5-oxo-2-azabicyclo[2.2.1]heptanes-2-carboxylate (0.736 g, 3.00 mmol) and p-anisidine (0.370 g, 3.00 mmol) in 1,2-dichloroethane (10.0 mL) under nitrogen atmosphere at 23° C. The resulting mixture was stirred for 3 h at 23° C. The heterogeneous mixture was cooled to 0° C. and quenched with saturated sodium bicarbonate (a 1 h.) (150 mL). The mixture was extracted with ethyl acetate (200 mL×3) and the organic extracts were washed with brine, dried over magnesium sulfate and concentrated in vacuo. The crude material as clear yellow oil was purified by column chromatography (SiO$_2$, EtOAc:n-Hex. 1:2 (v/v)) to provide the title compound B15 (0.964 g, 2.73 mmol, 91%) as a white solid.

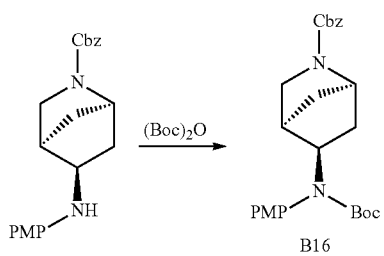

(1R,4R,5R)-Benzyl 5-(tert-butoxycarbonyl(4-methoxyphenyl)amino)-2-azabicyclo[2.2.1]heptane-2-carboxylate (B16)

The mixture of (1R,4R,5R)-benzyl 5-(4-methoxyphenylamino)-2-azabicyclo[2.2.1]heptanes-2-carboxylate (0.352 g, 1.00 mmol) and KHMDS (1.30 mL, 1.30 mmol, 1.0 M solution of THF (15.0 mL) was stirred for 15 min under nitrogen atmosphere at 23° C. The resulting greenish mixture was treated with (Boc)$_2$O (0.470 g, 2.15 mmol) and then was stirred for 16 h at 23° C. The mixture was concentrated under reduced pressure to provide yellow oil. The crude material was purified by column chromatography (SiO$_2$, EtOAc:n-Hex. 1:2 (v/v)) to give the title compound B16 (0.408 g, 0.901 mmol, 90%) as a colorless oil.

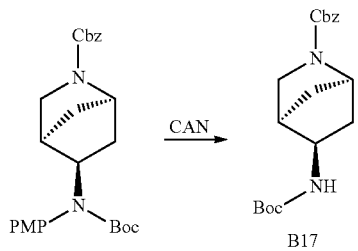

(1R,4R,5R)-Benzyl 5-(tert-butoxycarbonylamino)-2-azabicyclo[2.2.1]heptane-2-carboxylate (B17)

Ceric ammonium nitrate (1.73 g, 3.15 mmol) dissolved in H$_2$O (5.0 mL) was added to a solution of (1R,4R,5R)-benzyl 5-(tert-butoxycarbonyl(4-methoxyphenyl)amino)-2-azabicyclo[2.2.1]heptane-2-carboxylate (0.408 g, 0.901 mmol) in acetonitrile (25 mL) under nitrogen atmosphere at 0° C. The resulting mixture was stirred for 1 hr at 0° C. and then diluted with H$_2$O (100 mL), extracted with ethyl acetate (150 mL×3). The combined organic phase was washed with 1 N Ns$_2$SO$_3$ (75 mL), dried over MgSO4 and concentrated in vacuo. The crude material was purified by column chromatography (SiO$_2$, EtOAc:n-Hex. 1:2 (v/v)) to give the title compound B17 (0.229 g, 0.661 mmol, 73%) as a colorless oil.

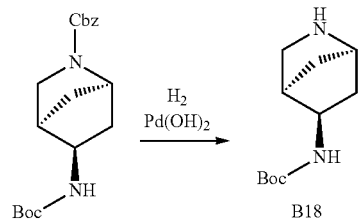 [SMILES: CC(C)(C)OC(=O)N[C@@H]1C[C@H]2C[C@@H]1CN2C(=O)OCc1ccccc1 ; "B18" ; CC(C)(C)OC(=O)N[C@@H]1C[C@H]2C[C@@H]1CN2]

tert-Butyl (1R,4R,5R)-2-azabicyclo[2.2.1]heptane-5-carboxylate (B18)

The mixture of palladium hydroxide (0.015 g, 0.022 mmol, 10.0 mol %, 20 wt. % on carbon, 50% wet) and (1R,4R,5R)-benzyl 5-(tert-butoxycarbonylamino)-2-azabicyclo[2.2.1]heptane-2-carboxylate (0.077 g, 0.222 mmol) in ethanol (5.0 mL) was stirred for 3 h 30 min under hydrogen atmosphere at 23° C. The resulting mixture was filter through Celite and the pad was washed with ethyl acetate (100 mL). The filtrate was concentrated under reduced pressure to provide the title compound B18 (0.045 g, 0.212 mmol, 95%) as colorless oil.

$^1$H NMR (300 MHz, MeOD): δ 3.89 (d, J=11.2 Hz, 1H), 3.42 (s, 1H), 3.01 (d, J=10.4 Hz, 1H), 2.74-2.69 (m, 1H), 2.58 (bs, 1H), 2.12-2.02 (m, 1H), 1.64 (s, 2H), 1.46 (s, 9H), 1.19-1.13 (m, 1H).

Asymmetric Synthesis of tert-butyl(S)-(2-azaspiro[3.3]heptan-5-yl)carbamate

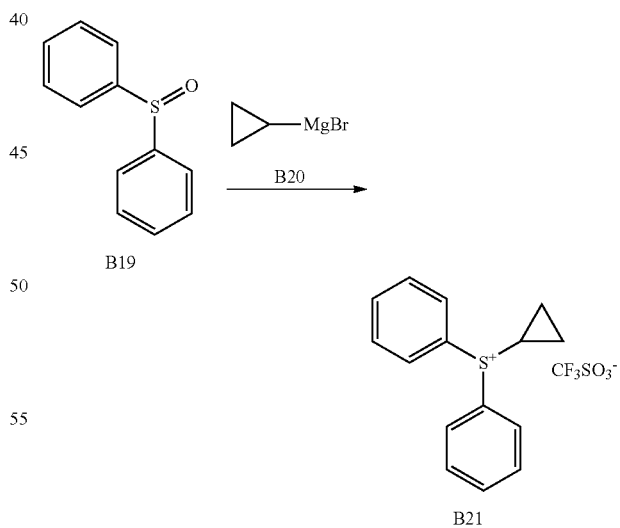

Synthesis of 2-Methylcyclopropyldiphenylsulfonium trifluomethanesulfonate (B21)

To a solution of phenyl sulfoxide (20.0 g, 9.9 mmol, 1.0 eq) in DCM (200 mL) was cooled to −78° C. and treated drop wise with trimethylsilyl triflate (23 mL, 12.0 mmol, 1.2 eq) over 5 min After the solution had been stirred for an additional 30 min at −78° C., The solution was warmed to 0° C. and kept the temperature for 30 min. The reaction mixture was recooled to −78° C. and treated drop wise with a 1.0 M solution of cycylpropyl magnesium bromide in THF (200 mL, 20.0 mmol, 2.0 eq). After an additional 30 min at −78° C., the reaction mixture was warmed to 0° C. and kept at temperature for 30 min. The reaction mixture was quenched with 3% aqueous triflic acid (300 mL) and diluted with ether. The organic layers was washed with additional riflic acid (600 mL). The combined aqueous fractions were extracted with chloroform, dried over Na₂SO₄ and concentrated to give 20 g crude as a yellow oil which was used next step without further purification.

Synthesis of 6-(diphenylmethyl)-6-azaspiro[3.3]heptan-1-one (B23)

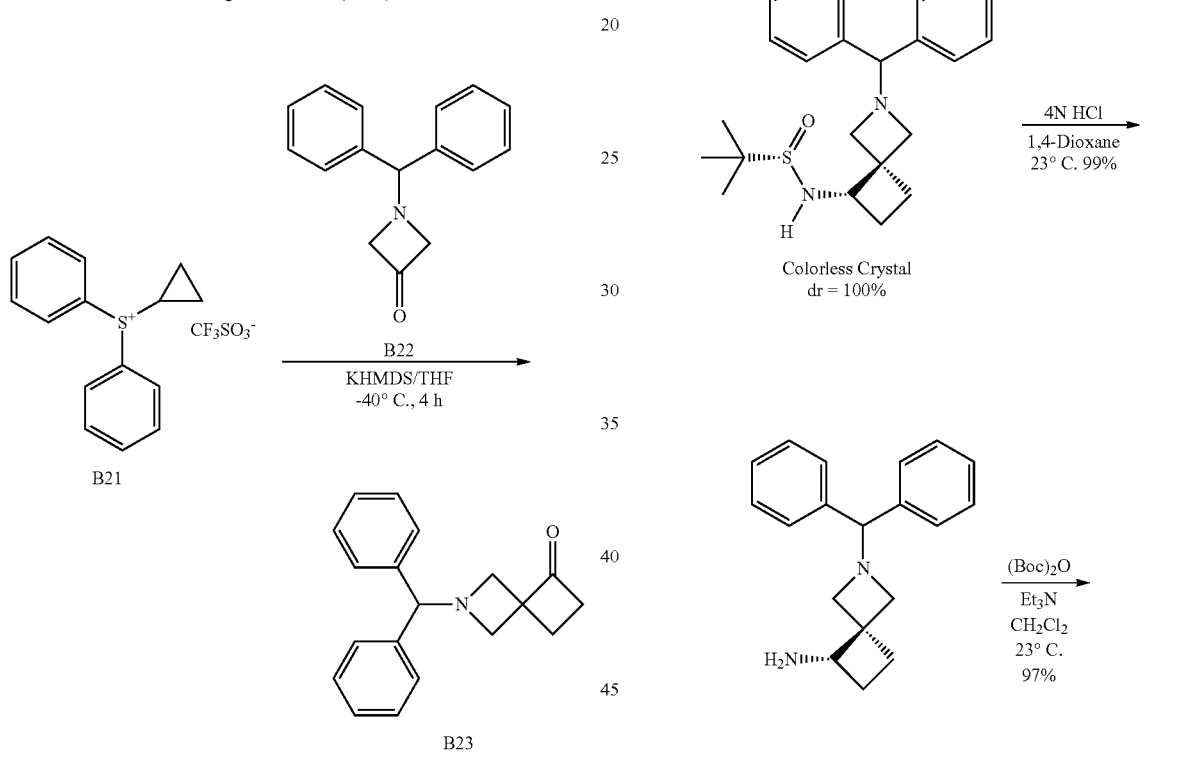

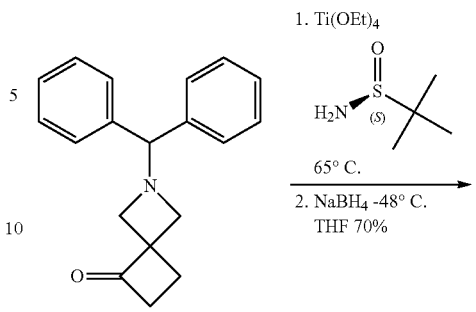

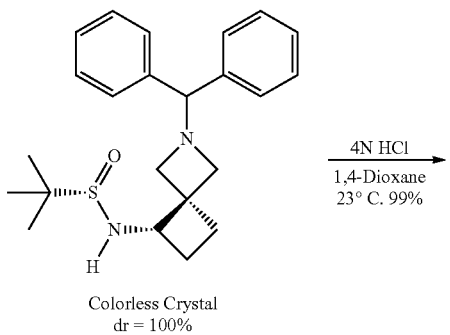

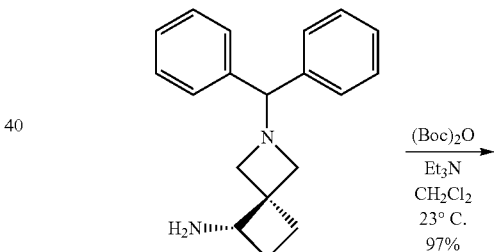

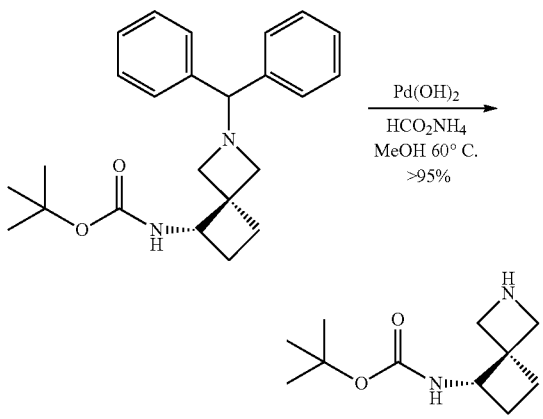

To a solution of B23 (100 g, 266 mmol, 1.0 eq) in 1800 mL THF under nitrogen was added KHMDS (330 mL, 293 mmol, 1.1 eq) below −70° C. The yellow-orange suspension was stirred for 30 min and then a solution of compound 4 (63.0 g, 266 mmol, 1.0 eq) in 250 mL THF was added. The reaction was stirred at −40° C. for 4 h, and then was allowed to warm to room temperature. LiI (21 g, 157.5 mmol, 0.5 eq) was added. The reaction was heated to 50° C. overnight and then quenched with water (500 mL). The mixture was extracted with EA (1500 mL) three times. The combined organic layer was washed with brine, dried over sodium sulfate, and then concentrated to obtain 60 g oil crude. The oil was purified through silica column to afford 18 g white solid (Y=24%)

¹H NMR (400 MHz, DMSO-d₆): δ 2.17 (t, J=8.0 Hz, 2H), 2.89 (t, J=8.8 Hz, 2H), 3.17 (d, J=7.6 Hz, 2H), 3.22 (d, J=7.6 Hz, 2H), 4.36 (s, 1H), 7.17 (t, J=7.6 Hz, 2H), 7.27 (t, J=7.2 Hz, 1H), 7.40 (d, J=7.6 Hz, 2H).

Synthesis of (S)—N—((S)-2-benzhydryl-2-azaspiro[3.3]heptan-5-yl)-2-methylpropane-2-sulfinamide (6)

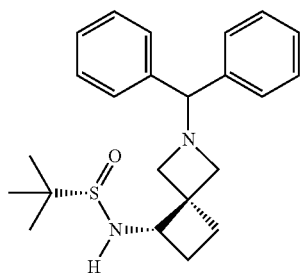

B24

To a solution of 2-benzhydryl-2-azaspiro[3.3]heptan-5-one (50.0 g, 180 mmol) and Ti(OEt)$_4$ (90.0 mL, 343 mmol, Sigma-Aldrich; technical grade) in anhydrous THF (360 mL) was added (S)-2-methylpropane-2-sulfinamide (20.7 g, 171 mmol) under nitrogen atmosphere at 23° C. The reaction mixture was heated for 5 h at 65° C. and monitored by LC/MS. Upon completion, the mixture was cooled to 23° C. first and then −48° C. NaBH$_4$ (22.2 g, 586 mmol) was slowly added into the mixture for 30 min under nitrogen. After the addition was successfully completed, the mixture was stirred for 2 h at −48° C. and checked by LC/MS. The diastereoselectivity of the crude material was determined to be 90:10 by HPLC analysis. The reaction mixture was warmed to 0° C. and then MeOH was dropwise added until gas was no longer evolved. Brine (360 mL) was slowly added into the mixture with vigorous stirring. The resulting white suspension was filtered through a plug of Celite and the filter cake was washed with EtOAc (300 mL×3). The filtrate was washed with brine (350 mL×2), and then the aqueous layer was extracted with EtOAc (500 mL×3). The combined organic layers were dried over MgSO$_4$, filtered, and concentrated in vacuo. The crude material as yellow oil was purified by column chromatography (SiO$_2$, n-Hex:EtOAc 20:80 (v/v)) to provide (S)—N—((S)-2-benzhydryl-2-azaspiro[3.3]heptan-5-yl)-2-methylpropane-2-sulfinamide (48.0 g, 126 mmol, 70%) as a colorless crystalline solid. After the column chromatography, the diastereomeric excess (de) of the title compound was determined to be 99.9% by LC/MS and $^1$H NMR analysis.

Synthesis of (S)-2-benzhydryl-2-azaspiro[3.3]heptan-5-amine (B25)

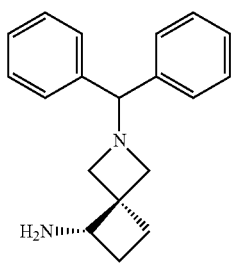

B25

4N HCl (156 mL, 622 mmol, Sigma-Aldrich) was slowly added to a solution of (S)—N—((S)-2-benzhydryl-2-azaspiro[3.3]heptan-5-yl)-2-methylpropane-2-sulfinamide (47.6 g, 124.4 mmol) in anhydrous 1,4-dioxane (1250 mL) under nitrogen atmosphere at 23° C. After being stirred for 3 h at 23° C., the resulting white precipitates mixture was concentrated under reduced pressure to give (S)-2-benzhydryl-2-azaspiro[3.3]heptan-5-amine (99%) as a white solid. The crude product was used for next reaction without further purification.

Synthesis of tert-butyl (S)-(2-benzhydryl-2-azaspiro[3.3]heptan-5-yl)carbamate (B26)

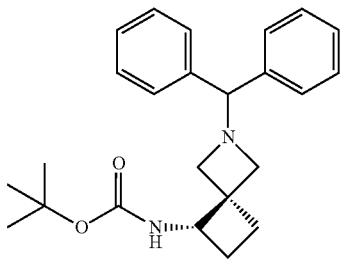

B26

To a solution of (S)-2-benzhydryl-2-azaspiro[3.3]heptan-5-amine as HCl salts form and Et3N (126 g, 1244 mmol) in CH$_2$Cl$_2$ (700 mL) was added (Boc)$_2$O (81.5 g, 373 mmol) under nitrogen atmosphere at 0° C. The resulting mixture was slowly warmed to 23° C. and stirred for 24 h at 23° C. The mixture was concentrated under reduced pressure and the crude material was purified by column chromatography (SiO$_2$, n-Hex:EtOAc 70:30 (v/v)) to give tert-butyl (S)-(2-benzhydryl-2-azaspiro[3.3]heptan-5-yl)carbamate (45.5 g, 120.2 mmol, 97%; two step yield) as a colorless oil.

Synthesis of tert-butyl (S)-(2-azaspiro[3.3]heptan-5-yl)carbamate (B27)

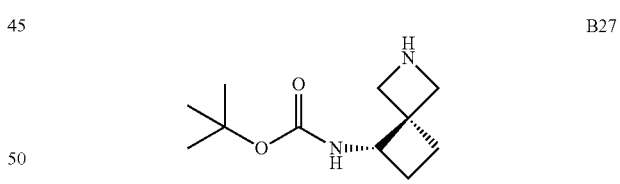

B27

Ammonium formate (26.5 g, 421 mmol, Sigma-Aldrich) was slowly added to a solution of tert-butyl (S)-(2-benzhydryl-2-azaspiro[3.3]heptan-5-yl)carbamate (45.5 g, 120.2 mmol) and palladium hydroxide (50.6 g, 72.1 mmol, 60 mol %, 20 wt. % on carbon, 50% wet) in MeOH (350 mL) under nitrogen atmosphere at 23° C. The resulting mixture was allowed to stir for 5 h at 60° C. After the reaction was completed, the mixture was cooled to 23° C. The heterogeneous mixture was filtered through Celite and the pad was washed with ethyl acetate (500 mL). The filtrate was concentrated under reduced pressure to provide tert-butyl (S)-(2-azaspiro[3.3]heptan-5-yl)carbamate (>95%) as a colorless oil (LC/MS and $^1$H NMR analysis).

$^1$H NMR (400 MHz, CDCl3): δ 1.46 (s, 1H), 1.50-1.58 (m, 9H), 1.86-1.88 (m, 1H), 2.03 (t, J=9.6 Hz, 1H), 2.16-

2.18 (m, 1H), 3.45-3.56 (m, 2H), 3.64 (s, 2H), 3.80 (d, J=8.0 Hz, 1H), 3.89-3.95 (m, 1H), 4.91 (s, 1H).

Example 7

Section C

General Scheme 1:

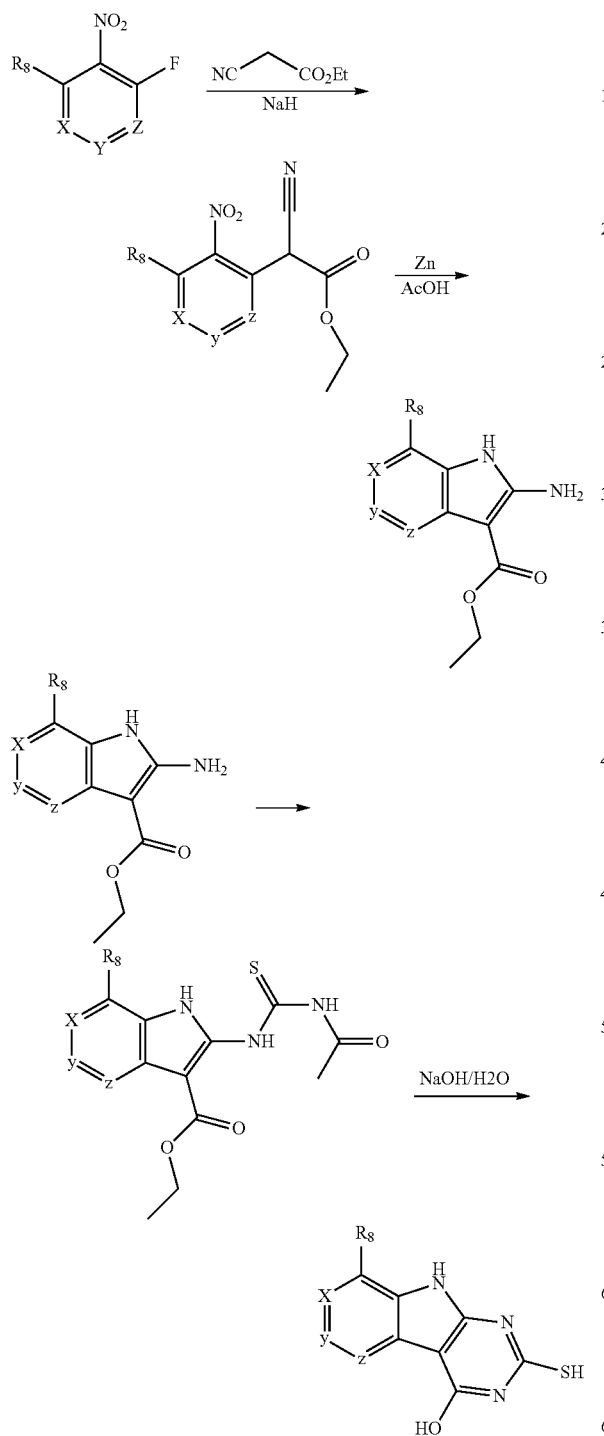

Processes for Compounds where L=S

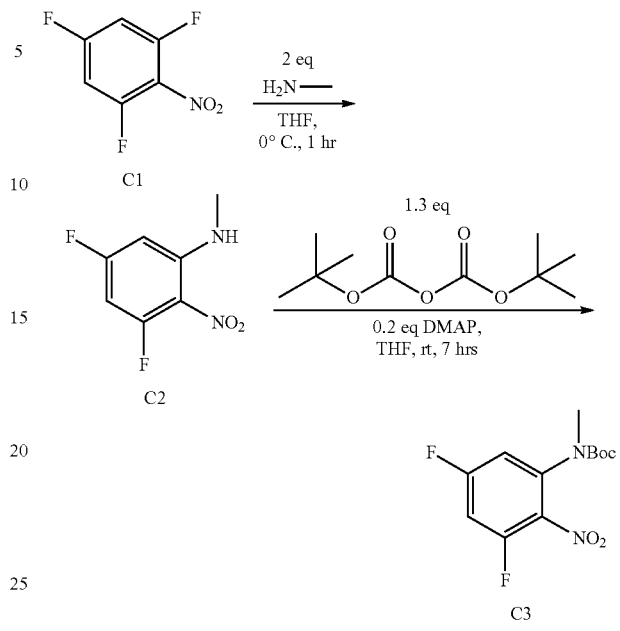

3,5-difluoro-N-methyl-2-nitroaniline (C2)

1,3,5-Trifluoro-2-nitrobenzene (35.16 g, 0.2 mol) was dissolved in 100 ml of THF and cooled in an ice-water bath. To this solution was added drop-wise the 40% aqueous solution of methylamine (23.25 g, 0.3 mol) over ~20 minutes through an additional funnel. The reaction mixture was stirred for 1 hour. It was then diluted with hexane (50 ml), and the solvents were partitioned into two layers. The aqueous solution was removed, and the organic layer was washed with water (20 ml). The solution was concentrated by gentle rotary evaporation at room temperature and further dried under high vacuum to afford the crude product (C2) as orange solid (36 g, 96%).

$^1$H NMR (CDCl$_3$, 300 MHz): δ=6.97-6.88 (m, 2H), 3.27 (s, 3H).

Tert-butyl 3,5-difluoro-2-nitrophenyl(methyl)carbamate (C3)

To the solution of crude 3,5-difluro-N-methyl-2-nitroaniline (C2) (36 g, 0.191 mol) in 100 ml of THF was added di-tert-butyl-dicarbonate (54.3 g, 0.249 mol) followed by 4-dimethylaminopyridine (4.68 g, 0.038 mol). The reaction mixture was stirred at room temperature for 7 hours. Water (50 ml) was then added and the resulting solution was stirred for 1.5 hours. After diluted with hexane (100 ml), the solution was partitioned into two layers, and the aqueous phase was removed through an extraction funnel and back extracted with ethyl acetate (50 ml). The combined organic layer was then washed first with 5% NH$_4$Cl solution (100 ml) and then with 5% K$_2$CO$_3$ solution (100 ml). After the combined organic solvent was concentrated by rotary evaporation at room temperature, the resulting residue was re-dissolved in MeOH (~50 ml) and then added drop-wise into 600 ml of ~0.01% K$_2$CO$_3$ solution. The orange solid product (C3) was filtered, washed with water, and dried under high vacuum (46.78 g, 85%).

$^1$H NMR (CDCl$_3$, 300 MHz): δ=6.93-6.85 (m, 2H), 3.20 (s, 3H), 1.32 (s, 9H).

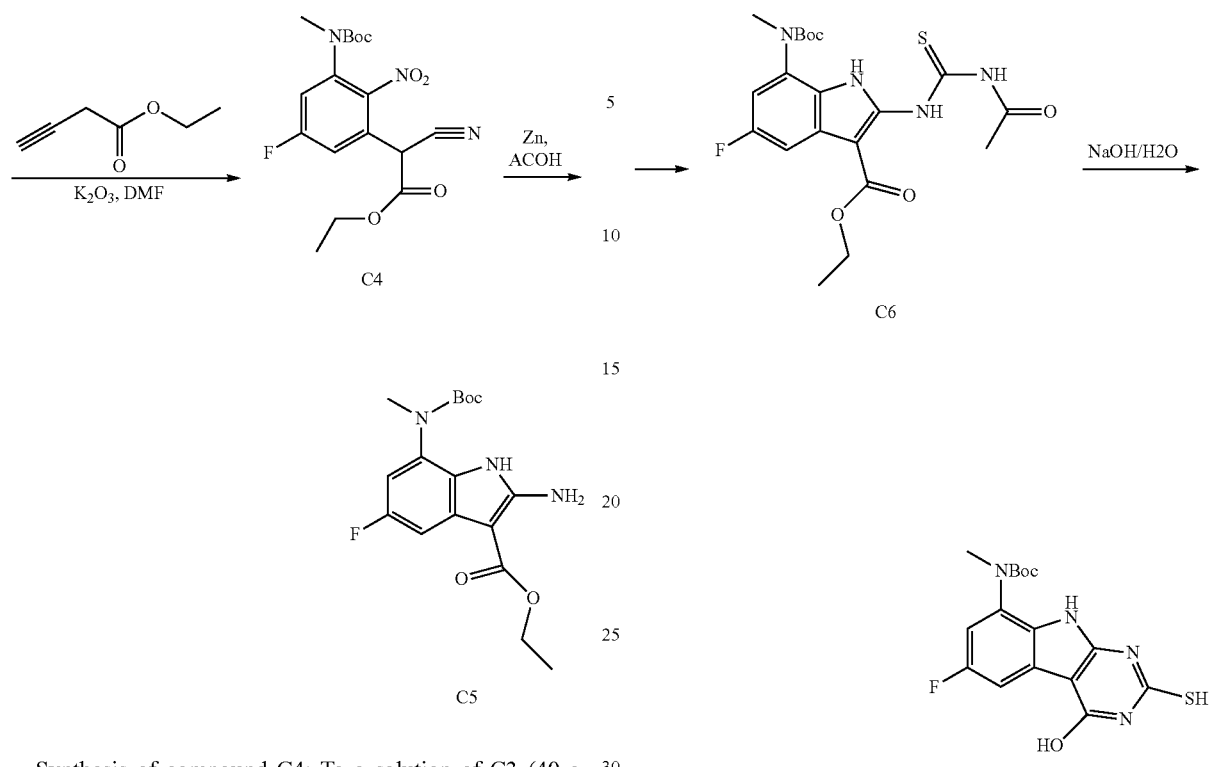

Synthesis of compound C4: To a solution of C3 (40 g, 0.14 mol) in DMF (200 mL) was added potassium carbonate (19 g, 0.14 mol), followed by a portion of ethyl cyano acetate (15 g, 0.14 mol). The mixture was stirred at room temperature for 2 h. Then an additional portion of potassium carbonate (19 g, 0.14 mol) and a portion of ethyl cyano acetate (15 g, 0.14 mol) were added. After the mixture was stirred at room temperature for 4 h, potassium carbonate (19 g, 0.14 mol) was added and the mixture was stirred at room temperature for another 12 h. Then the mixture was poured into ice water and extracted with ethyl acetate (2×200 mL). The organic layer was dried over $Na_2SO_4$, filtered, concentrated and purified by chromatography on silica gel (petroleum ether/ethyl acetate=5:1) to afford the compound C4 (33 g, yield: 63%) as yellow solid.

$^1$H NMR ($CDCl_3$, 300 MHz): δ=6.93-6.85 (m, 2H), 4.88 (m, 1H), 4.33 (m, 2H), 3.20 (s, 3H), 1.32 (s, 9H), 1.28 (t, 3H).

Synthesis of compound C5: To a solution of C4 (20 g, 52 mmol) in toluene (100 mL) and acetic acid (100 mL) was added zinc powder (30 g, 0.46 mol) and the mixture was stirred at 75° C. for 2 h. Then another Zn powder (10 g, 0.15 mol) was added. After stirred at 75° C. for more 0.5 h, the mixture was cooled to room temperature, filtered and poured into ice water. 2N NaOH was added to adjust the pH to 8-9 and the resultant mixture was extracted with ethyl acetate (2×200 mL). The organic layer was dried over $Na_2SO_4$, filtered, concentrated and purified by chromatography on silica gel (petroleum ether/ethyl acetate=5:1) to afford compound C5 as a brown solid (8.3 g, yield: 45%).

Synthesis of compound C7: To a stirred suspension of compound C5 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification. LC-MS: M+1: 453.21.

Above residue was dissolved into 50 ml methanol and 50 ml H2O, then was added 10 ml 10% KOH solution, the mixture solution was heated to reflux for 30 minutes. When LCMS showed the reaction was completed the reaction was cooled to room temperature, acidified to pH 5 with 1 M a 1 h. HCl, and the precipitate collected by filtration to give compound C7 as a solid (5 g, 65.4% in two steps). LC-MS: M+1: 365.13.

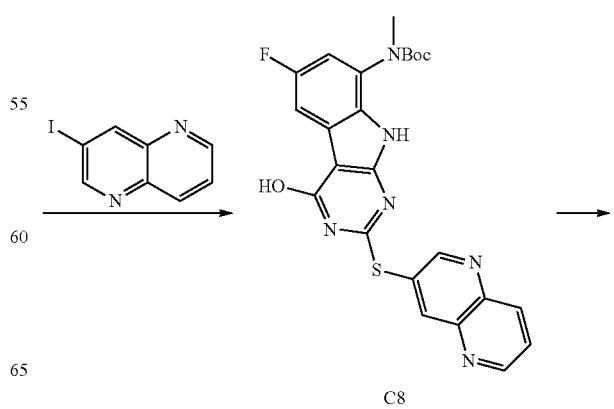

311

-continued

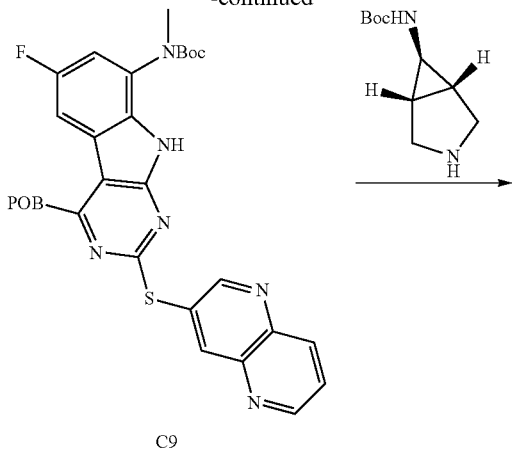

C9

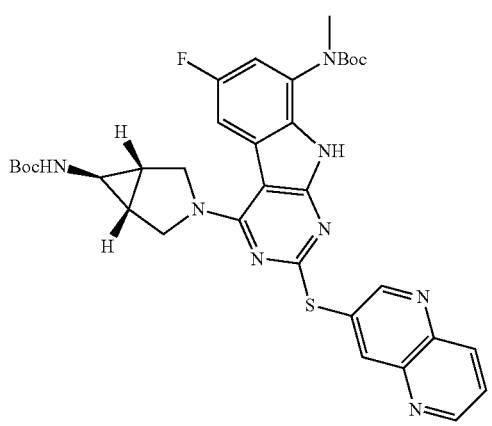

C10

Synthesis of compound C10: The solution of CuI (67 mg, 0.35 mmol), N,N'-dimethyl cyclohexane-1,2-diamine (100 mg, 0.70 mmol) in 9 mL of NMP was added to a stirring suspension of tert-butyl (4-hydroxy-2-mercapto-9H-pyrimido[4,5-b]indol-8-yl)(methyl) carbamate (5, 350 mg, 1.0 mmol), a proper I—Ar (1.17 mmol), $K_2CO_3$ (324 mg, 2.35 mmol) and $PPh_3$ (400 mg, 1.53 mmol) in NMP (9 mL). The mixture was heated to 130° C. for 2 to 12 hrs monitored by LC-MS for the completion of the reaction. When the reaction completed, the mixture was cooled to 0° C., BOP (621 mg, 1.40 mmol) and $Et_3N$ (0.41 mL, 2.93 mmol) was added, stirred for 30 minutes at 0° C., then warmed up to room temperature, a suitable Boc-protected diamine (2.34 mmol) was added. The reaction mixture was heated to 50° C. for 30 minutes. LC-MS indicated the completed reaction. After completed the reaction, the mixture was partitioned with ethyl acetate and water, the aqueous layer was extracted by ethyl acetate twice, the combined organic layer was dried and purified by flash chromatography to give products compound C10 as a solid (420 mg, 63% in two steps). LC-MS: M+1: 673.25.

312

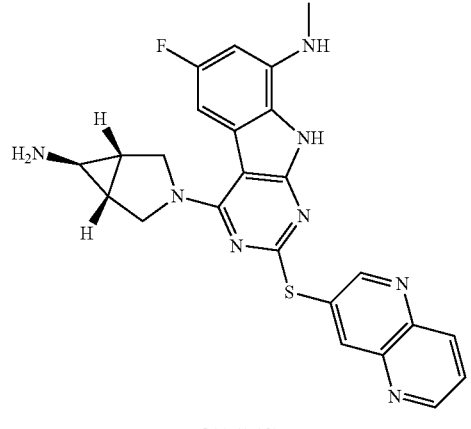

C11 (1.12)

Synthesis of compound C11: The above compound (420 mg, 0.63 mmol) was dissolved in 10 mL of TFA and stirred for 30 minute at room temperature. After removal of the solvents, the residue was re-dissolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipitate, and dried to gave final compounds as a white solid (200 mg, 70%). LC-MS: M+1: 473.13.

$^1$H NMR (300 MHz, DMSO) δ (ppm): 11.75 (s, 1H), 8.09 (d, 1H), 8.95 (s, 1H), 8.52 (m, 1H), 8.35 (s, 1H), 7.75 (m, 1H), 7.01 (d, J=11.2, 1H), 5.96 (d, 1H), 4.10 (s, 1H), 2.98 (s, 3H), 2.85 (m, 2H), 2.67 (m, 2H), 1.38 (m, 1H), 0.75 (br m, 2H).

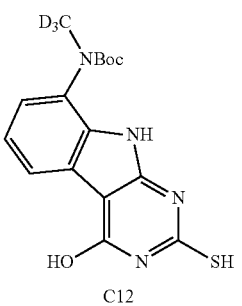

C12

+

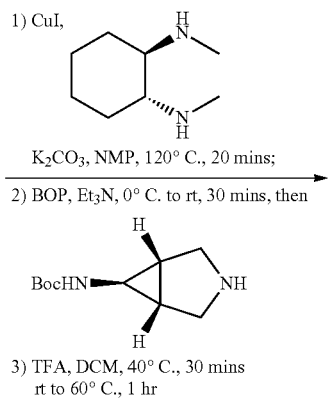

1) CuI, [diamine]
K₂CO₃, NMP, 120° C., 20 mins;
2) BOP, Et₃N, 0° C. to rt, 30 mins, then
[BocHN-pyrrolidine]
3) TFA, DCM, 40° C., 30 mins
rt to 60° C., 1 hr -continued

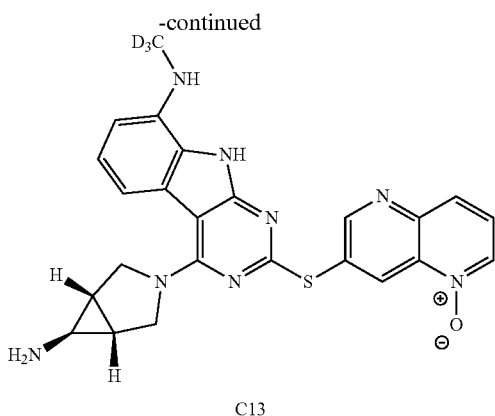

C13

Example 7b 7-(4-(6-amino-3-azabicyclo[3.1.0]hexan-3-yl)-8-(deuteratedmethylamino)-9H-pyrimido[4,5-b]indol-2-ylthio)-1,5-naphthyridine 1-oxide C13 (CD3 analog of 1.13): To the mixture of CuI (76 mg, 0.4 mmol) and $K_2CO_3$ (112 mg, 0.8 mmol) in NMP (1 ml) was added trans-N,N'-dimethylcyclohexane-1,2-diamine (113.6 mg (0.8 mmol). The mixture was stirred at 120° C. for 10 minutes. It was then added with compound (C12) (70 mg, 0.2 mmol) and 7-iodo-1,5-naphthyridine 1-oxide (59.8 mg, 0.22 mmol). The reaction was continued at 120° C. for 20 minutes. It was cooled down to −4° C. and then added with $Et_3N$ (0.3 ml) followed by [benzotriazole-1-yl-oxy-tris-(dimethylamino)phosphonium hexafluorophosphate](BOP reagent) (97.3 mg, 0.22 mmol). After stirred at −4° C. to room temperature for 30 minutes, the reaction mixture was added with the amine (79.3 mg, 0.4 mmol) and then heated at 60° C. for one hour. It was then purified through HPLC. Water in the collected Boc-adduct eluents was removed by extraction with DCM (20 ml×2). The combined organic layers were concentrated by rotary evaporation. The residue was re-dissolved in DCM (2 ml) and trifluoroacetic acid (~0.2 ml). It was stirred at 40° C. for 30 minutes to remove the BOC-protection. The reaction mixture was flash purified through HPLC to afford the title compound (C13) as white solid (52.1 mg, 55%).

$^1$H NMR (300 MHz, DMSO) δ (ppm): 11.75 (s, 1H), 8.09 (d, 1H), 8.95 (s, 1H), 8.52 (m, 1H), 8.35 (s, 1H), 7.75 (m, 1H), 7.01 (d, J=11.2, 1H), 5.96 (d, 1H), 4.10 (s, 1H), 2.85 (m, 2H), 2.67 (m, 2H), 1.38 (m, 1H), 0.75 (br m, 2H).

Table of Formula I' compounds where L = S

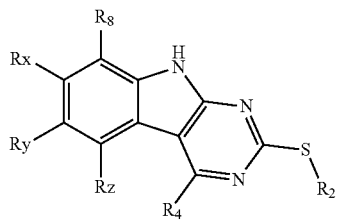

| Cmpd ID | R8 | Rx | Ry | Rz | R4 | R2 |
|---|---|---|---|---|---|---|
| 1.1 | cyclopropyl-NH- | H | F | H | 6-amino-3-azabicyclo[3.1.0]hexan-3-yl | 1,5-naphthyridin-3-yl |
| 1.2 | cyclopropyl-C(CH3)-NH- | H | F | H | 6-amino-5-azaspiro[2.4]heptan-5-yl | 1,5-naphthyridin-3-yl 1-oxide |
| 1.3 | Cl | H | H | H | 6-amino-3-azabicyclo[3.1.0]hexan-3-yl | 1,5-naphthyridin-3-yl 5-oxide |

-continued

Table of Formula I' compounds where L = S

| Cmpd ID | R8 | Rx | Ry | Rz | R4 | R2 |
|---|---|---|---|---|---|---|
| 1.4 | Cl | H | H | H | pyrrolidin-1-yl with 3-NH2 (stereo) | 1,5-naphthyridine N-oxide |
| 1.5 | H | H | H | H | azetidin-1-yl with 3-NH2 | pyrido[2,3-b]pyrazine |
| 1.6 | H | H | H | H | pyrrolidin-1-yl with 3-NH2 | pyrido[2,3-b]pyrazine |
| 1.7 | Me | H | H | H | 3-azabicyclo[3.1.0]hexyl-NH2 | pyrido[2,3-b]pyrazine |
| 1.8 | NH2 | H | H | H | 3-azabicyclo[3.1.0]hexyl-NH2 | 1,5-naphthyridine N-oxide |
| 1.9 | NH2 | H | H | H | 3-azabicyclo[3.1.0]hexyl-NH2 | 1,5-naphthyridine |
| 1.10 | NHEt | H | H | H | 3-azabicyclo[3.1.0]hexyl-NH2 | 1,5-naphthyridine N-oxide |

-continued

Table of Formula I' compounds where L = S

| Cmpd ID | R8 | Rx | Ry | Rz | R4 | R2 |
|---------|-----|----|----|----|----|-----|
| 1.11 | NHEt | H | H | H | 3-azabicyclo[3.1.0]hexyl-NH₂ | 1,5-naphthyridin-3-yl |
| 1.12 | NHMe | H | H | H | 3-azabicyclo[3.1.0]hexyl-NH₂ | 1,5-naphthyridin-3-yl |
| 1.13 | NHMe | H | H | H | 3-azabicyclo[3.1.0]hexyl-NH₂ | 1,5-naphthyridin-3-yl N-oxide |
| 1.14 | NHMe | H | H | H | (3R)-3-aminopyrrolidin-1-yl | 1,5-naphthyridin-3-yl N-oxide |
| 1.15 | NHMe | H | H | H | (3S)-3-aminopyrrolidin-1-yl | pyrido[2,3-b]pyrazin-7-yl |
| 1.16 | NHMe | H | H | H | 3-azabicyclo[3.1.0]hexyl-NH₂ | pyrido[2,3-b]pyrazin-7-yl |

-continued

Table of Formula I' compounds where L = S

| Cmpd ID | R8 | Rx | Ry | Rz | R4 | R2 |
|---|---|---|---|---|---|---|
| 1.17 | NHMe | H | H | H | azetidine-N-yl with 3-OH | [1,5]naphthyridine N-oxide |
| 1.18 | NHMe | H | H | H | pyrrolidine with CH2NH2 | [1,5]naphthyridine N-oxide |
| 1.19 | NHMe | H | H | H | N-methyl-3-azabicyclo[3.1.0]hexane with NH2 and C(O)NH2 | [1,5]naphthyridine N-oxide |
| 1.20 | NHMe | H | H | H | azetidine-N-yl with 3-CH2NH2 | [1,5]naphthyridine N-oxide |
| 1.21 | NHMe | H | H | H | azetidinyl-CH2-NHC(O)-(1-methyl-3-CF3-pyrazol-4-yl) | [1,5]naphthyridine N-oxide |
| 1.22 | NHMe | H | H | H | 3-azabicyclo[3.1.0]hexane with NH2 | 5-(N,N-dimethylsulfamoyl)pyridin-3-yl |

Table of Formula I' compounds where L = S

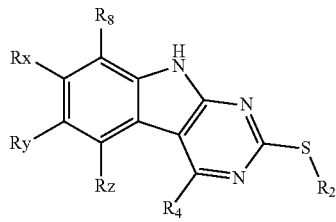

| Cmpd ID | R8 | Rx | Ry | Rz | R4 | R2 |
|---|---|---|---|---|---|---|
| 1.23 | NHMe | H | H | H | 3-amino-3-azabicyclo[3.1.0]hexan-6-amine | 1,5-naphthyridine N-oxide |
| 1.24 | NHMe | H | H | H | 3-amino-3-azabicyclo[3.1.0]hexan-6-amine | 1,5-naphthyridine |
| 1.25 | NHMe | H | H | H | 5-azaspiro[2.4]heptan-1-amine | 1,5-naphthyridine |
| 1.26 | NHMe | H | H | H | 5-azaspiro[2.4]heptan-1-amine | 1,5-naphthyridine |
| 1.27 | NHMe | H | H | H | 6-azaspiro[2.4]heptan-4-amine (pyrrolidine-cyclopropane) | 1,5-naphthyridine |
| 1.28 | NHMe | H | H | H | octahydro-pyrrolo[3,4-b]pyridine | 1,5-naphthyridine |
| 1.29 | NHMe | H | H | H | 3-aminoazetidine | 1,5-naphthyridine |
| 1.30 | NHMe | H | H | H | 6-amino-6-(hydroxymethyl)-3-azabicyclo[3.1.0]hexane | 1,5-naphthyridine |

-continued

Table of Formula I' compounds where L = S

| Cmpd ID | R8 | Rx | Ry | Rz | R4 | R2 |
|---|---|---|---|---|---|---|
| 1.31 | NHMe | H | H | H | 3-amino-3-azabicyclo[3.1.0]hexane (exo-NH2) | 1,5-naphthyridine 1-oxide |
| 1.32 | NHMe | H | H | H | 3,6-diazabicyclo[3.2.0]heptane | 1,5-naphthyridine 5-oxide |
| 1.33 | NHMe | H | H | H | 3-(1-aminocyclopropyl)azetidine | 1,5-naphthyridine 5-oxide |
| 1.34 | NHMe | H | H | H | 3-aminopiperidine | 1,5-naphthyridine 1-oxide |
| 1.35 | NHMe | H | H | H | 3-amino-4-methylpiperidine | 1,5-naphthyridine 5-oxide |
| 1.36 | NHMe | H | H | H | 3-amino-3-azabicyclo[3.1.0]hexane | N-methylpyridine-3-sulfonamide |
| 1.37 | NHMe | H | H | H | (R)-3-aminopiperidine | 1,5-naphthyridine |

-continued

Table of Formula I' compounds where L = S

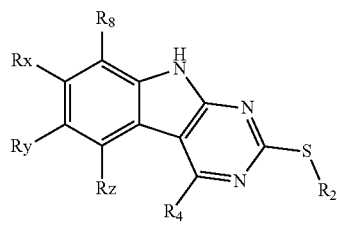

| Cmpd ID | R8 | Rx | Ry | Rz | R4 | R2 |
|---|---|---|---|---|---|---|
| 1.38 | NHMe | H | H | H | pyrrolidine-spirocyclopropyl-NH₂ | 1,5-naphthyridine N-oxide |
| 1.39 | NHMe | H | H | H | pyrrolidine-spirocyclopropyl-NH₂ | 1,5-naphthyridine N-oxide |
| 1.40 | NHMe | H | H | H | aminopyrrolidine-spirocyclopropyl | 1,5-naphthyridine N-oxide |
| 1.41 | NHMe | H | H | H | azabicyclo[3.1.0]hexyl-NH₂ | pyridinyl sulfonamide |
| 1.42 | NHMe | H | H | H | azabicyclo[3.1.0]hexyl-NH₂ | pyridinyl sulfonamide-NH-CH₂CH₂-OH |

Table of Formula I' compounds where L = S
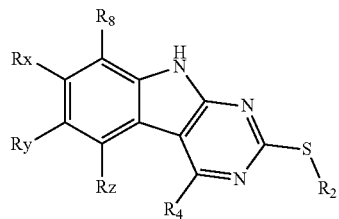
| Cmpd ID | R8 | Rx | Ry | Rz | R4 | R2 |
|---|---|---|---|---|---|---|
| 1.43 | NHMe | H | H | H | 3-amino-bicyclo[3.1.0] pyrrolidinyl | pyrimidin-5-yl |
| 1.44 | NHMe | H | H | H | aminospiro pyrrolidinyl | pyrimidin-5-yl |
| 1.45 | NHMe | H | H | H | 3-aminoazepan-1-yl | 1,5-naphthyridin-3-yl |
| 1.46 | NHMe | H | H | H | piperazin-1-yl | 1,5-naphthyridin-3-yl |
| 1.47 | NHMe | H | H | H | 3,8-diazabicyclo[3.2.1]octan-3-yl | 1,5-naphthyridin-3-yl |
| 1.48 | NHMe | H | H | H | 3-(aminomethyl)pyrrolidin-1-yl | 1,5-naphthyridin-3-yl |

-continued

Table of Formula I' compounds where L = S

| Cmpd ID | R8 | Rx | Ry | Rz | R4 | R2 |
|---|---|---|---|---|---|---|
| 1.49 | NHMe | H | H | H | N-bicyclic-NH₂ | 1,5-naphthyridine N-oxide |
| 1.50 | NHMe | H | F | H | N-bicyclic-NH₂ | 1,5-naphthyridine N-oxide |
| 1.51 | NHMe | H | F | H | N-bicyclic-NH₂ | 1,5-naphthyridine |
| 1.52 | NHMe | H | H | H | N-bicyclic-NH-C(O)-CH(NH₂)CH₃ | 1,5-naphthyridine N-oxide |
| 1.53 | NHMe | H | H | H | pyrrolidin-1-yl-CH₂OH | 1,5-naphthyridine |
| 1.54 | NHMe | H | H | H | piperazinyl-pyrazine | 1,5-naphthyridine |
| 1.55 | NHMe | H | H | H | octahydropyrrolo[3,4-b]pyrrole | 1,5-naphthyridine |
| 1.56 | NHMe | H | H | H | 2,8-diazaspiro[4.5]decane | 1,5-naphthyridine |

-continued
Table of Formula I' compounds where L = S
| Cmpd ID | R8 | Rx | Ry | Rz | R4 | R2 |
|---|---|---|---|---|---|---|
| 1.57 | NHMe | H | H | H | 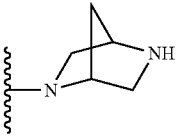 [SMILES: *N1CC2CC1CN2] | 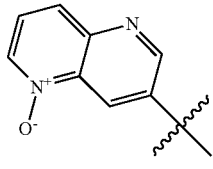 [SMILES: *c1cnc2ccc[n+]([O-])c2c1] |
| 1.58 | NHMe | H | H | Me | 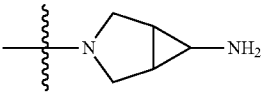 [SMILES: *N1CC2C(N)C2C1] | 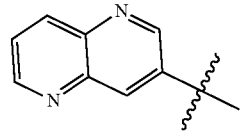 [SMILES: *c1cnc2cccnc2c1] |
| 1.59 | NHMe | H | H | H | 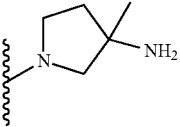 | 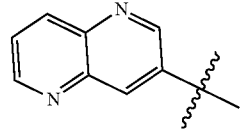 [SMILES: *c1cnc2cccnc2c1] |
| 1.60 | NHMe | H | H | H | 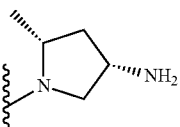 | 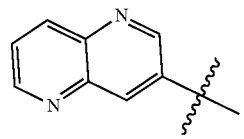 [SMILES: *c1cnc2cccnc2c1] |
| 1.61 | NHMe | H | H | H | 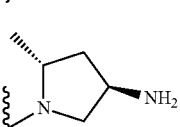 | 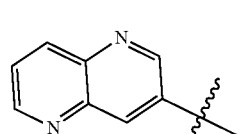 |
| 1.62 | NHMe | H | F | H | 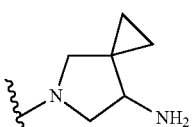 | 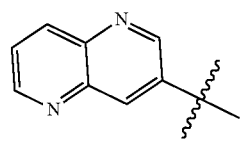 [SMILES: *c1cnc2cccnc2c1] |
| 1.63 | NHMe | H | F | H | 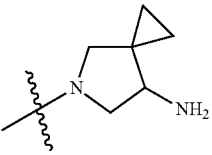 [SMILES: *N1CC(N)C2(CC2)C1] | 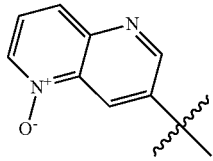 [SMILES: *c1cnc2ccc[n+]([O-])c2c1] |
| 1.64 | NHMe | H | F | H | 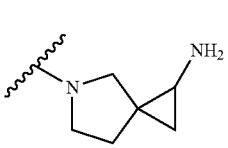 [SMILES: *N1CCC2(CC2N)C1] | 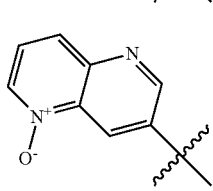 |

Table of Formula I' compounds where L = S

| Cmpd ID | R8 | Rx | Ry | Rz | R4 | R2 |
|---|---|---|---|---|---|---|
| 1.65 | NHMe | H | F | H | N-linked 2-amino-5-azaspiro[2.4]heptane | 1,5-naphthyridine N-oxide |
| 1.66 | NHMe | H | H | H | N-linked 6-amino-3-azabicyclo[3.1.0]hexane | 1,5-naphthyridine N-oxide |
| 1.67 | NHMe | H | H | H | 4-acetylpiperazin-1-yl | 1,5-naphthyridine |
| 1.68 | NHMe | H | H | H | (2S,4S)-4-amino-2-(hydroxymethyl)pyrrolidin-1-yl | 1,5-naphthyridine |
| 1.69 | NHMe | H | H | H | 4-(tetrahydrofuran-2-carbonyl)piperazin-1-yl | 1,5-naphthyridine |
| 1.70 | NHMe | H | H | H | 4-(hydroxy(thiophen-2-yl)methyl)piperidin-1-yl | 1,5-naphthyridine |
| 1.71 | NHMe | H | H | H | N-linked 6-amino-3-azabicyclo[3.1.0]hexane | 1,5-naphthyridine N-oxide |

-continued

Table of Formula I' compounds where L = S

| Cmpd ID | R8 | Rx | Ry | Rz | R4 | R2 |
|---|---|---|---|---|---|---|
| 1.72 | NHMe | H | H | Me | 4-amino-2-azaspiro[3.4] pyrrolidine | 1,5-naphthyridine N-oxide |
| 1.73 | NHMe | H | H | Me | 3-amino-3-azabicyclo[3.1.0]hexane | 1,5-naphthyridine N-oxide |
| 1.74 | NHMe | H | H | H | 3-amino-3-azabicyclo[3.1.0]hexane | quinoline-2-carboxylic acid |
| 1.75 | OMe | H | H | H | 3-amino-3-azabicyclo[3.1.0]hexane | 1,5-naphthyridine |
| 1.76 | OMe | H | H | H | 3-amino-3-azabicyclo[3.1.0]hexane | pyrido[2,3-b]pyrazine |
| 1.77 | OMe | H | H | H | 3-aminoazetidine | 1,5-naphthyridine N-oxide |

Table of Formula I' compounds where L = S

| Cmpd ID | R8 | Rx | Ry | Rz | R4 | R2 |
|---|---|---|---|---|---|---|
| 1.78 | OMe | H | H | H | (pyrrolidin-3-yl-CH-NH₂) | (1,5-naphthyridine N-oxide) |

Example 8

Section D: Synthesis of Formula 1 Compounds where L=O

Example 8a—Synthesis of Tricyclic Cores L=O where $R^8$ is not NHAlkyl

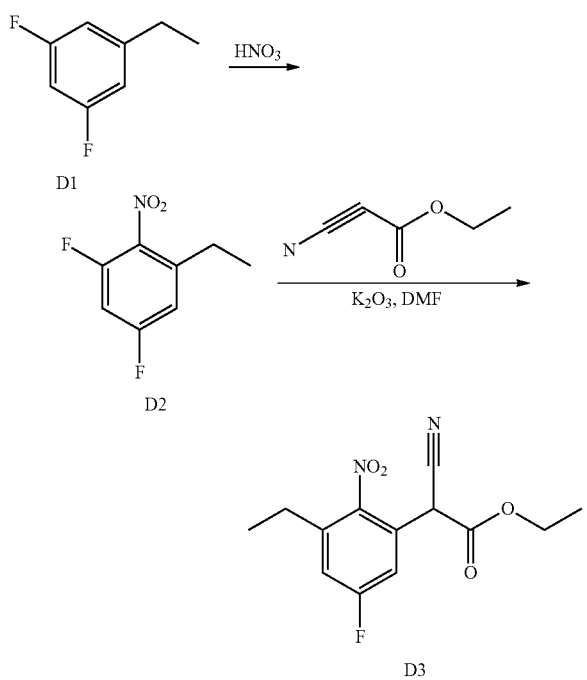

Synthesis of compound D2: To a solution of D1 (40 g, 0.28 mol) in $H_2SO_4$ (200 mL) was added HNO3 (26 g, 0.42 mol) at 0° C. After stirred at 0° C. for 1 h, the mixture was poured into ice water and extracted with ethyl acetate (2×200 mL). The organic layer was dried over $Na_2SO_4$, filtered, concentrated and purified by chromatography on silica gel (petroleum ether/ethyl acetate=15:1) to afford the compound D2 (37 g, yield: 70%) as yellow oil.

$^1$H NMR (400 MHz, CDCl$_3$): δ: 6.93 (s, 1H), 6.91 (s, 1H), 4.33-4.27 (m, 2H), 2.73-2.68 (m, 2H), 1.29-1.25 (t, J=7.6 Hz, 2H).

Synthesis of compound D3: To a solution of 2 (37 g, 0.20 mol) in DMF (200 mL) was added potassium carbonate (54.8 g, 0.40 mol), followed by a portion of ethyl cyano acetate (22.3 g, 0.20 mol). The mixture was stirred at room temperature for 2 h. Then an additional portion of potassium carbonate (54.8 g, 0.40 mol) and a portion of ethyl cyano acetate (22.3 g, 0.20 mol) were added. After the mixture was stirred at room temperature for 4 h, potassium carbonate (27.4 g, 0.2 mol) was added and the mixture was stirred at room temperature for another 12 h. Then the mixture was poured into ice water and extracted with ethyl acetate (2×200 mL). The organic layer was dried over $Na_2SO_4$, filtered, concentrated and purified by chromatography on silica gel (petroleum ether/ethyl acetate=5:1) to afford the compound D3 (25 g, yield: 67%) as yellow solid.

$^1$H NMR (400 MHz, CDCl$_3$): δ: 7.33-7.04 (dd, J=4.4, 2.4 Hz, 1H), 7.16-7.13 (dd, J=4.4, 2.4 Hz, 1H), 5.06 (s, 1H), 4.32-4.27 (m, 2H), 2.74-2.68 (m, 2H), 1.35-1.26 (m, 6H).

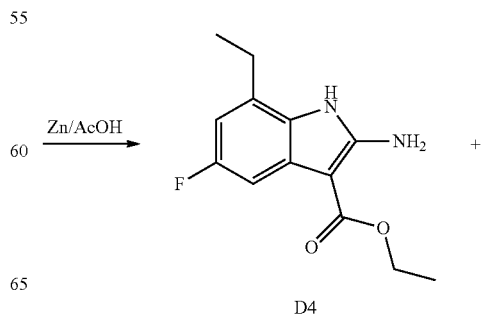

-continued

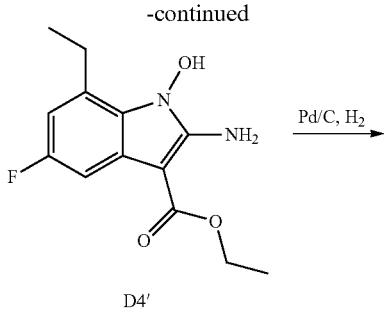

D4'

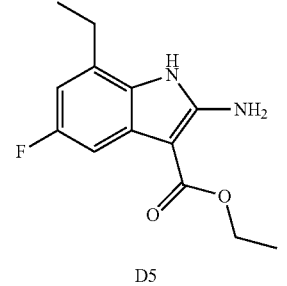

D5

-continued

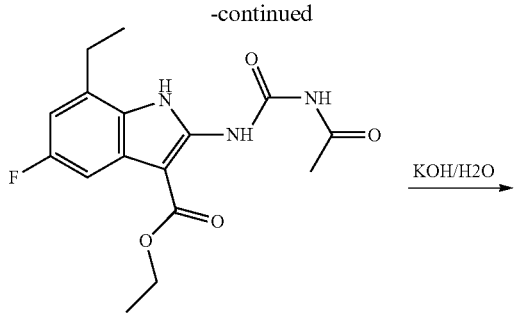

D6

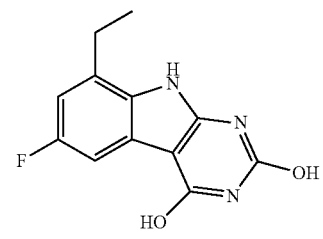

D7

Synthesis of compound D4 and D4': To a solution of D3 (22 g, 79 mmol) in toluene (100 mL) and acetic acid (100 mL) was added zinc powder (30 g, 0.46 mol) and the mixture was stirred at 75° C. for 2 h. Then another Zn powder (10 g, 0.15 mol) was added. After stirred at 75° C. for more 0.5 h, the mixture was cooled to room temperature, filtered and poured into ice water. 2N NaOH was added to adjust the pH to 8-9 and the resultant mixture was extracted with ethyl acetate (2×200 mL). The organic layer was dried over $Na_2SO_4$, filtered, concentrated and purified by chromatography on silica gel (petroleum ether/ethyl acetate=5:1) to afford a brown solid, which was recrystallized in petroleum ether/EtOAc (10:1) to give a mixture of compound D4 and D4' (7.2 g, yield: 35%) as brown solid.

Synthesis of compound D5: A solution of mixture of compound D4 and D4' (5.8 g) in EtOH (100 mL)/HOAc (5 mL) was hydrogenated with catalyst of 10% Pd/C (580 mg) for overnight under 50 Psi pressure. The catalyst was filtered off and the filtrate was concentrated to get compound D5 (5.3 g, yield: 93%).

$^1$H NMR (400 MHz, DMSO-$d_6$): δ: 10.75 (s, 1H), 7.08 (dd, J=9.6, 2.4 Hz, 1H), 6.55 (dd, J=10.8, 2.4 Hz, 1H), 6.44 (s, 2H), 4.21 (1 h, J=7.2 Hz, 2H), 2.71 (1 h, J=7.6 Hz, 2H), 1.31 (t, J=6.8 Hz, 3H), 1.20 (t, J=7.6 Hz, 3H). LCMS [mobile phase: 30%-95% Acetonitrile-0.02% NH4Ac in 6 min, finally under these conditions for 0.5 min.] purity is >95%, Rt=2.953 min; MS Calcd.: 250; MS Found: 251 ([M+1]).

To a stirred suspension of compound D5 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification. LC-MS: M+1: 453.21.

To a stirred suspension of D6 (9.13 g, 20.0 mmoL) in water/EtOH (75 mL/25 mL) was added a KOH solution in 20 mL of water at r.t. After addition, the resulting mixture was reflux for 4 h. TLC showed the reaction was completed, then the reaction was cooled to r.t., acidified with 1M HCl a 1 h. until pH=5, the precipitate was collected by filter, washed with water (200 mL×1) then ethyl acetate (200 mL×1) to give the product D7 as a pale yellow solid (5.90 g, 87.1% yield). TLC: $R_{f=0.05}$ (silica gel, methanol:DCM=1:10, v/v). LC-MS: M-1: 248.10

$^1$H NMR (400 MHz, DMSO-$d_6$): δ: 11.44 (s, 1H), 10.75 (s, 1H), 7.22 (s, 1H), 7.08 (dd, J=9.6, 2.4 Hz, 1H), 6.55 (dd, J=10.8, 2.4 Hz, 1H), 2.70 (1 h, J=7.6 Hz,

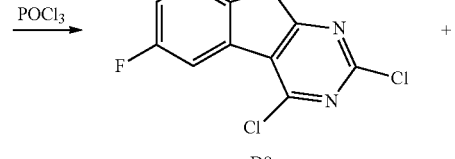

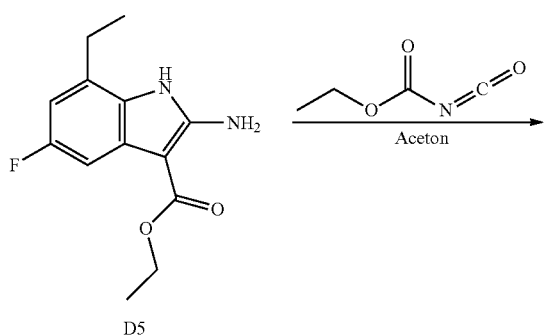

D5

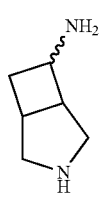

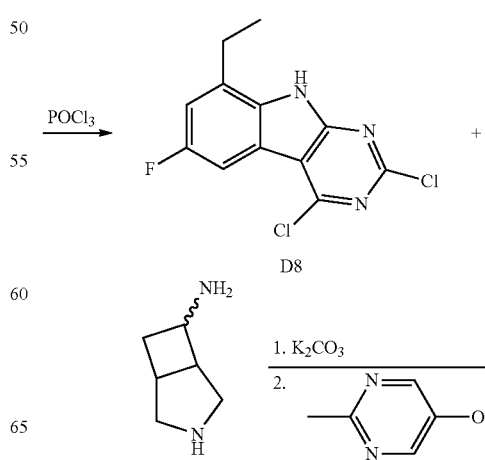

D8

341
-continued

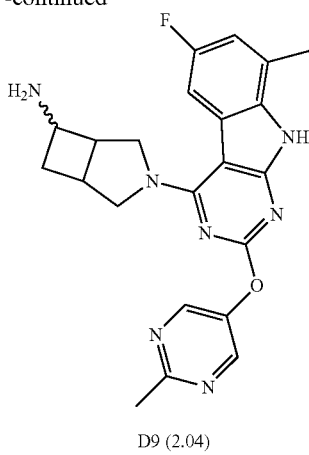

D9 (2.04)

Compound D7 (2 g, 8.06 mmol) was placed with a solution of POCl$_3$ (50 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D8 (2.1 g, 95% yield) as a yellow solid. LC-MS: M+1: 285.01

To a stirred solution of compound D8 (250 mg, 0.88 mmol) in 2 mL of NMP at 110° C. was added (R)-tert-butyl 5-azaspiro[2.4]heptan-7-ylcarbamate (98 mg, 0.88 mmol) and K$_2$CO$_3$ (7 mg, 0.05 mmol). After the completion of the reaction in 10 minutes, the reaction mixture was sealed and placed in Microwave at 180° C. for 10 minutes. The desired product was obtained by HPLC purification to give D9 (115 mg, 30%) as a white solid. LC-MS: M+1: 434.25.

$^1$H NMR (300 MHz, DMSO-d$_6$): δ: 11.44 (s, 1H), 10.75 (s, 1H), 7.22 (s, 1H), 7.08 (dd, J=9.6, 2.4 Hz, 1H), 6.55 (dd, J=10.8, 2.4 Hz, 1H), 2.70 (q, J=7.6 Hz, 2H), 2.64 (m, 2H), 2.62 (m, 2H), 2.01-2.41 (m, 4H), 1.22 (t, J=7.6 Hz, 3H).

342
Example 8b

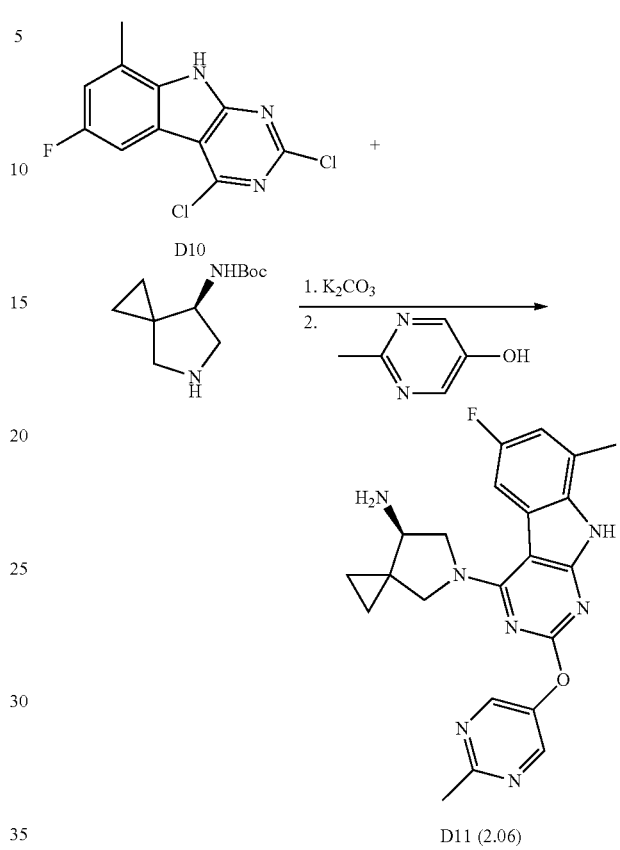

Synthesis of compound D11 (2.06): The subtitle compound was synthesised using the same method described for compound D9 starting with 2,4-dichloro-6-fluoro-8-methyl-9H-pyrimido[4,5-b]indole and (R)-tert-butyl 5-azaspiro[2.4]heptan-7-ylcarbamate. LC-MS: M+1 : 434.25.

$^1$H NMR (300 MHz, DMSO) δ (ppm): 11.75 (s, 1H), 8.72 (s, 2H), 8.09 (br s, 3H), 7.01 (d, J=11.2, 1H), 6.31 (d, J=9.7, 1H), 4.40 (d, J=9.9, 1H), 4.32 (dd, J=7.6, 4.5, 1H), 4.03 (d, J=12.3, 1H), 3.50 (d, J=9.8, 2H), 2.67 (s, 3H), 2.05 (s, 3H), 1.09 (m, 1H), 0.81 (br m, 3H).

Table of Formula I' Compounds Where L is O and R8 is not NHCH$_3$

| Compd ID | L-R2 | R4 | Rz | Ry | Rx | R8 |
|---|---|---|---|---|---|---|
| 2.1 | 2-methylpyrimidin-5-yloxy | 3-azabicyclo[3.1.0]hexan-6-ylamino pyrrolidinyl | H | F | H | NHNHCH$_3$ |

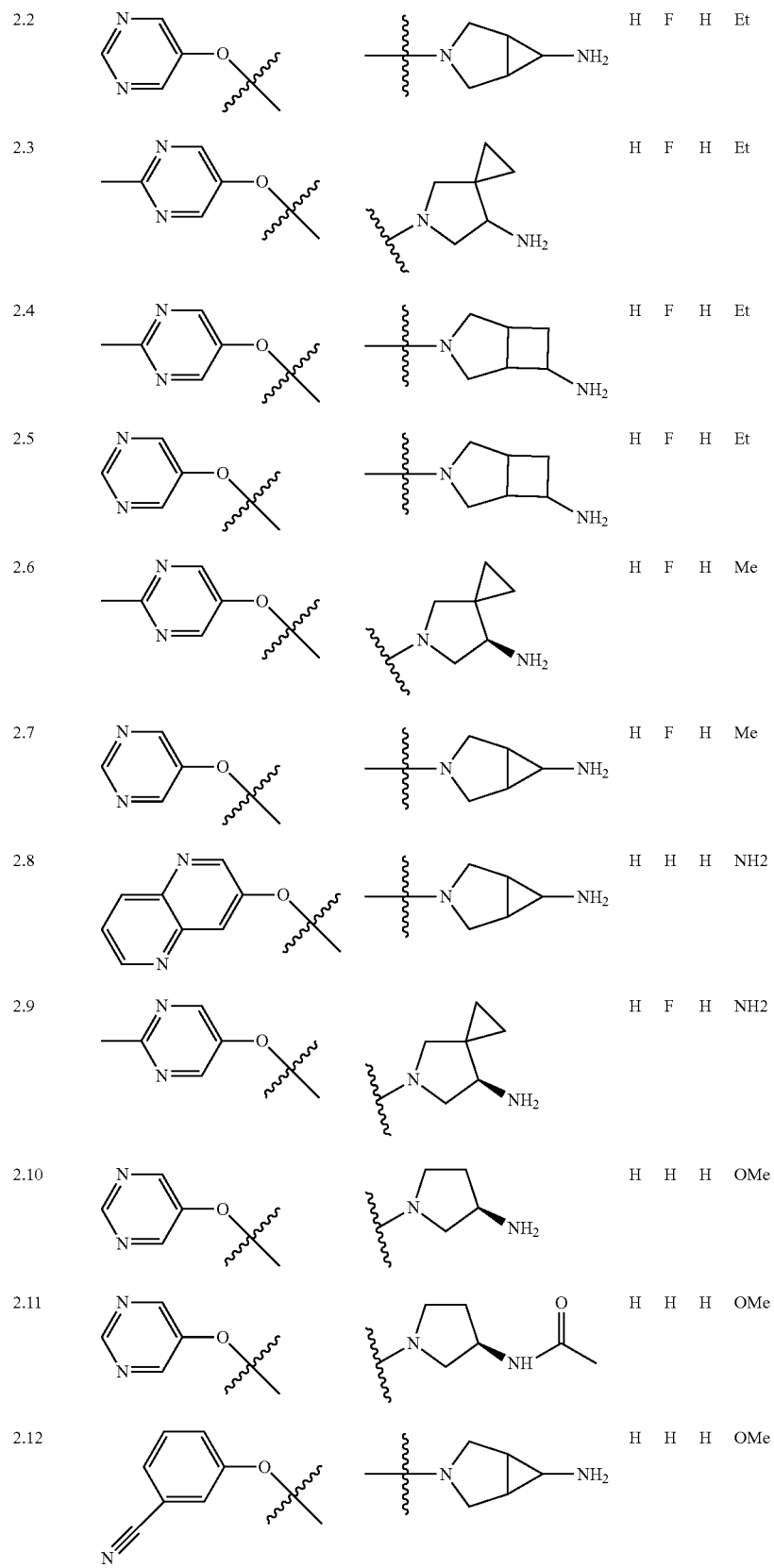

-continued
| | | | | | | | |
|---|---|---|---|---|---|---|---|
| 2.13 | pyrimidin-5-yloxy | azabicyclo-NH2 | H | H | H | OMe | |
| 2.14 | 1,5-naphthyridin-3-yloxy | azabicyclo-NH2 | H | H | H | OMe | |
| 2.15 | 3-cyanophenoxy | azabicyclo-NH2 | H | H | H | OMe | |
| Cmpd ID | |
|---|---|
| 2.160 | 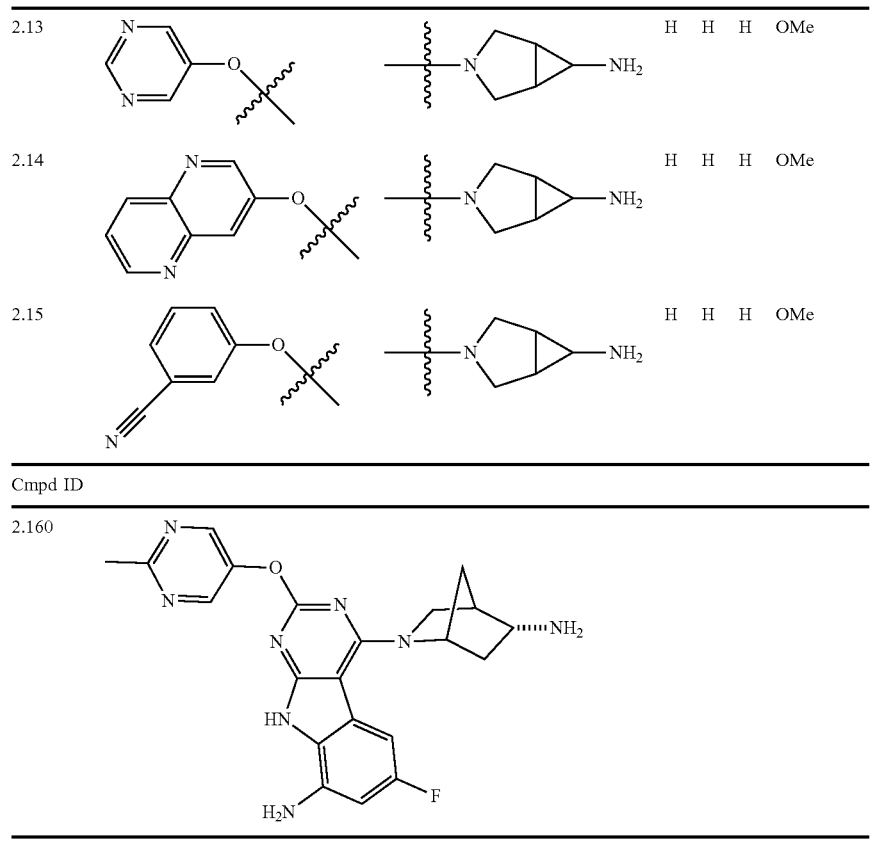 |
Example 9
Synthesis of Formula 1 compounds where L=O and R$^8$ is NHalkyl
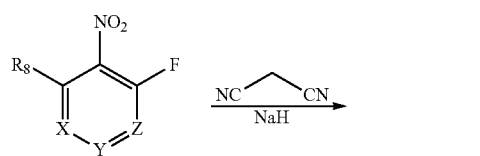
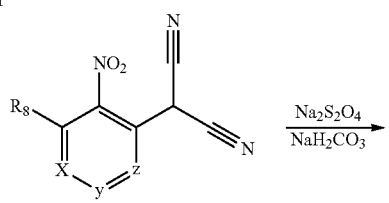
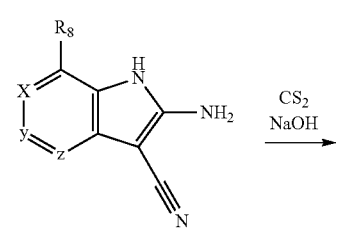
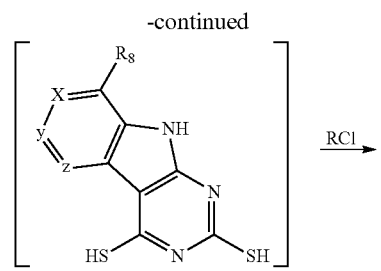
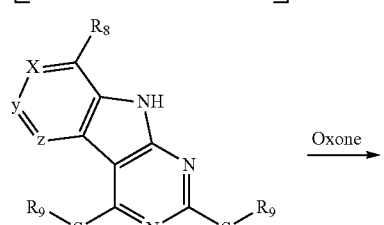
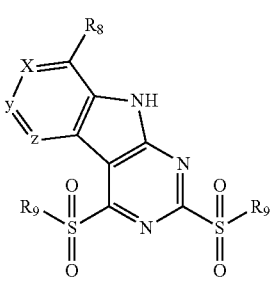

General Scheme for the Bis-Sulfone Route:

Example 9a

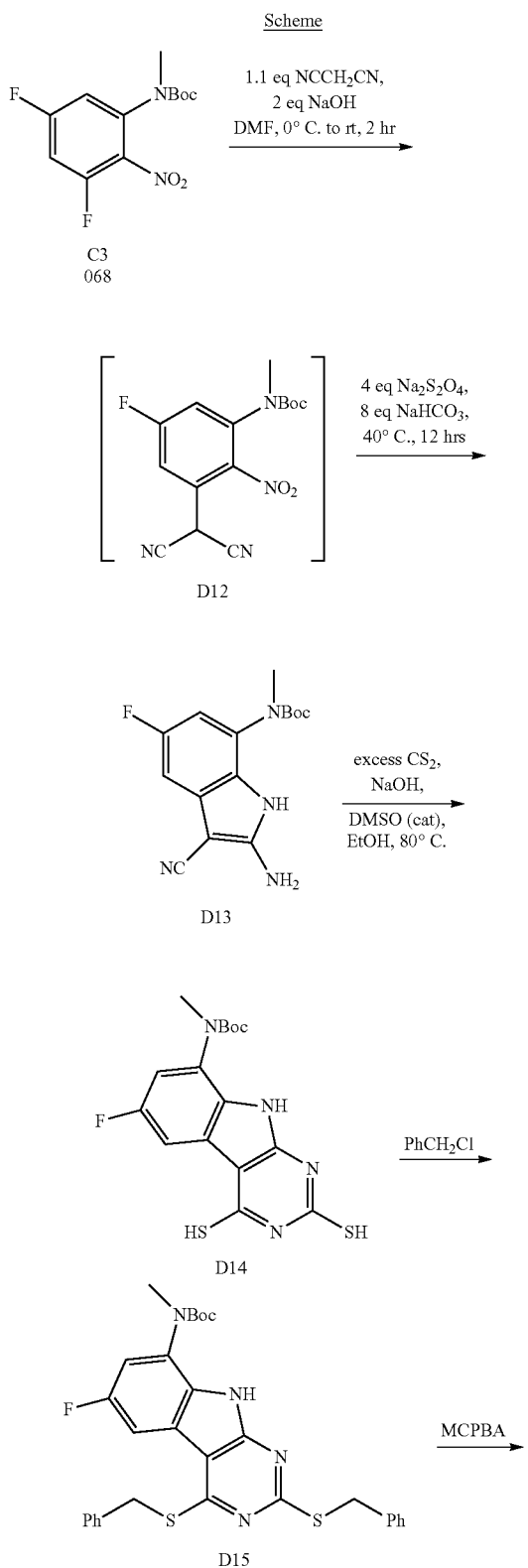

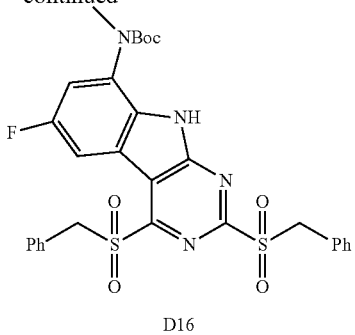

Tert-butyl 2-amino-3-cyano-5-fluoro-1H-indol-7-yl(methyl)carbamate (D13)

Crude tert-butyl 3,5-difluoro-2-nitrophenyl(methyl)carbamate (C3) (46.12 g, 0.162 mol) was dissolved in DMF (80 ml) and cooled in an ice-water bath. To it was added malononitrile (11.8 g, 179 mmol) followed by the addition of the NaOH solution (12.98 g, 325 mmol) in water (20 ml). After the exothermic reaction mixture was stirred for one hour, the ice-water bath was removed and the reaction was stirred for another one hour. It was then diluted with DMF (80 ml) and water (80 ml), and the atmosphere was displaced with argon. Sodium bicarbonate (109 g, 1.3 mol) followed by sodium hydrosulfite (123 g, 649 mmol) was added. The mixture was well stirred under argon at 40° C. for 12 hours (Additional sodium hydrosulfite could be added if the reaction took longer time to complete). After the reaction was cooled down to room temperature, it was diluted with EtOAc (100 ml) and then filtered through a fritted glass funnel. The solids were washed with EtOAc/hexane (1:1, 400 ml). The aqueous layer was separated, and the organic layer was extracted with 10% buffer 7 solution (3×100 ml). The combined aqueous layers were back extracted with EtOAc/hexane (1:1, 200 ml). The combined organic phases was washed with 5% $K_2CO_3$ solution (300 ml). The extractions were then dried over sodium sulfate and concentrated by rotary evaporation to afford the crude compound (D13) as brown color solid (32.6 g, 66%). LC-MS: M+1: 305.16.

$^1$H NMR (DMSO, 300 MHz): δ=10.77 (s, 1H), 6.84-6.80 (m, 1H), 6.69 (s, 2H), 6.69-6.66 (m, 1H), 3.14 (s, 3H), 1.33 (s, 9H).

Tert-butyl 2,4-bis(benzylthio)-6-fluoro-9H-pyrimido[4,5-b]indol-8-yl(methyl)carbamate (D15)

Crude tert-butyl 2-amino-3-cyano-5-fluoro-1H-indol-7-yl(methyl)carbamate (D13) (4 g, 13.14 mmol), sodium hydroxide (756 mg, 18.9 mmol), and EtOH (40 ml) were added in a 350 ml seal tube. The mixture was stirred at 50° C. for 15 mins to dissolve all NaOH and then cooled down to room temperature. After the atmosphere was displaced with argon, the solution was added with carbon disulfide (10 ml) and dimethyl sulfoxide (1 ml). The reaction was stirred at room temperature for 1 hour then refluxed at 80° C. for 42 hours. It was then cooled down to room temperature and placed in an ice-water bath. Water (20 ml) was added followed by the addition of benzyl chloride (3.33 g, 26.27 mmol). The ice-water bath was removed, and the reaction was stirred at ambient temperature for 5 hours. An additional of benzyl chloride (1.66 g, 13.13 mmol) was added, and the resulting solution was stirred at room temperature overnight.

It was diluted with EtOAc (60 ml) and water (100 ml). The resulting solution was partitioned into two layers, and the aqueous phase was removed through an extraction funnel and back extracted with 50 ml of ethyl acetate. The combined organic layers were concentrated by rotary evaporation, and the residue was purified through silica gel column chromatography (15% EtOAc in hexane) to afford the tile compound (D15) as yellow foam (2.65 g, 36%). LC-MS: M+1: 561.05.

$^1$H NMR (CDCl$_3$, 300 MHz): δ=8.72 (s, 1H), 7.66-7.62 (dd, J=8.37, 2.28 Hz, 1H), 7.48-7.27 (m, 10H), 7.05-7.01 (dd, J=10.14, 2.28 Hz, 1H), 4.69 (s, 2H), 4.55 (s, 2H), 3.37 (s, 3H), 1.48 (s, 9H).

Tert-butyl 2,4-bis(benzylsulfonyl)-6-fluoro-9H-pyrimido[4,5-b]indol-8-yl(methyl)carbamate (D16)

The solution of tert-butyl 2,4-bis(benzylthio)-6-fluoro-9H-pyrimido[4,5-b]indol-8-yl(methyl)carbamate (D15) (2.28 g, 4.07 mmol) in DCM (50 ml) was cooled in an ice-water bath and added with 3-chloroperoxybenzoic acid 77% (2.01 g, 8.95 mmol). After the reaction was stirred for 1 hour, the ice-water bath was removed and an additional mCPBA (2.01 g) was added. The resulting solution was stirred at ambient temperature for 7 hours. It was then extract with 5% K$_2$CO$_3$ solution (100 ml), and the aqueous layer was back extracted with DCM (100 ml). The combined organic layers were washed first with 5% K$_2$CO$_3$ (100 ml) then with 5% NaCl solution (50 ml). It was dried over sodium sulfate and concentrated by rotary evaporation to afford the crude title compound (D16) as bright yellow solid (2.54 g, quantitative yield). LC-MS: M+1: 625.05.

$^1$H NMR (CDCl$_3$, 300 MHz): δ=10.07 (s, 1H), 8.49-8.46 (dd, J=8.64, 2.22 Hz, 1H), 7.54-7.51 (m, 1H), 7.38-7.27 (m, 10H), 4.95 (s, 2H), 4.84 (s, 2H), 3.40 (s, 3H), 1.52 (s, 9H).

Scheme:

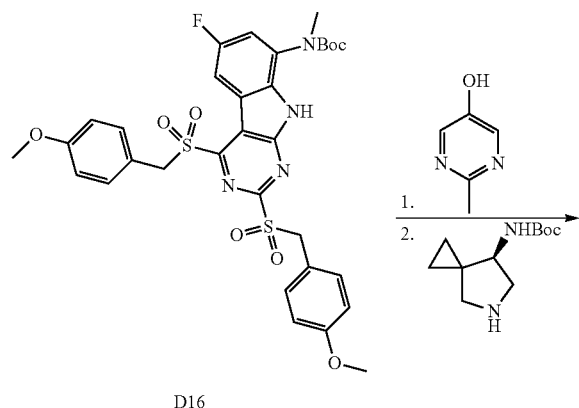

D16

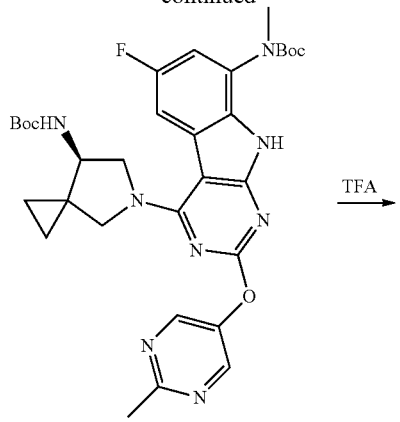

D17

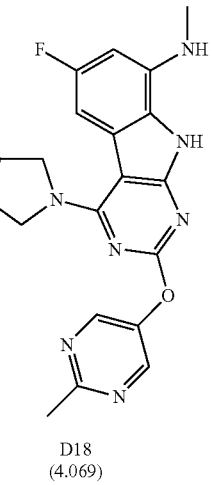

D18
(4.069)

Preparation of D17: The bis-sulfone 2 (11.80 g, 17.23 mmol) was dissolved in NMP (60 mL), followed by adding 2-methylpyrimidin-5-ol 1 (7.59 g, 68.93 mmol). The homogeneous solution was obtained. K$_2$CO$_3$ (9.53 g, 68.93 mmol) was added and the resulting suspension was heated to 100 C for 1 hr, then Boc protected amine (7.32 g, 34.46 mmol) was added and the resulting mixture was heated to 100 C for one more hour, cooled to the room temperature and water (450 mL) was poured into the mixture with stirring. The mixture was cooled to 0 C, filtered and washed the precipitates with water (2×25 mL), dried to give about 12 g of the white solid crude product. The crude solid was dissolved in dichloromethane and silica gel was added. Solvents were removed. Flash chromatography of the residue over silica gel (EtOAc/hexane: 20% to 50% to 90%) to give the pure D17 as a white solid (7.76 g, 75%). LC-MS: M+1: 635.30.

Preparation of D18 (4.069):

The compound D17 was dissolved in 50 mL of TFA and stirred for 1 minute at room temperature. After removal of the solvent, water (50 mL) and EtOH (25 mL) was added. The homogeneous solution was neutralized with 1N NaOH (about 150 mL, PH>10). The gummy solid was formed and separated. The gummy solid was suspended in water (50 mL) and broke the gummy solid into small pieces with spatula. The precipitates were filtered, washed with water twice and dried in the air to give 4.40 gram pure D18 (4.069) as a light white solid (85%, overall 63% from D16). LC-MS: M+1: 435.24.

351
¹H NMR (300 MHz, DMSO) δ (ppm): 11.75 (s, 1H), 8.72 (s, 2H), 8.09 (br s, 3H), 7.01 (d, J=11.2, 1H), 6.31 (d, J=9.7, 1H), 4.40 (d, J=9.9, 1H), 4.32 (dd, J=7.6, 4.5, 1H), 4.03 (d, J=12.3, 1H), 3.50 (d, J=9.8, 2H), 2.85 (s, 3H), 2.67 (s, 3H), 1.09 (m, 1H), 0.81 (br m, 3H).
Example 9b
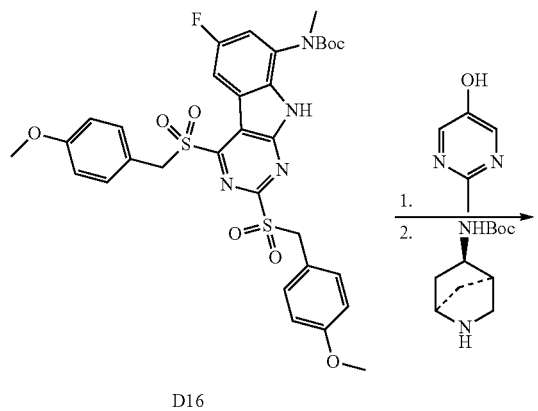
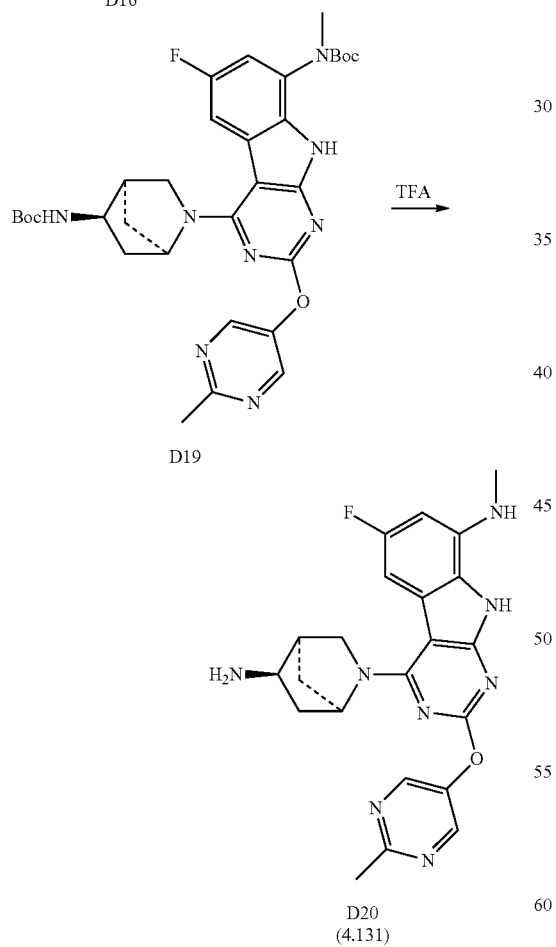
Preparation of D20 (4.131): The subtitle compound was synthesised using the method described in Example 9a above starting with tert-butyl (1R,4R,5R)-2-azabicyclo[2.2.1]heptan-5-ylcarbamate. LC-MS: M+1: 435.24.
352
¹H NMR (500 MHz, DMSO) δ (ppm): 11.75 (brm, 1H), 8.92 (brm, 1H), 8.66 (brs, 1H), 7.44 (d, J=9.7, 1H), 7.04 (d, J=5.2), 6.31 (d, J=12.2, 1H), 5.56 (s, 1H), 4.38 (m, 1H), 4.04 (s, 1H), 3.37 (m, 1H), 3.01 (m, 1H), 2.87 (m, 1H), 2.85 (m, 3H), 2.66 (s, 3H), 2.16 (m, 1H), 1.86 (m, 1H), 1.79 (m, 1H), 1.75 (m, 1H).
Example 9c
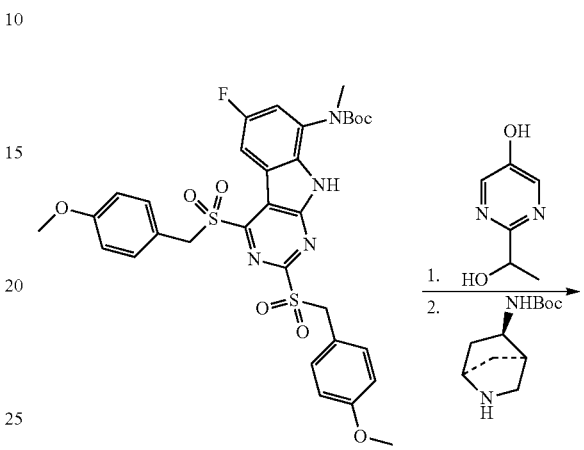
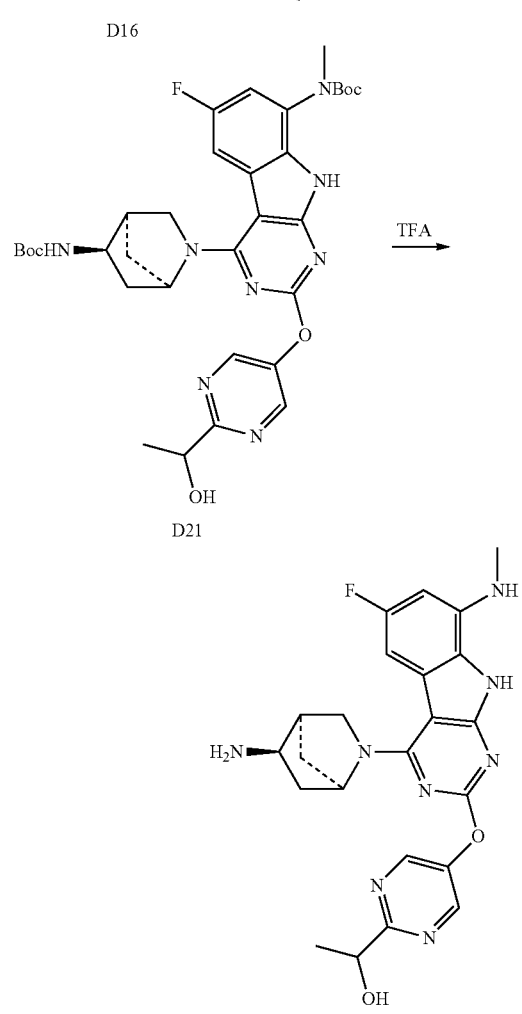

Preparation of D22 (4.408): The subtitle compound was synthesised using the method described above in Example 9a starting with 2-(1-hydroxyethyl)pyrimidin-5-ol. LC-MS: M+1: 465.22.

¹H NMR (300 MHz, DMSO) δ (ppm): 11.75 (s, 1H), 8.72 (s, 2H), 7.01 (d, J=11.2, 1H), 6.31 (d, J=9.7, 1H), 4.82 (brm, 1H), 4.02 (m, 1H), 3.81 (m, 1H), 3.49 (m, 1H), 2.85 (s, 3H), 2.63 (brs, 1H), 2.14 (m, 1H), 1.65-182 (m, 2H), 1.47 (d, 3H), 1.38 (m, 1H).

Example 9d

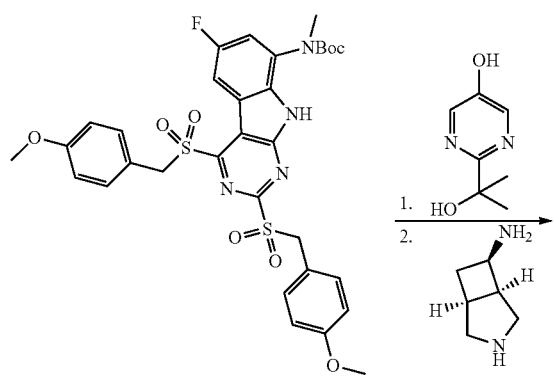

D16

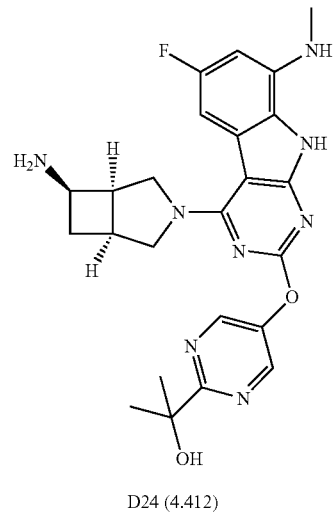

D24 (4.412)

Preparation of D24 (4.412): The subtitle compound was synthesised using the method described in Example 9a above starting with 2-(2-hydroxypropan-2-yl)pyrimidin-5-ol and (6R)-3-azabicyclo[3.2.0]heptan-6-amine. LC-MS: M+1: 479.25.

¹H NMR (500 MHz, DMSO) δ (ppm): 11.35 (brm, 1H), 8.82 (s, 2H), 7.07 (d, J=9.7, 1H), 6.31 (d, J=12.2, 1H), 5.63 (m, 2H), 5.11 (brs, 1H), 4.67 (m, 1H), 3.96 (m, 1H), 3.33-3.53 (m, 6H), 3.01 (m, 1H), 2.85 (s, 3H), 2.70 (m, 1H), 2.51 (m, 1H), 1.55 (s, 6H).

Example 9e

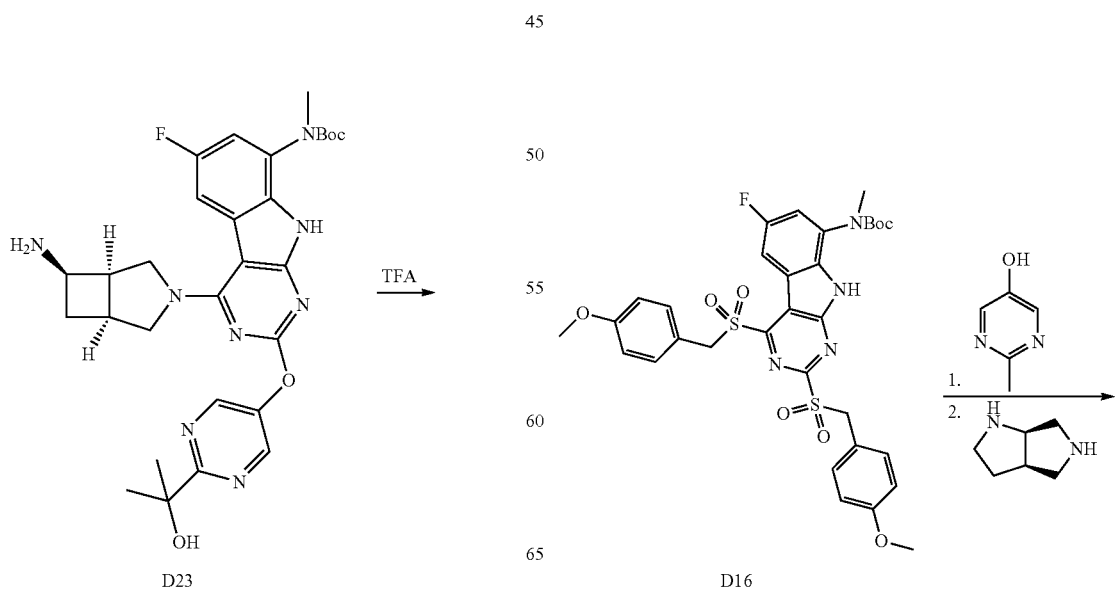

D23                                           D16

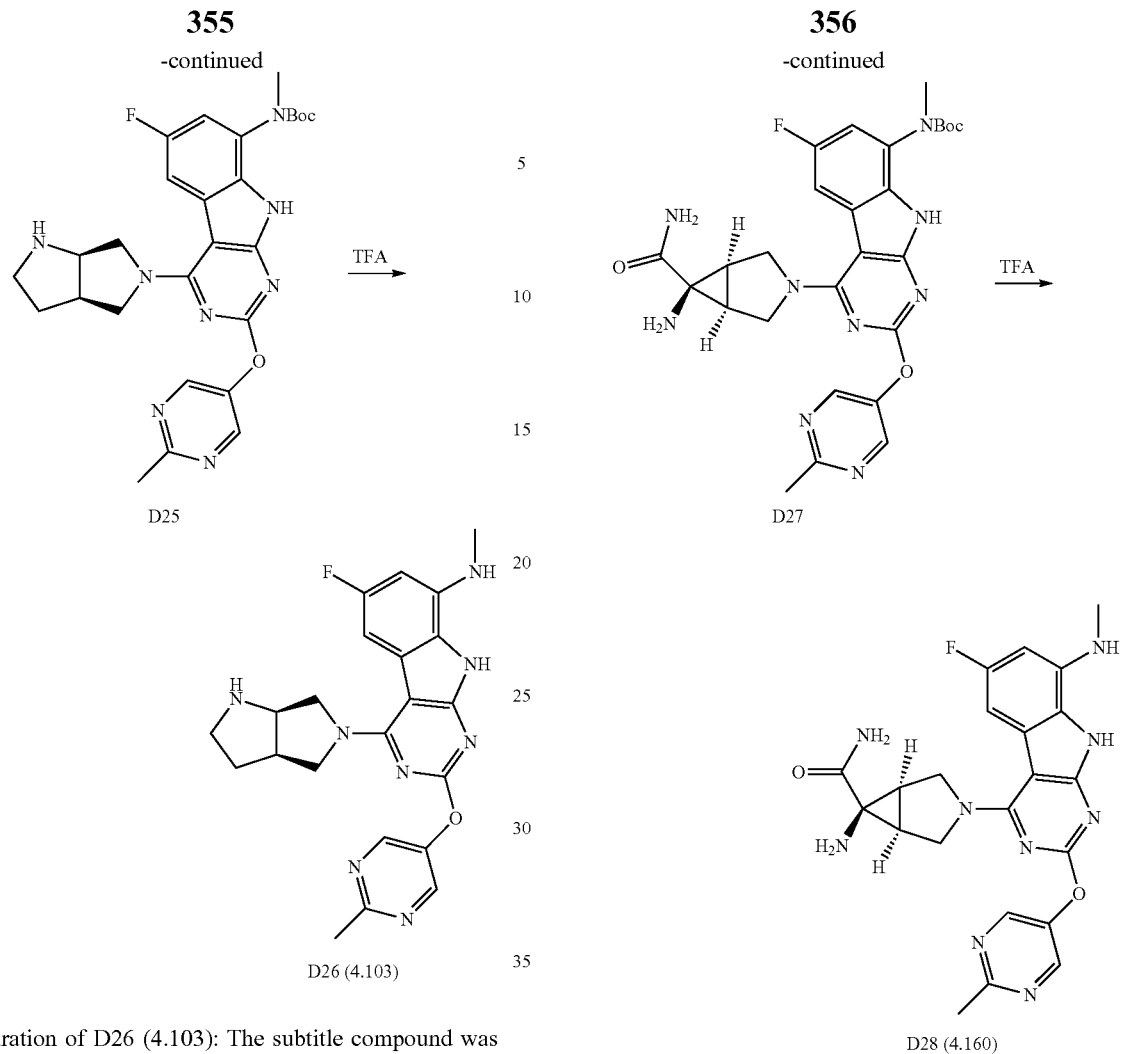

Preparation of D26 (4.103): The subtitle compound was synthesised using the method described in Example 9a above starting with (3aR,6aR)-octahydropyrrolo[3,4-b]pyrrole. LC-MS: M+1: 435.21.

¹H NMR (300 MHz, DMSO) δ (ppm): 8.71 (s, 2H), 6.96 (d, J=11.2, 1H), 6.28 (d, J=11.9, 1H), 5.56 (m, 1H), 3.85 (m, 1H), 3.73 (m, 1H), 3.68 (d, J=11.2, 1H), 3.60 (d, J=11.3, 1H), 2.92 (m, 1H), 2.83 (m, 4H), 2.77 (m, 1H), 2.67 (s, 3H), 1.85 (m, 1H), 1.62 (m, 1H).

Example 9f

Preparation of D28 (4.160): The subtitle compound was synthesised using the method described in Example 9a above starting with (1R,5S,6r)-6-amino-3-azabicyclo[3.1.0]hexane-6-carboxamide. LC-MS: M+1: 435.24.

¹H NMR (300 MHz, DMSO) δ (ppm): 11.05 (s, 1H), 8.72 (s, 2H), 7.21 (s, 2H), 7.01 (d, J=11.2, 1H), 6.11 (d, J=9.7, 1H), 5.01 (s, 2H), 4.03 (d, J=12.3, 1H), 2.95 (s, 3H), 2.81 (m, 2H), 2.75 (m, 2H), 2.67 (s, 3H), 0.85 (br m, 2H).

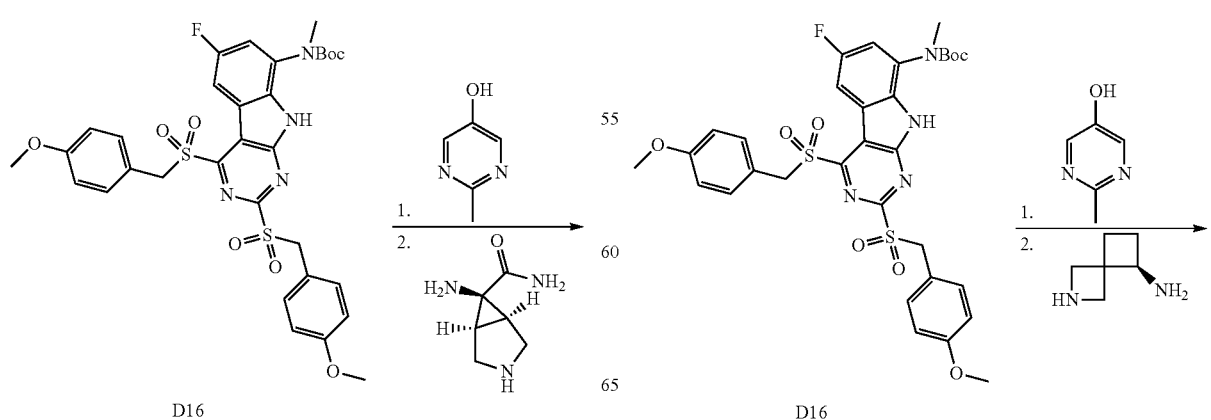

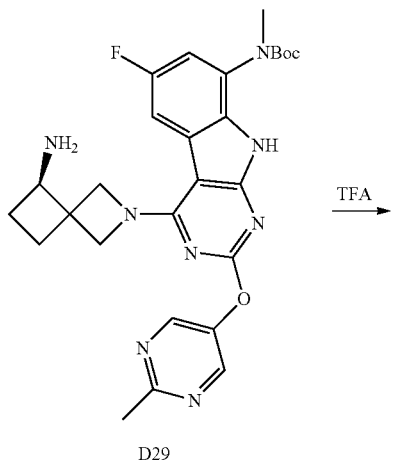

D29

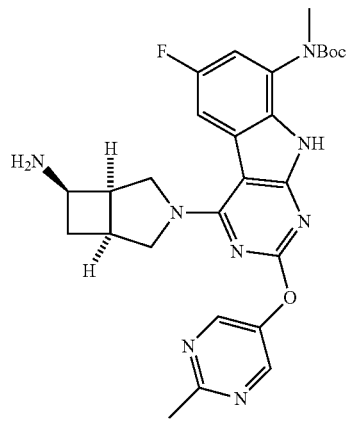

D31

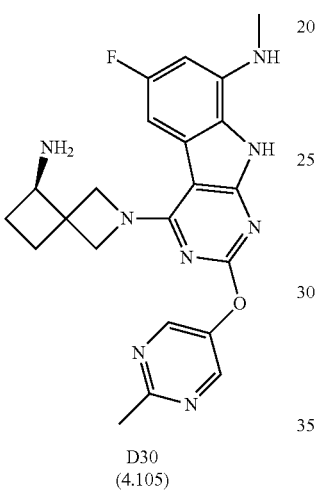

D30
(4.105)

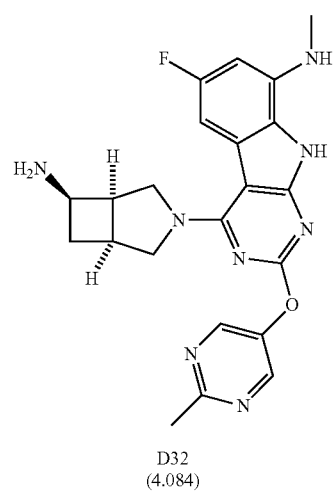

D32
(4.084)

The subtitle compound D30 was synthesised using the same method described for the above compound in Example 9a starting with bis-sulfone and (R)-2-azaspiro[3.3]heptan-5-amine (the diamine was prepared from chiro column separation from commercially available racemics). LC-MS: M+1: 435.21.

Example 9g

The subtitle compound D32 was synthesised using the same method described for the above compound in Example 9a starting with bis-sulfone and (1S,5R,6R)-3-azabicyclo[3.2.0]heptan-6-amine (the diamine was prepared according patent procedure PCT Int. Appl. (1994), WO 9415933 A1 19940721 and the separation from chiro column). LC-MS: M+1: 435.21.

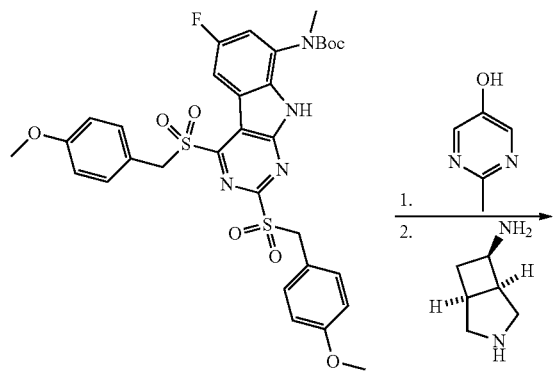

D16

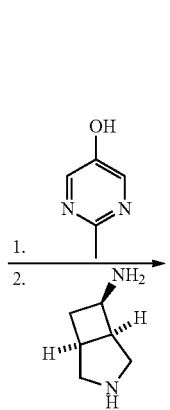

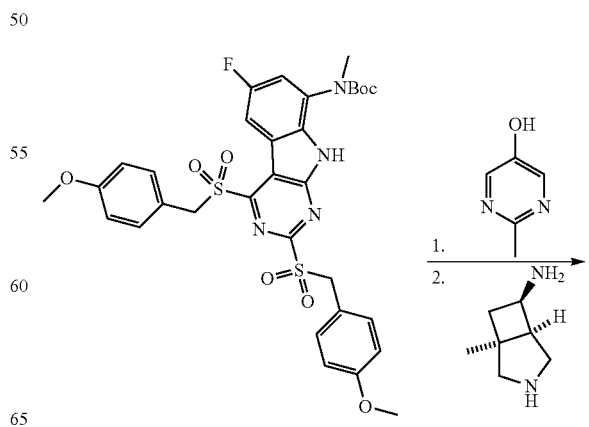

D16

359
-continued

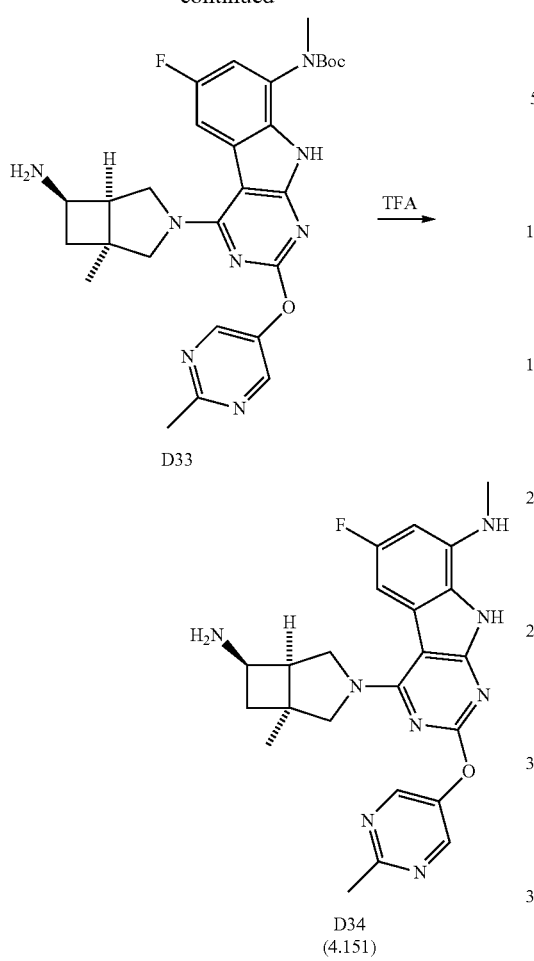

D33

D34
(4.151)

Example 9h

The subtitle compound D34 was synthesized using the same method described for the above compound in Example 9a starting with bis-sulfone and (1S,5R,6R)-1-methyl-3-azabicyclo[3.2.0]heptan-6-amine (the diamine was prepared according patent procedure WO 2001053273 A1 and the separation from chiro column). LC-MS: M+1: 449.25

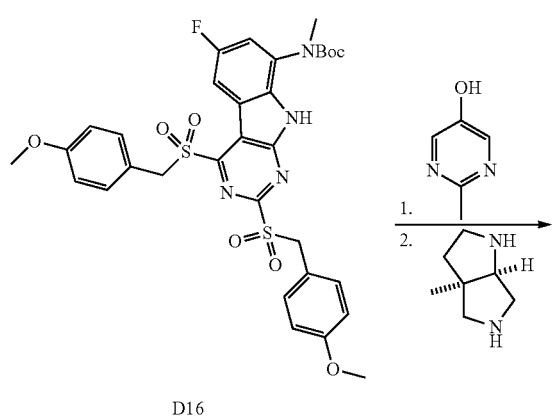

D16

360
-continued

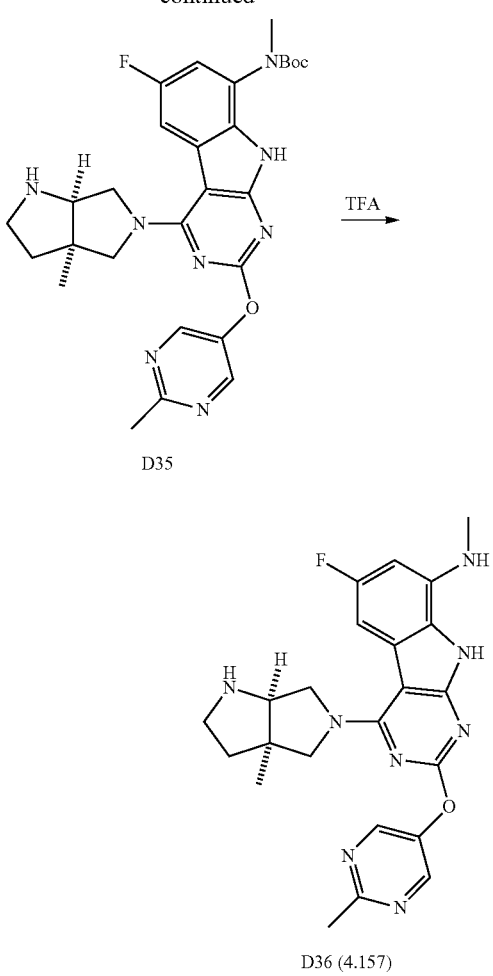

D35

D36 (4.157)

Example 9i

The subtitle compound D36 was synthesized using the same method described for the above compound in Example 9a starting with bis-sulfone and (3aR,6aR)-3a-methyloctahydropyrrolo[3,4-b]pyrrole (the diamine was prepared according patent procedure from U.S. Pat. No. 5,202,337 (A) and the separation from chiro column). LC-MS: M+1: 449.23.

Dichloro Route

General Scheme

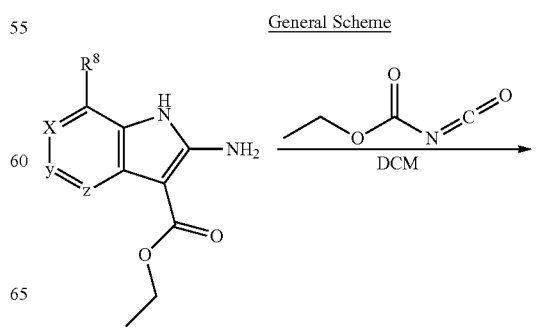

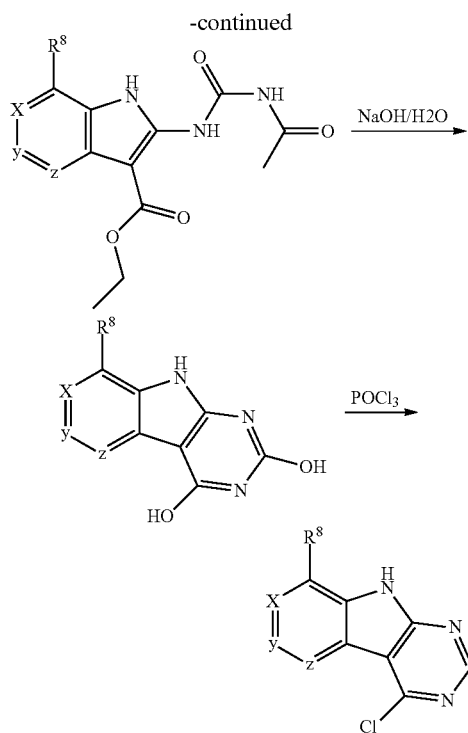

TCL showed the reaction was completed; the reaction mixture was concentrated under vacuum. The residue was partitioned by ethyl acetate (300 mL) and water (500 mL), the organic layer was washed with brine (300 mL×3), dried over $Na_2SO_4$, filtered, and concentrated under vacuum. The crude product was purified by flash chromatography (pet. ether/EtOAc, 100/1 to 50/1, v/v) to give the product D37 as a pale yellow solid (69.0 g, 87.9% yield). LC-MS: M+1: 279

$^1$H-NMR (400 MHz, $CDCl_3$) δ (ppm):=7.37 (5H, m), 6.43 (2H, m), 4.40 (2H, s),2.84 (3H, s).

To a stirred suspension of $K_2CO_3$ (57.6 g, 0.417 mol) and ethyl cyanoacetate (35.4 g, 0.313 mol) in 200 mL DMF was added a solution of compound D37 (58.0 g, 0.208 mol) in 100 mL DMF under $N_2$ protection. After addition, the reaction was stirred at r.t. for two days. TLC showed the SM was consumed, then the reaction mixture was diluted with ethyl acetate (400 mL) and water (1500 mL), the organic layer was separated, the aqueous layer extracted by ethyl acetate (200 mL). The combined organic layer was washed with brine (300 mL×3), dried over $Na_2SO_4$, filtered, and concentrated in vacuum. The crude product was purified by chromatography (pet. ether/EtOAc, 100/1 to 20/1, v/v) to give the product D38 as a pale yellow solid (61.0 g, 79.2% yield). LC-MS: M+1: 371

$^1$H-NMR (400 MHz, $CDCl_3$) δ (ppm): 7.33 (5H, m), 6.92 (1H, d, J=8 Hz), 6.84 (1H, d, J=8 Hz), 5.13 (1H, s), 4.37 (2H, s). 4.30 (2H. dd, J=14.4 Hz), 2.78 (3H. s), 1.35 (3H, t, J=7.2 Hz).

Example 9j

Example of compounds made by the $R^4$ addition first then $R^2$

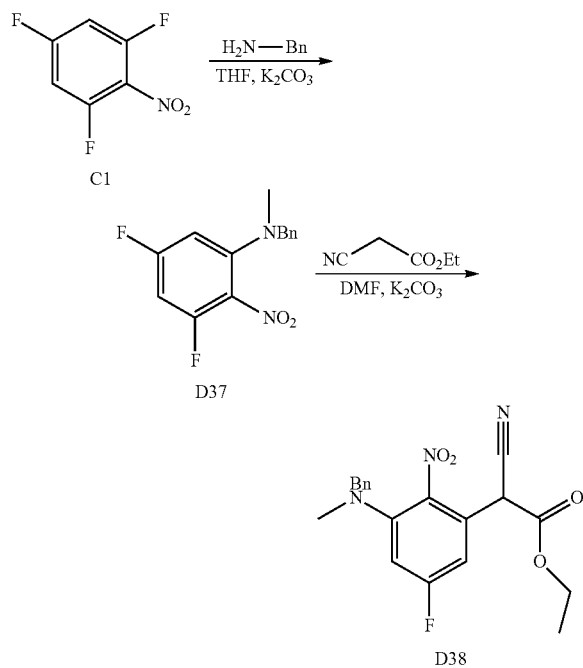

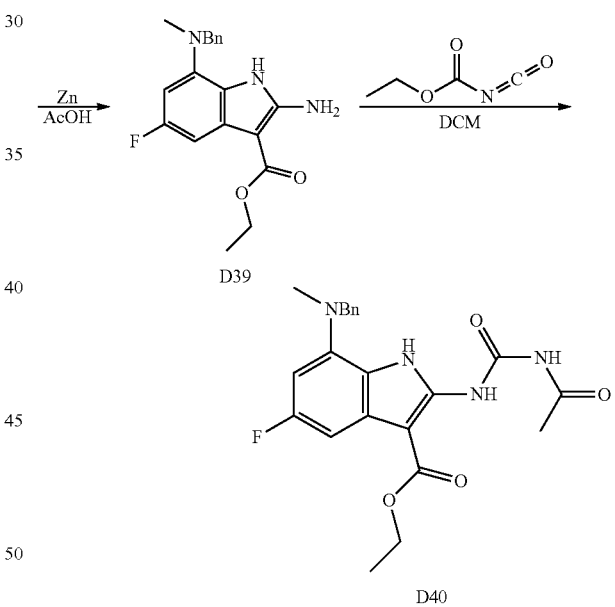

To a stirred suspension of BnNHMe (34.2 g, 0.282 mol) and $K_2CO_3$ (50.6 g, 0.367 mol) in 400 mL of THF was added dropwise a solution of compound 1 (50.0 g, 0.282 mol) in 100 mL THF below 10° C. After addition, the reaction was warmed to r.t. slowly and stirred overnight.

To a stirred solution of compound D38 (61.0 g, 0.164 mol) in 400 mL AcOH cooled on an ice bath was added zinc powder in portions. After addition, the reaction was heated to 60° C. and stirred at this temperature for 5 h. TLC showed the reaction was completed. The reaction mixture was cooled to r.t., filtered, the filtrate was concentrated under vacuum, the residue was dissolved in ethyl acetate (400 mL), basified by saturated $NaHCO_3$ aqueous solution (400 mL), then the organic layer was separated, washed with brine (200 mL×3), dried over $Na_2SO_4$, filtered and concentrated in vacuo to give a dark oil which was purified by chromatography (pet. ether/DCM, 5/1 to DCM, v/v) to give the product D39 as a pale yellow solid (26.0 g, 46.4% yield). LC-MS: M+1: 342

¹H-NMR (400 MHz, CDCl₃) δ (ppm): 8.02 (1H, S), 7.33 (5H, m), 6.52 (1H, d, J=2.4 Hz), 6.49 (1H, d, J=2.4 Hz), 5.73 (2H, s), 4.35 (2H, dd, J=15.2 Hz). 4.19 (2H. s), 2.73 (3H. s), 1.44 (3H, t, J=7.2 Hz).

To a stirred suspension of D39 (16.0 g, 46.9 mmoL) in 200 mL of DCM was added dropwise ethyl isocyanatoformate (resolved in 50 mL of DCM) with an ice bath cooling. After addition, the resulting mixture was stirred at r.t. the SM was dissolved gradually then precipitate was generated from the reaction. 4 hours later, TLC showed the reaction was completed. The reaction mixture was filtered. The filtration was concentrated in vacuo. The residue was suspended in 50 mL of DCM, stirred then filtered. The two batch filter cakes were combined, dried in vacuo to give the product D40 as a pale yellow solid (14.4 g, 67.3% yield). LC-MS: M+1: 457

¹H-NMR (400 MHz, DMSO-d6) δ (ppm): 12.01 (1H, S), 11.12 (1H, S), 11.06 (1H, S), 10.41 (1H, S), 7.33 (5H, m), 6.63 (1H, d, J=2.0 Hz), 6.60 (1H, d, J=2.4 Hz), 4.34 (2H, dd, J=7.2 Hz), 4.28 (2H, s), 4.24 (2H, dd, J=7.2 Hz), 4.14 (2H, dd, J=7.2 Hz), 2.75 (3H. s), 1.37 (3H, t, J=7.2 Hz) 1.27 (3H, t, J=7.2 Hz), 1.22 (3H, t, J=6.8 Hz).

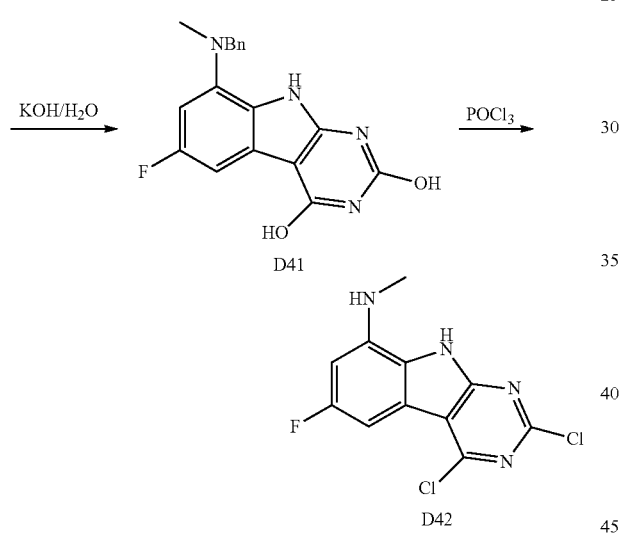

To a stirred suspension of D40 (9.13 g, 20.0 mmoL) in water/EtOH (75 mL/25 mL) was added a KOH solution in 20 mL of water at r.t. After addition, the resulting mixture was reflux for 4 h. TLC showed the reaction was completed, then the reaction was cooled to r.t., acidified with 1M HCl a 1 h. until pH=5, the precipitate was collected by filter, washed with water (200 mL×1) then ethyl acetate (200 mL×1) to give the product D41 as a pale yellow solid (5.90 g, 87.1% yield). LC-MS: M−1: 337.

¹H-NMR (400 MHz, DMSO-d6) δ (ppm): 7.25 (5H, m), 7.01 (1H, dd, J=8.8 Hz), 6.35 (1H, d, J=12.0 Hz), 4.45 (2H, s), 2.76 (3H. s).

Compound D41 (2 g, 5.75 mmol) was placed with a solution of POCl₃ (100 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D42 (1.6 g, 98% yield) as a yellow solid. LC-MS: M+1: 286.02

Example 9k

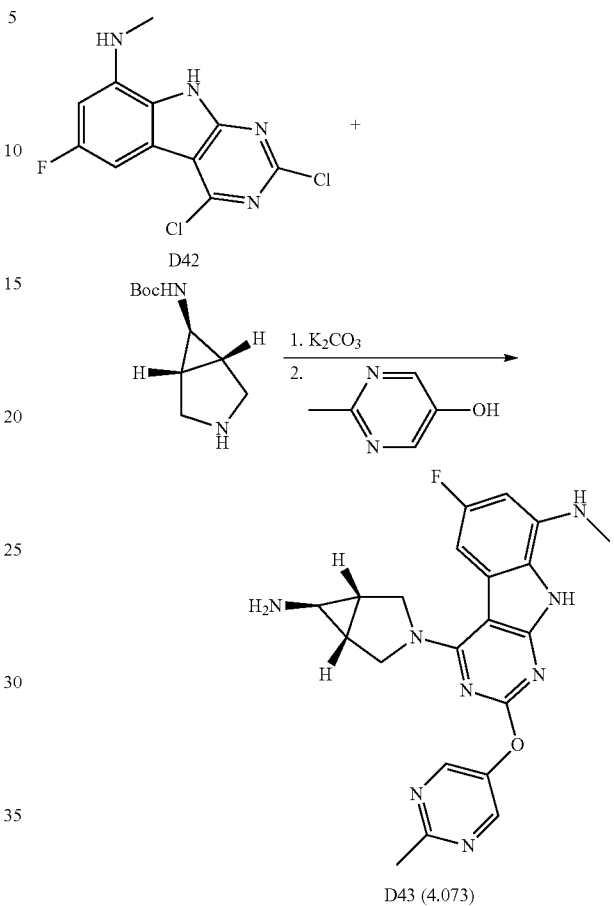

To a stirred solution of compound D42 (250 mg, 0.87 mmol) in 5 mL of NMP at 110° C. was added (R)-tert-butyl 5-azaspiro[2.4]heptan-7-ylcarbamate (175 mg, 0.88 mmol) and K₂CO₃ (7 mg, 0.05 mmol). After the completion of the reaction in 10 minutes, the reaction mixture added to a solution of 2-methylpymiridin-5-ol (90 mg, 0.90 mmol) in a microwave tube. The reaction mixture was sealed and placed in Microwave at 220° C. for 10 minutes. The desired product was obtained by HPLC purification to give D43 (90 mg, 25%) as a white solid. LC-MS: M+1: 421.18.

Example 9l

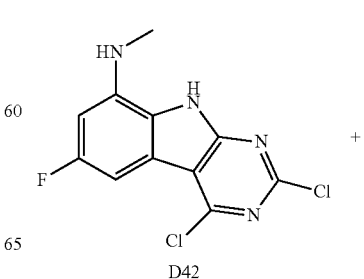

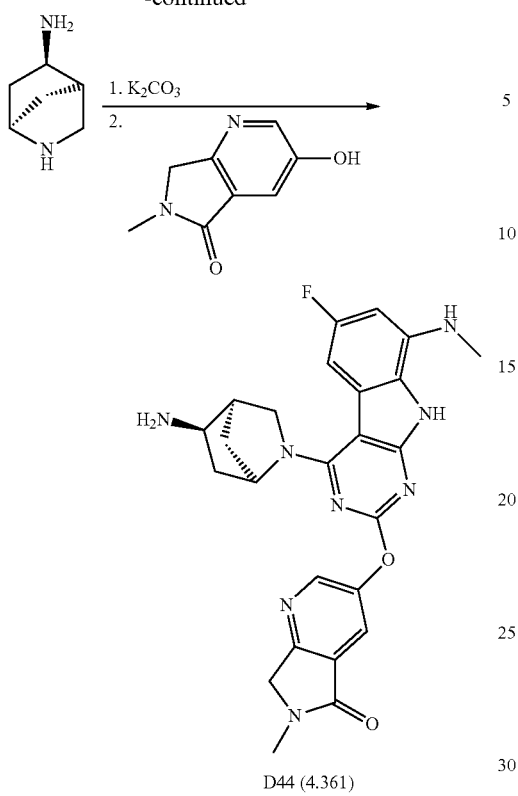

D44 (4.361)

The subtitle compound D44 was synthesized using the method described in Example 9j above starting with (1R,4R,5R)-2-azabicyclo[2.2.1]heptan-5-amine and 3-hydroxy-6-methyl-6,7-dihydro-5H-pyrrolo[3,4-b]pyridin-5-one. LC-MS: M+1: 489.22.

Example 9m

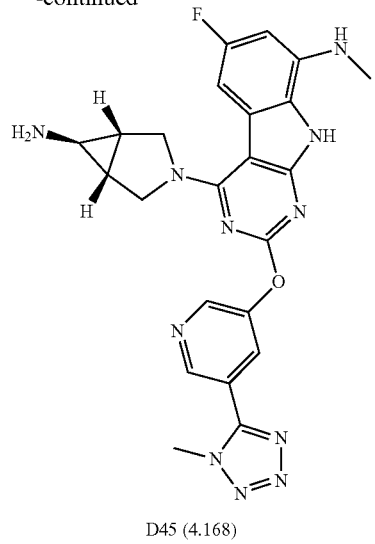

D45 (4.168)

The subtitle compound D45 was synthesized using the method described in Example 9j above starting with tert-butyl 3-azabicyclo[3.1.0]hexan-6-ylcarbamate and 5-(1-methyl-1H-tetrazol-5-yl)pyridin-3-ol. LC-MS: M+1:488.20.

Example 9n

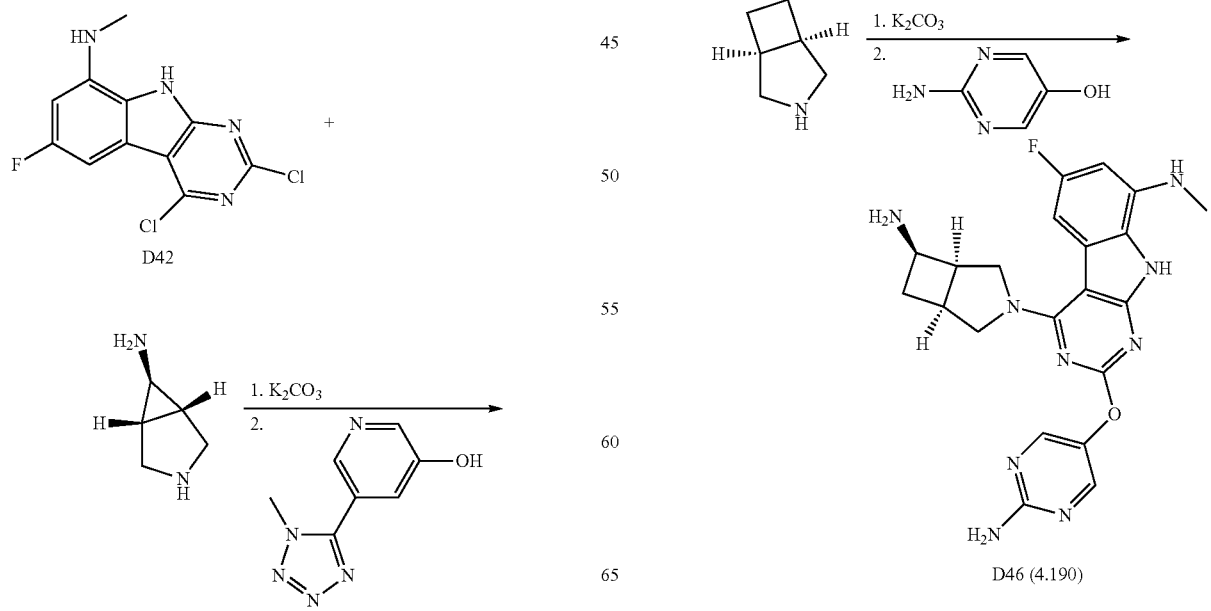

D46 (4.190)

The subtitle compound D46 was synthesized using the method described in Example 9j starting with (6R)-3-azabicyclo[3.2.0]heptan-6-amine and 2-aminopyrimidin-5-ol. LC-MS: M+1: 436.20.

Example 9o

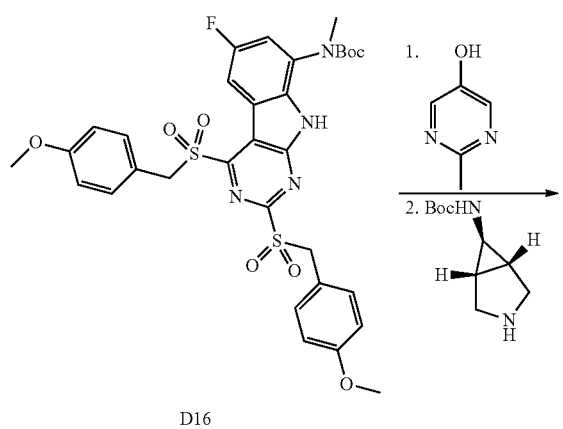

D16

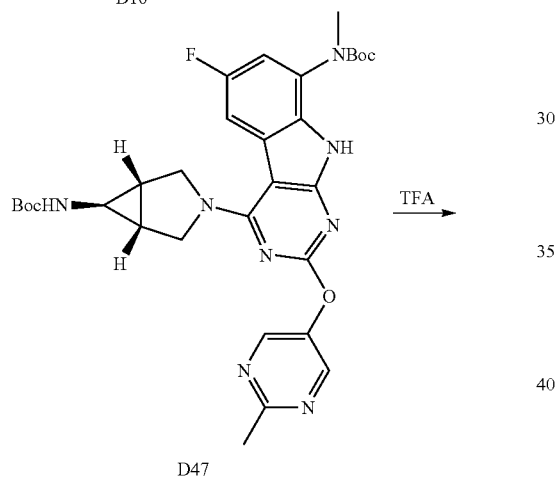

D47

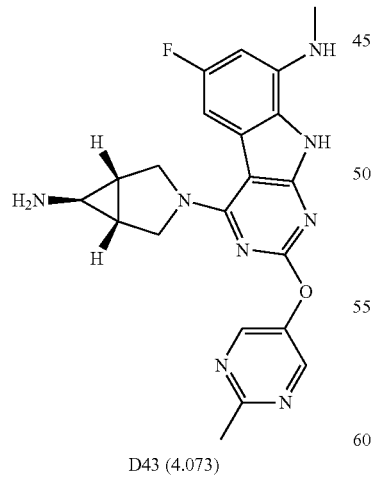

D43 (4.073)

The subtitle compound D43 was synthesized using the same method described for the above compound D18 starting with bis-sulfone and tert-butyl 3-azabicyclo[3.1.0]hexan-6-ylcarbamate. LC-MS: M+1: 421.18.

Example 9p

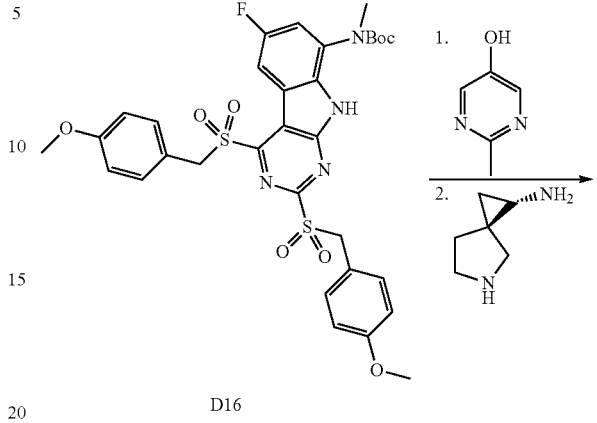

D16

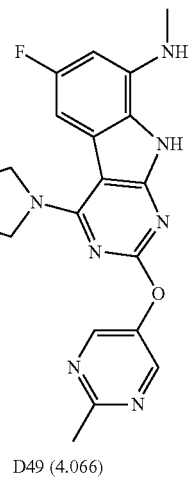

D48

D49 (4.066)

The subtitle compound D49 was synthesised using the same method described for the above compound in Example 9a starting with bis-sulfone and (1R)-5-azaspiro[2.4]heptan-1-amine. LC-MS: M+1:435.23.

369
Example 91 h

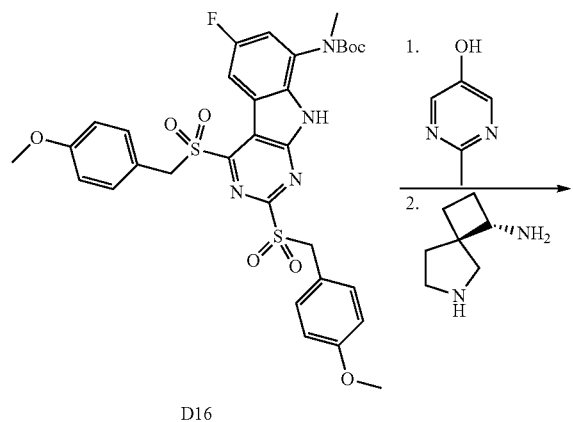

D16

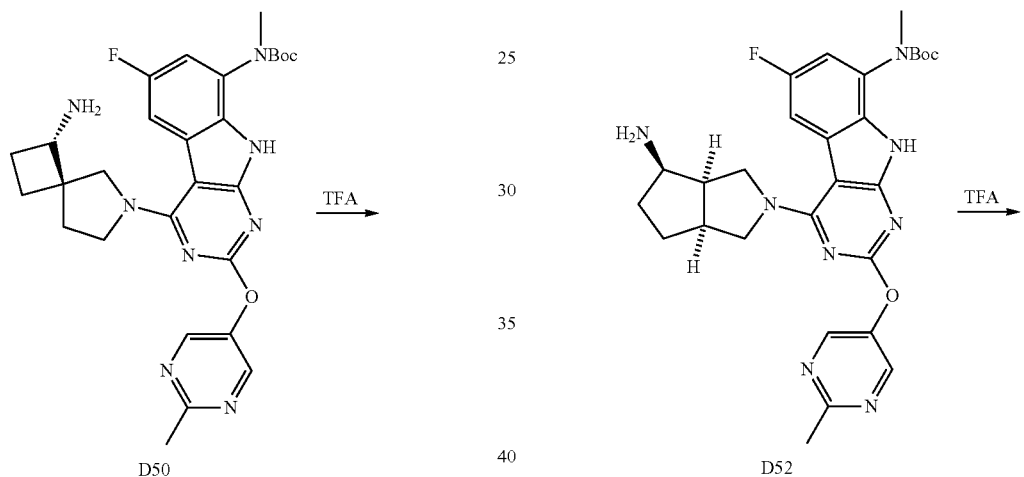

D50

D51 (4.117)

370
Example 9r

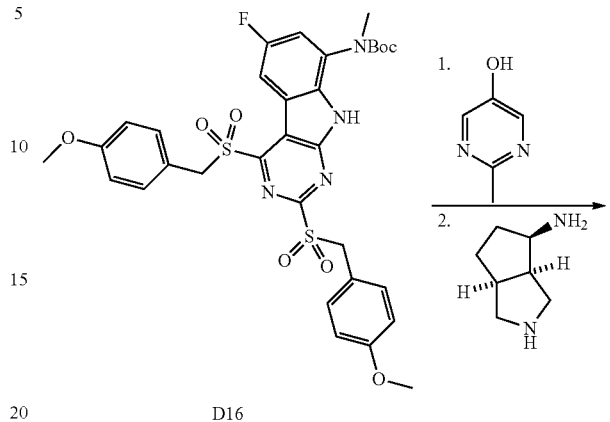

D16

D52

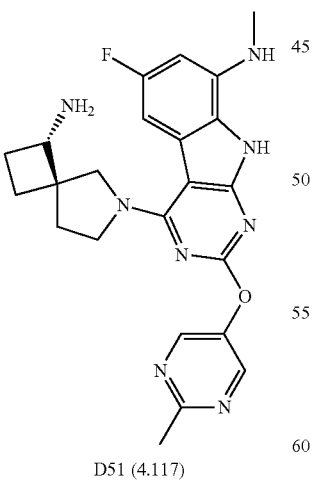

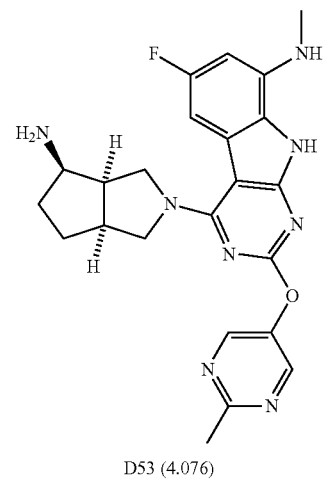

D53 (4.076)

The subtitle compound D51 was synthesized using the same method described for the above in Example 9a compound starting with bis-sulfone and (1S,4R)-6-azaspiro[3.4]octan-1-amine. LC-MS: M+1: 449.25.

The subtitle compound D53 was synthesized using the same method described for the above compound in Example 9a starting with bis-sulfone and (3aR,4R,6aS)-octahydrocyclopenta[c]pyrrol-4-amine. LC-MS: M+1: 449.21.

371
Example 9s

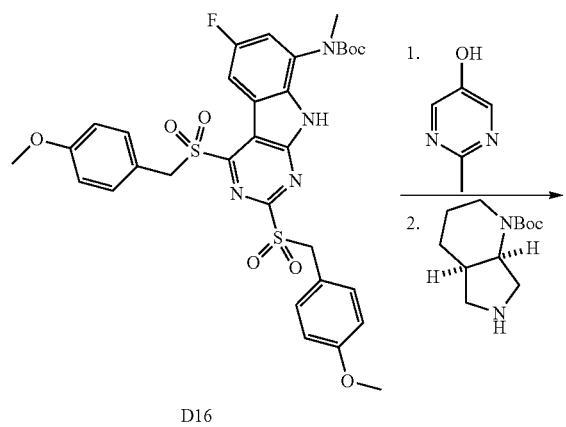

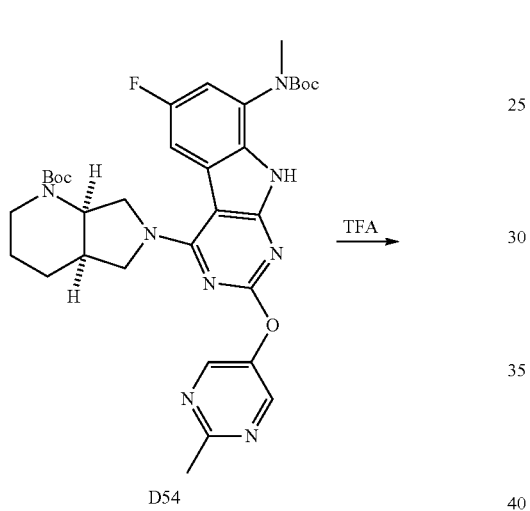

372
Example 9t

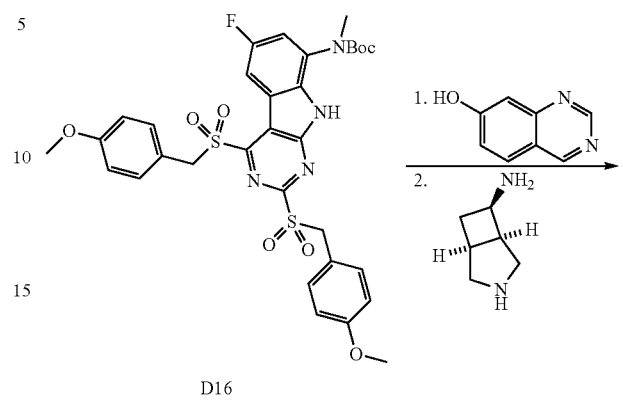

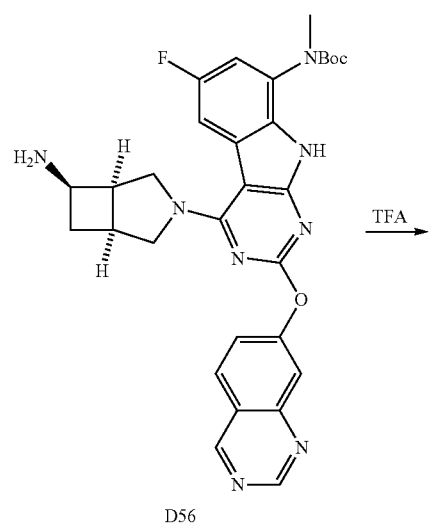

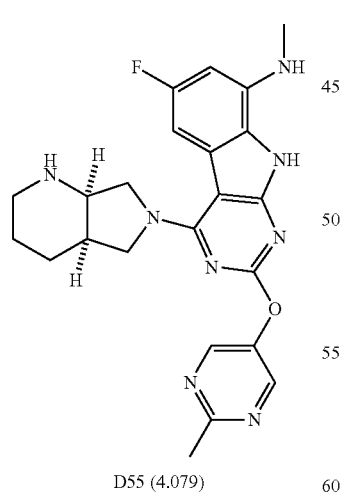

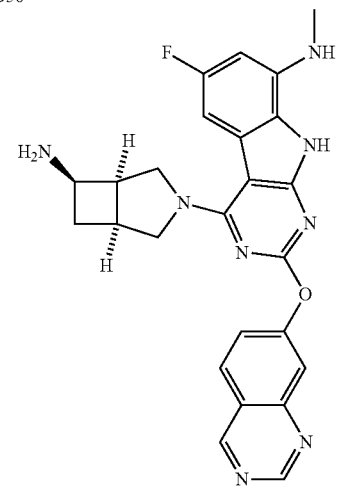

The subtitle compound D55 was synthesized using the same method described for the above compound in Example 9a starting with bis-sulfone and (4aR,7aR)-tert-butyl octahydro-1H-pyrrolo[3,4-b]pyridine-1-carboxylate. LC-MS: M+1: 449.23.

The subtitle compound D57 was synthesized using the same method described for the above compound in Example 9a starting with bis-sulfone, quinazolin-7-ol and (1S,5R,6R)-3-azabicyclo[3.2.0]heptan-6-amine. LC-MS: M+1: 471.26.

Example 9u

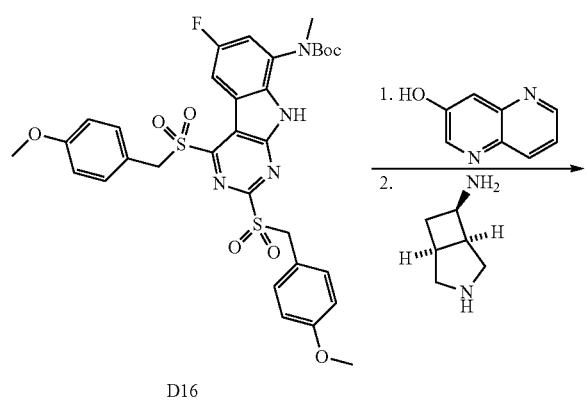

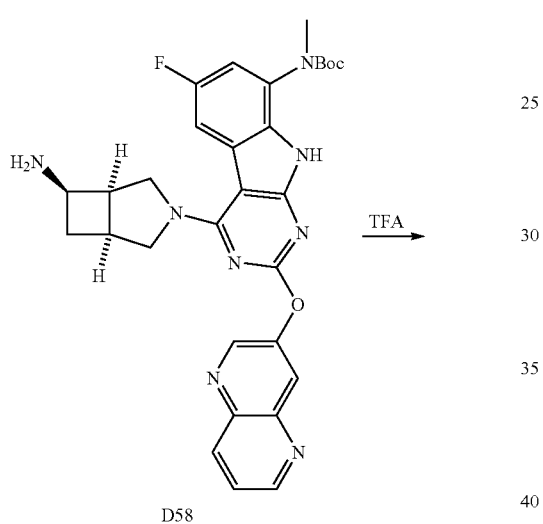

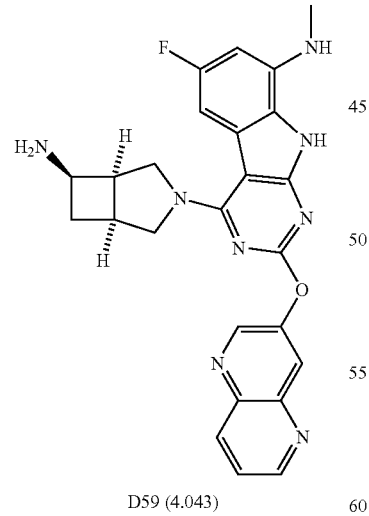

The subtitle compound D59 was synthesized using the same method described for the above compound in Example 9a starting with bis-sulfone, 1,5-naphthyridin-3-ol and (1S,5R,6R)-3-azabicyclo[3.2.0]heptan-6-amine. LC-MS: M+1: 471.20.

Example 9v

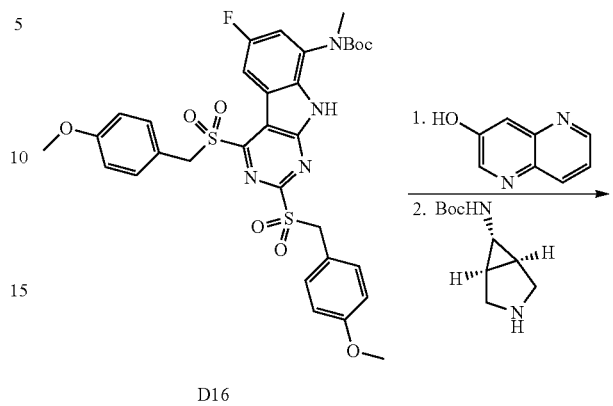

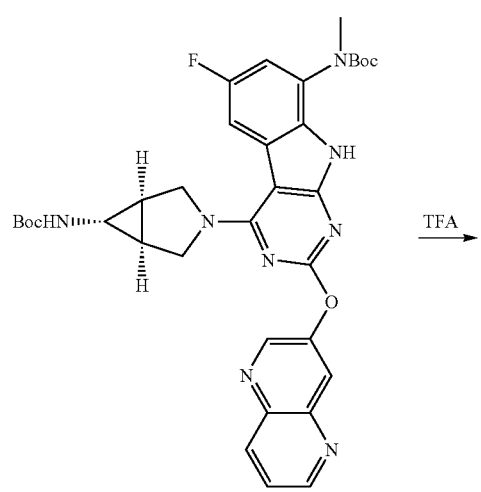

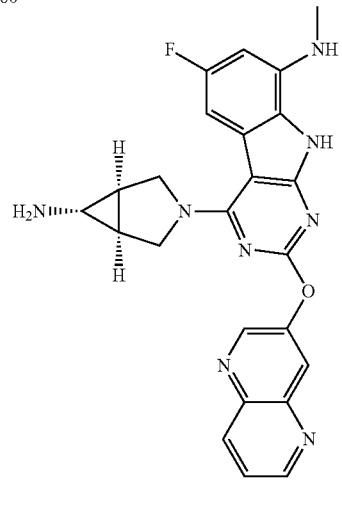

The subtitle compound D61 was synthesized using the same method described for the above compound in Example 9a starting with bis-sulfone, 1,5-naphthyridin-3-ol and tert-butyl 3-azabicyclo[3.1.0]hexan-6-ylcarbamate. LC-MS: M+1: 457.20.

375
Example 9w

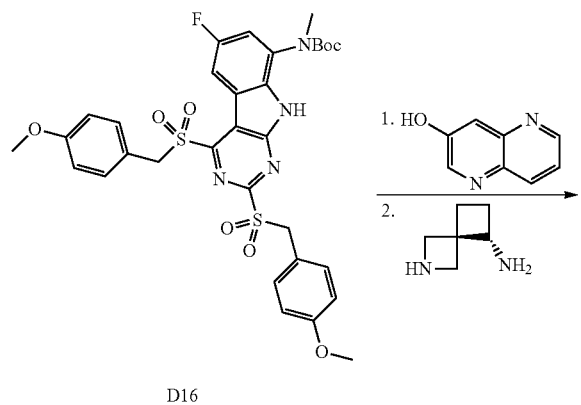

D16

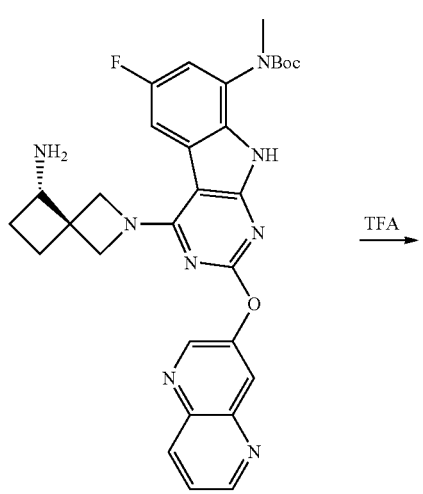

D62

→ TFA →

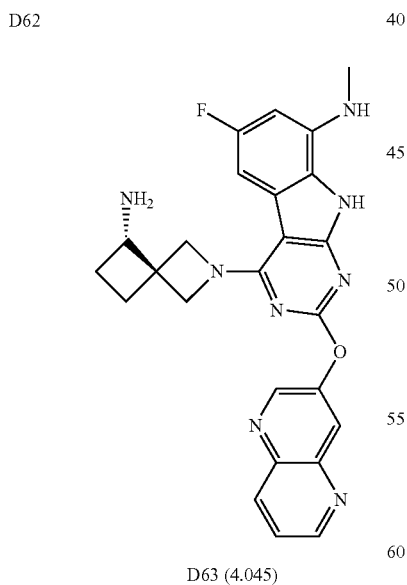

D63 (4.045)

The subtitle compound D63 was synthesized using the same method described for the above compound in Example 9a starting with bis-sulfone, 1,5-naphthyridin-3-ol and (S)-2-azaspiro[3.3]heptan-5-amine. LC-MS: M+1: 471.22.

376
Example 9x

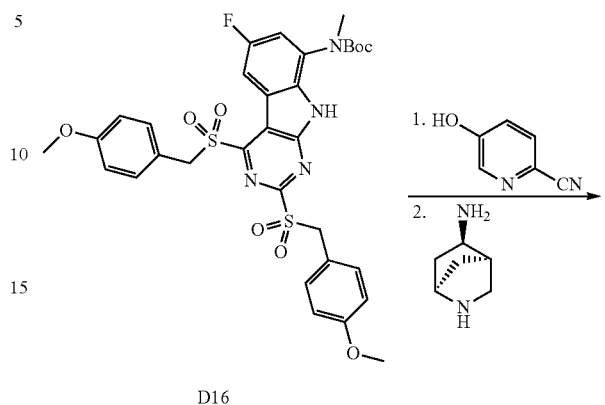

D16

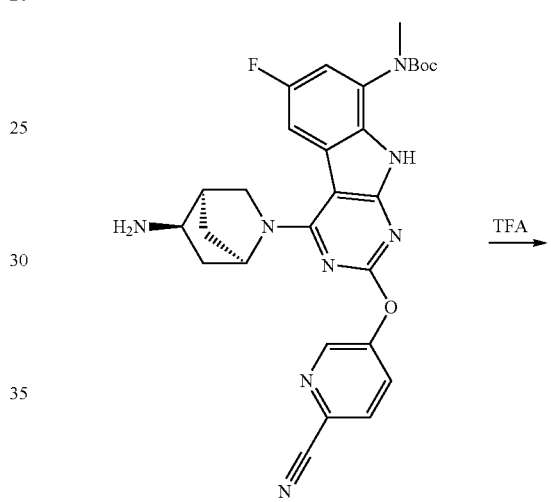

D64

→ TFA →

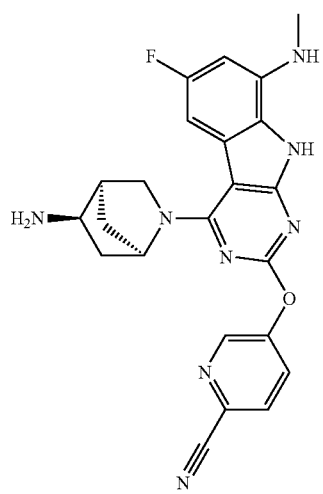

D65 (4.434)

The subtitle compound D65 was synthesized using the same method described for the above compound in Example 9a starting with bis-sulfone, 5-hydroxypicolinonitrile and (1R,4R,5R)-2-azabicyclo[2.2.1]heptan-5-amine. LC-MS: M+1: 445.18.

Example 10: Synthesis of Analogs where R⁴ not Attached by a Nitrogen

Example 10a

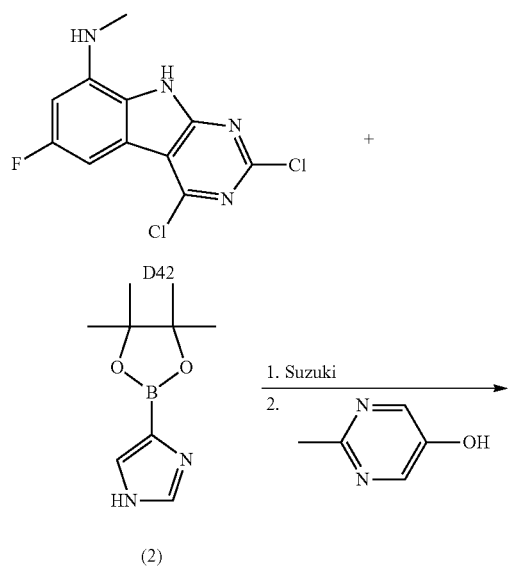

(2)

2-chloro-6-fluoro-4-(1H-imidazol-4-yl)-N-methyl-9H-pyrimido[4,5-b]indol-8-amine The mixture of compound (D42) (150 mg, 0.52 mmol), 4-(4,4,5,5-tetramethyl-1,3,2-dioxaborolan-2-yl)-1H-imidazole (2) (100 mg, 0.52 mmol), $K_2CO_3$ (100 mg, 0.5 mmol), and catalytic amount of Pd[(PPh$_3$)]Cl$_2$ was dissolved in DMF (3 ml) and water (0.3 ml). It was heated at 150° C. at microwave for 10 minutes. The mixture was then purified through HPLC to afford the title compound as yellow solid (91 mg; 55% yield). LC-MS: M+1:317.08.

¹H NMR (300 MHz, DMSO) δ (ppm): 14.01 (S, 1H), 11.71 (s, 1H), 7.98 (s, 2H), 7.51 (d, J=11.2, 1H), 6.30 (d, J=9.7, 1H), 4.12 (s, 1H), 3.15 (s, 3H).

6-fluoro-4-(1H-imidazol-4-yl)-N-methyl-2-(2-methylpyrimidin-5-yloxy)-9H-pyrimido[4,5-b]indol-8-amine D66

To the solution of the coupling compound of D42 and (2) (80 mg, 2.52 mmol) in NMP (5 ml) was added 2-methylpyrimidine-5-ol (33 mg, 3.0 mmol) and potassium carbonate (43.6 mg, 0.31 mmol). It was then heated at 160° C. under microwave condition for 15 minutes. The mixture was then purified through HPLC to afford the title compound as yellow solid (59 mg, 60%). LC-MS: M+1: 391.15. [0567]¹H NMR (300 MHz, DMSO) δ (ppm): 14.01 (S, 1H), 11.71 (s, 1H), 7.98 (s, 2H), 7.69 (s, 2H), 7.51 (d, J=11.2, 1H), 5.98 (d, J=9.7, 1H), 4.02 (s, 1H), 3.10 (s, 3H), 2.65 (s, 3H).

Example 10b

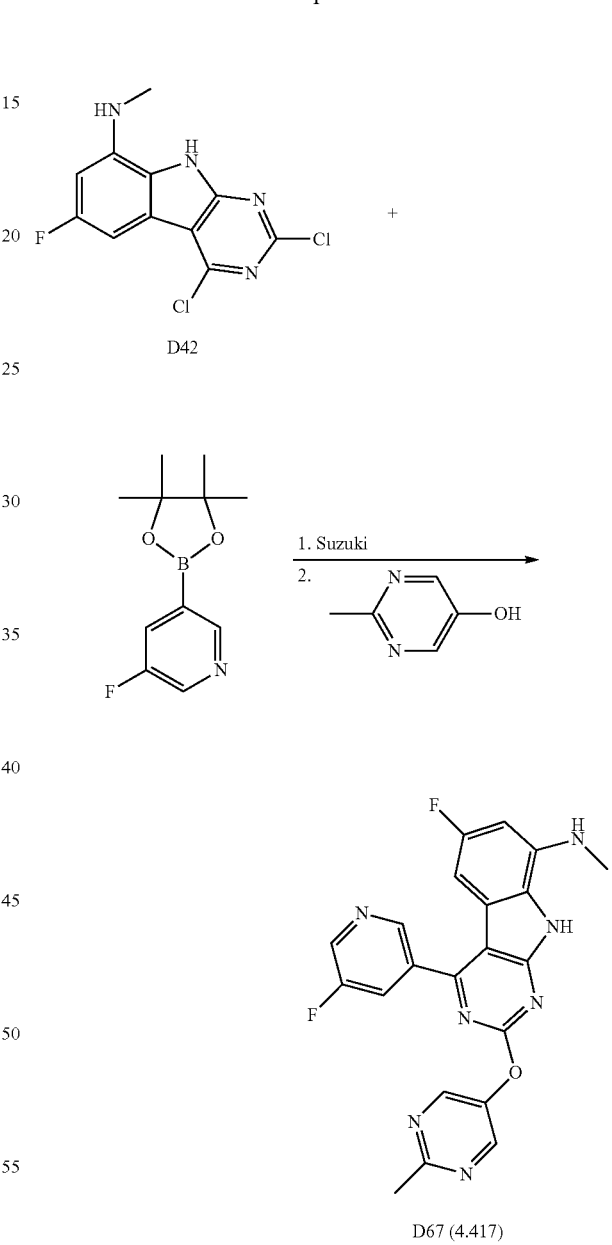

The subtitle compound D67 was synthesized using the method described above starting with 3-fluoro-5-(4,4,5,5-tetramethyl-1,3,2-dioxaborolan-2-yl)pyridine. LC-MS: M+1: 420.16.

¹H NMR (300 MHz, DMSO) δ (ppm): 11.71 (s, 1H), 9.10 (s, 1H), 8.52 (d, 1H), 7.63-7.80 (m, 3H), 7.31 (brs, 1H), 5.98 (d, J=9.7, 1H), 4.10 (s, 1H), 2.98 (s, 3H), 2.66 (s, 3H).

Example 10c

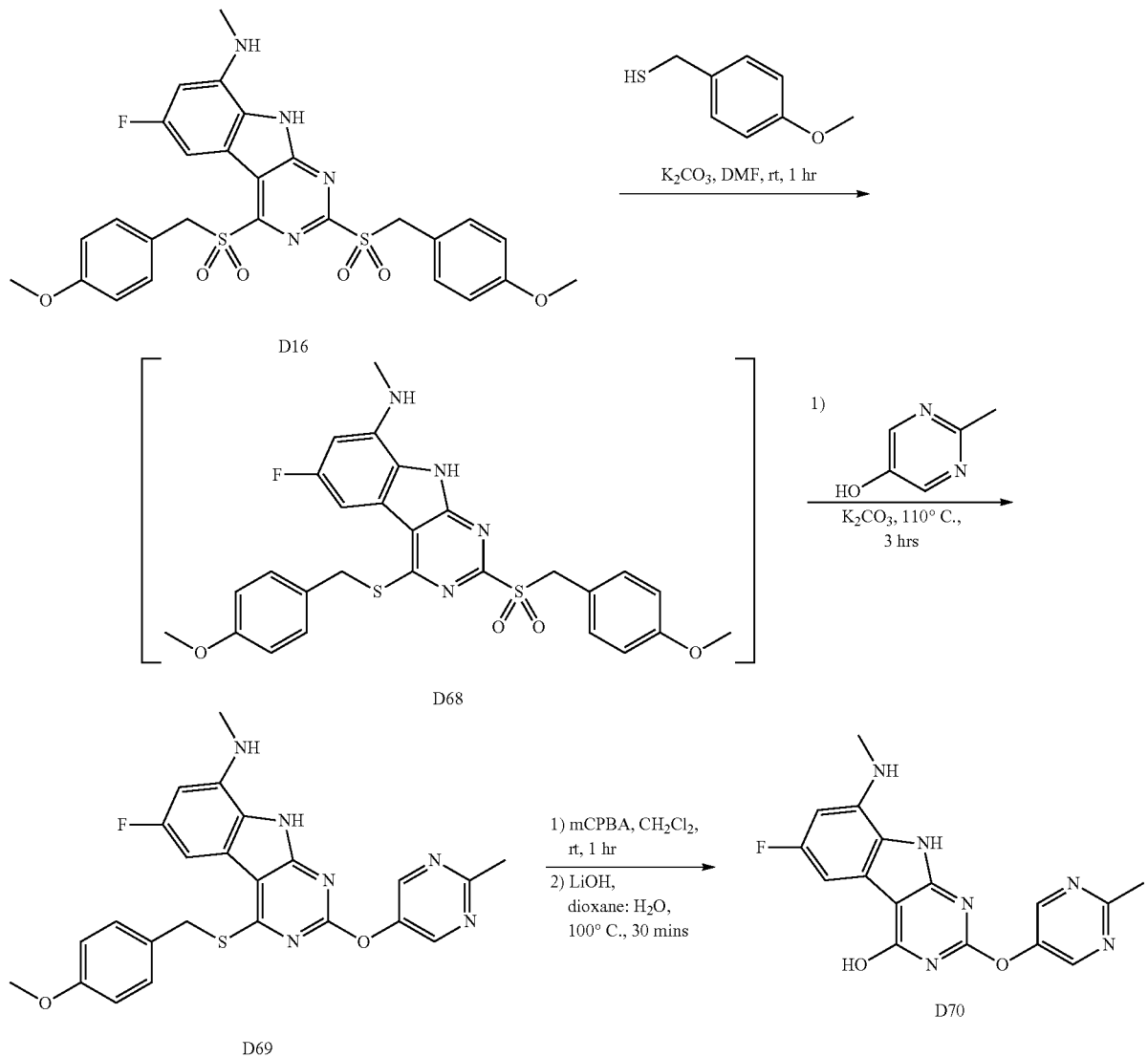

6-Fluoro-4-(4-methoxybenzylthio)-N-methyl-2-(2-methylpyrimidin-5-yloxy)-9H-pyrimido[4,5-b]indol-8-amine (D69)

To the solution of compound (D16) (2.923 g, 5 mmol) in NMP (12 ml) was added potassium carbonate (2.073 g, 15 mmol) followed by 4-methoxyphenyl)methanethiol (0.771 g, 5 mmol). The reaction mixture was stirred at room temperature for one hour. 2-Methylpyrimidine-5-ol (1.101 g, 10 mmol) was then added. The resulting mixture was heated at 100° C. for 3 hours. It was purified through C18 column chromatography to afford the title compound as light yellow solid (2.4 g, 83%).

6-Fluoro-8-(methylamino)-2-(2-methylpyrimidin-5-yloxy)-9H-pyrimido[4,5-b]indol-4-ol (D70)

To the solution of compound (D69) (2.48 g, 4.3 mmol) in dioxane (12 ml) was added 3-chloroperoxy benzoic acid (1.484 g, 8.6 mmol) by portion over 10 minutes. After the reaction was stirred at room temperature for 30 minutes, lithium hydroxide (1.8 g, 75 mmol) and water (5 ml) were added. The resulting solution was stirred at room temperature to 100° C. for one hour. It was then purified through C18 column chromatography to afford the title compound as white solid (1.39 g, 95%). [0572]4-Chloro-6-fluoro-N-methyl-2-(2-methylpyrimidin-5-yloxy)-9H-pyrimido[4,5-b]indol-8-amine (D71): Compound (D70) (1.06 g, 2.407 mmol) was dissolved in POCl$_3$ (20 ml) and N-ethyl-isopropylpropan-2-amine (0.43 g, 3.33 mmol). The mixture was heated at 50° C. for 4 hours. After the reaction was cooled down to room temperature, it was poured into a 1 L-flask containing ice (~500 g) and NaOH (20 g) and the resulting was sat for one hour. It was then extracted with ethyl acetate (100 ml×3). The combined organic layers were dried over Na$_2$SO$_4$ and concentrated by rotary evaporation to afford the title compound as white solid (492 mg, 57%).

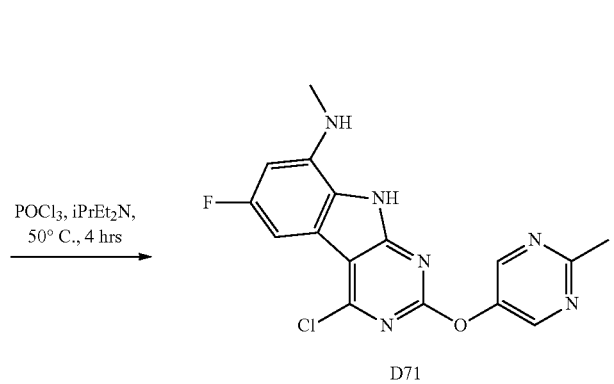
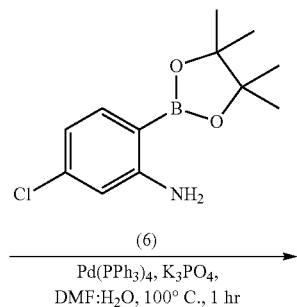

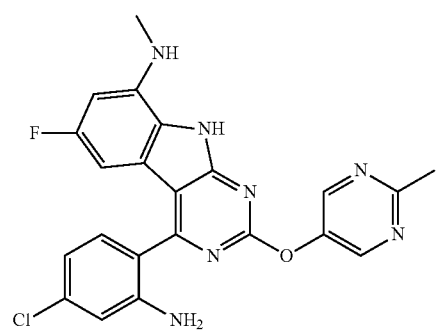

D72 (4.161)

4-(2-amino-4-chlorophenyl)-6-fluoro-N-methyl-2-(2-methylpyrimidin-5-yloxy)-9H-pyrimido[4,5-b]indol-8-amine (D72)

The mixture of compound (D71) (36 mg, 0.1 mmol), the boronic acid pinacol ester (6) (38 mg, 0.15 mmol), potassium phosphate (64 mg, 0.3 mmol), and catalytic amount of Pd(PPh$_3$)$_4$ was dissolved in DMF (1 ml) and water (0.3 ml). The reaction mixture was refluxed at 100° C. for one hour. It was then purified through HPLC to afford the title compound as yellow product (17 mg, 37.8%).

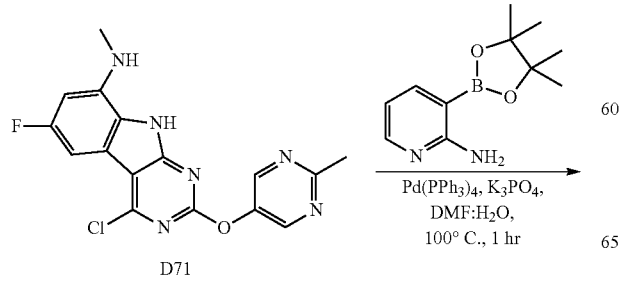

-continued

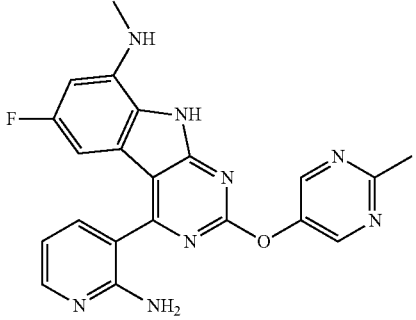

D73 (4.448)

The subtitle compound D73 was synthesized using the method described above starting with 3-(4,4,5,5-tetramethyl-1,3,2-dioxaborolan-2-yl)pyridin-2-amine.

Example 11
Synthesis of Prodrugs at R[4]
(S)-2-Amino-N—((R)-5-(6-fluoro-8-(methylamino)-2-(2-methylpyrimidin-5-yloxy)-9H-pyrimido[4.5-b]indol-4-yl)-5-azaspiro[2.4]heptan-7yl)propanamide D76 (4.424)
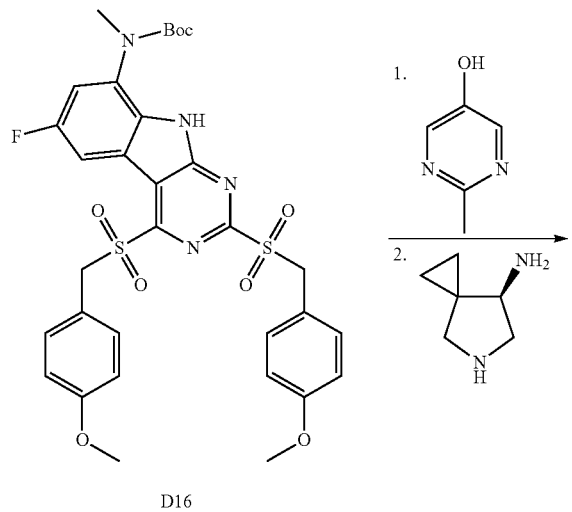
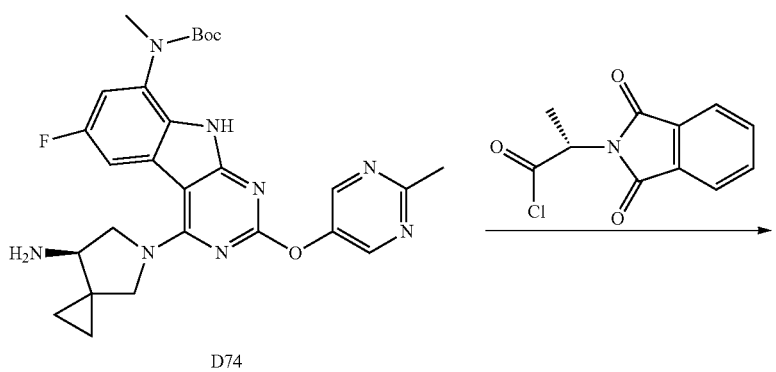
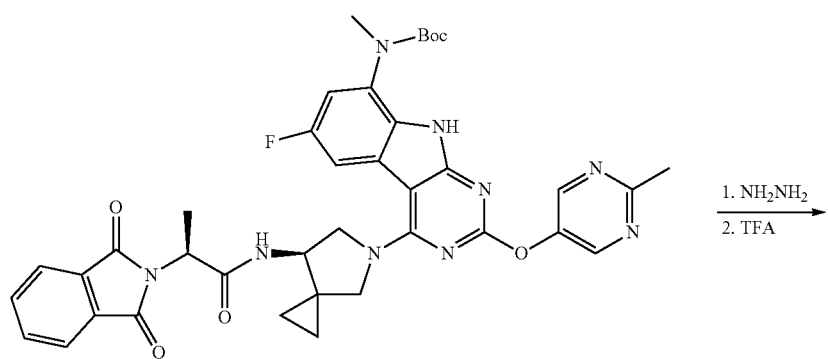

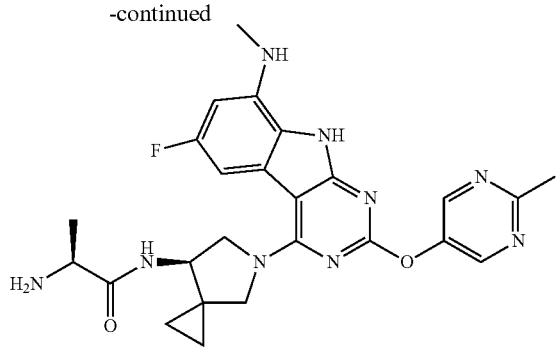

D76

The mixture of D16 (0.342 g, 0.500 mmol), 2-methylpyrimidin-5-ol (0.165 g, 1.50 mmol) and K$_2$CO$_3$ (0.276 g, 2.00 mmol) in NMP (5.0 mL) was stirred for 1 hr 30 min at 100° C. After being stirred for 1 hr 30 min, the reaction was checked by LC/MS. (R)-5-azaspiro[2.4]hepten-7-amine (0.168 g, 1.50 mmol) was added at once, the mixture was allowed to stir for 1 hr 30 min at 100° C. The resulting heterogeneous mixture was cooled to 23° C. and purified by HPLC to give D74 (0.100 g, 0.187 mmol) as light yellow solid. LC/MS (ESI, M+H$^+$)=535. To a solution of D74 (0.100 g, 0.187 mmol) and K$_2$CO$_3$ (0.052 g, 0.374 mmol) in CH$_2$Cl$_2$ (8.0 mL) was added (S)-2-(1,3-dioxoisoindolin-2-yl)propanoyl chloride (0.089 g, 0.374 mmol) dissolved in CH$_2$Cl$_2$ (2.0 mL) at 23° C. The mixture was allowed to stir for 1 hr 30 min at 60° C. and then cooled to 23° C. The reaction mixture was concentrated by Rotavap and the crude material was purified by HPLC to give D75 as yellow solid. LC/MS (ESI, M+H$^+$)=736. To a solution of D75 in ethanol (7.0 mL) was added hydrazine (1.5 mL, 30 wt. % solution in water) via syringe at 23° C. The mixture was stirred for 1 hr at 23° C. The reaction mixture was concentrated by Rotavap and the crude material was purified by HPLC to provide D76 as light yellow solid. LC/MS (ESI, M+H$^+$)=606. The mixture of D76 in trifluoroacetic acid (1.00 mL) was stirred for 1 hr at 23° C. The crude material was purified by HPLC to provide a title compound D76 (0.026 g, 0.051 mmol) as white solid. LC/MS (ESI, M+H$^+$)= 506.

Example 12

Synthesis of Prodrugs at R$^8$ (S)-2-Amino-N-(4-((R)-7-amino-5-azaspiro[2.4] heptan-5-yl)-6-fluoro-2-(2-methylpyrimidin-5-yloxy)-9H-pyrimido[4.5-b]indol-8-yl)-N-methylpropanamide

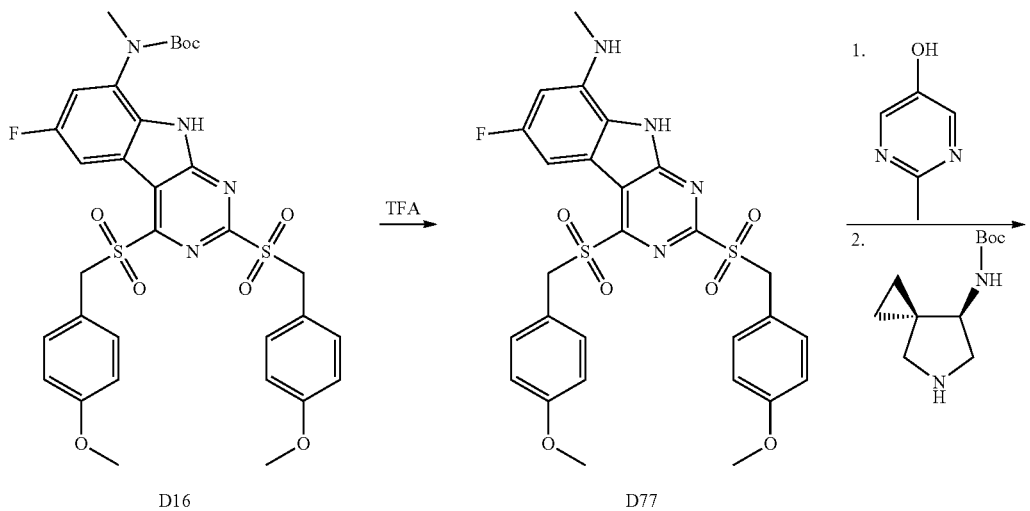

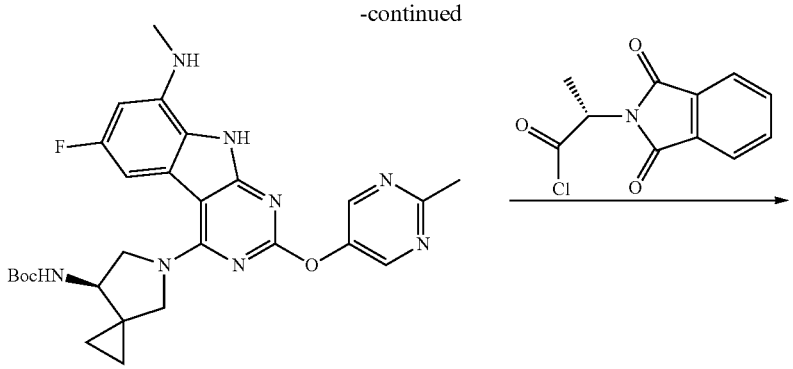

D78

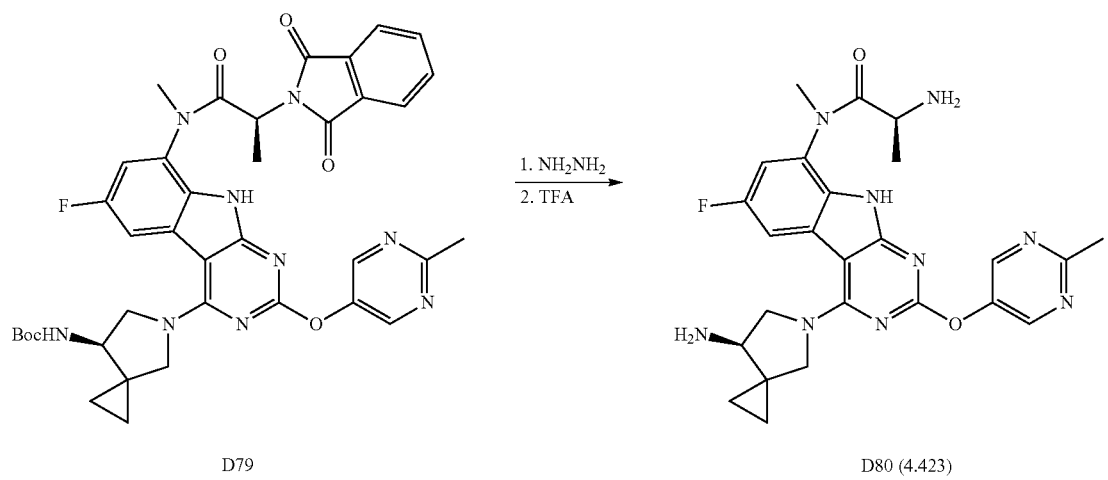

D79

D80 (4.423)

The mixture of D16 (1.00 g, 1.46 mmol) in trifluoroacetic acid (3.0 mL) was stirred for 30 min at 23° C. Trifluoroacetic acid was evaporated by reduced pressure to provide D77 (quantitative yield) as deep orange solid. This crude material was used for next reaction without further purification. LC/MS (ESI, M+H$^+$)=585. The mixture of D77 (0.292 g, 0.50 mmol), 2-methylpyrimidin-5-ol (0.165 g, 1.50 mmol) and K$_2$CO$_3$ (0.276 g, 2.00 mmol) in NMP (5.0 mL) was stirred for 2 hr at 100° C. After being stirred for 2 hr, the reaction was checked by LC/MS. (R)-tert-butyl 5-azaspiro[2.4]hepten-7-ylcarbamate (0.318 g, 1.50 mmol) was added at once, the mixture was allowed to stir for 1 hr 30 min at 100° C.

The resulting heterogeneous mixture was cooled to 23° C. and purified by HPLC to provide D78 (0.182 g, 0.34 mmol) as yellow solid. LC/MS (ESI, M+H$^+$)=535. To a solution of D78 (0.182 g, 0.34 mmol) and K$_2$CO$_3$ (0.094 g, 0.68 mmol) in CH$_2$Cl$_2$ (10.0 mL) was added (S)-2-(1,3-dioxoisoindolin-2-yl)propanoyl chloride (0.161 g, 0.68 mmol) dissolved in CH$_2$Cl$_2$ (2.0 mL) at 23° C. The mixture was allowed to stir for 2 hr at 60° C. and then cooled to 23° C. The reaction mixture was concentrated by Rotavap and the crude material was purified by HPLC to give D79 as yellow solid. LC/MS (ESI, M+H$^+$)=736. To a solution of D79 in ethanol (7.0 mL) was added hydrazine (1.5 mL, 30 wt. % solution in water) via syringe at 23° C. The mixture was stirred for 1 hr at 23° C. The reaction mixture was concentrated by Rotavap and the crude material was purified by HPLC to provide 5 as light yellow solid. LC/MS (ESI, M+H$^+$)=606. The mixture of 5 in trifluoroacetic acid (1.50 mL) was stirred for 30 min at 23° C. The crude material was purified by HPLC to provide a title compound D80 (0.031 g, 0.061 mmol) as white solid. LC/MS (ESI, M+H$^+$)=506.

Example 13: Prodrug at R[4] and R[8]

(R)-2-Amino-N-(4-(7-(2-aminoacetamido)-5-azaspiro[2.4]heptan-5-yl)-6-fluoro-2-(2-methylpyrimidin-5-yloxy)-9H-pyrimido[4,5-b]ondol-8-yl)-N-methylacetamide

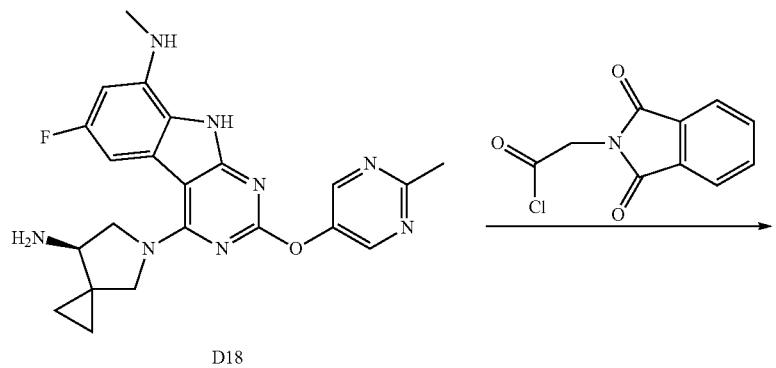

D18

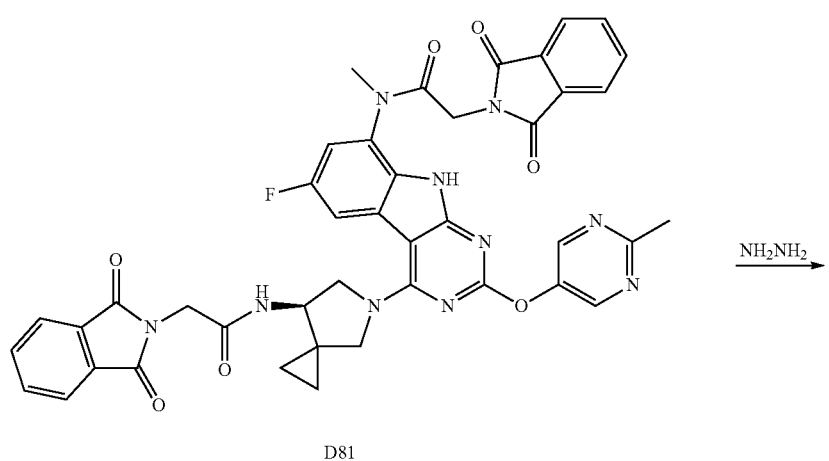

D81

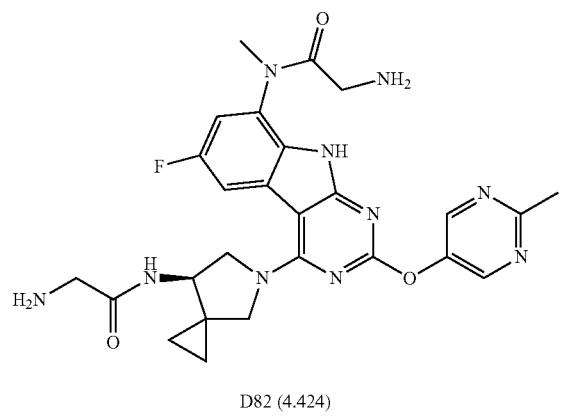

D82 (4.424)

To a solution of D16 (0.075 g, 0.173 mmol) and $K_2CO_3$ (0.084 g, 0.606 mmol) in $CH_2Cl_2$ (8.0 mL) was added 2-(1,3-dioxoisoindolin-2-yl)acetyl chloride (0.136 g, 0.606 mmol) dissolved in $CH_2Cl_2$ (2.0 mL) at 23° C. The mixture was allowed to stir for 3 hr 30 min at 60° C. and then cooled to 23° C. The reaction mixture was concentrated by Rotavap and the crude material was purified by HPLC to give D81 as light yellow solid. LC/MS (ESI, M+H$^+$)=809. To a solution of D81 in ethanol (5.0 mL) was added hydrazine (1.0 mL, 30 wt. % solution in water) via syringe at 23° C. The mixture was stirred for 1 hr at 23° C. The reaction mixture was concentrated by Rotavap and the crude material was purified by HPLC to provide a title compound D82 (0.084 g, 0.153 mmol) as white solid. LC/MS (ESI, M+H$^+$)=549.

Example 14
Table of Formula I' compounds where L = O, R$^x$, R$^y$, R$^z$ = H, R$^8$ = NHCH$_3$
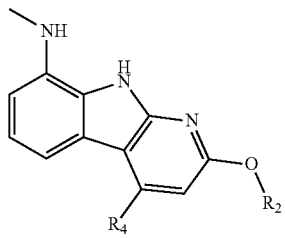
| Compd ID | R2 | R4 |
|---|---|---|
| 3.1 | pyrimidin-5-yl | 1-amino-3-azabicyclo[3.1.0]hexan-3-yl |
| 3.2 | 2,4-dimethoxypyrimidin-5-yl | (3R)-3-aminopyrrolidin-1-yl |
| 3.3 | 5-cyanopyridin-3-yl | (3R)-3-aminopyrrolidin-1-yl |
| 3.4 | pyrimidin-5-yl | (3R)-3-aminopyrrolidin-1-yl |
| 3.5 | 2-methylpyrimidin-5-yl | (3R)-3-aminopyrrolidin-1-yl |
| 3.6 | 5-fluoropyridin-3-yl | (3R)-3-aminopyrrolidin-1-yl |

-continued

Table of Formula I' compounds where L = O, R^x, R^y, R^z = H, R^8 = NHCH_3

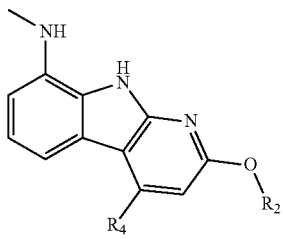

| Compd ID | R2 | R4 |
|---|---|---|
| 3.7 | 5-fluoropyridin-3-yl | 3,6-diazabicyclo[3.2.0]heptan-3-yl |
| 3.8 | pyrimidin-5-yl | 3-amino-4-hydroxypyrrolidin-1-yl |
| 3.9 | pyrimidin-5-yl | 1H-pyrazol-4-yl |
| 3.10 | 2-methylpyrimidin-5-yl | 3-((2-cyanoethyl)amino)pyrrolidin-1-yl |
| 3.11 | 2-methylpyrimidin-5-yl | 6-((2-cyanoethyl)amino)-3-azabicyclo[3.1.0]hexan-3-yl |
| 3.12 | pyrimidin-5-yl | 7-((cyclopropylmethyl)amino)-5-azaspiro[2.4]heptan-5-yl |
| 3.13 | pyrimidin-5-yl | 6-((cyclopropylmethyl)amino)-3-azabicyclo[3.1.0]hexan-3-yl |

Table of Formula I' compounds where L = O, R$^x$, R$^y$, R$^z$ = H, R$^8$ = NHCH$_3$

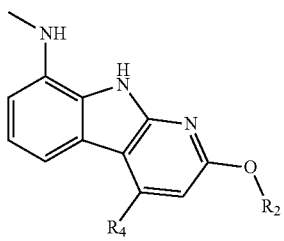

| Compd ID | R2 | R4 |
|---|---|---|
| 3.14 | 2-methylpyrimidin-5-yl | 3-azabicyclo[3.1.0]hexan-6-yl-NH-CH$_2$-cyclopropyl |
| 3.15 | pyrimidin-5-yl | octahydrocyclopenta[c]pyrrol-4-amine |
| 3.16 | pyrimidin-5-yl | (3R)-3-aminopiperidin-1-yl |
| 3.17 | pyrimidin-5-yl | 3-carbamoylpyrrolidin-1-yl |
| 3.18 | pyrimidin-5-yl | N-(3-azabicyclo[3.1.0]hexan-6-yl)-2-aminoacetamide |
| 3.19 | 5-carbamoylpyridin-3-yl | 3-azabicyclo[3.1.0]hexan-6-amine |

Table of Formula I' compounds where L = O, $R^x$, $R^y$, $R^z$ = H, $R^8$ = NHCH$_3$

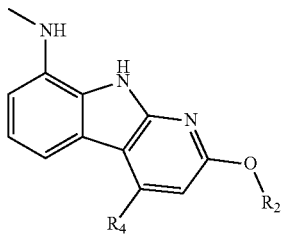

| Compd ID | R2 | R4 |
|---|---|---|
| 3.20 | 5-(carboxy)pyridin-3-yl | 3-azabicyclo[3.1.0]hexan-6-amine (N-linked) |
| 3.21 | 6-(methoxycarbonyl)pyridin-3-yl | 3-azabicyclo[3.1.0]hexan-6-amine (N-linked) |
| 3.22 | 6-(carboxy)pyridin-3-yl | 3-azabicyclo[3.1.0]hexan-6-amine (N-linked) |
| 3.23 | furo[3,2-b]pyridin-6-yl | 3-azabicyclo[3.1.0]hexan-6-amine (N-linked) |
| 3.24 | 2-(1-methyl-1H-tetrazol-5-yl)pyrimidin-5-yl | 3-azabicyclo[3.1.0]hexan-6-amine (N-linked) |
| 3.25 | 2-(cyclopropylamino)pyrimidin-5-yl | 3-azabicyclo[3.1.0]hexan-6-amine (N-linked) |
| 3.26 | 2-(morpholin-4-yl)pyrimidin-5-yl | 3-azabicyclo[3.1.0]hexan-6-amine (N-linked) |
| 3.27 | 5-cyanopyridin-3-yl | 3-azabicyclo[3.1.0]hexan-6-amine (N-linked) |

Table of Formula I' compounds where L = O, R$^x$, R$^y$, R$^z$ = H, R$^8$ = NHCH$_3$

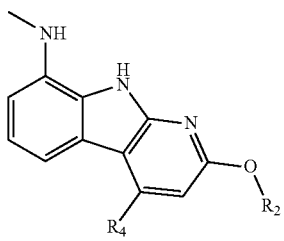

| Compd ID | R2 | R4 |
|---|---|---|
| 3.28 | pyrimidin-5-yl | 3-aminobicyclo[3.1.0]hexan-N-yl |
| 3.29 | 2-methylpyrimidin-5-yl | 3-aminobicyclo[3.1.0]hexan-N-yl |
| 3.30 | pyridin-3-yl N-oxide | 3-aminobicyclo[3.1.0]hexan-N-yl |
| 3.31 | quinoxalin-6-yl | 3-aminobicyclo[3.1.0]hexan-N-yl |
| 3.32 | 2-aminopyrimidin-5-yl | 3-aminobicyclo[3.1.0]hexan-N-yl |
| 3.33 | 5-fluoropyridin-3-yl | 3-aminobicyclo[3.1.0]hexan-N-yl |
| 3.34 | 1,5-naphthyridin-3-yl | 3-aminobicyclo[3.1.0]hexan-N-yl |
| 3.35 | 5-methoxypyridin-3-yl | 3-aminobicyclo[3.1.0]hexan-N-yl |
| 3.36 | 1-methyl-1H-imidazo[4,5-b]pyridin-6-yl | 3-aminobicyclo[3.1.0]hexan-N-yl |

Table of Formula I' compounds where L = O, $R^x$, $R^y$, $R^z$ = H, $R^8$ = $NHCH_3$

| Compd ID | R2 | R4 |
|---|---|---|
| 3.37 | pyrimidin-5-yl | O-pyrimidin-5-yl |
| 3.38 | 2-methylpyrimidin-5-yl | O-(2-methylpyrimidin-5-yl) |
| 3.39 | pyridin-3-yl N-oxide | O-(2-methylpyrimidin-5-yl) |
| 3.40 | 5-cyanopyridin-3-yl | 1-amino-5-azaspiro[2.4]heptan-5-yl |
| 3.41 | pyrimidin-5-yl | 1-amino-5-azaspiro[2.4]heptan-5-yl |
| 3.42 | 2-methylpyrimidin-5-yl | 1-amino-5-azaspiro[2.4]heptan-5-yl |
| 3.43 | 5-cyanopyridin-3-yl | 7-amino-5-azaspiro[2.4]heptan-5-yl |
| 3.44 | 5-cyanopyridin-3-yl | (7S)-7-amino-5-azaspiro[2.4]heptan-5-yl |

Table of Formula I' compounds where L = O, R^x, R^y, R^z = H, R^8 = NHCH_3
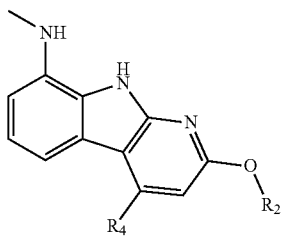
| Compd ID | R2 | R4 |
|---|---|---|
| 3.45 | 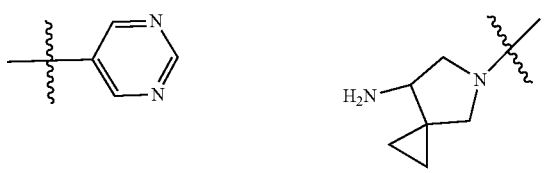 | |
| 3.46 | 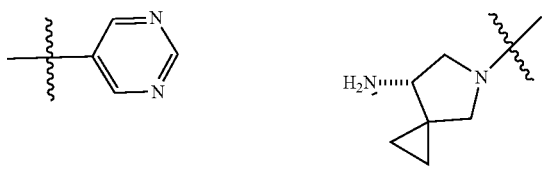 | |
| 3.47 | 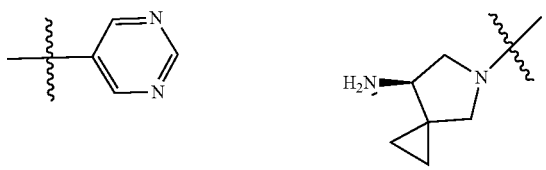 | |
| 3.48 | 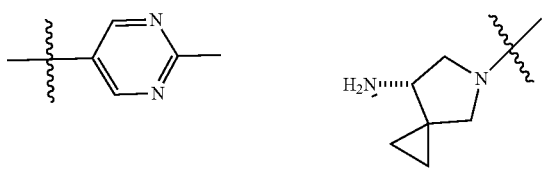 | |
| 3.49 | 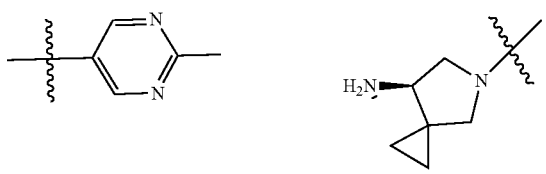 | |
| 3.50 | 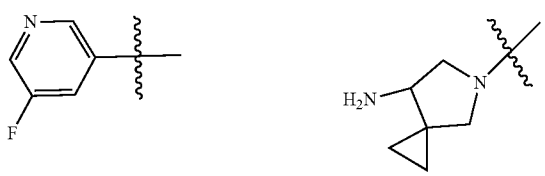 | |
| 3.51 | 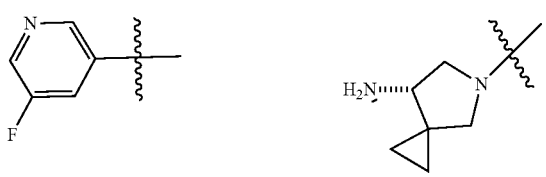 | |

-continued
Table of Formula I' compounds where L = O, R$^x$, R$^y$, R$^z$ = H, R$^8$ = NHCH$_3$
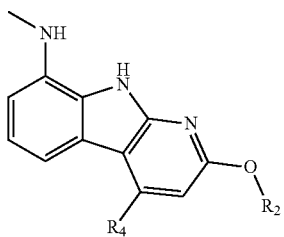
| Compd ID | R2 | R4 |
|---|---|---|
| 3.52 | 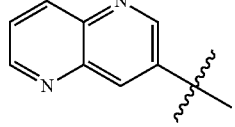 | 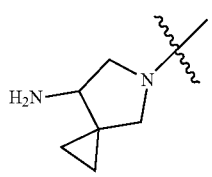 |
| 3.53 | 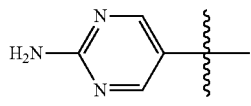 | 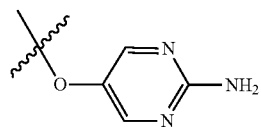 |
| 3.54 | 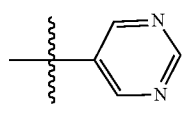 | 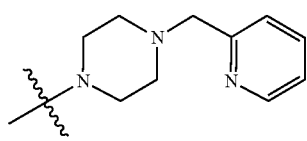 [SMILES: *N1CCN(Cc2ccccn2)CC1] |
| 3.55 | 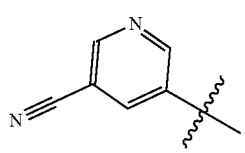 [SMILES: *c1cncc(C#N)c1] | 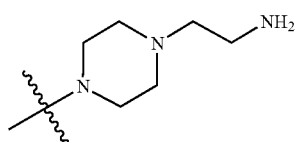 [SMILES: *N1CCN(CCN)CC1] |
| 3.56 | 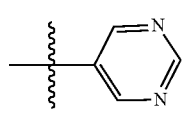 | 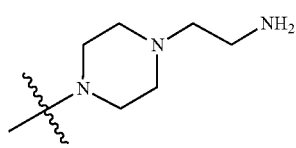 [SMILES: *N1CCN(CCN)CC1] |
| 3.57 | 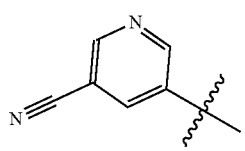 [SMILES: *c1cncc(C#N)c1] | 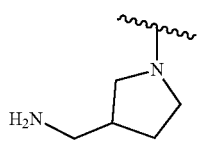 |
| 3.58 | 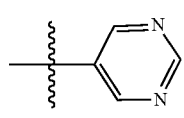 [SMILES: *c1cncnc1] | 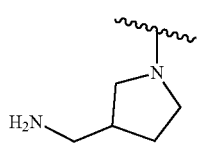 |
| 3.59 | 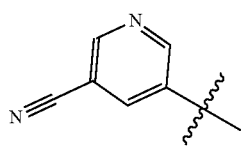 [SMILES: *c1cncc(C#N)c1] | 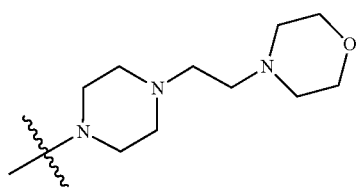 [SMILES: *N1CCN(CCN2CCOCC2)CC1] |

-continued

Table of Formula I' compounds where L = O, R$^x$, R$^y$, R$^z$ = H, R$^8$ = NHCH$_3$

| Compd ID | R2 | R4 |
|---|---|---|
| 3.60 | pyrimidin-5-yl | 4-(2-morpholinoethyl)piperazin-1-yl |
| 3.61 | pyrimidin-5-yl | octahydropyrrolo[3,4-b]pyrrol-2-yl |
| 3.62 | pyrimidin-5-yl | 3-amino-4-(methoxyimino)pyrrolidin-1-yl |
| 3.63 | pyrimidin-5-yl | 3-amino-4-fluoropyrrolidin-1-yl |
| 3.64 | pyrimidin-5-yl | 4-aminopiperidin-1-yl |
| 3.65 | pyrimidin-5-yl | 2,7-diazaspiro[3.4]octan-7-yl |
| 3.66 | 5-fluoropyridin-3-yl | 2,7-diazaspiro[3.4]octan-7-yl |

Table of Formula I' compounds where L = O, R$^x$, R$^y$, R$^z$ = H, R$^8$ = NHCH$_3$

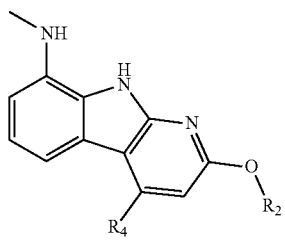

| Compd ID | R2 | R4 |
|---|---|---|
| 3.67 | pyrimidin-5-yl | 2,6-diazaspiro[3.4]octan-2-yl |

Table of Formula I' Compounds Where L is O R$^x$, R$^z$ is CH, R$^y$ is F and R$^8$ is NHCH$_3$

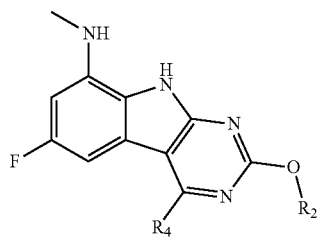

| Cmpd ID | R2 | R4 |
|---|---|---|
| 4.001 | pyrimidin-5-yl | 6-amino-3-azabicyclo[3.1.0]hexan-3-yl |
| 4.002 | pyrimidin-5-yl | 5-aminospiro[2.4]heptan-6-yl (N-linked) |
| 4.003 | pyrimidin-5-yl | 1-aminospiro[2.4]heptan-5-yl (N-linked) |
| 4.004 | pyrimidin-5-yl | 6-(aminomethyl)-3-azabicyclo[3.1.0]hexan-3-yl |

| | | |
|---|---|---|
| 4.005 | 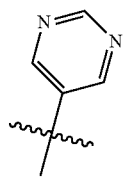 [SMILES: *c1cncnc1] | 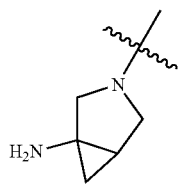 |
| 4.006 | 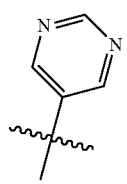 [SMILES: *c1cncnc1] | 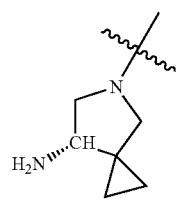 [SMILES: *N1C[C@@H](N)C2(CC2)C1] |
| 4.007 | 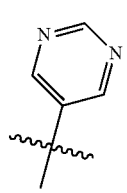 [SMILES: *c1cncnc1] | 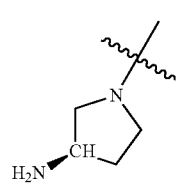 [SMILES: *N1CC[C@@H](N)C1] |
| 4.008 | 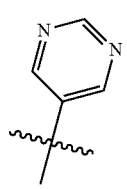 [SMILES: *c1cncnc1] | 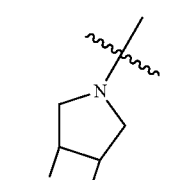 |
| 4.009 | 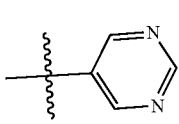 | 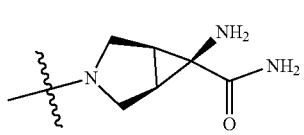 [SMILES: *N1C[C@@H]2[C@H](C1)[C@@]2(N)C(N)=O] |
| 4.010 | 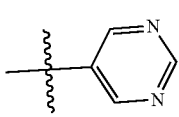 [SMILES: *c1cncnc1] | 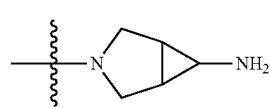 |
| 4.011 | 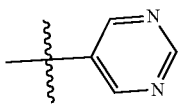 [SMILES: *c1cncnc1] | 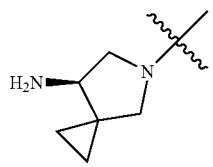 [SMILES: *N1C[C@H](N)C2(CC2)C1] |
| 4.012 | 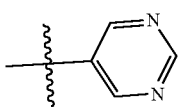 [SMILES: *c1cncnc1] | 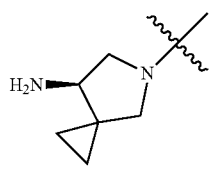 |
| 4.013 | 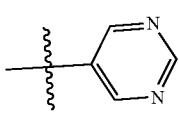 | 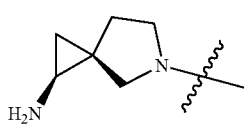 [SMILES: *N1CC[C@]2(C[C@@H]2N)C1] |

-continued
| | | |
|---|---|---|
| 4.014 | 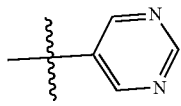 [SMILES: *c1cncnc1] |  |
| 4.015 | 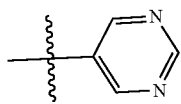 [SMILES: *c1cncnc1] | 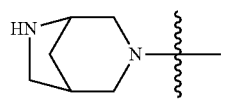 |
| 4.016 | 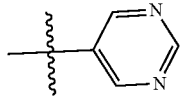 [SMILES: *c1cncnc1] | 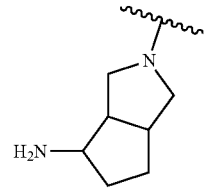 [SMILES: *N1CC2CCC(N)C2C1] |
| 4.017 | 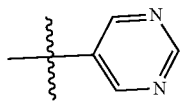 [SMILES: *c1cncnc1] | 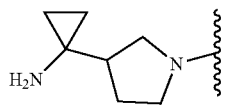 |
| 4.018 | 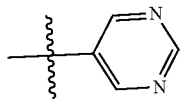 [SMILES: *c1cncnc1] | 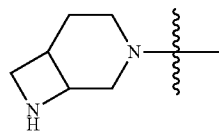 |
| 4.019 | 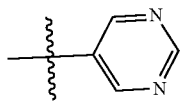 | 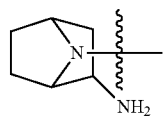 |
| 4.020 | 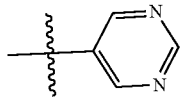 | 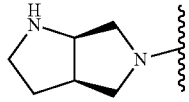 |
| 4.021 | 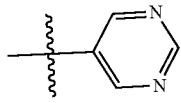 [SMILES: *c1cncnc1] | 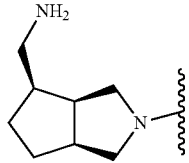 [SMILES: *N1C[C@H]2CC[C@@H](CN)[C@H]2C1] |
| 4.022 | 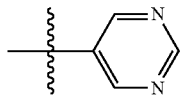 [SMILES: *c1cncnc1] | 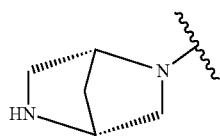 [SMILES: *N1C[C@H]2C[C@@H]1CN2] |
| 4.023 | 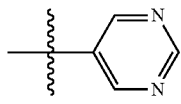 | 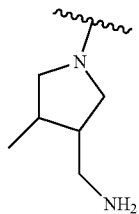 |

-continued
| | | |
|---|---|---|
| 4.024 | 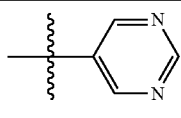 | 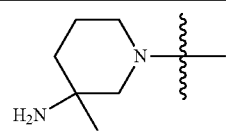 |
| 4.025 | 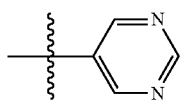 | 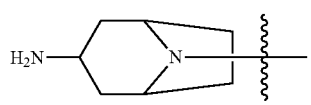 |
| 4.026 | 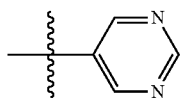 [SMILES: *c1cncnc1] | 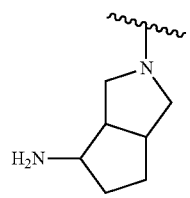 |
| 4.027 | 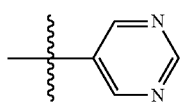 [SMILES: *c1cncnc1] | 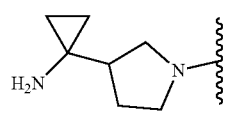 |
| 4.028 | 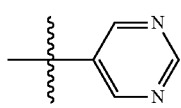 | 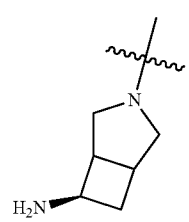 [SMILES: *N1CC2C[C@@H](N)C2C1] |
| 4.029 | 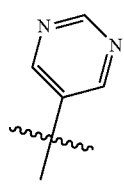 [SMILES: *c1cncnc1] | 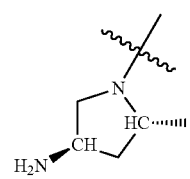 |
| 4.030 | 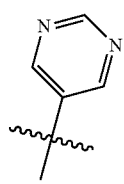 [SMILES: *c1cncnc1] | 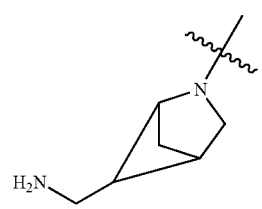 [SMILES: *N1CC2CC1C2CN] |
| 4.031 | 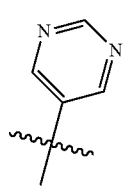 [SMILES: *c1cncnc1] |  |
| 4.032 | 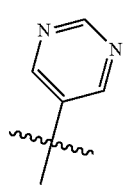 [SMILES: *c1cncnc1] | 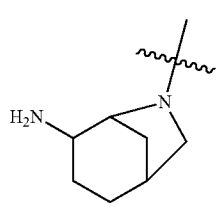 [SMILES: *N1CC2CCC(N)C1C2] |

-continued
| | | |
|---|---|---|
| 4.033 | 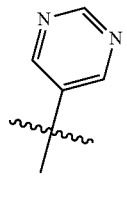 [SMILES: *c1cncnc1] | 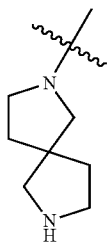 [SMILES: *N1CCC2(CCNC2)C1] |
| 4.034 | 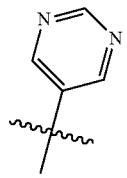 [SMILES: *c1cncnc1] | 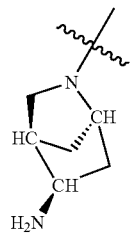 |
| 4.035 | 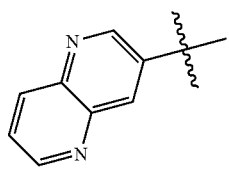 [SMILES: *c1cnc2cccnc2c1] | 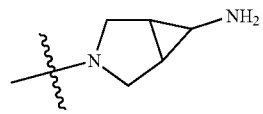 [SMILES: *N1CC2C(N)C2C1] |
| 4.036 | 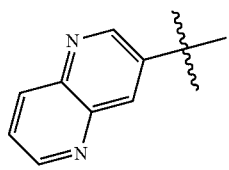 [SMILES: *c1cnc2cccnc2c1] | 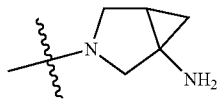 |
| 4.037 | 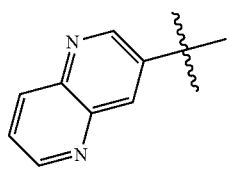 [SMILES: *c1cnc2cccnc2c1] | 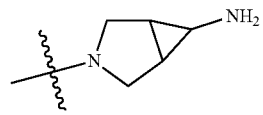 [SMILES: *N1CC2C(N)C2C1] |
| 4.038 | 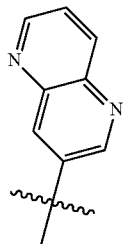 [SMILES: *c1cnc2cccnc2c1] | 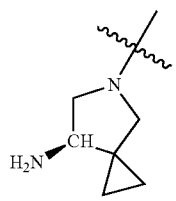 |
| 4.039 | 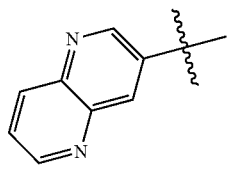 [SMILES: *c1cnc2cccnc2c1] | 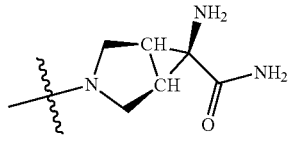 [SMILES: *N1C[C@@H]2[C@H](C1)[C@@]2(N)C(N)=O] |

| | | |
|---|---|---|
| 4.040 | 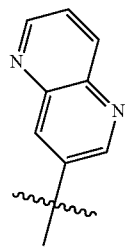 [SMILES: *c1cnc2cccnc2c1] | 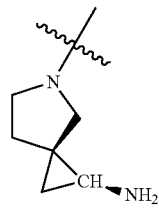 |
| 4.041 | 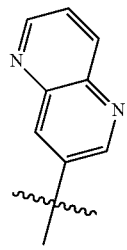 [SMILES: *c1cnc2cccnc2c1] | 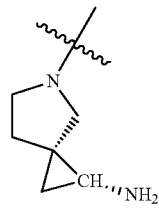 |
| 4.042 | 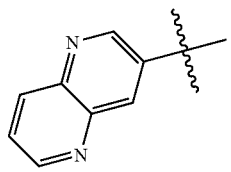 [SMILES: *c1cnc2cccnc2c1] | 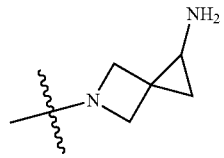 [SMILES: *N1CC2(CC2N)C1] |
| 4.043 | 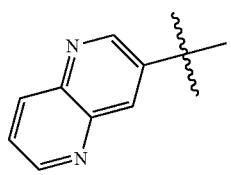 [SMILES: *c1cnc2cccnc2c1] | 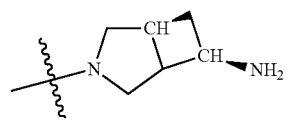 |
| 4.044 | 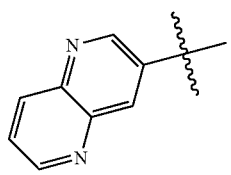 [SMILES: *c1cnc2cccnc2c1] | 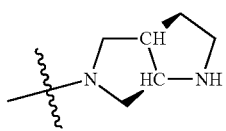 |
| 4.045 | 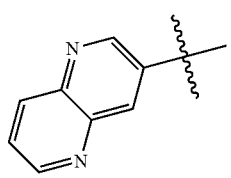 [SMILES: *c1cnc2cccnc2c1] | 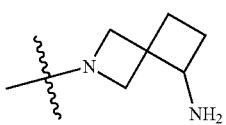 |
| 4.046 | 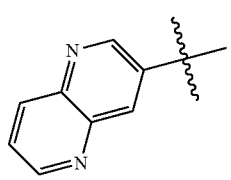 [SMILES: *c1cnc2cccnc2c1] | 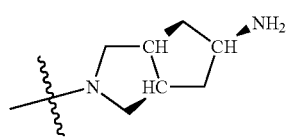 |
| 4.047 | 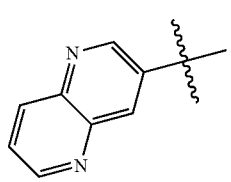 [SMILES: *c1cnc2cccnc2c1] | 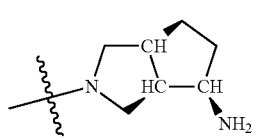 |

-continued
| | | | |
|---|---|---|---|
| 4.048 | 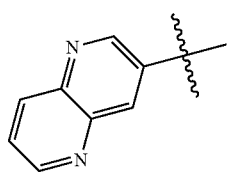 [SMILES: *c1cnc2cccnc2c1] | | 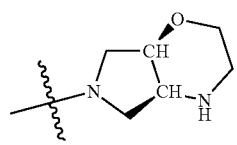 [SMILES: *N1C[C@@H]2NCCO[C@@H]2C1] |
| 4.049 | 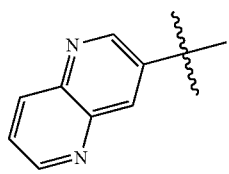 [SMILES: *c1cnc2cccnc2c1] | | 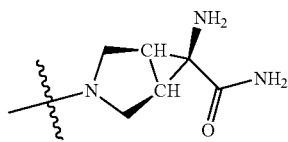 [SMILES: *N1C[C@@H]2[C@H](C1)[C@@]2(N)C(N)=O] |
| 4.050 | 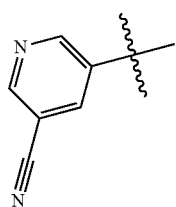 [SMILES: *c1cncc(C#N)c1] | | 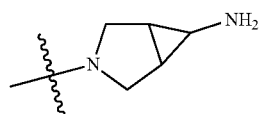 [SMILES: *N1CC2C(N)C2C1] |
| 4.051 | 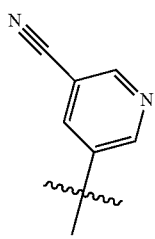 [SMILES: *c1cncc(C#N)c1] | | 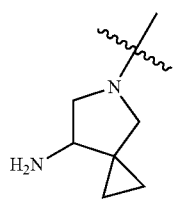 [SMILES: *N1CC(N)C2(CC2)C1] |
| 4.052 | 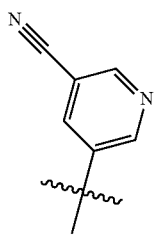 | | 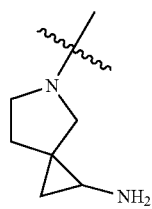 |
| 4.053 | 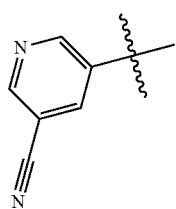 [SMILES: *c1cncc(C#N)c1] | | 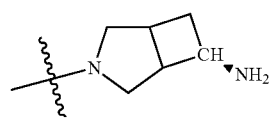 [SMILES: *N1CC2C[C@@H](N)C2C1] |
| 4.054 | 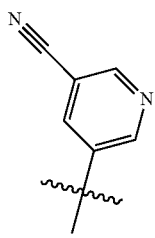 [SMILES: *c1cncc(C#N)c1] | | 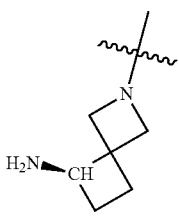 [SMILES: *N1CC2(CC[C@H]2N)C1] |

| | | |
|---|---|---|
| 4.055 | 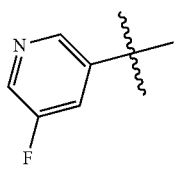 | 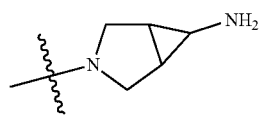 |
| 4.056 | 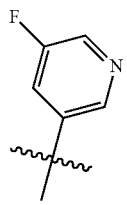 | 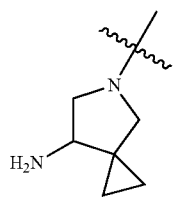 [SMILES: *N1CC(N)C2(CC2)C1] |
| 4.057 | 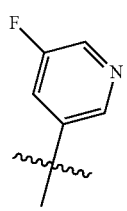 | 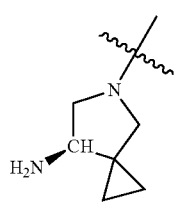 [SMILES: *N1C[C@H](N)C2(CC2)C1] |
| 4.058 | 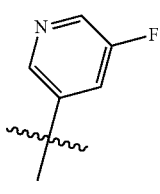 [SMILES: *c1cncc(F)c1] | 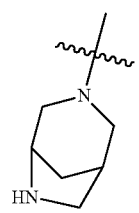 |
| 4.059 | 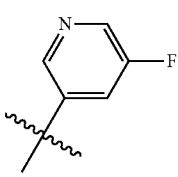 [SMILES: *c1cncc(F)c1] | 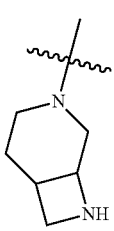 [SMILES: *N1CCC2CNC2C1] |
| 4.060 | 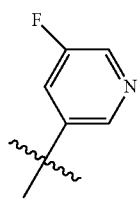 | 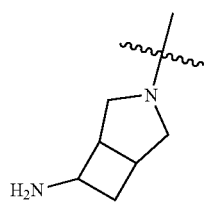 [SMILES: *N1CC2CC(N)C2C1] |
| 4.061 | 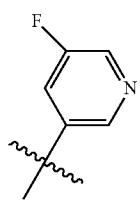 [SMILES: *c1cncc(F)c1] | 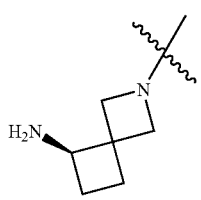 [SMILES: *N1CC2(CC[C@H]2N)C1] |

-continued
| | | |
|---|---|---|
| 4.062 | 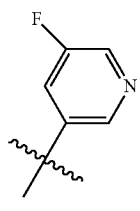 [SMILES: *c1cncc(F)c1] | 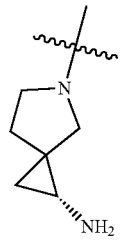 |
| 4.063 | 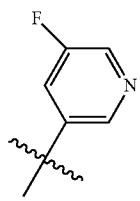 | 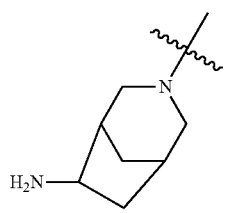 [SMILES: *N1CC2CC(N)C(C2)C1] |
| 4.064 | 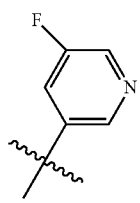 [SMILES: *c1cncc(F)c1] | 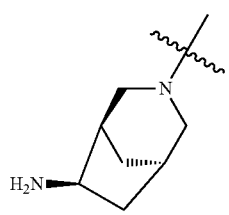 [SMILES: *N1C[C@@H]2C[C@H](C1)[C@H](N)C2] |
| 4.065 | 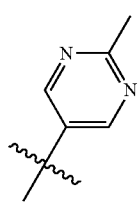 [SMILES: *c1cnc(C)nc1] | 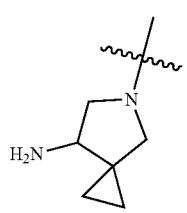 [SMILES: *N1CC(N)C2(CC2)C1] |
| 4.066 | 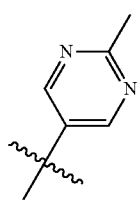 [SMILES: *c1cnc(C)nc1] | 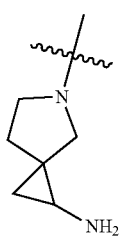 |
| 4.067 | 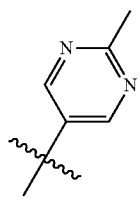 [SMILES: *c1cnc(C)nc1] | 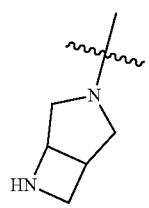 |
| 4.068 | 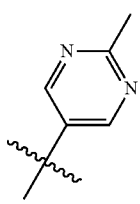 [SMILES: *c1cnc(C)nc1] | 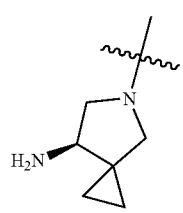 [SMILES: *N1C[C@H](N)C2(CC2)C1] |

-continued

| | | |
|---|---|---|
| 4.069 | pyrimidine (5-yl, 2-methyl) | 2-amino-5-azaspiro[3.4] with NH2 |
| 4.070 | pyrimidine (5-yl, 2-methyl) | 3-aminopyrrolidine |
| 4.071 | pyrimidine (5-yl, 2-methyl) | azepane with NH2 |
| 4.072 | pyrimidine (5-yl, 2-methyl) | 3,8-diazabicyclo[3.2.1]octane |
| 4.073 | pyrimidine (5-yl, 2-methyl) | 3-azabicyclo[3.1.0]hexan-6-amine |
| 4.074 | pyrimidine (5-yl, 2-methyl) | aminocyclopropane-spiro-pyrrolidine |
| 4.075 | pyrimidine (5-yl, 2-methyl) | octahydrocyclopenta[c]pyrrole amine |
| 4.076 | pyrimidine (5-yl, 2-methyl) | octahydrocyclopenta[c]pyrrole amine |
| 4.077 | pyrimidine (5-yl, 2-methyl) | 3-aminopiperidine |
| 4.078 | pyrimidine (5-yl, 2-methyl) | N-(3-azabicyclo[3.1.0]hexan-6-yl)glycinamide |
| 4.079 | pyrimidine (5-yl, 2-methyl) | octahydro-1H-pyrrolo[3,4-b]pyridine |

| | | |
|---|---|---|
| 4.080 | 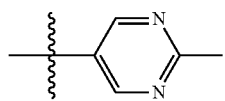 [SMILES: *c1cnc(C)nc1] | 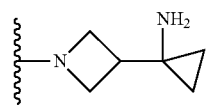 |
| 4.081 | 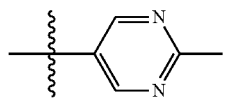 [SMILES: *c1cnc(C)nc1] | 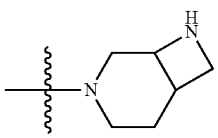 |
| 4.082 | 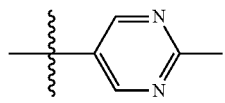 [SMILES: *c1cnc(C)nc1] | 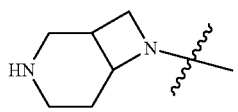 |
| 4.083 | 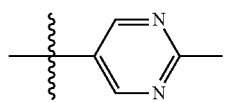 | 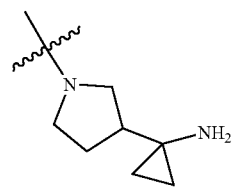 |
| 4.084 | 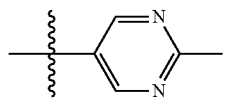 [SMILES: *c1cnc(C)nc1] | 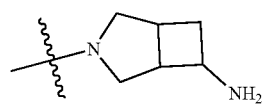 |
| 4.085 | 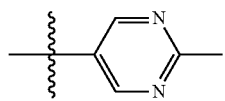 [SMILES: *c1cnc(C)nc1] | 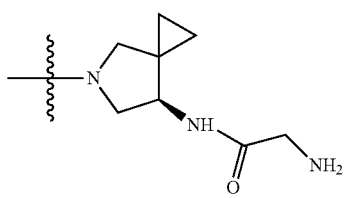 [SMILES: *N1C[C@H](NC(=O)CN)C2(CC2)C1] |
| 4.086 | 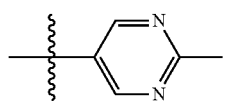 | 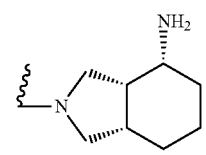 |
| 4.087 | 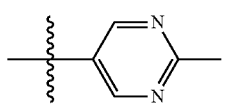 | 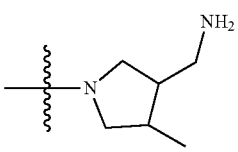 [SMILES: *N1CC(C)C(CN)C1] |
| 4.088 | 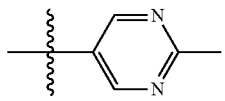 | 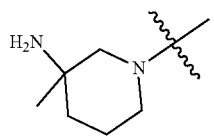 [SMILES: *N1CCCC(C)(N)C1] |
| 4.080 | 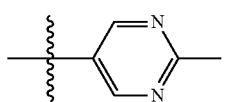 | 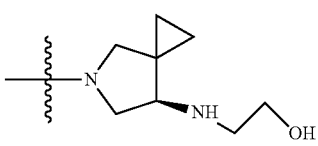 [SMILES: *N1C[C@H](NCCO)C2(CC2)C1] |

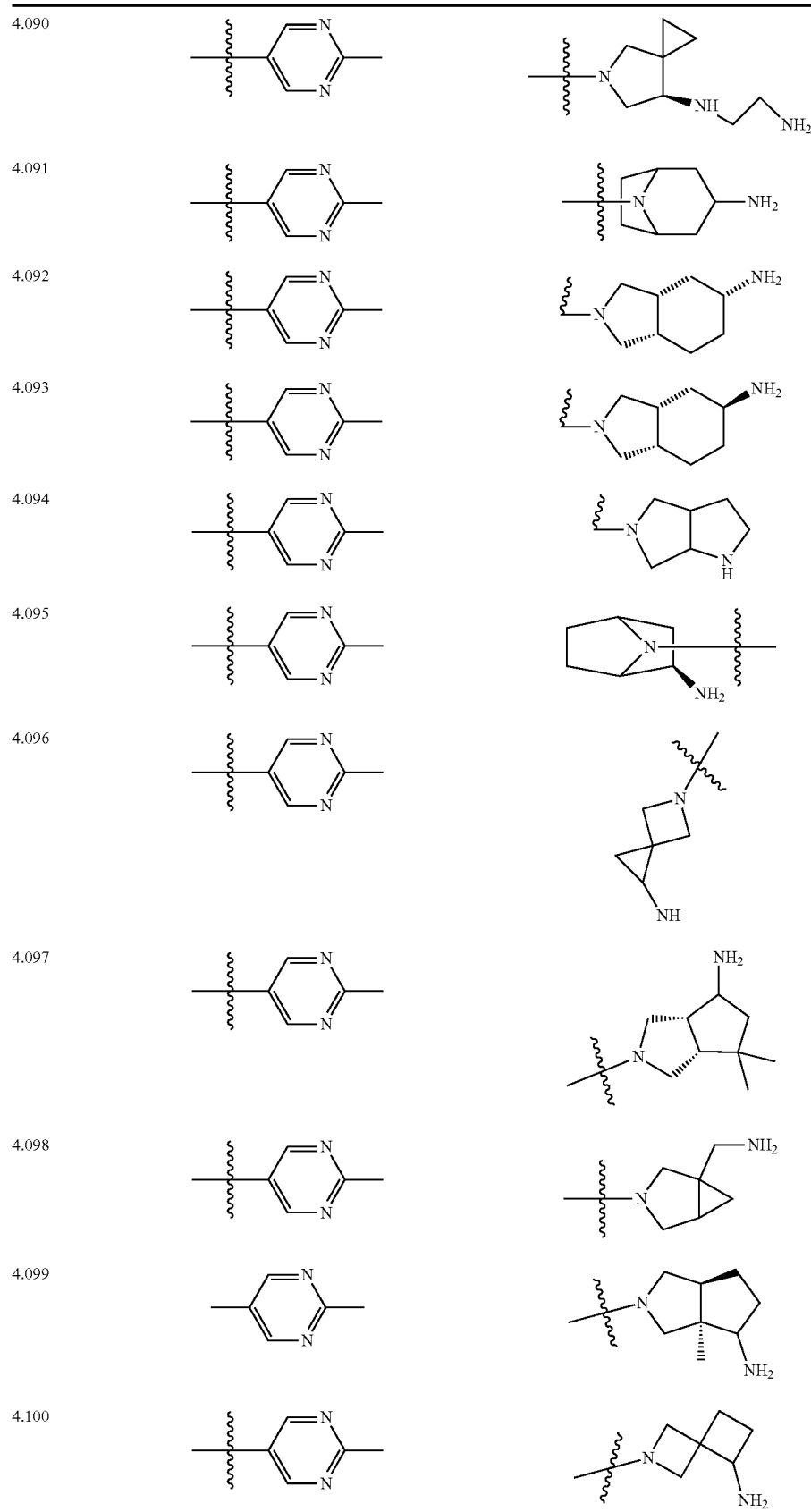

-continued
| | | |
|---|---|---|
| 4.101 | 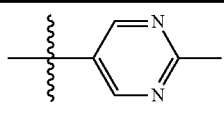 | 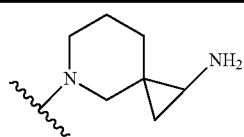 |
| 4.102 | 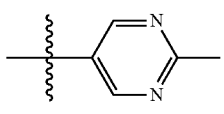 [SMILES: *c1cnc(C)nc1] | 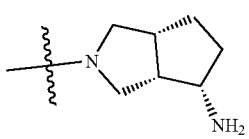 [SMILES: *N1C[C@@H]2CC[C@H](N)[C@@H]2C1] |
| 4.103 | 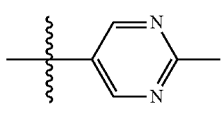 [SMILES: *c1cnc(C)nc1] | 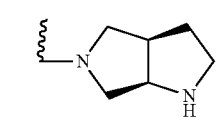 |
| 4.104 | 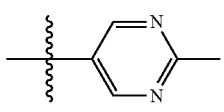 | 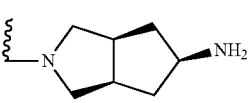 |
| 4.105 | 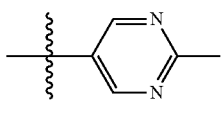 | 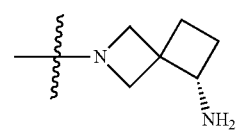 |
| 4.106 | 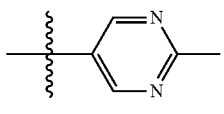 | 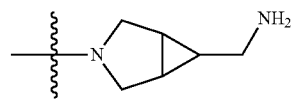 [SMILES: *N1CC2C(CN)C2C1] |
| 4.107 | 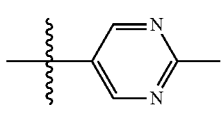 | 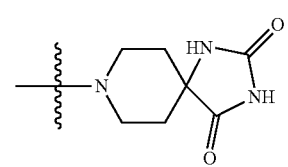 [SMILES: *N1CCC2(CC1)NC(=O)NC2=O] |
| 4.108 | 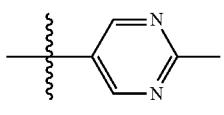 | 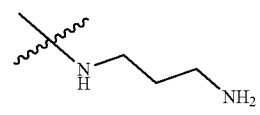 |
| 4.109 | 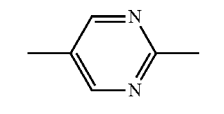 | 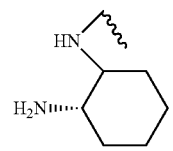 |
| 4.110 | 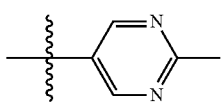 [SMILES: *c1cnc(C)nc1] | 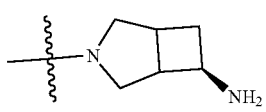 |
| 4.111 | 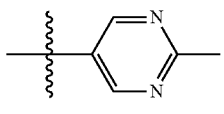 [SMILES: *c1cnc(C)nc1] | 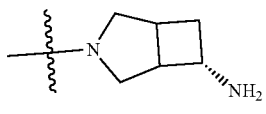 |
| 4.112 | 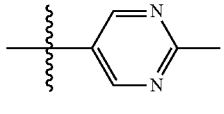 [SMILES: *c1cnc(C)nc1] | 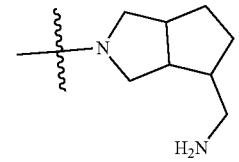 [SMILES: *N1CC2CCC(CN)C2C1] |

-continued
| | | |
|---|---|---|
| 4.113 | 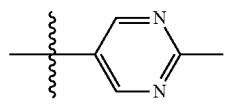 [SMILES: *c1cnc(C)nc1] | 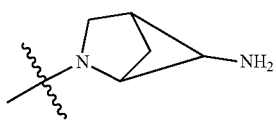 [SMILES: *N1CC2CC1C2N] |
| 4.114 | 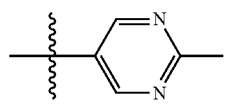 [SMILES: *c1cnc(C)nc1] | 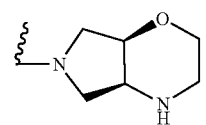 |
| 4.115 | 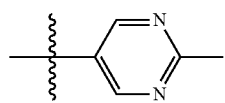 [SMILES: *c1cnc(C)nc1] | 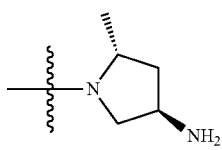 [SMILES: *N1C[C@H](N)C[C@H]1C] |
| 4.116 | 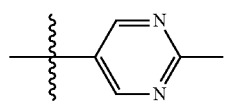 | 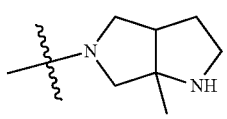 [SMILES: *N1CC2CCNC2(C)C1] |
| 4.117 | 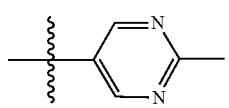 | 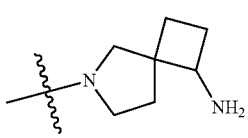 [SMILES: *N1CCC2(CCC2N)C1] |
| 4.118 | 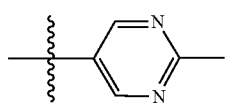 | 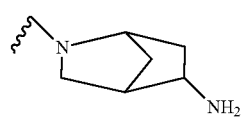 |
| 4.119 | 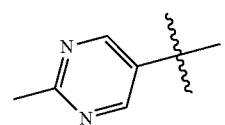 [SMILES: *c1cnc(C)nc1] | 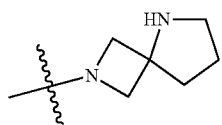 [SMILES: *N1CC2(CCCN2)C1] |
| 4.120 | 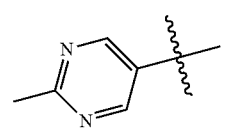 [SMILES: *c1cnc(C)nc1] | 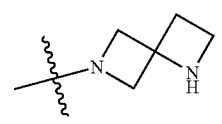 |
| 4.121 | 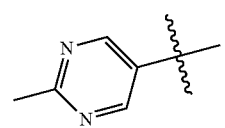 [SMILES: *c1cnc(C)nc1] | 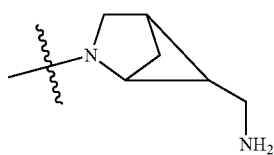 |
| 4.122 | 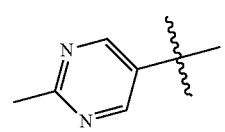 [SMILES: *c1cnc(C)nc1] | 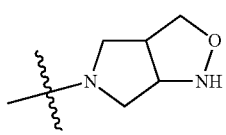 [SMILES: *N1CC2CONC2C1] |
| 4.123 | 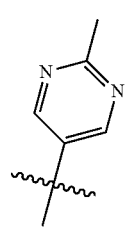 [SMILES: *c1cnc(C)nc1] | 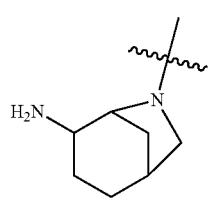 [SMILES: *N1CC2CCC(N)C1C2] |

-continued
| | | |
|---|---|---|
| 4.124 | 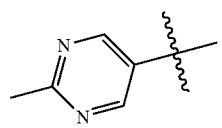 | 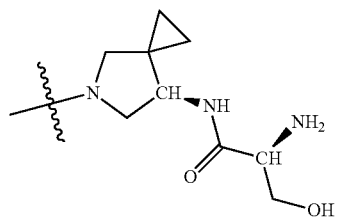 [SMILES: *N1C[C@H](NC(=O)[C@@H](N)CO)C2(CC2)C1] |
| 4.125 | 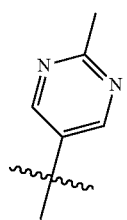 [SMILES: *c1cnc(C)nc1] | 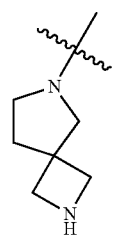 [SMILES: *N1CCC2(CNC2)C1] |
| 4.126 | 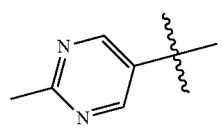 [SMILES: *c1cnc(C)nc1] | 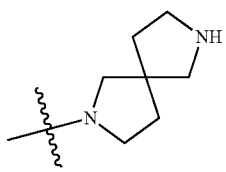 [SMILES: *N1CCC2(CCNC2)C1] |
| 4.127 | 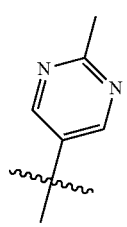 [SMILES: *c1cnc(C)nc1] | 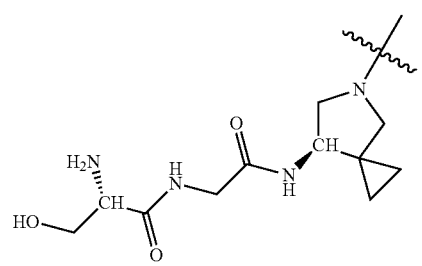 [SMILES: *N1C[C@H](NC(=O)CNC(=O)[C@@H](N)CO)C2(CC2)C1] |
| 4.128 | 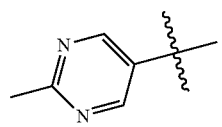 [SMILES: *c1cnc(C)nc1] | 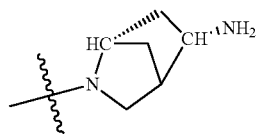 [SMILES: *N1CC2C[C@H]1C[C@@H]2N] |
| 4.129 | 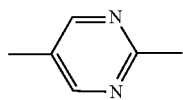 | 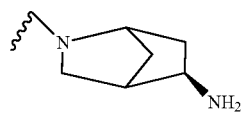 |
| 4.130 | 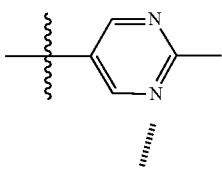 | 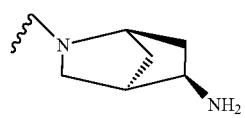 |
| 4.131 | 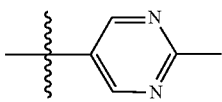 [SMILES: *c1cnc(C)nc1] | 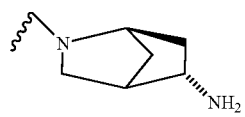 |

-continued
| | | |
|---|---|---|
| 4.132 | 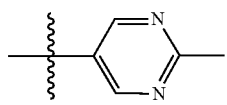 | 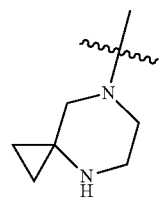 |
| 4.133 | 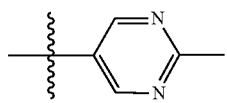 [SMILES: *c1cnc(C)nc1] | 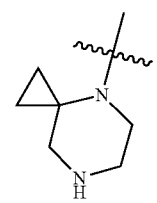 |
| 4.134 | 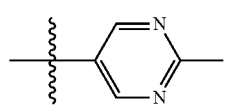 [SMILES: *c1cnc(C)nc1] | 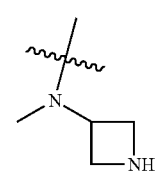 [SMILES: *N(C)C1CNC1] |
| 4.135 | 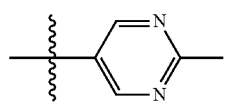 | 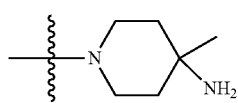 |
| 4.136 | 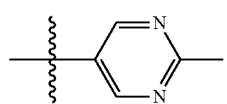 | 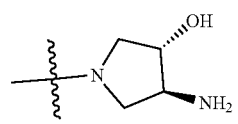 [SMILES: *N1C[C@H](N)[C@@H](O)C1] |
| 4.137 | 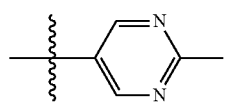 | 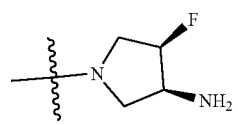 [SMILES: *N1C[C@@H](F)[C@@H](N)C1] |
| 4.138 | 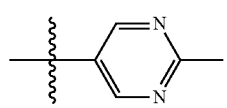 [SMILES: *c1cnc(C)nc1] | 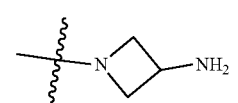 |
| 4.139 | 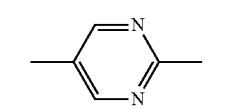 | 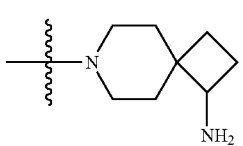 |
| 4.140 | 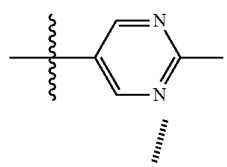 | 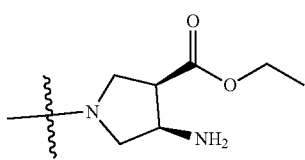 [SMILES: *N1C[C@H](N)[C@H](C(=O)OCC)C1] |
| 4.141 | 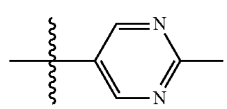 | 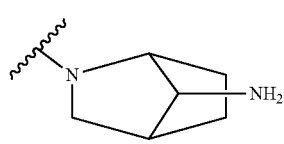 [SMILES: *N1CC2CCC1C2N] |

| | | |
|---|---|---|
| 4.142 | 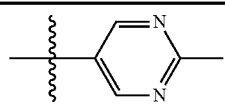 | 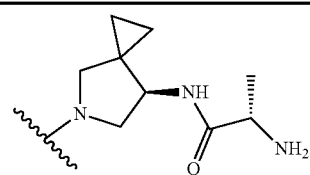 |
| 4.143 | 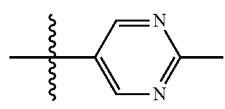 | 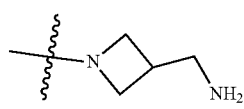 |
| 4.144 | 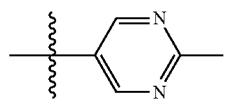 | 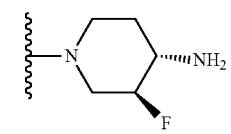 [SMILES: *N1CC[C@H](N)[C@@H](F)C1] |
| 4.145 | 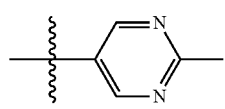 | 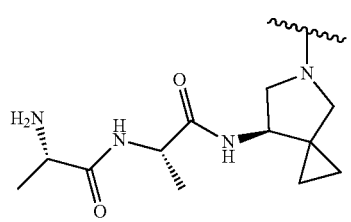 [SMILES: *N1C[C@H](NC(=O)[C@H](C)NC(=O)[C@H](C)N)C2(CC2)C1] |
| 4.146 | 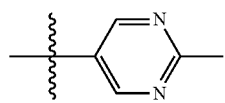 | 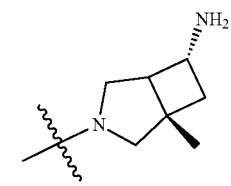 [SMILES: *N1CC2[C@H](N)C[C@]2(C)C1] |
| 4.147 | 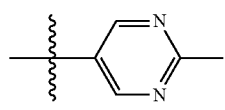 | 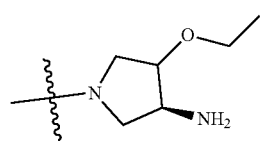 [SMILES: *N1CC(OCC)[C@@H](N)C1] |
| 4.148 | 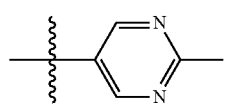 [SMILES: *c1cnc(C)nc1] | 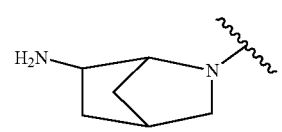 |
| 4.149 | 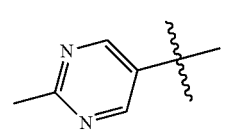 [SMILES: *c1cnc(C)nc1] | 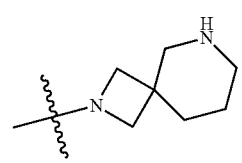 [SMILES: *N1CC2(CCCNC2)C1] |
| 4.150 | 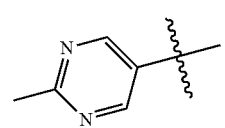 [SMILES: *c1cnc(C)nc1] | 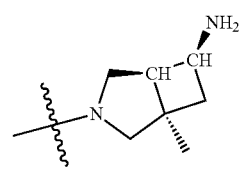 [SMILES: *N1C[C@H]2[C@@H](N)C[C@@]2(C)C1] |
| 4.151 | 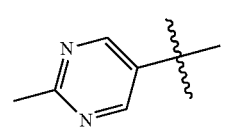 | 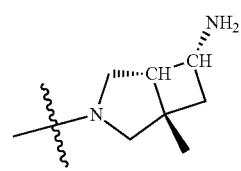 [SMILES: *N1C[C@@H]2[C@H](N)C[C@]2(C)C1] |

-continued
| | | |
|---|---|---|
| 4.152 | 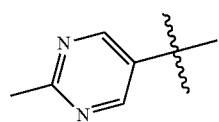 [SMILES: *c1cnc(C)nc1] | 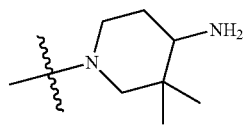 [SMILES: *N1CCC(N)C(C)(C)C1] |
| 4.153 | 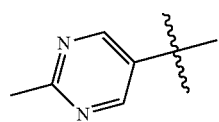 [SMILES: *c1cnc(C)nc1] | 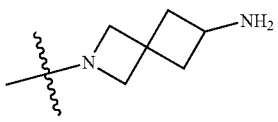 [SMILES: *N1CC2(CC(N)C2)C1] |
| 4.154 | 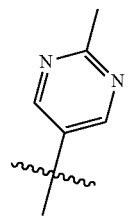 [SMILES: *c1cnc(C)nc1] | 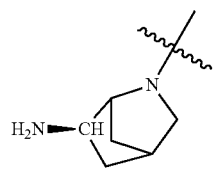 |
| 4.155 | 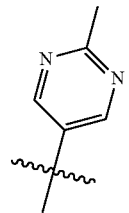 [SMILES: *c1cnc(C)nc1] | 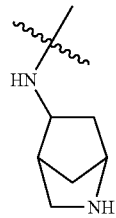 |
| 4.156 | 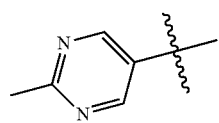 [SMILES: *c1cnc(C)nc1] | 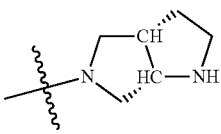 [SMILES: *N1C[C@@H]2CCN[C@@H]2C1] |
| 4.157 | 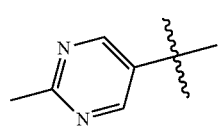 [SMILES: *c1cnc(C)nc1] | 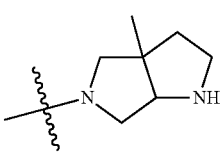 [SMILES: *N1CC2NCCC2(C)C1] |
| 4.158 | 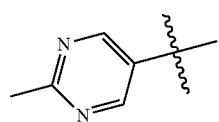 [SMILES: *c1cnc(C)nc1] | 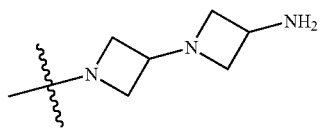 [SMILES: *N1CC(N2CC(N)C2)C1] |
| 4.159 | 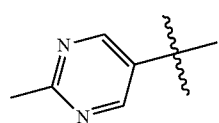 [SMILES: *c1cnc(C)nc1] | 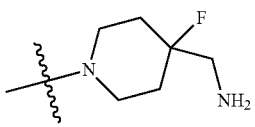 [SMILES: *N1CCC(F)(CN)CC1] |
| 4.160 | 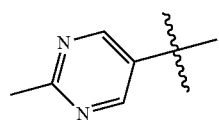 [SMILES: *c1cnc(C)nc1] | 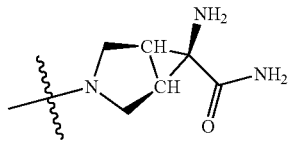 [SMILES: *N1C[C@@H]2[C@H](C1)[C@@]2(N)C(N)=O] |
| 4.161 | 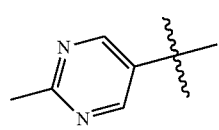 [SMILES: *c1cnc(C)nc1] | 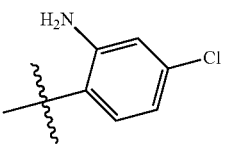 [SMILES: *c1ccc(Cl)cc1N] |

| | | |
|---|---|---|
| 4.162 | 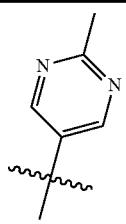 | 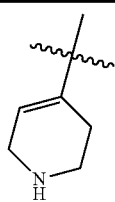 |
| 4.163 | 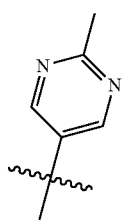 [SMILES: *c1cnc(C)nc1] | 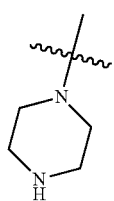 [SMILES: *N1CCNCC1] |
| 4.164 | 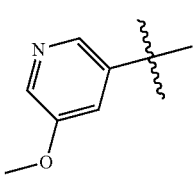 [SMILES: *c1cncc(OC)c1] | 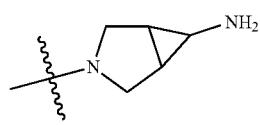 |
| 4.165 | 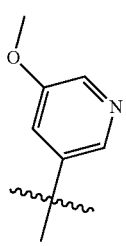 [SMILES: *c1cncc(OC)c1] | 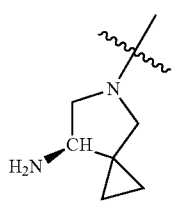 [SMILES: *N1C[C@H](N)C2(CC2)C1] |
| 4.166 | 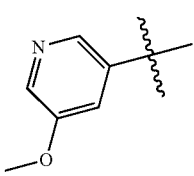 [SMILES: *c1cncc(OC)c1] | 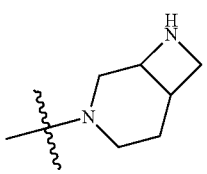 [SMILES: *N1CCC2CNC2C1] |
| 4.167 | 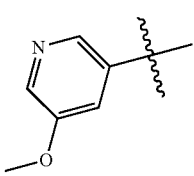 [SMILES: *c1cncc(OC)c1] | 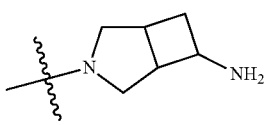 [SMILES: *N1CC2CC(N)C2C1] |
| 4.168 | 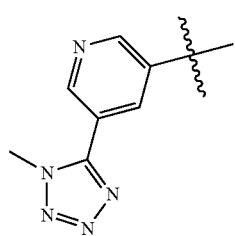 [SMILES: *c1cncc(-c2nnnn2C)c1] | 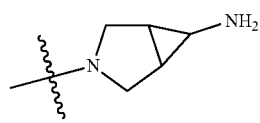 [SMILES: *N1CC2C(N)C2C1] |
| 4.169 | 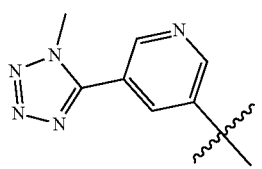 [SMILES: *c1cncc(-c2nnnn2C)c1] | 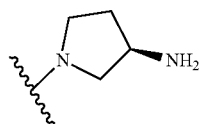 [SMILES: *N1CC[C@@H](N)C1] |

-continued
| | | | |
|---|---|---|---|
| 4.170 | 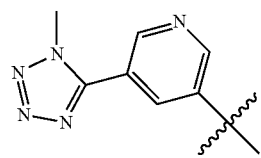 [SMILES: *c1cncc(-c2nnnn2C)c1] | | 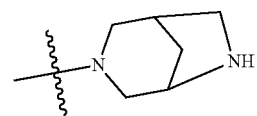 [SMILES: *N1CC2CNC(C2)C1] |
| 4.171 | 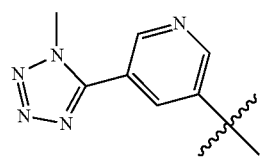 [SMILES: *c1cncc(-c2nnnn2C)c1] | | 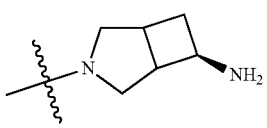 [SMILES: *N1CC2C[C@@H](N)C2C1] |
| 4.172 | 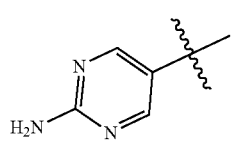 [SMILES: *c1cnc(N)nc1] | | 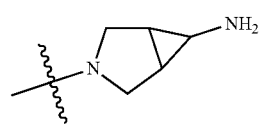 [SMILES: *N1CC2C(N)C2C1] |
| 4.173 | 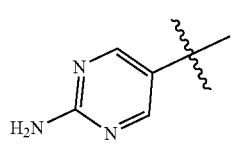 [SMILES: *c1cnc(N)nc1] | | 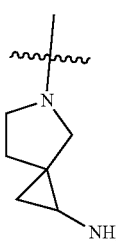 |
| 4.174 | 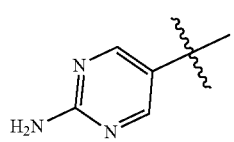 [SMILES: *c1cnc(N)nc1] | | 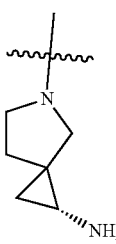 |
| 4.175 | 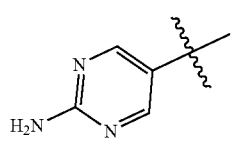 [SMILES: *c1cnc(N)nc1] | | 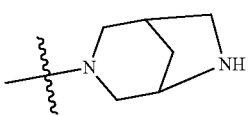 |
| 4.176 | 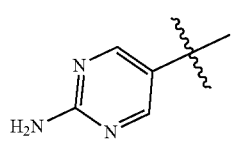 [SMILES: *c1cnc(N)nc1] | | 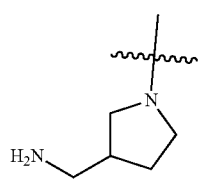 |
| 4.177 | 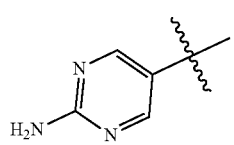 [SMILES: *c1cnc(N)nc1] | | 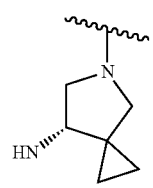 [SMILES: *N1C[C@@H](N)C2(CC2)C1] |

-continued
| | | |
|---|---|---|
| 4.178 | 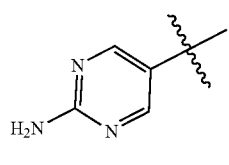 | 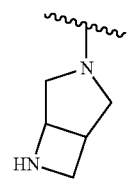 |
| 4.179 | 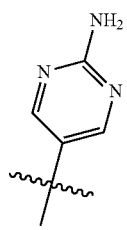 [SMILES: *c1cnc(N)nc1] | 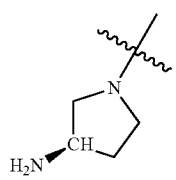 |
| 4.180 | 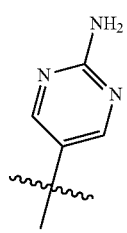 [SMILES: *c1cnc(N)nc1] | 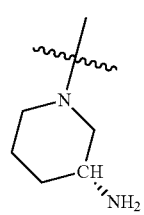 |
| 4.181 | 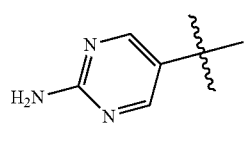 | 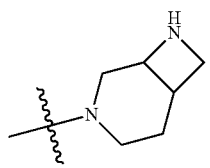 [SMILES: *N1CCC2CNC2C1] |
| 4.182 | 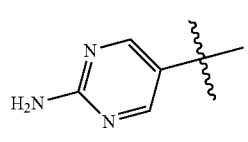 | 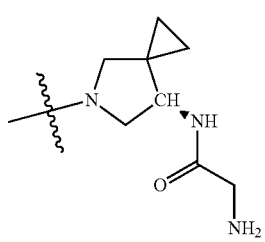 [SMILES: *N1C[C@H](NC(=O)CN)C2(CC2)C1] |
| 4.183 | 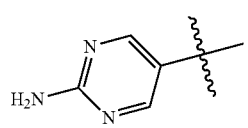 | 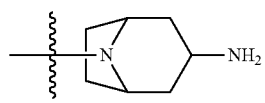 |
| 4.184 | 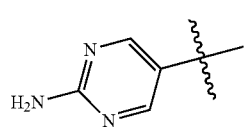 [SMILES: *c1cnc(N)nc1] | 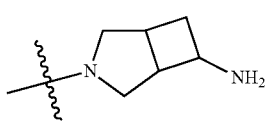 |
| 4.185 | 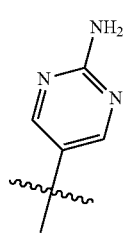 [SMILES: *c1cnc(N)nc1] | 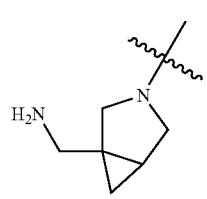 [SMILES: *N1CC2CC2(CN)C1] |

-continued
| | | | |
|---|---|---|---|
| 4.186 | 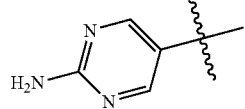 [SMILES: *c1cnc(N)nc1] | | 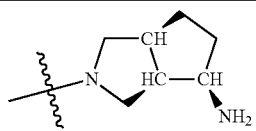 |
| 4.187 | 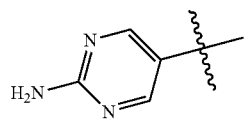 [SMILES: *c1cnc(N)nc1] | | 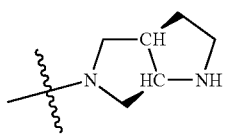 |
| 4.188 | 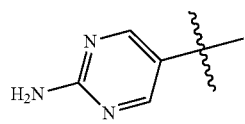 [SMILES: *c1cnc(N)nc1] | | 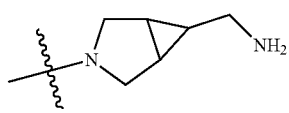 [SMILES: *N1CC2C(CN)C2C1] |
| 4.189 | 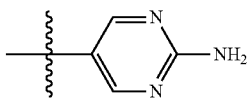 | | 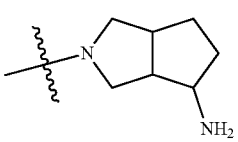 [SMILES: *N1CC2CCC(N)C2C1] |
| 4.190 | 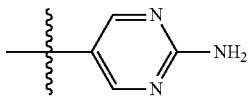 | | 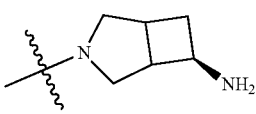 [SMILES: *N1CC2C[C@@H](N)C2C1] |
| 4.191 | 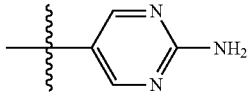 | | 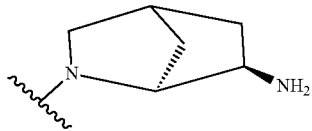 [SMILES: *N1CC2C[C@@H](N)[C@@H]1C2] |
| 4.192 | 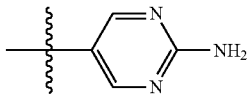 | | 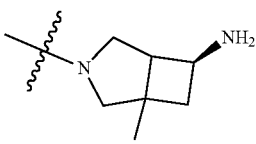 [SMILES: *N1CC2[C@@H](N)CC2(C)C1] |
| 4.193 | 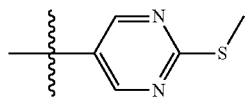 | | 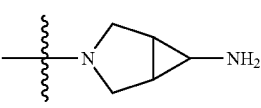 [SMILES: *N1CC2C(N)C2C1] |
| 4.194 | 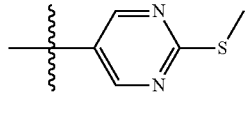 [SMILES: *c1cnc(SC)nc1] | | 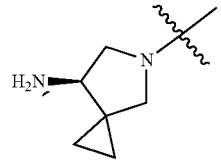 |
| 4.195 | 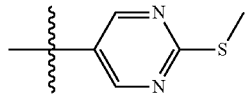 [SMILES: *c1cnc(SC)nc1] | | 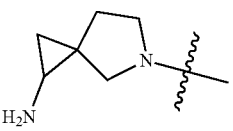 |
| 4.196 | 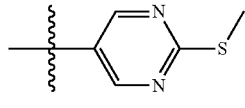 | | 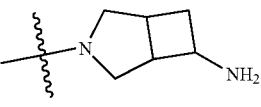 [SMILES: *N1CC2CC(N)C2C1] |
| 4.197 | 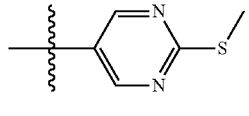 | | 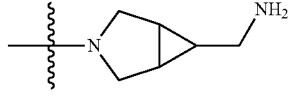 [SMILES: *N1CC2C(CN)C2C1] |

| | | |
|---|---|---|
| 4.198 | pyrimidine-SMe | octahydropyrrolo[3,4-b]pyrrole |
| 4.199 | pyrimidine-SMe | 3-aminopyrrolidine |
| 4.200 | pyrimidine-SMe | octahydrocyclopenta[c]pyrrol-4-amine |
| 4.201 | pyrimidine-SMe | 6-amino-3-azabicyclo[3.2.0]heptane |
| 4.202 | pyrimidine-SMe | 2-azaspiro[3.3]heptan-6-amine |
| 4.203 | pyrimidine-SMe | 5-azaspiro[2.4]heptan-1-amine |
| 4.204 | pyrimidine-SMe | 2-azabicyclo[2.2.1]heptan-5-amine |
| 4.205 | 5-(pyrimidin-5-yl)pyridine | 3-azabicyclo[3.1.0]hexan-6-amine |
| 4.206 | 5-(1H-pyrazol-4-yl)pyridine | 3-azabicyclo[3.1.0]hexan-6-amine |
| 4.207 | 2-(dimethylamino)pyrimidine | 3-aminopyrrolidine |
| 4.208 | 2-(dimethylamino)pyrimidine | 3-azabicyclo[3.1.0]hexan-6-amine |

-continued
| | | |
|---|---|---|
| 4.209 | 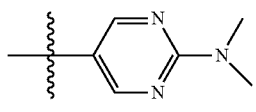 [SMILES: *c1cnc(N(C)C)nc1] | 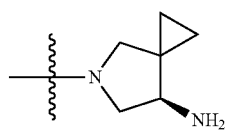 |
| 4.210 | 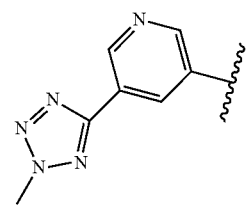 [SMILES: *c1cncc(-c2nnn(C)n2)c1] | 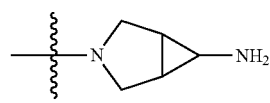 [SMILES: *N1CC2C(N)C2C1] |
| 4.211 | 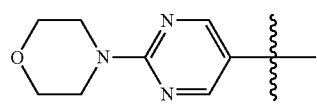 [SMILES: *c1cnc(N2CCOCC2)nc1] | 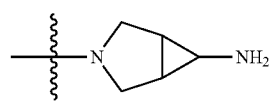 [SMILES: *N1CC2C(N)C2C1] |
| 4.212 | 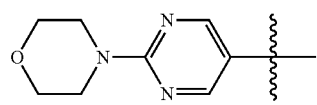 [SMILES: *c1cnc(N2CCOCC2)nc1] | 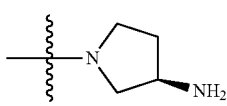 [SMILES: *N1CC[C@@H](N)C1] |
| 4.213 | 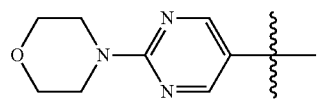 | 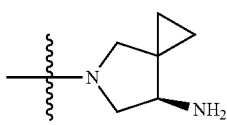 |
| 4.214 | 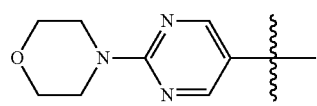 | 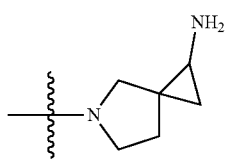 [SMILES: *N1CCC2(CC2N)C1] |
| 4.215 | 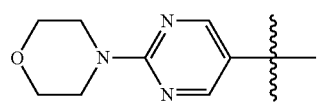 [SMILES: *c1cnc(N2CCOCC2)nc1] | 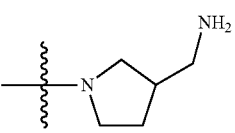 [SMILES: *N1CCC(CN)C1] |
| 4.216 | 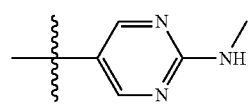 | 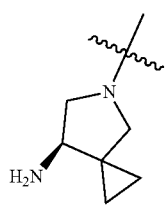 [SMILES: *N1C[C@H](N)C2(CC2)C1] |
| 4.217 | 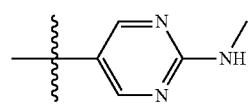 | 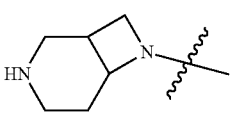 |
| 4.218 | 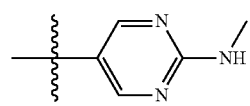 | 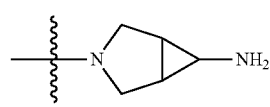 [SMILES: *N1CC2C(N)C2C1] |
| 4.219 | 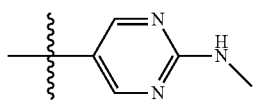 [SMILES: *c1cnc(NC)nc1] | 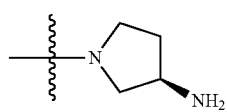 |

-continued
| | | |
|---|---|---|
| 4.220 | 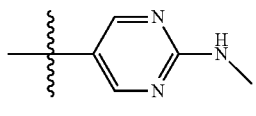 | 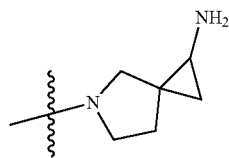 [SMILES: *N1CCC2(CC2N)C1] |
| 4.221 | 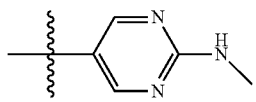 | 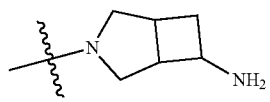 [SMILES: *N1CC2CC(N)C2C1] |
| 4.222 | 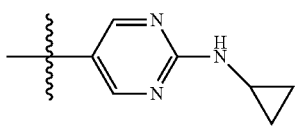 | 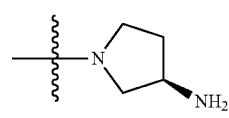 |
| 4.223 | 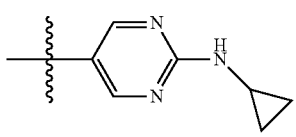 [SMILES: *c1cnc(NC2CC2)nc1] | 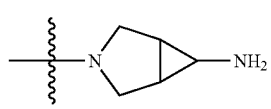 [SMILES: *N1CC2C(N)C2C1] |
| 4.224 | 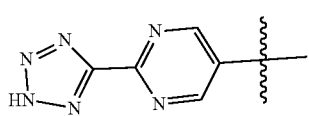 | 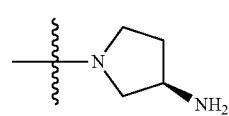 |
| 4.225 | 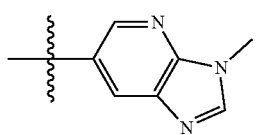 [SMILES: *c1cnc2c(c1)ncn2C] | 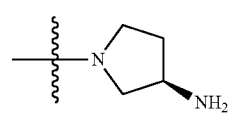 |
| 4.226 | 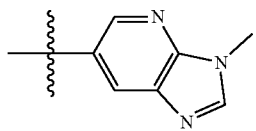 [SMILES: *c1cnc2c(c1)ncn2C] | 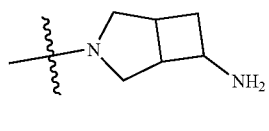 [SMILES: *N1CC2CC(N)C2C1] |
| 4.227 | 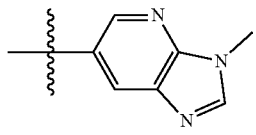 [SMILES: *c1cnc2c(c1)ncn2C] | 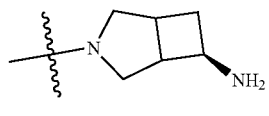 [SMILES: *N1CC2C[C@@H](N)C2C1] |
| 4.228 | 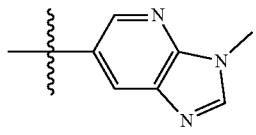 [SMILES: *c1cnc2c(c1)ncn2C] | 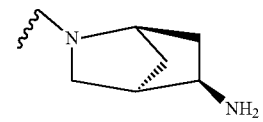 |
| 4.229 | 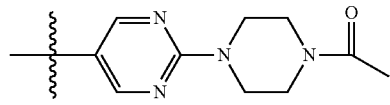 [SMILES: *c1cnc(N2CCN(C(C)=O)CC2)nc1] | 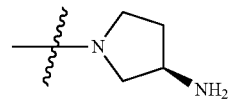 |
| 4.230 | 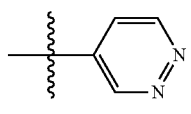 [SMILES: *c1ccnnc1] | 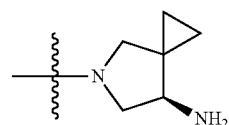 |

| | | |
|---|---|---|
| 4.231 | 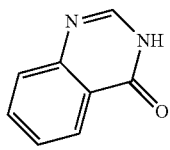 [SMILES: O=c1[nH]cnc2ccccc12] | 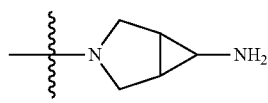 [SMILES: *N1CC2C(N)C2C1] |
| 4.232 | 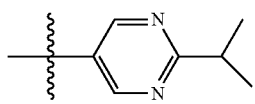 [SMILES: *c1cnc(C(C)C)nc1] | 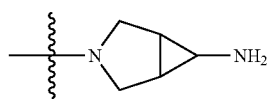 [SMILES: *N1CC2C(N)C2C1] |
| 4.233 | 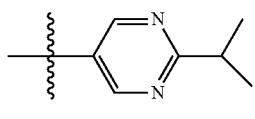 [SMILES: *c1cnc(C(C)C)nc1] | 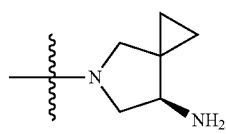 [SMILES: *N1C[C@H](N)C2(CC2)C1] |
| 4.234 | 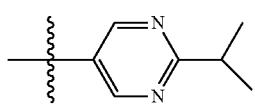 [SMILES: *c1cnc(C(C)C)nc1] | 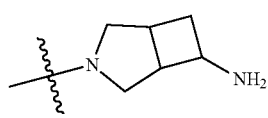 [SMILES: *N1CC2CC(N)C2C1] |
| 4.235 | 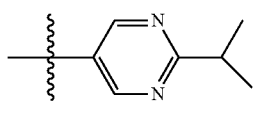 [SMILES: *c1cnc(C(C)C)nc1] | 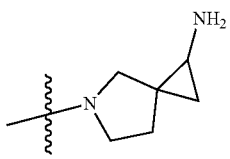 [SMILES: *N1CCC2(CC2N)C1] |
| 4.236 | 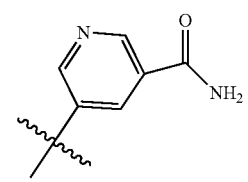 [SMILES: *c1cncc(C(N)=O)c1] | 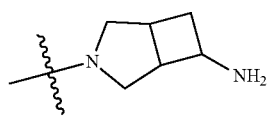 [SMILES: *N1CC2CC(N)C2C1] |
| 4.237 | 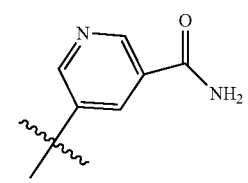 [SMILES: *c1cncc(C(N)=O)c1] | 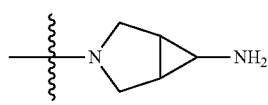 [SMILES: *N1CC2C(N)C2C1] |
| 4.238 | 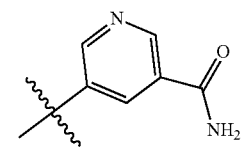 [SMILES: *c1cncc(C(N)=O)c1] | 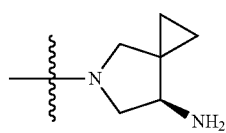 |
| 4.239 | 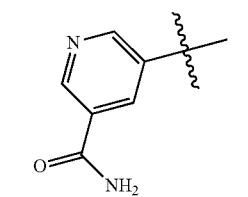 [SMILES: *c1cncc(C(N)=O)c1] |  |
| 4.240 | 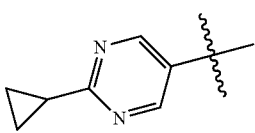 [SMILES: *c1cnc(C2CC2)nc1] | 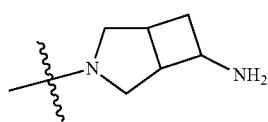 [SMILES: *N1CC2CC(N)C2C1] |

| | | |
|---|---|---|
| 4.241 | 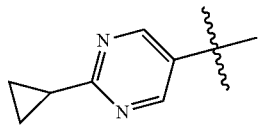 | 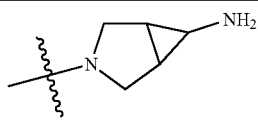 |
| 4.242 | 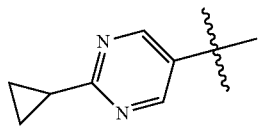 | 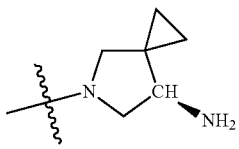 [SMILES: *N1C[C@H](N)C2(CC2)C1] |
| 4.243 | 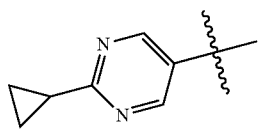 [SMILES: *c1cnc(C2CC2)nc1] | 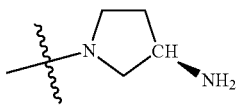 |
| 4.244 | 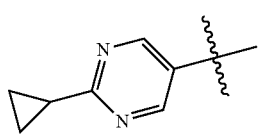 [SMILES: *c1cnc(C2CC2)nc1] | 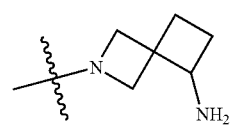 [SMILES: *N1CC2(CCC2N)C1] |
| 4.245 | 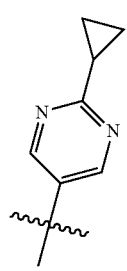 [SMILES: *c1cnc(C2CC2)nc1] | 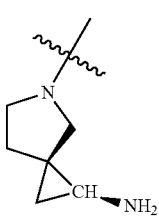 |
| 4.246 | 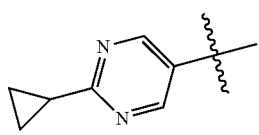 [SMILES: *c1cnc(C2CC2)nc1] | 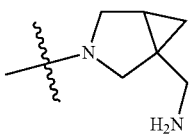 [SMILES: *N1CC2CC2(CN)C1] |
| 4.247 | 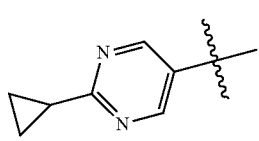 | 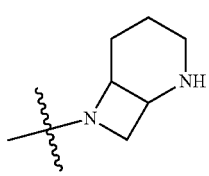 [SMILES: *N1CC2NCCCC21] |
| 4.248 | 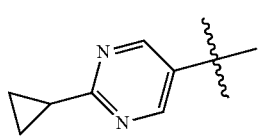 [SMILES: *c1cnc(C2CC2)nc1] | 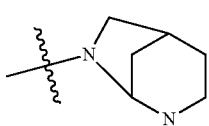 |
| 4.249 | 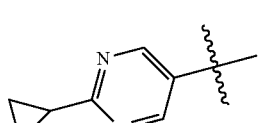 | 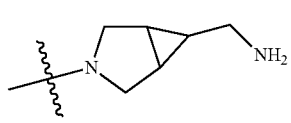 [SMILES: *N1CC2C(CN)C2C1] |
| 4.250 | 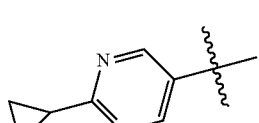 | 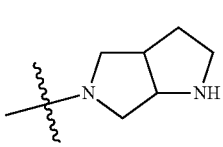 [SMILES: *N1CC2CCNC2C1] |

-continued
| | | |
|---|---|---|
| 4.251 | 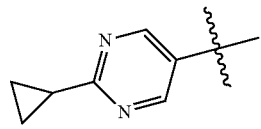 [SMILES: *c1cnc(C2CC2)nc1] | 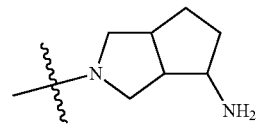 [SMILES: *N1CC2CCC(N)C2C1] |
| 4.252 | 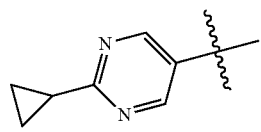 [SMILES: *c1cnc(C2CC2)nc1] | 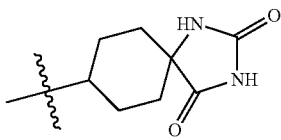 [SMILES: *C1CCC2(CC1)NC(=O)NC2=O] |
| 4.253 | 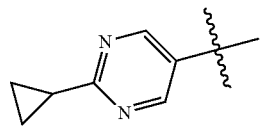 [SMILES: *c1cnc(C2CC2)nc1] | 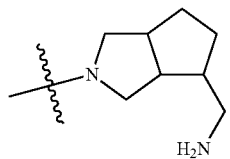 |
| 4.254 | 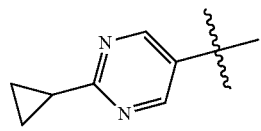 |  |
| 4.255 | 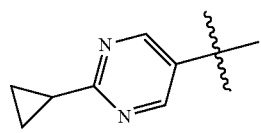 [SMILES: *c1cnc(C2CC2)nc1] | 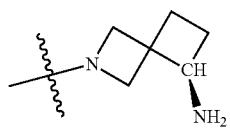 [SMILES: *N1CC2(CC[C@H]2N)C1] |
| 4.256 | 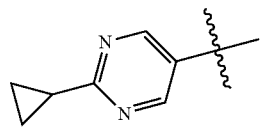 [SMILES: *c1cnc(C2CC2)nc1] | 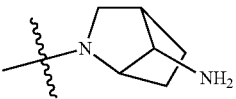 [SMILES: *N1CC2CCC1C2N] |
| 4.257 | 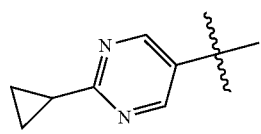 [SMILES: *c1cnc(C2CC2)nc1] | 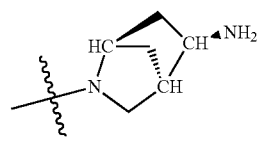 [SMILES: *N1C[C@H]2C[C@@H]1C[C@H]2N] |
| 4.258 | 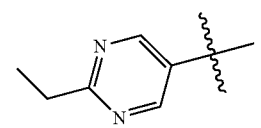 [SMILES: *c1cnc(CC)nc1] | 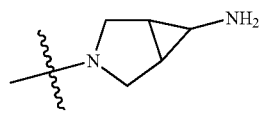 |
| 4.259 | 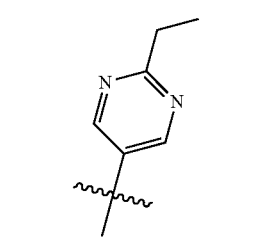 [SMILES: *c1cnc(CC)nc1] | 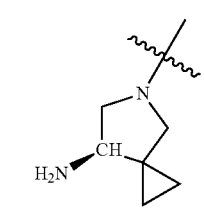 [SMILES: *N1C[C@H](N)C2(CC2)C1] |
| 4.260 | 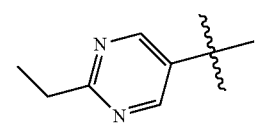 [SMILES: *c1cnc(CC)nc1] | 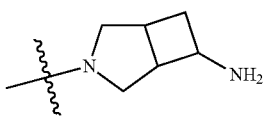 [SMILES: *N1CC2CC(N)C2C1] |

| | | |
|---|---|---|
| 4.261 | 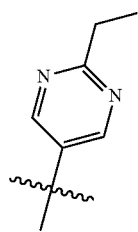 [SMILES: *c1cnc(CC)nc1] | 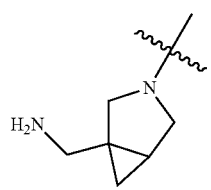 [SMILES: *N1CC2CC2(CN)C1] |
| 4.262 | 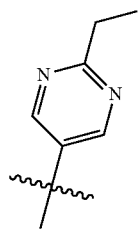 [SMILES: *c1cnc(CC)nc1] | 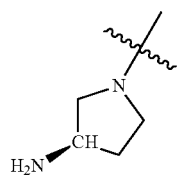 |
| 4.263 | 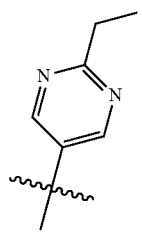 [SMILES: *c1cnc(CC)nc1] | 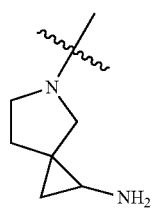 |
| 4.264 | 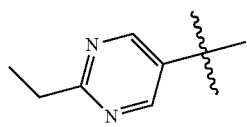 | 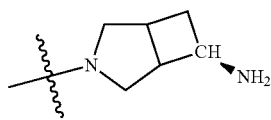 [SMILES: *N1CC2C[C@@H](N)C2C1] |
| 4.265 | 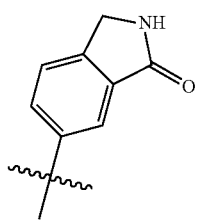 [SMILES: *c1ccc2c(c1)C(=O)NC2] | 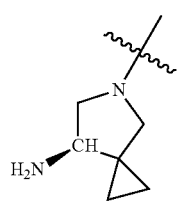 [SMILES: *N1C[C@H](N)C2(CC2)C1] |
| 4.266 | 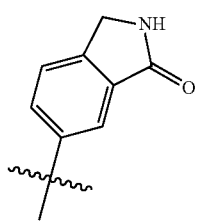 [SMILES: *c1ccc2c(c1)C(=O)NC2] | 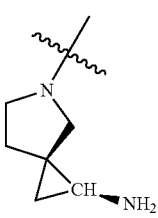 [SMILES: *N1CC[C@]2(C[C@@H]2N)C1] |
| 4.267 | 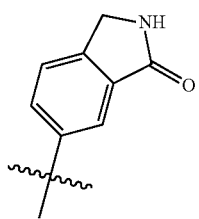 [SMILES: *c1ccc2c(c1)C(=O)NC2] | 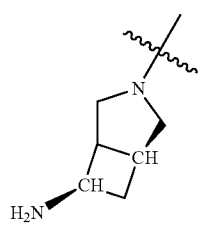 |

| | | |
|---|---|---|
| 4.269 | 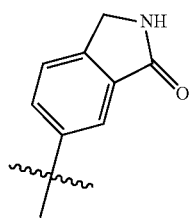 [SMILES: *c1ccc2c(c1)C(=O)NC2] | 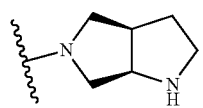 [SMILES: *N1C[C@H]2CCN[C@H]2C1] |
| 4.270 | 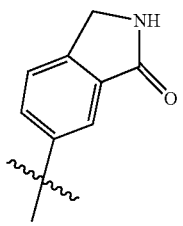 [SMILES: *c1ccc2c(c1)C(=O)NC2] | 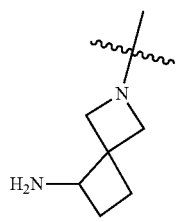 |
| 4.271 | 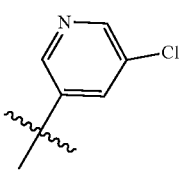 [SMILES: *c1cncc(Cl)c1] | 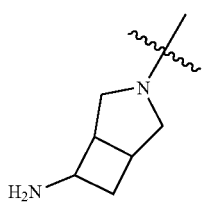 [SMILES: *N1CC2CC(N)C2C1] |
| 4.272 | 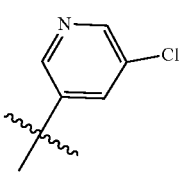 [SMILES: *c1cncc(Cl)c1] | 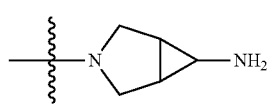 [SMILES: *N1CC2C(N)C2C1] |
| 4.273 | 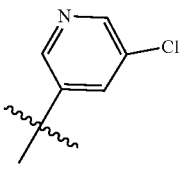 | 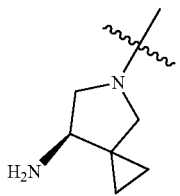 |
| 4.274 | 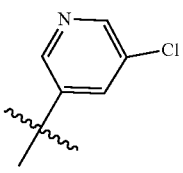 [SMILES: *c1cncc(Cl)c1] | 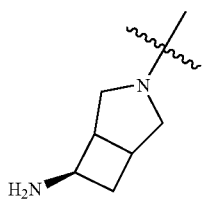 [SMILES: *N1CC2C[C@@H](N)C2C1] |
| 4.275 | 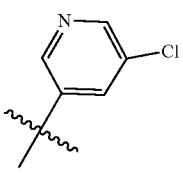 [SMILES: *c1cncc(Cl)c1] | 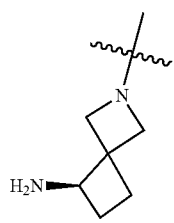 |

| | | |
|---|---|---|
| 4.276 |  | |
| 4.277 |  | |
| 4.278 |  | |
| 4.279 |  | |
| 4.280 |  | |
| 4.281 |  | |
| 4.282 |  | |
| 4.283 |  | |

-continued
| | | |
|---|---|---|
| 4.284 | 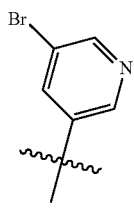 [SMILES: *c1cncc(Cl)c1] | 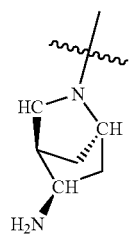 |
| 4.285 | 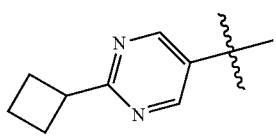 [SMILES: *c1cnc(C2CCC2)nc1] | 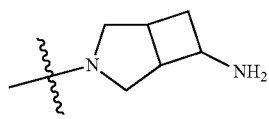 |
| 4.286 | 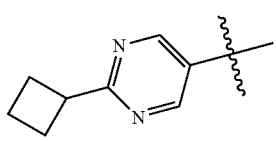 | 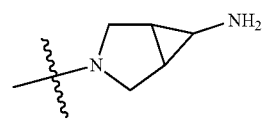 [SMILES: *N1CC2C(N)C2C1] |
| 4.287 | 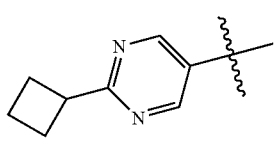 [SMILES: *c1cnc(C2CCC2)nc1] | 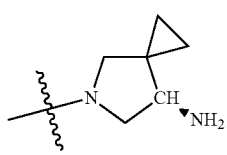 [SMILES: *N1C[C@H](N)C2(CC2)C1] |
| 4.288 | 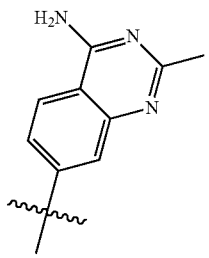 [SMILES: *c1ccc2c(N)nc(C)nc2c1] | 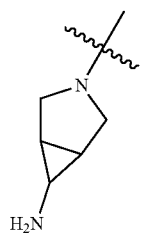 [SMILES: *N1CC2C(N)C2C1] |
| 4.290 | 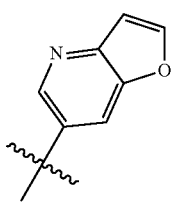 [SMILES: *c1cnc2ccoc2c1] | 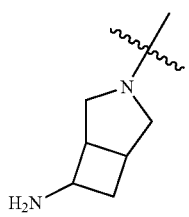 |
| 4.291 | 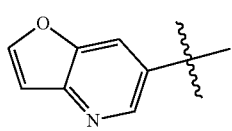 [SMILES: *c1cnc2ccoc2c1] | 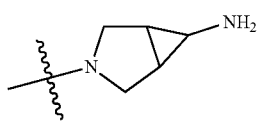 |
| 4.292 | 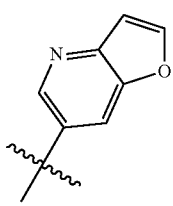 [SMILES: *c1cnc2ccoc2c1] | 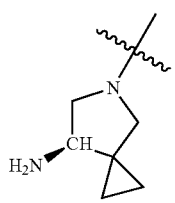 [SMILES: *N1C[C@H](N)C2(CC2)C1] |

-continued
| | | | |
|---|---|---|---|
| 4.293 | 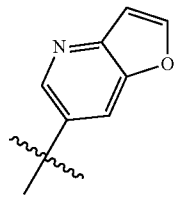 [SMILES: *c1cnc2ccoc2c1] | | 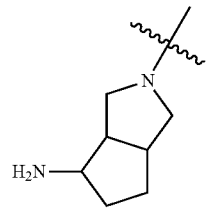 [SMILES: *N1CC2CCC(N)C2C1] |
| 4.294 | 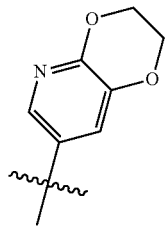 [SMILES: *c1cnc2c(c1)OCCO2] | | 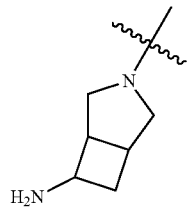 |
| 4.295 | 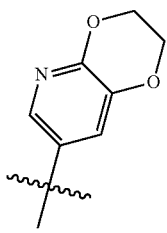 [SMILES: *c1cnc2c(c1)OCCO2] | | 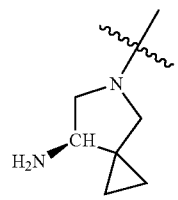 [SMILES: *N1C[C@H](N)C2(CC2)C1] |
| 4.296 | 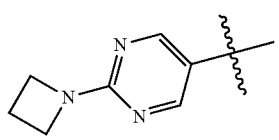 | | 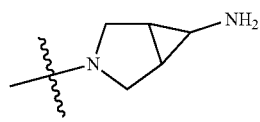 [SMILES: *N1CC2C(N)C2C1] |
| 4.297 | 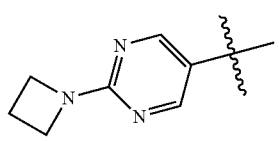 [SMILES: *c1cnc(N2CCC2)nc1] | | 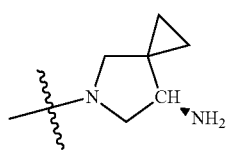 [SMILES: *N1C[C@H](N)C2(CC2)C1] |
| 4.298 | 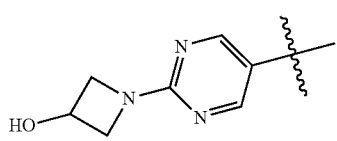 [SMILES: *c1cnc(N2CC(O)C2)nc1] | | 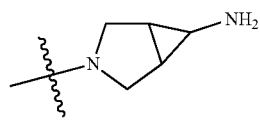 |
| 4.299 | 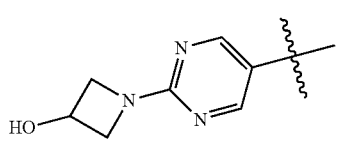 [SMILES: *c1cnc(N2CC(O)C2)nc1] | | 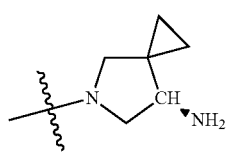 |
| 4.300 | 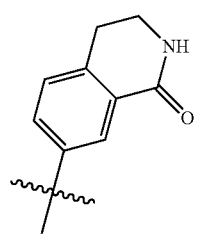 [SMILES: *c1ccc2c(c1)C(=O)NCC2] | | 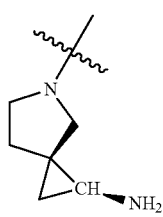 [SMILES: *N1CC[C@]2(C[C@@H]2N)C1] |

-continued
| | | |
|---|---|---|
| 4.301 | 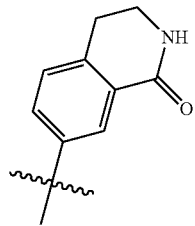 [SMILES: *c1ccc2c(c1)C(=O)NCC2] | 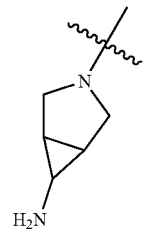 [SMILES: *N1CC2C(N)C2C1] |
| 4.302 | 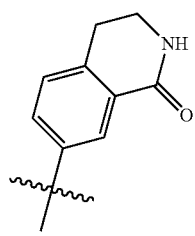 [SMILES: *c1ccc2c(c1)C(=O)NCC2] | 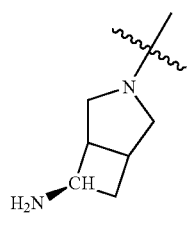 |
| 4.303 | 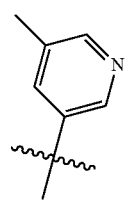 [SMILES: *c1cncc(C)c1] | 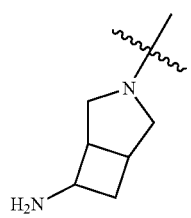 |
| 4.304 | 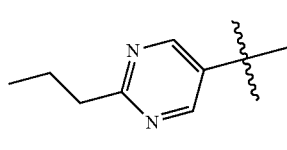 [SMILES: *c1cnc(CCC)nc1] | 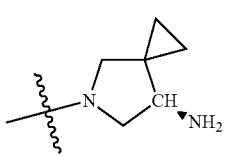 [SMILES: *N1C[C@H](N)C2(CC2)C1] |
| 4.305 | 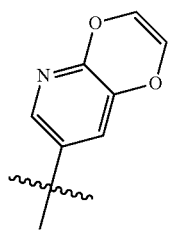 [SMILES: *c1cnc2c(c1)OC=CO2] | 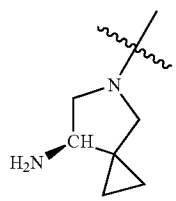 [SMILES: *N1C[C@H](N)C2(CC2)C1] |
| 4.309 | 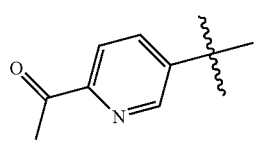 [SMILES: *c1ccc(C(C)=O)nc1] | 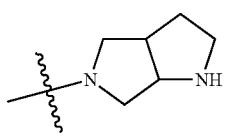 [SMILES: *N1CC2CCNC2C1] |
| 4.310 | 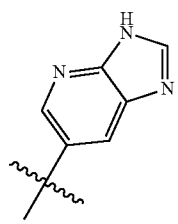 [SMILES: *c1cnc2[nH]cnc2c1] | 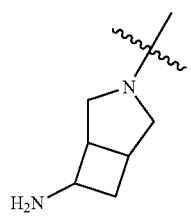 |
| 4.311 | 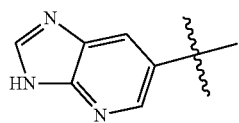 | 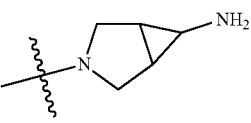 [SMILES: *N1CC2C(N)C2C1] |

| | | |
|---|---|---|
| 4.312 | 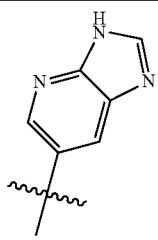 | 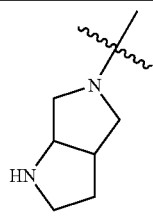 |
| 4.313 | 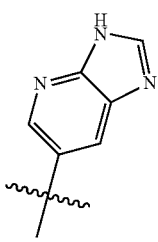 [SMILES: *c1cnc2[nH]cnc2c1] | 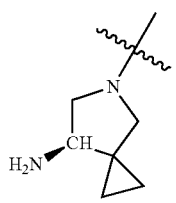 |
| 4.314 | 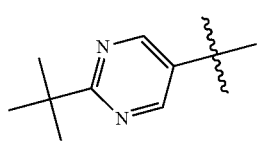 [SMILES: *c1cnc(C(C)(C)C)nc1] | 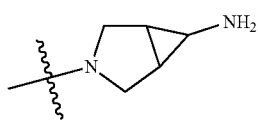 [SMILES: *N1CC2C(N)C2C1] |
| 4.315 | 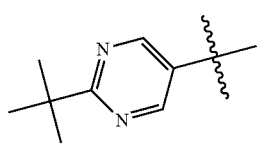 [SMILES: *c1cnc(C(C)(C)C)nc1] | 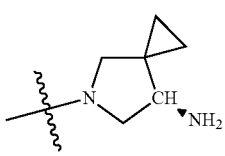 |
| 4.316 | 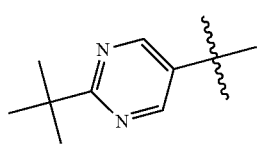 [SMILES: *c1cnc(C(C)(C)C)nc1] | 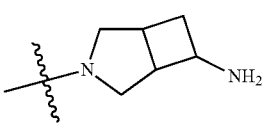 [SMILES: *N1CC2CC(N)C2C1] |
| 4.317 | 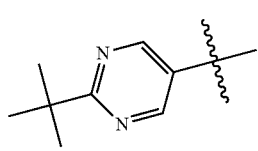 [SMILES: *c1cnc(C(C)(C)C)nc1] | 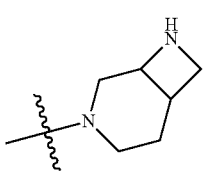 [SMILES: *N1CCC2CNC2C1] |
| 4.318 | 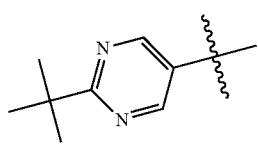 [SMILES: *c1cnc(C(C)(C)C)nc1] | 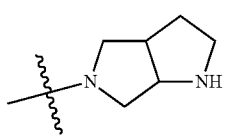 [SMILES: *N1CC2CCNC2C1] |
| 4.319 | 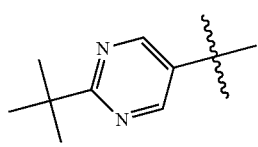 [SMILES: *c1cnc(C(C)(C)C)nc1] | 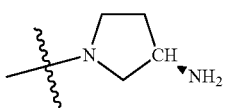 [SMILES: *N1CC[C@@H](N)C1] |
| 4.320 | 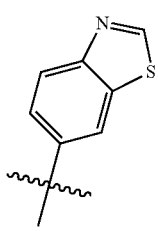 [SMILES: *c1ccc2ncsc2c1] | 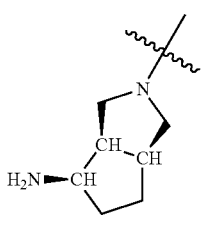 [SMILES: *N1C[C@H]2CC[C@@H](N)[C@H]2C1] |

| | | |
|---|---|---|
| 4.321 | 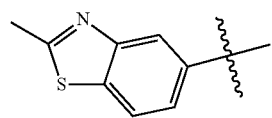 [SMILES: *c1ccc2sc(C)nc2c1] | 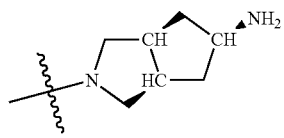 [SMILES: *N1C[C@H]2C[C@@H](N)C[C@H]2C1] |
| 4.322 | 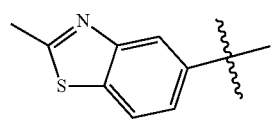 [SMILES: *c1ccc2sc(C)nc2c1] | 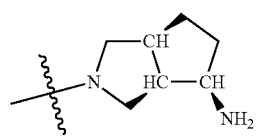 [SMILES: *N1C[C@H]2CC[C@@H](N)[C@H]2C1] |
| 4.323 | 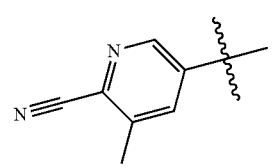 [SMILES: *c1cnc(C#N)c(C)c1] | 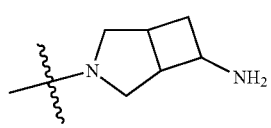 [SMILES: *N1CC2CC(N)C2C1] |
| 4.324 | 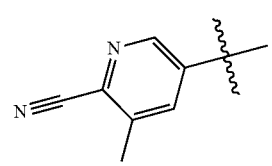 [SMILES: *c1cnc(C#N)c(C)c1] | 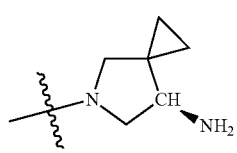 [SMILES: *N1C[C@H](N)C2(CC2)C1] |
| 4.325 | 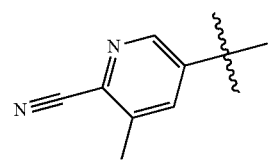 [SMILES: *c1cnc(C#N)c(C)c1] | 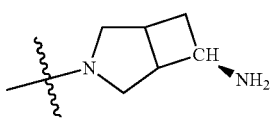 |
| 4.326 | 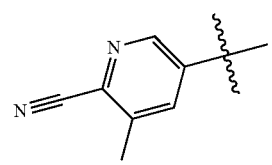 [SMILES: *c1cnc(C#N)c(C)c1] | 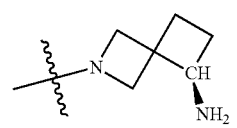 |
| 4.327 | 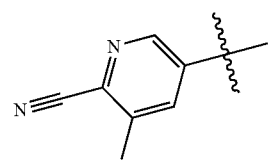 [SMILES: *c1cnc(C#N)c(C)c1] | 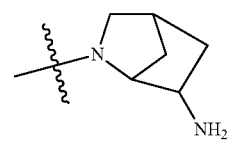 [SMILES: *N1CC2CC(N)C1C2] |
| 4.328 | 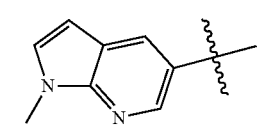 | 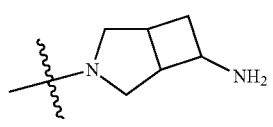 [SMILES: *N1CC2CC(N)C2C1] |
| 4.329 | 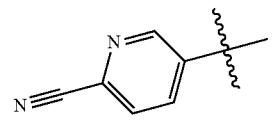 | 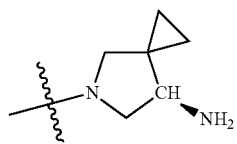 |
| 4.330 | 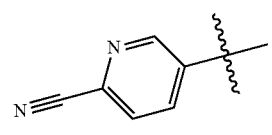 | 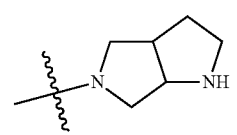 [SMILES: *N1CC2CCNC2C1] |

-continued
| | | |
|---|---|---|
| 4.331 | 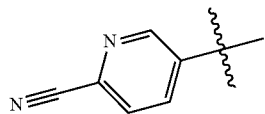 | 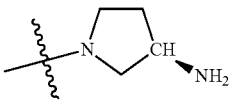 [SMILES: *N1CC[C@@H](N)C1] |
| 4.332 | 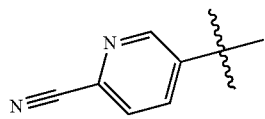 [SMILES: *c1ccc(C#N)nc1] | 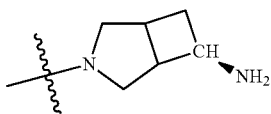 |
| 4.333 | 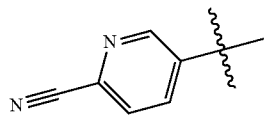 | 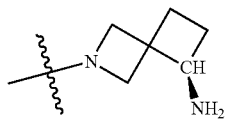 |
| 4.334 | 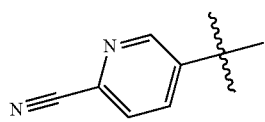 [SMILES: *c1ccc(C#N)nc1] | 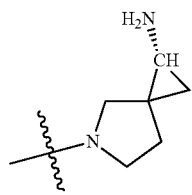 [SMILES: *N1CCC2(C[C@H]2N)C1] |
| 4.335 | 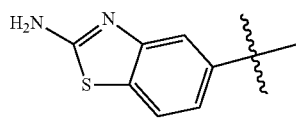 [SMILES: *c1ccc2sc(N)nc2c1] | 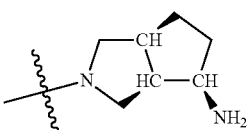 |
| 4.336 | 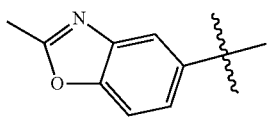 | 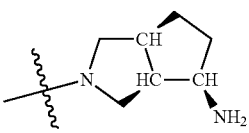 [SMILES: *N1C[C@H]2CC[C@@H](N)[C@H]2C1] |
| 4.337 | 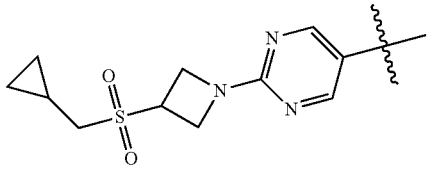 [SMILES: *c1cnc(N2CC(S(=O)(=O)CC3CC3)C2)nc1] | 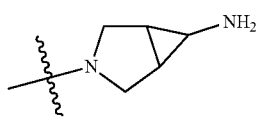 [SMILES: *N1CC2C(N)C2C1] |
| 4.338 | 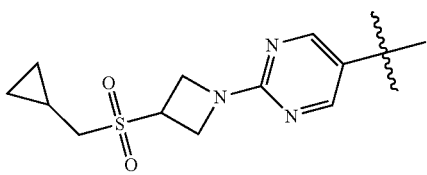 [SMILES: *c1cnc(N2CC(S(=O)(=O)CC3CC3)C2)nc1] | 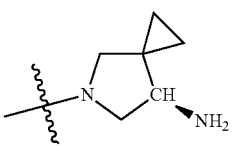 |
| 4.339 | 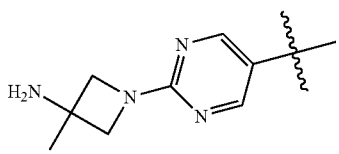 [SMILES: *c1cnc(N2CC(C)(N)C2)nc1] | 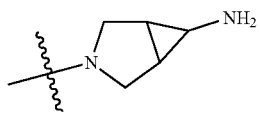 [SMILES: *N1CC2C(N)C2C1] |
| 4.340 | 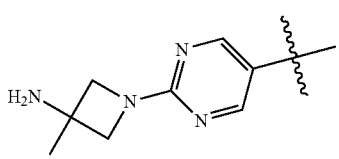 [SMILES: *c1cnc(N2CC(C)(N)C2)nc1] | 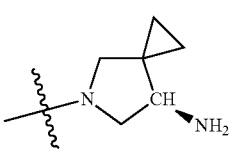 [SMILES: *N1C[C@H](N)C2(CC2)C1] |

-continued
| | | |
|---|---|---|
| 4.341 | 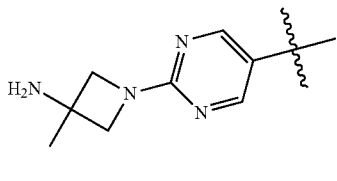 [SMILES: *c1cnc(N2CC(C)(N)C2)nc1] | 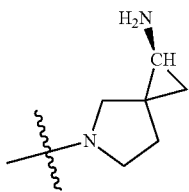 [SMILES: *N1CCC2(C[C@@H]2N)C1] |
| 4.342 | 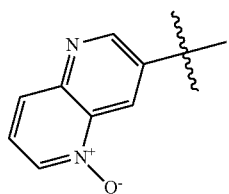 [SMILES: *c1cnc2ccc[n+]([O-])c2c1] | 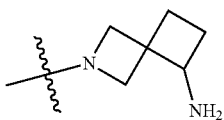 |
| 4.343 | 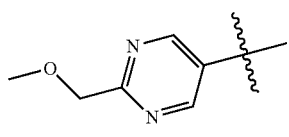 [SMILES: *c1cnc(COC)nc1] | 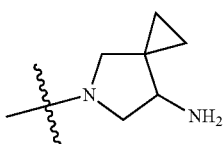 [SMILES: *N1CC(N)C2(CC2)C1] |
| 4.344 | 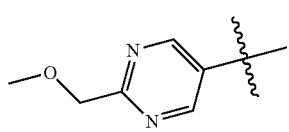 [SMILES: *c1cnc(COC)nc1] | 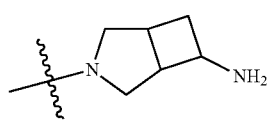 [SMILES: *N1CC2CC(N)C2C1] |
| 4.345 | 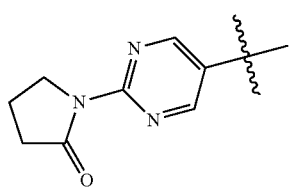 [SMILES: *c1cnc(N2CCCC2=O)nc1] | 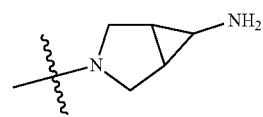 [SMILES: *N1CC2C(N)C2C1] |
| 4.346 | 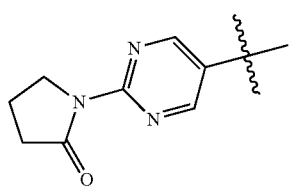 [SMILES: *c1cnc(N2CCCC2=O)nc1] | 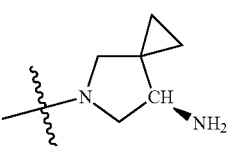 [SMILES: *N1C[C@H](N)C2(CC2)C1] |
| 4.347 | 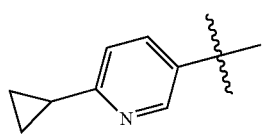 [SMILES: *c1ccc(C2CC2)nc1] | 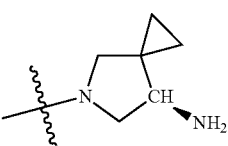 [SMILES: *N1C[C@H](N)C2(CC2)C1] |
| 4.348 | 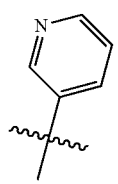 [SMILES: *c1cccnc1] | 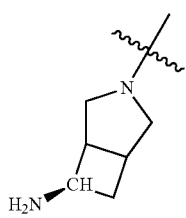 |

| | | |
|---|---|---|
| 4.349 | 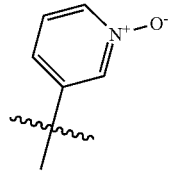 [SMILES: *c1ccc[n+]([O-])c1] | 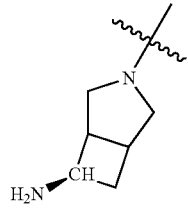 |
| 4.350 | 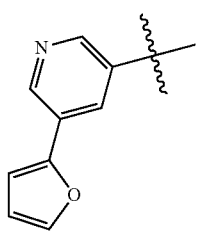 [SMILES: *c1cncc(-c2ccco2)c1] | 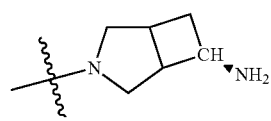 [SMILES: *N1CC2C[C@@H](N)C2C1] |
| 4.351 | 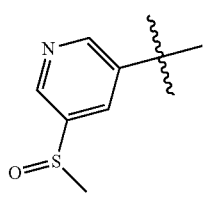 [SMILES: *c1cncc(S(C)=O)c1] | 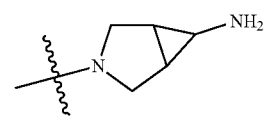 |
| 4.352 | 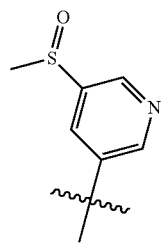 [SMILES: *c1cncc(S(C)=O)c1] | 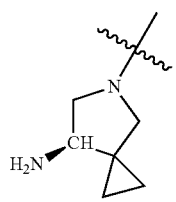 [SMILES: *N1C[C@H](N)C2(CC2)C1] |
| 4.353 | 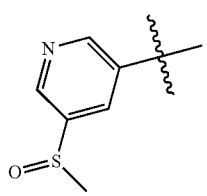 [SMILES: *c1cncc(S(C)=O)c1] | 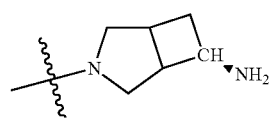 |
| 4.354 | 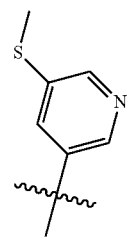 [SMILES: *c1cncc(SC)c1] | 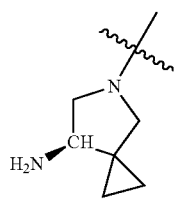 [SMILES: *N1C[C@H](N)C2(CC2)C1] |
| 4.355 | 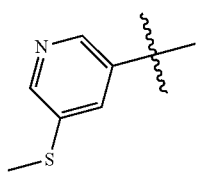 [SMILES: *c1cncc(SC)c1] | 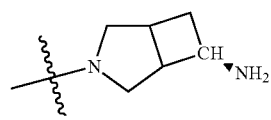 [SMILES: *N1CC2C[C@@H](N)C2C1] |

-continued
| | | |
|---|---|---|
| 4.356 | 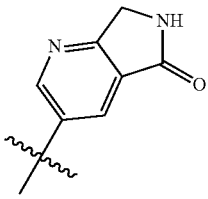 [SMILES: *c1cnc2c(c1)C(=O)NC2] | 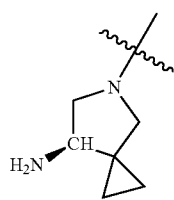 [SMILES: *N1C[C@H](N)C2(CC2)C1] |
| 4.357 | 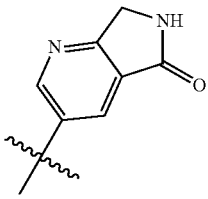 [SMILES: *c1cnc2c(c1)C(=O)NC2] | 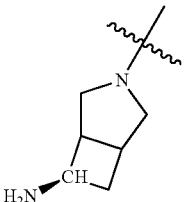 |
| 4.358 | 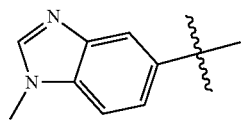 [SMILES: *c1ccc2c(c1)ncn2C] | 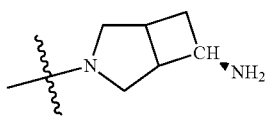 |
| 4.359 | 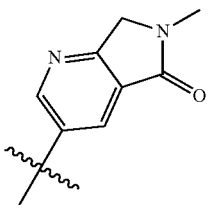 [SMILES: *c1cnc2c(c1)C(=O)N(C)C2] | 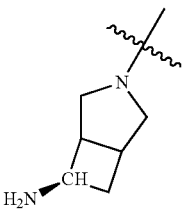 |
| 4.360 | 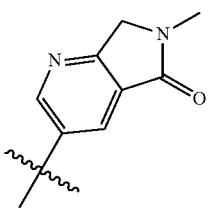 [SMILES: *c1cnc2c(c1)C(=O)N(C)C2] | 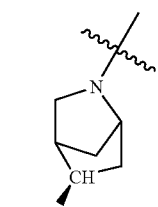 |
| 4.361 | 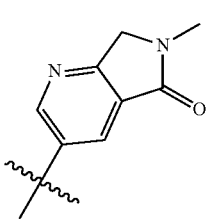 [SMILES: *c1cnc2c(c1)C(=O)N(C)C2] | 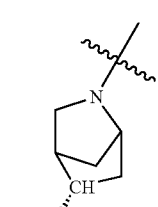 |
| 4.362 | 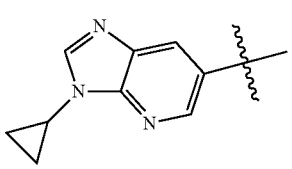 [SMILES: *c1cnc2c(c1)ncn2C1CC1] | 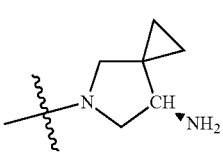 [SMILES: *N1C[C@H](N)C2(CC2)C1] |
| 4.363 | 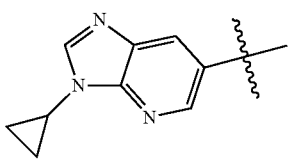 [SMILES: *c1cnc2c(c1)ncn2C1CC1] | 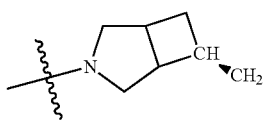 [SMILES: *N1CC2C[C@@H](C)C2C1] |

-continued
| | | |
|---|---|---|
| 4.364 | 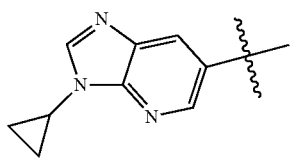 | 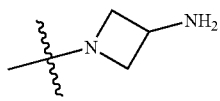 [SMILES: *N1CC(N)C1] |
| 4.365 | 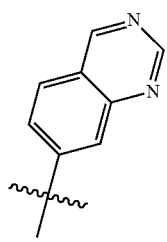 [SMILES: *c1ccc2cncnc2c1] | 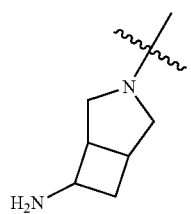 [SMILES: *N1CC2CC(N)C2C1] |
| 4.366 | 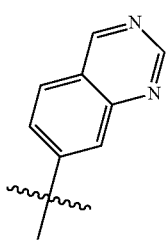 [SMILES: *c1ccc2cncnc2c1] | 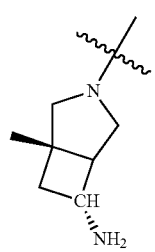 |
| 4.367 | 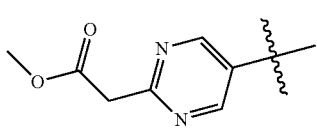 [SMILES: *c1cnc(CC(=O)OC)nc1] | 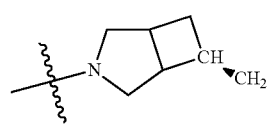 [SMILES: *N1CC2C[C@@H](C)C2C1] |
| 4.368 | 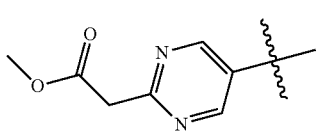 [SMILES: *c1cnc(CC(=O)OC)nc1] | 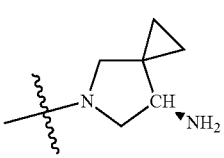 [SMILES: *N1C[C@H](N)C2(CC2)C1] |
| 4.369 | 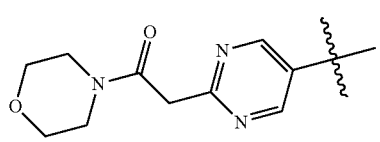 [SMILES: *c1cnc(CC(=O)N2CCOCC2)nc1] | 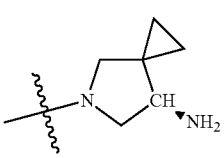 [SMILES: *N1C[C@H](N)C2(CC2)C1] |
| 4.370 | 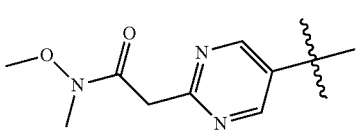 [SMILES: *c1cnc(CC(=O)N(C)OC)nc1] | 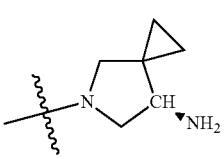 [SMILES: *N1C[C@H](N)C2(CC2)C1] |
| 4.371 | 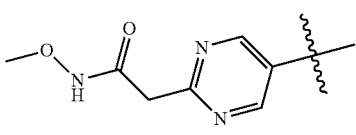 [SMILES: *c1cnc(CC(=O)NOC)nc1] | 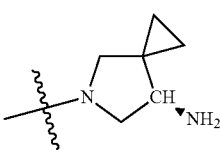 [SMILES: *N1C[C@H](N)C2(CC2)C1] |
| 4.372 | 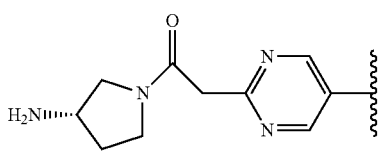 | 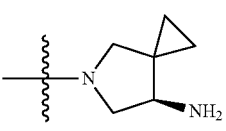 [SMILES: *N1C[C@H](N)C2(CC2)C1] |

-continued
| | | | |
|---|---|---|---|
| 4.373 | 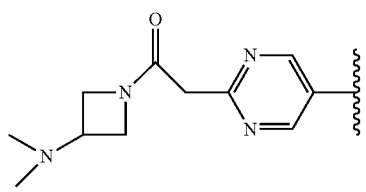 [SMILES: *c1cnc(CC(=O)N2CC(N(C)C)C2)nc1] | | 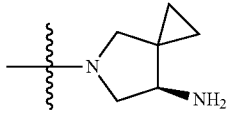 [SMILES: *N1C[C@H](N)C2(CC2)C1] |
| 4.374 | 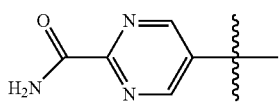 | | 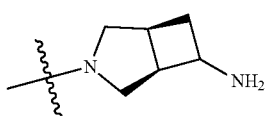 |
| 4.375 | 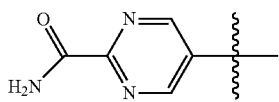 | | 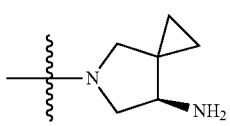 [SMILES: *N1C[C@H](N)C2(CC2)C1] |
| 4.376 | 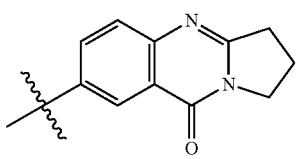 [SMILES: *c1ccc2nc3n(c(=O)c2c1)CCC3] | | 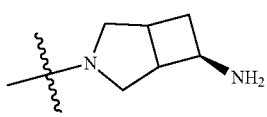 [SMILES: *N1CC2C[C@@H](N)C2C1] |
| 4.377 | 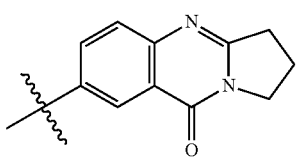 [SMILES: *c1ccc2nc3n(c(=O)c2c1)CCC3] | | 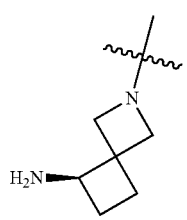 [SMILES: *N1CC2(CC[C@H]2N)C1] |
| 4.378 | 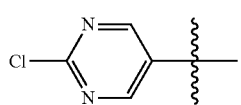 | | 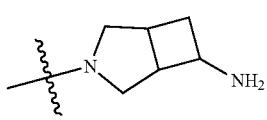 [SMILES: *N1CC2CC(N)C2C1] |
| 4.379 | 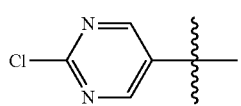 | | 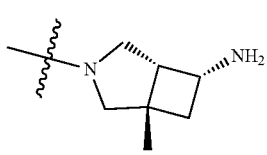 [SMILES: *N1C[C@@H]2[C@H](N)C[C@]2(C)C1] |
| 4.380 | 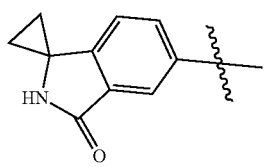 [SMILES: *c1ccc2c(c1)C(=O)NC21CC1] | | 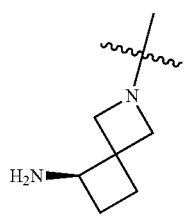 [SMILES: *N1CC2(CC[C@H]2N)C1] |
| 4.381 | 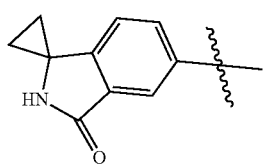 [SMILES: *c1ccc2c(c1)C(=O)NC21CC1] | | 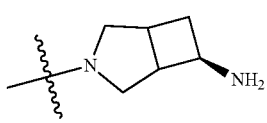 [SMILES: *N1CC2C[C@@H](N)C2C1] |

-continued
| | | |
|---|---|---|
| 4.382 | 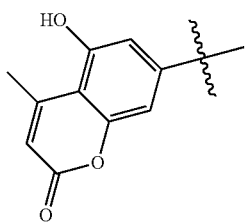 [SMILES: *c1cc(O)c2c(C)cc(=O)oc2c1] | 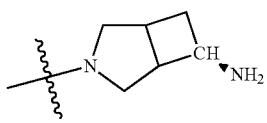 [SMILES: *N1CC2C[C@@H](N)C2C1] |
| 4.383 | 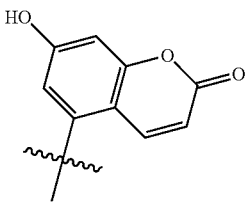 | 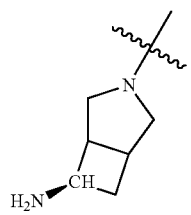 [SMILES: *N1CC2C[C@@H](N)C2C1] |
| 4.384 | 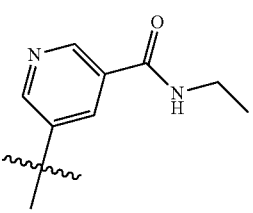 [SMILES: *c1cncc(C(=O)NCC)c1] |  |
| 4.385 | 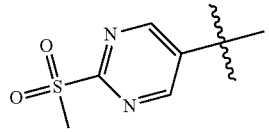 [SMILES: *c1cnc(S(C)(=O)=O)nc1] | 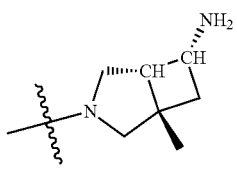 [SMILES: *N1C[C@@H]2[C@H](N)C[C@]2(C)C1] |
| 4.386 | 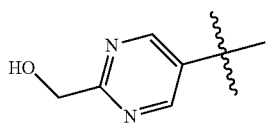 [SMILES: *c1cnc(CO)nc1] | 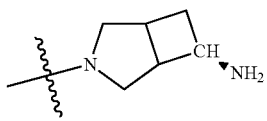 [SMILES: *N1CC2C[C@@H](N)C2C1] |
| 4.387 | 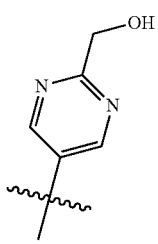 [SMILES: *c1cnc(CO)nc1] | 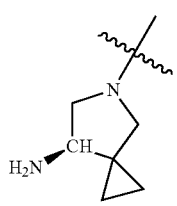 |
| 4.388 | 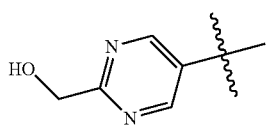 | 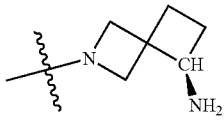 |
| 4.389 | 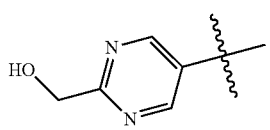 | 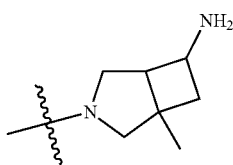 [SMILES: *N1CC2C(N)CC2(C)C1] |

-continued
| | | |
|---|---|---|
| 4.390 | 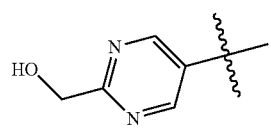 [SMILES: *c1cnc(CO)nc1] | 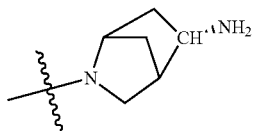 [SMILES: *N1CC2CC1C[C@@H]2N] |
| 4.391 | 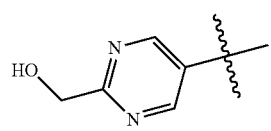 | 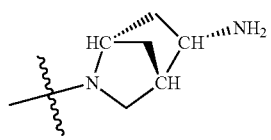 [SMILES: *N1C[C@@H]2C[C@H]1C[C@@H]2N] |
| 4.392 | 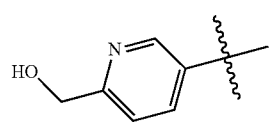 [SMILES: *c1ccc(CO)nc1] | 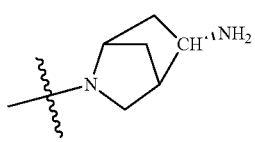 [SMILES: *N1CC2CC1C[C@@H]2N] |
| 4.393 | 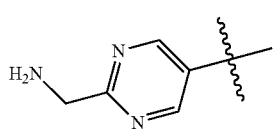 [SMILES: *c1cnc(CN)nc1] | 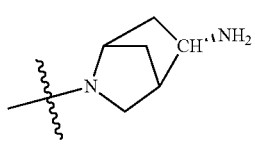 [SMILES: *N1CC2CC1C[C@@H]2N] |
| 4.394 | 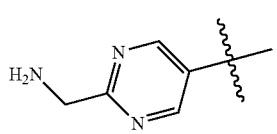 | 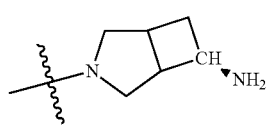 [SMILES: *N1CC2C[C@@H](N)C2C1] |
| 4.395 | 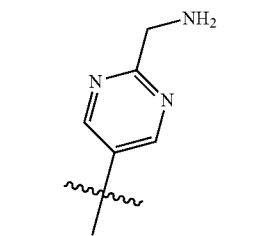 [SMILES: *c1cnc(CN)nc1] | 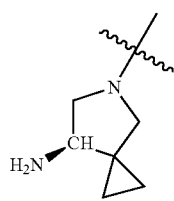 [SMILES: *N1C[C@H](N)C2(CC2)C1] |
| 4.396 | 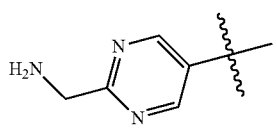 | 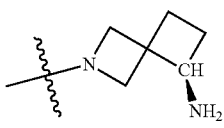 |
| 4.397 | 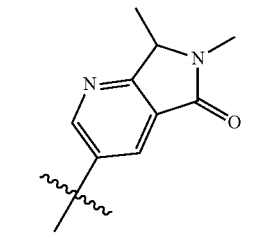 [SMILES: *c1cnc2c(c1)C(=O)N(C)C2C] | 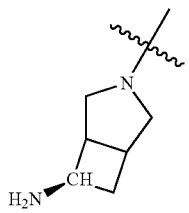 [SMILES: *N1CC2C[C@@H](N)C2C1] |
| 4.398 | 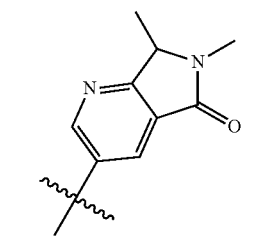 [SMILES: *c1cnc2c(c1)C(=O)N(C)C2C] | 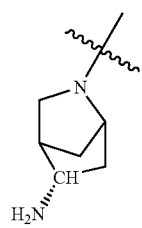 |

| | | |
|---|---|---|
| 4.399 | 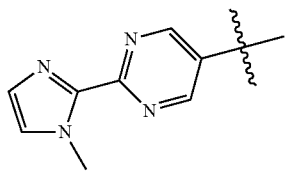 [SMILES: *c1cnc(-c2nccn2C)nc1] | 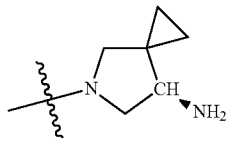 [SMILES: *N1C[C@H](N)C2(CC2)C1] |
| 4.400 | 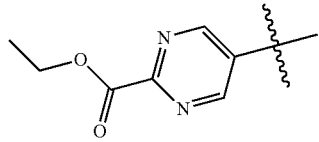 | 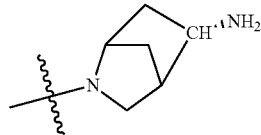 [SMILES: *N1CC2CC1C[C@@H]2N] |
| 4.401 | 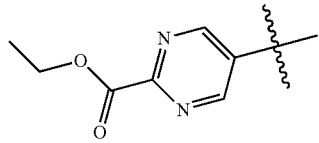 [SMILES: *c1cnc(C(=O)OCC)nc1] | 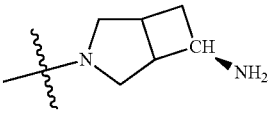 [SMILES: *N1CC2C[C@@H](N)C2C1] |
| 4.402 | 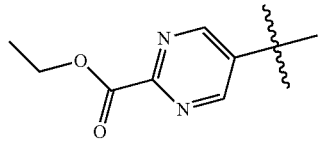 [SMILES: *c1cnc(C(=O)OCC)nc1] | 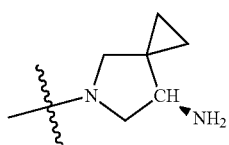 [SMILES: *N1C[C@H](N)C2(CC2)C1] |
| 4.403 | 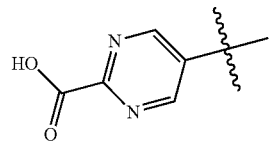 [SMILES: *c1cnc(C(=O)O)nc1] | 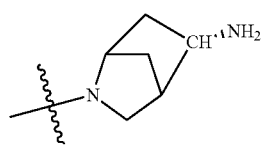 [SMILES: *N1CC2CC1C[C@@H]2N] |
| 4.404 | 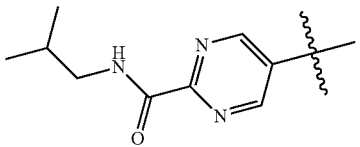 [SMILES: *c1cnc(C(=O)NCC(C)C)nc1] | 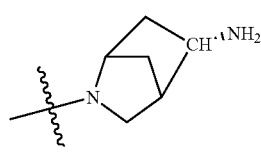 [SMILES: *N1CC2CC1C[C@@H]2N] |
| 4.405 | 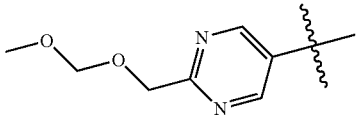 [SMILES: *c1cnc(COCOC)nc1] | 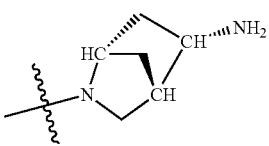 [SMILES: *N1C[C@@H]2C[C@H]1C[C@@H]2N] |
| 4.406 | 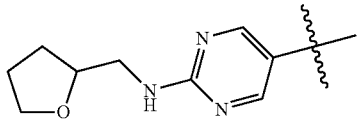 [SMILES: *c1cnc(NCC2CCCO2)nc1] | 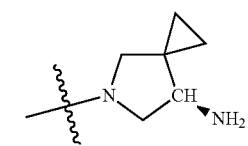 [SMILES: *N1C[C@H](N)C2(CC2)C1] |
| 4.407 | 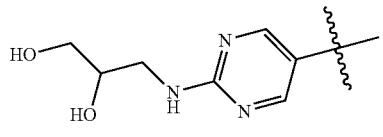 [SMILES: *c1cnc(NCC(O)CO)nc1] | 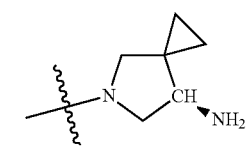 |
| 4.408 | 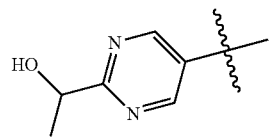 | 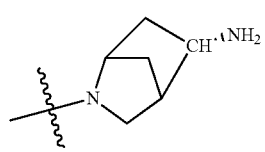 [SMILES: *N1CC2CC1C[C@@H]2N] |

-continued
| | | |
|---|---|---|
| 4.409 | 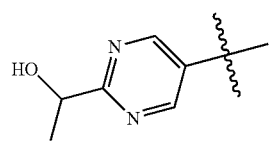 [SMILES: *c1cnc(C(C)O)nc1] | 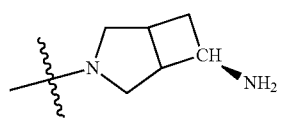 |
| 4.410 | 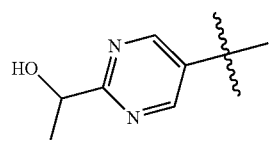 [SMILES: *c1cnc(C(C)O)nc1] | 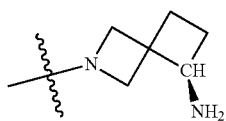 [SMILES: *N1CC2(CC[C@H]2N)C1] |
| 4.411 | 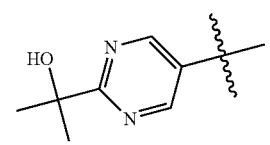 [SMILES: *c1cnc(C(C)(C)O)nc1] | 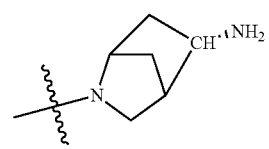 [SMILES: *N1CC2CC1C[C@@H]2N] |
| 4.412 | 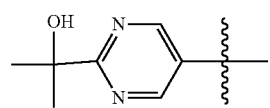 [SMILES: *c1cnc(C(C)(C)O)nc1] | 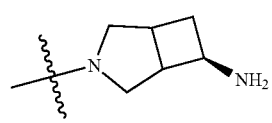 [SMILES: *N1CC2C[C@@H](N)C2C1] |
| 4.413 | 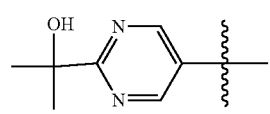 [SMILES: *c1cnc(C(C)(C)O)nc1] | 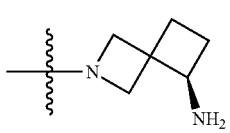 |
| 4.414 | 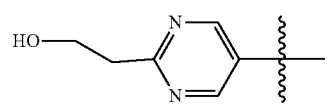 | 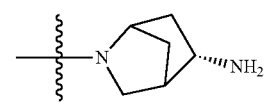 [SMILES: *N1CC2CC1C[C@@H]2N] |
| 4.415 | 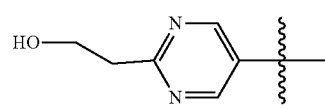 | 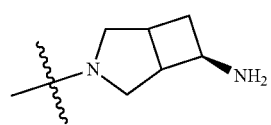 [SMILES: *N1CC2C[C@@H](N)C2C1] |
| 4.416 | 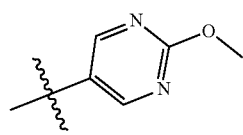 [SMILES: *c1cnc(OC)nc1] | 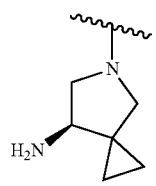 |
| 4.417 | 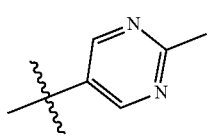 [SMILES: *c1cnc(C)nc1] | 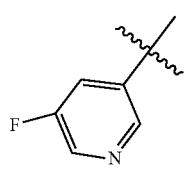 |
| 4.418 | 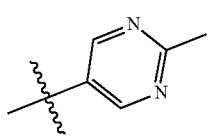 [SMILES: *c1cnc(C)nc1] | 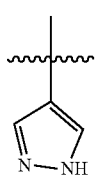 |

-continued
| | | | |
|---|---|---|---|
| 4.419 | 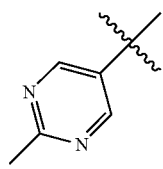 [SMILES: *c1cnc(C)nc1] | | 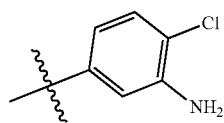 [SMILES: *c1ccc(Cl)c(N)c1] |
| 4.420 | 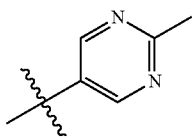 [SMILES: *c1cnc(C)nc1] | | 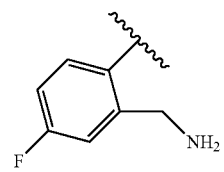 |
| 4.421 | 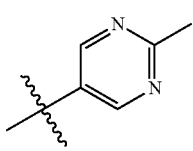 [SMILES: *c1cnc(C)nc1] | | 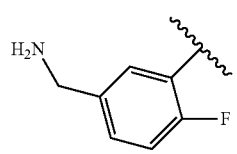 [SMILES: *c1cc(CN)ccc1F] |
| 4.422 | 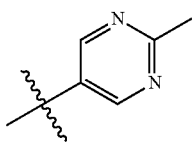 [SMILES: *c1cnc(C)nc1] | | 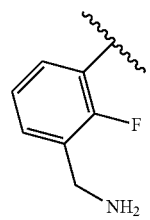 |
4.423 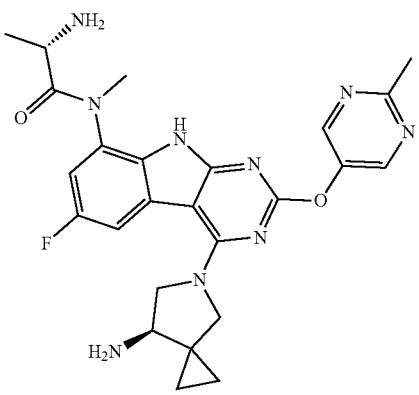 [SMILES: Cc1ncc(Oc2nc(N3C[C@H](N)C4(CC4)C3)c3c(n2)[nH]c2c(N(C)C(=O)[C@H](C)N)cc(F)cc23)cn1]
4.424 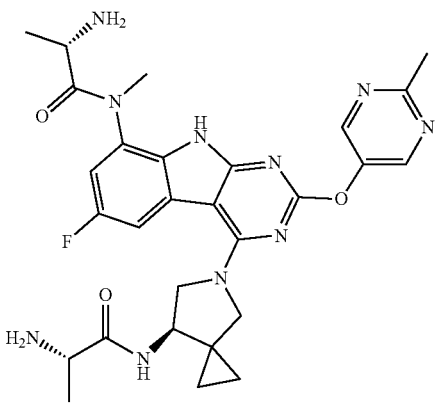 [SMILES: Cc1ncc(Oc2nc(N3C[C@H](NC(=O)[C@H](C)N)C4(CC4)C3)c3c(n2)[nH]c2c(N(C)C(=O)[C@H](C)N)cc(F)cc23)cn1]

| Cmpd ID | |
|---|---|
| 4.425 | 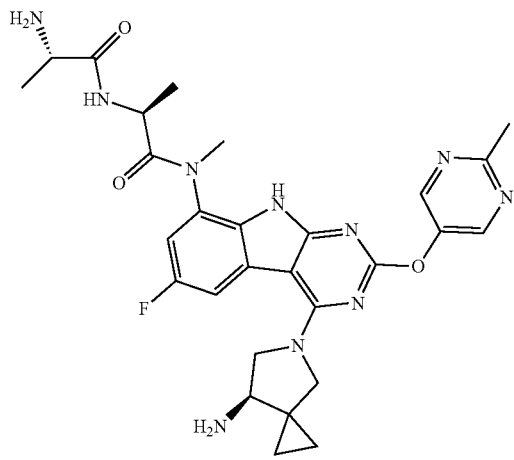 [SMILES: Cc1ncc(Oc2nc(N3C[C@H](N)C4(CC4)C3)c3c(n2)[nH]c2c(N(C)C(=O)[C@H](C)NC(=O)[C@H](C)N)cc(F)cc23)cn1] |
| 4.426 | 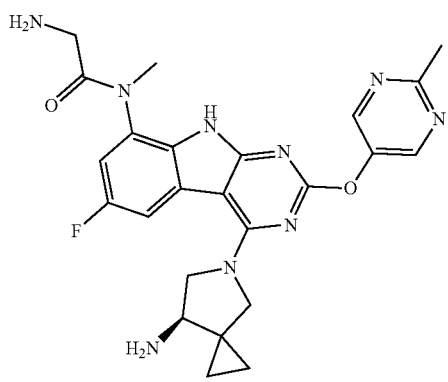 [SMILES: Cc1ncc(Oc2nc(N3C[C@H](N)C4(CC4)C3)c3c(n2)[nH]c2c(N(C)C(=O)CN)cc(F)cc23)cn1] |
| 4.427 | 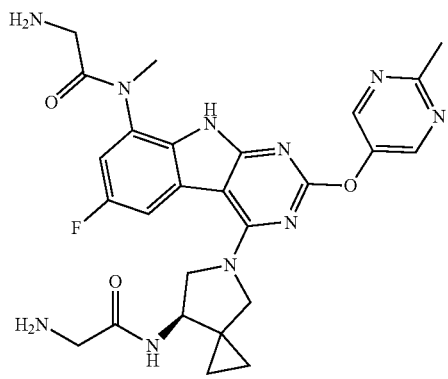 [SMILES: Cc1ncc(Oc2nc(N3C[C@H](NC(=O)CN)C4(CC4)C3)c3c(n2)[nH]c2c(N(C)C(=O)CN)cc(F)cc23)cn1] |
| Cmpd ID | |
|---|---|
| 4.428 | 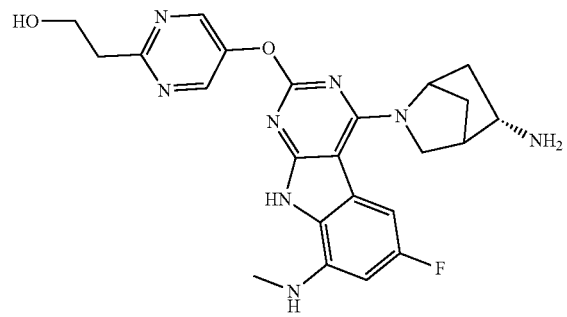 [SMILES: CNc1cc(F)cc2c1[nH]c1nc(Oc3cnc(CCO)nc3)nc(N3CC4CC3C[C@@H]4N)c12] |

4.429 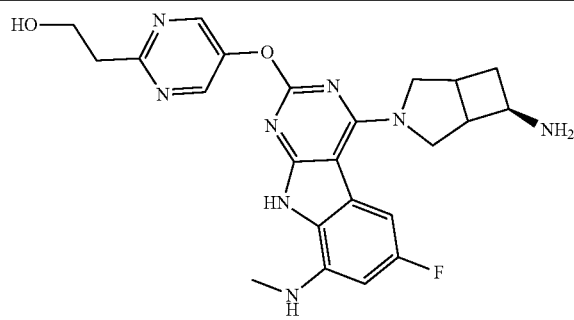
4.430 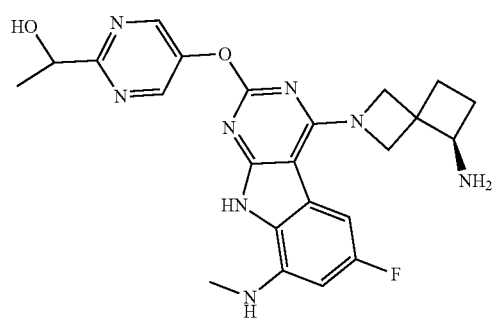 [SMILES: CNc1cc(F)cc2c1[nH]c1nc(Oc3cnc(C(C)O)nc3)nc(N3CC4(CC[C@H]4N)C3)c12]
4.431 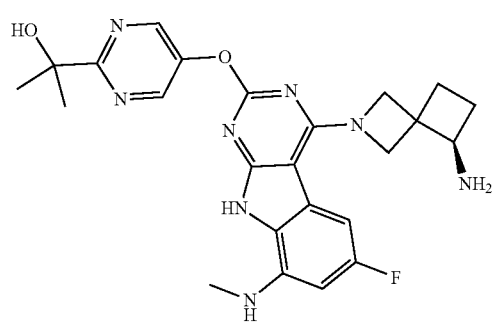 [SMILES: CNc1cc(F)cc2c1[nH]c1nc(Oc3cnc(C(C)(C)O)nc3)nc(N3CC4(CC[C@H]4N)C3)c12]
4.432 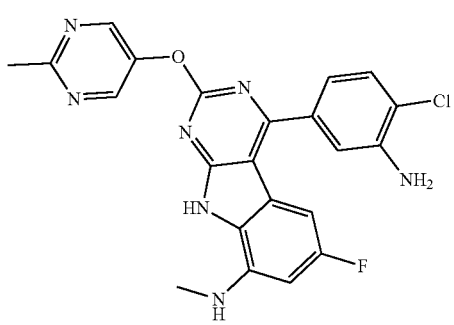 [SMILES: CNc1cc(F)cc2c1[nH]c1nc(Oc3cnc(C)nc3)nc(-c3ccc(Cl)c(N)c3)c12]
4.433 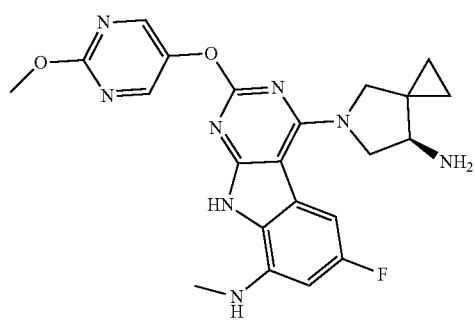 [SMILES: CNc1cc(F)cc2c1[nH]c1nc(Oc3cnc(OC)nc3)nc(N3C[C@H](N)C4(CC4)C3)c12]

4.434 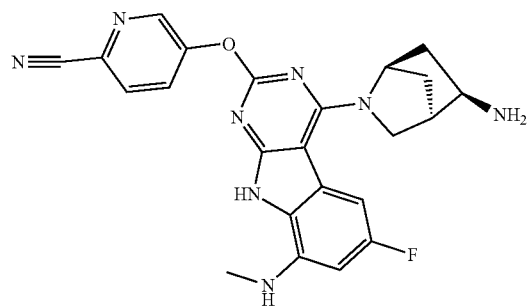 [SMILES: CNc1cc(F)cc2c1[nH]c1nc(Oc3ccc(C#N)nc3)nc(N3C[C@H]4C[C@@H]3C[C@H]4N)c12]
4.435 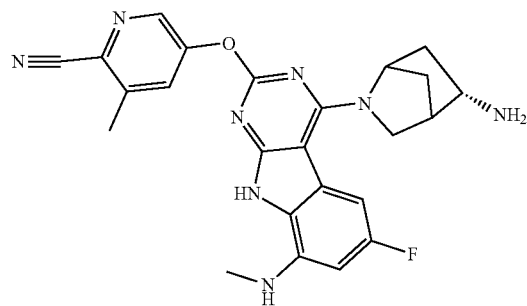 [SMILES: CNc1cc(F)cc2c1[nH]c1nc(Oc3cnc(C#N)c(C)c3)nc(N3CC4CC3C[C@@H]4N)c12]
4.436 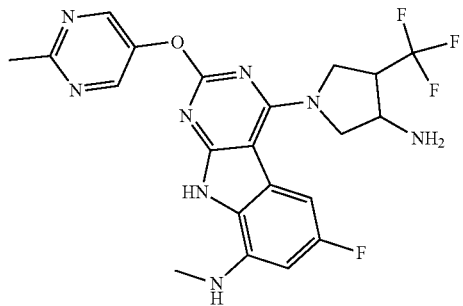 [SMILES: CNc1cc(F)cc2c1[nH]c1nc(Oc3cnc(C)nc3)nc(N3CC(N)C(C(F)(F)F)C3)c12]
4.437 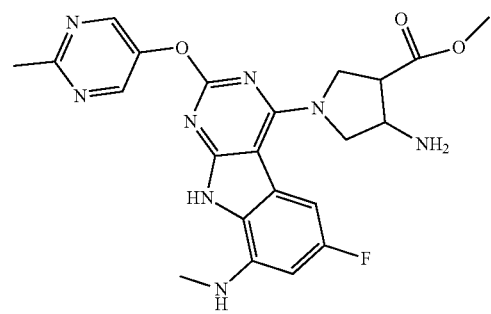
4.438 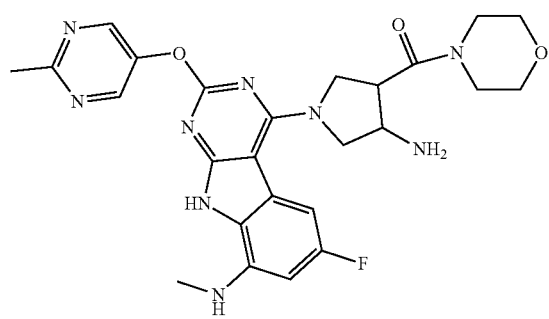 [SMILES: CNc1cc(F)cc2c1[nH]c1nc(Oc3cnc(C)nc3)nc(N3CC(N)C(C(=O)N4CCOCC4)C3)c12]

-continued
4.439
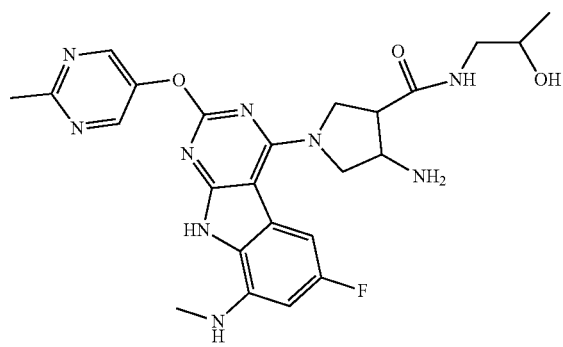 [SMILES: CNc1cc(F)cc2c1[nH]c1nc(Oc3cnc(C)nc3)nc(N3CC(N)C(C(=O)NCC(C)O)C3)c12]
4.440
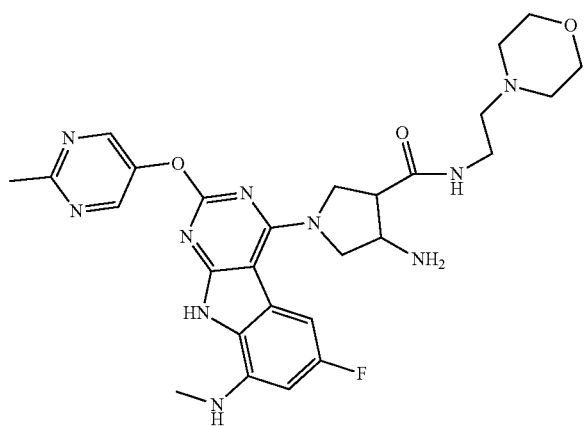 [SMILES: CNc1cc(F)cc2c1[nH]c1nc(Oc3cnc(C)nc3)nc(N3CC(N)C(C(=O)NCCN4CCOCC4)C3)c12]
4.441
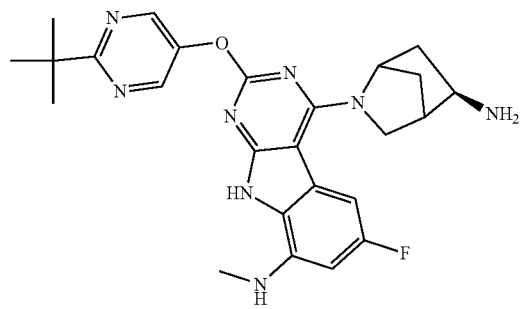 [SMILES: CNc1cc(F)cc2c1[nH]c1nc(Oc3cnc(C(C)(C)C)nc3)nc(N3CC4CC3C[C@H]4N)c12]
4.442
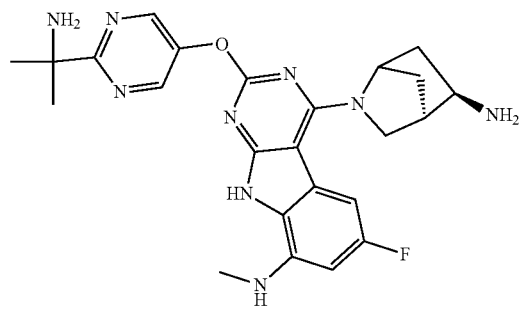 [SMILES: CNc1cc(F)cc2c1[nH]c1nc(Oc3cnc(C(C)(C)N)nc3)nc(N3C[C@H]4CC3C[C@H]4N)c12]

4.443 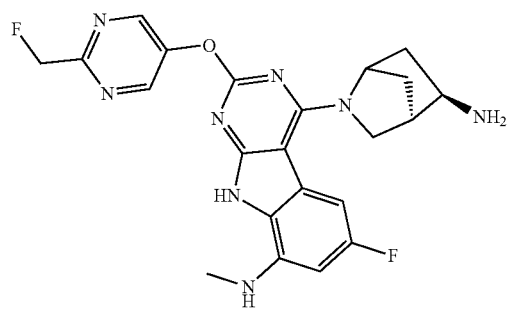 [SMILES: CNc1cc(F)cc2c1[nH]c1nc(Oc3cnc(CF)nc3)nc(N3C[C@H]4CC3C[C@H]4N)c12]
4.445 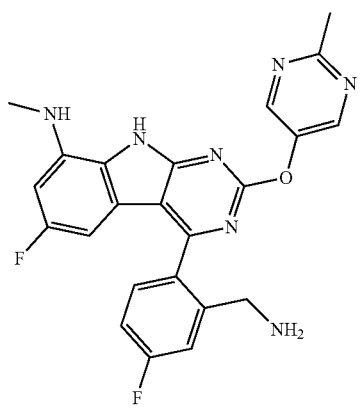 [SMILES: CNc1cc(F)cc2c1[nH]c1nc(Oc3cnc(C)nc3)nc(-c3ccc(F)cc3CN)c12]
4.446 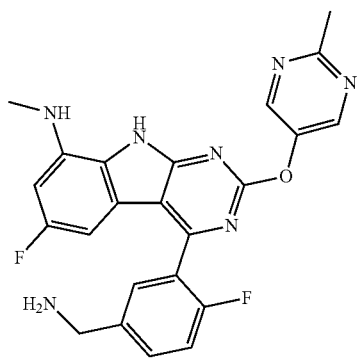 [SMILES: CNc1cc(F)cc2c1[nH]c1nc(Oc3cnc(C)nc3)nc(-c3cc(CN)ccc3F)c12]
4.447 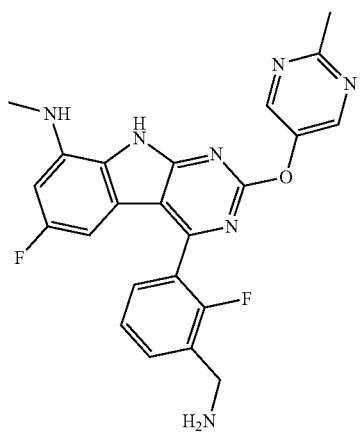 [SMILES: CNc1cc(F)cc2c1[nH]c1nc(Oc3cnc(C)nc3)nc(-c3cccc(CN)c3F)c12]

-continued 4.448

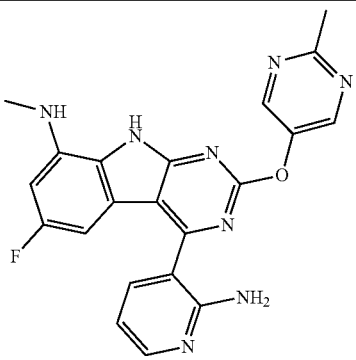

4.449

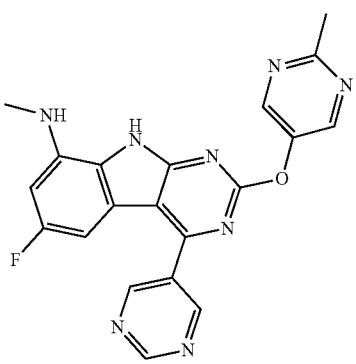 [SMILES: CNc1cc(F)cc2c1[nH]c1nc(Oc3cnc(C)nc3)nc(-c3cncnc3)c12]

4.450

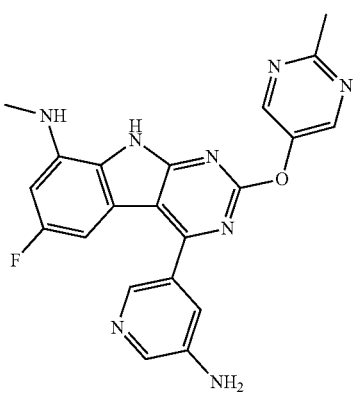 [SMILES: CNc1cc(F)cc2c1[nH]c1nc(Oc3cnc(C)nc3)nc(-c3cncc(N)c3)c12]

Example 15

Difluorophenyl Analogs

Experimental

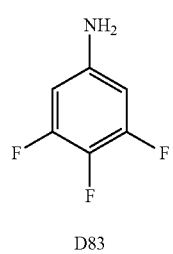 → 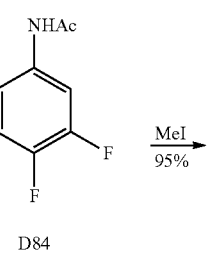 →

Ac₂O / 100%   MeI / 95%

D83   D84

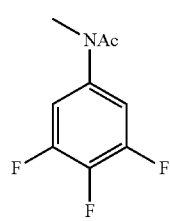

D85

Preparation of Compound D84:

Tri-fluroaniline (250 g) was portionly added into 500 ml acetic anhydride under the ice-water bath, after addition, the reaction was stirred vigorously for 4 hours, then poured into crashed ice, the precipitate (white granular solid) was collected and dry for next step (quantitative yield).

Preparation of Compound D85:

The above made acetyl aniline (126 g, 666 mmol) was portionly added into sodium hydride (40 g, 1 mmol, 60% in oil) solution in dry THF (1 L) under the ice water bath, then the solution was stirred for another 1 hours, then MeI (64 ml, 1 mol) in 100 ml THF was added dropwisely into the solution, the mixture was stirred for overnight (12 hours), and quenched with ice water. The aqueous solution was extracted with 3×500 ml ethyl acetate, the combined solution was dried and concentrated for next steps without purification.

Preparation of compound D86: The above crude compounds was dissolved into 1500 ml trifluoro acetice anydride under the ice-water bath, then $KNO_3$(168 g, 1.66 mol) was added portionly into the TFAA solution, keep the temperature under 35° C. by controlling the rate of $KNO_3$, after addition, the reaction was stirred for further 36 hours, then quenched the reaction with ice-water, the red solution was extracted with 3×500 ml ethyl acetate, the combined solution was dried and concentrated for next steps without purification.

Preparation of Compound D87:

The above sticky solid was dissolved into 1 L (2M HCl), the reaction solution was refluxed for 4 hours, TLC monitored the reaction, cooled down to room temperature when the starting material disappeared, the dark-red solution was extracted with 3×500 ml DCM, the combined solution was dried and concentrated. the residue was purified by flash chromatography, nice dark granular solids (105 g) was obtained with 75% yield.

Preparation of Compound D88:

The above N-methyl-aniline (21 g, 100 mmol) was portionly added into sodium hydride (40 g, 1 mmol, 60% in oil) solution in dry THF (1 L) under the ice water bath, then the solution was stirred for another 1 hours, then Boc anhydride (24 g, 110 mol) in 100 ml THF was added dropwisely into the solution, the mixture was stirred for overnight (12 hours), and quenched with 10% HOAc/ice water. the aqueous solution was extracted with 3×500 ml ethyl acetate, the combined solution was dried and concentrated to remove solvent, then the residue was purified by flash chromatography to gave 26 g desired products, 82% yield.

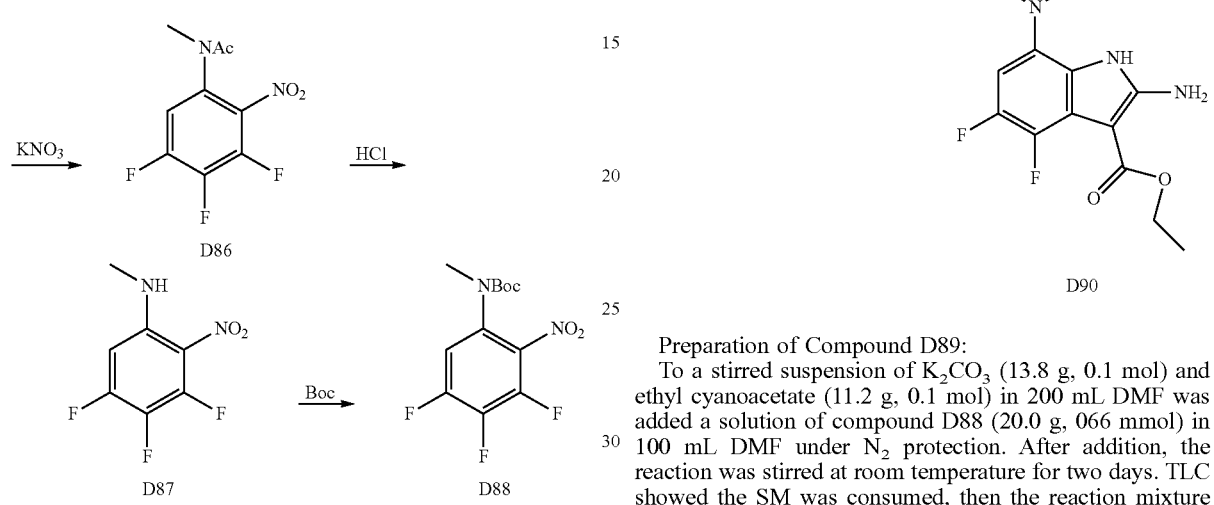

Preparation of Compound D89:

To a stirred suspension of $K_2CO_3$ (13.8 g, 0.1 mol) and ethyl cyanoacetate (11.2 g, 0.1 mol) in 200 mL DMF was added a solution of compound D88 (20.0 g, 066 mmol) in 100 mL DMF under $N_2$ protection. After addition, the reaction was stirred at room temperature for two days. TLC showed the SM was consumed, then the reaction mixture was diluted with ethyl acetate (400 mL) and water (1500 mL), the organic layer was separated, the aqueous layer extracted by ethyl acetate (200 mL). The combined organic layer was washed with brine (300 mL×3), dried over $Na_2SO_4$, filtered, and concentrated in vacuum. The crude product was purified by chromatography (pet. ether/EtOAc, 100/1 to 20/1, v/v) to give compound D89 as a pale yellow solid (12.0 g, 45% yield).

Preparation of Compound:

To a solution of compounds D89 (12 g, 30 mmol) in acetic acid (200 ml) was added portionly Zinc dust (13 g, 200 mmol). After addition, the reaction mixture was warmed to 50 degree, LCMS monitored the reaction process. The reaction was concentrated after the reaction completed (about 4 hours), and the residue was partitioned with $H_2O$ (200 ml) and ethyl acetate (200 ml), the aqueous layer was extracted twice with ethyl acetate, the combined solvent was dried and concentrated, the residue was purified by flash chromatography to produce products D90 (9 g, 81% yield). %). LC-MS: M+1: 370.

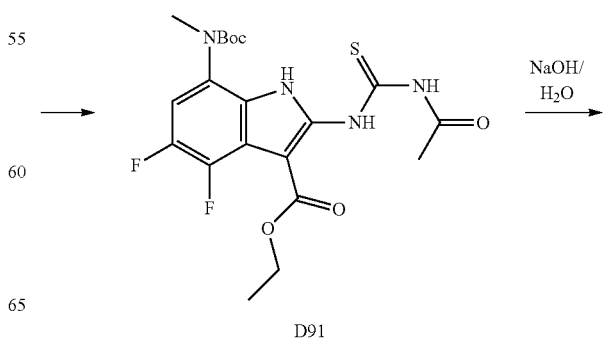

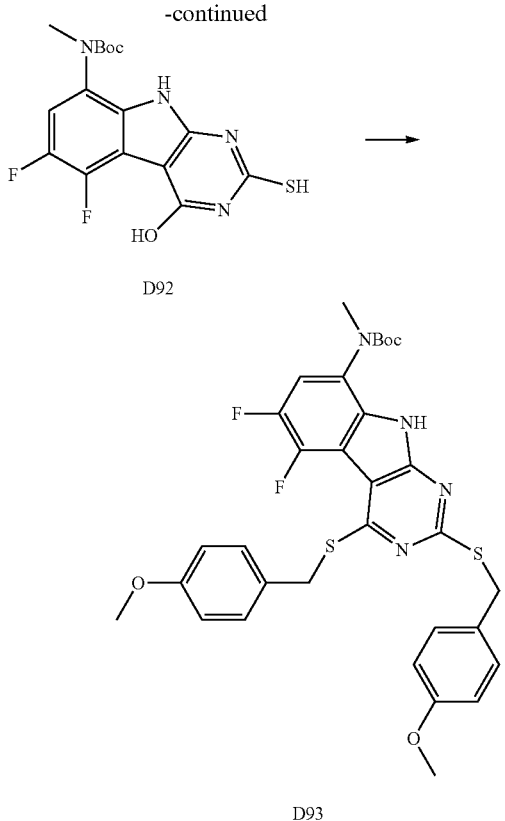

Preparation of Compound D92:

Above residue was dissolved into 50 ml methanol and 50 ml H2O, then was added 10 ml 10% KOH solution, the mixture solution was heated to reflux for 30 minutes. When LCMS showed the reaction was completed the reaction was cooled to room temperature, acidified to pH 5 with 1 M a 1 h. HCl, and the precipitate collected by filtration to give compound D92 as a solid (5 g, 65.4% in two steps). LC-MS: M+1: 383.

Preparation of Compound D93:

To a stirred suspension of compound D92 (3.8 g, 10 mol) and $K_2CO_3$ (2.8 g, 20 mol) in 50 mL of NMP was added dropwise a solution of 1-(chloromethyl)-4-methoxybenzene (1.5 g, 9.6 mol) in 5 mL NMP at room temperature. LCMS showed the reaction was completed in 40 minutes. The reaction mixture was cooled to 0° C., BOP (4.86 g, 11 mmol) and $Et_3N$ (1.5 g, 15 mmol) were added. After 30 minutes, (4-methoxyphenyl)methanethiol (2 g, 12 mmol) was added to the reaction mixture, and was warmed to room temperature then heated to 40° C. for 1 h. The reaction mixture was diluted with ethyl acetate (200 mL) and water (500 mL), the organic layer was separated, the aqueous layer extracted by ethyl acetate (200 mL). The combined organic layer was washed with brine (100 mL×3), dried over $Na_2SO_4$, filtered, and concentrated in vacuum. The crude product was purified by chromatography (pet. ether/EtOAc, 100/1 to 20/1, v/v) to give compound D93 as a pale yellow solid (5.4 g, 84% yield). LC-MS: M+1: 639

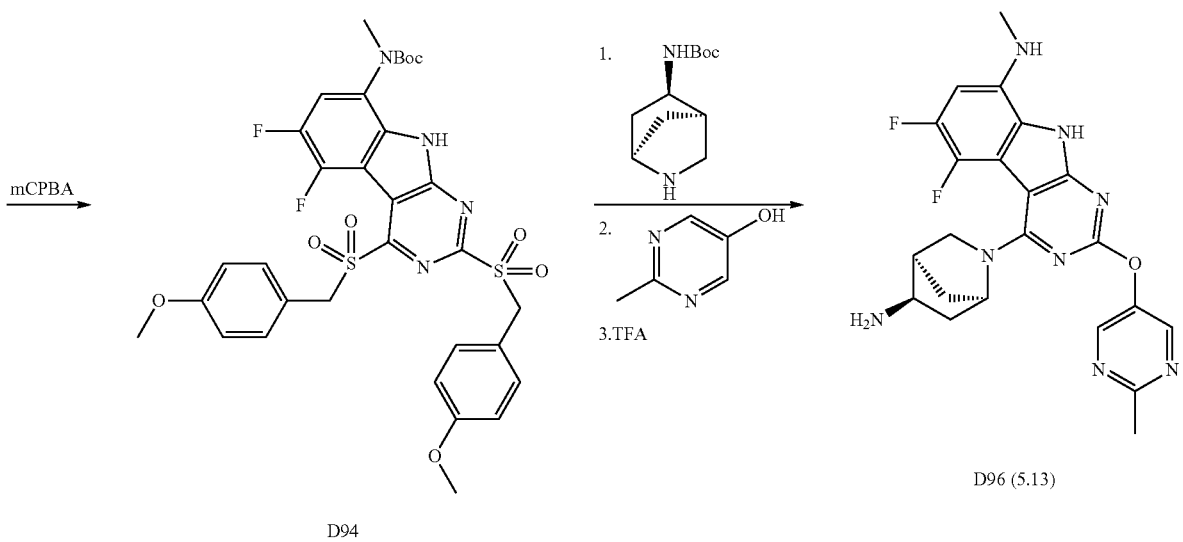

Preparation of Compound D91:

To a stirred suspension of compound D90 (7.4 g, 20 mmol) in acetone (140 mL) was added dropwise a solution of acetyl thioisocynate (12 mL, 140 mmol) in acetone (50 mL) at room temperature. The reaction mixture was heated to reflux for 16 h. LCMS showed the reaction was completed. The reaction mixture was concentrated for next step without purification.

Preparation of Compound D94:

To a stirred suspension of compound D93 (2 g, 3.1 mmol) in 200 mL of $CH_2Cl_2$ at 0° C. was added MCPBA (2.8 g, 21 mmol) portion wise. The reaction mixture was stirred at room temperature for 16 h, 30 mL of saturated $Na_2S_2O_3$ was added. The reaction mixture was diluted with ethyl acetate (200 mL) and water (500 mL), the organic layer was separated, the aqueous layer extracted by ethyl acetate (100 mL). The combined organic layer was washed with 100 mL of saturated $Na_2CO_3$, brine (100 mL×3), dried over $Na_2SO_4$, filtered, and concentrated in vacuum. The crude product was purified by chromatography to give compound D94 as a yellow solid (1.4 g, 64%). LC-MS: M+1: 703.

Preparation of Compound D95:

The mixture of tert-butyl (1R,4R,5R)-2-azabicyclo[2.2.1]heptan-5-ylcarbamate (430 mg, 2 mmol), 7 (1.40 g, 2 mmol), and $K_2CO_3$ (280 mg, 2 mmol) in NMP (5 mL) was stirred for overnight at room temperature, then 2-methylpyrimidin-5-ol (330 mg, 3 mmol) was added and the resulting mixture was heated to 50° C. for overnight. The crude product was purified by HPLC to give compound D95 (the BOC protected D96) as a white solid (700 g, 54%). LC-MS: M+1: 653.

Preparation of Compound D96:

The above compound (700 mg, 1.1 mmol) was dissolved in 10 mL of TFA and stirred for 1 minute at room temperature. After removal of the solvents, the residue was redesolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipitate, and dried to gave final compounds D96 as a white solid (400 mg, 80%). LC-MS: M+1: 453.20.

$^1$H NMR (300 MHz, DMSO) δ (ppm): 11.75 (s, 1H), 8.72 (s, 2H), 6.45 (dd, J=2.7, J=5.2, 1H), 5.37 (brm, 1H), 4.46 (s, 1H), 3.78 (m, 1H), 3.67 (m, 1H), 3.33 (brs, 1H), 2.83 (brs, 3H), 2.67 (s, 3H), 2.37 (brs, 1H), 2.01 (brt, 1H), 1.20 (brt, 1H).

Preparation of Compound D97:

The subtitle compound was synthesized using the same method described for the above compound starting with (R)-2-azaspiro[3.3]heptan-5-amine. LC-MS: M+1: 453.18. [0593]$^1$H NMR (300 MHz, DMSO) δ (ppm): 11.75 (s, 1H), 8.72 (s, 2H), 6.37 (dd, J=2.7, J=5.2, 1H), 5.45 (brs, 1H), 4.63 (d, J=3, 1H), 4.12 (s, 3H), 3.20 (t, 1H), 2.83 (d, J=2, 3H), 2.67 (s, 3H), 1.75-2.01 (m, 7H), 1.39 (m, 1H).

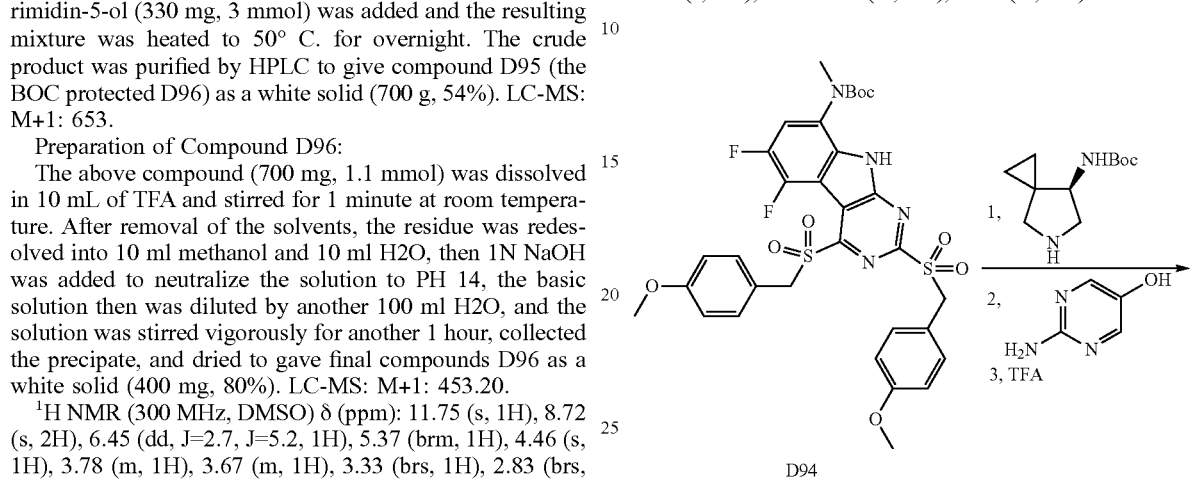

D94

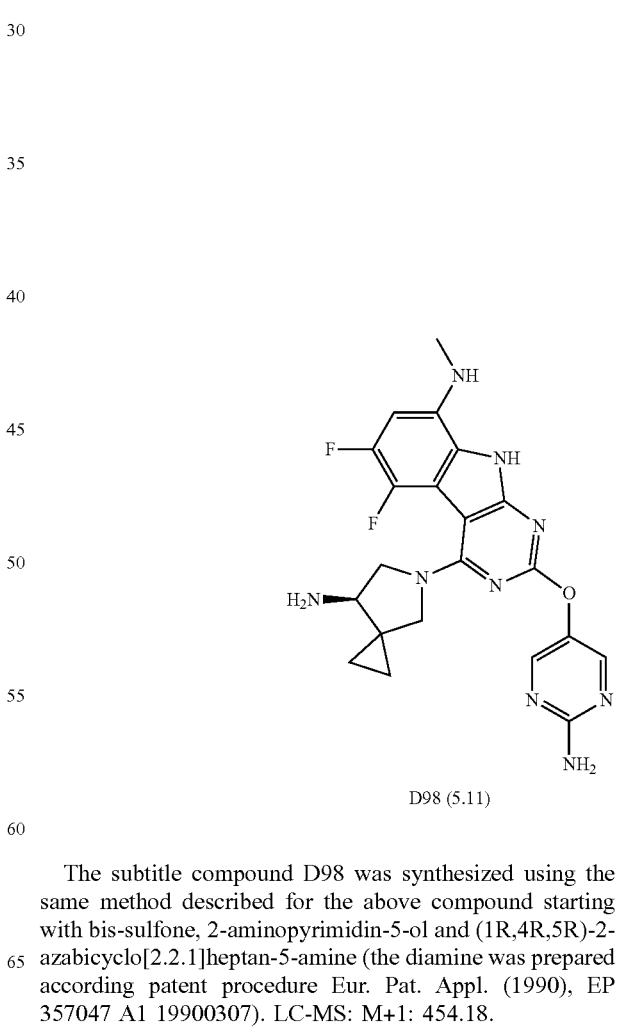

D97 (5.01)

D98 (5.11)

The subtitle compound D98 was synthesized using the same method described for the above compound starting with bis-sulfone, 2-aminopyrimidin-5-ol and (1R,4R,5R)-2-azabicyclo[2.2.1]heptan-5-amine (the diamine was prepared according patent procedure Eur. Pat. Appl. (1990), EP 357047 A1 19900307). LC-MS: M+1: 454.18.

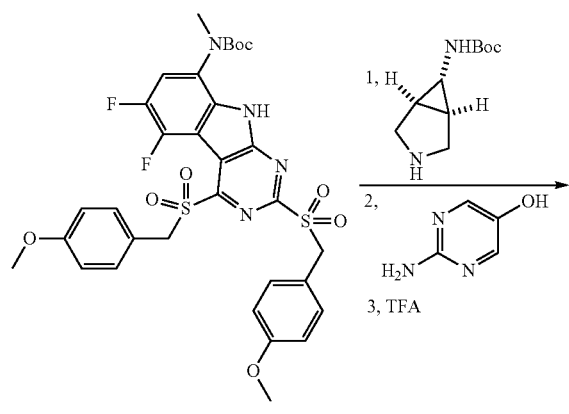

D94

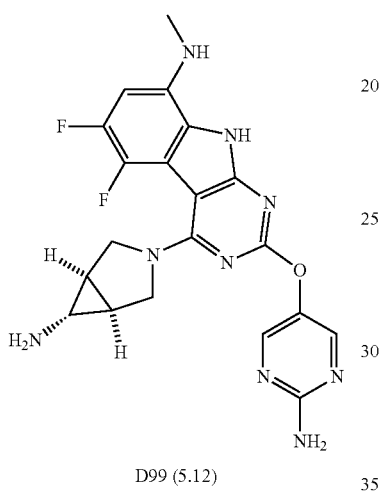

D99 (5.12)

The subtitle compound D99 was synthesized using the same method described for the above compound starting with bis-sulfone, 2-aminopyrimidin-5-ol and tert-butyl (1R, 5S,6r)-3-azabicyclo[3.1.0]hexan-6-ylcarbamate. LC-MS: M+1: 440.15.

Preparation of Compound 9.1:

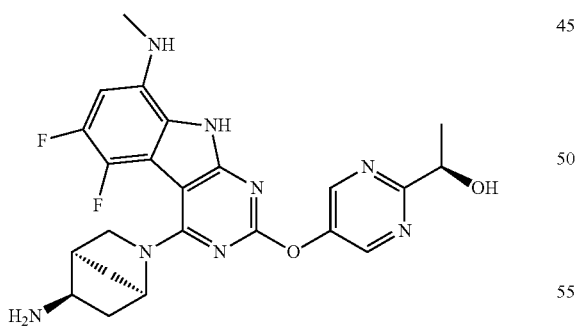

The title compound was prepared using the same method described above to make Compound 5.12 starting with (R)-tert-butyl 2-azabicyclo[2.2.1]heptan-5-ylcarbamate and (S)-2-(1-hydroxyethyl)pyrimidin-5-ol. LC-MS: 465.23.

$^1$H NMR (300 MHz, DMSO) δ (ppm):
8.81 (2H, s), 6.45 (1H, dd, J1=6 Hz, J2=12 Hz), 5.36 (2H, d, J=6 Hz), 4.84 (1H, dd, J1=6 Hz, J2=12 Hz), 4.46 (1H, s), 3.73 (2H, m), 3.35 (3H, m), 2.84 (3H, d, J=6 Hz), 2.38 (1H, s), 2.04 (1H, m), 1.61 (2H, m), 1.46 (3H, d, J=6 Hz), 1.18 (1H, m).

Preparation of Compound 9.2:

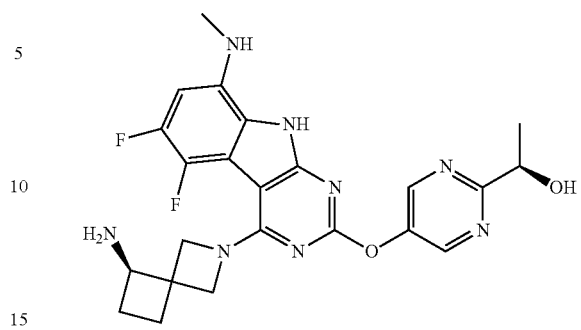

The title compound was prepared using the same method described above to make Compound 5.12 starting with (S)-tert-butyl 2-azaspiro[3.3]heptan-5-ylcarbamate and (S)-2-(1-hydroxyethyl)pyrimidin-5-ol. LC-MS: 465.15. (Compound 10.118 may be made by the same method using corresponding starting materials.)

$^1$H NMR (300 MHz, DMSO) δ (ppm):
8.83 (2H, s), 6.46 (1H, dd, J1=6 Hz, J2=12 Hz), 5.31 (2H, d, J=6 Hz), 4.85 (1H, m), 4.70 (1H, d, J2=12 Hz), 4.18 (3H, m), 3.18 (1H, t, J=9 Hz), 2.82 (3H, d, J=3 Hz), 1.85 (3H, m), 1.46 (3H, d, J=6 Hz), 1.18 (1H, m).

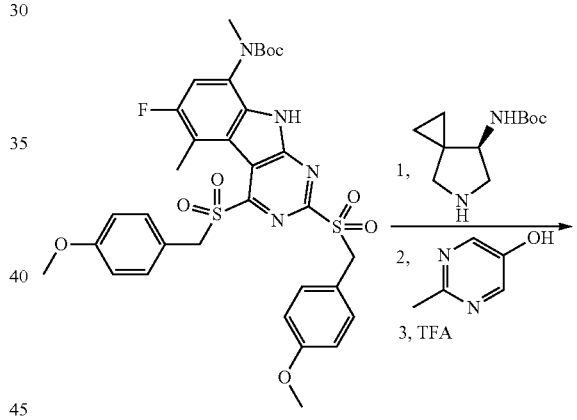

D100

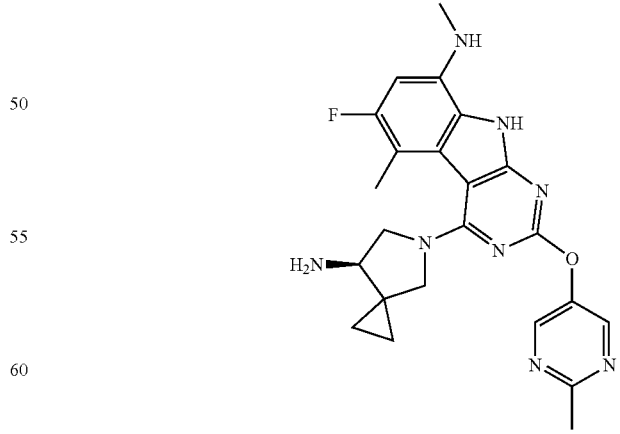

D101 (6.29)

The subtitle compound D101 was synthesized using the same method described for the above compound starting with bis-sulfone and (R)-tert-butyl 5-azaspiro[2.4]heptan-7-ylcarbamate. LC-MS: M+1: 449.24.

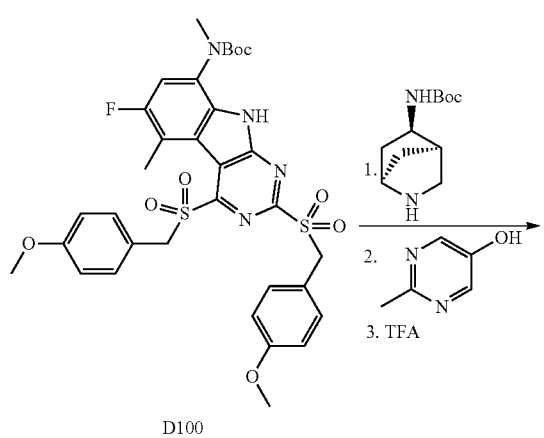

D100

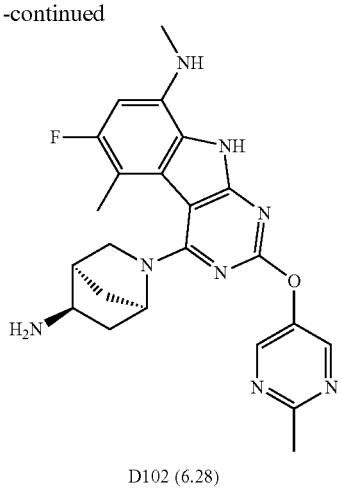

D102 (6.28)

The subtitle compound D102 was synthesized using the same method described for the above compound starting with bis-sulfone and tert-butyl (1R,4R,5R)-2-azabicyclo[2.2.1]heptan-5-ylcarbamate. LC-MS: M+1: 449.21.

Table of Formula I' Compounds Where L is O, $R^x$, is CH, $R^y$ and $R^z$ are F and $R^8$ is $NHCH_3$

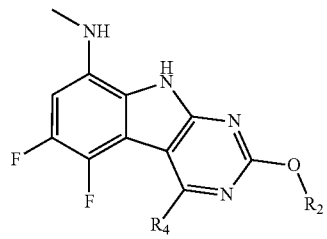

| Compd ID | R2 | R4 |
|---|---|---|
| 5.01 | | ![](2-azaspiro[3.3]heptan-6-amine) |
| 5.02 | | ![](5-azaspiro[2.4]heptan-1-amine) |
| 5.03 | | ![](octahydrocyclopenta[c]pyrrol-5-amine) |
| 5.04 | | ![](3-azabicyclo[3.1.0]hexan-6-amine) |

-continued

Table of Formula I' Compounds Where L is O, R$^x$, is CH, R$^y$ and R$^z$ are F and R$^8$ is NHCH$_3$

| Compd ID | R2 | R4 |
|---|---|---|
| 5.05 | 5-methylpyrimidin-2-yloxy | 6-amino-5-azaspiro[3.4]octan-5-yl (with H$_2$N) |
| 5.06 | 5-methylpyrimidin-2-yloxy | 3-aminoazetidin-1-yl |
| 5.07 | 5-aminopyrimidin-2-yloxy | 6-amino-2-azaspiro[3.3]heptan-2-yl |
| 5.08 | 5-methylpyrimidin-2-yloxy | 5-amino-2-azabicyclo[2.2.1]heptan-2-yl |
| 5.09 | pyrimidin-2-yloxy | 6-amino-5-azaspiro[3.4]octan-5-yl |
| 5.1 | 5-methylpyrimidin-2-yloxy | amino-methyl-octahydrocyclobuta[b]pyrrol-yl |
| 5.11 | 5-aminopyrimidin-2-yloxy | 6-amino-5-azaspiro[3.4]octan-5-yl |
| 5.12 | 5-methylpyrimidin-2-yloxy | 6-amino-3-azabicyclo[3.1.0]hexan-3-yl |

Table of Formula I' Compounds Where L is O, $R^x$ is CH, $R^y$ and $R^z$ are F and $R^8$ is NHCH$_3$
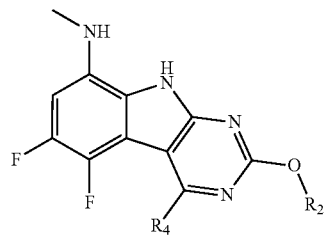
| Compd ID | R2 | R4 |
|---|---|---|
| 5.13 | 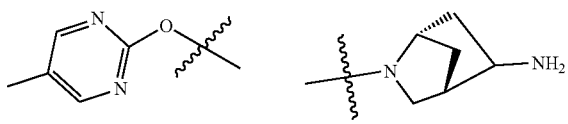 | |
5.14
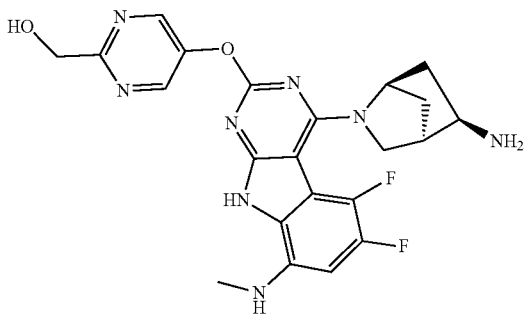 [SMILES: CNc1cc(F)c(F)c2c1[nH]c1nc(Oc3cnc(CO)nc3)nc(N3C[C@H]4C[C@@H]3C[C@H]4N)c12]
5.15
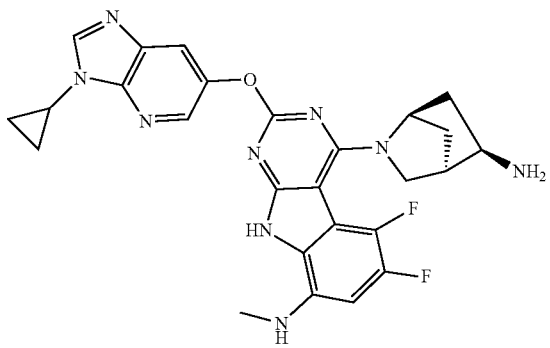 [SMILES: CNc1cc(F)c(F)c2c1[nH]c1nc(Oc3cnc4c(c3)ncn4C3CC3)nc(N3C[C@H]4C[C@@H]3C[C@H]4N)c12]

Table of Formula I' Compounds
Where L is O, $R^8$ is $NHCH_3$ Alternative $R^x$ $R^y$, $R^z$ combinations

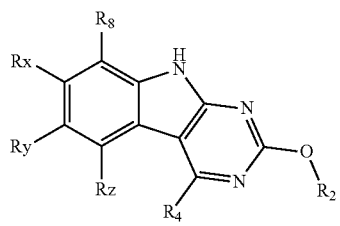

| Cmpd ID | L—R2 | R4 | Rz | Ry | Rx | R8 |
|---|---|---|---|---|---|---|
| 6.01 | 5-methylpyrimidin-2-yloxy | 3-aminopyrrolidin-1-yl | H | H | F | NHMe |
| 6.02 | pyrimidin-2-yloxy | 6-amino-3-azabicyclo[3.1.0]hexan-3-yl | H | H | F | NHMe |
| 6.03 | 1,5-naphthyridin-2-yloxy | (3-amino)pyrrolidin-1-yl (stereo) spiro cyclopropane | H | H | F | NHMe |
| 6.04 | 1,5-naphthyridin-2-yloxy | 6-amino-3-azabicyclo[3.1.0]hexan-3-yl | H | H | F | NHMe |
| 6.05 | 1,5-naphthyridin-2-yloxy | 3-aminopyrrolidin-1-yl | H | H | F | NHMe |
| 6.06 | 5-methylpyrimidin-2-yloxy | 6-amino-3-azabicyclo[3.1.0]hexan-3-yl | F | H | F | NHMe |
| 6.07 | 5-methylpyrimidin-2-yloxy | aminopyrrolidinyl-spirocyclopropane | F | H | F | NHMe |
| 6.08 | 5-methylpyrimidin-2-yloxy | 6-amino-2-azaspiro[3.3]heptan-2-yl | F | H | F | NHMe |

-continued

Table of Formula I' Compounds
Where L is O, $R^8$ is $NHCH_3$ Alternative $R^x$ $R^y$, $R^z$ combinations

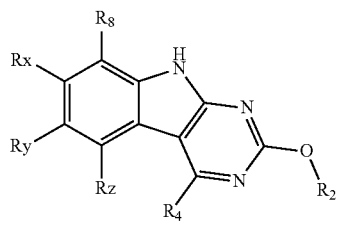

| Cmpd ID | L—R2 | R4 | Rz | Ry | Rx | R8 |
|---|---|---|---|---|---|---|
| 6.09 | 5-methylpyrimidin-2-yloxy | octahydrocyclobuta[c]pyrrol-amine | F | H | F | NHMe |
| 6.10 | 5-methylpyrimidin-2-yloxy | 3-azabicyclo[3.1.0]hexan-6-amine | H | CF3 | H | NHMe |
| 6.11 | pyrimidin-2-yloxy | 5-azaspiro[2.4]heptan-amine | H | Cl | H | NHMe |
| 6.12 | pyrimidin-2-yloxy | 5-azaspiro[2.4]heptan-amine | H | Cl | H | NHMe |
| 6.13 | 5-methylpyrimidin-2-yloxy | octahydro-1,6-naphthyridine | H | Cl | H | NHMe |
| 6.14 | 1,5-naphthyridin-2-yloxy | 6-azaspiro[2.5]octan-amine | H | Cl | H | NHMe |
| 6.15 | 5-aminopyrimidin-2-yloxy | 5-azaspiro[2.4]heptan-amine | H | Cl | H | NHMe |

-continued

Table of Formula I' Compounds
Where L is O, R⁸ is NHCH₃ Alternative Rˣ Rʸ, Rᶻ combinations

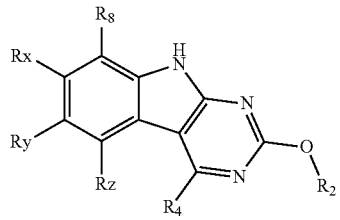

| Cmpd ID | L—R2 | R4 | Rz | Ry | Rx | R8 |
|---|---|---|---|---|---|---|
| 6.16 | 5-aminopyrimidin-2-yloxy | 3-azabicyclo[3.2.0] with NH₂ | H | Cl | H | NHMe |
| 6.17 | 5-aminopyrimidin-2-yloxy | 3-azabicyclo[3.1.0]hexyl-NH₂ | H | Cl | H | NHMe |
| 6.18 | 2-methoxypyrimidin-5-yl | 6-methoxypyridin-3-yl | H | F | H | NHMe |
| 6.19 | pyrimidin-5-yloxy | 3-azabicyclo[3.1.0]hexyl-NH₂ | F | F | H | NHMe |
| 6.20 | 2-methylpyrimidin-5-yloxy | 2-azaspiro[3.3]heptyl-NH₂ | Me | F | H | NHMe |
| 6.21 | 2-methylpyrimidin-5-yloxy | HN-CH₂CH₂CH₂-NH₂ | Me | F | H | NHMe |
| 6.22 | 2-methylpyrimidin-5-yloxy | trans-2-aminocyclohexylamino | Me | F | H | NHMe |
| 6.23 | pyrimidin-5-yloxy | 3-azabicyclo[3.1.0]hexyl-NH₂ | F | H | H | NHMe |

-continued

Table of Formula I' Compounds
Where L is O, R⁸ is NHCH₃ Alternative Rˣ Rʸ, Rᶻ combinations

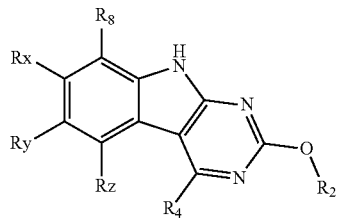

| Cmpd ID | L—R2 | R4 | Rz | Ry | Rx | R8 |
|---|---|---|---|---|---|---|
| 6.24 | pyrimidin-2-amine-5-yloxy | 2-amino-5-azaspiro[2.4]heptane | F | H | H | NHMe |
| 6.25 | pyrimidin-2-amine-5-yloxy | 3-azabicyclo[3.1.0]hexan-6-amine | F | H | H | NHMe |
| 6.26 | 2-methylpyrimidin-5-yloxy | 3-azabicyclo[3.1.0]hexan-6-amine | H | Me | H | NHMe |
| 6.27 | pyrimidin-5-yloxy | 3-azabicyclo[3.1.0]hexan-6-amine | H | Me | H | NHMe |
| 6.28 | (full structure shown) | | | | | |
| 6.29 | (full structure shown) | | | | | |

Example 16: Synthesis of Analogs where either X, Y or Z is N

Example 16a—Pyrimidines

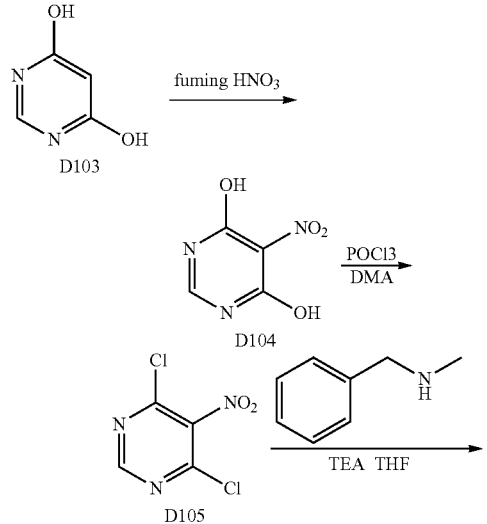

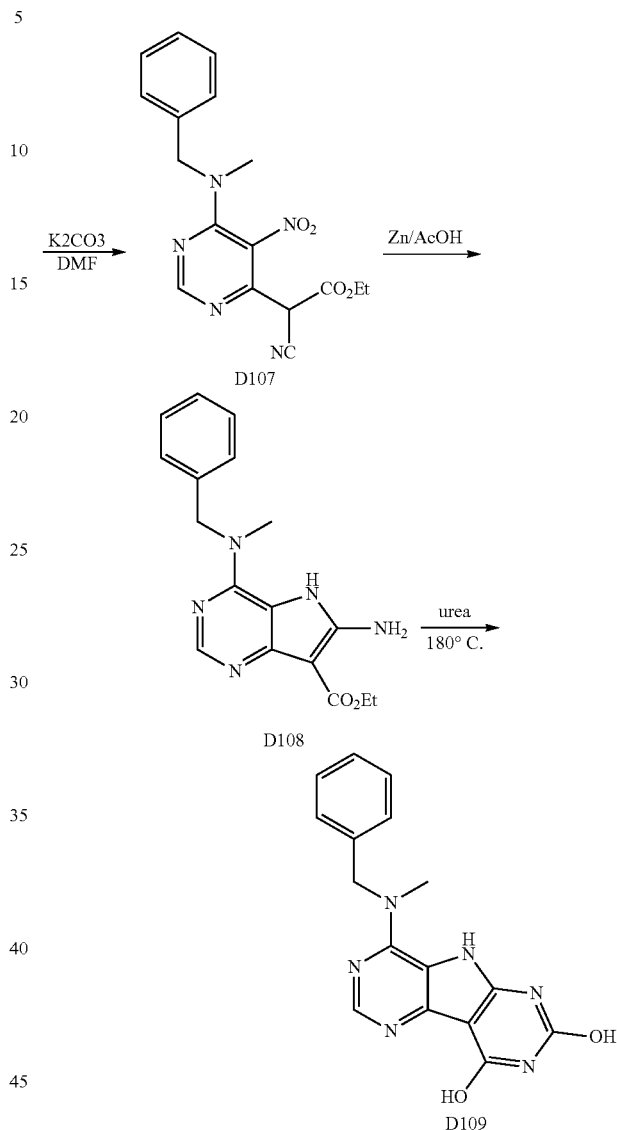

Preparation of Compound D104:

Compound D103 (280 g, 2.50 mol) was added to a solution of nitric acid (90%, 1120 ml) at −10° C. over 1 h and the whole was stirred at −10° C. for further 1.5 h, followed by warming to r.t. and stirred for 2 h. The mixture was poured into ice water and the yellow solid was collected by filtration, dried under reduced press to give D104 (200 g, 51% yield) as a yellow solid. LC-MS: M+1: 158 Preparation of compound D105: Compound D104 (200 g, 1.27 mol) was added to the mixture of $POCl_3$ (1300 ml) and DMA (255 ml) at r.t, and the whole was heated to reflux for 2-3 h and the reaction is monitored by TLC. The reaction mixture was poured into ice water, extracted with EtOAc (1 L*3), washed with sat. brine, dried ($Na_2SO_4$), and concentrated in vacuo to give crude product compound D105 (170 g) as a black solid. It was used in next step directly without further purification. LC-MS: M+1: 194

Preparation of Compound D106:

To a mixture of compound D105 (170 g, 1.27 mol) obtained above and triethyl amine (107 g, 1.06 mol) in THF (500 ml) was added the solution of N-methyl(phenyl)methane amine (38.4 g, 316 mmol) in THF at −40° C. drop-wise, and the whole was stirred at that temperature. After the reaction was completed (monitored by TLC), the reaction mixture was diluted with $H_2O$ and extracted with EtOAc, washed with sat. NaCl, dried ($Na_2SO_4$) and concentrated in vacuo to give the crude product.

It was purified by column chromatography to give the product of compound D106 (101 g, 41.4%) as an oil. LC-MS: M+1: 279.

Preparation of Compound D107:

To a mixture of compound D106 (5.0 g, 17.94 mmol) and $K_2CO_3$ (5.25 g, 35.89 mmol) in DMF (30 ml) was added ethyl 2-cyanoacetate (4.06 g, 35.89 mmol) at r.t., it was heated to 50° C. for 3 h and monitored by TLC. The reaction mixture was diluted with $H_2O$ and extracted with EtOAc. The organic layer was washed with sat. brine, dried ($Na_2SO_4$) and concentrated in vacuo to give the crude product. It was purified by column chromatography to give the product compound D107 (2.67 g, 42% yield) as a yellow solid. LC-MS: M+1: 356

Preparation of Compound D108:

To a mixture of compound D107 (39 g 110 mmol) in acetic acid (300 ml) was added Zn (56 g, 858 mmol) at 80° C. over 0.5 h, and the whole was heated to 90° C. for further 3 h and the reaction was monitored by TLC. After the reaction was completed the mixture was cooled to r.t. and filtered to remove inorganic salts. The filtrate was concentrated in vacuo, and the residue was diluted with $H_2O$ and basified with NaHCO₃ to PH 7-8. Then it was extracted with EtOAc. The organic layer was washed with sat. brine, dried (Na₂SO₄), and concentrated in vacuo to give the product compound D108 (35 g, 98.0% yield) as a white solid. It was used in next step directly. LC-MS: M+1: 326. Preparation of compound D109: The mixture of compound D108 (10.00 g, 30.73 mmol) and urea (50.0 g) was heated to 180° C. overnight, TLC and LCMS showed the reaction was completed. It was diluted with DMSO and heated to 180° C. for 10 min. After it was cooled to r,t, the insoluble material was filtered off and the filtrate was poured into H₂O. The solid precipitated put was collected by filtration. The solid was treated with H₂O, and the suspension was heated to reflux. It was filtered while hot. The collected solid was washed with hot water for 4 more times. Then it was washed with hot MeOH and EtOAc, dried in vacuo to give the pure enough product compound D109 (6.20 g, 62% yield) as a white sold. LC-MS: M+1: 323.

¹H-NMR (300 MHz, DMSO-d6) δ (ppm): 8.23 (1H, s), 7.25-7.36 (5H, m), 3.37 (2H. s), 2.51 (3H. s).

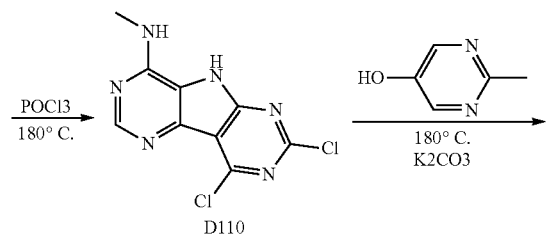

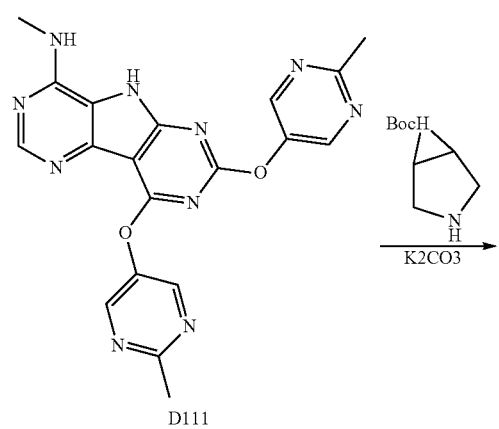

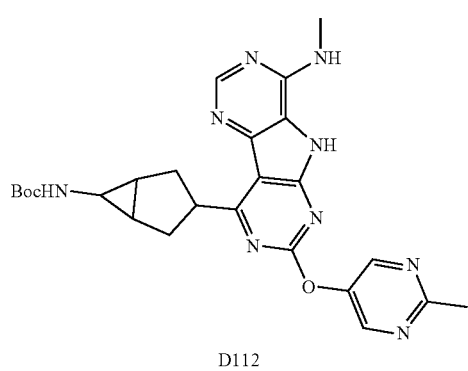

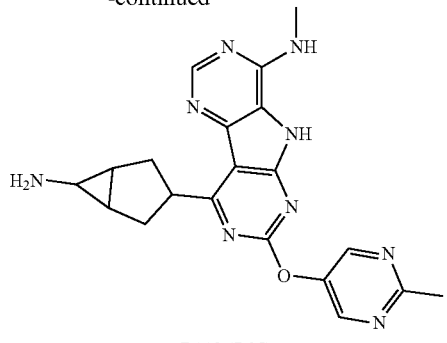

D113 (7.05)

Preparation of Compound D110:

Compound D109 (1.5 g, 4.64 mmol) was placed with a solution of POCl₃ (50 ml) in a pressure tube and few drops of N-ethyldiisopropyl amine. The reaction mixture was heated to at 185° C. under sealed condition over 10 h. The mixture was cooled and poured into ice water and the yellow solid was collected by filtration, dried under reduced press to give D110 (1.2 g, 98% yield) as a yellow solid. LC-MS: M+1: 270.

Preparation of Compound D11:

Compound D110 (100 mg, 0.37 mmol) was added to a solution of 2-methylpymiridin-5-ol (120 mg, 1.1 mmol) and K₂CO₃ (15 mg, 1.0 mmol) in NMP (4 mL) in a microwave tube. The reaction mixture was sealed and placed in Microwave at 150° C. for 10 minutes. The desired product was obtained by HPLC purification to give D111 (100 mg, 75%) as a white solid. LC-MS: M+1: 417.

Preparation of Compound D112:

To a stirred solution of compound D111 (50 mg, 0.12 mmol) in 2 mL of NMP at 110° C. was added tert-butyl 3-azabicyclo[3.1.0]hexan-6-ylcarbamate (27 mg, 0.1 mmol) and K₂CO₃ (2 mg, 0.05 mmol). After the completion of the reaction in 10 minutes, the reaction mixture was purified by HPLC to give the product D112 (38 mg, 63%) as a white solid. LC-MS: M+1: 505.

Preparation of Compound D113:

To a stirred solution of compound D112 (38 mg, 0.07 mmol) in 5 mL of acetonitrile at room temperature was added 2 mL of TFA. After the completion of the reaction in 20 minutes. The reaction mixture was concentrated and purified by HPLC to give the product D113 (28 mg, 95%) as a white solid. LC-MS: M+1: 405.

¹H-NMR (300 MHz, DMSO-d6) δ (ppm): 8.23 (1H, s), 7.26 (2H, s), 2.51 (3H. s), 2.55 (3H. s), 2.88 (2H. m), 2.63 (2H. m), 1.22 (1H. m), 0.66 (2H. m).

Example 16b—Pyridines

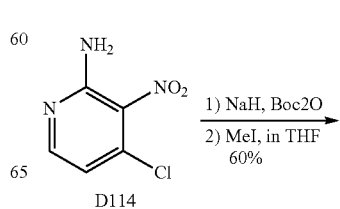

D114

-continued

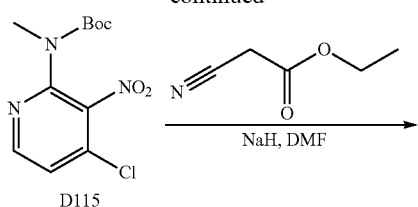

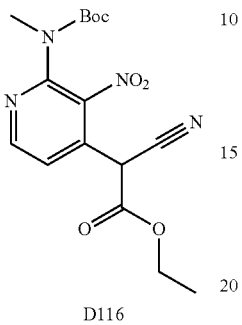

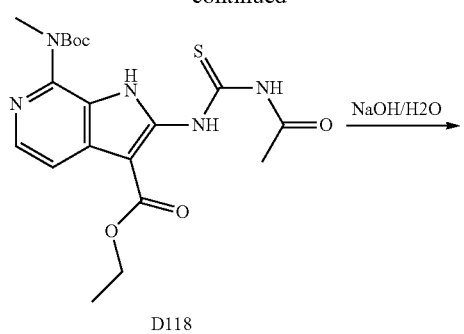

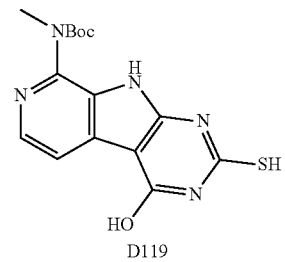

4-chloro-3-nitropyridin-2-amine (1.73 g, 10 mmol) in 10 ml THF was portionly added into sodium hydride (2 g, 50 mmol, 60% in oil) solution in dry THF (200 ml) under the ice water bath, then the solution was stirred for another 1 hours, then Boc2O (2.4 g, 11 mol) in 10 ml THF was added dropwisely into the solution, the solution was stirred for 4 hours at room temperature, then MeI (2.8 g, 20 mol) in 10 ml THF was added dropwisely into the solution, the mixture was stirred for overnight (12 hours), and quenched with ice water. The aqueous solution was extracted with 3×100 ml ethyl acetate, the combined organic solution was dried and concentrated. The residue was purified by flash chromatography to give 2.1 g desired products D115 with 73% yield.

To the mixture of NaH (0.8 g, 20 mmol, 60% in oil) and ethyl 2-cyanoacetate (2.2 g, 20 mmol) in dry DMF (100 ml) at room temperature was added tert-butyl (4-chloro-3-nitro-pyridin-2-yl)(methyl)carbamate (2 g, 7 mmol), the mixture was stirred for overnight at 100° C. for 12 hours, then the reaction mixture was carefully quenched by water, then the solution was partitioned by water and ethyl acetate (100 ml+100 ml), then organic layer was dried and concentrated. The residue was purified by flash chromatography to give 2.4 g desired products D116 with 66% yield. LC-MS: M+1: 365.15.

To a stirred suspension of compound ethyl 2-amino-7-((tert-butoxycarbonyl)(methyl)amino)-1H-pyrrolo[2,3-c]pyridine-3-carboxylate (500 mg, 1.5 mmol) in acetone (20 mL) was added dropwise a solution of acetyl isothiocyanate (0.24 mL, 3 mmol) in acetone (5 mL) at room temperature. The reaction mixture was heated to reflux for 16 h. LCMS showed the reaction was completed. The reaction mixture was concentrated for next step without purification.

Above residue was dissolved into 20 ml methanol and 20 ml H2O, and then added 5 ml 10% KOH solution, the mixture solution was heated to reflux for 30 minutes. When LCMS showed the reaction was completed the reaction was cooled to room temperature, acidified to pH 5 with 1 M a 1 h. HCl, and the precipitate collected by filtration to give desired compound tert-butyl (4-hydroxy-2-mercapto-9H-pyrido[4',3':4,5]pyrrolo[2,3-d]pyrimidin-8-yl)(methyl)carbamate D119 as a solid (340 mg, 65.4% in two steps). LC-MS: M+1: 348.

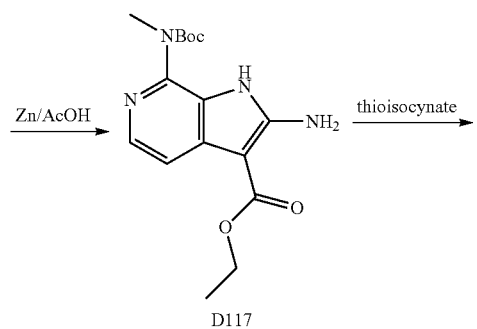

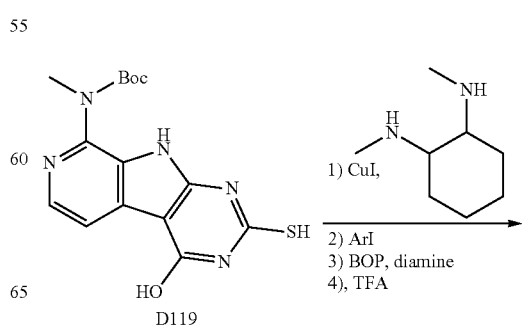

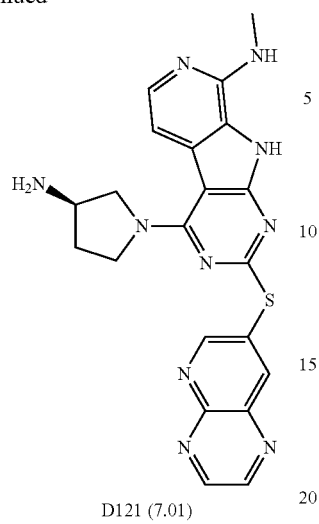

D121 (7.01)

The solution of CuI (67 mg, 0.35 mmol), N,N'-dimethylcyclohexane-1,2-diamine (100 mg, 0.70 mmol) in 9 mL of NMP was added to a stirring suspension tert-butyl (4-hydroxy-2-mercapto-9H-pyrido[4',3':4,5]pyrrolo[2,3-d]pyrimidin-8-yl)(methyl)carbamate (350 mg, 1.0 mmol), a proper I—Ar (1.17 mmol), $K_2CO_3$ (324 mg, 2.35 mmol) and $PPh_3$ (400 mg, 1.53 mmol) in NMP (9 mL). The mixture was heated to 130° C. for 2 to 12 hrs monitored by LC-MS for the completion of the reaction. When the reaction completed, the mixture was cooled to 0° C., BOP (621 mg, 1.40 mmol) and $Et_3N$ (0.41 mL, 2.93 mmol) was added, stirred for 30 minutes at 0° C., then warmed up to room temperature, a suitable Boc-protected diamine (2.34 mmol) was added. The reaction mixture was heated to 50° C. for 30 minutes. LC-MS indicated the completed reaction. After completed the reaction, the mixture was partitioned with ethyl acetate and water, the aqueous layer was extracted by ethyl acetate twice, the combined organic layer was dried and purified by flash chromatography to give products compound D120 as a solid (420 mg, 65% in two steps). LC-MS: M+1: 644.

The above compound (420 mg, 0.64 mmol) was dissolved in 10 mL of TFA and stirred for 30 minute at room temperature. After removal of the solvents, the residue was re-dissolved into 10 ml methanol and 10 ml H2O, then 1N NaOH was added to neutralize the solution to PH 14, the basic solution then was diluted by another 100 ml H2O, and the solution was stirred vigorously for another 1 hour, collected the precipitate, and dried to gave final compound D121 as a white solid (200 mg, 70%). LC-MS: M+1: 444.

Table of Formula I' Compounds Where L is O, where one or more $R^x, R^y, R^z$ is N and $R^8$ NHCH$_3$

| Compd ID | Structure |
|---|---|
| 7.01 | 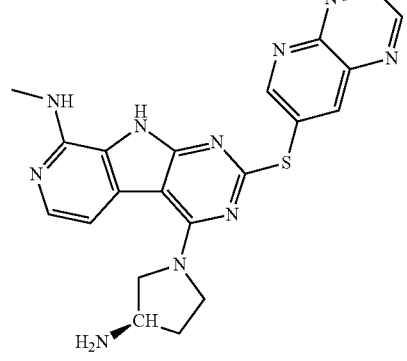 |
| 7.02 | 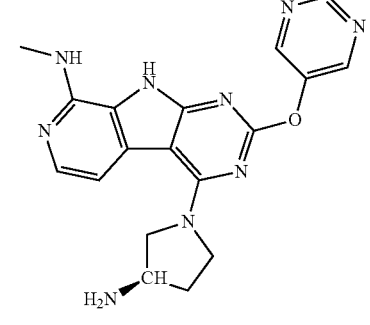 |
| 7.03 | 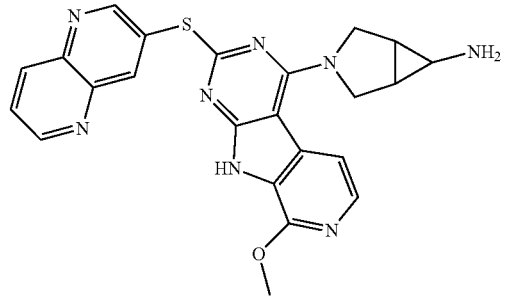 [SMILES: COc1nccc2c1[nH]c1nc(Sc3cnc4cccnc4c3)nc(N3CC4C(N)C4C3)c12] |
| 7.04 | 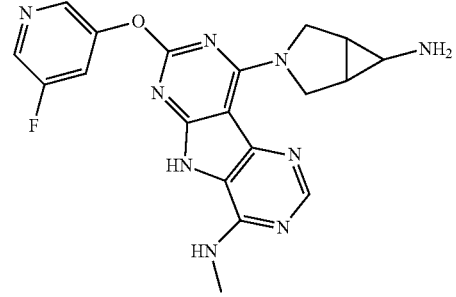 [SMILES: CNc1ncnc2c1[nH]c1nc(Oc3cncc(F)c3)nc(N3CC4C(N)C4C3)c12] |

TABLE: Table of Formula I' Compounds Where L is O, where one or more R^x, R^y, R^z is N and R^8 NHCH_3

| Compd ID | Structure |
|---|---|
| 7.05 | (structure) |
| 7.06 | (structure) |
| 7.07 | (structure) |
| 7.08 | (structure) |
| 7.09 | (structure) |
| 7.10 | (structure) |
| 7.11 | (structure) |
| 7.12 | (structure) |

Example 17: Bis aryloxys

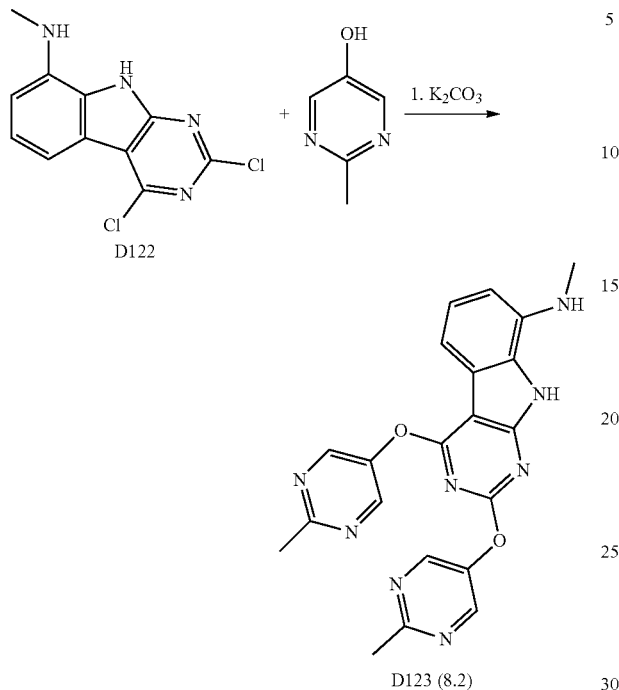

N-methyl-2,4-bis(2-methylpyrimidin-5-yloxy)-9H-pyrimido[4,5-b]indol-8-amine

To the solution of compound (D122)(100 mg, 0.37 mmol) in NMP (5 ml) was added 2-methylpyrimidine-5-ol (100 mg, 0.9 mmol) and potassium carbonate (43.6 mg, 0.31 mmol). It was then heated at 180° C. under microwave condition for 15 minutes. The mixture was then purified through HPLC to afford the title compound D123 as yellow solid (80 mg, 52%). LC-MS: M+1:415.15.

$^1$H NMR (300 MHz, DMSO) δ (ppm): 14.01 (S, 1H), 11.71 (s, 1H), 8.98 (s, 2H), 8.78 (s, 2H), 7.84 (d, J=7.5, 1H), 7.47 (m, 1H), 6.90 (d, J=9.7, 1H), 4.18 (s, 1H), 3.10 (s, 3H), 2.65 (s, 3H), 2.64 (s, 3H).

Table of Formula I' Compounds Where $R^4$ is OR

| Cmpd ID | Structure |
| --- | --- |
| 8.1 | 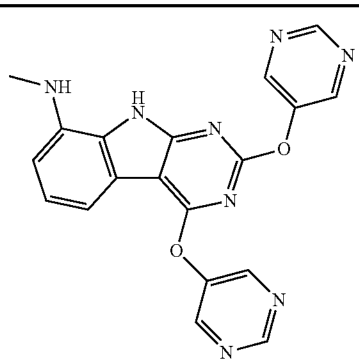 |
| 8.2 | 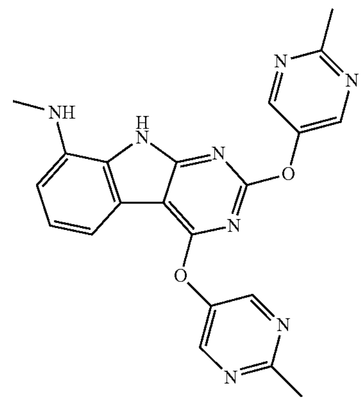 [SMILES: CNc1cccc2c1[nH]c1nc(Oc3cnc(C)nc3)nc(Oc3cnc(C)nc3)c12] |
| 8.3 | 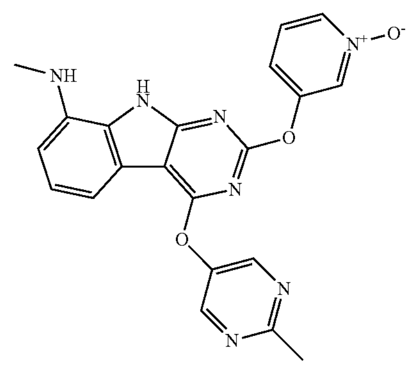 [SMILES: CNc1cccc2c1[nH]c1nc(Oc3ccc[n+]([O-])c3)nc(Oc3cnc(C)nc3)c12] |
| 8.4 | 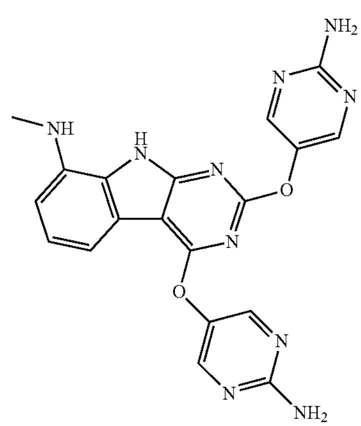 [SMILES: CNc1cccc2c1[nH]c1nc(Oc3cnc(N)nc3)nc(Oc3cnc(N)nc3)c12] |

Example 18

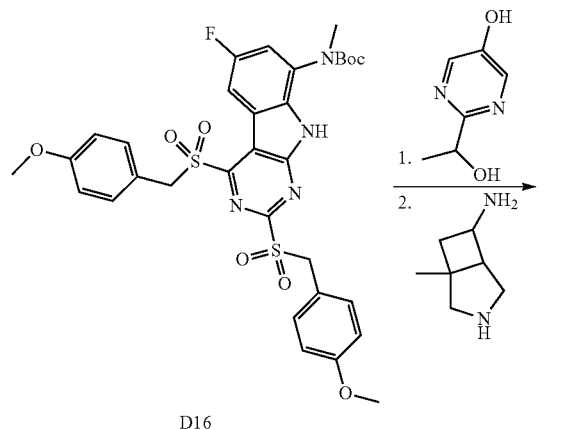

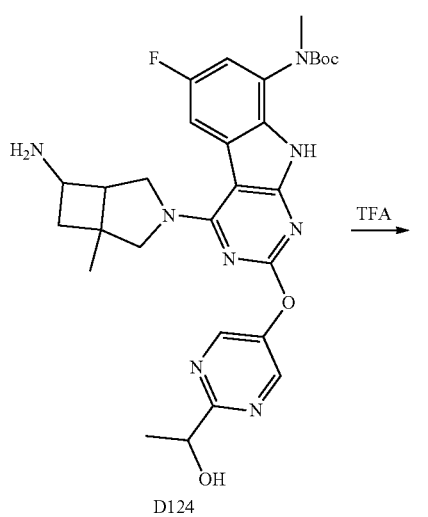

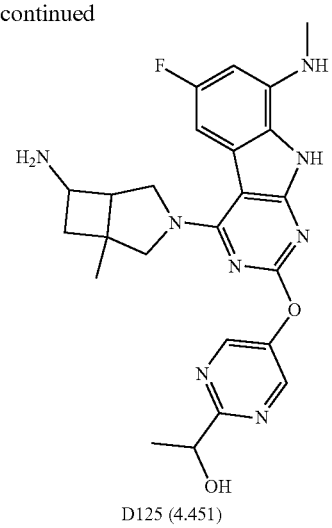

The subtitle compound D125 was synthesized using the same method described for the above compound starting with bis-sulfone, 2-(1-hydroxyethyl)pyrimidin-5-ol and 1-methyl-3-azabicyclo[3.2.0]heptan-6-amine (the diamine was prepared in accordance with the procedure described in PCT Int. Appl. (1994), WO 9415933 A1 19940721). LC-MS: M+1: 479.25.

Example 19: Determination of Anti-Bacterial Efficacy

Colonies of *H. influenzae, E. coli, S. aureus, A. baumannii, S. pneumoniae, P. aeruginosa*, and *B. thailandensis* were picked from overnight plates and resuspended in 3 mL DPBS solution. Absorbance was read at 600 nM and suspensions were diluted to an OD of 0.1.

Inocula were added to appropriate growth medium, and 98 μL of the mixture were plated into columns 1-11 of a 96 well flat-bottomed cell-culture plate. Column 12 was plated with medium only.

|  |  | Resuspended Cells | Medium | Incubation |
|---|---|---|---|---|
| *S. aureus* | ATCC 13709 | 50 uL | 20 mL Mueller Hinton cationic adjusted | Ambient 18 h |
| SA + serum | ATCC 13709 | 50 uL | 16 mL MHCA + 4 mL mouse serum | Ambient 18 h |
| *S. pneumoniae* | ATCC 51916 | 100 uL | 20 mL MHCA + 3% Laked Horse Blood | 5% CO$_2$ 18 h |
| *E. coli* | ATCC 25922 | 100 uL | 20 mL MHCA | Ambient 18 h |
| EC + serum | ATCC 25922 | 100 uL | 16 mL MHCA + 4 mL mouse serum | Ambient 18 h |
| *E. coli* | MX1313 | 100 uL | 20 mL MHCA | Ambient 18 h |
| *E. coli* imp | Benson BAS849 | 100 uL | 20 mL MHCA | Ambient 18 h |
| *E. coli* Δtolc | BW25113 Δtolc | 100 uL | 20 mL MHCA | Ambient 18 h |
| *P. aeruginosa* | ATCC 15692 | 100 uL | 20 mL MHCA | Ambient 18 h |
| *A. baumannii* | ATCC 19606 | 100 uL | 20 mL MHCA | Ambient 18 h |
| *A. baumannii* | MX2585 | 100 uL | 20 mL MHCA | Ambient 18 h |
| *K. pneumoniae* | ATCC 700603 | 100 uL | 20 mL MHCA | Ambient 18 h |
| *S. enteritidis* | ATCC 53000 | 100 uL | 20 mL MHCA | Ambient 18 h |
| *S. typhi* | ATCC 33459 | 100 uL | 20 mL MHCA | Ambient 18 h |
| *S. typhimurium* | ATCC 14028 | 100 uL | 20 mL MHCA | Ambient 18 h |
| *S. dysenteriae* | ATCC 13313 | 100 uL | 20 mL MHCA | Ambient 18 h |
| *Y. pestis* | CO92 pgm- | 100 uL | 20 mL MHCA | Ambient 42 h |
| *B. thailandensis* | ATCC E264 | 100 uL | 20 mL MHCA | Ambient 18 h |
| *C. jejuni* | ATCC 33560 | 100 uL | 20 mL MHCA | GasPak EZ Campy Container System 42 h |

|  |  | Resuspended Cells | Medium | Incubation |
|---|---|---|---|---|
| F. tularensis | holarctica LVS | 100 uL | 20 mL MHCA with Isovitalex | Ambient 42 h |
| F. tularensis | novicida Utah 112 | 100 uL | 20 mL MHCA with Isovitalex | Ambient 42 h |

2 μL of compound dilution series in 100% DMSO were added to columns 1-10. Plates were agitated in a plate-shaker for 1 min.

Mixtures of cells and media were diluted 1000× in DPBS and 100 μL were plated onto appropriate media and incubated overnight in order to count CFUs.

Plates were incubated overnight at 35° C. H. influenzae* and *S. pneumoniae* plates were incubated with 5% $CO_2$.

10 μL of Alamar Blue (Invitrogen) were added to plates, and plates were agitated for 1 min in a plate-shaker. Plates were incubated at 35° C. for 1 h. Plates were read visually, with any change in color from blue read as alive.

TABLE 9

MIC data for Compounds in Tables 1-8 (Concentration in μg/mL)

| Cmpd ID | Sa | Ec |
|---|---|---|
| 1.01 | 4 | 64 |
| 1.02 | 32 | >64 |
| 1.03 | 32 | >64 |
| 1.04 | 32 | 64 |
| 1.05 | >64 | >64 |
| 1.06 | 32 | >64 |
| 1.07 | 4 | >32 |
| 1.08 | 64 | >64 |
| 1.09 | 64 | >64 |
| 1.10 | ≤0.5 | 4 |
| 1.11 | ≤0.5 | 8 |
| 1.12 | ≤0.5 | 1 |
| 1.13 | ≤0.5 | ≤0.5 |
| 1.14 | ≤0.5 | 1 |
| 1.15 | 1 | 2 |
| 1.16 | ≤0.5 | 1 |
| 1.17 | ≤0.5 | >64 |
| 1.18 | ≤0.5 | 2 |
| 1.19 | >64 | >64 |
| 1.20 | 4 | 16 |
| 1.21 | ≤0.5 | >64 |
| 1.22 | 1 | 8 |
| 1.23 | ≤0.5 | ≤0.5 |
| 1.24 | ≤0.5 | 1 |
| 1.25 | ≤0.5 | 4 |
| 1.26 | ≤0.5 | 1 |
| 1.27 | ≤0.5 | 1 |
| 1.28 | 4 | 16 |
| 1.29 | 1 | >64 |
| 1.30 | 16 | >64 |
| 1.31 | ≤0.5 | ≤0.5 |
| 1.32 | ≤0.5 | 4 |
| 1.33 | ≤0.5 | 4 |
| 1.34 | 1 | 4 |
| 1.35 | ≤0.5 | 2 |
| 1.36 | 2 | 4 |
| 1.37 | 1 | 4 |
| 1.38 | ≤0.5 | 2 |
| 1.39 | ≤0.5 | 1 |
| 1.40 | ≤0.5 | 1 |
| 1.41 | 4 | 8 |
| 1.42 | 8 | 32 |
| 1.43 | 2 | 8 |
| 1.44 | 1 | 2 |
| 1.45 | 1 | 4 |
| 1.46 | 2 | 4 |
| 1.47 | ≤0.5 | 2 |
| 1.48 | ≤0.5 | 2 |
| 1.49 | ≤0.5 | ≤0.5 |

TABLE 9-continued

MIC data for Compounds in Tables 1-8 (Concentration in μg/mL)

| Cmpd ID | Sa | Ec |
|---|---|---|
| 1.50 | ≤0.5 | ≤0.5 |
| 1.51 | ≤0.5 | ≤0.5 |
| 1.52 | 1 | 16 |
| 1.53 | ≤0.5 | 8 |
| 1.54 | ≤0.5 | >64 |
| 1.55 | 1 | 8 |
| 1.56 | 4 | 32 |
| 1.57 | >32 | >32 |
| 1.58 | ≤0.5 | 8 |
| 1.59 | 1 | 4 |
| 1.60 | 0.5 | 2 |
| 1.61 | 8 | 64 |
| 1.62 | ≤0.5 | ≤0.5 |
| 1.63 | ≤0.5 | ≤0.5 |
| 1.64 | ≤0.5 | ≤0.5 |
| 1.65 | ≤0.5 | ≤0.5 |
| 1.66 | ≤0.13 | ≤0.5 |
| 1.67 | ≤0.5 | >64 |
| 1.68 | 16 | 32 |
| 1.69 | ≤0.5 | 8 |
| 1.70 | 1 | >32 |
| 1.71 | ≤0.5 | ≤0.5 |
| 1.72 | ≤0.5 | 1 |
| 1.73 | ≤0.5 | 8 |
| 1.74 | 4 | >64 |
| 1.75 | ≤0.5 | >64 |
| 1.76 | 1 | >64 |
| 1.77 | 2 | >64 |
| 1.78 | ≤0.5 | 64 |
| 2.01 | ≤0.5 | >16 |
| 2.02 | 2 | 4 |
| 2.03 | 1 | 16 |
| 2.04 | ≤0.5 | 1 |
| 20.5 | ≤0.5 | 2 |
| 2.06 | 1 | 16 |
| 2.07 | 4 | >16 |
| 2.08 | 16 | >64 |
| 2.09 | 16 | 16 |
| 2.10 | 2 | 32 |
| 2.11 | 4 | >64 |
| 2.12 | 16 | >64 |
| 2.13 | 2 | 64 |
| 2.14 | 1 | >64 |
| 2.15 | 1 | >32 |
| 2.16 | 8 | 16 |
| 3.01 | 1 | 4 |
| 3.02 | 4 | 16 |
| 3.03 | 0.5 | 1 |
| 3.04 | 0.5 | ≤0.5 |
| 3.05 | 0.25 | ≤0.5 |
| 3.06 | 0.5 | 1 |
| 3.07 | 1 | 4 |
| 3.08 | 16 | >64 |
| 3.09 | 2 | 32 |
| 3.10 | 32 | >64 |
| 3.11 | ≤0.5 | 2 |
| 3.12 | 1 | 8 |
| 3.13 | ≤0.5 | 1 |
| 3.14 | ≤0.5 | 2 |
| 3.15 | 1 | 8 |
| 3.16 | 4 | 4 |
| 3.17 | 2 | >16 |
| 3.18 | 4 | >16 |
| 3.19 | 8 | 32 |
| 3.20 | >8 | >8 |

TABLE 9-continued

MIC data for Compounds in Tables 1-8 (Concentration in μg/mL)

| Cmpd ID | Sa | Ec |
|---|---|---|
| 3.21 | ≤0.5 | 1 |
| 3.22 | 16 | 64 |
| 3.23 | ≤0.5 | 2 |
| 3.24 | 2 | 8 |
| 3.26 | >16 | >16 |
| 3.27 | 1 | 4 |
| 3.28 | 1 | 2 |
| 3.29 | ≤0.5 | ≤0.5 |
| 3.30 | 16 | 16 |
| 3.31 | 2 | 8 |
| 3.32 | ≤0.5 | 2 |
| 3.33 | ≤0.5 | 1 |
| 3.34 | ≤0.5 | ≤0.5 |
| 3.35 | ≤0.5 | 1 |
| 3.36 | ≤0.5 | 2 |
| 3.37 | 2 | >64 |
| 3.38 | 1 | >32 |
| 3.39 | 2 | 64 |
| 3.40 | ≤0.5 | 1 |
| 3.41 | ≤0.5 | ≤0.5 |
| 3.42 | ≤0.5 | 2 |
| 3.43 | ≤0.5 | 1 |
| 3.44 | 8 | 16 |
| 3.45 | ≤0.5 | ≤0.5 |
| 3.46 | 2 | 4 |
| 3.47 | ≤0.5 | ≤0.5 |
| 3.48 | 2 | 8 |
| 3.49 | ≤0.5 | ≤0.5 |
| 3.50 | ≤0.5 | 2 |
| 3.51 | 8 | 32 |
| 3.52 | ≤0.5 | ≤0.5 |
| 3.53 | 8 | >64 |
| 3.54 | 8 | >32 |
| 3.55 | 64 | >64 |
| 3.56 | >64 | >64 |
| 3.57 | 1 | 8 |
| 3.58 | 32 | >64 |
| 3.59 | 4 | >64 |
| 3.60 | 8 | >64 |
| 3.61 | 4 | 16 |
| 3.62 | ≤0.5 | 8 |
| 3.63 | ≤0.5 | 8 |
| 3.64 | 16 | 64 |
| 3.65 | 8 | 64 |
| 3.66 | 8 | >32 |
| 3.67 | 16 | 64 |
| 4.001 | ≤0.5 | ≤0.5 |
| 4.002 | ≤0.5 | ≤0.5 |
| 4.003 | ≤0.5 | ≤0.5 |
| 4.004 | ≤0.5 | 2 |
| 4.005 | ≤0.5 | ≤0.5 |
| 4.006 | ≤0.5 | 1 |
| 4.007 | ≤0.5 | ≤0.5 |
| 4.008 | ≤0.5 | ≤0.5 |
| 4.009 | ≤0.5 | >64 |
| 4.010 | ≤0.5 | ≤0.5 |
| 4.011 | ≤0.5 | ≤0.5 |
| 4.012 | ≤0.5 | ≤0.5 |
| 4.013 | ≤0.5 | ≤0.5 |
| 4.014 | ≤0.5 | 1 |
| 4.015 | ≤0.5 | 1 |
| 4.016 | ≤0.5 | 1 |
| 4.017 | ≤0.5 | ≤0.5 |
| 4.018 | ≤0.5 | ≤0.5 |
| 4.019 | 2 | 16 |
| 4.020 | ≤0.5 | ≤0.5 |
| 4.021 | ≤0.5 | 2 |
| 4.022 | 8 | 16 |
| 4.023 | ≤0.5 | 1 |
| 4.024 | ≤0.5 | 2 |
| 4.025 | ≤0.5 | 2 |
| 4.026 | ≤0.5 | ≤0.5 |
| 4.027 | ≤0.5 | 1 |
| 4.028 | ≤0.5 | ≤0.5 |
| 4.029 | 4 | 16 |
| 4.030 | 2 | 16 |
| 4.031 | 2 | >16 |
| 4.032 | ≤0.5 | 2 |
| 4.033 | ≤0.5 | 4 |
| 4.034 | ≤0.5 | ≤0.5 |
| 4.035 | ≤0.5 | ≤0.5 |
| 4.036 | ≤0.5 | ≤0.5 |
| 4.037 | ≤0.5 | ≤0.5 |
| 4.038 | ≤0.5 | ≤0.5 |
| 4.039 | ≤0.5 | 2 |
| 4.040 | ≤0.5 | ≤0.5 |
| 4.041 | ≤0.5 | 1 |
| 4.042 | ≤0.5 | ≤0.5 |
| 4.043 | ≤0.5 | ≤0.5 |
| 4.044 | ≤0.5 | ≤0.5 |
| 4.045 | ≤0.5 | ≤0.5 |
| 4.046 | ≤0.5 | 1 |
| 4.047 | ≤0.5 | ≤0.5 |
| 4.048 | ≤0.5 | 1 |
| 4.049 | ≤0.5 | 2 |
| 4.050 | ≤0.5 | ≤0.5 |
| 4.051 | ≤0.5 | 2 |
| 4.052 | ≤0.5 | ≤0.5 |
| 4.053 | ≤0.5 | ≤0.5 |
| 4.054 | ≤0.5 | ≤0.5 |
| 4.055 | ≤0.5 | ≤0.5 |
| 4.056 | ≤0.5 | ≤0.5 |
| 4.057 | ≤0.5 | ≤0.5 |
| 4.058 | ≤0.5 | ≤0.5 |
| 4.059 | ≤0.5 | 1 |
| 4.060 | ≤0.5 | ≤0.5 |
| 4.061 | ≤0.5 | ≤0.5 |
| 4.062 | ≤0.5 | ≤0.5 |
| 4.063 | 1 | 8 |
| 4.064 | ≤0.5 | ≤0.5 |
| 4.065 | ≤0.5 | ≤0.5 |
| 4.066 | ≤0.5 | ≤0.5 |
| 4.067 | ≤0.5 | ≤0.5 |
| 4.068 | ≤0.5 | ≤0.5 |
| 4.069 | ≤0.5 | ≤0.5 |
| 4.070 | ≤0.5 | 1 |
| 4.071 | ≤0.5 | 2 |
| 4.072 | ≤0.5 | 1 |
| 4.073 | ≤0.5 | ≤0.5 |
| 4.074 | ≤0.5 | ≤0.5 |
| 4.075 | ≤0.5 | ≤0.5 |
| 4.076 | ≤0.5 | ≤0.5 |
| 4.077 | ≤0.5 | ≤0.5 |
| 4.078 | ≤0.5 | 8 |
| 4.079 | ≤0.5 | ≤0.5 |
| 4.080 | ≤0.5 | 1 |
| 4.081 | ≤0.5 | 1 |
| 4.082 | 1 | 8 |
| 4.083 | ≤0.5 | ≤0.5 |
| 4.084 | ≤0.5 | ≤0.5 |
| 4.085 | ≤0.5 | 2 |
| 4.086 | ≤0.5 | 2 |
| 4.087 | ≤0.5 | 1 |
| 4.088 | ≤0.5 | 1 |
| 4.089 | ≤0.5 | ≤0.5 |
| 4.090 | ≤0.5 | 4 |
| 4.091 | ≤0.5 | 1 |
| 4.092 | ≤0.5 | 2 |
| 4.093 | ≤0.5 | 4 |
| 4.094 | ≤0.5 | ≤0.5 |
| 4.095 | 2 | 8 |
| 4.096 | ≤0.5 | ≤0.5 |
| 4.097 | ≤0.5 | 2 |
| 4.098 | ≤0.5 | 1 |
| 4.099 | ≤0.5 | 4 |
| 4.100 | ≤0.5 | ≤0.5 |
| 4.101 | ≤0.5 | ≤0.5 |
| 4.102 | ≤0.5 | 2 |
| 4.103 | ≤0.5 | ≤0.5 |
| 4.104 | ≤0.5 | ≤0.5 |
| 4.105 | ≤0.5 | ≤0.5 |
| 4.106 | ≤0.5 | 2 |

TABLE 9-continued

MIC data for Compounds in Tables 1-8 (Concentration in µg/mL)

| Cmpd ID | Sa | Ec |
|---|---|---|
| 4.107 | >16 | >16 |
| 4.108 | 4 | >16 |
| 4.109 | ≤0.5 | 1 |
| 4.110 | ≤0.5 | ≤0.5 |
| 4.111 | ≤0.5 | ≤0.5 |
| 4.112 | ≤0.5 | 1 |
| 4.113 | ≤0.5 | 4 |
| 4.114 | ≤0.5 | 2 |
| 4.115 | 1 | 8 |
| 4.116 | ≤0.5 | ≤0.5 |
| 4.117 | ≤0.5 | ≤0.5 |
| 4.118 | ≤0.5 | ≤0.5 |
| 4.119 | ≤0.5 | 2 |
| 4.120 | ≤0.5 | 1 |
| 4.121 | 1 | 8 |
| 4.122 | ≤0.5 | 1 |
| 4.123 | 16 | >16 |
| 4.124 | ≤0.5 | 8 |
| 4.125 | ≤0.5 | 4 |
| 4.126 | ≤0.5 | 2 |
| 4.127 | 8 | >16 |
| 4.128 | ≤0.5 | 4 |
| 4.129 | ≤0.5 | ≤0.5 |
| 4.130 | ≤0.5 | ≤0.5 |
| 4.131 | ≤0.5 | ≤0.5 |
| 4.132 | ≤0.5 | 2 |
| 4.133 | >16 | >16 |
| 4.134 | >16 | >16 |
| 4.135 | ≤0.5 | 1 |
| 4.136 | 2 | 8 |
| 4.137 | ≤0.5 | 1 |
| 4.138 | ≤0.5 | ≤0.5 |
| 4.139 | ≤0.5 | ≤0.5 |
| 4.140 | ≤0.5 | 2 |
| 4.141 | ≤0.5 | ≤0.5 |
| 4.142 | ≤0.5 | 1 |
| 4.143 | ≤0.5 | 2 |
| 4.144 | ≤0.5 | 1 |
| 4.145 | 1 | 8 |
| 4.146 | ≤0.5 | ≤0.5 |
| 4.147 | ≤0.5 | 1 |
| 4.148 | ≤0.5 | 4 |
| 4.149 | ≤0.5 | 2 |
| 4.150 | ≤0.5 | 1 |
| 4.151 | ≤0.5 | ≤0.5 |
| 4.152 | ≤0.5 | 1 |
| 4.153 | ≤0.5 | 2 |
| 4.154 | 2 | 16 |
| 4.155 | 2 | >16 |
| 4.156 | ≤0.5 | ≤0.5 |
| 4.157 | ≤0.5 | ≤0.5 |
| 4.158 | ≤0.5 | 4 |
| 4.159 | ≤0.5 | ≤0.5 |
| 4.160 | ≤0.5 | 2 |
| 4.161 | ≤0.5 | ≤0.5 |
| 4.162 | 8 | >16 |
| 4.163 | ≤0.5 | ≤0.5 |
| 4.164 | ≤0.5 | 1 |
| 4.165 | ≤0.5 | 1 |
| 4.166 | ≤0.5 | 2 |
| 4.167 | ≤0.5 | ≤0.5 |
| 4.168 | ≤0.5 | 2 |
| 4.169 | 2 | 8 |
| 4.170 | 2 | >16 |
| 4.171 | ≤0.5 | 4 |
| 4.172 | ≤0.5 | ≤0.5 |
| 4.173 | ≤0.5 | 1 |
| 4.174 | ≤0.5 | ≤0.5 |
| 4.175 | ≤0.5 | 8 |
| 4.176 | ≤0.5 | 1 |
| 4.177 | ≤0.5 | ≤0.5 |
| 4.178 | ≤0.5 | 8 |
| 4.179 | ≤0.5 | 1 |
| 4.180 | 1 | 8 |
| 4.181 | ≤0.5 | 8 |
| 4.182 | 2 | 16 |
| 4.183 | 1 | 8 |
| 4.184 | ≤0.5 | 1 |
| 4.185 | ≤0.5 | 8 |
| 4.186 | ≤0.5 | 2 |
| 4.187 | ≤0.5 | 2 |
| 4.188 | ≤0.5 | 8 |
| 4.189 | ≤0.5 | 2 |
| 4.190 | ≤0.5 | 1 |
| 4.191 | ≤0.5 | 2 |
| 4.192 | ≤0.5 | 4 |
| 4.193 | ≤0.5 | ≤0.5 |
| 4.194 | ≤0.5 | ≤0.5 |
| 4.195 | ≤0.5 | 1 |
| 4.196 | ≤0.5 | ≤0.5 |
| 4.197 | ≤0.5 | ≤0.5 |
| 4.198 | ≤0.5 | ≤0.5 |
| 4.199 | ≤0.5 | ≤0.5 |
| 4.200 | ≤0.5 | ≤0.5 |
| 4.201 | ≤0.5 | ≤0.5 |
| 4.202 | ≤0.5 | ≤0.5 |
| 4.203 | ≤0.5 | ≤0.5 |
| 4.204 | ≤0.5 | ≤0.5 |
| 4.205 | ≤0.5 | ≤0.5 |
| 4.206 | ≤0.5 | 4 |
| 4.207 | ≤0.5 | ≤0.5 |
| 4.208 | ≤0.5 | ≤0.5 |
| 4.209 | ≤0.5 | ≤0.5 |
| 4.210 | ≤0.5 | 1 |
| 4.211 | 16 | >16 |
| 4.212 | ≤0.5 | ≤0.5 |
| 4.213 | ≤0.5 | 1 |
| 4.214 | ≤0.5 | 2 |
| 4.215 | ≤0.5 | 4 |
| 4.216 | ≤0.5 | ≤0.5 |
| 4.217 | ≤0.5 | 4 |
| 4.218 | ≤0.5 | ≤0.5 |
| 4.219 | ≤0.5 | ≤0.5 |
| 4.220 | ≤0.5 | ≤0.5 |
| 4.221 | ≤0.5 | 2 |
| 4.222 | ≤0.5 | ≤0.5 |
| 4.223 | ≤0.5 | ≤0.5 |
| 4.224 | 1 | >16 |
| 4.225 | ≤0.5 | 2 |
| 4.226 | ≤0.5 | 2 |
| 4.227 | ≤0.5 | 1 |
| 4.228 | ≤0.5 | 1 |
| 4.229 | ≤0.5 | 2 |
| 4.230 | 32 | >16 |
| 4.231 | ≤0.5 | 2 |
| 4.232 | ≤0.5 | ≤0.5 |
| 4.233 | ≤0.5 | 1 |
| 4.234 | ≤0.5 | 1 |
| 4.235 | ≤0.5 | ≤0.5 |
| 4.236 | ≤0.5 | ≤0.5 |
| 4.237 | ≤0.5 | 2 |
| 4.238 | 2 | >16 |
| 4.239 | ≤0.5 | 8 |
| 4.240 | ≤0.5 | ≤0.5 |
| 4.241 | ≤0.5 | ≤0.5 |
| 4.242 | ≤0.5 | ≤0.5 |
| 4.243 | ≤0.5 | ≤0.5 |
| 4.244 | ≤0.5 | ≤0.5 |
| 4.245 | ≤0.5 | ≤0.5 |
| 4.246 | ≤0.5 | ≤0.5 |
| 4.247 | 1 | 8 |
| 4.248 | ≤0.5 | ≤0.5 |
| 4.249 | ≤0.5 | ≤0.5 |
| 4.250 | ≤0.5 | ≤0.5 |
| 4.251 | ≤0.5 | ≤0.5 |
| 4.252 | >16 | >16 |
| 4.253 | ≤0.5 | ≤0.5 |
| 4.254 | ≤0.5 | ≤0.5 |
| 4.255 | ≤0.5 | ≤0.5 |
| 4.256 | ≤0.5 | ≤0.5 |
| 4.257 | ≤0.5 | ≤0.5 |
| 4.258 | ≤0.5 | ≤0.5 |

TABLE 9-continued

MIC data for Compounds in Tables 1-8 (Concentration in μg/mL)

| Cmpd ID | Sa | Ec |
|---|---|---|
| 4.259 | ≤0.5 | ≤0.5 |
| 4.260 | ≤0.5 | ≤0.5 |
| 4.261 | ≤0.5 | 1 |
| 4.262 | ≤0.5 | ≤0.5 |
| 4.263 | ≤0.5 | ≤0.5 |
| 4.264 | ≤0.5 | ≤0.5 |
| 4.265 | ≤0.5 | 4 |
| 4.266 | ≤0.5 | 1 |
| 4.267 | ≤0.5 | 4 |
| 4.269 | ≤0.5 | 4 |
| 4.270 | ≤0.5 | 2 |
| 4.271 | ≤0.5 | ≤0.5 |
| 4.272 | ≤0.5 | ≤0.5 |
| 4.273 | ≤0.5 | 2 |
| 4.274 | ≤0.5 | ≤0.5 |
| 4.275 | ≤0.5 | ≤0.5 |
| 4.276 | ≤0.5 | 8 |
| 4.277 | ≤0.5 | ≤0.5 |
| 4.278 | ≤0.5 | ≤0.5 |
| 4.279 | ≤0.5 | ≤0.5 |
| 4.280 | ≤0.5 | ≤0.5 |
| 4.281 | ≤0.5 | ≤0.5 |
| 4.282 | ≤0.5 | ≤0.5 |
| 4.283 | ≤0.5 | ≤0.5 |
| 4.284 | ≤0.5 | ≤0.5 |
| 4.285 | ≤0.5 | ≤0.5 |
| 4.286 | ≤0.5 | ≤0.5 |
| 4.287 | ≤0.5 | ≤0.5 |
| 4.288 | 4 | >16 |
| 4.290 | ≤0.5 | ≤0.5 |
| 4.291 | ≤0.5 | ≤0.5 |
| 4.292 | ≤0.5 | ≤0.5 |
| 4.293 | ≤0.5 | 1 |
| 4.294 | ≤0.5 | 1 |
| 4.295 | ≤0.5 | ≤0.5 |
| 4.296 | ≤0.5 | ≤0.5 |
| 4.297 | ≤0.5 | ≤0.5 |
| 4.298 | ≤0.5 | 2 |
| 4.299 | ≤0.5 | 4 |
| 4.300 | ≤0.5 | ≤0.5 |
| 4.301 | ≤0.5 | 1 |
| 4.302 | ≤0.5 | 2 |
| 4.303 | ≤0.5 | ≤0.5 |
| 4.304 | ≤0.5 | ≤0.5 |
| 4.305 | ≤0.5 | 1 |
| 4.309 | ≤0.5 | ≤0.5 |
| 4.310 | 8 | >16 |
| 4.311 | 4 | >16 |
| 4.312 | 16 | >16 |
| 4.313 | 8 | >16 |
| 4.314 | ≤0.5 | ≤0.5 |
| 4.315 | ≤0.5 | ≤0.5 |
| 4.316 | ≤0.5 | 1 |
| 4.317 | ≤0.5 | 2 |
| 4.318 | ≤0.5 | 8 |
| 4.319 | ≤0.5 | ≤0.5 |
| 4.320 | ≤0.5 | 1 |
| 4.321 | ≤0.5 | 1 |
| 4.322 | ≤0.5 | ≤0.5 |
| 4.323 | ≤0.5 | 1 |
| 4.324 | ≤0.5 | ≤0.5 |
| 4.325 | ≤0.5 | ≤0.5 |
| 4.326 | ≤0.5 | ≤0.5 |
| 4.327 | ≤0.5 | 8 |
| 4.328 | ≤0.5 | 1 |
| 4.329 | ≤0.5 | ≤0.5 |
| 4.330 | ≤0.5 | ≤0.5 |
| 4.331 | ≤0.5 | ≤0.5 |
| 4.332 | ≤0.5 | ≤0.5 |
| 4.333 | ≤0.5 | ≤0.5 |
| 4.334 | ≤0.5 | 8 |
| 4.335 | ≤0.5 | 4 |
| 4.336 | ≤0.5 | 1 |
| 4.337 | ≤0.5 | 1 |
| 4.338 | ≤0.5 | 2 |
| 4.339 | ≤0.5 | 1 |
| 4.340 | 1 | 2 |
| 4.341 | ≤0.5 | 1 |
| 4.342 | ≤0.5 | 4 |
| 4.343 | ≤0.5 | ≤0.5 |
| 4.344 | ≤0.5 | 2 |
| 4.345 | ≤0.5 | 2 |
| 4.346 | ≤0.5 | 4 |
| 4.347 | ≤0.5 | 1 |
| 4.348 | ≤0.5 | ≤0.5 |
| 4.349 | ≤0.5 | 1 |
| 4.350 | ≤0.5 | 4 |
| 4.351 | ≤0.5 | 2 |
| 4.352 | ≤0.5 | 4 |
| 4.353 | ≤0.5 | 2 |
| 4.354 | ≤0.5 | 1 |
| 4.355 | ≤0.5 | ≤0.5 |
| 4.356 | ≤0.5 | 4 |
| 4.357 | ≤0.5 | 4 |
| 4.358 | ≤0.5 | 4 |
| 4.359 | ≤0.5 | ≤0.5 |
| 4.360 | ≤0.5 | 2 |
| 4.361 | ≤0.5 | 1 |
| 4.362 | ≤0.5 | 1 |
| 4.363 | ≤0.5 | 1 |
| 4.364 | ≤0.5 | 4 |
| 4.365 | ≤0.5 | ≤0.5 |
| 4.366 | ≤0.5 | 1 |
| 4.367 | ≤0.5 | ≤0.5 |
| 4.368 | ≤0.5 | ≤0.5 |
| 4.369 | ≤0.5 | 1 |
| 4.370 | ≤0.5 | 1 |
| 4.371 | 1 | 16 |
| 4.372 | 4 | 16 |
| 4.373 | 2 | 8 |
| 4.374 | ≤0.5 | 4 |
| 4.375 | ≤0.5 | 4 |
| 4.376 | >16 | >16 |
| 4.377 | 4 | 16 |
| 4.378 | ≤0.5 | ≤0.5 |
| 4.379 | ≤0.5 | ≤0.5 |
| 4.380 | 4 | 16 |
| 4.381 | 4 | 16 |
| 4.382 | 1 | 16 |
| 4.383 | 4 | >16 |
| 4.384 | 1 | >16 |
| 4.385 | ≤0.5 | ≤0.5 |
| 4.386 | ≤0.5 | ≤0.5 |
| 4.387 | ≤0.5 | ≤0.5 |
| 4.388 | ≤0.5 | ≤0.5 |
| 4.389 | ≤0.5 | ≤0.5 |
| 4.390 | ≤0.5 | ≤0.5 |
| 4.391 | ≤0.5 | ≤0.5 |
| 4.392 | 16 | >16 |
| 4.393 | ≤0.5 | 1 |
| 4.394 | ≤0.5 | ≤0.5 |
| 4.395 | 1 | 1 |
| 4.396 | ≤0.5 | 2 |
| 4.397 | ≤0.5 | ≤0.5 |
| 4.398 | ≤0.5 | ≤0.5 |
| 4.399 | ≤0.5 | 2 |
| 4.400 | ≤0.5 | ≤0.5 |
| 4.401 | ≤0.5 | ≤0.5 |
| 4.402 | ≤0.5 | ≤0.5 |
| 4.403 | 4 | >16 |
| 4.404 | ≤0.5 | 1 |
| 4.405 | ≤0.5 | ≤0.5 |
| 4.406 | ≤0.5 | 1 |
| 4.407 | 2 | >16 |
| 4.408 | ≤0.5 | ≤0.5 |
| 4.409 | ≤0.5 | ≤0.5 |
| 4.410 | ≤0.5 | ≤0.5 |
| 4.411 | ≤0.5 | ≤0.5 |
| 4.412 | ≤0.5 | ≤0.5 |
| 4.413 | ≤0.5 | ≤0.5 |
| 4.414 | ≤0.5 | 2 |
| 4.415 | ≤0.5 | 1 |

TABLE 9-continued

MIC data for Compounds in Tables 1-8 (Concentration in μg/mL)

| Cmpd ID | Sa | Ec |
|---|---|---|
| 4.416 | ≤0.5 | ≤0.5 |
| 4.417 | ≤0.5 | 1 |
| 4.418 | ≤0.5 | 1 |
| 4.419 | ≤0.5 | >16 |
| 4.420 | 2 | >16 |
| 4.421 | 2 | 8 |
| 4.422 | 4 | 16 |
| 4.423 | >16 | >16 |
| 4.424 | >16 | >16 |
| 4.425 | >16 | >16 |
| 4.426 | 8 | >16 |
| 4.427 | >16 | >16 |
| 4.428 | ≤0.5 | 2 |
| 4.429 | ≤0.5 | 1 |
| 4.430 | ≤0.5 | ≤0.5 |
| 4.431 | ≤0.5 | ≤0.5 |
| 4.432 | ≤0.5 | >16 |
| 4.433 | ≤0.5 | ≤0.5 |
| 4.434 | ≤0.5 | ≤0.5 |
| 4.435 | ≤0.5 | ≤0.5 |
| 4.436 | ≤0.5 | >16 |
| 4.437 | ≤0.5 | 1 |
| 4.438 | 1 | 16 |
| 4.439 | 8 | >16 |
| 4.440 | 16 | >16 |
| 4.441 | ≤0.5 | ≤0.5 |
| 4.442 | 1 | 2 |
| 4.443 | ≤0.5 | ≤0.5 |
| 4.445 | 2 | >16 |
| 4.446 | 2 | 8 |
| 4.447 | 4 | 16 |
| 4.448 | ≤0.5 | 1 |
| 4.449 | ≤0.5 | >16 |
| 4.450 | ≤0.5 | 2 |
| 4.451 | ≤0.5 | ≤0.5 |
| 5.01 | ≤0.5 | ≤0.5 |
| 5.02 | ≤0.5 | ≤0.5 |
| 5.03 | ≤0.5 | ≤0.5 |
| 5.04 | ≤0.5 | ≤0.5 |
| 5.05 | ≤0.5 | ≤0.5 |
| 5.06 | ≤0.5 | ≤0.5 |
| 5.07 | ≤0.5 | 1 |
| 5.08 | ≤0.5 | ≤0.5 |
| 5.09 | ≤0.5 | ≤0.5 |
| 5.10 | ≤0.5 | ≤0.5 |
| 5.11 | ≤0.5 | ≤0.5 |
| 5.12 | ≤0.5 | ≤0.5 |
| 5.13 | ≤0.5 | ≤0.5 |
| 5.14 | ≤0.5 | ≤0.5 |
| 5.15 | ≤0.5 | 1 |
| 6.01 | ≤0.5 | 1 |
| 6.02 | ≤0.5 | ≤0.5 |
| 6.03 | ≤0.5 | ≤0.5 |
| 6.04 | ≤0.5 | ≤0.5 |
| 6.05 | ≤0.5 | ≤0.5 |
| 6.06 | ≤0.5 | ≤0.5 |
| 6.07 | ≤0.5 | ≤0.5 |
| 6.08 | ≤0.5 | ≤0.5 |
| 6.09 | ≤0.5 | 1 |
| 6.10 | ≤0.5 | ≤0.5 |
| 6.11 | ≤0.5 | ≤0.5 |
| 6.12 | ≤0.5 | ≤0.5 |
| 6.13 | ≤0.5 | ≤0.5 |
| 6.14 | ≤0.5 | 1 |
| 6.15 | ≤0.5 | ≤0.5 |
| 6.16 | ≤0.5 | 1 |
| 6.17 | ≤0.5 | ≤0.5 |
| 6.18 | >64 | >64 |
| 6.19 | >16 | >16 |
| 6.20 | 4 | >16 |
| 6.21 | >16 | >16 |
| 6.22 | >16 | >16 |
| 6.23 | ≤0.5 | ≤0.5 |
| 6.24 | ≤0.5 | 1 |
| 6.25 | ≤0.5 | ≤0.5 |
| 6.26 | ≤0.5 | 1 |
| 6.27 | ≤0.5 | 1 |
| 6.28 | ≤0.5 | ≤0.5 |
| 6.29 | ≤0.5 | ≤0.5 |
| 7.01 | 8 | >64 |
| 7.02 | >64 | 32 |
| 7.03 | 2 | >64 |
| 7.04 | 8 | 32 |
| 7.05 | 8 | 64 |
| 7.06 | 8 | 64 |
| 7.07 | 16 | >64 |
| 7.08 | 16 | >64 |
| 7.09 | 8 | >64 |
| 7.10 | >64 | >64 |
| 7.11 | >64 | >64 |
| 7.12 | >64 | >64 |
| 8.1 | 2 | >64 |
| 8.2 | 1 | >32 |
| 8.3 | 2 | 64 |
| 8.4 | 8 | >64 |

TABLE 10

MIC data for Select Formula 1 Compounds versus a Broad Bacterial Panel

| Cmpd. # | Sa | Spn | Ec | Ab | Kpn | Pa | Bt | Ft | Yp |
|---|---|---|---|---|---|---|---|---|---|
| | | | | MIC (μg/mL) | | | | | |
| 4.035 | ≤0.5 | ≤0.5 | ≤0.5 | ≤0.5 | 2 | 4 | ≤0.5 | 1 | ≤0.5 |
| 4.045 | ≤0.5 | ≤0.5 | ≤0.5 | ≤0.5 | 8 | 4 | 1 | 2 | ≤0.5 |
| 4.066 | ≤0.5 | ≤0.5 | ≤0.5 | ≤0.5 | 2 | 2 | ≤0.5 | 1 | ≤0.5 |
| 4.069 | ≤0.5 | ≤0.5 | ≤0.5 | ≤0.5 | 2 | 4 | ≤0.5 | 2 | ≤0.5 |
| 4.073 | ≤0.5 | ≤0.5 | ≤0.5 | ≤0.5 | 2 | 4 | ≤0.5 | 1 | ≤0.5 |
| 4.076 | ≤0.5 | ≤0.5 | ≤0.5 | ≤0.5 | 4 | 4 | 1 | 2 | ≤0.5 |
| 4.079 | ≤0.5 | ≤0.5 | ≤0.5 | ≤0.5 | 8 | 4 | 1 | 4 | ≤0.5 |
| 4.084 | ≤0.5 | ≤0.5 | ≤0.5 | ≤0.5 | 4 | 1 | ≤0.5 | ≤0.5 | ≤0.5 |
| 4.103 | ≤0.5 | ≤0.5 | ≤0.5 | ≤0.5 | 2 | 2 | ≤0.5 | 1 | ≤0.5 |
| 4.105 | ≤0.5 | ≤0.5 | ≤0.5 | ≤0.5 | 2 | 1 | ≤0.5 | 1 | ≤0.5 |
| 4.117 | ≤0.5 | ≤0.5 | ≤0.5 | ≤0.5 | 2 | 1 | ≤0.5 | 1 | ≤0.5 |
| 4.131 | ≤0.5 | ≤0.5 | ≤0.5 | ≤0.5 | 2 | 1 | ≤0.5 | ≤0.5 | ≤0.5 |
| 4.151 | ≤0.5 | ≤0.5 | ≤0.5 | ≤0.5 | 1 | 1 | | | |
| 4.157 | ≤0.5 | ≤0.5 | ≤0.5 | ≤0.5 | 4 | 8 | | | |
| 4.160 | ≤0.5 | ≤0.5 | 2 | >16 | >16 | >16 | | | |
| 4.365 | ≤0.5 | ≤0.5 | ≤0.5 | ≤0.5 | 4 | 1 | ≤0.5 | 1 | ≤0.5 |
| 4.409 | ≤0.5 | ≤0.5 | ≤0.5 | 1 | 4 | 1 | | | |
| 4.410 | ≤0.5 | ≤0.5 | ≤0.5 | 2 | 2 | 1 | | | |
| 4.434 | ≤0.5 | ≤0.5 | ≤0.5 | ≤0.5 | 1 | 1 | | | |
| 4.451 | ≤0.5 | ≤0.5 | ≤0.5 | ≤0.5 | 1 | 2 | | | |
| 5.010 | ≤0.5 | ≤0.5 | ≤0.5 | ≤0.5 | 1 | ≤0.5 | | | |
| 5.110 | ≤0.5 | ≤0.5 | ≤0.5 | 2 | 4 | 4 | | | |
| 5.120 | ≤0.5 | ≤0.5 | ≤0.5 | ≤0.5 | 1 | 4 | | | |
| 5.130 | ≤0.5 | ≤0.5 | ≤0.5 | ≤0.5 | 1 | ≤0.5 | | | |
| 6.280 | ≤0.5 | ≤0.5 | ≤0.5 | ≤0.5 | 2 | 1 | | | |
| 6.290 | ≤0.5 | ≤0.5 | ≤0.5 | ≤0.5 | 2 | 2 | | | |

Sa = *S. aureus*,
Spn = *S. pneumoniae*,
Ec = *E. coli*,
Ab = *A. baumannii*,
Kpn = *K. pneumoniae*,
Pa = *P. aeruginosa*,
Bt = *B. thailandensis*,
Ft = *F. tularensis*,
Yp = *Y. pestis*

TABLE 11
MIC data for Select Formula 1 Compounds wherein L = CH$_2$.
| ID | SA | EC8 |
|---|---|---|
| 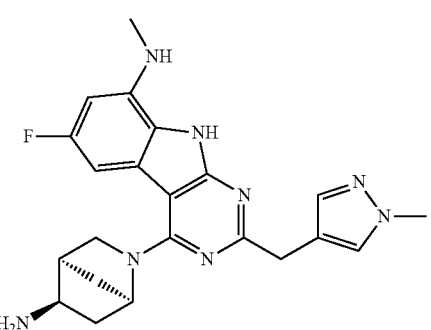 | 1 | 8 |
| 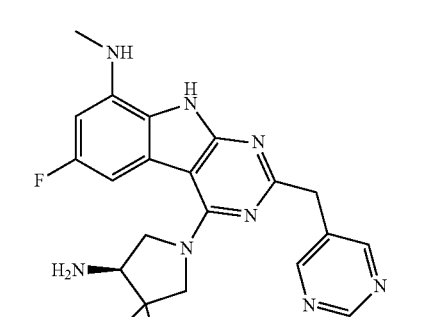 | ≤0.5 | 1 |
| 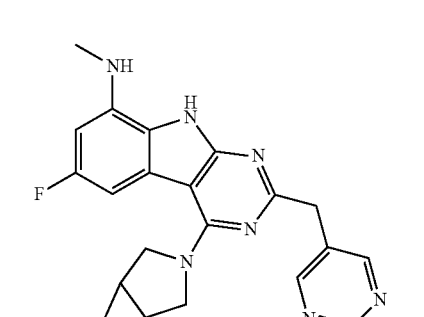 | ≤0.5 | 0.25 |
|  | ≤0.5 | 0.25 |
TABLE 11-continued
MIC data for Select Formula 1 Compounds wherein L = CH$_2$.
| ID | SA | EC8 |
|---|---|---|
| 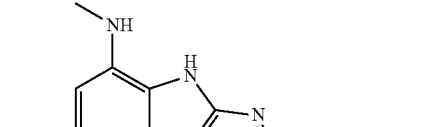 | ≤0.5 | 2 |
| 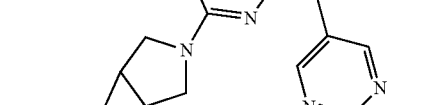 | 1 | 8 |
|  | ≤0.5 | 1 |
|  | ≤0.5 | 1 |

TABLE 12

MIC data for Select Formula 1 Compounds wherein Z is C and connected to R⁴

| ID | SA | EC8 |
|---|---|---|
| (structure) | ≤0.5 | ≤0.5 |
| (structure) | 16 | >16 |
| (structure) | 4 | 8 |
| (structure) | ≤0.5 | 4 |

TABLE 12-continued

MIC data for Select Formula 1 Compounds wherein Z is C and connected to R⁴

| ID | SA | EC8 |
|---|---|---|
| (structure) | ≤0.5 | >16 |
| (structure) | ≤0.5 | >16 |

TABLE 13

MIC data for Select Formula 1 Compounds wherein L = NH

| | SA | EC |
|---|---|---|
| (structure) | ≤0.5 | ≤0.5 |

TABLE 13-continued

MIC data for Select Formula 1 Compounds wherein L = NH

| structures | SA | EC |
|---|---|---|
| (structure) | ≤0.5 | 1 |
| (structure) 702207 | ≤0.5 | ≤0.5 |
| (structure) | ≤0.5 | ≤0.5 |
| (structure) | ≤0.5 | 1 |

TABLE 13-continued

MIC data for Select Formula 1 Compounds wherein L = NH

| structures | SA | EC |
|---|---|---|
| (structure) | ≤0.5 | 16 |

TABLE 14

MIC data for Select Formula 1 Compounds wherein R² is a 5 membered hereocycle

| structures | SA | SA+ serum | EC8 |
|---|---|---|---|
| (structure) | <≤0.5 | ≤0.5 | ≤0.5 |
| (structure) | 1 | 4 | 16 |

TABLE 14-continued

MIC data for Select Formula 1 Compounds wherein R² is a 5 membered hereocycle

| structures | SA | SA+ serum | EC8 |
|---|---|---|---|
| (structure) | ≤0.5 | ≤0.5 | ≤0.5 |
| (structure) | ≤0.5 | 2 | ≤0.5 |
| (structure) | ≤0.5 | 2 | >16 |
| (structure) | ≤0.5 | ≤0.5 | ≤0.5 |
| (structure) | ≤0.5 | >16 | 1 |

TABLE 15

MIC data for Select Formula 1 Compounds wherein R² is is joind to R⁴

| | MIC (µg/ml) | |
|---|---|---|
| | SA | EC8 |
| (structure) | ≤0.5 | 1 |

TABLE 15-continued
MIC data for Select Formula 1 Compounds wherein R² is is joind to R⁴
| | MIC (µg/ml) | |
|---|---|---|
| | SA | EC8 |
| 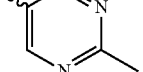 | ≤0.5 | >16 |
| 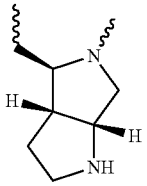 | ≤0.5 | 2 |
| 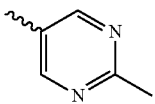 | 2 | 8 |
TABLE 15a
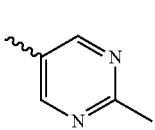
| | L | R2 | SA | EC8 |
|---|---|---|---|---|
| 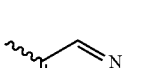 | O | 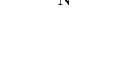 | >16 | >16 |
| 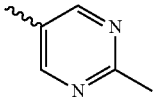 | O | 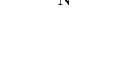 | ≤0.5 | ≤0.5 |
| 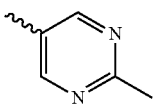 | O | 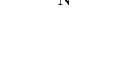 | ≤0.5 | 8 |
|  | O | 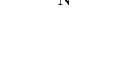 | 8 | >16 |
| 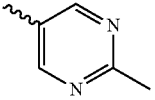 | O | 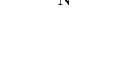 | ≤0.5 | ≤0.5 |
| 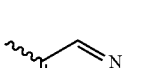 | O | 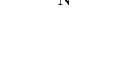 | ≤0.5 | ≤0.5 |
|  | O | 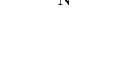 | 4 | 16 |

TABLE 15a-continued
| | L | R2 | SA | EC8 |
|---|---|---|---|---|
| 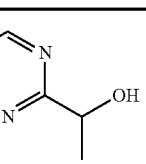 | O | 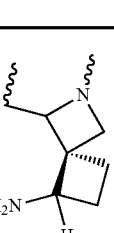 | ≤0.5 | 1 |
| 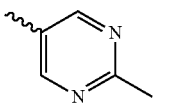 | O | 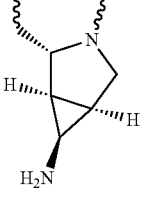 | 4 | >16 |
| 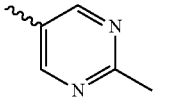 | O | 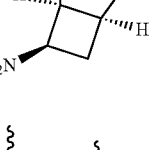 | ≤0.5 | ≤0.5 |
| 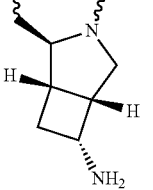 | O | 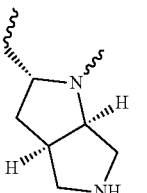 | 4 | 16 |
| 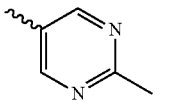 | O | 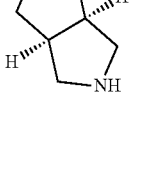 | ≤0.5 | 2 |
| 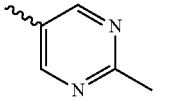 | O |  | ≤0.5 | 2 |
| 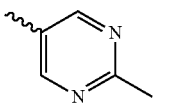 | O | 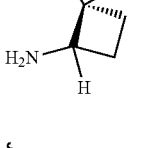 | ≤0.5 | 4 |
TABLE 15a-continued
| | L | R2 | SA | EC8 |
|---|---|---|---|---|
| 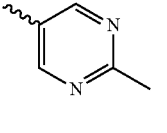 | O | 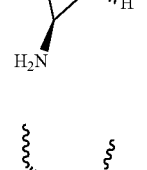 | ≤0.5 | 2 |
| 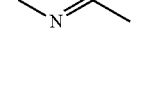 | O | 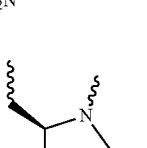 | 2 | 8 |
| 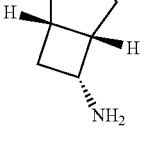 | O | 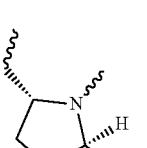 | ≤0.5 | ≤0.5 |
|  | O |  | ≤0.5 | 4 |
| 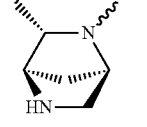 | O | 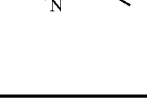 | 16 | >16 |
|  | O |  | ≤0.5 | ≤0.5 |

TABLE 16

MIC data for Select Formula 1 Compounds having new R⁴ substituents

| Structure | MIC (µg/ml) SA | MIC (µg/ml) EC8 |
|---|---|---|
| (structure 1) | ≤0.5 | 0.5 |
| (structure 2) | ≤0.5 | 8 |
| (structure 3) | ≤0.5 | ≤0.5 |
| (structure 4) | ≤0.5 | ≤0.5 |
| (structure 5) | 1 | >16 |
| (structure 6) | ≤0.5 | 4 |
| (structure 7) | ≤0.5 | 16 |
| (structure 8) | ≤0.5 | 1 |
| (structure 9) | ≤0.5 | ≤0.5 |

TABLE 16-continued

MIC data for Select Formula 1 Compounds having new R⁴ substituents

| Structure | MIC (µg/ml) SA | EC8 |
|---|---|---|
| [structure] | ≤0.5 | ≤0.5 |
| [structure] | ≤0.5 | ≤0.5 |
| [structure] | ≤0.5 | ≤0.5 |
| [structure] | 4 | 16 |
| [structure] | 1 | 2 |
| [structure] | 1 | 2 |
| [structure] | ≤0.5 | 8 |
| [structure] | 8 | >16 |

TABLE 16-continued

MIC data for Select Formula 1 Compounds having new R⁴ substituents

| | MIC (µg/ml) | |
|---|---|---|
| | SA | EC8 |
| 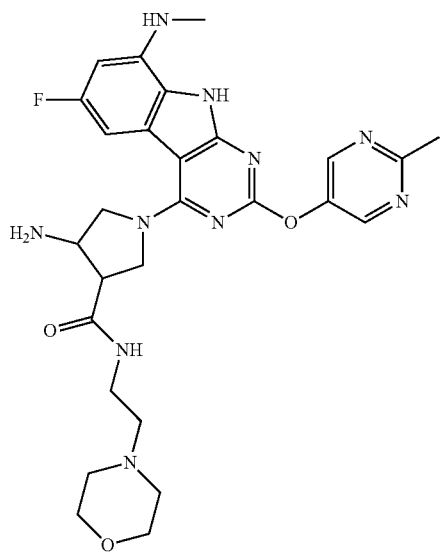 [SMILES: CNc1cc(F)cc2c1[nH]c1nc(Oc3cnc(C)nc3)nc(N3CC(N)C(C(=O)NCCN4CCOCC4)C3)c12] | 16 | >16 |
| 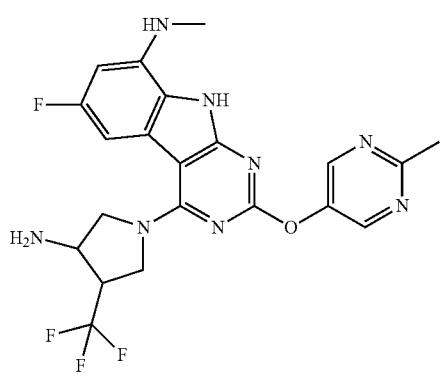 [SMILES: CNc1cc(F)cc2c1[nH]c1nc(Oc3cnc(C)nc3)nc(N3CC(N)C(C(F)(F)F)C3)c12] | ≤0.5 | >16 |
| 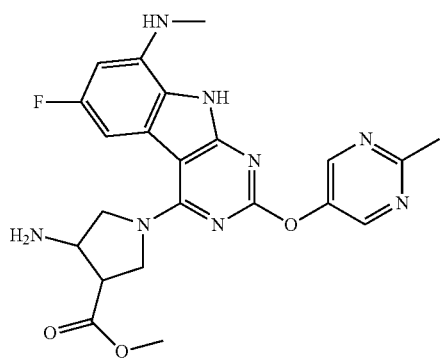 [SMILES: CNc1cc(F)cc2c1[nH]c1nc(Oc3cnc(C)nc3)nc(N3CC(N)C(C(=O)OC)C3)c12] | ≤0.5 | 1 |

TABLE 16-continued

MIC data for Select Formula 1 Compounds having new R⁴ substituents

| | MIC (µg/ml) | |
|---|---|---|
| | SA | EC8 |
| 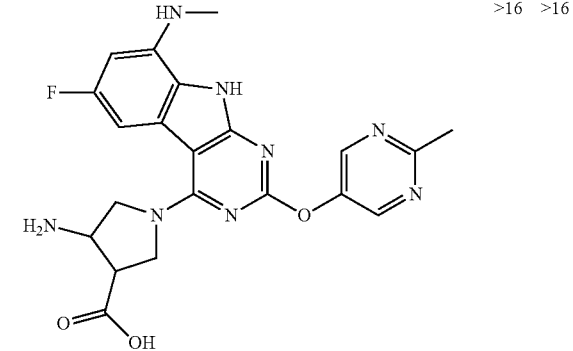 | >16 | >16 |
| 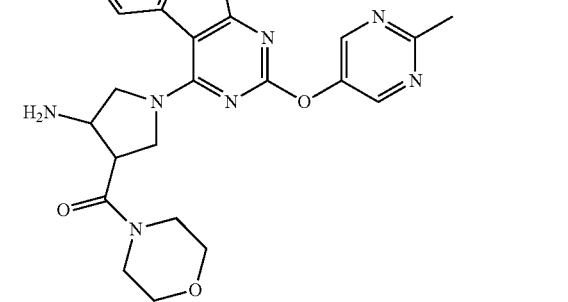 | 1 | 16 |

TABLE 17

Comparative MIC data for Select Formula 1 Compounds wherein new species of R² generally give better MIC and cell penetration compared to leading compounds in PCT/US2012/029104.

| | SA | Spn52 | PA |
|---|---|---|---|
| 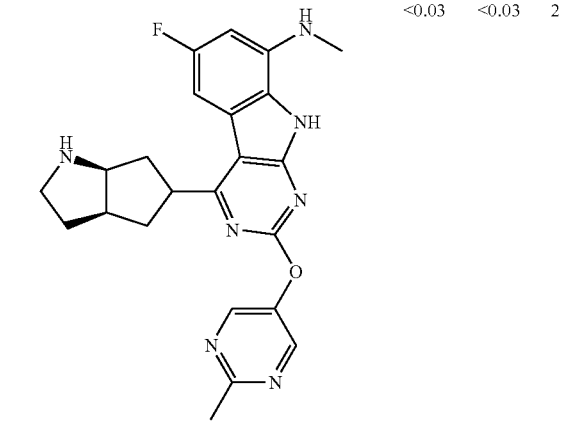 | <0.03 | <0.03 | 2 |

TABLE 17-continued

Comparative MIC data for Select Formula 1 Compounds wherein new species of $R^2$ generally give better MIC and cell penetration compared to leading compounds in PCT/US2012/029104.

| Structure | SA | Spn52 | PA |
|---|---|---|---|
| (structure with F, NHMe, NH, H₂N-bicyclic-N, O-pyrimidine-methyl) | ≤0.016 | ≤0.016 | 1 |
| (structure with F, NHMe, NH, H₂N-bicyclic-N, O-pyrazolopyridazine) | ≤0.016 | ≤0.001 | 0.5 |
| (structure with F, NHMe, NH, H₂N-bicyclic-N, O-methylpyrazolopyrimidine) | ≤0.016 | ≤0.001 | 0.5 |

TABLE 18

MIC data for Select MIC data for Select Compounds

| number | Sa | Ec |
|---|---|---|
| 10.01 | ≤0.5 | ≤0.5 |
| 10.02 | ≤0.5 | ≤0.5 |
| 10.03 | ≤0.5 | ≤0.5 |
| 10.04 | ≤0.5 | ≤0.5 |
| 10.05 | ≤0.5 | ≤0.5 |
| 10.06 | ≤0.5 | ≤0.5 |
| 10.07 | ≤0.5 | ≤0.5 |
| 10.08 | ≤0.5 | ≤0.5 |
| 10.09 | ≤0.5 | ≤0.5 |
| 10.10 | ≤0.5 | 1 |
| 10.11 | ≤0.5 | ≤0.5 |
| 10.12 | ≤0.5 | ≤0.5 |
| 10.13 | ≤0.5 | ≤0.5 |
| 10.14 | ≤0.5 | ≤0.5 |
| 10.15 | ≤0.5 | ≤0.5 |
| 10.16 | ≤0.5 | ≤0.5 |
| 10.17 | ≤0.5 | ≤0.5 |
| 10.18 | ≤0.5 | ≤0.5 |
| 10.19 | ≤0.5 | ≤0.5 |
| 10.20 | ≤0.5 | ≤0.5 |
| 10.21 | ≤0.5 | ≤0.5 |
| 10.22 | ≤0.5 | ≤0.5 |
| 10.23 | ≤0.5 | ≤0.5 |
| 10.24 | ≤0.5 | ≤0.5 |
| 10.25 | ≤0.5 | ≤0.5 |
| 10.26 | ≤0.5 | ≤0.5 |
| 10.27 | ≤0.5 | ≤0.5 |
| 10.28 | ≤0.5 | ≤0.5 |
| 10.29 | ≤0.5 | ≤0.5 |
| 10.30 | ≤0.5 | ≤0.5 |
| 10.31 | ≤0.5 | ≤0.5 |
| 10.32 | ≤0.5 | ≤0.5 |
| 10.33 | ≤0.5 | ≤0.5 |
| 10.34 | ≤0.5 | ≤0.5 |
| 10.35 | ≤0.5 | ≤0.5 |
| 10.36 | ≤0.5 | ≤0.5 |
| 10.37 | ≤0.5 | ≤0.5 |
| 10.38 | ≤0.5 | ≤0.5 |
| 10.39 | ≤0.5 | ≤0.5 |
| 10.40 | ≤0.5 | ≤0.5 |
| 10.41 | ≤0.5 | ≤0.5 |
| 10.42 | ≤0.5 | 1 |
| 10.43 | ≤0.5 | 1 |
| 10.44 | ≤0.5 | ≤0.5 |
| 10.45 | ≤0.5 | ≤0.5 |
| 10.46 | ≤0.5 | ≤0.5 |
| 10.47 | 1 | 8 |
| 10.48 | 8 | 16 |
| 10.49 | ≤0.5 | 2 |
| 10.50 | ≤0.5 | ≤0.5 |
| 10.51 | 4 | 16 |
| 10.52 | ≤0.5 | ≤0.5 |
| 10.53 | ≤0.5 | ≤0.5 |
| 10.54 | ≤0.5 | ≤0.5 |
| 10.55 | ≤0.5 | 1 |
| 10.56 | ≤0.5 | ≤0.5 |
| 10.57 | ≤0.5 | ≤0.5 |
| 10.58 | ≤0.5 | ≤0.5 |
| 10.59 | ≤0.5 | ≤0.5 |
| 10.60 | 8 | 16 |
| 10.61 | 0.03 | 2 |
| 10.62 | ≤0.5 | ≤0.5 |
| 10.63 | ≤0.5 | ≤0.5 |
| 10.64 | ≤0.5 | ≤0.5 |
| 10.65 | ≤0.5 | ≤0.5 |
| 10.66 | ≤0.5 | ≤0.5 |
| 10.67 | ≤0.5 | ≤0.5 |
| 10.68 | ≤0.5 | ≤0.5 |
| 10.69 | ≤0.5 | ≤0.5 |
| 10.70 | ≤0.5 | ≤0.5 |
| 10.71 | ≤0.5 | ≤0.5 |
| 10.72 | ≤0.5 | ≤0.5 |
| 10.73 | ≤0.5 | ≤0.5 |
| 10.74 | ≤0.5 | 1 |
| 10.75 | ≤0.5 | 1 |
| 10.76 | ≤0.5 | ≤0.5 |

TABLE 18-continued

MIC data for Select MIC data for Select Compounds

| number | Sa | Ec |
|---|---|---|
| 10.77 | ≤0.5 | 2 |
| 10.78 | 1 | 4 |
| 10.79 | ≤0.5 | ≤0.5 |
| 10.80 | 0.06 | 2 |
| 10.81 | ≤0.5 | 0.5 |
| 10.82 | 0.13 | 0.5 |
| 10.83 | ≤0.5 | 1 |
| 10.84 | ≤0.5 | ≤0.5 |
| 10.85 | ≤0.5 | ≤0.5 |
| 10.86 | ≤0.5 | 0.25 |
| 10.87 | ≤0.5 | ≤0.5 |
| 10.88 | ≤0.5 | ≤0.5 |
| 10.89 | ≤0.5 | 2 |
| 10.90 | ≤0.5 | ≤0.5 |
| 10.91 | 4 | >16 |
| 10.92 | ≤0.5 | ≤0.5 |
| 10.93 | ≤0.5 | ≤0.5 |
| 10.94 | ≤0.5 | ≤0.5 |
| 10.95 | ≤0.5 | ≤0.5 |
| 10.96 | ≤0.5 | ≤0.5 |
| 10.97 | ≤0.5 | 2 |
| 10.98 | ≤0.5 | ≤0.5 |
| 10.99 | ≤0.5 | ≤0.5 |
| 10.10 | ≤0.5 | ≤0.5 |
| 10.101 | ≤0.5 | ≤0.5 |
| 10.102 | ≤0.5 | ≤0.5 |
| 10.103 | ≤0.5 | ≤0.5 |
| 10.104 | ≤0.5 | 8 |
| 10.105 | ≤0.5 | 1 |
| 10.106 | ≤0.5 | 2 |
| 10.107 | ≤0.5 | ≤0.5 |
| 10.108 | ≤0.5 | >16 |
| 10.109 | ≤0.5 | ≤0.5 |
| 10.110 | ≤0.5 | ≤0.5 |
| 10.111 | ≤0.5 | ≤0.5 |
| 10.112 | ≤0.5 | ≤0.5 |
| 10.113 | ≤0.5 | ≤0.5 |
| 10.114 | ≤0.5 | ≤0.5 |
| 10.115 | ≤0.5 | 1 |
| 10.116 | ≤0.5 | ≤0.5 |
| 10.117 | ≤0.5 | ≤0.5 |

Example 20

A Cerep automated patch-clamp assay using Chinese Hamster Ovary K1 cells was used to measure hERG $IC_{50}$ values. The degree of inhibition (%) was obtained by measuring the tail current amplitude, which is induced by a one second test pulse to −40 mV after a two second pulse to +20 mV, before and after drug incubation (the difference in current was normalized to control and multiplied by 100 to obtain the percent inhibition).

Concentration (log) response curves were fitted to a logistic equation (three parameters assuming complete block of the current at very high test compound concentrations) to generate estimates of the 50% inhibitory concentration (IC50). The concentration-response relationship of each compound was constructed from the percentage reductions of current amplitude by sequential concentrations. The hERG IC50 values are provided in Table 19 below for the compounds tested.

TABLE 19

| Compound | | hERG $IC_{50}$ |
|---|---|---|
| 4.408 | 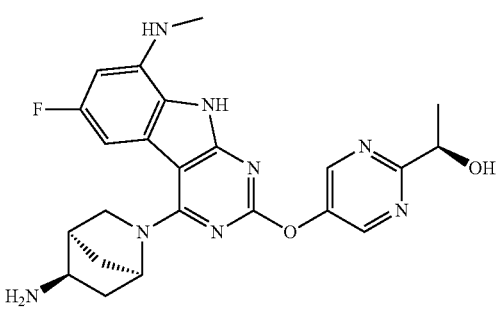 [SMILES: CNc1cc(F)cc2c1[nH]c1nc(Oc3cnc([C@@H](C)O)nc3)nc(N3C[C@H]4C[C@@H]3C[C@H]4N)c12] | 6.4 μM |
| 4.409 | 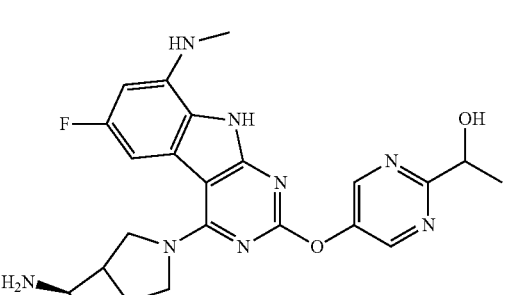 | 7.5 μM |

TABLE 19-continued

| Compound | | hERG IC$_{50}$ |
|---|---|---|
| 9.1 | (structure) | 80-100 μM |
| 9.2 | (structure) | 37 μM |

It is expected that Compound 10.118 would show similar hERG values as Compound 9.2.

TABLE 20

| | MIC data for selected compounds (μg/mL) | | | | | | | | |
|---|---|---|---|---|---|---|---|---|---|
| Cmpd # | Sa | Spn | Ec | Ab | Kpn | Pa | Bt | Ft | Bp |
| 9.1 | ≤0.5 | ≤0.5 | ≤0.5 | 1 | 4 | 2 | 0.5 | 0.5 | 0.5 |
| 9.2 | ≤0.5 | ≤0.5 | ≤0.5 | 0.5 | 2 | 1 | 0.5 | 0.5 | 0.5 |

Sa = *S. aureus*,
Spn = *S. pneumoniae*,
Ec = *E. coli*,
Ab = *A. baumannii*,
Kpn = *K. pneumoniae*,
Pa = *P. aeruginosa*,
Bt = *B. thailandensis*,
Ft = *F. tularensis*,
Yp = *Y. pestis*

The stereoisomers, Compounds 10.25 and 10.118, showed similar MIC activity as Compounds 9.1 and 9.2 respectively.

What is claimed is:

1. A compound having the structure of Formula I

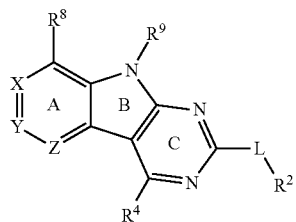

Formula I or pharmaceutically suitable salts thereof, wherein

L is:
a) O or S; or
b) NH, CH$_2$, CHF, CF$_2$, SCH$_2$, OCH$_2$, NHCH$_2$, CH=CH, CH$_2$CH$_2$, SCH$_2$CONH, OCH$_2$CONH, NHCH$_2$CONH, OCH$_2$CH=CH, or SCH$_2$CH=CH;

R$^8$ is:
a) H or an interacting substituent selected from the group consisting of H, F, Cl, Br, NH$_2$, OH, 1-3C alkyl, amino-1-3C alkyl, aminocyclopropyl, OCH$_3$, OCH$_2$CH$_3$, cyclopropyl, CH$_2$cyclopropyl, CH$_2$Cl, CH$_2$F, CHF$_2$, CF$_3$, CH$_2$CH$_2$F, CH$_2$CHF$_2$, CH$_2$CF$_3$, NHNH$_2$, NHOH, NHNHCH$_3$, NHOCH$_3$, NHCD$_3$, SCH$_3$, NHCOH, CHCl$_2$, and CHCH$_2$; or b) a substituent having the following structure:

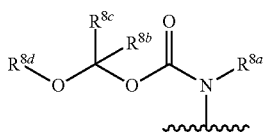

wherein $R^{8a}$ is H or an interacting substituent selected from the group consisting of H, methyl, ethyl, and cyclopropyl;
wherein $R^{8b}$ and $R^{8c}$ are independently H or C1-C6 alkyl;
wherein $R^{8d}$ is

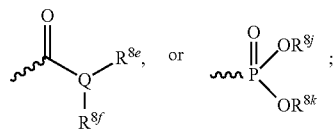

wherein Q is CH or N;
wherein $R^{8e}$ is $(CR^{8g}_2)_n$-basic amine, wherein each $R^{8g}$ is independently H or C1-C3 alkyl;
wherein n is 0-2;
wherein $R^{8f}$ is hydrogen or C1-C6 alkyl optionally substituted with OH or $NH_2$;
alternatively wherein $R^{8e}$ and $R^{8f}$ join to form a C3-C12 hydrocarbyl ring containing 0-3 heteroatoms selected from O, N and S;
wherein $R^{8j}$ and $R^{8k}$ are independently H or C1-C8 hydrocarbyl residue;
c) a substituent having the following structure:

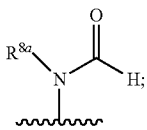

$R^9$ is H;
$R^2$ is
a) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH at each position immediately adjacent the position where $R^2$ attaches to L, if L is O or S;
b) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S;
c) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH or CF independently at each position immediately adjacent the position where $R^2$ attaches to L, if L is NH, $CH_2$, CHF, or $CF_2$;
d) a 5-membered heteroaryl ring containing 1-4 O, S, or N heteroatoms, optionally substituted with 0-2 noninterfering substituents;

wherein the 5-membered heteroaryl ring of $R^2$ has O, S, N, NH, CH, CF, or
CCl, independently at each of the positions immediately adjacent the position where $R^2$ attaches to L, if L is O, S, NH, $CH_2$, CHF, or $CF_2$;
e) a 6-membered or 5-membered non-aryl or non-heteroaryl ring containing 0-3 O, S, or N heteroatoms, optionally substituted with 0-3 noninterfering substituents;
wherein the 6-membered or 5-membered non-aryl or non-heteroaryl ring of $R^2$ has O, S, N, NH, CH, CF, or $CH_2$, independently at each position immediately adjacent the position where $R^2$ attaches to L, if L is O, S, NH, $CH_2$, CHF, or $CF_2$;
f) i) a 6-membered aryl or heteroaryl ring containing 0-3 O, S, or N heteroatoms, optionally substituted with 0-3 noninterfering substituents,
ii) a 5-membered heteroaryl ring containing 1-4 O, S, or N heteroatoms, optionally substituted with 0-2 noninterfering substituents, or
iii) a 6-membered or 5-membered non-aryl or non-heteroaryl ring containing 0-3 O, S, or N heteroatoms, optionally with 0-3 noninterfering substituents,
when L is selected from the group consisting of $SCH_2$, $OCH_2$, $NHCH_2$, CH=CH, $CH_2CH_2$, $SCH_2CONH$, $OCH_2CONH$, $NHCH_2CONH$, $OCH_2CH=CH$, and $SCH_2CH=CH$ in any of f)i) to f)iii);
alternatively wherein 2 adjacent noninterfering substituents of $R^2$ in a)-f) form one or more fused rings with the 6-membered aryl or heteroaryl ring, the 5-membered heteroaryl ring, or the 6-membered or 5-membered non-aryl or non-heteroaryl ring;
g) a substituent having the following structure:

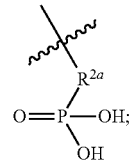

wherein $R^{2a}$ contains an oxygen residue derived from an $R^2$ as in a)-f), wherein $R^2$ has an OH group, wherein the $R^2$ OH is replaced with an oxygen residue in $R^{2a}$, and wherein the oxygen residue is linked to P;
h)

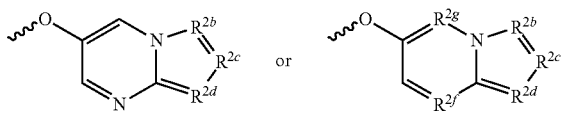

wherein $R^{2b}$, $R^{2c}$, $R^{2d}$, $R^{2f}$, and $R^{2g}$ independently are each N or $CR^{2e}$ wherein $R^{2e}$ is H or C1-C4 alkyl optionally substituted with a noninterfering substituent; or
i) selected from the group consisting of

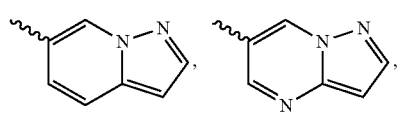

-continued

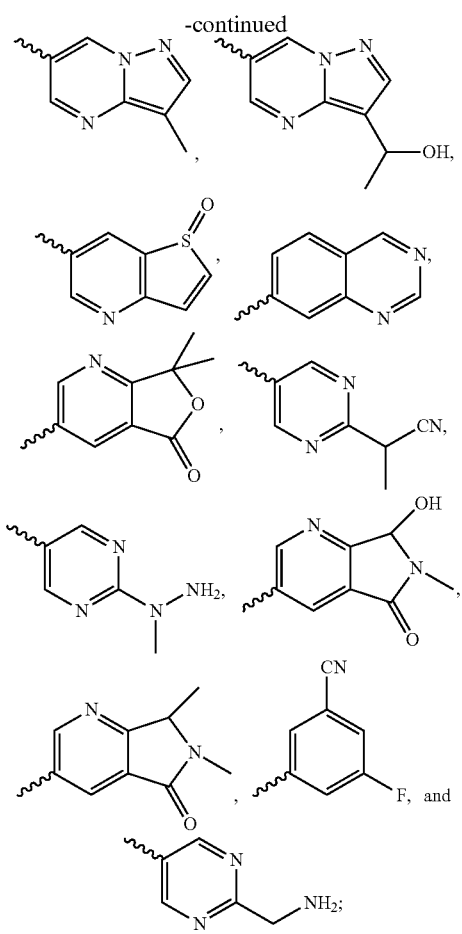

wherein the noninterfering substituents in a)-h) of $R^2$ are independently selected from the group consisting of OH, $CO_2H$, CN, $NH_2$, Br, Cl, F, $SO_3H$, $SO_2NH_2$, $SO_2CH_3$, $SOCH_3$, NHOH, $NHOCH_3$, $NO_2$, and C1-15 hydrocarbyl residue containing 0-5 O, S, or N heteroatoms optionally substituted with a substituent selected from the group consisting of OH, CN, =O, $NH_2$, NHOH, =NOH, =$NNH_2$, =$NOCH_3$, Br, F, Cl, $SO_3H$, and $NO_2$;

$R^4$ is a) H;

b) an optionally substituted ORa; wherein Ra is a 5-6 membered aryl or heteroaryl containing 0-3 O, S, or N heteroatoms optionally substituted with 0-3 noninterfering substituents;

c) an optionally substituted secondary or tertiary amine attached to the C Ring through the secondary or tertiary amine N;

d) an optionally substituted 5-10 membered unsaturated cyclic or heterocyclic residue containing 0-3 N, O or S heteroatoms;

wherein the optional substituent is 0-3 noninterfering substituents;

wherein the $R^4$ substituent of a)-d) does not project greater than about 3 A below the plane of the A, B and C Rings toward the GyrB/ParE binding pocket floor in the bound conformation; and wherein $R^4$ does not sterically interfere with $R^2$ or Z when the compound is in the bound conformation;

e) a substituent having the following structure:

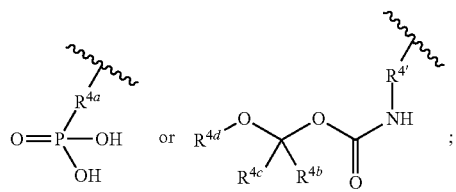

wherein $R^{4a}$ contains an oxygen residue derived from the $R^4$ as in b)-d) or g), wherein the $R^4$ has an OH group, wherein the $R^4$ OH is replaced with an oxygen residue in $R^{4a}$, and wherein the oxygen residue is linked to P;

wherein $R^{4'}$—NH is derived from the $R^4$ as in b)-d) or g), wherein the $R^4$ contains a primary amine and wherein the NH in the primary amine links the $R^{4'}$ residue to the C=O;

wherein $R^{4b}$ and $R^{4c}$ are independently H or C1-C6 alkyl;

wherein $R^{4d}$ is

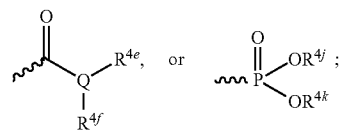

wherein Q is CH or N;

wherein $R^{4e}$ is $(CR^{4g}_2)_n$-basic amine, wherein each $R^{4g}$ is independently H or C1-C3 alkyl;

wherein n is 0-2;

wherein $R^{4f}$ is hydrogen or C1-C6 alkyl optionally substituted with OH or $NH_2$;

alternatively wherein $R^{4e}$ and $R^{4f}$ join to form a ring;

wherein $R^{4j}$ and $R^{4k}$ are independently H or C1-C8 hydrocarbyl residue;

f) a substituent having the following structure

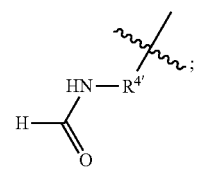

g) selected from the group consisting of:

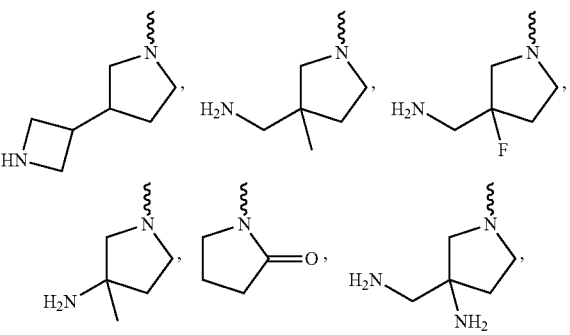

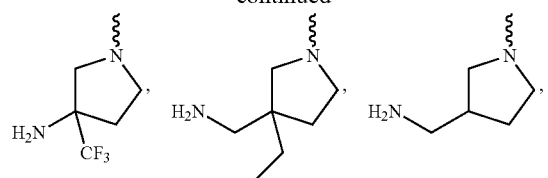
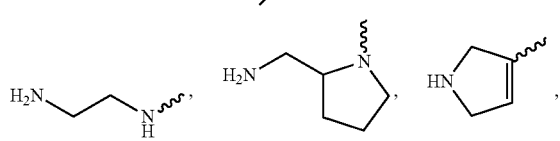
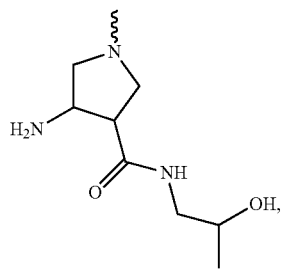
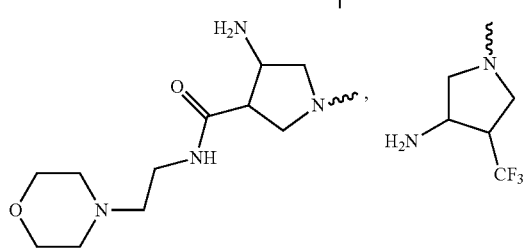
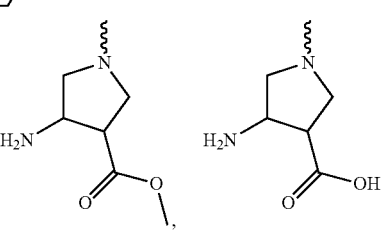
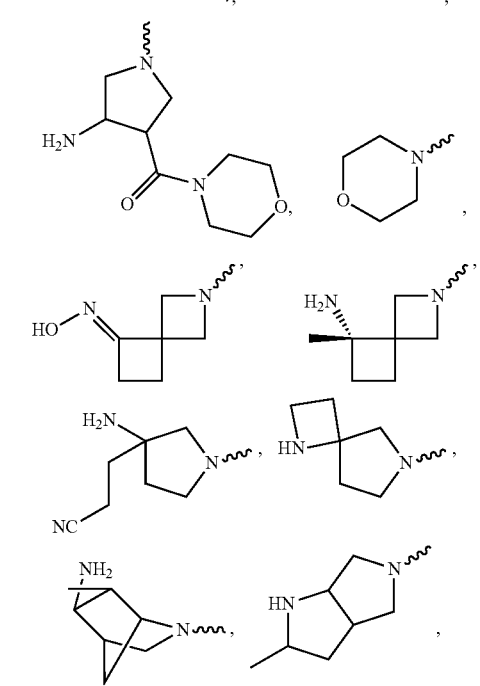

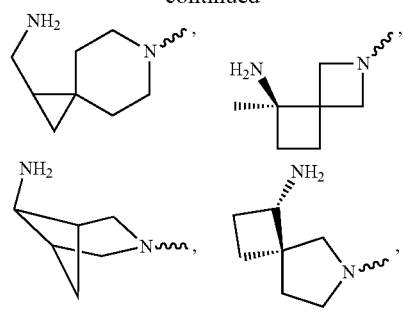
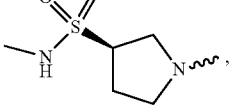
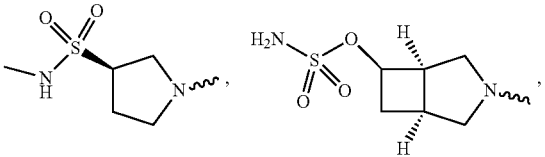
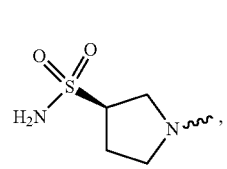
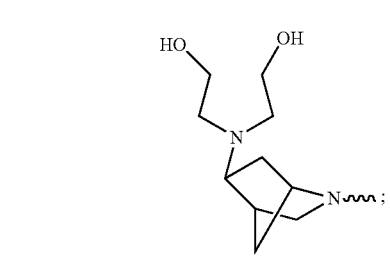
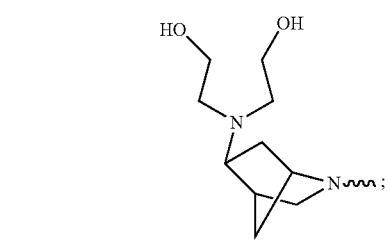

and

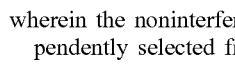
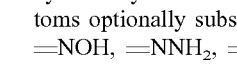
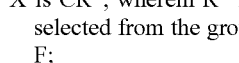
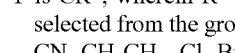
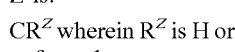

wherein the noninterfering substituents for $R^4$ are independently selected from the group consisting of OH, $CO_2H$, CN, $NH_2$, Br, Cl, F, $SO_3H$, $NO_2$, and C1-15 hydrocarbyl residue containing 0-5 O, S, or N heteroatoms optionally substituted with OH, CN, =O, $NH_2$, =NOH, =$NNH_2$, =$NOCH_3$, Br, F, Cl, $SO_3H$, and $NO_2$;

X is $CR^X$, wherein $R^X$ is H or an interacting substituent selected from the group consisting of $CH_3$, Cl, Br, and F;

Y is $CR^Y$, wherein $R^Y$ is H or an interacting substituent selected from the group consisting of $CH_3$, $CHF_2$, $CF_3$, CN, $CH_2CH_3$, Cl, Br, and F;

Z is:

$CR^Z$ wherein $R^Z$ is H or an interacting substituent selected from the group consisting of $CH_3$, CN, Cl, Br, and F;

provided that the compound of Formula I has at least one of the following moieties i)-iv):

i) L is NH, $CH_2$, CHF, $CF_2$, $SCH_2$, $OCH_2$, $NHCH_2$, CH=CH, $CH_2CH_2$, $SCH_2CONH$, $OCH_2CONH$, $NHCH_2CONH$, $OCH_2CH$=CH, or $SCH_2CH$=CH;

ii) R⁸ is:
a) a substituent having the following structure:

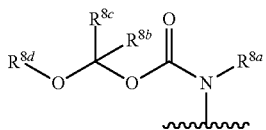

wherein R⁸ᵃ is H or an interacting substituent selected from the group consisting of H, methyl, ethyl, and cyclopropyl;
wherein R⁸ᵇ and R⁸ᶜ are independently H or C1-C6 alkyl;
wherein R⁸ᵈ is

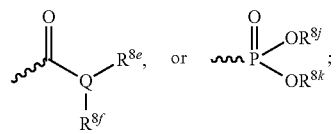

wherein Q is CH or N;
wherein R⁸ᵉ is (CR⁸ᵍ₂)ₙ-basic amine, wherein each R⁸ᵍ is independently H or C1-C3 alkyl;
wherein n is 0-2;
wherein R⁸ᶠ is hydrogen or C1-C6 alkyl optionally substituted with OH or NH₂;
alternatively wherein R⁸ᵉ and R⁸ᶠ join to form a C3-C12 hydrocarbyl ring containing 0-3 heteroatoms selected from O, N and S;
wherein R⁸ʲ and R⁸ᵏ are independently H or C1-C8 hydrocarbyl residue; or
b) a substituent having the following structure:

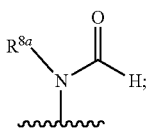

iii) R² is
a) a 6-membered aryl or heteroaryl ring containing 0-3 O, S, or N heteroatoms, optionally substituted with 0-3 noninterfering substituents,
wherein the 6-membered aryl or heteroaryl ring of R² has a CF at each position immediately adjacent to the position where R² attaches to L, if L is 0 or S;
b) a 6-membered aryl or heteroaryl ring containing 0-3 O, S, or N heteroatoms, optionally substituted with 0-3 noninterfering substituents,
wherein the 6-membered aryl or heteroaryl ring of R² has a CH or CF independently at each position immediately adjacent to the position where R² attaches to L, if L is NH, CH₂, CHF, or CF₂;
c) a 5-membered heteroaryl ring containing 1-4 O, S, or N heteroatoms, optionally substituted with 0-2 noninterfering substituents;
wherein the 5-membered heteroaryl ring of R² has O, S, N, NH, CH, CF, or CCl, independently at each of the positions immediately adjacent to the position where R² attaches to L, if L is O, S, NH, CH₂, CHF, or CF₂;
d) a 6-membered or 5-membered non-aryl or non-heteroaryl ring containing 0-3 O, S, or N heteroatoms, optionally substituted with 0-3 noninterfering substituents;
wherein the 6-membered or 5-membered non-aryl or non-heteroaryl ring of R² has O, S, N, NH, CH, CF, or CH₂, independently at each position immediately adjacent to the position where R² attaches to L, if L is O, S, NH, CH₂, CHF, or CF₂;
e) i) a 6-membered aryl or heteroaryl ring containing 0-3 O, S, or N heteroatoms, optionally substituted with 0-3 noninterfering substituents,
ii) a 5-membered heteroaryl ring containing 1-4 O, S, or N heteroatoms, optionally substituted with 0-2 noninterfering substituents, or
iii) a 6-membered or 5-membered non-aryl or non-heteroaryl ring containing 0-3 O, S, or N heteroatoms, optionally with 0-3 noninterfering substituents,
when L is selected from the group consisting of SCH₂, OCH₂, NHCH₂, CH=CH, CH₂CH₂, SCH₂CONH, OCH₂CONH, NHCH₂CONH, OCH₂CH=CH, and SCH₂CH=CH in any of e.i. to e.iii.;
alternatively wherein 2 adjacent noninterfering substituents of R² in a)-e) form one or more fused rings with the 6-membered aryl or heteroaryl ring, the 5-membered heteroaryl ring, or the 6-membered or 5-membered non-aryl or non-heteroaryl ring;
f) a substituent having the following structure:

wherein R²ᵃ contains an oxygen residue derived from an R² as in a)-e), wherein R² has an OH group, wherein the R² OH is replaced with an oxygen residue in R²ᵃ, and wherein the oxygen residue is linked to P;

g)

wherein R²ᵇ, R²ᶜ, R²ᵈ, R²ᶠ and R²ᵍ independently are each N or CR²ᵉ wherein R²ᵉ is H or C1-C4 alkyl optionally substituted with a noninterfering substituent; or
h) selected from the group consisting of -continued

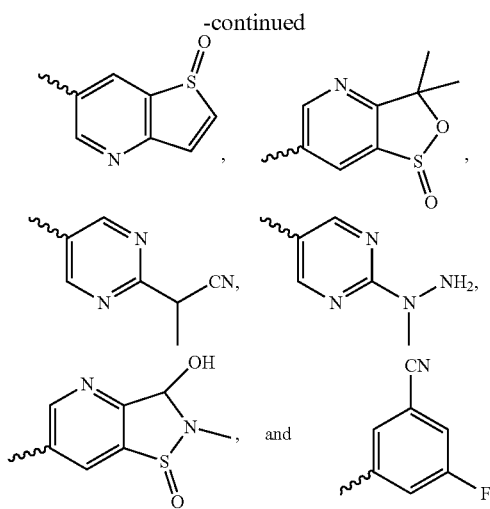

wherein the noninterfering substitutents for $R^2$ are the same as described above;

iv) $R^4$ is:

a) a substituent having the following structure:

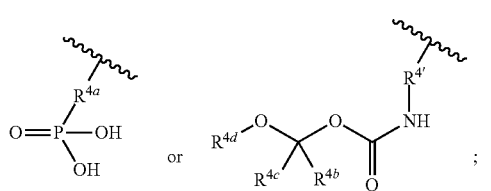

wherein $R^{4a}$ contains an oxygen residue derived from $R^4$ as in b)-d) or g), wherein the $R^4$ has an OH group, wherein the $R^4$ OH is replaced with an oxygen residue in $R^{4a}$, and wherein the oxygen residue is linked to P;

wherein $R^{4'}$—NH is derived from $R^4$ as in b)-d) or g), wherein the $R^4$ contains a primary amine and wherein the NH in the primary amine links the $R^{4'}$ residue to the C=O;

wherein $R^{4b}$ and $R^{4c}$ are independently H or C1-C6 alkyl;

wherein $R^{4d}$ is

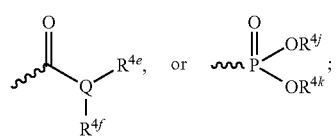

wherein Q is CH or N;

wherein $R^{4e}$ is $(CR^{4g}_2)_n$-basic amine, wherein each $R^{4g}$ are independently H or C1-C3 alkyl;

wherein n is 0-2;

wherein $R^{4f}$ is hydrogen or C1-C6 alkyl optionally substituted with OH or $NH_2$;

alternatively wherein $R^{4e}$ and $R^{4f}$ join to form a ring;

wherein $R^{4j}$ and $R^{4k}$ are independently H or C1-C8 hydrocarbyl residue:, b) a substituent having the following structure

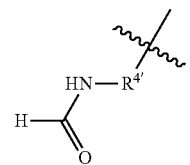

c) selected from the group consisting of:

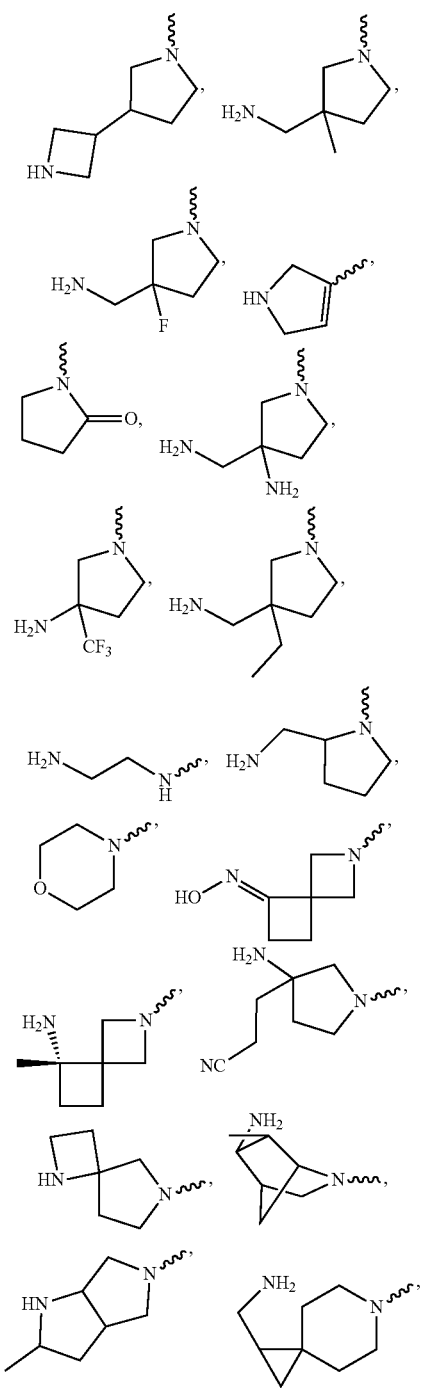

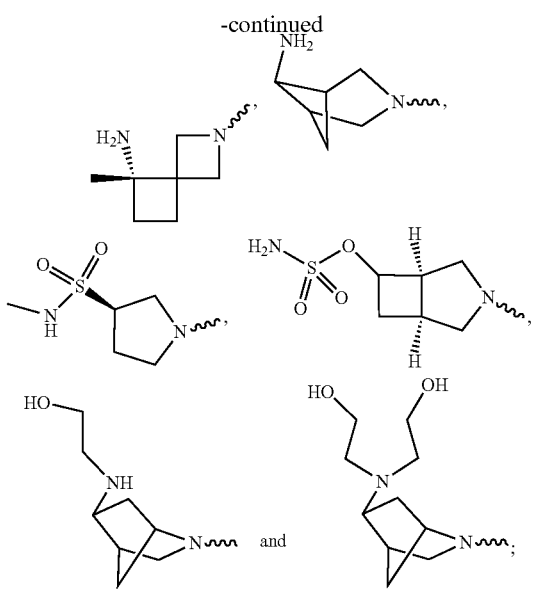

wherein the noninterfering substitutents for $R^4$ are the same as described above.

2. A compound having the formula:

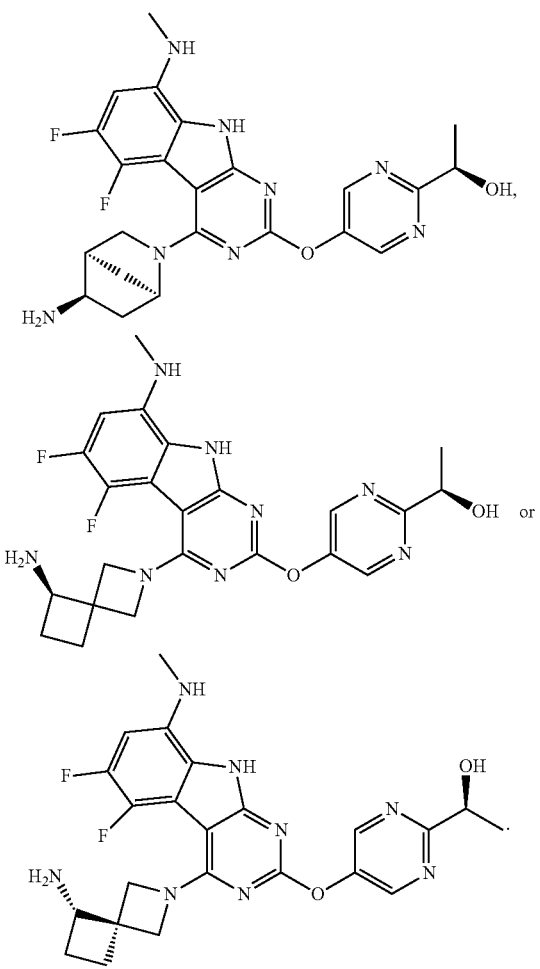

3. A composition comprising an effective amount of compound of claim 1 and a pharmaceutically acceptable carrier.

4. A method of treating a bacterial infection comprising administering to a patient in need thereof an effective amount of compound of claim 1.

5. The compound of claim 1, wherein
L is O, S, NH, $CH_2$, $SCH_2$, or $NHCH_2$;
$R^8$ is H or an interacting substituent selected from the group consisting of Cl, F, Br, $NH_2$, $C_{1-3}$ alkyl, amino $C_{1-3}$ alkyl, aminocyclopropyl, $OCH_3$, cyclopropyl, and $CH_2$cyclopropyl;
$R^9$ is H;
$R^2$ is a) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH at each position immediately adjacent the position where $R^2$ attaches to L, if L is O or S;

b) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CF at each positions immediately adjacent the position where $R^2$ attaches to L, if L is O or S;

c) a 6-membered aryl or heteroaryl ring containing 0-3 O, S, or N heteroatoms, optionally substituted with 0-3 noninterfering substituents, wherein the 6-membered aryl or heteroaryl ring of $R^2$ has a CH or CF independently at each position immediately adjacent the position where $R^2$ attaches to L, if L is NH, $CH_2$, CHF, or $CF_2$;

d) a 5-membered heteroaryl ring containing 1-4 O, S, or N heteroatoms, optionally substituted with 0-2 noninterfering substituents;
wherein the 5-membered heteroaryl ring of $R^2$ has O, S, N, NH, CH, CF, or CCl, independently at each of the positions immediately adjacent the position where $R^2$ attaches to L, if L is O, S, NH, $CH_2$, CHF, or $CF_2$;

e) a 6-membered or 5-membered non-aryl or non-heteroaryl ring containing 0-3 O, S, or N heteroatoms, optionally substituted with 0-3 noninterfering substituents;
wherein the 6-membered or 5-membered non-aryl or non-heteroaryl ring of $R^2$ has O, S, N, NH, CH, CF, or $CH_2$, independently at each position immediately adjacent the position where R attaches to L, if L is O, S, NH, $CH_2$, CHF, or $CF_2$;

f)

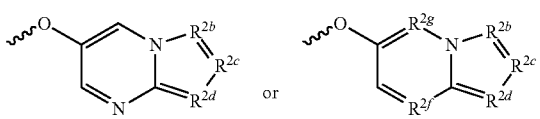

wherein $R^{2b}$, $R^{2c}$, $R^{2d}$, $R^{2f}$, and $R^{2g}$ independently is each N or $CR^{2e}$ wherein the $R^{2e}$ is C1-C4 alkyl optionally substituted with a noninterfering substituent; or g) selected from the group consisting of

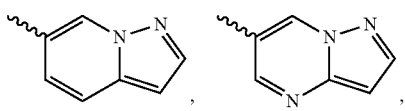

-continued

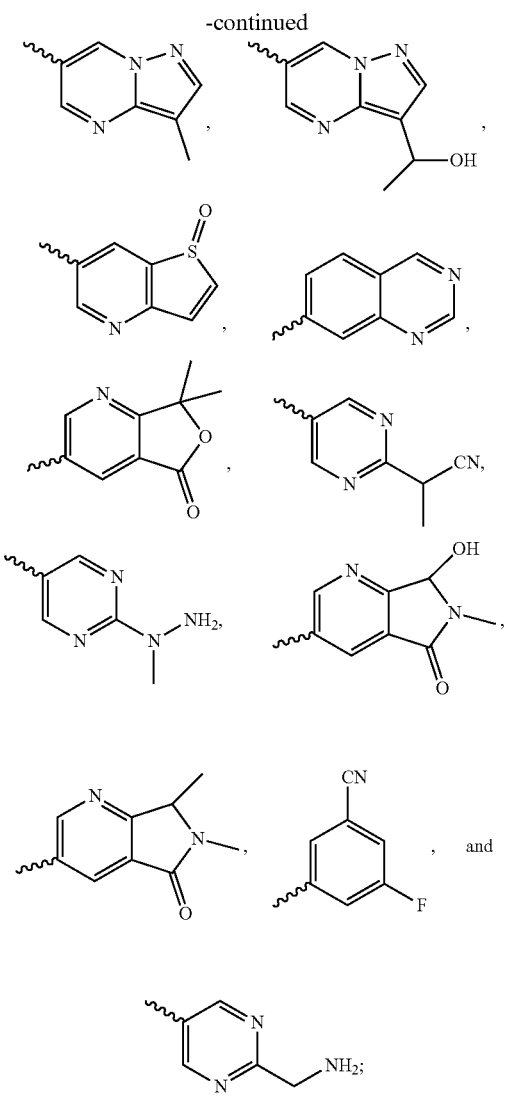

wherein the noninterfering substituents in a)-f) for $R^2$ are the same as in claim 1;

$R^4$ is a) H;

b) an optionally substituted $OR_a$; wherein $R_a$ is a 5-6 membered aryl or heteroaryl containing 0-3 O, S, or N heteroatoms optionally substituted with 0-3 noninterfering substituents;

c) an optionally substituted secondary or tertiary amine attached to the C Ring through the secondary or tertiary amine N;

d) an optionally substituted 5-10 membered unsaturated cyclic or heterocyclic residue containing 0-3 N, O or S heteroatoms;

wherein the optional substituent is 0-3 noninterfering substituents; wherein the $R^4$ substituent of a)-d) does not project greater than about 3 Å below the plane of the A, B and C Rings toward the GyrB/ParE binding pocket floor in the bound conformation; and wherein $R^4$ does not sterically interfere with $R^2$ or Z when the compound is in the bound conformation;

wherein the noninterfering substituents in a)-d) for $R^4$ are the same as in claim 1;

or e) selected from the group consisting of:

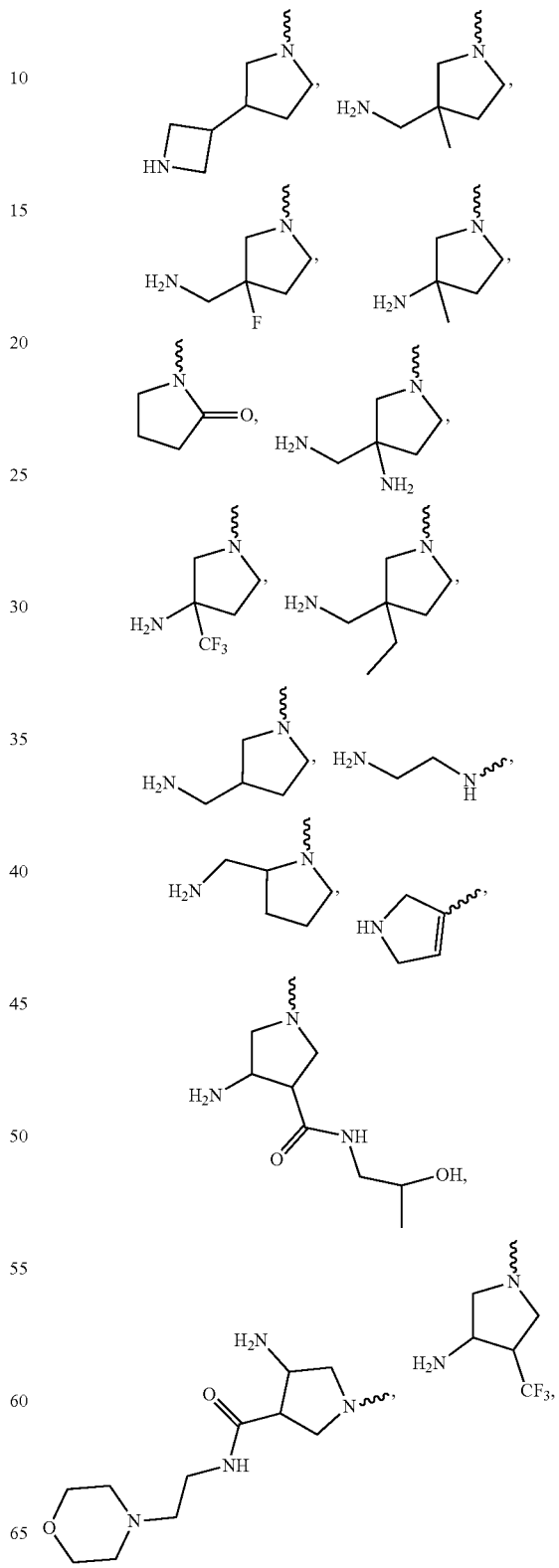

-continued

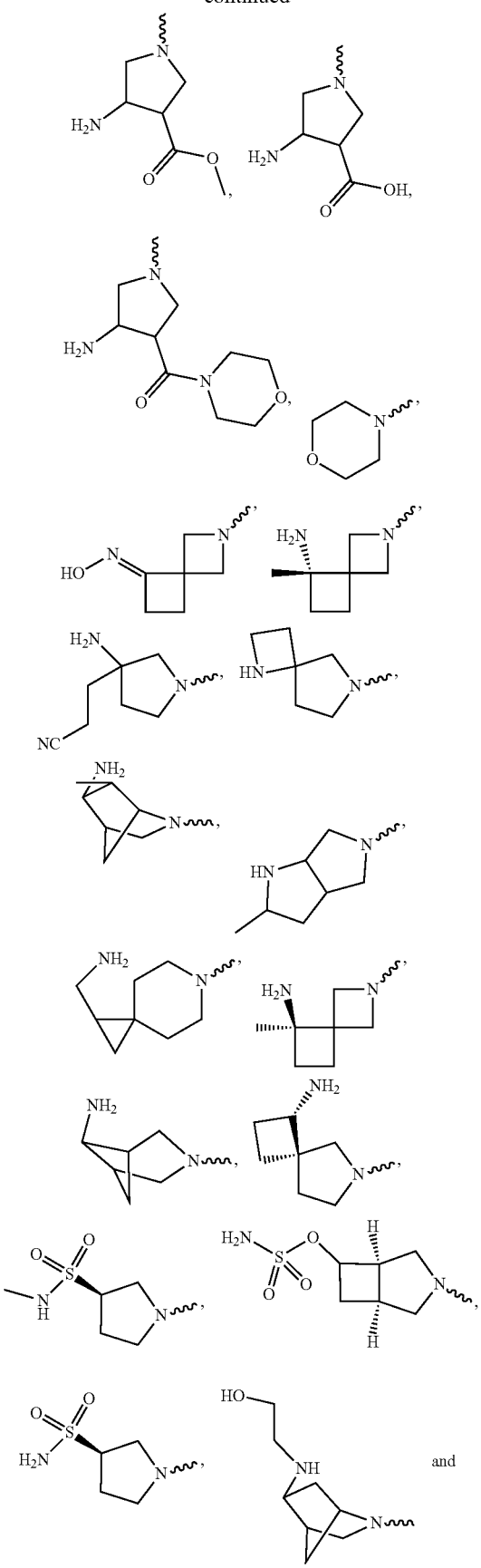

-continued

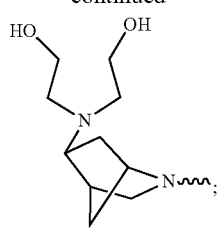

and the proviso is the same as in claim 1.

6. The compound of claim 5, wherein the noninterfering substituents in $R^2$ and $R^4$ are independently selected from the group consisting of $CO_2H$, CN, $NH_2$, Br, Cl, F, $SO_3H$, and C1-15 hydrocarbyl residue containing 0-5 O, S, or N heteroatoms optionally substituted with OH, CN, =O, $NH_2$;

and the proviso is the same as in claim 5.

7. The compound of claim 5, wherein $R^2$ is selected from the group consisting of

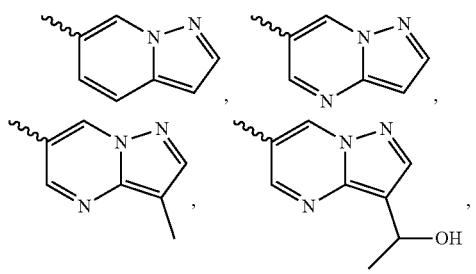

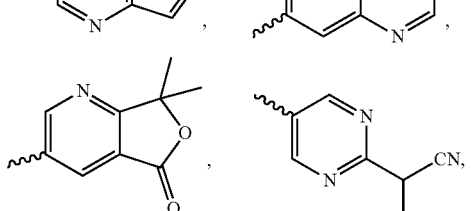

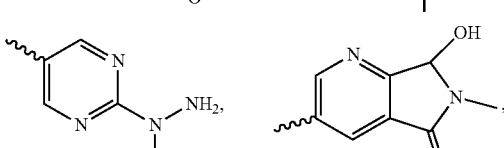

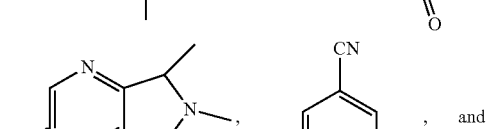

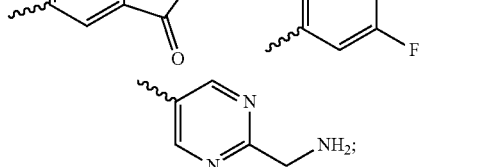

and the proviso is the same as in claim 5.

8. The compound of claim 5, wherein R[4] is selected from the group consisting of
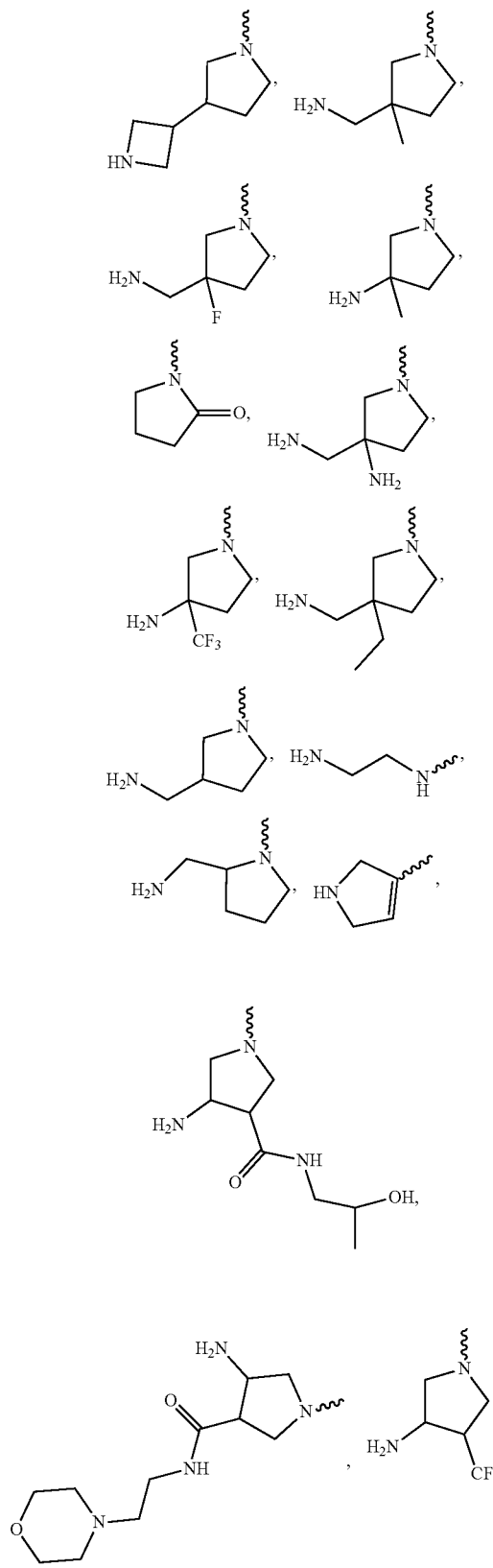
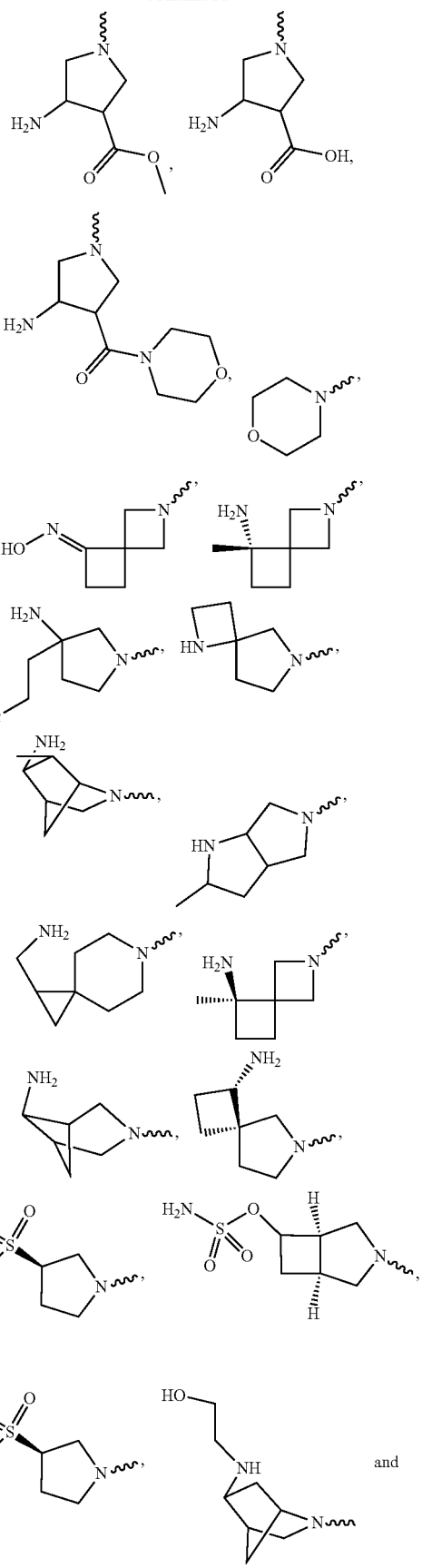

605

-continued

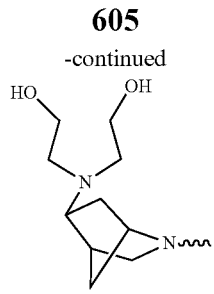

and the proviso is the same as in claim 5.

9. The compound of claim 5, wherein
L is O or S;
and the proviso is the same as in claim 5.

10. The compound of claim 5, wherein
L is NH, CH$_2$, SCH$_2$, or NHCH$_2$;
and the proviso is the same as in claim 5.

11. The compound of claim 1, wherein
R$^4$ is:

a)

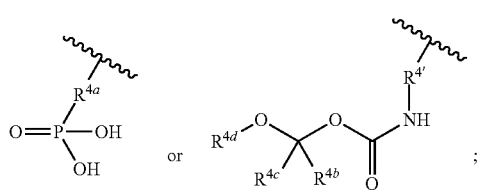

wherein R$^{4a}$ contains an oxygen residue derived from R$^4$ as in b)-d) or g) of claim 1, wherein the R$^4$ has an OH group, wherein the R$^4$ OH is replaced with an oxygen residue in R$^{4a}$, and wherein the oxygen residue is linked to P;

wherein R$^{4'}$—NH is derived from R$^4$ as in b)-d) or g), wherein the R$^4$ contains a primary amine and wherein the NH in the primary amine links the R$^{4'}$ residue to the C=O;

wherein R$^{4b}$ and R$^{4c}$ are independently H or C1-C6 alkyl;

wherein R$^{4d}$ is

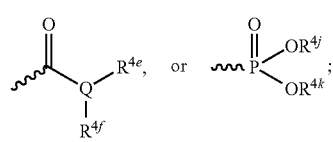

wherein Q is CH or N;

wherein R$^{4e}$ is (CR$^{4g}$$_2$)$_n$-basic amine, wherein each R$^{4g}$ is independently H or C1-C3 alkyl;

wherein n is 0-2;

wherein R$^{4f}$ is hydrogen or C1-C6 alkyl optionally substituted with OH or NH$_2$;

alternatively wherein R$^{4e}$ and R$^{4f}$ join to form a ring;

wherein R$^{4j}$ and R$^{4k}$ are independently H or C1-C8 hydrocarbyl residue

606 or b)

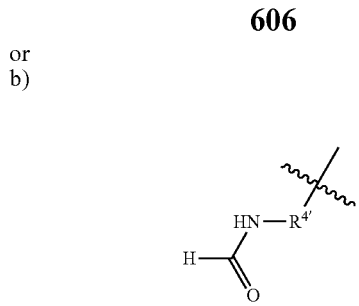

12. The compound of claim 1, wherein
L is O, S, NH, CH$_2$, SCH$_2$, or NHCH$_2$;
R$^8$ is H or an interacting substituent selected from the group consisting of H, F, Cl, Br, NH$_2$, OH, 1-3C alkyl, amino-1-3C alkyl, aminocyclopropyl, OCH$_3$, OCH$_2$CH$_3$, cyclopropyl, CH$_2$cyclopropyl, NHNH$_2$, NHOH, NHNHCH$_3$, NHOCH$_3$, NHCD$_3$, SCH$_3$, CHCl$_2$, and CHCH$_2$.

13. The compound of claim 12, wherein
L is O;
R$^2$ is a pyrimidine ring substituted with 0-3 noninterfering substituents selected from the group consisting of CN, NH$_2$, Br, Cl, F, and C1-15 hydrocarbyl residue;
R$^8$ is selected from the group consisting of Cl, F, Br, NH$_2$, 1-3Calkyl, amino-1-3C alkyl, aminocyclopropyl, OCH$_3$, cyclopropyl, and CH$_2$cyclopropyl.

14. The compound of claim 1, which is selected from the group consisting of

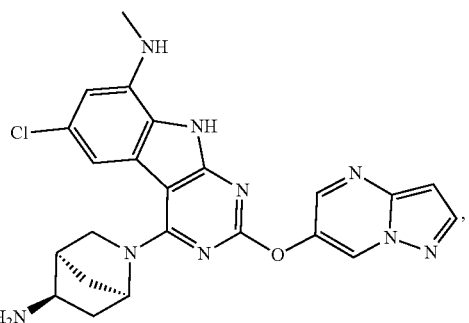

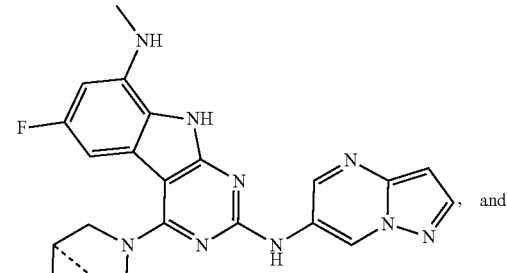

, and

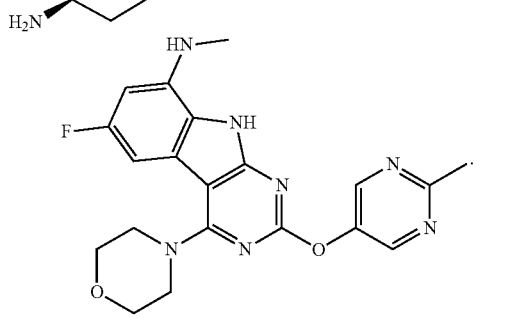

.

15. The compound of claim 12, wherein
L is O;
R² is a pyrimidine ring substituted with 0-3 noninterfering substituents selected from the group consisting of CN, NH₂, Br, Cl, F, and C1-15 hydrocarbyl residue; and
R⁴ is
a) an optionally substituted secondary or tertiary amine attached to the C Ring through the secondary or tertiary amine N; or
b) an optionally substituted 5-10 membered unsaturated cyclic or heterocyclic residue containing 0-3 N, O or S heteroatoms.

16. The compound of claim 1, which is selected from the group consisting of 10.3
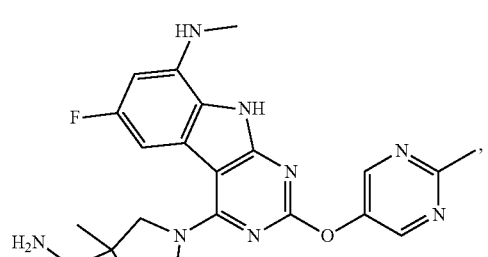

10.7
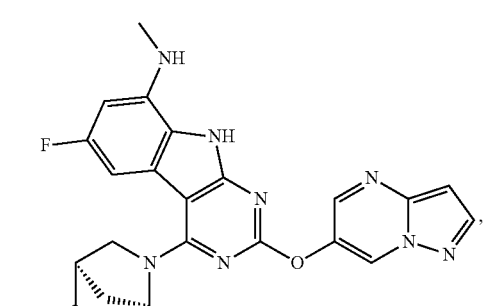

10.8
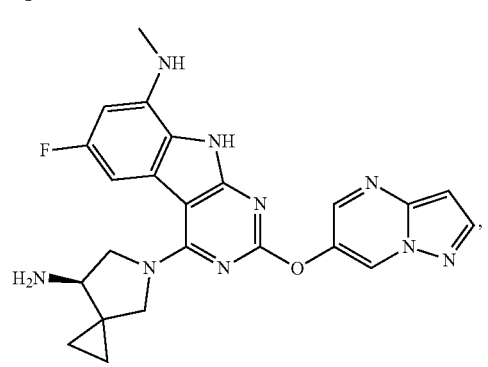

10.9
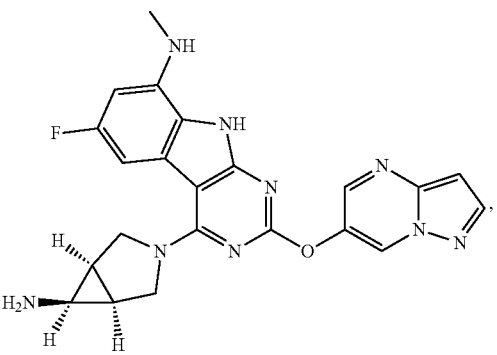

-continued 10.18
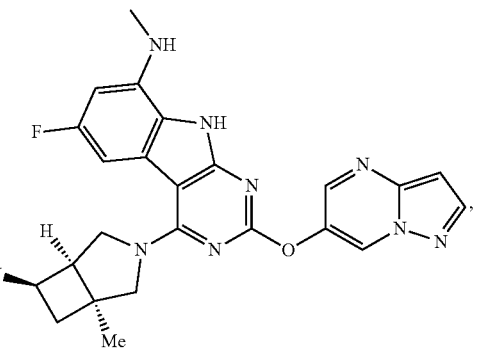

10.19
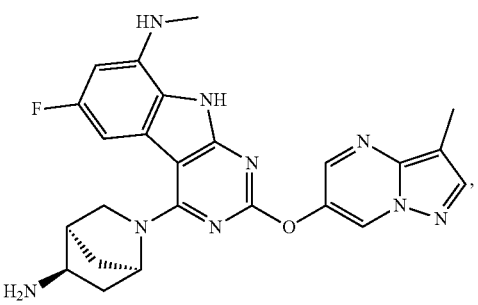

10.20
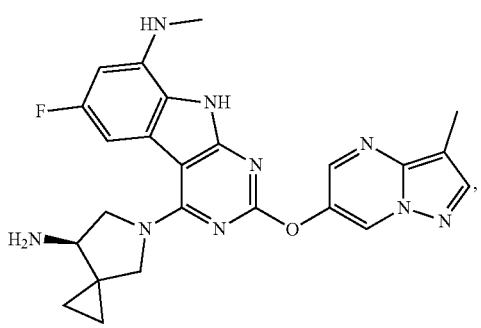

10.21
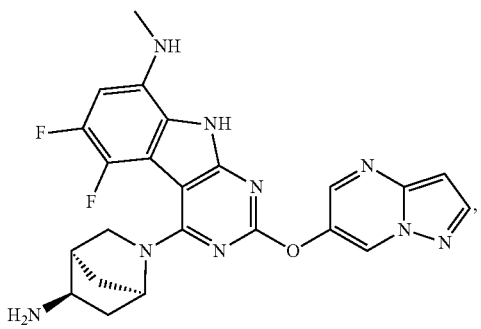

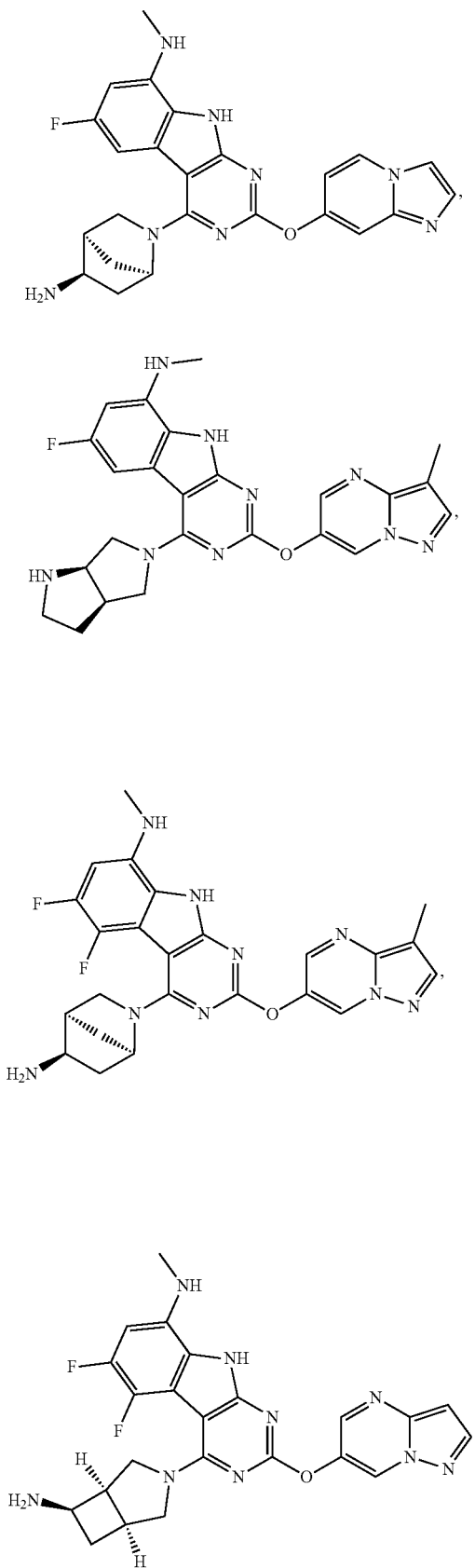
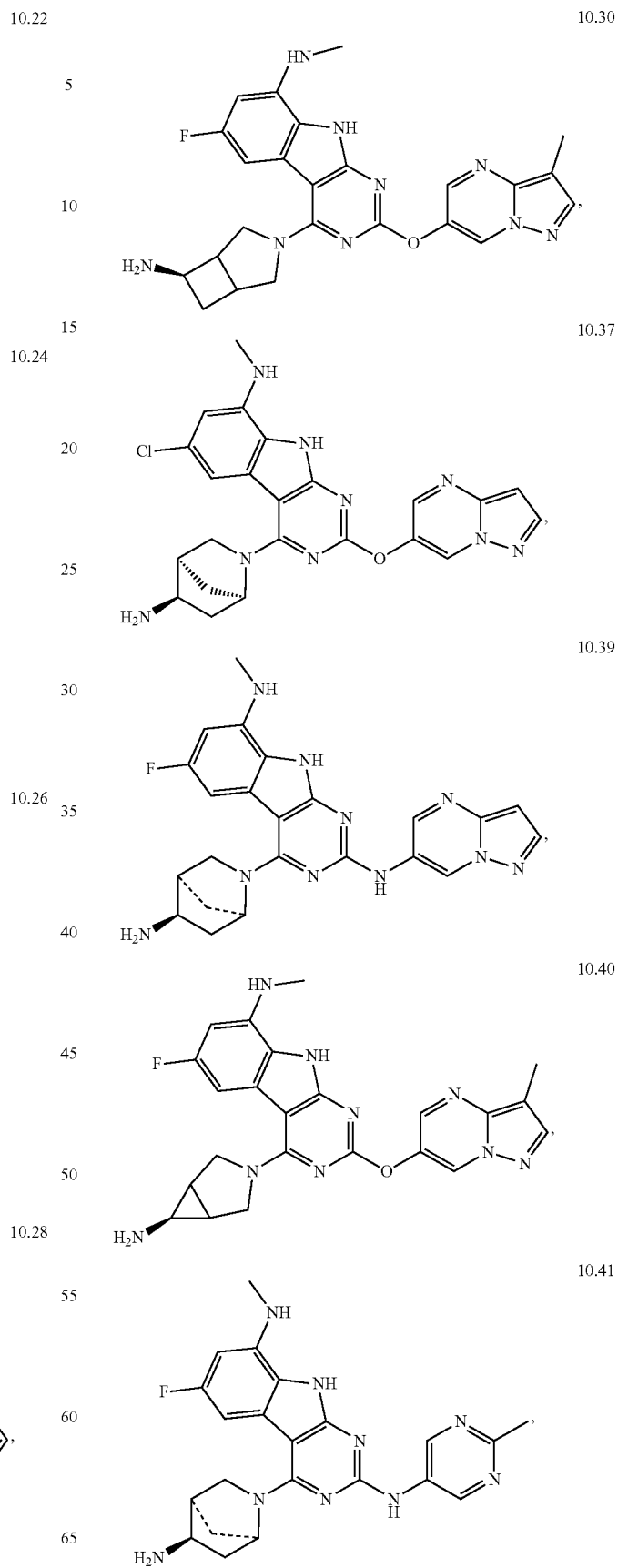

-continued
10.42
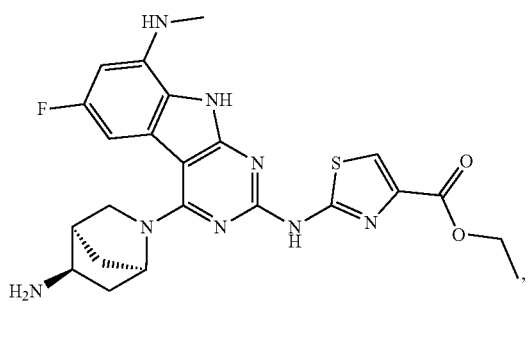
10.43
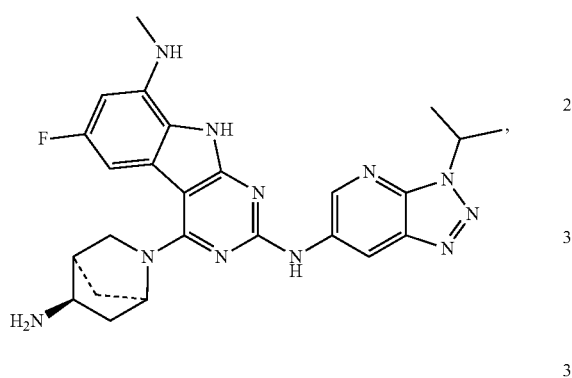
10.44
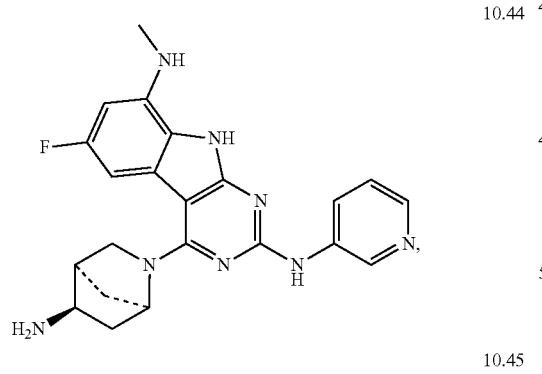
10.45
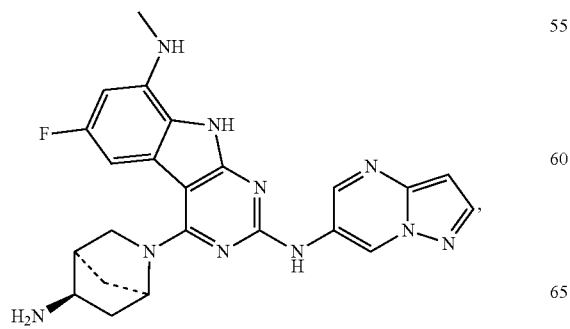
-continued
10.46
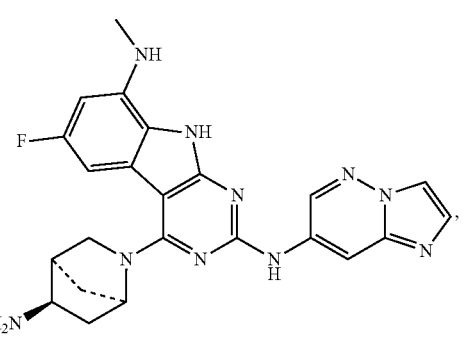
10.47
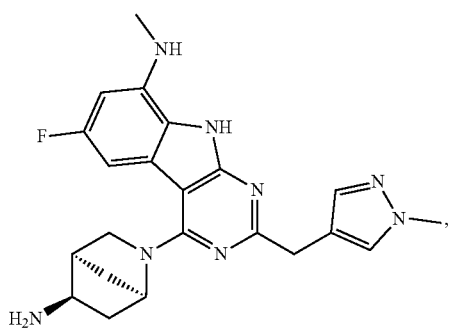
10.48
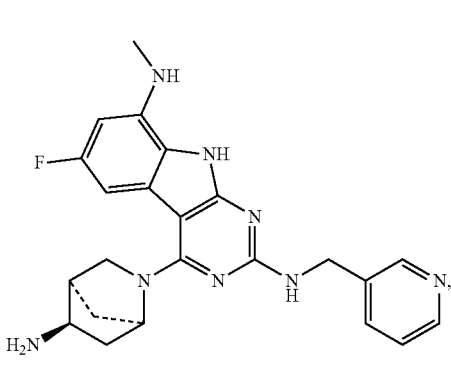
10.49
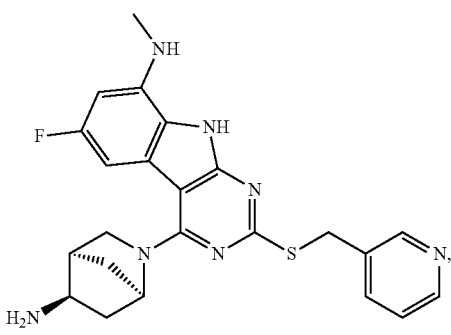

10.50
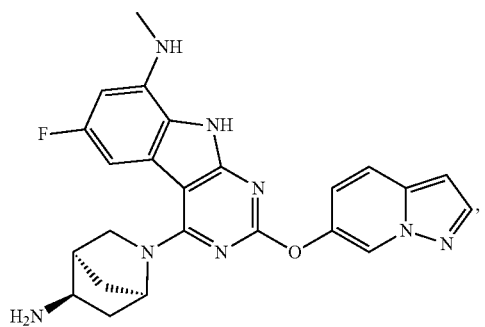
10.51
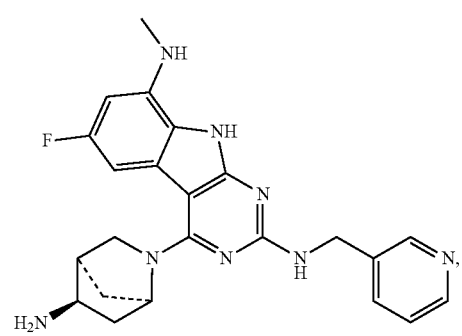
10.52
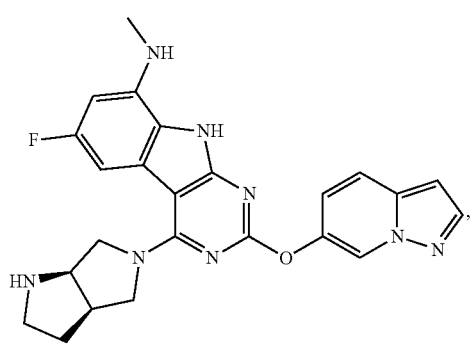
10.53
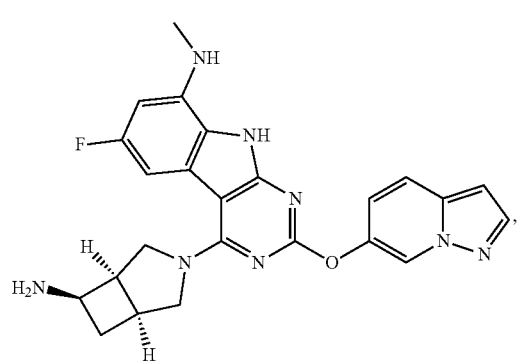
10.54
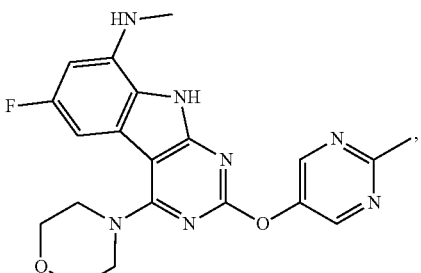
10.55
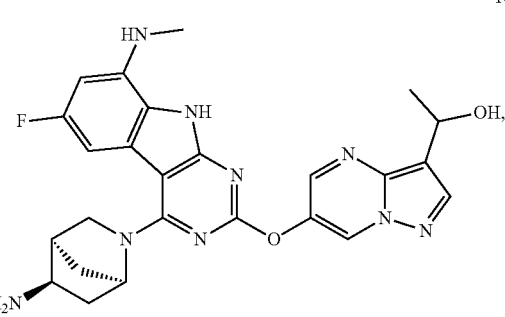
10.56
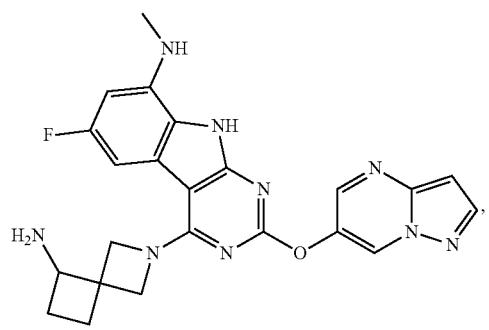
10.57
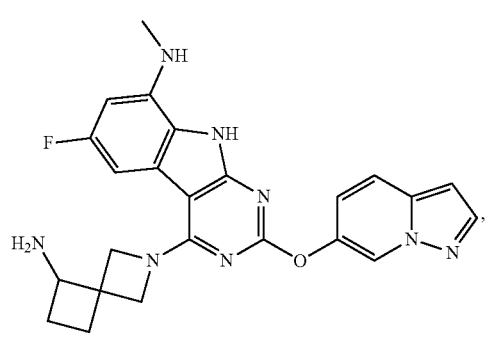
10.58
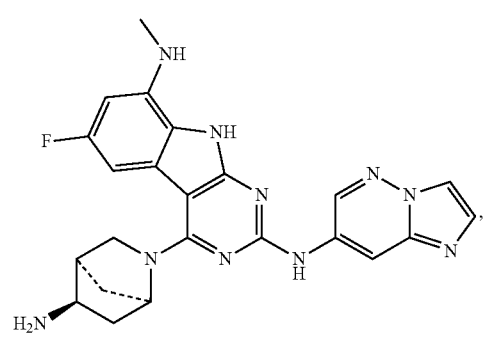

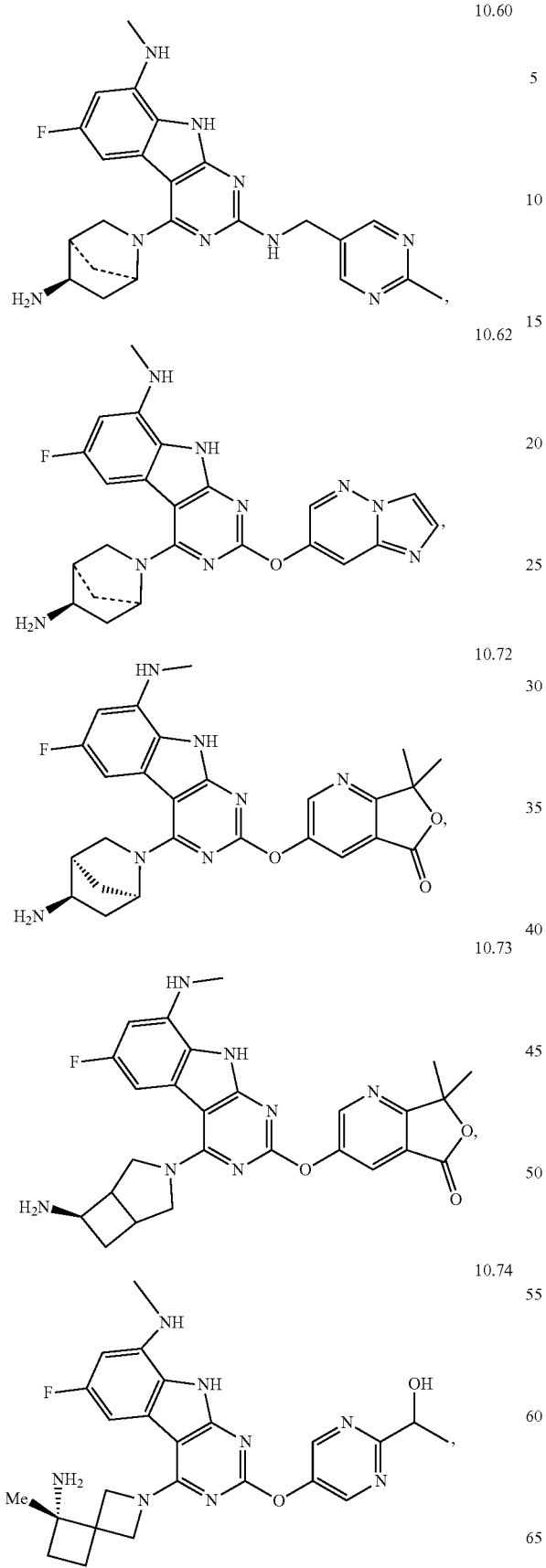
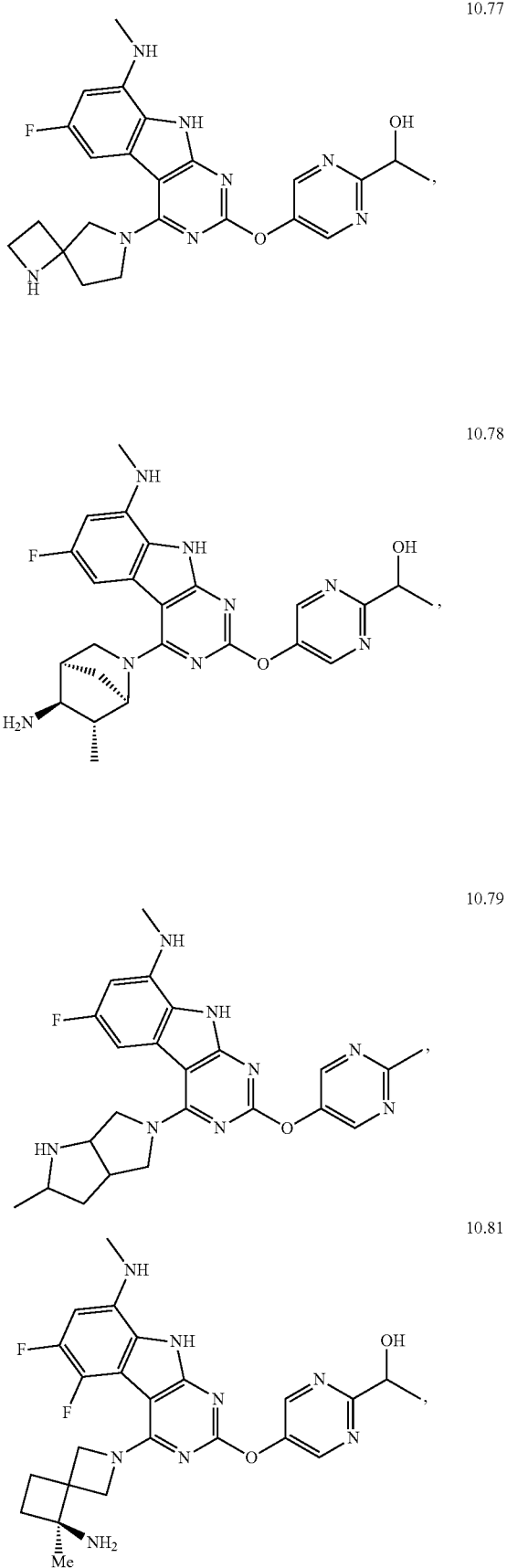

| | | |
|---|---|---|
| 10.85 | 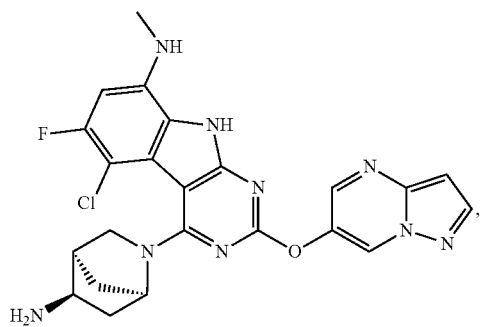 | 10.94 |
| | | 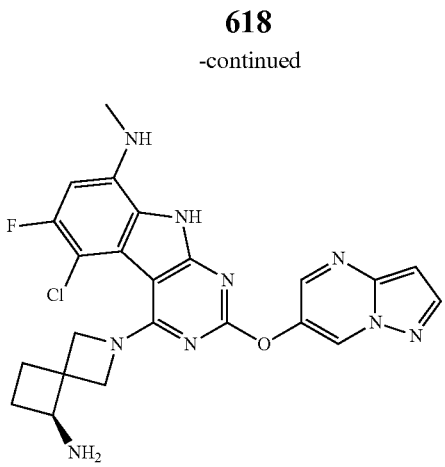 |
| 10.86 | 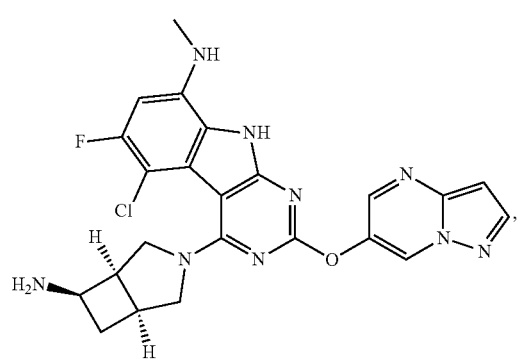 | 10.95 |
| | | 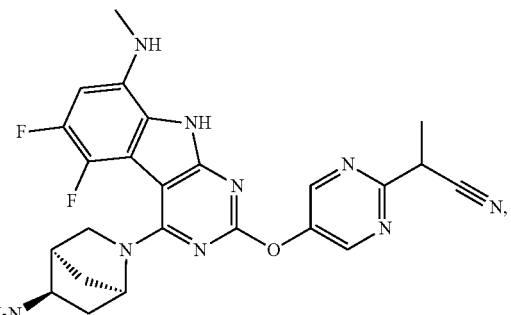 |
| 10.90 | 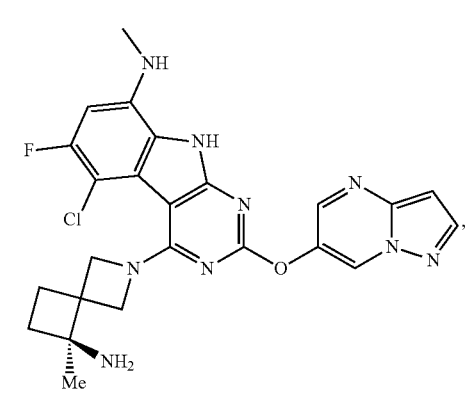 | 10.98 |
| | | 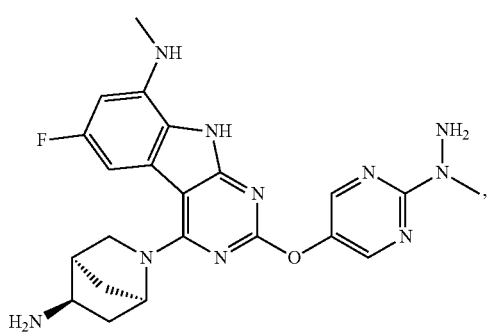 |
| 10.91 | 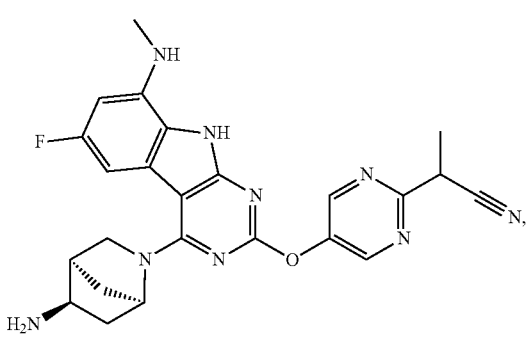 | 10.107 |
| | | 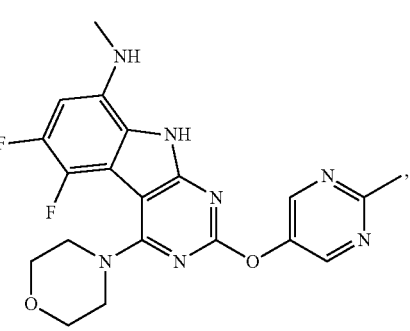 |

-continued
10.108
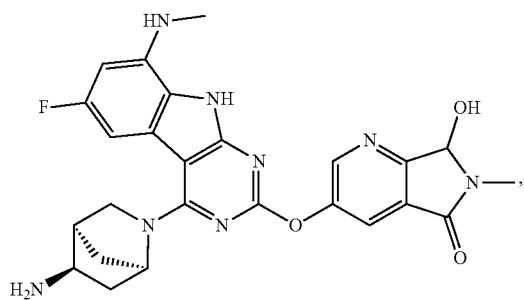
10.109
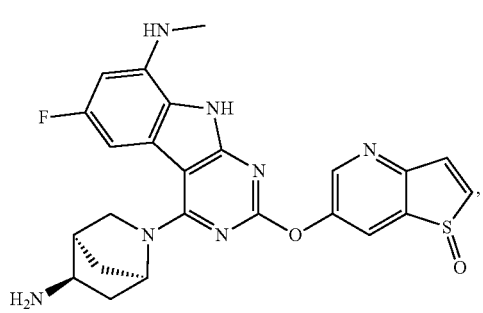
10.114
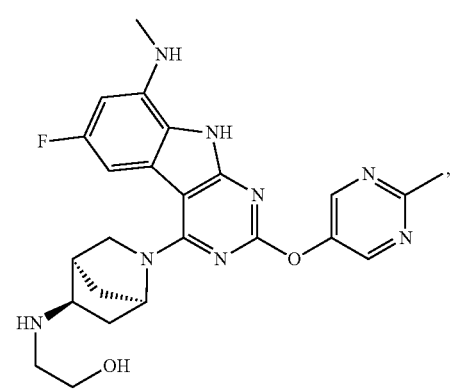
10.115
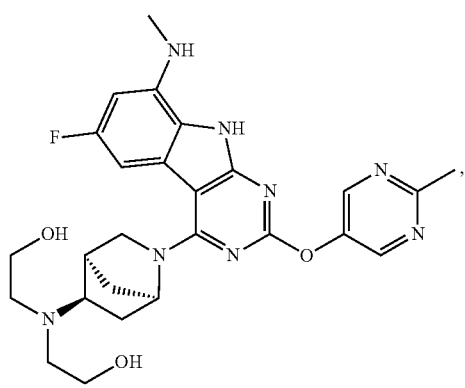
-continued
10.116
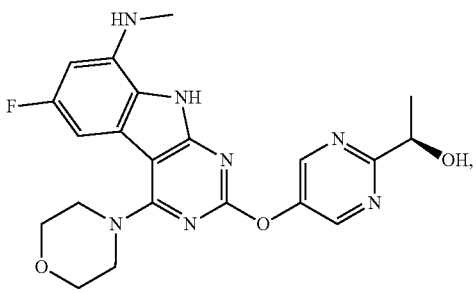
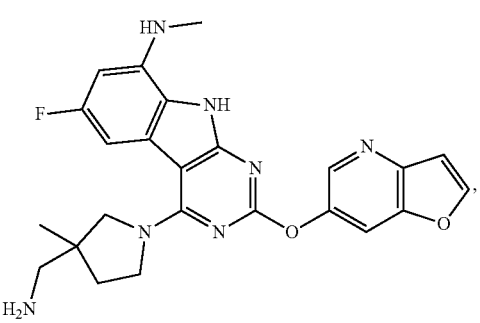
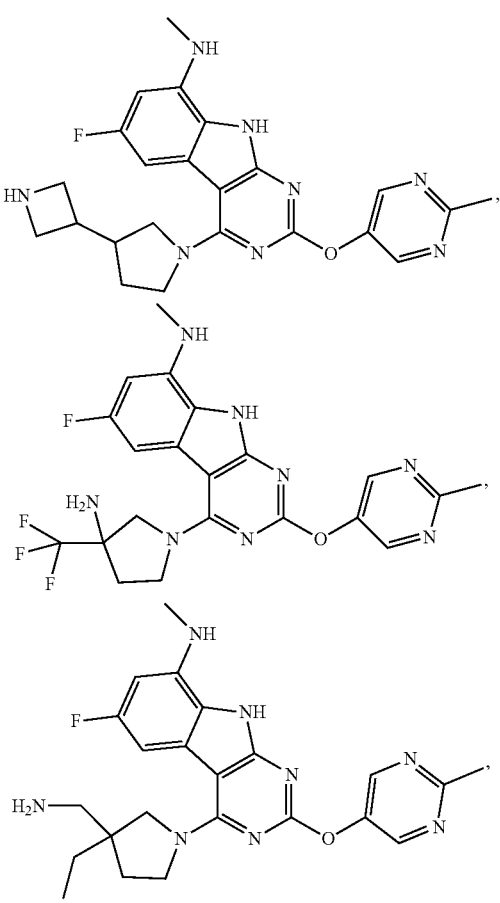

621
-continued
622
-continued
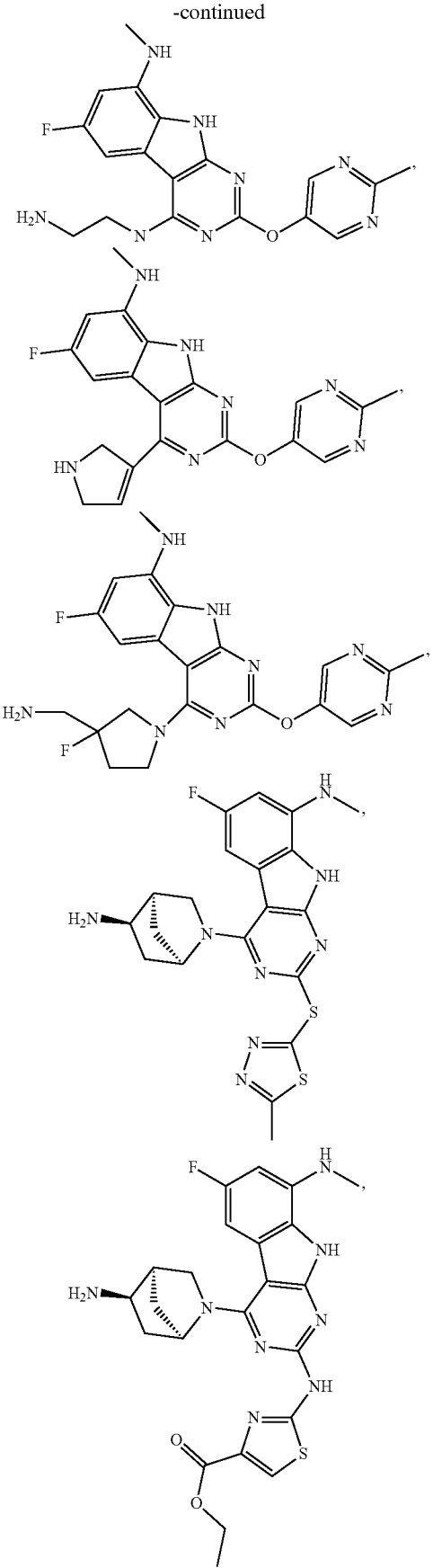
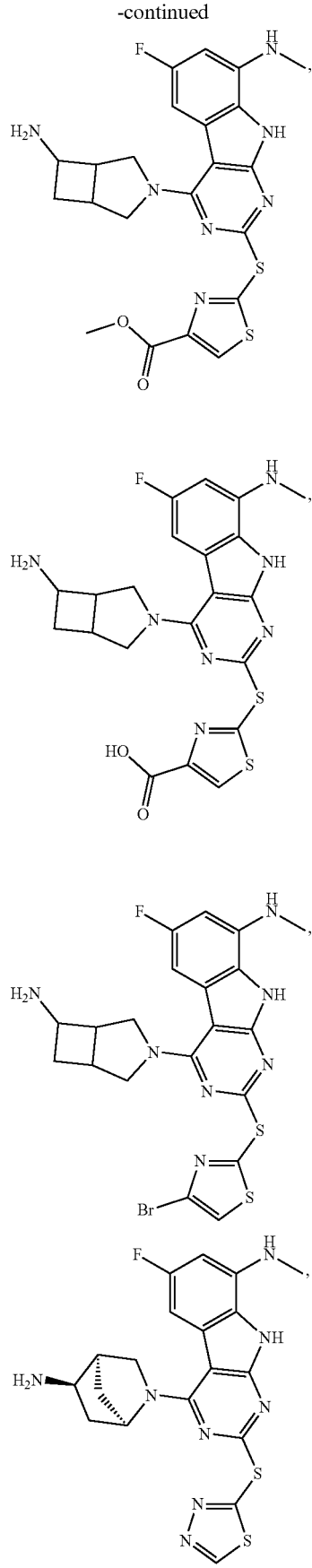

623
-continued
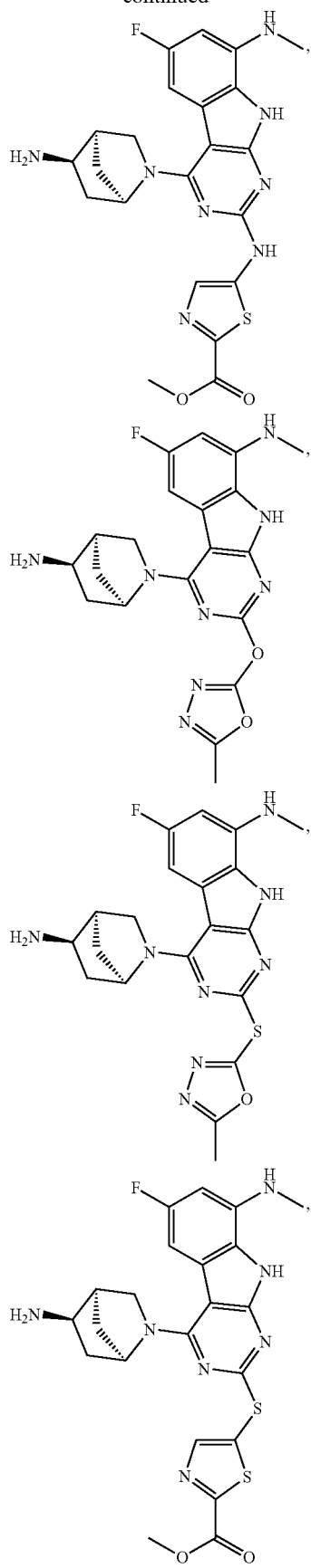
624
-continued
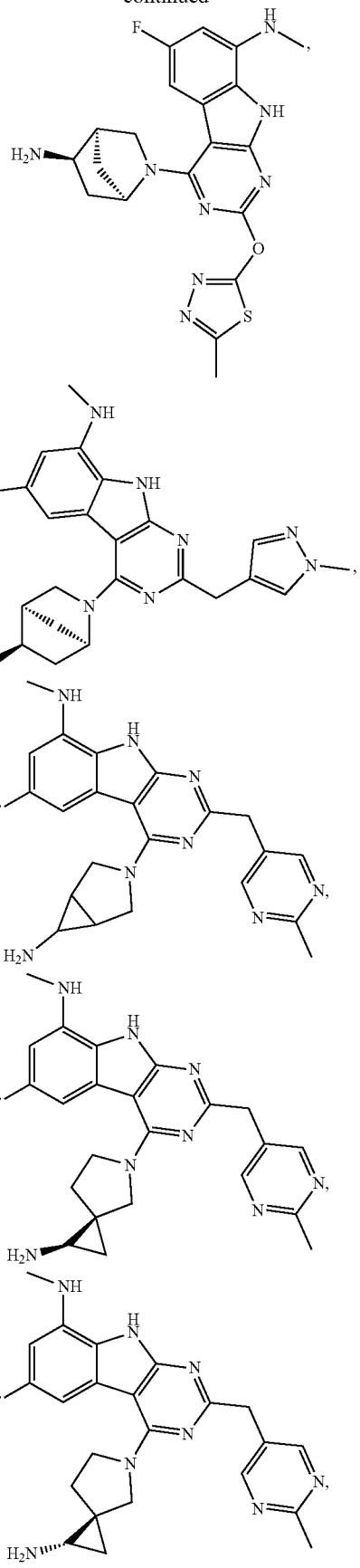

625
-continued
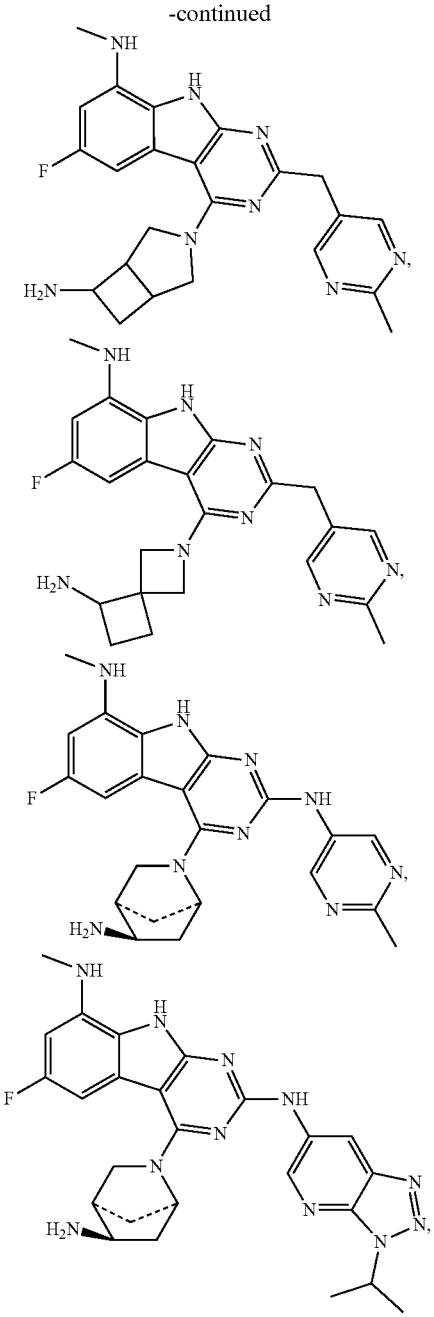
626
-continued
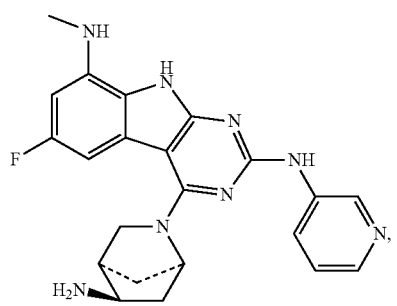
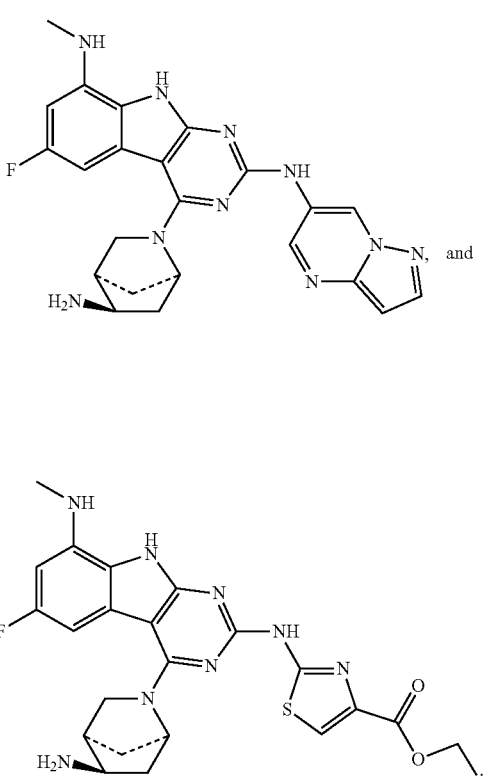
* * * * *